United States Patent
Norris et al.

(10) Patent No.: US 9,458,156 B2
(45) Date of Patent: Oct. 4, 2016

(54) TRICYCLIC COMPOUNDS AS ANTICANCER AGENTS

(71) Applicant: BRISTOL-MYERS SQUIBB COMPANY, Princeton, NJ (US)

(72) Inventors: Derek J. Norris, Pennington, NJ (US); George V. Delucca, Pennington, NJ (US); Ashvinikumar V. Gavai, Princeton Junction, NJ (US); Francis Y. Lee, Yardley, PA (US); John S. Tokarski, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/580,355

(22) Filed: Dec. 23, 2014

(65) Prior Publication Data

US 2016/0176864 A1    Jun. 23, 2016

(51) Int. Cl.
   *C07D 471/04*    (2006.01)
   *A61K 31/437*    (2006.01)

(52) U.S. Cl.
   CPC ........... *C07D 471/04* (2013.01); *A61K 31/437* (2013.01)

(58) Field of Classification Search
   CPC ... C07D 471/04; C07D 417/04; A61K 31/45

USPC ............................................ 546/81; 514/278
See application file for complete search history.

(56) References Cited

U.S. PATENT DOCUMENTS

2014/0256700 A1    9/2014   Poss et al.

FOREIGN PATENT DOCUMENTS

| WO | WO 2010/080429 | 7/2010 |
|----|----------------|--------|
| WO | WO 2012/145173 | 10/2012 |
| WO | WO 2013/046635 | 4/2013 |
| WO | PCT/US2014/018914 | 2/2014 |
| WO | WO 2014/086739 | 6/2014 |
| WO | WO 2014/134232 | 9/2014 |
| WO | WO 2014/134267 | 9/2014 |
| WO | WO 2014/164596 | 10/2014 |

OTHER PUBLICATIONS

Conway, S., ACS Med. Chem. Lett.; vol. 3 pp. 691-694 (2012).
Hewings et al., J. Med. Chem., vol. 55, pp. 9393-9413 (2012).
Gorlitzer, K. et. al., Die Pharmazie, Govi Verlag Pharmazeutischer Verlag GMBH, vol. 55 No. 4, pp. 273-281 (2000).

*Primary Examiner* — Rita Desai
(74) *Attorney, Agent, or Firm* — Elliott Korsen

(57) ABSTRACT

The present invention is directed to tricyclic compounds, pharmaceutically acceptable compositions comprising compounds of the invention and methods of using said compositions in the treatment of various disorders.

3 Claims, No Drawings

SEQUENCE LISTING

<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His Ser Ser Gly Glu Thr Val
1               5                   10                  15

Arg Phe Gln Ser Met
            20

<210> SEQ ID NO 2
<211> LENGTH: 39
<212> TYPE: PRT
<213> ORGANISM: Tobacco vein mottling virus

<400> SEQUENCE: 2

Met Gly Ser Ser His His His His His Ser Ser Gly Glu Thr Val
1               5                   10                  15

Arg Phe Gln Gly Leu Asn Asp Ile Phe Glu Ala Gln Lys Ile Glu Trp
            20                  25                  30

His Glu Asp Thr Gly His Met
        35

<210> SEQ ID NO 3
<211> LENGTH: 21
<212> TYPE: PRT
<213> ORGANISM: Artificial Sequence
<220> FEATURE:

```
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 3

Ser Gly Arg Gly Lys Gly Gly Lys Gly Leu Gly Lys Gly Gly Ala Lys
1               5                   10                  15

Arg His Arg Lys Val
            20
```

TRICYCLIC COMPOUNDS AS ANTICANCER AGENTS

This application claims priority from U.S. Provisional Application No. 61/920,500 filed Dec. 24, 2013, the disclosures of which are incorporated herein by reference in their entirety.

FIELD OF THE INVENTION

The invention provides novel tricyclic compounds, pharmaceutical compositions comprising the compounds, and methods of using them, for example, for the treatment or prophylaxis of certain cancers and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction.

BRD2 and BRD3 are reported to associate with histones along actively transcribed genes and may be involved in facilitating transcriptional elongation (Leroy et al., Mol. Cell. 2008 30(1):51-60), while BRD4 appears to be involved in the recruitment of the pTEF-I3 complex to inducible genes, resulting in phosphorylation of RNA polymerase and increased transcriptional output (Hargreaves et al., Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al., Cell, 2004 117(3): 349-60).

Recent articles relating to this target include Prinjha et al., Trends in Pharmacological Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in development include GSK-525762A, OTX-015, TEN-010 as well as others from the University of Oxford and Constellation Pharmaceuticals Inc.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

There is provided a compound of formula (I)

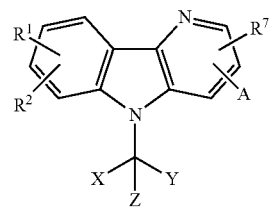

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, optionally substituted heterocyclo, $-OR^4$, $-CONR^3R^4$, $-NR^3R^4$, $NR^3R^4(C_1-C_6)$alkyl-, $-NR^6COR^3$, $-NR^6COR^3$, $NR^6COR^3(C_1-C_6)$alkyl-, $-NR^6CO_2R^3$, $NR^6CO_2R^3(C_1-C_6)$alkyl-, $-NR^6CONR^3R^4$, $-SO_2NR^3R^4$, $SO_2(C_1-C_6)$alkyl-, $-NR^6SO_2NR^3R^4$, $-NR^6SO_2R^4$ or $NR^6SO_2R^4(C_1-C_6)$alkyl-;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, $-OH$, $(C_1-C_6)$alkyl, $(C_1-C_6)$alkoxy, $-NR^3R^4$, $-CONR^3R^4$, $-OCONR^3R^4$, $-NR^6OCOR^3$, $-NR^6CONR^3R^4$, $-NR^6SO_2NR^3R^4$ or $-NR^6SO_2R^4$;

$R^1$ is, independently at each occurrence, one or more hydrogen, halogen, $-CN$, $-OR^4$, $-NR^3R^4$, $-CONR^3R^4$, $-COOH$, $-OCONR^3R^4$, $-NR^6OCOR^3$, $-NR^6CONR^3R^4$, $-NR^6SO_2NR^3R^4$, $-NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NR^6SO_2$-optionally substituted ($C_1$-$C_6$)alkyl, —$NR^6SO_2$-optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$)alkyl-$SO_2$—, optionally substituted aryl-$SO_2$, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring; $R^5$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$) alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$) alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

$R^6$ is hydrogen or optionally substituted ($C_1$-$C_6$)alkyl;

$R^7$ is hydrogen, optionally substituted ($C_1$-$C_6$)alkyl, —$OR^4$, CN or halogen;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect, there is provided a method of treating cancer which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

DETAILED DESCRIPTION OF THE INVENTION

In a first aspect of the present invention, there is provided a compound of formula (I)

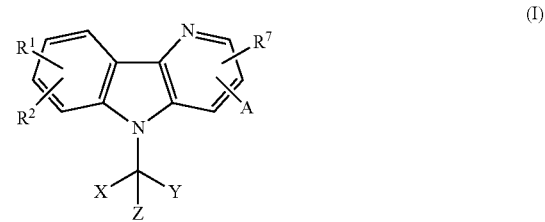

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$) alkoxy, optionally substituted ($C_3$-$C_6$)cycloalkyl, optionally substituted heterocyclo, —$OR^4$, —$CONR^3R^4$, —$NR^3R^4$, $NR^3R^4(C_1$-$C_6)$alkyl-, —$NR^6OCOR^3$, —$NR^6COR^3$, $NR^6COR^3(C_1$-$C_6)$alkyl-, —$NR^6CO_2R^3$, $NR^6CO_2R^3(C_1$-$C_6)$ alkyl-, —$NR^6CONR^3R^4$, —$SO_2NR^3R^4$, $SO_2(C_1$-$C_6)$alkyl-, —$NR^6SO_2NR^3R^4$, —$NR^6SO_2R^4$ or $NR^6SO_2R^4(C_1$-$C_6)$ alkyl-;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NR^6SO_2$-optionally substituted ($C_1$-$C_6$)alkyl, —$NR^6SO_2$-optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$)alkyl-$SO_2$—, optionally substituted aryl-$SO_2$, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^5$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

$R^6$ is hydrogen or optionally substituted ($C_1$-$C_6$)alkyl;

$R^7$ is hydrogen, optionally substituted ($C_1$-$C_6$)alkyl, —$OR^4$, CN or halogen;

and/or a pharmaceutically acceptable salt, tautomer or stereoisomer thereof.

In a second aspect of the invention, there is provided a compound according to claim 1 of formula (II)

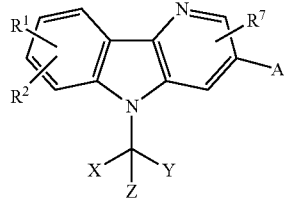

(II)

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$) alkoxy, optionally substituted ($C_3$-$C_6$)cycloalkyl, optionally substituted heterocyclo, —$OR^4$, —$CONR^3R^4$, —$NR^3R^4$, $NR^3R^4$($C_1$-$C_6$)alkyl-, —$NR^6OCOR^3$, —$NR^6COR^3$, $NR^6COR^3$($C_1$-$C_6$)alkyl-, —$NR^6CO_2R^3$, $NR^6CO_2R^3$($C_1$-$C_6$) alkyl-, —$NR^6CONR^3R^4$, —$SO_2NR^3R^4$, $SO_2$($C_1$-$C_6$)alkyl-, —$NR^6SO_2NR^3R^4$, —$NR^6SO_2R^4$ or $NR^6SO_2R^4$($C_1$-$C_6$) alkyl-;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NR^6SO_2$-optionally substituted ($C_1$-$C_6$)alkyl, —$NR^6SO_2$-optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$)alkyl-$SO_2$—, optionally substituted aryl-$SO_2$, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^5$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

$R^6$ is hydrogen or optionally substituted ($C_1$-$C_6$)alkyl;

$R^7$ is hydrogen, optionally substituted ($C_1$-$C_6$)alkyl, —$OR^4$, CN or halogen;

and/or a pharmaceutically acceptable salt, tautomer or stereoisomer thereof.

In a third aspect of the invention within the scope of the first two aspects, there is provided a compound of formula (II)

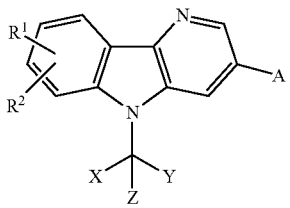

(II)

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, optionally substituted heterocyclo, —$OR^4$, —$CONR^3R^4$, —$NR^3R^4$, $NR^3R^4(C_1-C_6)$alkyl-, —$NR^6OCOR^3$, —$NR^6COR^3$, $NR^6COR^3(C_1-C_6)$alkyl-, —$NR^6CO_2R^3$, $NR^6CO_2R^3(C_1-C_6)$alkyl-, —$NR^6CONR^3R^4$, —$SO_2NR^3R^4$, $SO_2(C_1-C_6)$alkyl-, —$NR^6SO_2NR^3R^4$, —$NR^6SO_2R^4$ or $NR^6SO_2R^4(C_1-C_6)$alkyl-;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-$SO_2$—, —$NR^6SO_2$-optionally substituted $(C_1-C_6)$alkyl, —$NR^6SO_2$-optionally substituted heterocyclo, optionally substituted $(C_1-C_6)$alkyl-$NR^6SO_2$— or optionally substituted heterocyclo-$NR^6SO_2$—;

$R^2$ is hydrogen, halogen, —CN, OH, optionally substituted $(C_1-C_6)$alkyl, optionally substituted $(C_3-C_8)$cycloalkyl, optionally substituted $(C_1-C_6)$ alkoxy, optionally substituted aryl, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_4-C_8)$ heteroaryl or $(C_4-C_8)$ heterocyclic ring;

$R^6$ is hydrogen or optionally substituted $(C_1-C_6)$alkyl;

and/or a pharmaceutically acceptable salt, tautomer or stereoisomer thereof.

In a $4^{th}$ aspect within the scope of the prior aspects, there is provided a compound of the formula

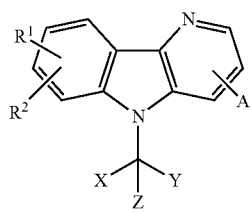

wherein

A is

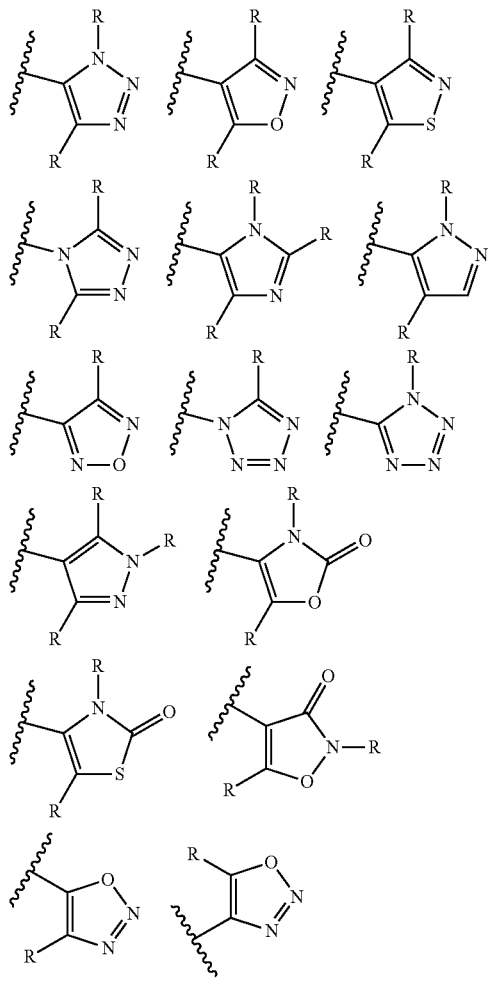

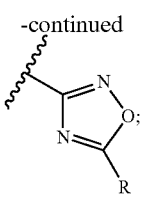

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, optionally substituted heterocyclo, $-OR^4$, $-CONR^3R^4$, $-NR^3R^4$, $NR^3R^4(C_1-C_6)$alkyl-, $-NR^6OCOR^3$, $-NR^6COR^3$, $NR^6COR^3(C_1-C_6)$alkyl-, $-NR^6CO_2R^3$, $NR^6CO_2R^3(C_1-C_6)$alkyl-, $-NR^6CONR^3R^4$, $-SO_2NR^3R^4$, $SO_2(C_1-C_6)$alkyl-, $-NR^6SO_2NR^3R^4$, $-NR^6SO_2R^4$ or $NR^6SO_2R^4(C_1-C_6)$alkyl-;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, $-OH$, $(C_1-C_6)$alkyl, $(C_1-C_6)$alkoxy, $-NR^3R^4$, $-CONR^3R^4$, $-OCONR^3R^4$, $-NR^6OCOR^3$, $-NR^6CONR^3R^4$, $-NR^6SO_2NR^3R^4$ or $-NR^6SO_2R^4$;

$R^1$ is, independently at each occurrence, one or more hydrogen, halogen, $-CN$, $-OR^4$, $-NR^3R^4$, $-CONR^3R^4$, $-COOH$, $-OCONR^3R^4$, $-NR^6OCOR^3$, $-NR^6CONR^3R^4$, $-NR^6SO_2NR^3R^4$, $-NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-SO_2—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-SO_2—, $-NR^6SO_2$-optionally substituted $(C_1-C_6)$alkyl, $-NR^6SO_2$-optionally substituted heterocyclo, optionally substituted $(C_1-C_6)$alkyl-NR^6SO_2$— or optionally substituted heterocyclo-NR^6SO_2$—;

$R^2$ is hydrogen, halogen, $-CN$, OH, optionally substituted $(C_1-C_6)$alkyl, optionally substituted $(C_3-C_8)$cycloalkyl, optionally substituted $(C_1-C_6)$ alkoxy, optionally substituted aryl, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO_2—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_4-C_8)$ heteroaryl or $(C_4-C_8)$ heterocyclic ring;

$R^6$ is hydrogen or optionally substituted $(C_1-C_6)$alkyl;
and/or a pharmaceutically acceptable salt, tautomer or stereoisomer thereof.

In a 5$^{th}$ aspect of the invention within the scope of the prior aspects, there is provided a compound of the formula (II)

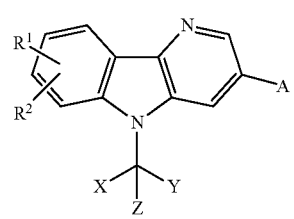

wherein:
A is

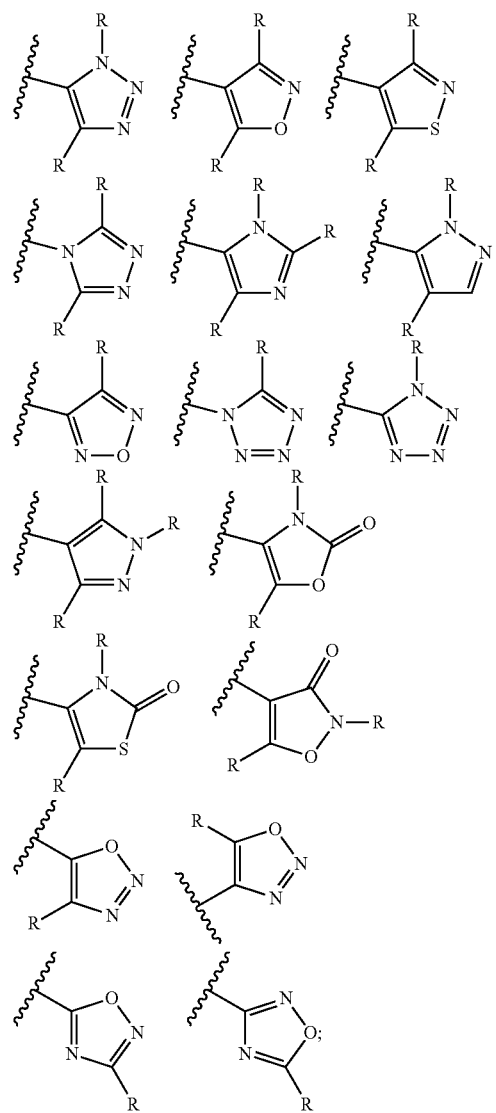

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, optionally substituted heterocyclo, —OR⁴, —CONR³R⁴, —NR³R⁴, NR³R⁴(C₁-C₆)alkyl-, —NR⁶OCOR³, —NR⁶COR³, NR⁶COR³(C₁-C₆)alkyl-, —NR⁶CO₂R³, NR⁶CO₂R³(C₁-C₆)alkyl-, —NR⁶CONR³R⁴, —SO₂NR³R⁴, SO₂(C₁-C₆)alkyl-, —NR⁶SO₂NR³R⁴, —NR⁶SO₂R⁴ or NR⁶SO₂R⁴(C₁-C₆)alkyl-;

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl, (C₁-C₆)alkoxy, —NR³R⁴, —CONR³R⁴, —OCONR³R⁴, —NR⁶OCOR³, —NR⁶CONR³R⁴, —NR⁶SO₂NR³R⁴ or —NR⁶SO₂R⁴;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl(C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted aryl, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈) heteroaryl or (C₄-C₈) heterocyclic ring;

R⁶ is hydrogen or optionally substituted (C₁-C₆)alkyl;

and/or a pharmaceutically acceptable salt, tautomer or stereoisomer thereof.

In a 6ᵗʰ aspect of the invention within the scope of the prior aspects, there is provided a compound of the formula (II)

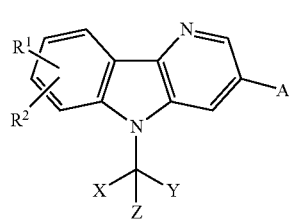

wherein:
A is

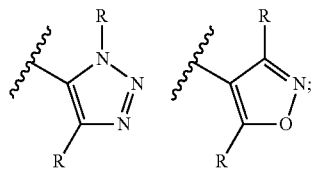

R is independently one or more hydrogen, CD₃, halogen, haloalkyl, hydroxyalkyl, CN, CF₃, CH₂F, CHF₂, optionally substituted (C₁-C₆)alkyl, optionally substituted (C₁-C₆)alkoxy, optionally substituted (C₃-C₆)cycloalkyl, optionally substituted heterocyclo, —OR⁴, —CONR³R⁴, —NR³R⁴, NR³R⁴(C₁-C₆)alkyl-, —NR⁶OCOR³, —NR⁶COR³, NR⁶COR³(C₁-C₆)alkyl-, —NR⁶CO₂R³, NR⁶CO₂R³(C₁-C₆)alkyl-, —NR⁶CONR³R⁴, —SO₂NR³R⁴, SO₂(C₁-C₆)alkyl-, —NR⁶SO₂NR³R⁴, —NR⁶SO₂R⁴ or NR⁶SO₂R⁴(C₁-C₆)alkyl-;

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl, (C₁-C₆)alkoxy, —NR³R⁴, —CONR³R⁴, —OCONR³R⁴, —NR⁶OCOR³, —NR⁶CONR³R⁴, —NR⁶SO₂NR³R⁴ or —NR⁶SO₂R⁴;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl(C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted aryl, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

or $R^3$ and $R^4$ may be taken together with the nitrogen atom to which they are attached to form an optionally substituted $(C_4-C_8)$ heteroaryl or $(C_4-C_8)$ heterocyclic ring;

$R^6$ is hydrogen or optionally substituted $(C_1-C_6)$alkyl;

and/or a pharmaceutically acceptable salt, tautomer or stereoisomer thereof.

In a 7$^{th}$ aspect of the invention within the scope of the prior aspects, there is provided a compound of the formula

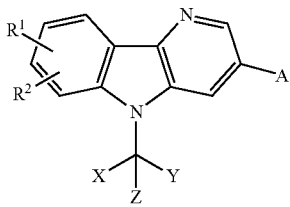

(II)

wherein:

A is

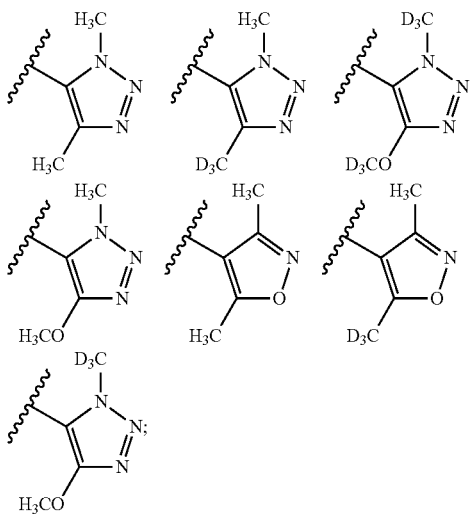

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$ alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-SO$_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-SO$_2$—, —NR$^6$SO$_2$-optionally substituted $(C_1-C_6)$alkyl, —NR$^6$SO$_2$-optionally substituted heterocyclo, optionally substituted $(C_1-C_6)$alkyl-NR$^6$SO$_2$— or optionally substituted heterocyclo-NR$^6$SO$_2$—;

$R^2$ is hydrogen, halogen, —CN, OH, optionally substituted $(C_1-C_6)$alkyl, optionally substituted $(C_3-C_8)$cycloalkyl, optionally substituted $(C_1-C_6)$ alkoxy, optionally substituted aryl, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_4-C_8)$ heteroaryl or $(C_4-C_8)$ heterocyclic ring;

$R^6$ is hydrogen or optionally substituted $(C_1-C_6)$alkyl;

and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following

2-[3-(dimethyl-1H-1,2,3-triazol-5-yl)-5-(1,1,1,7,7,7-hexafluoroheptan-4-yl)-5H-pyrido[3,2-b]indol-7-yl]propan-2-ol, 2-[3-(dimethyl-1,2-oxazol-4-yl)-5-[(S)-oxan-4-yl(phenyl)methyl]-5H-pyrido[3,2-b]indol-7-yl]propan-2-ol, 2-[3-(dimethyl-1H-1,2,3-triazol-5-yl)-5-[(1S)-4,4,4-trifluoro-1-phenylbutyl]-5H-pyrido[3,2-b]indol-7-yl]propan-2-ol, 2-[3-(dimethyl-1H-1,2,3-triazol-5-yl)-5-[(S)-oxan-4-yl(phenyl)methyl]-5H-pyrido[3,2-b]indol-7-yl]propan-2-ol, 2-[3-(dimethyl-1,2-oxazol-4-yl)-5-[(S)-(4-fluorophenyl)(oxan-4-yl)methyl]-5H-pyrido[3,2-b]indol-7-yl]propan-2-ol, 2-[3-(dimethyl-1H-1,2,3-triazol-5-yl)-5-[(4-fluorophenyl)(oxan-4-yl)methyl]-5H-pyrido[3,2-b]indol-7-yl]propan-2-ol, 2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-ol, 2-{3-[4-(hydroxymethyl)-1-methyl-1H-1,2,3-triazol-5-yl]-5-[(S)-oxan-4-yl(phenyl)methyl]-5H-pyrido[3,2-b]indol-7-yl}propan-2-ol, 5-{7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 5-{5-[(S)-(4-fluorophenyl)(oxan-4-yl)methyl]-7-methanesulfonyl-5H-pyrido[3,2-b]indol-3-yl}-4-($^2$H$_3$)methyl-1-methyl-1H-1,2,3-triazole, 2-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, (1R)-1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol, 2-{3-[5-($^2$H$_3$)methyl-3-methyl-1,2-oxazol-4-yl]-5-[(S)-oxan-4-yl(phenyl)methyl]-5H-pyrido[3,2-b]indol-7-yl}propan-2-ol 2-{3-[4-($^2$H$_3$)methoxy-1-methyl-1H-1,2,3-triazol-5-yl]-5-[(S)-oxan-4-yl(phenyl)methyl]-5H-pyrido[3,2-b]indol-7-yl}propan-2-ol, 2-[3-(4-methoxy-1-methyl-1H-1,2,3-triazol-5-yl)-5-[(S)-oxan-4-yl(phenyl)methyl]-5H-pyrido[3,2-b]indol-7-yl]propan-2-ol, (1R)-1-cyclopropyl-1-[3-(dimethyl-1H-1,2,3-triazol-5-yl)-6-fluoro-5-[(S)-(2-fluorophenyl)(oxan-4-yl)methyl]-5H-pyrido[3,2-b]indol-7-yl]ethan-1-ol, 2-{6-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, (1S)-1-cyclopropyl-1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol, (1R)-1-cyclopropyl-1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol, 2-{5-[(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{8-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol, 2-{5-[(S)-(4,4-difluorocyclohexyl)(phenyl)methyl]-3-[4-($^2$H$_3$)methyl-1-methyl-1H-1,2,3-triazol-5-yl]-5H-pyrido[3,2-b]indol-7-yl}propan-2-ol, 2-{8-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol, (1R)-1-cyclopropyl-1-{6-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}ethan-1-ol, 2-{6-fluoro-5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{6-chloro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol, 2-[(R)-(4,4-difluorocyclohexyl)({9-fluoro-7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine, (1S)-1-cyclopropyl-1-{6-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}ethan-1-ol, 2-{8-fluoro-5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{5-[(5-chloropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{5-[(3-chloropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{5-[(4-chloropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{5-[(4,4-difluorocyclohexyl)(3-fluoropyridin-2-yl)methyl]-6-fluoro-3-[4-($^2$H$_3$)methyl-1-methyl-1H-1,2,3-triazol-5-yl]-5H-pyrido[3,2-b]indol-7-yl}propan-2-ol, 2-{6-fluoro-5-[(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{8-fluoro-5-[(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{3-[4-($^2$H$_3$)methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol, 2-{3-[4-methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol, 5-{7-methanesulfonyl-5-[(S)-oxan-4-yl(phenyl)methyl]-5H-pyrido[3,2-b]indol-3-yl}-4-methoxy-1-methyl-1H-1,2,3-triazole, 2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-amine, N-{2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-yl}acetamide, N-{2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-yl}methanesulfonamide, methyl N-{2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-yl}carbamate, 5-{6-methanesulfonyl-5-[(S)-oxan-4-yl(phenyl)methyl]-5H-pyrido[3,2-b]indol-3-yl}-1,4-dimethyl-1H-1,2,3-triazole, 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 5-{9-fluoro-7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 5-{6-methanesulfonyl-9-methoxy-5-[(S)-oxan-4-yl(phenyl)methyl]-5H-pyrido[3,2-b]indol-3-yl}-1,4-dimethyl-1H-1,2,3-triazole, N-[3-(dimethyl-1H-1,2,3-triazol-5-yl)-6-methanesulfonyl-5-[(S)-oxan-4-yl(phenyl)methyl]-5H-pyrido[3,2-b]indol-9-yl]cyclopropanesulfonamide, 5-{9-methanesulfonyl-5-[(S)-oxan-4-yl(phenyl)methyl]-5H-pyrido[3,2-b]indol-3-yl}-1,4-dimethyl-1H-1,2,3-triazole, 5-{9-methanesulfonyl-6,7-dimethoxy-5-[(S)-oxan-4-yl(phenyl)methyl]-5H-pyrido[3,2-b]indol-3-yl}-4-($^2$H$_3$)methyl-1-methyl-1H-1,2,3-triazole, and 2-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol and/or a pharmaceutically acceptable salt, tautomer or stereoisomer thereof.

One embodiment of the invention provides compounds wherein A is optionally substituted heterocyclo or optionally substituted heteroaryl, wherein the substituents are one or more R;

Another embodiment of the invention provides compounds wherein A is

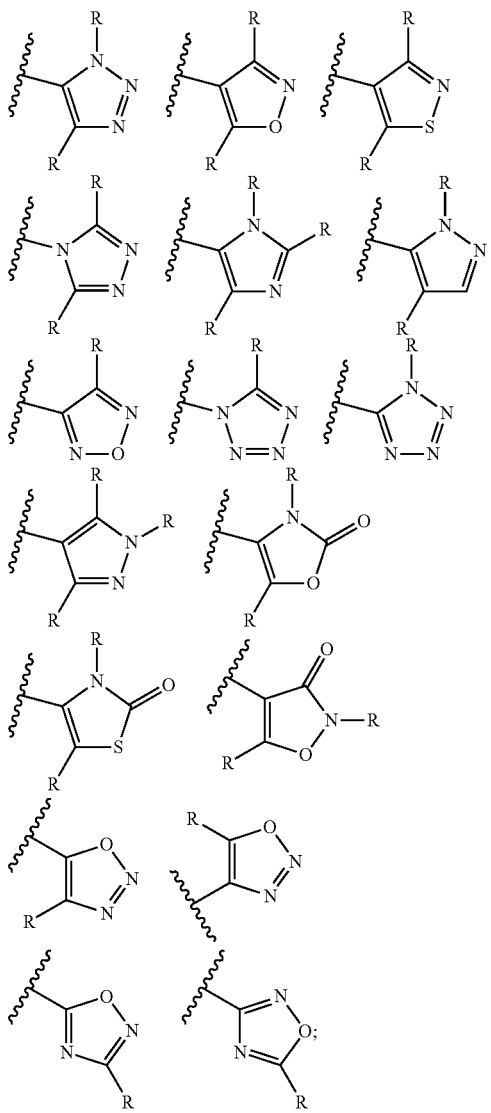

and R is independently one or more hydrogen, $CD_3$, $OCD_3$, $CF_3$, $CHF_2$ or $(C_1-C_3)$alkyl.

Another embodiment of the invention provides compounds wherein A is

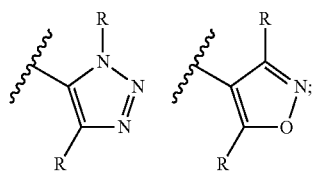

and R is independently one or more hydrogen, $CD_3$, $OCD_3$, $CF_3$, $CHF_2$ or $(C_1-C_3)$alkyl.

In another embodiment, the compounds of the invention have $IC_{50}$ values ≤250 nM.

In another embodiment, the compounds of the invention have $IC_{50}$ values ≤25 nM.

In another embodiment, the compounds of the invention have $IC_{50}$ values ≤5 nM.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, colorectal cancer, multiple myeloma or AML.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment, the bromodomain inhibitor would be administered at the point of diagnosis to reduce the incidence of SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (1) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; and (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

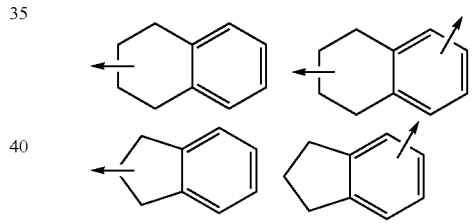

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1H$ (hydrogen), $^2H$ (deuterium) and $^3H$ (tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy,* $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I)

is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

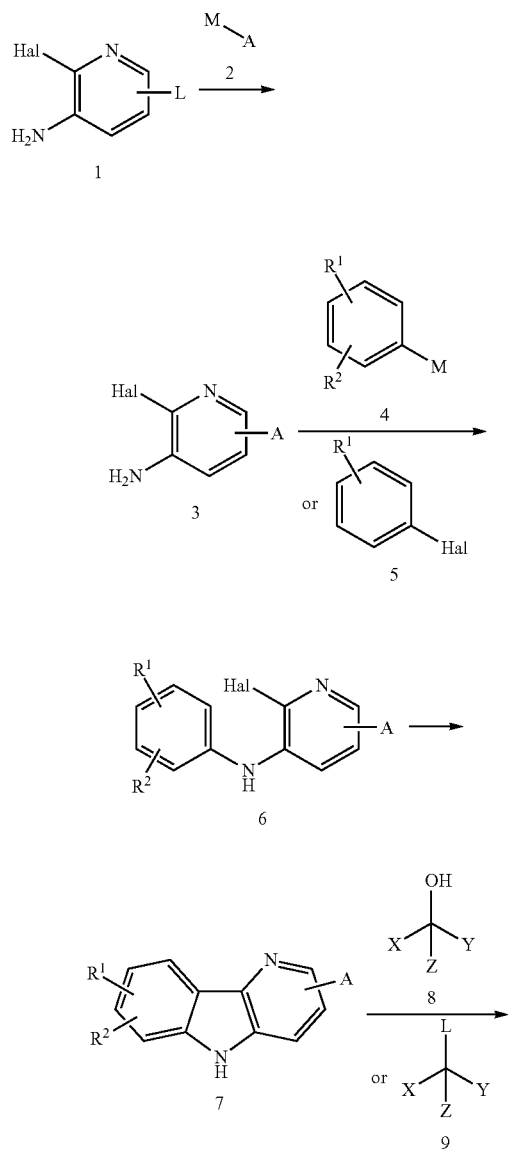

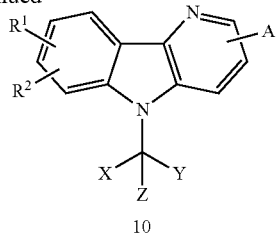

General routes to compounds described in the invention are illustrated in Schemes 1-13, where the $R^1$, $R^2$, X, Y, Z and A substituents are defined previously in the text or a functional group that can be converted to the desired final substituent. The substituent Hal is a halide. L is a leaving group such as a halide or OH that can be easily converted to a leaving group such as a triflate. As shown in Scheme 1, a general procedure for the preparation of compounds of the invention involves starting with the substituted aminopyridine 1. Coupling of 1 with the aromatic heterocycle A (2, where M is a suitable coupling partner, such as boronic acid, boronic ester or stannane) using a suitable catalyst can yield functionalized aminopyridines 3. For example, 3 could arise from a Suzuki coupling reaction between 5-bromo-2-chloropyridin-3-amine and a heteroaromatic boronic acid using Pd(dppf)Cl$_2$ as a catalyst. Subsequent coupling to give the functionalized aniline 6 can be achieved using a variety of conditions known in the literature. For example, aminopyridine 3 can undergo copper-mediated coupling with a suitably substituted arene 4 (where M is a boronic acid, boronic ester or stannane) to give aniline 6. Alternatively, 6 could arise from a Buchwald N-arylation reaction of 3 with an aromatic halide 5 (where Hal is a halide). Ring closure to generate carboline 7 can be achieved using a Pd catalyst in the presence of a base, such as sodium acetate. In the final step, the carboline nitrogen can be substituted under Mitsunobu conditions using triphenylphosphine and diisopropyl azodicarboxylate (DIAD) with an alkylating agent 8 (where X is OH). Alternatively, functionalized carboline 10 can be generated from a displacement reaction between the carboline 7 and an alkylating agent 9, where L is a leaving group such as a halide, mesylate or triflate, in the presence of a base, such as potassium carbonate. In cases where 10 is a racemate, chiral separation can provide enantiomerically pure products. Further derivatization of $R^1$ can provide additional compounds of the invention. For example, when $R^1$ is an ester, addition of a Grignard reagent or alkyl lithium can generate tertiary alcohols. The same $R^1$ ester could instead be hydrolyzed using, for example, sodium hydroxide to give a carboxylic acid ($R^1$=CO$_2$H) as the final substituent.

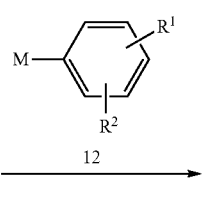

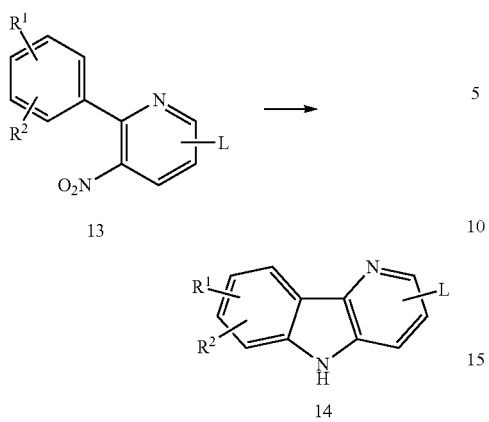

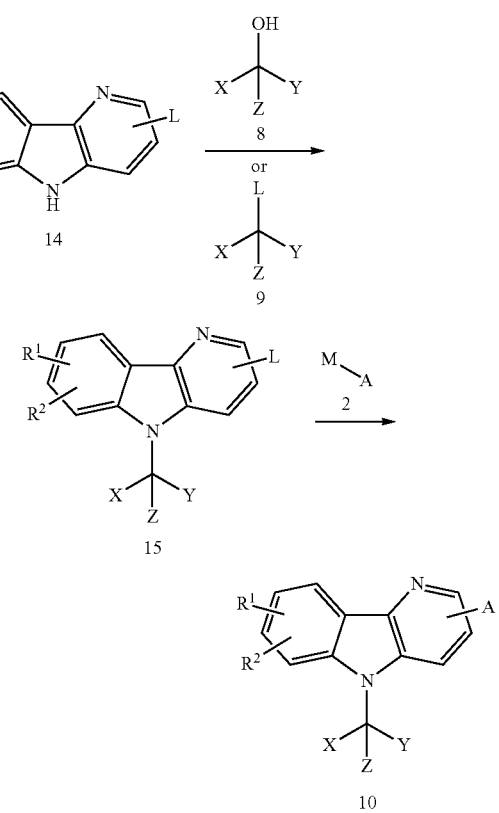

An alternative synthesis of the carbolines 7 and 10 starts from nitropyridine 11 as shown in Schemes 2 to 4. A Suzuki reaction between, for example, 2,5-dibromo-3-nitropyridine and an appropriately substituted arene (12, where M is a suitable coupling partner, such as boronic acid or boronic ester) can give the functionalized pyridine 13. Reductive cyclization mediated by a phosphine reagent, such as 1,2-bis(diphenylphosphino)ethane (dppe), can provide carboline 14. Coupling of 14 with the aromatic heterocycle A (2, where M is a suitable coupling partner, such as boronic acid, boronic ester or stannane) using a suitable catalyst then generates carboline 7 as shown in Scheme 3.

Alternately, the carboline nitrogen of intermediate 14 can be first substituted under Mitsunobu conditions with an alkylating agent 8 (where X is OH) or with alkylating agent 9, where L is a leaving group such as a halide, mesylate or triflate, in the presence of a base, such as potassium carbonate as previously described in Scheme 1 to give intermediate 15. Then coupling of 15 with the aromatic heterocycle A (2, where M is a suitable coupling partner, such as boronic acid, boronic ester or stannane) using a suitable catalyst then generates the final carboline 10 as shown in Scheme 4.

An alternate synthesis of carbolines 10 can be achieved as outlined in Scheme 5. The leaving group, L, of 15 (prepared as in Scheme 4) can be converted to a suitable coupling partner, M (preferably a boronic ester or boronic acid) by the action of a palladium catalyst, affording 16. Coupling of 16 with the aromatic heterocycle A (17, where L is a suitable leaving group, such as a halogen or triflate) using a suitable catalyst can give carbolines 10.

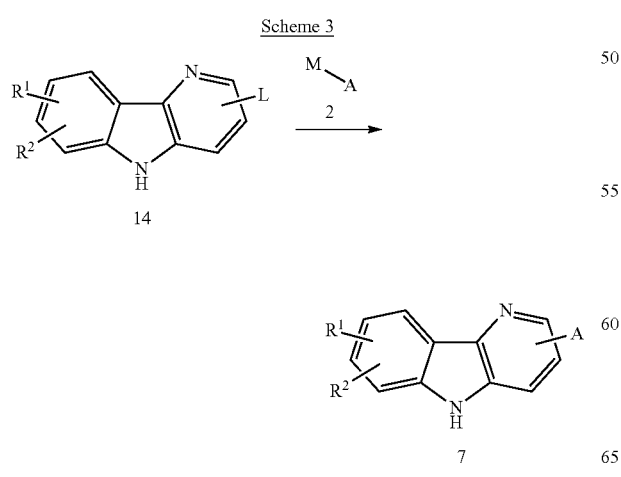

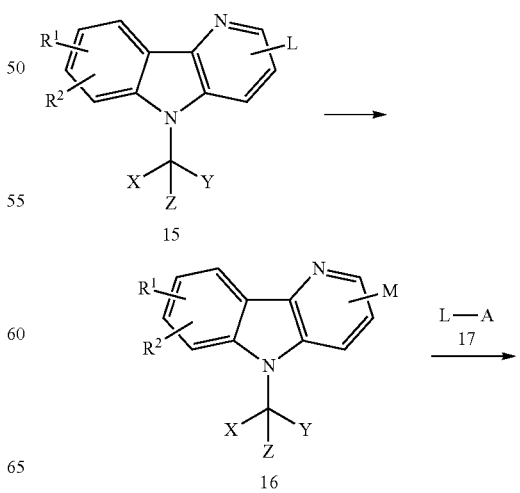

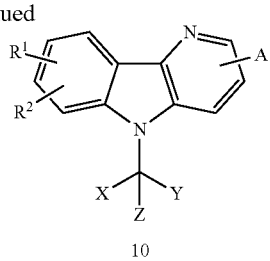

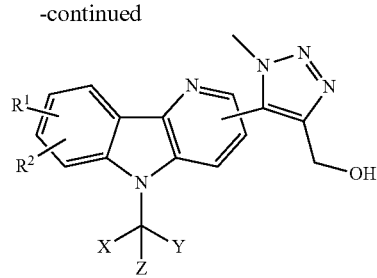

Hydroxymethyl pyrazole derivatives such as 20 can be accessed according to Scheme 6. Intermediate 16 (where M is a suitable coupling partner such as a boronic acid or boronic ester; prepared as in Scheme 5) can be coupled to an appropriately protected triazole 18 by the action of a suitable catalyst. Triazole 18 is available in one step from a copper-mediated cycloaddition reaction of (azidomethyl)trimethylsilane with a protected propargyl alcohol. Intermediate 19 can then be deprotected using a variety of conditions. For example, when PG is tert-butyldimethylsilyl, treatment with tetrabutylammonium fluoride can give the final compound 20. Further derivatization of the hydroxyl group (for example: alkylation, conversion to a leaving group and displacement, oxidation to either an aldehyde or carboxylic acid and subsequent elaboration) can provide additional compounds of the invention by application of methods which will be readily apparent to one of ordinary skill in the art.

Alternately, intermediate 15 (prepared as in Scheme 4) can be directly coupled with a suitable aromatic heterocycle, 21, via palladium-mediated C—H activation to afford compounds 10. This is illustrated in Scheme 7.

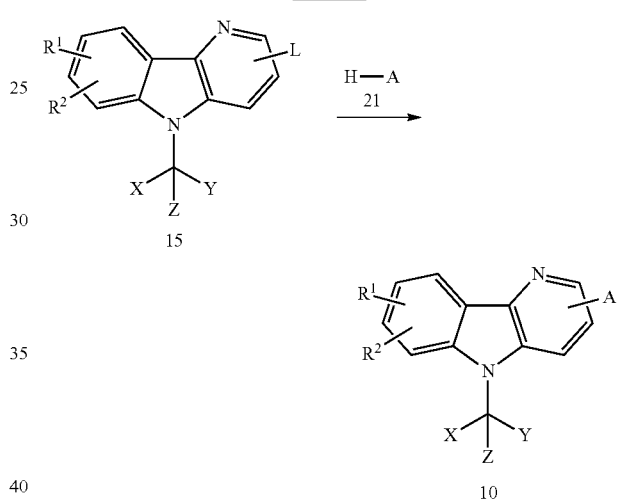

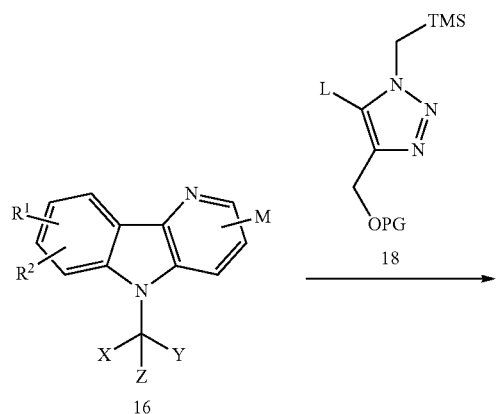

Alternately, aromatic heterocycle 21 can be deprotonated with a strong base such as n-BuLi and transmetallated to zinc, tin, or boron to afford compounds 2. Compounds 2 can then be coupled in a Negishi, Stille, or Suzuki coupling to intermediate 15 (prepared as in Scheme 4) by the action of a suitable palladium catalyst to afford compounds 10. This is illustrated in Scheme 8.

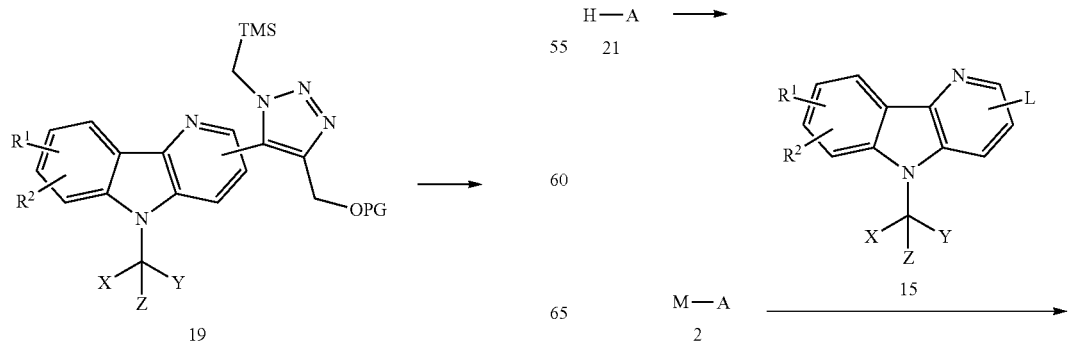

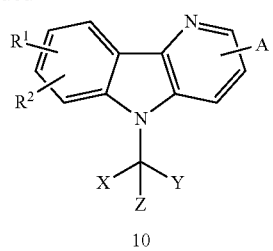

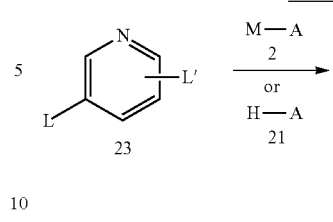

An alternate synthesis of carbolines 14 can be achieved as outlined in Scheme 9. Aniline 22 can be coupled to pyridine 23, where L and L' are two leaving groups such as halide or triflate, using a Buchwald N-arylation reaction to give intermediate 24. For example, 24 could arise from a Buchwald N-arylation reaction between 3,5-dibromopyridine and a suitable aniline. Oxidative ring closure, using an appropriate catalyst such as Pd(OAc)$_2$ in an acidic media such as trifluoroacetic acid, can afford carbolines 14. This is illustrated in Scheme 9.

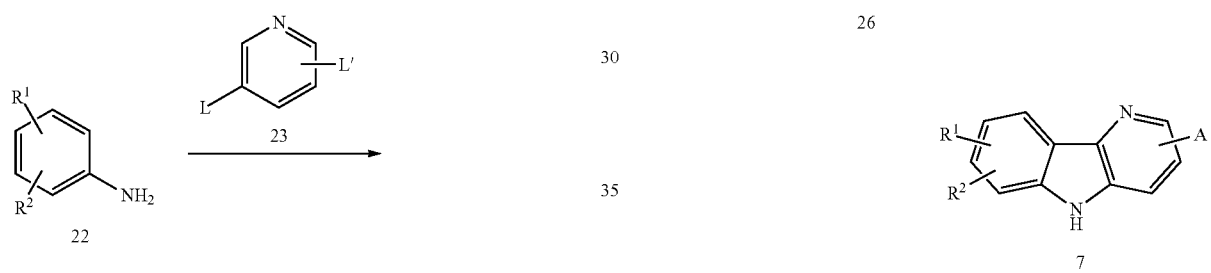

Pyridines 23 (where L and L' are suitable leaving groups such as halides or triflates) can also be coupled to aromatic heterocycles 2 (where M is a suitable coupling partner such as a boronic ester, boronic acid, or stannane) or 21 by methods analogous to those illustrated in Schemes 1, 3, 4, 7, and 8. Pyridines 25 can be coupled to anilines 22, using a Buchwald N-arylation reaction to give intermediate 26. Oxidative ring closure, using an appropriate catalyst such as Pd(OAc)$_2$ in an acidic media such as trifluoroacetic acid, can afford carbolines 7. This is illustrated in Scheme 10.

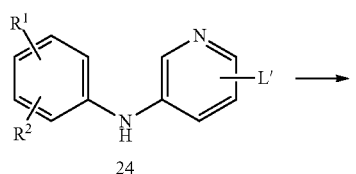

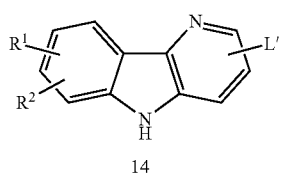

Alkoxy-substituted triazoles 32 can be prepared as illustrated in Scheme 11. Aldehyde 27 can be converted to acetal 29 by treatment with alcohol 28 (where Alk is a $C_1$-$C_6$ alkyl or $C_3$-$C_6$ cycloalkyl optionally substituted with deuterium) in the presence of acid or a dehydrating agent such as CaCl$_2$. Acetal 29 can be converted to alkoxy-substituted alkynes 30 by treatment with a strong base such as lithium diethylamide or sodium amide. Compounds 30 can be converted to triazoles 32 through a copper-catalyzed 3+2 cycoaddition reaction with azide 31. Triazoles 32 can be directly coupled to carbolines as illustrated in Scheme 7. In most cases, said coupling results in loss of the trimethylsilyl group. In cases where the trimethylsilyl group is not lost, it can be removed by treatment with tetrabutylammonium fluoride.

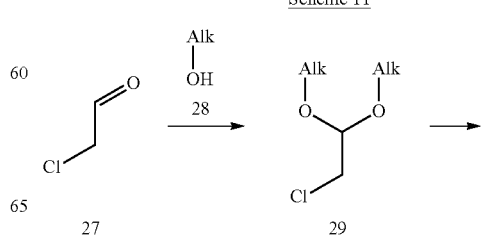

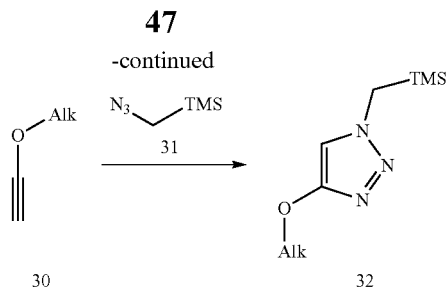

Alkyl-substituted triazoles 39 can be prepared as illustrated in Scheme 12. Acetylene 33 can be alkylated with 34 (where Alk is a $C_1$-$C_6$ alkyl or $C_3$-$C_6$ cycloalkyl optionally substituted with deuterium and where L is an appropriate leaving group such as iodide, bromide, chloride, or sulfonate) by the action of a strong base such as n-BuLi. Alkyne 35 can be converted to triazoles 36 through a copper-catalyzed 3+2 cycoaddition reaction with 31. Triazoles 36 can be directly coupled to carbolines as illustrated in Scheme 7. Alternately, the trimethylsilyl group of 36 can be removed directly by the action of tetrabutyl ammonium fluoride to give N-methyl-triazole 37. Deprotonation of 37 with a strong base such as n-BuLi, followed by reaction with an appropriate electrophile 38 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 39 which can readily be coupled as illustrated in Schemes 1, 3, 4, 8, and 10.

Scheme 12

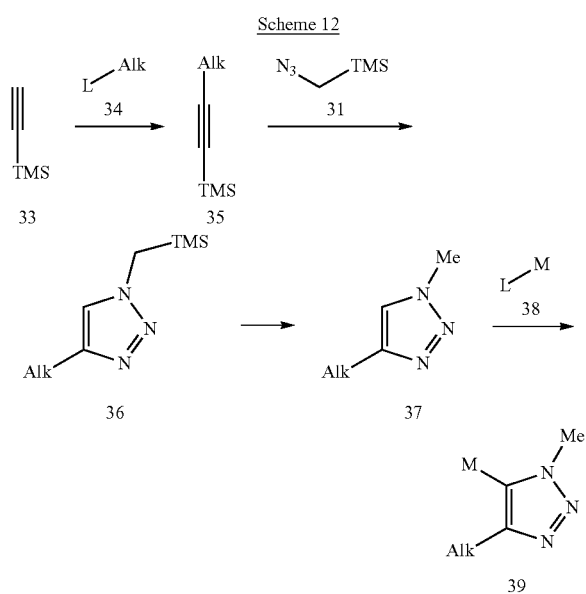

One can vary the substituents of the triazole as shown in Scheme 13. The leaving group of 34 (where Alk is a $C_1$-$C_6$ alkyl or $C_3$-$C_6$ cycloalkyl optionally substituted with deuterium and where L is an appropriate leaving group such as iodide, bromide, chloride, or sulfonate) can be displaced by treatment with sodium azide to afford 40. Alkynes 41 or 42 can be coupled to azides 40 to give triazoles 43 through a copper-catalyzed 3+2 cycoaddition reaction. Triazoles 43 can be directly coupled to carbolines as illustrated in Scheme 7. Alternately, deprotonation of 43 with a strong base such as n-BuLi, followed by reaction with an appropriate electrophile 38 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 44 which can readily be coupled as illustrated in Schemes 1, 3, 4, 8, and 10.

Scheme 13

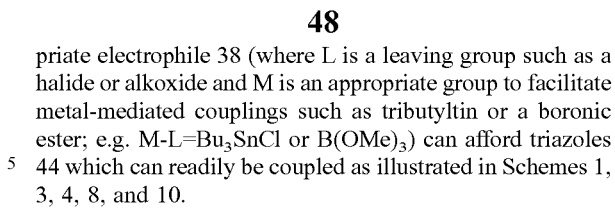

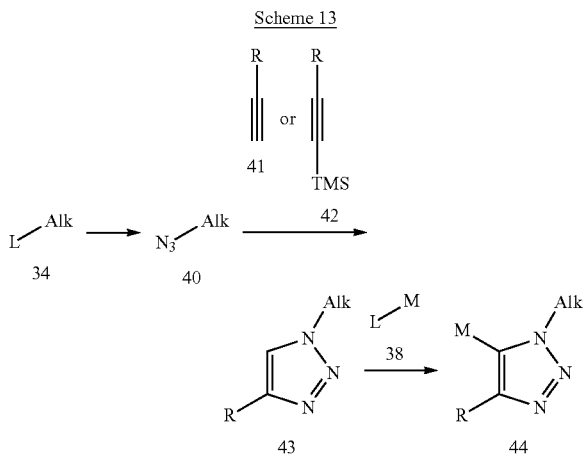

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

| ABBREVIATIONS | |
|---|---|
| MeCN | Acetonitrile |
| AcOH | acetic acid |
| $AlMe_3$ | trimethyl aluminum |
| aq | Aqueous |
| Bn | Benzyl |
| Boc | tert-butoxycarbonyl |
| $Boc_2O$ | di-tert-butyl dicarbonate |
| CBz | benzyloxycarbonyl |
| DCC | 1,3-dicyclohexylcarbodiimide |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-dimethylaminopyridine |
| DMA | dimethylacetamide |
| DME | dimethoxyethane |
| DMF | dimethylformamide |
| DMSO | dimethyl sulfoxide |
| EDC | 1-(3-dimethylaminopropyl)-3-ethylcarbodiimide hydrochloride |
| $Et_2AlCl$ | diethyl aluminum chloride |
| $Et_3N$ | triethyl amine |
| $Et_2O$ | diethyl ether |
| EtOH | Ethanol |
| EtOAc | ethyl acetate |
| equiv. | equivalent(s) |
| g | gram(s) |
| h or hr | hour(s) |

-continued

| ABBREVIATIONS | |
|---|---|
| HOBt | hydroxybenzotriazole |
| HPLC | high pressure liquid chromatography |
| iPrOH | isopropyl alcohol |
| KOtBu | potassium tert-butoxide |
| LCMS | Liquid Chromatography-Mass Spectroscopy |
| LDA | lithium diisopropylamide |
| LiHMDS | lithium bis(trimethylsilyl)amide |
| Me | Methyl |
| MeI | methyl iodide |
| MeOH | Methanol |
| min | minute(s) |
| mL | milliliter(s) |
| mmol | Millimolar |
| MTBE | methyl t-butyl ether |
| NaHMDS | sodium bis(trimethylsilyl)amide |
| n-BuLi | n-butyl lithium |
| $NH_4OAc$ | ammonium acetate |
| NMP | N-methylpyrrolidinone |
| $Pd(OAc)_2$ | palladium acetate |
| $Pd(dppf)Cl_2$ | [1,1'-bis(diphenylphosphino)ferrocene]dichloropalladium(II) |
| RT or Rt | retention time |
| sat | Saturated |
| SFC | Supercritical fluid chromatography |
| t-Bu | tertiary butyl |
| t-BuLi | t-butyl lithium |
| t-BuOH | tertiary butyl alcohol |
| t-BuOMe | tert-butyl methyl ether |
| TBTU | O-(1H-benzotriazol-1-yl)-N,N,N',N'-tetramethyluronium tetrafluoroborate |
| TCTU | O-(1H-6-chlorobenzotriazol-1-yl)-N,N,N',N'-tetramethyluronium tetrafluoroborate |
| TEA | Triethylamine |
| TFA | trifluoroacetic acid |
| $Tf_2O$ | trifluoromethylsulfonic anhydride |
| THF | Tetrahydrofuran |

The following HPLC conditions may be used where indicated:

Analytical HPLC Method 1: Column: Waters Acquity UPLC BEH C18, 2.1×50 mm, 1.7 μm particles; Mobile Phase A: water with 0.05% TFA; Mobile Phase B: acetonitrile 0.05% TFA; Gradient: 2-98% B over 1 min, then a 0.5-min hold at 98% B; Flow: 0.8 mL/min; Detection: UV at 254 nm.

Analytical HPLC Method 2: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Gradient: 0-100% B over 3 min, then a 0.7-min hold at 100% B; Flow: 1.11 mL/min; Detection: UV at 254 nm.

LC/MS Method 1: Column: Phenomenex-Luna 2.0×30 mm, 3 um particles; Mobile Phase A: 10/90 methanol:water, 0.1% TFA; Mobile Phase B: 90/10 methanol:water, 0.1% TFA; Temperature 40° C.; Gradient 0% —100% B over 2 min; Flow 1 mL/min; Detection: UV at 220 nm.

LC/MS Method 2: Column: Waters Acquity SDS; Mobile Phase A: 100% Water, 0.1% TFA; Mobile Phase B: 100% acetonitrile, 0.1% TFA; Temperature 50° C.; Gradient 2%-98% B over 2.2 min; Flow 0.8 mL/min; Detection: UV at 220 nm.

LC/MS Method 3: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 min, then a 0.5-min hold at 100% B; Flow: 1 mL/min; Detection: UV at 220 nm.

LC/MS Method 4: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0%-100% B over 3 min, then a 0.5-min hold at 100% B; Flow: 0.5 mL/min; Detection: UV at 220 nm.

Preparative HPLC Method 1: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-min hold at 100% B; Flow: 20 mL/min.

Preparative HPLC Method 2: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 20 min, then a 5-min hold at 100% B; Flow: 20 mL/min.

Preparative HPLC Method 3: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 min, then a 5-min hold at 100% B; Flow: 20 mL/min.

Examples 1 & 2

2-[3-(Dimethyl-1,2-oxazol-4-yl)-5-[oxan-4-yl(phenyl)methyl]-5H-pyrido[3,2-b]indol-7-yl]propan-2-ol Enantiomer A, Example 1

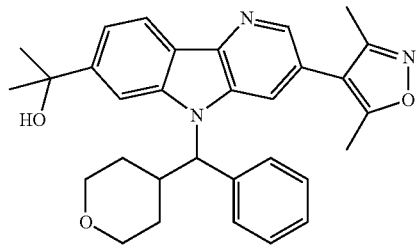

Enantiomer B, Example 2

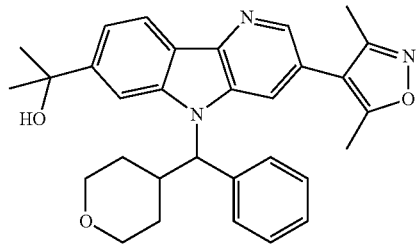

Step 1: 2-Chloro-5-(3,5-dimethylisoxazol-4-yl)pyridin-3-amine

To a 500 mL round bottom flask containing 5-bromo-2-chloropyridin-3-amine (Matrix, 4.0 g, 19.3 mmol) and (3,5-dimethylisoxazol-4-yl)boronic acid (AOBChem, 3.26 g, 23.1 mmol) in THF (150 mL) was added tripotassium phosphate (2M aq., 28.9 mL, 57.8 mmol) to give a yellow suspension. $Pd(dppf)Cl_2$—$CH_2Cl_2$ (1.58 g, 1.93 mmol) was then added and $N_2$ was bubbled into the mixture for 4 min. The resulting reaction mixture was heated at 80° C. for 1 h, concentrated and then diluted with 10% LiCl solution and extracted with $CH_2Cl_2$. The organic layer was concentrated and filtered through Celite®. The mother liquor was purified using ISCO silica gel chromatography (220 g column, gradient from 0% to 50% EtOAc/$CH_2Cl_2$). Trituration with cold $Et_2O$ gave the title compound (3.14 g, 73%) as a pale orange solid. $^1$H NMR (400 MHz, $CDCl_3$) δ 7.71 (d, J=2.1 Hz, 1H), 6.92 (d, J=2.1 Hz, 1H), 4.20 (br. s., 2H), 2.42 (s, 3H), 2.27 (s, 3H); LCMS (M+H)=224.1. HPLC RT=1.39 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 3-((2-chloro-5-(3,5-dimethylisoxazol-4-yl)pyridin-3-yl)amino)benzoate To a 250 mL round bottom flask containing 2-chloro-5-(3,5-dimethylisoxazol-4-yl)pyridin-3-amine (2.0 g, 8.9 mmol), (3-(methoxycarbonyl)phenyl)boronic acid (Aldrich, 3.22 g, 17.9 mmol), $Cu(OAc)_2$ (2.43 g, 13.4 mmol) and powdered 4 Å molecular sieves (7.0 g) was added $CHCl_3$ (50 mL) and pyridine (1.45 mL, 17.9 mL). The atmosphere was exchanged with $O_2$, and the reaction was stirred under an $O_2$ balloon for 6 h. Additional (3-(methoxycarbonyl)phenyl) boronic acid (3.22 g, 17.9 mmol), pyridine (1.45 mL, 17.9 mmol) and 4 Å molecular sieves (1.7 g) were added. The reaction mixture was stirred at room temperature overnight. Additional (3-(methoxycarbonyl)phenyl)boronic acid (3.22 g, 17.9 mmol), pyridine (1.45 mL, 17.9 mmol) and $Cu(OAc)_2$ (400 mg) were added to the reaction. After stirring at room temperature for 7 h, the reaction mixture was filtered through Celite® rinsing with $CHCl_3$. The filtrate was diluted with water and ammonium hydroxide (18.6 mL, 143 mmol) was added. The aqueous layer was extracted with $CHCl_3$ and the combined organic layers were washed with 10% LiCl. The organic layer was concentrated and purified by silica gel chromatography (220 g column, gradient from 0% to 50% EtOAc/$CH_2Cl_2$). The fractions were concentrated in vacuo until a white precipitate formed which collected via filtration and rinsed with EtOAc to give the title compound (1.33 g, 57%) as a white solid. $^1$H NMR (400 MHz, $CDCl_3$) δ 7.94 (t, J=1.8 Hz, 1H), 7.85 (d, J=2.1 Hz, 1H), 7.82 (dt, J=7.7, 1.3 Hz, 1H), 7.48 (t, J=7.9 Hz, 1H), 7.40 (d, J=2.1 Hz, 1H), 7.36 (ddd, J=8.0, 2.3, 1.0 Hz, 1H), 6.32 (s, 1H), 3.94 (s, 3H), 2.45 (s, 3H), 2.29 (s, 3H); LCMS (M+H)=358.2; HPLC RT=2.70 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: Methyl 3-(3,5-dimethylisoxazol-4-yl)-5H-pyrido[3,2-b]indole-7-carboxylate To a 40 mL vial containing methyl 3-((2-chloro-5-(3,5-dimethylisoxazol-4-yl)pyridin-3-yl)amino)benzoate (515 mg, 1.44 mmol) and sodium acetate trihydrate (480 mg, 3.52 mmol) in DMA (5.0 mL) was added bis(triphenylphosphine) palladium(II) chloride (81 mg, 0.12 mmol). $N_2$ was bubbled through the reaction mixture for 1 min. The vial was capped and heated at 180° C. for 15-30 min. The reaction mixture was then concentrated and purified directly using ISCO silica gel chromatography (40 g column, gradient from 0% to 100% EtOAc/$CH_2Cl_2$). The resulting orange oil was dissolved in EtOAc (7 mL) and stirred at room temperature overnight. The resulting yellow precipitate was collected via filtration and washed with EtOAc. The mother liquor was concentrated and repurified using ISCO silica gel chromatography (40 g column, gradient from 0% to 50% EtOAc/$CH_2Cl_2$). After trituration with cold EtOAc, the solids were combined to give the title compound (301 mg, 65%). HPLC RT=2.01 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: Methyl 3-(3,5-dimethylisoxazol-4-yl)-5-(phenyl(tetrahydro-2H-pyran-4-yl)methyl)-5H-pyrido[3,2-b]indole-7-carboxylate To a 5 mL vial containing methyl 3-(3,5-dimethylisoxazol-4-yl)-5H-pyrido[3,2-b]indole-7-carboxylate (87 mg, 0.27 mmol) and phenyl(tetrahydro-2H-pyran-4-yl)methanol (104 mg, 0.54 mmol) [Orjales, A. et al. *J. Med. Chem.* 2003, 46, 5512-5532] in THF (2.0 mL) was added $Ph_3P$ (141 mg, 0.54 mmol) and DIAD (0.11 mL, 0.54 mmol). The resulting suspension was stirred at room temperature overnight and then concentrated. The residue was purified using ISCO silica gel chromatography (40 g column, gradient from 0% to 50% EtOAc/$CH_2Cl_2$) to give the title compound (139 mg) as an impure mixture which was carried on to the subsequent step without further purification. LCMS (M+H)=496.2; HPLC RT=3.06 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 5: 2-[3-(Dimethyl-1,2-oxazol-4-yl)-5-[oxan-4-yl)phenyl)methyl]-5H-pyrido[3,2-b]indol-7-yl]propan-2-ol A 250 mL round bottom flask containing methyl 3-(3,5-dimethylisoxazol-4-yl)-5-(phenyl(tetrahydro-2H-pyran-4-yl)methyl)-5H-pyrido[3,2-b]indole-7-carboxylate (1.58 g, 3.19 mmol) in $CH_2Cl_2$ (50 mL) was cooled in an ice/MeOH bath. MeMgBr, (3M in $Et_2O$, 17.0 mL, 51.0 mmol) was added slowly over 2 min. The resulting suspension was stirred for 2.5 h and then quenched carefully with sat. $NH_4Cl$. Ice was added to the reaction mixture followed by 10% LiCl solution. The aqueous layer was extracted with $CH_2Cl_2$ (2×). The organic layer was dried over $MgSO_4$, filtered and concentrated to give racemic 2-[3-(dimethyl-1,2-oxazol-4-yl)-5-[oxan-4-yl(phenyl)methyl]-5H-pyrido[3,2-b]indol-7-yl]propan-2-ol, which was separated using chiral prep SFC (Column: Chiral OD-H 25×3 cm, 5 µm; Mobile Phase: 70/30 $CO_2$/MeOH; Flow: 85 mL/min). The faster eluting peak was concentrated to a small volume. Water was added to form a white precipitate which was collected via filtration, rinsing with water, to give a white solid which was assigned as Enantiomer A (0.59 g, 36%). The slower eluting peak was treated in an identical manner and assigned as Enantiomer B (0.51 g, 31%). Enantiomer A: $^1$H NMR (500 MHz, $CDCl_3$) δ 8.40 (d, J=1.8 Hz, 1H), 8.33 (d, J=8.2 Hz, 1H), 7.93 (s, 1H), 7.53 (d, J=1.8 Hz, 1H), 7.46 (d, J=7.3 Hz, 2H), 7.42 (dd, J=8.2, 1.4 Hz, 1H), 7.37-7.31 (m, 2H), 7.30-7.28 (m, 1H), 5.56 (d, J=10.5 Hz, 1H), 4.06 (d, J=8.9 Hz, 1H), 3.89-3.83 (m, 1H), 3.55 (td, J=11.9, 2.1 Hz, 1H), 3.35 (td, J=11.9, 2.1 Hz, 1H), 3.10 (q, J=10.8 Hz, 1H), 2.39 (s, 3H), 2.23 (s, 3H), 2.03 (d, J=14.2 Hz, 1H), 1.89 (s, 1H), 1.74 (s, 6H), 1.68-1.59 (m, 1H), 1.46-1.36 (m, 1H), 1.12 (d, J=12.2 Hz, 1H); LCMS (M+H)=496.4; HPLC RT=2.46 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=5.36 min (Column: Chiralcel OD-H 250×4.6 mm, 5 μm; Mobile Phase: 70/30 CO$_2$/MeOH; Flow: 2 mL/min). Enantiomer B: $^1$H NMR (500 MHz, CDCl$_3$) δ 8.40 (d, J=1.8 Hz, 1H), 8.33 (d, J=8.2 Hz, 1H), 7.94 (s, 1H), 7.53 (d, J=1.8 Hz, 1H), 7.46 (d, J=7.3 Hz, 2H), 7.42 (dd, J=8.2, 1.4 Hz, 1H), 7.36-7.31 (m, 2H), 7.30-7.28 (m, 1H), 5.56 (d, J=10.7 Hz, 1H), 4.06 (dd, J=11.7, 2.5 Hz, 1H), 3.86 (dd, J=11.5, 2.8 Hz, 1H), 3.55 (td, J=11.9, 2.1 Hz, 1H), 3.35 (td, J=11.9, 2.0 Hz, 1H), 3.15-3.05 (m, 1H), 2.39 (s, 3H), 2.23 (s, 3H), 2.03 (d, J=13.6 Hz, 1H), 1.90 (s, 1H), 1.74 (s, 6H), 1.68-1.58 (m, 1H), 1.46-1.36 (m, 1H), 1.12 (d, J=12.4 Hz, 1H); LCMS (M+H)=496.4; HPLC RT=2.46 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=14.95 min (Column: Chiralcel OD-H 250×4.6 mm, 5 μm; Mobile Phase: 70/30 CO$_2$/MeOH; Flow: 2 mL/min).

Examples 3-24

The compounds in Table 1 were prepared according to the procedures described for Example 1:

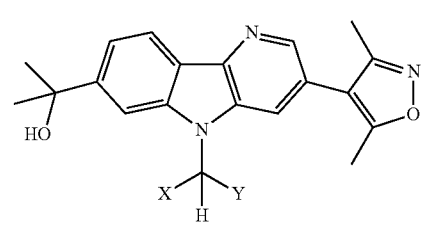

TABLE 1

| Example | X | Y | HPLC RT (min) | LCMS (M + H) | Optical Rotation $[α]_D^{20}$ | HPLC Method |
|---|---|---|---|---|---|---|
| 3 | benzyl | benzyl | 2.92 | 488.1 | N/A | A |
| 4 | ethyl | ethyl | 1.79 | 392.2 | N/A | B |
| 5 (racemate) | methoxymethyl | benzyl | 2.42 | 456.4 | N/A | A |
| 6 | CH$_2$CH$_2$CF$_3$ | CH$_2$CH$_2$CF$_3$ | 1.98 | 527.2 | N/A | B |
| 7 | methoxymethyl | methoxymethyl | 1.51 | 423.2 | N/A | B |
| 8 | propyl | propyl | 2.66 | 420.4 | N/A | A |
| 9 Enantiomer A | CH$_2$CH$_2$CF$_3$ | benzyl | 3.25 | 508.4 | −43.39 (c = 0.10, CHCl$_3$) | C |
| 10 Enantiomer B | CH$_2$CH$_2$CF$_3$ | benzyl | 9.44 | 508.4 | N/A | C |

TABLE 1-continued

| Example | X | Y | HPLC RT (min) | LCMS (M + H) | Optical Rotation $[\alpha]_D^{20}$ | HPLC Method |
|---|---|---|---|---|---|---|
| 11 Enantiomer A | cyclopropyl | phenyl | 9.40 | 452.4 | N/A | D |
| 12 Enantiomer B | cyclopropyl | phenyl | 14.11 | 452.4 | +32.61 (c = 0.07, CHCl$_3$) | D |
| 13 Enantiomer A | cyclobutyl | phenyl | 6.50 | 466.5 | −73.83 (c = 0.06, CHCl$_3$) | D |
| 14 Enantiomer B | cyclobutyl | phenyl | 10.66 | 466.5 | +75.20 (c = 0.09, CHCl$_3$) | D |
| 15 Enantiomer A | cyclobutyl | 4-F-phenyl | 13.60 | 484.4 | −70.71 (c = 0.54, MeOH) | E |
| 16 Enantiomer B | cyclobutyl | 4-F-phenyl | 16.61 | 484.4 | +52.84 (c = 0.60, MeOH) | E |
| 17 Enantiomer A | 2,2-dimethyltetrahydropyran-4-yl | 4-F-phenyl | 14.82 | 542.5 | −118.89 (c = 0.11, MeOH) | E |
| 18 Enantiomer B | 2,2-dimethyltetrahydropyran-4-yl | 4-F-phenyl | 9.14 | 542.5 | N/A | E |
| 19 Enantiomer A | thiazol-4-yl | CH$_2$CH$_2$CF$_3$ | 5.06 | 515.3 | −52.83 (c = 0.41, MeOH) | C |
| 20 Enantiomer B | thiazol-4-yl | CH$_2$CH$_2$CF$_3$ | 6.82 | 515.3 | +50.15 (c = 0.43, MeOH) | C |

TABLE 1-continued

| Example | X | Y | HPLC RT (min) | LCMS (M + H) | Optical Rotation $[\alpha]_D^{20}$ | HPLC Method |
|---|---|---|---|---|---|---|
| 21 Enantiomer A | tetrahydropyran-4-yl | pyridin-2-yl | 9.20 | 497.5 | −133.04 (c = 0.08, MeOH) | C |
| 22 Enantiomer B | tetrahydropyran-4-yl | pyridin-2-yl | 11.94 | 497.5 | +133.47 (c = 0.08, MeOH) | C |
| 23 Enantiomer A | F₃C-CH₂CH₂- | pyridin-2-yl | 4.38 | 509.4 | −79.87 (c = 0.30, MeOH) | C |
| 24 Enantiomer B | F₃C-CH₂CH₂- | pyridin-2-yl | 5.31 | 509.4 | +79.60 (c = 0.33, MeOH) | C |

HPLC Conditions for Table 1:

Method A:

Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min; Detection: UV at 220 nm.

Method B:

Column: Waters Acquity UPLC BEH C18, 2.1×50 mm, 1.7 μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm.

Method C:

Column: Chiralcel OD-H 250×4.6 mm, 5 μm particles; Mobile Phase: 80/20 CO₂/MeOH; Flow: 2 mL/min; Detection UV at 220 nm.

Method D:

Column: Chiralpak IB, 250×4.6 mm, 5 μm particles; Mobile Phase: 80/20 CO₂/MeOH; Flow: 2 mL/min; Detection UV at 220 nm.

Method E:

Column: Phenomenex Lux Cellulose 2, 250×4.6 mm, 5 μm particles; Mobile Phase: 75/25 CO₂/MeOH; Flow: 2 mL/min; Detection UV at 220 nm.

Examples 25 & 26

2-[3-(Dimethyl-1,2-oxazol-4-yl)-5-[oxan-4-yl(phenyl)methyl]-5H-pyrido[3,2-b]indol-7-yl]propan-2-ol Enantiomer A, Example 25

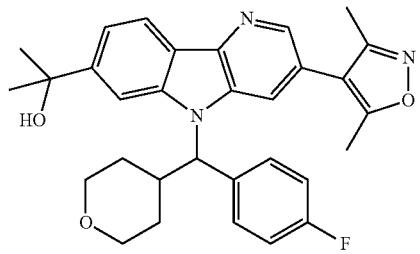

Enantiomer B, Example 26

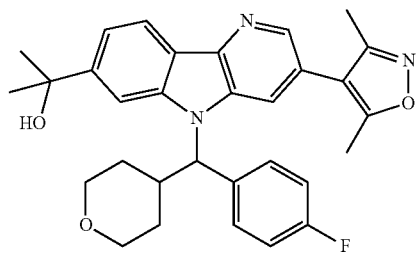

Step 1:
(4-Fluorophenyl)(tetrahydro-2H-pyran-4-yl)methanol

To a 40 mL vial containing magnesium (0.39 g, 16.1 mmol) in THF (15 mL) was slowly added 4-bromotetrahydro-2H-pyran (PharmaBlock, 1.8 mL, 16.1 mmol) cooling in a water bath as needed. The resulting reaction mixture was stirred at room temperature for 1.5 h and then cooled in a water bath. 4-Fluorobenzaldehyde (Aldrich, 1.2 mL, 10.7 mmol) was added slowly. The resulting orange reaction mixture was removed from the water bath and quenched with sat. NH₄Cl after 10 min. 10% LiCl solution was added and the mixture was extracted with Et₂O (2×). The organic layer was dried over MgSO₄, filtered and concentrated. The residue was purified using ISCO silica gel chromatography (80 g column, gradient from 0% to 50% EtOAc/hexanes) to give the title compound (1.12 g, 33%) as a colorless oil. $^1$H NMR (500 MHz, CDCl₃) δ 7.31-7.27 (m, 2H), 7.08-7.02 (m, 2H), 4.37 (dd, J=0.7, 2.4 Hz, 1H), 4.06-3.99 (m, 1H), 3.94-3.87 (m, 1H), 3.37 (td, J=11.9, 2.2 Hz, 1H), 3.29 (td, J=11.8, 2.3 Hz, 1H), 1.94-1.87 (m, 2H), 1.81 (tdt, J=11.6, 7.7, 3.8 Hz, 1H), 1.45 (qd, J=12.3, 4.7 Hz, 1H), 1.36-1.27 (m, 1H), 1.16 (ddq, J=13.2, 3.9, 2.0 Hz, 1H); LCMS (M+H-H₂O)=193.1; HPLC RT=1.65 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-[3-(Dimethyl-1,2-oxazol-4-yl)-5-[oxan-4-yl(phenyl)methyl]-5H-pyrido[3,2-b]indol-7-yl]propan-2-ol Following procedures analogous to those described in Steps 4 and 5 of Example 1, methyl 3-(3,5-dimethylisoxazol-4-yl)-5H-pyrido[3,2-b]indole-7-carboxylate (100 mg, 0.31 mmol) and (4-fluorophenyl)(tetrahydro-2H-pyran-4-yl)methanol (131 mg, 0.62 mmol) were converted to racemic 2-[3-(dimethyl-1,2-oxazol-4-yl)-5-[oxan-4-yl(phenyl)methyl]-5H-pyrido[3,2-b]indol-7-yl]propan-2-ol, which was separated by chiral prep SFC to give Enantiomer A (18 mg, 11%) and Enantiomer B (22 mg, 12%). Enantiomer A: $^1$H NMR (500 MHz, CDCl₃) δ 8.41 (d, J=1.8 Hz, 1H), 8.33 (d, J=8.2 Hz, 1H), 7.91 (s, 1H), 7.50 (d, J=1.5 Hz, 1H), 7.46-7.37 (m, 3H), 7.06-6.99 (m, 2H), 5.53 (d, J=10.5 Hz, 1H), 4.07 (dd, J=11.7, 2.5 Hz, 1H), 3.87 (dd, J=11.8, 3.0 Hz, 1H), 3.54 (td, J=11.9, 2.1 Hz, 1H), 3.34 (td, J=11.9, 2.1 Hz, 1H), 3.11-3.01 (m, 1H), 2.41 (s, 3H), 2.25 (s, 3H), 1.98 (d, J=13.4 Hz, 1H), 1.89 (s, 1H), 1.73 (s, 6H), 1.66-1.59 (m, 1H), 1.46-1.36 (m, 1H), 1.13 (d, J=13.3 Hz, 1H); LCMS (M+H)=514.4; HPLC RT=2.55 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=6.56 min (Column: Chiralcel OD-H 250×4.6 mm, 5 μm; Mobile Phase: 75/25 CO₂/MeOH; Flow: 2 mL/min). Enantiomer B: $^1$H NMR (500 MHz, CDCl₃) δ 8.41 (d, J=1.8 Hz, 1H), 8.33 (d, J=8.2 Hz, 1H), 7.91 (s, 1H), 7.50 (d, J=1.5 Hz, 1H), 7.46-7.37 (m, 3H), 7.06-6.99 (m, 2H), 5.53 (d, J=10.5 Hz, 1H), 4.07 (dd, J=11.7, 2.5 Hz, 1H), 3.87 (dd, J=11.8, 3.0 Hz, 1H), 3.54 (td, J=11.9, 2.1 Hz, 1H), 3.34 (td, J=11.9, 2.1 Hz, 1H), 3.11-3.01 (m, 1H), 2.41 (s, 3H), 2.25 (s, 3H), 1.98 (d, J=13.4 Hz, 1H), 1.89 (s, 1H), 1.73 (s, 6H), 1.66-1.59 (m, 1H), 1.46-1.36 (m, 1H), 1.13 (d, J=13.3 Hz, 1H); LCMS (M+H)=514.4; HPLC RT=2.55 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=8.58 min (Column: Chiralcel OD-H 250×4.6 mm, 5 μm; Mobile Phase: 75/25 CO₂/MeOH; Flow: 2 mL/min); $[\alpha]_D^{20}$=+89.91, (c=0.14, CHCl₃).

Examples 27 & 28

2-{5-[(4,4-Difluorocyclohexyl)(phenyl)methyl]-3-(dimethyl-1,2-oxazol-4-yl)-5H-pyrido[3,2-b]indol-7-yl}propan-2-ol

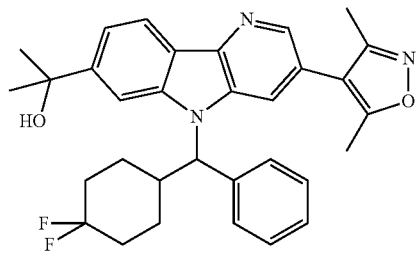

Enantiomer A, Example 27

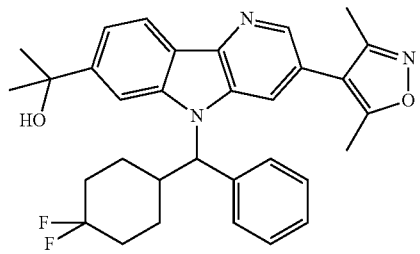

Enantiomer B, Example 28

Step 1: (4,4-Difluorocyclohexyl)(phenyl)methanone

To a 50 mL round bottom flask containing 4,4-difluoro-N-methoxy-N-methylcyclohexanecarboxamide (500 mg, 2.41 mmol) [Lehmann-Lintz, T. et al. PCT Int. Appl., 2011, WO2011104334] in THF (10 mL) at −78° C. was slowly added phenyllithium (1.8M in dibutyl ether, 4.69 mL, 8.45 mmol). After 1 h, the reaction mixture was poured into ice and 1M HCl (10.8 mL, 10.8 mmol) with stirring. The mixture was diluted with sat. NaCl and extracted with Et₂O. The organic layer was dried over MgSO₄, filtered and concentrated to give the title compound (532 mg, 98%) as a white solid. $^1$H NMR (400 MHz, CDCl₃) δ 7.98-7.89 (m, 2H), 7.64-7.55 (m, 1H), 7.54-7.44 (m, 2H), 3.46-3.27 (m, 1H), 2.36-2.11 (m, 2H), 2.09-1.73 (m, 6H); HPLC RT=2.39 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: (4,4-Difluorocyclohexyl)(phenyl)methanol

To a 100 mL round bottom flask containing (4,4-difluorocyclohexyl)(phenyl) methanone (532 mg, 2.37 mmol) in MeOH (15 mL) in an ice water bath was added NaBH₄ (135 mg, 3.56 mmol) in small portions over 20 seconds. After stirring in the ice water bath for 30 min, the reaction mixture was diluted with water and concentrated. The residue was acidified to pH 6 with 1N citric acid and extracted with CH₂Cl₂ (2×). The organic layer was dried over MgSO₄, filtered and concentrated to give the crude title compound (562 mg) which was used in the subsequent step without further purification. HPLC RT=2.35 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 2-{5-[(4,4-Difluorocyclohexyl)(phenyl)methyl]-3-(dimethyl-1,2-oxazol-4-yl)-5H-pyrido[3,2-b]indol-7-yl}propan-2-ol Following procedures analogous to those described in Steps 4 and 5 of Example 1, methyl 3-(3,5-dimethylisoxazol-4-yl)-5H-pyrido[3,2-b]indole-7-carboxylate (80 mg, 0.25 mmol) and (4,4-difluorocyclohexyl)(phenyl)methanol (141 mg, 0.62 mmol) were converted to racemic 2-{5-[(4,4-difluorocyclohexyl)(phenyl)methyl]-3-(dimethyl-1,2-oxazol-4-yl)-5H-pyrido[3,2-b]indol-7-yl}propan-2-ol, which was separated by chiral prep SFC to give Enantiomer A (23 mg, 30%) and Enantiomer B (23 mg, 30%). Enantiomer A: $^1$H NMR (500 MHz, CDCl$_3$) δ 8.40 (d, J=1.7 Hz, 1H), 8.33 (d, J=8.1 Hz, 1H), 7.93 (s, 1H), 7.51 (d, J=1.7 Hz, 1H), 7.47-7.39 (m, 3H), 7.37-7.32 (m, 2H), 7.31-7.28 (m, 1H), 5.56 (d, J=10.5 Hz, 1H), 2.94 (d, J=8.1 Hz, 1H), 2.39 (s, 3H), 2.28-2.15 (m, 5H), 2.05-1.83 (m, 3H), 1.77-1.72 (m, 6H), 1.71-1.58 (m, 2H), 1.44-1.31 (m, 2H); LCMS (M+H)=530.4; HPLC RT=2.81 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=3.54 min (Column: Chiralcel OD-H 250×4.6 mm, 5 μm; Mobile Phase: 70/30 CO$_2$/MeOH; Flow: 2 mL/min); $[α]_D^{20}$=−101.98, (c=0.07, CHCl$_3$). Enantiomer B: $^1$H NMR (500 MHz, CDCl$_3$) δ 8.40 (d, J=1.7 Hz, 1H), 8.33 (d, J=8.1 Hz, 1H), 7.93 (s, 1H), 7.51 (d, J=1.7 Hz, 1H), 7.47-7.39 (m, 3H), 7.37-7.32 (m, 2H), 7.31-7.28 (m, 1H), 5.56 (d, J=10.5 Hz, 1H), 2.94 (d, J=8.1 Hz, 1H), 2.39 (s, 3H), 2.28-2.15 (m, 5H), 2.05-1.83 (m, 3H), 1.77-1.72 (m, 6H), 1.71-1.58 (m, 2H), 1.44-1.31 (m, 2H); LCMS (M+H)=530.4; HPLC RT=2.81 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.58 min (Column: Chiralcel OD-H 250×4.6 mm, 5 μm; Mobile Phase: 70/30 CO$_2$/MeOH; Flow: 2 mL/min); $[α]_D^{20}$=+104.36, (c=0.10, CHCl$_3$).

Examples 29 & 30

2-[3-(Dimethyl-1,2-oxazol-4-yl)-5-[phenyl(1,3-thiazol-4-yl)methyl]-5H-pyrido[3,2-b]indol-7-yl]propan-2-ol Enantiomer A, Example 29

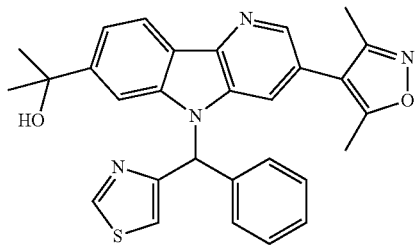

Enantiomer B, Example 30

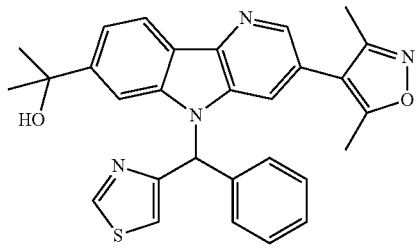

Step 1: Phenyl(thiazol-4-yl)methanol

A solution of thiazole-4-carbaldehyde (0.32 g, 2.83 mmol) in THF (18.9 mL) was cooled to 0° C. Phenylmagnesium bromide (3M in Et$_2$O, 2.83 mL, 8.49 mmol) was added. After 1.5 h, the reaction was quenched with sat. NH$_4$Cl, then diluted with water. The reaction was extracted with EtOAc, and the organic layer was washed with sat. NaCl, dried with Na$_2$SO$_4$ and concentrated. The residue was purified using ISCO silica gel chromatography (40 g column, gradient from 0% to 100% EtOAc/hexanes) to give the title compound (0.45 g, 82%). $^1$H NMR (400 MHz, CDCl$_3$) δ 8.80 (d, J=2.1 Hz, 1H), 7.49-7.44 (m, 2H), 7.42-7.36 (m, 2H), 7.35-7.29 (m, 1H), 7.13 (dd, J=2.0, 0.9 Hz, 1H), 6.01 (d, J=4.2 Hz, 1H), 2.94 (d, J=4.3 Hz, 1H); LCMS (M+H—H$_2$O)=174.1.

Step 2: 2-[3-(Dimethyl-1,2-oxazol-4-yl)-5-[phenyl(1,3-thiazol-4-yl)methyl]-5H-pyrido[3,2-b]indol-7-yl]propan-2-ol Following procedures analogous to those described in Steps 4 and 5 of Example 1, methyl 3-(3,5-dimethylisoxazol-4-yl)-5H-pyrido[3,2-b]indole-7-carboxylate (80 mg, 0.25 mmol) and phenyl(thiazol-4-yl)methanol (95 mg, 0.50 mmol) were converted to racemic 2-[3-(dimethyl-1,2-oxazol-4-yl)-5-[phenyl(1,3-thiazol-4-yl)methyl]-5H-pyrido[3,2-b]indol-7-yl]propan-2-ol, which was separated by chiral prep SFC to give Enantiomer A (10 mg, 8%) and Enantiomer B (10 mg, 8%). Enantiomer A: $^1$H NMR (400 MHz, CD$_3$OD) δ 9.05 (d, J=2.0 Hz, 1H), 8.35 (d, J=1.5 Hz, 1H), 8.30 (d, J=8.4 Hz, 1H), 7.72 (s, 1H), 7.57 (s, 1H), 7.53-7.44 (m, 3H), 7.39-7.33 (m, 3H), 7.27-7.18 (m, 2H), 2.32 (s, 3H), 2.14 (s, 3H), 1.58 (s, 6H); LCMS (M+H)=495.4; HPLC RT=7.24 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm); SFC RT=8.45 min (Column: Chiralpak AD-H, 250×4.6 mm, 5 μm; Mobile Phase: 80/20 CO$_2$/MeOH; Flow: 2 mL/min); $[α]_D^{20}$=+42.45, (c=0.06, CHCl$_3$). Enantiomer B: $^1$H NMR (400 MHz, CD$_3$OD) δ 9.05 (d, J=2.0 Hz, 1H), 8.35 (d, J=1.5 Hz, 1H), 8.30 (d, J=8.4 Hz, 1H), 7.72 (s, 1H), 7.57 (s, 1H), 7.53-7.44 (m, 3H), 7.39-7.33 (m, 3H), 7.27-7.18 (m, 2H), 2.32 (s, 3H), 2.14 (s, 3H), 1.58 (s, 6H); LCMS (M+H)=495.4; HPLC RT=7.24 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm); SFC RT=11.91 min (Column: Chiralpak AD-H, 250×4.6

Example 31

2-[5-(Dicyclobutylmethyl)-3-(dimethyl-1,2-oxazol-4-yl)-5H-pyrido[3,2-b]indol-7-yl]propan-2-ol

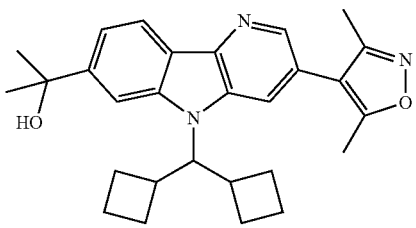 [SMILES: Cc1noc(C)c1-c1cnc2c3ccc(C(C)(C)O)cc3n(C(C3CCC3)C3CCC3)c2c1]

Step 1: Dicyclobutylmethanol

To a suspension of magnesium (0.58 g, 23.8 mmol) in THF (32 mL) was added 4 drops of 1,2-dibromoethane. The suspension was heated to 50° C., then bromocyclobutane (3.21 g, 23.8 mmol) was added dropwise. The reaction was cooled in an ice bath, then cyclobutanecarbaldehyde (1.0 g, 11.9 mmol) in THF (7.9 mL) was added. After 1 h, the reaction was quenched with sat. $NH_4Cl$, then extracted with EtOAc. The organic layer was washed with sat. NaCl, dried with $Na_2SO_4$ and concentrated. The residue was purified using ISCO silica gel chromatography (40 g column, gradient form 0% to 50% EtOAc/hexanes) to give the title compound (1.04 g, 62%). $^1$H NMR (400 MHz, $CDCl_3$) δ 3.40 (td, J=6.9, 4.8 Hz, 1H), 2.38-2.23 (m, 2H), 1.98-1.68 (m, 12H), 1.30-1.27 (m, 1H).

Step 2: Methyl 5-(dicyclobutylmethyl)-3-(3,5-dimethylisoxazol-4-yl)-5H-pyrido[3,2-b]indole-7-carboxylate To a suspension of methyl 3-(3,5-dimethylisoxazol-4-yl)-5H-pyrido[3,2-b]indole-7-carboxylate (100 mg, 0.31 mmol) and dicyclobutylmethanol (87 mg, 0.62 mmol) in toluene (3.1 mL) was added 2-(trimethylphosphoranylidene)acetonitrile (0.5M in THF, 1.2 mL, 0.62 mmol). The reaction mixture was heated to 110° C. overnight. Additional dicyclobutylmethanol (87 mg, 0.62 mmol) and 2-(trimethylphosphoranylidene)acetonitrile (0.5M in THF, 1.2 mL, 0.62 mmol) were added and stirring was continued overnight. The reaction mixture was concentrated, and the residue was purified using ISCO silica gel chromatography (24 g column, gradient from 0% to 50% EtOAc/hexanes) to give the title compound (57 mg, 41%). LCMS (M+H)=444.5.

Step 3: 2-[5-(Dicyclobutylmethyl)-3-(dimethyl-1,2-oxazol-4-yl)-5H-pyrido[3,2-b]indol-7-yl]propan-2-ol Following a procedure analogous to that described in Step 5 of Example 1, methyl 5-(dicyclobutylmethyl)-3-(3,5-dimethylisoxazol-4-yl)-5H-pyrido[3,2-b]indole-7-carboxylate (80 mg, 0.25 mmol) was converted to the title compound (19 mg, 30%) as an inseparable mixture of atropisomers after purification by prep HPLC (Column: Phen Luna C18, 30×100 mm, 5 µm particles; Mobile Phase A: 5:95 acetonitrile:water with 0.1% TFA; Mobile Phase B: 95:5 acetonitrile:water with 0.1% TFA; Gradient: 10-100% B over 14 min, then a 2-min hold at 100% B; Flow: 40 mL/min). LCMS (M+H)=444.5; HPLC RT=6.96 min (Column: Sunfire C18 3.5 µm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm).

Example 32 & 33

2-[3-(Dimethyl-1,2-oxazol-4-yl)-5-[(1-fluorocyclobutyl)(phenyl)methyl]-5H-pyrido[3,2-b]indol-7-yl]propan-2-ol

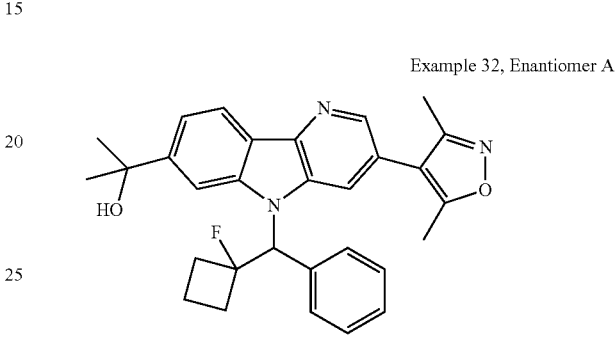

Example 32, Enantiomer A

Example, 33 Enantiomer B

Step 1: (1-Fluorocyclobutyl)(phenyl)methanone

A suspension of Accufluor™ NFTh (Aldrich, 50% on alumina, 6.03 g, 9.36 mmol) and cyclobutyl(phenyl)methanone (0.75 g, 4.68 mmol) [Bauser, M. et al. *PCT Int. Appl.,* 2005, WO2005039569] in MeOH (46.8 ml) was divided between two 40 mL pressure vials and stirred overnight at 70° C. Additional Accufluor™ NFTh (2.0 g) was added and heating was continued overnight. The reaction was cooled, then decanted and concentrated. $CH_2Cl_2$ was added, and the insoluble material was filtered off. The organic layer was washed sequentially with water and sat. NaCl, then dried with $Na_2SO_4$ and concentrated to give the crude title compound (600 mg, 72%), which was used in the subsequent step without further purification. $^1$H NMR (400 MHz, $CDCl_3$) δ 7.90-8.05 (2H, m), 7.52-7.63 (1H, m), 7.41-7.50 (2H, m), 2.71-2.91 (2H, m), 2.42-2.64 (2H, m), 2.00 (1H, dd, J=11.1, 3.7 Hz), 1.74 (1H, dtd, J=11.2, 8.9, 8.9, 2.3 Hz)

Step 2: (1-Fluorocyclobutyl)(phenyl)methanol

A solution of (1-fluorocyclobutyl)(phenyl)methanone (0.780 g, 4.38 mmol) in MeOH (14.59 ml) was cooled to 0° C. and $NaBH_4$ (0.248 g, 6.57 mmol) was added portionwise. After 1 hour a small amount of water was added, then the reaction was concentrated. The residue was suspended in $CH_2Cl_2$, then sat. NH4Cl solution was added carefully. The layers were separated, and then the aqueous layer was reextracted with CH₂Cl₂. The organic layer was washed with brine, dried with sodium sulfate and concentrated. The residue was purified via ISCO (40 g column; Hex/EtOAc; 0 to 30% gradient) to give (1-fluorocyclobutyl)(phenyl) methanol (0.651 g, 3.61 mmol, 83% yield). 1H NMR (400 MHz, CDCl₃) δ 7.48-7.43 (m, 2H), 7.41-7.31 (m, 3H), 4.77 (dd, J=18.5, 4.7 Hz, 1H), 2.48-2.13 (m, 5H), 1.83-1.70 (m, 1H), 1.25-1.13 (m, 1H). 19F NMR (376 MHz, CDCl₃) δ −142.70 (s, 1F)

Step 3: 2-[3-(Dimethyl-1,2-oxazol-4-yl)-5-[(1-fluorocyclobutyl)(phenyl)methyl]-5H-pyrido[3,2-b]indol-7-yl]propan-2-ol Following procedures analogous to those described in Steps 4 and 5 of Example 1, methyl 3-(3,5-dimethylisoxazol-4-yl)-5H-pyrido[3,2-b]indole-7-carboxylate (75 mg, 0.23 mmol) and (1-fluorocyclobutyl)(phenyl)methanol (84 mg, 0.47 mmol) were converted to racemic 2-[3-(dimethyl-1,2-oxazol-4-yl)-5-[(1-fluorocyclobutyl)(phenyl)methyl]-5H-pyrido[3,2-b]indol-7-yl]propan-2-ol, which was separated by chiral prep SFC to give Enantiomer A (29 mg, 18%) and Enantiomer B (30 mg, 19%). Enantiomer A: ¹H NMR (400 MHz, CDCl₃) δ 8.39-8.35 (m, 2H), 7.89 (br s, 1H), 7.47 (dd, J=8.2, 1.3 Hz, 1H), 7.31-7.28 (m, 6H), 6.27-6.10 (m, 1H), 2.92-2.65 (m, 2H), 2.40-2.26 (m, 2H), 2.25 (s, 3H), 2.06 (s, 3H), 1.95-1.83 (m, 2H), 1.74 (s, 6H); LCMS (M+H)=484.5; HPLC RT=8.20 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=6.57 (Column: Chiralcel OD-H 250×4.6 mm, 5 μm; Mobile Phase: 80/20 CO₂/MeOH; Flow: 2 mL/min); [α]$_D^{20}$=−10.66 (c=0.08, CHCl₃). Enantiomer B: ¹H NMR (400 MHz, CDCl₃) δ 8.39-8.35 (m, 2H), 7.89 (br s, 1H), 7.47 (dd, J=8.2, 1.3 Hz, 1H), 7.31-7.28 (m, 6H), 6.27-6.10 (m, 1H), 2.92-2.65 (m, 2H), 2.40-2.26 (m, 2H), 2.25 (s, 3H), 2.06 (s, 3H), 1.95-1.83 (m, 2H), 1.74 (s, 6H); LCMS (M+H)=484.5; HPLC RT=8.20 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=13.73 (Column: Chiralcel OD-H 250×4.6 mm, 5 μm; Mobile Phase: 80/20 CO₂/MeOH; Flow: 2 mL/min); [α]$_D^{20}$=+15.73 (c=0.08, CHCl₃).

Example 34 and 35

2-[3-(Dimethyl-1,2-oxazol-4-yl)-5-[4,4,4-trifluoro-1-(1,3-oxazol-4-yl)butyl]-5H-pyrido[3,2-b]indol-7-yl]propan-2-ol Enantiomer A, Example 34

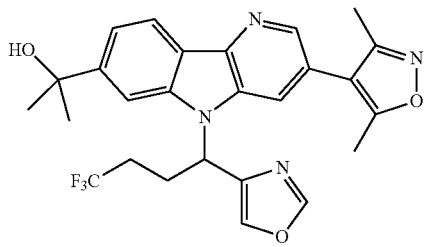

Enantiomer B, Example 35

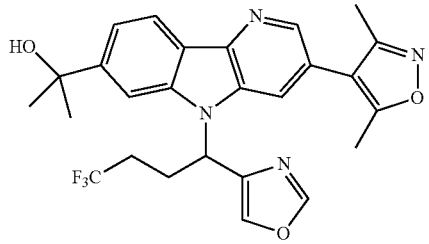

Step 1:
N-Methoxy-N-methyloxazole-4-carboxamide

A suspension of oxazole-4-carboxylic acid (0.50 g, 4.42 mmol) and HOBT (0.74 g, 4.86 mmol) was stirred for 10 min and then N,O-dimethylhydroxylamine, HCl (0.47 g, 4.86 mmol) and DIEA (0.85 mL, 4.86 mmol) were added. After 10 min, EDC (0.93 g, 4.86 mmol) was added. The resulting reaction mixture was stirred overnight and then diluted with 1M HCl. The layers were separated, and the aqueous layer was extracted with CH₂Cl₂. The organic layer was washed sequentially with sat. NaHCO₃ and sat. NaCl, dried over Na₂SO₄ and concentrated to give the title compound (0.22 g, 33%). ¹H NMR (400 MHz, CDCl₃) δ 8.22 (s, 1H), 7.93 (s, 1H), 3.78 (s, 3H), 3.41 (s, 3H).

Step 2: 4,4,4-Trifluoro-1-(oxazol-4-yl)butan-1-one

To a suspension of magnesium (0.070 g, 2.88 mmol) in THF (15 mL) was added 2 drops of 1,2-dibromoethane followed by a solution of 3-bromo-1,1,1-trifluoropropane (0.51 g, 2.88 mmol) in THF (5.0 mL). The resulting reaction mixture was cooled to 0° C., and then a suspension of N-methoxy-N-methyloxazole-4-carboxamide (0.22 g, 1.44 mmol) in THF (5.0 mL) was added. After 1.5 h, the reaction was quenched with sat. NH₄Cl, and then extracted with EtOAc (2×). The combined organic layer was washed with sat. NaCl, dried with Na₂SO₄ and concentrated to the title compound (0.25 g, 89% yield), which was used without further purification in the subsequent step. ¹H NMR (400 MHz, CDCl₃) δ 8.30 (d, J=1.0 Hz, 1H), 7.94 (d, J=0.7 Hz, 1H), 3.31-3.19 (m, 2H), 2.57 (dt, J=10.8, 7.7 Hz, 2H).

Step 3: 4,4,4-Trifluoro-1-(oxazol-4-yl)butan-1-ol

A solution of 4,4,4-trifluoro-1-(oxazol-4-yl)butan-1-one (0.25 g, 1.28 mmol) in MeOH (4.3 mL) was cooled to 0° C. and NaBH₄ (0.073 g, 1.92 mmol) was added. After 1.5 h, a small amount of water was added and the reaction mixture was concentrated. The residue was diluted with CH₂Cl₂, then carefully quenched with sat. NH₄Cl. The layers were separated, and the aqueous layer extracted with CH₂Cl₂. The combined organic layer was dried with Na₂SO₄ and concentrated. The residue was purified using ISCO silica gel chromatography (24 g column, gradient from 0% to 100% EtOAc/hexanes) to give the title compound (0.16 g, 63%). ¹H NMR (400 MHz, CDCl₃) δ 7.88 (s, 1H), 7.62 (t, J=0.9 Hz, 1H), 4.85-4.76 (m, 1H), 2.40 (d, J=5.4 Hz, 1H), 2.38-2.19 (m, 2H), 2.16-2.06 (m, 2H).

Step 4: 2-[3-(Dimethyl-1,2-oxazol-4-yl)-5-[4,4,4-trifluoro-1-(1,3-oxazol-4-yl)butyl]-5H-pyrido[3,2-b]indol-7-yl]propan-2-ol Following procedures analogous to those described in Steps 4 and 5 of Example 1, methyl 3-(3,5-dimethylisoxazol-4-yl)-5H-pyrido[3,2-b]indole-7-carboxylate (100 mg, 0.31 mmol) and 4,4,4-trifluoro-1-(oxazol-4-yl)butan-1-ol, (91 mg, 0.47 mmol) were converted to racemic 2-[3-(dimethyl-1,2-oxazol-4-yl)-5-[4,4,4-trifluoro-1-(1,3-oxazol-4-yl)butyl]-5H-pyrido[3,2-b]indol-7-yl]propan-2-ol, which was separated by chiral prep SFC to give Enantiomer A (26 mg, 17%) and Enantiomer B (27 mg, 17%). Enantiomer A: $^1$H NMR (500 MHz, CD$_3$OD) δ 8.41 (d, J=1.7 Hz, 1H), 8.30 (d, J=8.4 Hz, 1H), 8.17 (s, 1H), 8.12 (s, 1H), 8.04 (d, J=1.6 Hz, 1H), 7.88 (s, 1H), 7.51 (dd, J=8.4, 1.3 Hz, 1H), 6.16 (dd, J=10.2, 5.4 Hz, 1H), 2.98-2.73 (m, 2H), 2.47 (s, 3H), 2.37 (dt, J=14.9, 5.6 Hz, 1H), 2.30 (s, 3H), 1.91-1.76 (m, 1H), 1.64 (s, 6H); LCMS (M+H)=499.5; HPLC RT=7.19 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=4.21 min (Column: Phenomenex LUX Cellulose 2 250×4.6 mm, 5 μm; Mobile Phase: 80/20 CO$_2$/MeOH; Flow: 2 mL/min); $[α]_D^{20}$=+16.38 (c=0.17, CHCl$_3$). Enantiomer B: $^1$H NMR (500 MHz, CD$_3$OD) δ 8.41 (d, J=1.7 Hz, 1H), 8.30 (d, J=8.4 Hz, 1H), 8.17 (s, 1H), 8.12 (s, 1H), 8.04 (d, J=1.6 Hz, 1H), 7.88 (s, 1H), 7.51 (dd, J=8.4, 1.3 Hz, 1H), 6.16 (dd, J=10.2, 5.4 Hz, 1H), 2.98-2.73 (m, 2H), 2.47 (s, 3H), 2.37 (dt, J=14.9, 5.6 Hz, 1H), 2.30 (s, 3H), 1.91-1.76 (m, 1H), 1.64 (s, 6H); LCMS (M+H)=499.5; HPLC RT=7.19 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=5.10 min (Column: Phenomenex LUX Cellulose 2 250×4.6 mm, 5 μm; Mobile Phase: 80/20 CO$_2$/MeOH; Flow: 2 mL/min); $[α]_D^{20}$=−9.16 (c=0.08, CHCl$_3$).

Example 36 & Example 37

2-[3-(Dimethyl-1,2-oxazol-4-yl)-5-[4,4,4-trifluoro-1-(1,2-oxazol-4-yl)butyl]-5H-pyrido[3,2-b]indol-7-yl]propan-2-ol Enantiomer A, Example 36

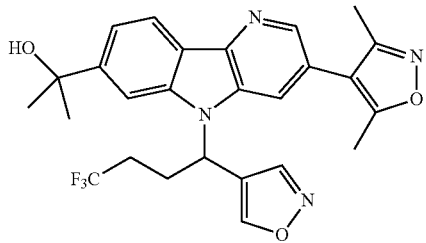

Enantiomer B, Example 37

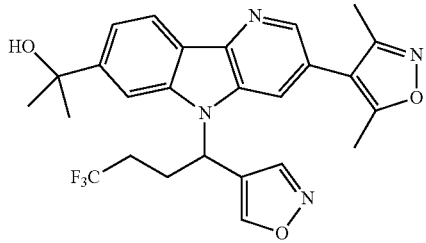

Step 1: 4,4,4-Trifluoro-1-(isoxazol-4-yl)butan-1-ol

A mixture of 3-bromo-1,1,1-trifluoropropane (1.37 g, 7.73 mmol), magnesium (0.19 g, 7.73 mmol) and dibromoethane (2-3 drops) in THF (13 mL) was heated to 50° C. for 30 min. The reaction mixture was then cooled in ice bath and isoxazole-4-carbaldehyde (0.50 g, 5.15 mmol) in THF (5.0 mL) was added slowly. The mixture was stirred at room temperature for 3 h and then quenched with sat. NH$_4$Cl (3 mL) and diluted with water. The aqueous layer was extracted with EtOAc (3×). The organic layer was separated, concentrated and the residue was purified by ISCO silica gel chromatography (40 g column, gradient from 0% to 40% EtOAc/hexanes) to afford the title compound (710 mg, 71%) as a colorless solid. $^1$H NMR (400 MHz, CD$_3$OD) δ 8.63 (d, J=0.7 Hz, 1H), 8.45 (s, 1H), 4.77 (dd, J=8.1, 4.9 Hz, 1H), 2.48-2.17 (m, 2H), 2.08-1.86 (m, 2H).

Step 2: 2-[3-(Dimethyl-1,2-oxazol-4-yl)-5-[4,4,4-trifluoro-1-(1,2-oxazol-4-yl)butyl]-5H-pyrido[3,2-b]indol-7-yl]propan-2-ol Following procedures analogous to those described in Steps 4 and 5 of Example 1, methyl 3-(3,5-dimethylisoxazol-4-yl)-5H-pyrido[3,2-b]indole-7-carboxylate (75 mg, 0.23 mmol) and 4,4,4-trifluoro-1-(isoxazol-4-yl)butan-1-ol, (68 mg, 0.35 mmol) were converted to racemic 2-[3-(dimethyl-1,2-oxazol-4-yl)-5-[4,4,4-trifluoro-1-(1,2-oxazol-4-yl)butyl]-5H-pyrido[3,2-b]indol-7-yl]propan-2-ol, which was separated by chiral prep SFC to give Enantiomer A (6 mg, 5%) and Enantiomer B (5 mg, 4%). Enantiomer A: $^1$H NMR (400 MHz, CD$_3$OD) δ $^1$H NMR (400 MHz, CD$_3$OD) δ 8.89 (d, J=1.1 Hz, 1H), 8.43 (d, J=1.5 Hz, 1H), 8.34 (d, J=8.4 Hz, 1H), 8.25 (s, 1H), 7.84 (d, J=14.5 Hz, 2H), 7.53 (dd, J=8.3, 1.2 Hz, 1H), 6.21 (dd, J=11.1, 4.5 Hz, 1H), 3.01-2.87 (m, 1H), 2.83-2.71 (m, 1H), 2.44 (s, 3H), 2.40-2.29 (m, 1H), 2.26 (s, 3H), 1.84-1.67 (m, 1H), 1.64 (s, 6H); LCMS (M+H)=499.4; HPLC RT=9.35 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=8.36 min (Column: Chiralpak IC, 250×4.6 mm, 5 μm; Mobile Phase: 75/25 CO$_2$/MeOH; Flow: 2 mL/min). Enantiomer B: $^1$H NMR (400 MHz, CD$_3$OD) δ 8.89 (d, J=1.1 Hz, 1H), 8.43 (d, J=1.5 Hz, 1H), 8.34 (d, J=8.4 Hz, 1H), 8.25 (s, 1H), 7.84 (d, J=14.5 Hz, 2H), 7.53 (dd, J=8.4, 1.3 Hz, 1H), 6.21 (dd, J=11.2, 4.4 Hz, 1H), 3.02-2.88 (m, 1H), 2.82-2.72 (m, 1H), 2.44 (s, 3H), 2.39-2.29 (m, 1H), 2.26 (s, 3H), 1.82-1.68 (m, 1H), 1.64 (s, 6H); LCMS (M+H)=499.3; HPLC RT=9.28 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm); SFC RT=12.41 min (Column: Chiralpak IC, 250×4.6 mm, 5 μm; Mobile Phase: 75/25 CO$_2$/MeOH; Flow: 2 mL/min).

Examples 38 & 39

4-[7-Methanesulfonyl-5-(4,4,4-trifluoro-1-phenylbutyl)-5H-pyrido[3,2-b]indol-3-yl]-3,5-dimethyl-1,2-oxazole Enantiomer A, Example 38

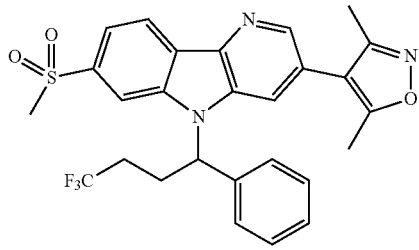

Enantiomer A, Example 39

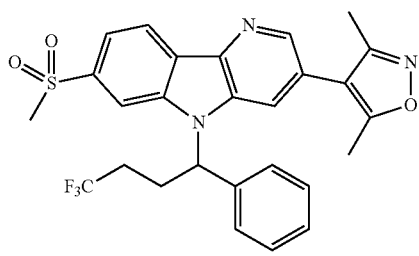

Racemic 4-[7-methanesulfonyl-5-(4,4,4-trifluoro-1-phenylbutyl)-5H-pyrido[3,2-b]indol-3-yl]-3,5-dimethyl-1,2-oxazole was prepared according to the procedures described for Example 1, substituting (3-(methylsulfonyl)phenyl)boronic acid (CombiBlocks) for (3-(methoxycarbonyl)phenyl) boronic acid in Step 2. Separation using chiral prep SFC gave Enantiomers A and B. Enantiomer A: $^1$H NMR (500 MHz, CDCl$_3$) δ 8.63 (d, J=8.2 Hz, 1H), 8.56 (d, J=1.7 Hz, 1H), 8.17 (s, 1H), 7.95 (dd, J=8.2, 1.4 Hz, 1H), 7.42-7.32 (m, 4H), 7.28 (d, J=1.7 Hz, 2H), 6.06 (dd, J=10.9, 5.1 Hz, 1H), 3.17 (s, 3H), 2.98-2.89 (m, 1H), 2.81 (ddt, J=19.7, 10.6, 5.2 Hz, 1H), 2.33 (s, 3H), 2.25-2.16 (m, 1H), 2.15 (s, 3H), 1.88-1.76 (m, 1H); LCMS (M+H)=528.3; HPLC RT=2.87 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=10.03 min (Column: Chiralcel OD-H 250×4.6 mm, 5 μm; Mobile Phase: 75/25 CO$_2$/MeOH; Flow: 2 mL/min); $[α]_D^{20}$=−56.9 (c=0.12, CHCl$_3$). Enantiomer B: $^1$H NMR (500 MHz, CDCl$_3$) δ 8.63 (d, J=8.2 Hz, 1H), 8.56 (d, J=1.7 Hz, 1H), 8.17 (s, 1H), 7.95 (dd, J=8.2, 1.4 Hz, 1H), 7.42-7.32 (m, 4H), 7.28 (d, J=1.7 Hz, 2H), 6.06 (dd, J=10.9, 5.1 Hz, 1H), 3.17 (s, 3H), 2.98-2.89 (m, 1H), 2.81 (ddt, J=19.7, 10.6, 5.2 Hz, 1H), 2.33 (s, 3H), 2.25-2.16 (m, 1H), 2.15 (s, 3H), 1.88-1.76 (m, 1H); LCMS (M+H)=528.3; HPLC RT=2.87 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=19.50 min (Column: Chiralcel OD-H 250×4.6 mm, 5 μm; Mobile Phase: 75/25 CO$_2$/MeOH; Flow: 2 mL/min); $[α]_D^{20}$=+62.7 (c=0.14, CHCl$_3$).

Examples 40 & 41

2-{5-[(4-Fluorophenyl)(oxan-4-yl)methyl]-3-(5-methyl-1,2-oxazol-4-yl)-5H-pyrido[3,2-b]indol-7-yl}propan-2-ol Enantiomer A, Example 40

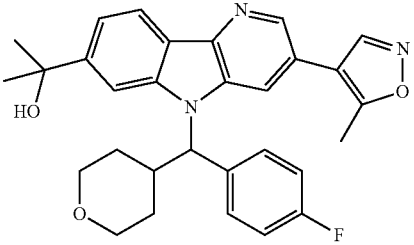

Enantiomer B, Example 41

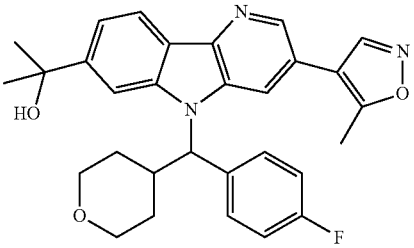

Step 1: Methyl 4-(5-bromo-3-nitropyridin-2-yl)benzoate

To a mixture of 2,5-dibromo-3-nitropyridine (2.00 g, 7.09 mmol), (4-(methoxycarbonyl)phenyl)boronic acid (1.28 g, 7.09 mmol) Pd(dppf)Cl$_2$ (0.36 g, 0.50 mmol) in THF (30 mL) was added tripotassium phosphate (3M in water) (7.09 mL, 21.3 mmol). The reaction mixture was purged with N$_2$ (3×) and then stirred at 80° C. for 3 h. The aqueous layer was separated. The organic layer dried with Na$_2$SO$_4$, filtered through a small plug of Celite® washing with EtOAc and concentrated. The crude residue was purified using ISCO silica gel chromatography (120 g column, gradient from 0% to 50% EtOAc/CH$_2$Cl$_2$) to give the title compound (1.64 g, 69%) as a white solid. $^1$H NMR (400 MHz, DMSO-d$_6$) δ 9.15 (d, J=2.0 Hz, 1H), 8.88 (d, J=2.2 Hz, 1H), 8.17-8.02 (m, 2H), 7.78-7.63 (m, 2H), 3.90 (s, 3H).

Step 2: Methyl 3-bromo-5H-pyrido[3,2-b]indole-7-carboxylate

A mixture of methyl 4-(5-bromo-3-nitropyridin-2-yl)benzoate (1.64 g, 4.86 mmol) and 1,2-bis(diphenylphosphino)ethane (2.42 g, 6.08 mmol) in 1,2-dichlorobenzene (30 mL) was purged with N$_2$ (3×) and then warmed to reflux. After 4 h, the mixture was cooled to room temperature and concentrated. The residue was suspended in CHCl$_3$, sonicated and then filtered. The solid was washed with CHCl$_3$ and dried to give the title compound (0.84 g, 57%) as a beige solid. $^1$H NMR (400 MHz, DMSO-d$_6$) δ 11.85 (s, 1H), 8.60 (d, J=2.0 Hz, 1H), 8.29 (dd, J=5.1, 3.1 Hz, 2H), 8.22 (s, 1H), 7.88 (dd, J=8.3, 1.4 Hz, 1H), 3.93 (s, 3H); LCMS (M+H)=305.1.

Step 3: Methyl 3-bromo-5-((4-fluorophenyl)(tetrahydro-2H-pyran-4-yl)methyl)-5H-pyrido[3,2-b]indole-7-carboxylate Following a procedure analogous to that described in Step 4 Example 1, methyl 3-bromo-5H-pyrido[3,2-b]indole-7-carboxylate (840 mg, 2.75 mmol) and (4-fluorophenyl)(tetrahydro-2H-pyran-4-yl)methanol (Step 1 of Example 25, 868 mg, 4.13 mmol) was converted to the title compound as a racemate (1.26 g, 92%), which was used without further purification in the subsequent step. LCMS (M+H)=497.2.

Step 4: Methyl 5-((4-fluorophenyl)(tetrahydro-2H-pyran-4-yl)methyl)-3-(4,4,5,5-tetramethyl-1,3,2-dioxaborolan-2-yl)-5H-pyrido[3,2-b]indole-7-carboxylate To a mixture of methyl 3-bromo-5-((4-fluorophenyl)(tetrahydro-2H-pyran-4-yl)methyl)-5H-pyrido[3,2-b]indole-7-carboxylate (500 mg, 1.01 mmol), 4,4,4',4',5,5,5',5'-octamethyl-2,2'-bi(1,3,2-dioxaborolane) (306 mg, 1.21 mmol), Pd(dppf)Cl$_2$ (37 mg, 0.050 mmol) and KOAc (197 mg, 2.01 mmol) in a screw cap vial was added dioxane (10 mL). The vial was fitted with a teflon lined septum cap and purged with N$_2$ (3×). The reaction mixture was heated at 90° C. for 16 h, then cooled to room temperature and filtered. The filtrate was purified using ISCO silica gel chromatography (40 g column, gradient from 0% to 90% EtOAc/CH$_2$Cl$_2$) to give the title compound (254 mg, 46%). LCMS (M+H)=463.4.

Step 5: Methyl 5-((4-fluorophenyl)(tetrahydro-2H-pyran-4-yl)methyl)-3-(5-methylisoxazol-4-yl)-5H-pyrido[3,2-b]indole-7-carboxylate To a screw top vial was added methyl 5-((4-fluorophenyl)(tetrahydro-2H-pyran-4-yl)methyl)-3-(4,4,5,5-tetramethyl-1,3,2-dioxaborolan-2-yl)-5H-pyrido[3,2-b]indole-7-carboxylate (125 mg, 0.23 mmol), 4-iodo-5-methylisoxazole (48 mg, 0.23 mmol), Pd(dppf)Cl$_2$ (8 mg, 0.011 mmol) and phosphoric acid, potassium salt (0.23 mL, 0.69 mmol) followed by THF (1.5 mL). The resulting suspension was heated at 80° C. for 45 min, then cooled to room temperature, diluted with EtOAc and quenched with water. The organic layer was washed with water, sat. NaCl, dried and concentrated in vacuo. The crude product was purified using ISCO silica gel chromatography (24 g column, gradient from 0% to 100% EtOAc/CH$_2$Cl$_2$) to give the title compound (83 mg, 72%). LCMS (M+H)=500.1; HPLC RT=3.68 min (Column: Waters Sunfire C18 5 μm, 2.1×50 mm; Mobile Phase A: 10:90 MeOH:water with 0.1% TFA; Mobile Phase B: 90:10 MeOH:water with 0.1% TFA; Gradient 0-100% B over 4 min; Flow: 1 mL/min; Detection: UV at 220 nm).

Step 6: 2-{5-[(4-Fluorophenyl)(oxan-4-yl)methyl]-3-(5-methyl-1,2-oxazol-4-yl)-5H-pyrido[3,2-b]indol-7-yl}propan-2-ol Following a procedure analogous to that described in Step 5 Example 1, methyl 5-((4-fluorophenyl)(tetrahydro-2H-pyran-4-yl)methyl)-3-(5-methylisoxazol-4-yl)-5H-pyrido[3,2-b]indole-7-carboxylate (105 mg, 0.21 mmol) was converted to racemic 2-{5-[(4-fluorophenyl)(oxan-4-yl)methyl]-3-(5-methyl-1,2-oxazol-4-yl)-5H-pyrido[3,2-b]indol-7-yl}propan-2-ol, (60 mg, 57%) which was separated by chiral prep SFC to give Enantiomers A and B. Enantiomer A: $^1$H NMR (400 MHz, CD$_3$OD) δ 8.75 (s, 1H), 8.52 (d, J=1.8 Hz, 1H), 8.34-8.13 (m, 2H), 8.05 (s, 1H), 7.79-7.62 (m, 2H), 7.46 (dd, J=8.4, 1.3 Hz, 1H), 7.10 (t, J=8.8 Hz, 2H), 5.76 (d, J=11.0 Hz, 1H), 4.19-3.75 (m, 3H), 3.68-3.54 (m, 1H), 3.50-3.35 (m, 2H), 2.64 (s, 2H), 2.08-1.86 (m, 1H), 1.86-1.74 (m, 1H), 1.74-1.53 (m, 6H), 1.53-0.99 (m, 4H); LCMS (M+H)=500.5; SFC RT=7.68 (Column: Chiralcel OD-H 250×4.6 mm, 5 μm; Mobile Phase: 75/25 CO$_2$/MeOH; Flow: 2 mL/min); $[α]_D^{20}$=−79.08 (c=0.11, MeOH). Enantiomer B: $^1$H NMR (400 MHz, CD$_3$OD) δ 8.75 (s, 1H), 8.52 (d, J=1.5 Hz, 1H), 8.26 (s, 2H), 8.12-7.90 (m, 1H), 7.81-7.60 (m, 2H), 7.58-7.34 (m, 1H), 7.10 (s, 2H), 5.88-5.64 (m, 1H), 4.15-3.74 (m, 3H), 3.72-3.55 (m, 1H), 3.37 (s, 2H), 2.64 (s, 2H), 2.10-1.90 (m, 1H), 1.68 (d, J=3.7 Hz, 6H), 1.51-1.26 (m, 2H), 1.25-1.01 (m, 2H); LCMS (M+H)=500.5; SFC RT=10.51 (Column: Chiralcel OD-H 250×4.6 mm, 5 μm; Mobile Phase: 75/25 CO$_2$/MeOH; Flow: 2 mL/min).

Examples 42 & 43

2-{5-[(4-Fluorophenyl)(oxan-4-yl)methyl]-3-(3-methyl-1,2-oxazol-4-yl)-5H-pyrido[3,2-b]indol-7-yl}propan-2-ol

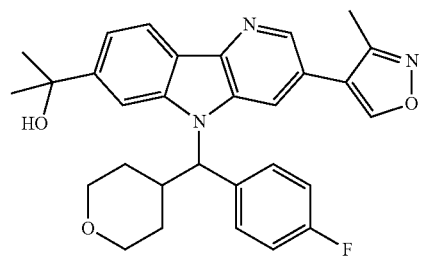

Enantiomer A, Example 42

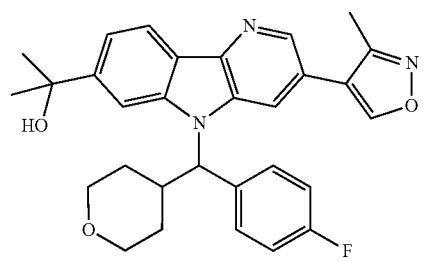

Enantiomer B, Example 43

Racemic 2-{5-[(4-fluorophenyl)(oxan-4-yl)methyl]-3-(3-methyl-1,2-oxazol-4-yl)-5H-pyrido[3,2-b]indol-7-yl}propan-2-ol, was prepared according to the procedures described for Example 40, substituting 4-bromo-3-methylisoxazole [Gibson, C. et al. *J. Med. Chem.* 2009, 52, 4370-4279] for 4-iodo-5-methylisoxazole in Step 5. Separation using chiral prep SFC gave Enantiomers A and B. Enantiomer A: $^1$H NMR (400 MHz, CD$_3$OD) δ 8.96 (s, 1H), 8.51 (d, J=1.8 Hz, 1H), 8.40-8.16 (m, 2H), 8.05 (s, 1H), 7.68 (dd, J=8.6, 5.3 Hz, 2H), 7.47 (dd, J=8.4, 1.3 Hz, 1H), 7.10 (t, J=8.8 Hz, 2H), 5.76 (d, J=11.0 Hz, 1H), 4.18-3.76 (m, 3H), 3.37 (s, 4H), 2.46 (s, 3H), 2.39-2.21 (m, 1H), 1.68 (d, J=3.7 Hz, 11H), 1.46-0.95 (m, 3H); LCMS (M+H)=500.5; SFC RT=7.92 (Column: Chiralcel OD-H 250×4.6 mm, 5 μm; Mobile Phase: 75/25 CO$_2$/MeOH; Flow: 2 mL/min); $[α]_D^{20}$=−25.54 (c=0.35, CHCl$_3$). Enantiomer B: $^1$H NMR (400 MHz, CD$_3$OD) δ 8.96 (s, 1H), 8.51 (d, J=1.8 Hz, 1H), 8.40-8.16 (m, 2H), 8.05 (s, 1H), 7.68 (dd, J=8.6, 5.3 Hz, 2H), 7.47 (dd, J=8.4, 1.3 Hz, 1H), 7.10 (t, J=8.8 Hz, 2H), 5.76 (d, J=11.0 Hz, 1H), 4.18-3.76 (m, 3H), 3.37 (s, 4H), 2.46 (s, 3H), 2.39-2.21 (m, 1H), 1.68 (d, J=3.7 Hz, 11H), 1.46-0.95 (m, 3H); LCMS (M+H)=500.5; SFC RT=10.45 (Column: Chiralcel OD-H 250×4.6 mm, 5 μm; Mobile Phase: 75/25 CO$_2$/MeOH; Flow: 2 mL/min).

Example 44

3-(Dimethyl-1,2-oxazol-4-yl)-5-[oxan-4-yl(phenyl)methyl]-5H-pyrido[3,2-b]indole-7-carboxylic acid

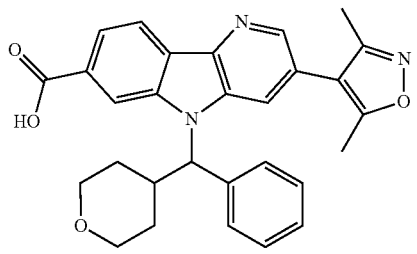 [SMILES: Cc1noc(C)c1-c1cnc2c3ccc(C(=O)O)cc3n(C(c3ccccc3)C3CCOCC3)c2c1]

To a 5 mL vial containing methyl 3-(3,5-dimethylisoxazol-4-yl)-5-(phenyl(tetrahydro-2H-pyran-4-yl)methyl)-5H-pyrido[3,2-b]indole-7-carboxylate (Step 4 of Example 1, 54 mg, 0.11 mmol) in MeOH (2.0 mL) was added 1N NaOH (1.10 mL, 1.10 mmol). The resulting reaction mixture was heated at 80° C. for 30 min and then concentrated. 1M citric acid (1.10 mL, 1.10 mmol) was added, and the white solid was collected via filtration, rinsed with water and dried under vacuum to give the title compound as a racemate (17 mg, 31%). $^1$H NMR (500 MHz, CDCl$_3$) δ 8.57-8.47 (m, 3H), 8.15 (dd, J=8.3, 1.1 Hz, 1H), 7.63 (d, J=1.4 Hz, 1H), 7.48 (d, J=7.5 Hz, 2H), 7.40-7.34 (m, 2H), 7.31 (d, J=7.2 Hz, 1H), 5.62 (d, J=10.5 Hz, 1H), 4.13-4.04 (m, 1H), 3.92-3.81 (m, 1H), 3.62-3.52 (m, 1H), 3.42-3.33 (m, 1H), 3.14 (q, J=10.9 Hz, 1H), 2.41 (s, 3H), 2.25 (s, 3H), 2.05 (d, J=13.0 Hz, 1H), 1.69-1.63 (m, 1H), 1.48-1.40 (m, 1H), 1.12 (d, J=13.3 Hz, 1H); LCMS (M+H)=482.1; HPLC RT=2.74 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 45

3-(Dimethyl-1,2-oxazol-4-yl)-5-(diphenylmethyl)-5H-pyrido[3,2-b]indole-7-carboxylic acid

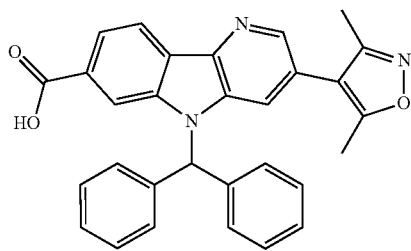 [SMILES: Cc1noc(C)c1-c1cnc2c3ccc(C(=O)O)cc3n(C(c3ccccc3)c3ccccc3)c2c1]

Following a procedure analogous to that described for Example 44, methyl 5-benzhydryl-3-(3,5-dimethylisoxazol-4-yl)-5H-pyrido[3,2-b]indole-7-carboxylate (Step 4 of Example 3, 17 mg, 0.035 mmol) was converted to the title compound (14 mg, 84%). $^1$H NMR (500 MHz, CDCl$_3$) δ 8.57-8.48 (m, 2H), 8.26 (s, 1H), 8.16 (d, J=8.0 Hz, 1H), 7.42-7.34 (m, 6H), 7.31 (s, 1H), 7.25-7.19 (m, 4H), 6.96 (d, J=1.7 Hz, 1H), 2.25 (s, 3H), 2.07 (s, 3H); LCMS (M+H)=474.0; HPLC RT=3.11 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 46

2-[5-Benzyl-3-(dimethyl-1,2-oxazol-4-yl)-5H-pyrido[3,2-b]indol-7-yl]propan-2-ol

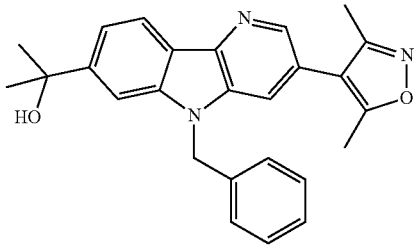 [SMILES: Cc1noc(C)c1-c1cnc2c3ccc(C(C)(C)O)cc3n(Cc3ccccc3)c2c1]

Step 1: Methyl 5-benzyl-3-(3,5-dimethylisoxazol-4-yl)-5H-pyrido[3,2-b]indole-7-carboxylate To a 5 mL vial containing methyl 3-(3,5-dimethylisoxazol-4-yl)-5H-pyrido[3,2-b]indole-7-carboxylate (Step 3 of Example 1, 39 mg, 0.12 mmol) and K$_2$CO$_3$ (50 mg, 0.36 mmol) in DMF (0.5 mL) was added benzyl bromide (0.021 mL, 0.18 mmol). The resulting reaction mixture was heated at 70° C. for 1 h. Additional benzyl bromide (0.021 mL, 0.18 mmol) was added and heating was continued at 70° C. for 10 min and then at 80° C. for 1 h. The reaction mixture was cooled to room temperature and purified directly using ISCO silica gel chromatography (40 g column, gradient form 0% to 50% EtOAc/CH$_2$Cl$_2$) to give the title compound (36 mg, 74%) as a yellow solid. $^1$H NMR (500 MHz, CDCl$_3$) δ 8.52 (d, J=1.9 Hz, 1H), 8.48 (dd, J=8.0, 0.6 Hz, 1H), 8.28 (d, J=0.6 Hz, 1H), 8.08 (dd, J=8.2, 1.2 Hz, 1H), 7.45 (d, J=1.9 Hz, 1H), 7.34-7.28 (m, 3H), 7.16 (dd, J=7.6, 1.8 Hz, 2H), 5.61 (s, 2H), 3.99 (s, 3H), 2.39 (s, 3H), 2.22 (s, 3H); LCMS (M+H)=412.1; HPLC RT=3.03 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-[5-Benzyl-3-(dimethyl-1,2-oxazol-4-yl)-5H-pyrido[3,2-b]indol-7-yl]propan-2-ol Following a procedure analogous to that described in Step 5 of Example 1, methyl 5-benzyl-3-(3,5-dimethylisoxazol-4-yl)-5H-pyrido[3,2-b]indole-7-carboxylate (36 mg, 0.087 mmol) was converted to the title compound (2 mg, 4%) after purification by prep HPLC (Column: Phen Luna C18, 30×100 mm, 5 μm particles; Mobile Phase A: 5:95 acetonitrile:water with 0.1% TFA; Mobile Phase B: 95:5 acetonitrile:water with 0.1% TFA; Gradient: 10-100% B over 12 min, then a 2-min hold at 100% B; Flow: 40 mL/min). $^1$H NMR (500 MHz, CDCl$_3$) δ 8.45 (d, J=1.7 Hz, 1H), 8.38 (d, J=8.3 Hz, 1H), 7.74 (s, 1H), 7.45 (dd, J=8.3, 1.4 Hz, 1H), 7.38 (d, J=1.9 Hz, 1H), 7.34-7.29 (m, 4H), 7.19-7.15 (m, 2H), 5.57 (s, 2H), 2.38 (s, 3H), 2.22 (s, 3H), 1.70 (s, 6H); LCMS (M+H)=412.1; HPLC RT=2.42 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 47-49

The compounds in Table 2 were prepared according to the procedures described for Example 46:

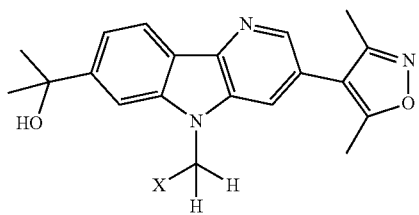

TABLE 2

| Example | X | HPLC RT (min) | LCMS (M + H) | HPLC Method |
|---|---|---|---|---|
| 47 | tetrahydropyran-4-yl | 1.94 | 420.4 | A |
| 48 | 4-fluorophenyl | 2.41 | 430.4 | A |
| 49 | 4,4-difluorocyclohexyl | 2.40 | 454.5 | A |

HPLC Conditions for Table 2:

Method A:

Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min; Detection: UV at 220 nm.

Example 50

4-[5-Benzyl-7-(difluoromethyl)-5H-pyrido[3,2-b]indol-3-yl]-3,5-dimethyl-1,2-oxazole

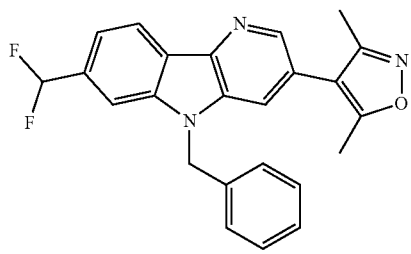 [SMILES: Cc1noc(C)c1-c1cnc2c3ccc(C(F)F)cc3n(Cc3ccccc3)c2c1]

Step 1: 3-((2-Chloro-5-(3,5-dimethylisoxazol-4-yl)pyridin-3-yl)amino)benzaldehyde To a 100 mL round bottom flask containing 2-chloro-5-(3,5-dimethylisoxazol-4-yl)pyridin-3-amine (Step 1 of Example 1, 1.00 g, 4.47 mmol), chloro(2-dicyclohexylphosphino-2',4',6'-triisopropyl-1,1'-biphenyl)[2-(2'-amino-1,1'-biphenyl)]palladium(II) (X-phos precatalyst, 0.21 g, 0.27 mmol) and 3-bromobenzaldehyde (1.56 mL, 13.4 mmol) in toluene (20 mL) was added cesium carbonate (2.91 g, 8.94 mmol). The reaction mixture was heated at 100° C. for 16 h, then cooled to room temperature and diluted with EtOAc (100 mL). Filtration through Celite® and concentration gave a crude residue which was purified using ISCO silica gel chromatography (24 g column, gradient from 0% to 100% EtOAc/hexanes) to give the title compound (359 mg, 24%). LCMS (M+H)=328.1; HPLC RT=1.63 min (Column: Waters Acquity BEH C18, 2.0×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient: 0-100% B over 1.5 min, then a 0.75-min hold at 100% B; Flow: 1 mL/min; Detection: UV at 220 nm)

Step 2: 3-(3,5-Dimethylisoxazol-4-yl)-5H-pyrido[3,2-b]indole-7-carbaldehyde

To a 5 mL microwave vial containing 3-((2-chloro-5-(3,5-dimethylisoxazol-4-yl)pyridin-3-yl)amino)benzaldehyde (359 mg, 1.10 mmol) and sodium acetate (225 mg, 2.74 mmol) in DMA (5.0 mL) was added bis(triphenylphosphine)palladium(II) chloride (62 mg, 0.088 mmol). The resulting suspension was heated at 170° C. in a microwave reactor for 20 min, then at 180° C. for 20 min, then at 200° C. for 40 min. The reaction mixture was purified directly using ISCO silica gel chromatography (24 g column, gradient from 0% to 100% EtOAc/hexanes) to give the title compound (69 mg, 22%). LCMS (M+H)=292.2; HPLC RT=0.88 min (Column: Waters Acquity BEH C18, 2.0×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient: 0-100% B over 1.5 min, then a 0.75-min hold at 100% B; Flow: 1 mL/min; Detection: UV at 220 nm)

Step 3: 5-Benzyl-3-(3,5-dimethylisoxazol-4-yl)-5H-pyrido[3,2-b]indole-7-carbaldehyde To a 25 mL round bottom flask containing 3-(3,5-dimethylisoxazol-4-yl)-5H-pyrido[3,2-b]indole-7-carbaldehyde (22 mg, 0.076 mmol) and cesium carbonate (98 mg, 0.30 mmol) in DMF (1.0 mL) was added benzyl bromide (0.018 mL, 0.15 mmol). The resulting suspension was stirred at room temperature for 3 h and then concentrated. The crude product was purified using ISCO silica gel chromatography (4 g column, gradient from 0% to 100% EtOAc/hexanes) to give the title compound (9 mg, 31%). LCMS (M+H)=382.2; HPLC RT=1.18 min (Column: Waters Acquity BEH C18, 2.0×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient: 0-100% B over 1.5 min, then a 0.75-min hold at 100% B; Flow: 1 mL/min; Detection: UV at 220 nm)

Step 4: 4-[5-Benzyl-7-(difluoromethyl)-5H-pyrido [3,2-b]indol-3-yl]-3,5-dimethyl-1,2-oxazole To a 25 mL round bottom flask containing 5-benzyl-3-(3, 5-dimethylisoxazol-4-yl)-5H-pyrido[3,2-b]indole-7-carbaldehyde (9 mg, 0.024 mmol) in CH$_2$Cl$_2$ (2.0 mL) was added deoxofluor (104 mg, 0.24 mmol). The resulting reaction mixture was stirred at room temperature under nitrogen overnight and then concentrated under reduced pressure. The crude material was purified via preparative LC-MS (Column: Waters XBridge C18, 19×200 mm, 5 μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 min, then a 5-min hold at 100% B; Flow: 20 mL/min) to give the title compound (1 mg, 14%). $^1$H NMR (500 MHz, DMSO-d$_6$) δ 8.58 (s, 1H), 8.40 (d, J=8.1 Hz, 1H), 8.21 (s, 1H), 8.04 (s, 1H), 7.53 (d, J=8.1 Hz, 1H), 7.36-7.20 (m, 6H), 5.83 (s, 2H), 2.47 (s, 3H), 2.29 (s, 3H); LCMS (M+H)=404.3; HPLC RT=1.98 min (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm).

Example 51

4-(5-Benzyl-5H-pyrido[3,2-b]indol-3-yl)-3,5-dimethyl-1,2-oxazole

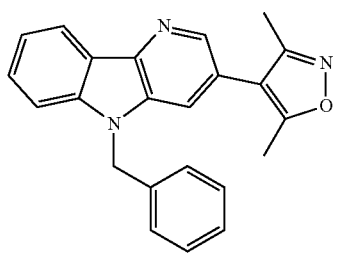 [SMILES: Cc1noc(C)c1-c1cnc2c3ccccc3n(Cc3ccccc3)c2c1]

Step 1: 2-Chloro-5-(3,5-dimethylisoxazol-4-yl)-N-phenylpyridin-3-amine

Following a procedure analogous to that described in Step 1 of Example 50, 2-chloro-5-(3,5-dimethylisoxazol-4-yl) pyridin-3-amine (Step 1 of Example 1, 0.50 g, 2.24 mmol) and bromobenzene (1.05 g, 6.71 mmol) were converted to the title compound (200 mg, 30%). $^1$H NMR (400 MHz, DMSO-d$_6$) δ 7.98 (s, 1H), 7.92 (d, J=2.2 Hz, 1H), 7.46 (d, J=2.0 Hz, 1H), 7.36-7.28 (m, 2H), 7.22 (d, J=7.5 Hz, 2H), 7.02 (t, J=7.3 Hz, 1H), 2.40 (s, 3H), 2.21 (s, 3H); LCMS (M+H)=300.2; HPLC RT=1.23 min (Column: Waters Acquity BEH C18, 2.0×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient: 0-100% B over 1.5 min, then a 0.75-min hold at 100% B; Flow: 1 mL/min; Detection: UV at 220 nm).

Step 2: 3,5-Dimethyl-4-(5H-pyrido[3,2-b]indol-3-yl) isoxazole

Following a procedure analogous to that described in Step 2 of Example 50, 2-chloro-5-(3,5-dimethylisoxazol-4-yl)-N-phenylpyridin-3-amine (200 mg, 0.67 mmol) was converted to the title compound (73 mg, 42%). $^1$H NMR (400 MHz, DMSO-d$_6$) δ 11.51 (s, 1H), 8.45 (d, J=2.0 Hz, 1H), 8.21 (d, J=7.9 Hz, 1H), 7.88 (d, J=2.0 Hz, 1H), 7.63-7.57 (m, 1H), 7.57-7.50 (m, 1H), 7.28 (td, J=7.4, 1.1 Hz, 1H), 2.49 (s, 3H), 2.30 (s, 3H); LCMS (M+H)=264.2; HPLC RT=0.84 min (Column: Waters Acquity BEH C18, 2.0×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient: 0-100% B over 1.5 min, then a 0.75-min hold at 100% B; Flow: 1 mL/min; Detection: UV at 220 nm).

Step 3: 4-(5-Benzyl-5H-pyrido[3,2-b]indol-3-yl)-3,5-dimethyl-1,2-oxazole

Following a procedure analogous to that described in Step 1 of Example 46, 3,5-dimethyl-4-(5H-pyrido[3,2-b]indol-3-yl)isoxazole (73 mg, 0.28 mmol) was converted to the title compound (51 mg, 52%). $^1$H NMR (500 MHz, DMSO-d$_6$) δ 8.55 (s, 1H), 8.30 (d, J=7.7 Hz, 1H), 8.24 (s, 1H), 7.80 (d, J=8.4 Hz, 1H), 7.62 (t, J=7.7 Hz, 1H), 7.36 (t, J=7.6 Hz, 1H), 7.31-7.18 (m, 5H), 5.77 (s, 2H), 2.46 (s, 3H), 2.28 (s, 3H); LCMS (M+H)=354.2; HPLC RT=1.98 min (Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm).

Example 52

4-(5-Benzyl-7-(methylsulfonyl)-5H-pyrido[3,2-b] indol-3-yl)-3,5-dimethyl-1,2-oxazole

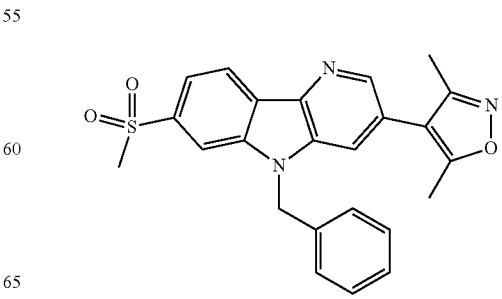

Step 1: 2-Chloro-5-(3,5-dimethylisoxazol-4-yl)-N-(3-(methylsulfonyl)phenyl)pyridin-3-amine Following a procedure analogous to that described in Step 2 of Example 1, 2-chloro-5-(3,5-dimethylisoxazol-4-yl)pyridin-3-amine (Step 1 of Example 1, 284 mg, 1.27 mmol) and (3-(methylsulfonyl)phenyl)boronic acid (CombiBlocks, 533 mg, 2.67 mmol) were converted to the title compound (100 mg, 21%). LCMS (M+H)=378.3; HPLC RT=2.08 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 4-(5-Benzyl-7-(methylsulfonyl)-5H-pyrido[3,2-b]indol-3-yl)-3,5-dimethyl-1,2-oxazole Following procedures analogous to those described in Steps 2 and 3 of Example 50, 2-chloro-5-(3,5-dimethylisoxazol-4-yl)-N-(3-(methylsulfonyl)phenyl)pyridin-3-amine (99 mg, 0.26 mmol) was converted to the title compound (23 mg, 20% over two steps). $^1$H NMR (400 MHz, CDCl$_3$) δ 8.61 (d, J=8.2 Hz, 1H), 8.57 (d, J=1.7 Hz, 1H), 8.17 (d, J=1.0 Hz, 1H), 7.93 (dd, J=8.3, 1.4 Hz, 1H), 7.49 (d, J=1.7 Hz, 1H), 7.38-7.30 (m, 3H), 7.15 (dd, J=7.2, 2.2 Hz, 2H), 5.63 (s, 2H), 3.16 (s, 3H), 2.40 (s, 3H), 2.23 (s, 3H); LCMS (M+H)=432.4; HPLC RT=2.55 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 53

2-[5-Benzyl-3-(dimethyl-1,2-oxazol-4-yl)-5H-pyrido[3,2-b]indol-9-yl]propan-2-ol

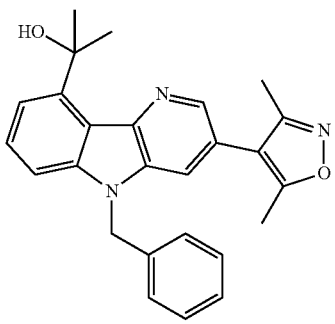 [SMILES: Cc1noc(C)c1-c1cnc2c3c(C(C)(C)O)cccc3n(Cc3ccccc3)c2c1]

Step 1: 5-(3,5-Dimethylisoxazol-4-yl)pyridin-3-amine

To a 40 mL vial containing 5-bromopyridin-3-amine (Aldrich, 200 mg, 1.16 mmol) and 3,5-dimethyl-4-(4,4,5,5-tetramethyl-1,3,2-dioxaborolan-2-yl)isoxazole (Aldrich, 516 mg, 2.31 mmol) in THF (10 mL) was added aq. tripotassium phosphate (2M, 1.7 mL, 3.47 mmol) to give a yellow suspension. Pd(dppf)Cl$_2$—CH$_2$Cl$_2$ (94 mg, 0.12 mmol) was then added and N$_2$ was bubbled into the mixture for 2 min. The resulting reaction mixture was heated at 80° C. for 1 h, concentrated and purified using ISCO silica gel chromatography (40 g column, gradient from 0% to 10% MeOH/CH$_2$Cl$_2$) to give the title compound (213 mg, 97%) as a pale orange solid. LCMS (M+H)=190; HPLC RT=0.51 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 3-((5-(3,5-dimethylisoxazol-4-yl)pyridin-3-yl)amino)benzoate

To a 40 mL pressure vial containing 5-(3,5-dimethylisoxazol-4-yl)pyridin-3-amine (212 mg, 1.12 mmol), methyl 3-bromobenzoate (Lancaster, 241 mg, 1.12 mmol) and Cs$_2$CO$_3$ (730 mg, 2.24 mmol) in toluene (10 mL) was added chloro(2-dicyclohexylphosphino-2',4',6'-triisopropyl-1,1'-biphenyl)[2-(2'-amino-1,1'-biphenyl)]palladium(II) (88 mg, 0.11 mmol). N$_2$ was bubbled through the reaction mixture for 1 min. The vial was sealed and heated to 100° C. for 16 h. After cooling to room temperature, the mixture was concentrated and purified using ISCO silica gel chromatography (80 g column, gradient from 0% to 100% EtOAc/CH$_2$Cl$_2$) to give the title compound (130 mg, 36%) as a white solid. $^1$H NMR (500 MHz, CDCl$_3$) δ 8.37 (d, J=2.5 Hz, 1H), 8.13 (d, J=1.9 Hz, 1H), 7.89-7.79 (m, 1H), 7.70 (dt, J=7.6, 1.2 Hz, 1H), 7.41 (t, J=7.9 Hz, 1H), 7.34-7.31 (m, 1H), 7.28 (dd, J=2.4, 1.0 Hz, 1H), 5.90 (s, 1H), 3.92 (s, 3H), 2.46 (s, 3H), 2.32 (s, 3H); LCMS (M+H)=324; HPLC RT=1.90 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: Methyl 3-(3,5-dimethylisoxazol-4-yl)-5H-pyrido[3,2-b]indole-9-carboxylate A 40 mL pressure vial containing methyl 3-((5-(3,5-dimethylisoxazol-4-yl)pyridin-3-yl)amino)benzoate (130 mg, 0.40 mmol), palladium (II) acetate (18 mg, 0.08 mmol) and K$_2$CO$_3$ (11.1 mg, 0.08 mmol) in pivalic acid (2 mL) was heated open to air at 110° C. for 12 h. After cooling to room temperature, the mixture was diluted with MTBE (6 mL), and the precipitate was filtered with MTBE rinses. In a 40 mL pressure vial, the solid was dissolved in TFA (3 mL) and palladium (II) acetate (18.1 mg, 0.08 mmol) was added. The vial was sealed and heated at 100° C. for 15 h. After cooling to room temperature, additional palladium (II) acetate (18 mg, 0.08 mmol) was added. The reaction was capped and heated for another 24 h. After cooling to room temperature, the reaction was concentrated and purified using preparative HPLC (Luna C18 30×100 column, 12 min gradient from 10% B to 100% B) to give the title compound (4 mg, 3%) as a yellow solid. $^1$H NMR (500 MHz, CD$_3$OD) δ 8.85 (d, J=1.7 Hz, 1H), 8.78 (d, J=1.7 Hz, 1H), 8.32 (dd, J=7.5, 0.8 Hz, 1H), 8.17 (dd, J=8.5, 0.7 Hz, 1H), 7.98 (dd, J=8.5, 7.6 Hz, 1H), 4.21 (s, 3H), 2.58 (s, 3H), 2.40 (s, 3H); LCMS (M+H)=322; HPLC RT=1.78 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: Methyl 5-benzyl-3-(3,5-dimethylisoxazol-4-yl)-5H-pyrido[3,2-b]indole-9-carboxylate Following a procedure analogous to that described in Step 1 of Example 46, methyl 3-(3,5-dimethylisoxazol-4-yl)-5H-pyrido[3,2-b]indole-9-carboxylate (4 mg, 0.012 mmol) was converted to the title compound (4 mg, 76%). $^1$H NMR (500 MHz, CDCl$_3$) δ 8.61 (d, J=1.9 Hz, 1H), 7.75 (dd, J=7.2, 1.1 Hz, 1H), 7.67-7.62 (m, 1H), 7.61-7.55 (m, 1H), 7.45 (d, J=1.9 Hz, 1H), 7.35-7.27 (m, 3H), 7.11 (dd, J=7.4, 2.1 Hz, 2H), 5.59 (s, 2H), 4.15 (s, 3H), 2.38 (s, 3H), 2.21 (s, 3H).

Step 5: 2-[5-Benzyl-3-(dimethyl-1,2-oxazol-4-yl)-5H-pyrido[3,2-b]indol-9-yl]propan-2-ol A 5 mL vial containing methyl 5-benzyl-3-(3,5-dimethylisoxazol-4-yl)-5H-pyrido[3,2-b]indole-9-carboxylate (4 mg, 9.5 μmol) in THF (0.2 mL) was cooled to −78° C. and MeLi (1.6M in Et$_2$O, 36 μL, 57 μmol) was added dropwise. The resulting reaction mixture was stirred at −78° C. for 30 min, then quenched with sat. NH$_4$Cl and extracted with EtOAc (2×). The organic layer was concentrated and purified using ISCO silica gel chromatography (12 g column, gradient from 50% to 100% EtOAc/CH$_2$Cl$_2$) and further purified using prep HPLC (Column: Phen Luna C18, 30×100 mm, 5 μm particles; Mobile Phase A: 5:95 acetonitrile:water with 0.1% TFA; Mobile Phase B: 95:5 acetonitrile:water with 0.1% TFA; Gradient: 10-100% B over 12 min, then a 2-min hold at 100% B; Flow: 40 mL/min). The fraction containing desired product was diluted with sat. NaHCO$_3$ solution and concentrated. The residue was rediluted in sat. NaHCO$_3$ solution and extracted with CHCl$_3$ (3×). The organic layer was dried over MgSO$_4$, filtered and concentrated to give the title compound (2 mg, 43%). $^1$H NMR (500 MHz, CDCl$_3$) δ 8.81 (br s, 1H), 8.42 (d, J=1.9 Hz, 1H), 7.58-7.52 (m, 1H), 7.48 (d, J=1.7 Hz, 1H), 7.42 (d, J=7.8 Hz, 1H), 7.36-7.28 (m, 4H), 7.18-7.12 (m, 2H), 5.57 (s, 2H), 2.39 (s, 3H), 2.23 (s, 3H), 1.85 (s, 6H); LCMS (M+H)=412.2; HPLC RT=2.73 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 54 & 55

2-[3-(Dimethyl-1H-1,2,3-triazol-5-yl)-5-[oxan-4-yl(phenyl)methyl]-5H-pyrido[3,2-b]indol-7-yl]propan-2-ol Enantiomer A, Example 54

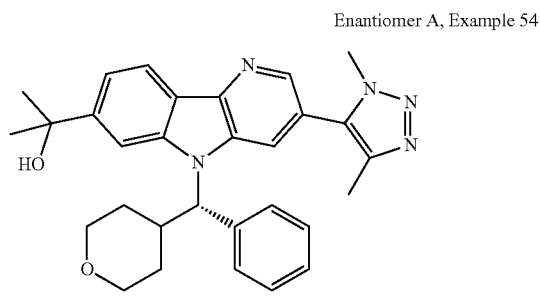 [SMILES: Cc1nnn(C)c1-c1cnc2c3ccc(C(C)(C)O)cc3n([C@H](c3ccccc3)C3CCOCC3)c2c1]

Enantiomer B, Example 55

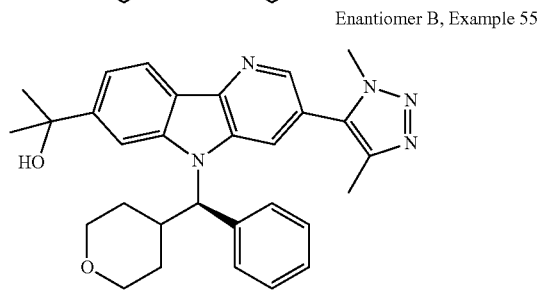

Step 1: 2-Chloro-5-(1,4-dimethyl-1H-1,2,3-triazol-5-yl)pyridin-3-amine

To a 100 mL round bottom flask containing 5-bromo-2-chloropyridin-3-amine (2.90 g, 14.0 mmol), 1,4-dimethyl-5-(tributylstannyl)-1H-1,2,3-triazole (2.70 g, 6.99 mmol) [Seefeld, M. A. et al. PCT Int. Appl., 2008, WO2008098104] and Pd(PPh$_3$)$_4$ (0.61 g, 0.52 mmol) in DMF (20 mL) was added cuprous iodide (0.20 g, 1.05 mmol) and Et$_3$N (1.9 mL, 14.0 mmol). The reaction mixture was purged with N$_2$ for 3 min and then heated at 100° C. for 1 h. After cooling to room temperature, the mixture was diluted with 10% LiCl solution and extracted with EtOAc (2×). The combined organics were washed with sat. NaCl, dried over MgSO$_4$, filtered and concentrated. CH$_2$Cl$_2$ was added, and the resulting precipitate was collected by filtration. The mother liquor was concentrated and purified using ISCO silica gel chromatography (40 g column, gradient from 0% to 100% EtOAc/CH$_2$Cl$_2$). The resulting solid was combined with the precipitate and triturated with cold EtOAc to give the title compound (740 mg, 47%) as a light tan solid. LCMS (M+H)=224.1; HPLC RT=1.03 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 3-((2-chloro-5-(1,4-dimethyl-1H-1,2,3-triazol-5-yl)pyridin-3-yl)amino)benzoate Following a procedure analogous to that described in Step 2 of Example 1, 2-chloro-5-(1,4-dimethyl-1H-1,2,3-triazol-5-yl)pyridin-3-amine (740 mg, 3.31 mmol) was converted to the title compound (644 mg, 54%). $^1$H NMR (400 MHz, CDCl$_3$) δ 7.94 (t, J=1.9 Hz, 1H), 7.88 (d, J=2.1 Hz, 1H), 7.83 (dt, J=7.8, 1.3 Hz, 1H), 7.49 (t, J=7.9 Hz, 1H), 7.40 (d, J=2.1 Hz, 1H), 7.36 (ddd, J=8.0, 2.3, 0.9 Hz, 1H), 6.38 (s, 1H), 3.99 (s, 3H), 3.93 (s, 3H), 2.34 (s, 3H); LCMS (M+H)=358.2; HPLC RT=2.34 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: Methyl 3-(1,4-dimethyl-1H-1,2,3-triazol-5-yl)-5H-pyrido[3,2-b]indole-7-carboxylate Following a procedure analogous to that described in Step 3 of Example 1, methyl 3-((2-chloro-5-(1,4-dimethyl-1H-1,2,3-triazol-5-yl)pyridin-3-yl)amino)benzoate (2.82 g, 7.88 mmol) was converted to the title compound (1.58 g, 62%). $^1$H NMR (500 MHz, DMSO-d$_6$) δ 11.93 (s, 1H), 8.62 (d, J=1.8 Hz, 1H), 8.36 (dd, J=8.2, 0.6 Hz, 1H), 8.29-8.22 (m, 1H), 8.16 (d, J=1.8 Hz, 1H), 7.91 (dd, J=8.2, 1.4 Hz, 1H), 4.02 (s, 3H), 3.94 (s, 3H), 2.31 (s, 3H); LCMS (M+H)=322.3; HPLC RT=1.98 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Alternate Synthesis of Methyl 3-(1,4-dimethyl-1H-1,2,3-triazol-5-yl)-5H-pyrido[3,2-b]indole-7-carboxylate A mixture of methyl 3-bromo-5H-pyrido[3,2-b]indole-7-carboxylate (Step 2 of Example 40, 3.000 g, 9.83 mmol), 1,4-dimethyl-5-(tributylstannyl)-1H-1,2,3-triazole (4.18 g, 10.82 mmol), copper (I) iodide (0.281 g, 1.475 mmol), Pd(Ph₃P)₄ (0.738 g, 0.639 mmol) and triethylamine (2.74 mL, 19.66 mmol) in DMF (25 mL) was purged under a nitrogen stream and then heated in a heating block at 95° C. for 2 hours. After cooling to room temperature the reaction mixture was diluted with water and extracted into ethyl acetate. Washed with water, NH₄OH, brine and concentrated. The residue was triturated with 100 mL CHCl₃, filtered off the solid and rinsed with CHCl₃ to give. 1.6 g of product. The filtrate was loaded unto the ISCO column (330 g column, A: DCM; B: 10% MeOH/DCM, 0 to 100% gradient) and chromatographed to give an additional 0.7 g. of methyl 3-(1,4-dimethyl-1H-1,2,3-triazol-5-yl)-5H-pyrido [3,2-b]indole-7-carboxylate (2.30 g total, 7.16 mmol, 72.8% yield).

Step 4: Methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate Following a procedure analogous to that described in Step 4 of Example 1, methyl 3-(1,4-dimethyl-1H-1,2,3-triazol-5-yl)-5H-pyrido[3,2-b]indole-7-carboxylate (80 mg, 0.25 mmol) was converted to the title compound (65 mg, 53%) after purification by prep HPLC (Column: Phen Luna C18, 30×100 mm, 5 μm particles; Mobile Phase A: 5:95 acetonitrile:water with 0.1% TFA; Mobile Phase B: 95:5 acetonitrile:water with 0.1% TFA; Gradient: 10-100% B over 14 min, then a 2-min hold at 100% B; Flow: 40 mL/min). ¹H NMR (400 MHz, CDCl₃) δ 8.51 (d, J=1.8 Hz, 1H), 8.50 (s, 1H), 8.47 (d, J=8.1 Hz, 1H), 8.10 (dd, J=8.1, 1.1 Hz, 1H), 7.63 (d, J=1.8 Hz, 1H), 7.46 (d, J=7.3 Hz, 2H), 7.40-7.30 (m, 3H), 5.62 (d, J=10.6 Hz, 1H), 4.11-4.03 (m, 4H), 3.92-3.83 (m, 4H), 3.56 (td, J=11.9, 1.8 Hz, 1H), 3.35 (td, J=11.9, 1.9 Hz, 1H), 3.18-3.05 (m, 1H), 2.30 (s, 3H), 2.04 (d, J=13.0 Hz, 1H), 1.71-1.58 (m, 1H), 1.50-1.37 (m, 1H), 1.09 (d, J=12.8 Hz, 1H); LCMS (M+H)=496.3; HPLC RT=2.93 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 5: 2-[3-(Dimethyl-1H-1,2,3-triazol-5-yl)-5-[oxan-4-yl(phenyl)methyl]-5H-pyrido[3,2-b]indol-7-yl]propan-2-ol Following a procedure analogous to that described in Step 5 of Example 1, methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate (65 mg, 0.13 mmol) was converted to racemic 2-[3-(dimethyl-1H-1,2,3-triazol-5-yl)-5-[oxan-4-yl(phenyl)methyl]-5H-pyrido[3,2-b]indol-7-yl]propan-2-ol, which was separated by chiral prep SFC (Column: Chiralpak IB 25×2 cm, 5 μm; Mobile Phase: 70/30 CO₂/MeOH; Flow: 50 mL/min); to give Enantiomer A (24 mg, 36%) and Enantiomer B (26 mg, 38%). Enantiomer A: ¹H NMR (500 MHz, CDCl₃) δ 8.44 (d, J=1.8 Hz, 1H), 8.36 (d, J=8.2 Hz, 1H), 7.98 (s, 1H), 7.56 (d, J=1.7 Hz, 1H), 7.47-7.41 (m, 3H), 7.37-7.32 (m, 2H), 7.31-7.28 (m, 1H), 5.59 (d, J=10.5 Hz, 1H), 4.06 (dd, J=11.8, 2.8 Hz, 1H), 3.90-3.84 (m, 4H), 3.55 (td, J=11.9, 2.0 Hz, 1H), 3.35 (td, J=11.9, 2.0 Hz, 1H), 3.15-3.04 (m, 1H), 2.30 (s, 3H), 2.04 (d, J=13.6 Hz, 1H), 1.92 (s, 1H), 1.75 (s, 6H), 1.69-1.58 (m, 1H), 1.47-1.38 (m, 1H), 1.12 (d, J=13.4 Hz, 1H); LCMS (M+H)=496.4; HPLC RT=2.46 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min). SFC RT=5.50 min (Column: Chiralpak IB 250×4.6 mm, 5 μm; Mobile Phase: 70/30 CO₂/MeOH; Flow: 2 mL/min); SFC RT=1.06 min (Column: Chiralcel OD-H 250×4.6 mm, 5 μm; Mobile Phase: 50/50 CO₂/(1:1 MeOH/CH3CN); Flow: 2 mL/min); $[\alpha]_D^{20}$=−117.23 (c=0.08, CHCl₃). Enantiomer B: ¹H NMR (500 MHz, CDCl₃) δ 8.44 (d, J=1.8 Hz, 1H), 8.36 (d, J=8.2 Hz, 1H), 7.98 (s, 1H), 7.56 (d, J=1.7 Hz, 1H), 7.47-7.41 (m, 3H), 7.37-7.32 (m, 2H), 7.31-7.28 (m, 1H), 5.59 (d, J=10.5 Hz, 1H), 4.06 (dd, J=11.8, 2.8 Hz, 1H), 3.90-3.84 (m, 4H), 3.55 (td, J=11.9, 2.0 Hz, 1H), 3.35 (td, J=11.9, 2.0 Hz, 1H), 3.15-3.04 (m, 1H), 2.30 (s, 3H), 2.04 (d, J=13.6 Hz, 1H), 1.92 (s, 1H), 1.75 (s, 6H), 1.69-1.58 (m, 1H), 1.47-1.38 (m, 1H), 1.12 (d, J=13.4 Hz, 1H); LCMS (M+H)=496.4; HPLC RT=2.46 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min). SFC RT=8.30 min (Column: Chiralpak IB 250×4.6 mm, 5 μm; Mobile Phase: 70/30 CO₂/MeOH; Flow: 2 mL/min); SFC RT=2.83 min (Column: Chiralcel OD-H 250×4.6 mm, 5 μm; Mobile Phase: 50/50 CO₂/(1:1 MeOH/CH3CN); Flow: 2 mL/min); $[\alpha]_D^{20}$=+88.78 (c=0.10, CHCl₃).

Alternate Synthesis of Examples 54

2-[3-(Dimethyl-1H-1,2,3-triazol-5-yl)-5-[oxan-4-yl(phenyl)methyl]-5H-pyrido[3,2-b]indol-7-yl]propan-2-ol

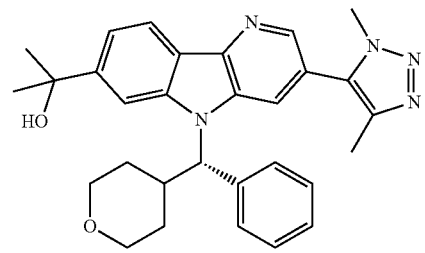

Enantiomer A, Example 54

Step 1: (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate The enantiomers of phenyl(tetrahydro-2H-pyran-4-yl) methanol (2.0 g, 10.4 mmol) [Orjales, A. et al. *J. Med. Chem.* 2003, 46, 5512-5532], were separated on preperative SFC. (Column: Chiralpak AD 5×25 cm, 5 μm; Mobile Phase: 74/26 CO₂/MeOH; Flow: 270 mL/min; Temperature 30° C.). The separated peaks were concentrated and dried under vacuum to give white solids. Enantiomer A: (S)-phenyl(tetrahydro-2H-pyran-4-yl)methanol: (0.91 g, 45.5%) SFC RT=2.32 min (Column: Chiralpac AD 250×4.6 mm, 5 μm; Mobile Phase: 70/30 CO₂/MeOH; Flow: 3 mL/min); Temperature 40° C. Enantiomer B: (R)-phenyl(tetrahydro-2H-pyran-4-yl)methanol. (0.92 g, 46%) SFC RT=3.09 min (Column: Chiralpac AD 250×4.6 mm, 5 μm; Mobile Phase: 70/30 CO₂/MeOH; Flow: 3 mL/min); Temperature 40° C.

Following a procedure analogous to that described in Step 4 of Example 1 except using toluene (120 mL) as the solvent, methyl 3-(1,4-dimethyl-1H-1,2,3-triazol-5-yl)-5H-pyrido[3,2-b]indole-7-carboxylate (4 g, 12.45 mmol) and (R)-phenyl(tetrahydro-2H-pyran-4-yl)methanol (Enantiomer B above, 5.86 g, 30.5 mmol) was converted to the title compound (5.0 g, 81%). HPLC RT=2.91 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2. (S)-2-[3-(Dimethyl-1H-1,2,3-triazol-5-yl)-5-[oxan-4-yl(phenyl)methyl]-5H-pyrido[3,2-b]indol-7-yl]propan-2-ol A 500 mL round bottom flask containing (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate (5.0 g, 10.09 mmol) in THF (150 mL) was cooled in an ice/MeOH bath. MeMgBr, (3M in Et$_2$O, 17.0 mL, 51.0 mmol) was added slowly over 4 min. The resulting solution was stirred for 2 h and then quenched carefully with sat. NH$_4$Cl. The reaction mixture was diluted with 10% LiCl solution extracted with EtOAc. The organic layer was dried over MgSO$_4$, filtered and concentrated. The crude material was purified using ISCO silica gel chromatography (120 g column, gradient from 0% to 6% MeOH/CH$_2$Cl$_2$). The product was collected and concentrated then dissolved in hot MeOH (35 mL). To the mixture was added 15 mL water and the mixture was cooled to room temperature. The resulting white precipitate was collected by filtration with 2:1 MeOH/water rinse then dried under vacuum to give the title compound (3.2 g, 62%). $^1$H NMR (500 MHz, CDCl$_3$) δ 8.40 (d, J=1.8 Hz, 1H), 8.33 (d, J=8.2 Hz, 1H), 7.93 (s, 1H), 7.53 (d, J=1.8 Hz, 1H), 7.46 (d, J=7.3 Hz, 2H), 7.42 (dd, J=8.2, 1.4 Hz, 1H), 7.37-7.31 (m, 2H), 7.30-7.28 (m, 1H), 5.56 (d, J=10.5 Hz, 1H), 4.06 (d, J=8.9 Hz, 1H), 3.89-3.83 (m, 1H), 3.55 (td, J=11.9, 2.1 Hz, 1H), 3.35 (td, J=11.9, 2.1 Hz, 1H), 3.10 (q, J=10.8 Hz, 1H), 2.39 (s, 3H), 2.23 (s, 3H), 2.03 (d, J=14.2 Hz, 1H), 1.89 (s, 1H), 1.74 (s, 6H), 1.68-1.59 (m, 1H), 1.46-1.36 (m, 1H), 1.12 (d, J=12.2 Hz, 1H); LCMS (M+H)=496.3; HPLC RT=2.44 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=2.01 min (Column: Chiralcel OD-H 250×4.6 mm, 5 μm; Mobile Phase: 60/40 CO$_2$/(1:1 MeOH/CH3CN); Flow: 2 mL/min). SFC RT=1.06 min (Column: Chiralcel OD-H 250×4.6 mm, 5 μm; Mobile Phase: 50/50 CO$_2$/(1:1 MeOH/CH3CN); Flow: 2 mL/min).

Examples 56-65

The compounds in Table 3 were prepared according to the procedures described for Example 54:

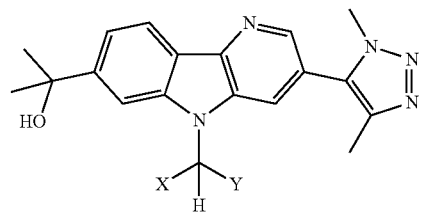

TABLE 3

| Example | X | Y | HPLC RT (min) | LCMS (M + H) | Optical Rotation [α]$_D^{20}$ | HPLC Method |
|---|---|---|---|---|---|---|
| 56 | F$_3$C~~~ | ~~~CF$_3$ | 2.67 | 528.4 | N/A | A |
| 57 Enantiomer A | F$_3$C~~~ | ~~~Ph | 4.14 | 508.4 | −42.34 (c = 0.14, CHCl$_3$) | B |
| 58 Enantiomer B | F$_3$C~~~ | ~~~Ph | 11.51 | 508.4 | +56.43 (c = 0.09, CHCl$_3$) | B |
| 59 Enantiomer A | oxan-4-yl | 4-F-C$_6$H$_4$ | 35.27 | 514.4 | −91.54 (c = 0.09, CHCl$_3$) | C |
| 60 Enantiomer B | oxan-4-yl | 4-F-C$_6$H$_4$ | 39.50 | 514.4 | +93.98 (c = 0.06, CHCl$_3$) | C |

TABLE 3-continued

| Example | X | Y | HPLC RT (min) | LCMS (M + H) | Optical Rotation $[\alpha]_D^{20}$ | HPLC Method |
|---|---|---|---|---|---|---|
| 61 | (butyl) | (butyl) | 2.58 | 420.4 | N/A | A |
| 62 Enantiomer A | (tetrahydropyran-4-yl) | (pyridin-2-yl) | 7.22 | 497.5 | N/A | B |
| 63 Enantiomer B | (tetrahydropyran-4-yl) | (pyridin-2-yl) | 9.68 | 497.5 | N/A | B |
| 64 Enantiomer A | (tetrahydropyran-4-yl) | (2-fluorophenyl) | 5.13 | 514.4 | −122.49 (c = 3.03, CHCl$_3$) | B |
| 65 Enantiomer B | (tetrahydropyran-4-yl) | (2-fluorophenyl) | 9.35 | 514.4 | +116.15 (c = 3.03, CHCl$_3$) | B |

HPLC Conditions for Table 3:
Method A:
Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min; Detection: UV at 220 nm.
Method B:
Column: Chiralcel OD-H 250×4.6 mm, 5 μm particles; Mobile Phase: 80/20 CO$_2$/MeOH; Flow: 2 mL/min; Detection: UV at 220 nm.
Method C:
Chiralpak IC 250×4.6 mm, 5 μm particles; Mobile Phase: 70/30 CO$_2$/MeOH; Flow: 2 mL/min; Detection: UV at 220 nm.

Examples 66 & 67

2-{5-[(4-Fluorophenyl)(oxan-4-yl)methyl]-3-(1-methyl-1H-1,2,3-triazol-5-yl)-5H-pyrido[3,2-b]indol-7-yl}propan-2-ol Enantiomer A, Example 66

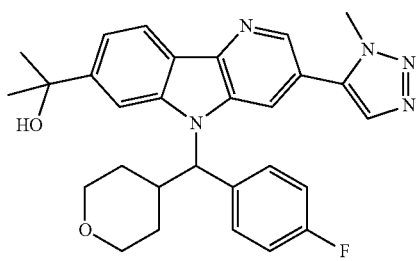

Enantiomer B, Example 67

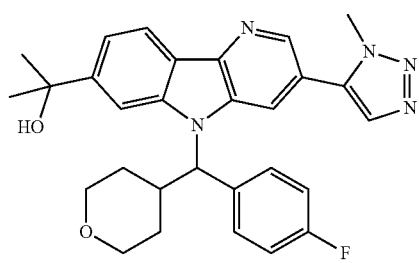

Step 1: Methyl 5-((4-fluorophenyl)(tetrahydro-2H-pyran-4-yl)methyl)-3-(1-methyl-1H-1,2,3-triazol-5-yl)-5H-pyrido[3,2-b]indole-7-carboxylate A mixture of 1-methyl-5-(tributylstannyl)-1H-1,2,3-triazole (244 mg, 0.66 mmol) [Allgeier, H. et al., PCT Int. Appl., 2006, WO2006108591], methyl 3-bromo-5-((4-fluorophenyl)(tetrahydro-2H-pyran-4-yl)methyl)-5H-pyrido[3,2-b]indole-7-carboxylate (Step 3 of Example 40, 163 mg, 0.33 mmol), copper (I) iodide (9 mg, 0.05 mmol), Pd(PPh$_3$)$_4$ (28 mg, 0.02 mmol) and triethylamine (0.091 mL, 0.65 mmol) in DMF (2.0 mL) was purged with N$_2$ (3×) and then warmed to 100° C. and stirred for 2 h. After cooling to room temperature, the reaction mixture was filtered through Celite® washing with EtOAc. The filtrate was washed with 10% LiCl solution and sat. NaCl, dried over Na$_2$SO$_4$, filtered and concentrated. The residue was purified using ISCO silica gel chromatography (24 g column, gradient from 0% to 100% EtOAc/hexanes) to give the title compound (64 mg, 39%). LCMS (M+H)=500.2.

Step 2: 2-{5-[(4-Fluorophenyl)(oxan-4-yl)methyl]-3-(1-methyl-1H-1,2,3-triazol-5-yl)-5H-pyrido[3,2-b]indol-7-yl}propan-2-ol Following a procedure analogous to that described in Step 5 of Example 1, methyl 5-((4-fluorophenyl)(tetrahydro-2H-pyran-4-yl)methyl)-3-(1-methyl-1H-1,2,3-triazol-5-yl)-5H-pyrido[3,2-b]indole-7-carboxylate (65 mg, 0.13 mmol) was converted to racemic 2-{5-[(4-fluorophenyl)(oxan-4-yl)methyl]-3-(1-methyl-1H-1,2,3-triazol-5-yl)-5H-pyrido[3,2-b]indol-7-yl}propan-2-ol, which was separated by chiral prep SFC to give Enantiomer A (20 mg, 30%) and Enantiomer B (20 mg, 30%). Enantiomer A: $^1$H NMR (400 MHz, DMSO-$d_6$) δ 8.59 (s, 1H), 8.56-8.47 (bs, 1H), 8.15 (d, J=8.4 Hz, 1H), 8.12-8.03 (m, 2H), 7.73 (dd, J=8.6, 5.5 Hz, 2H), 7.48 (d, J=8.4 Hz, 1H), 7.18 (t, J=8.8 Hz, 2H), 5.83 (d, J=11.2 Hz, 1H), 5.22 (s, 1H), 4.14 (s, 3H), 3.92 (d, J=9.7 Hz, 1H), 3.73 (d, J=8.8 Hz, 1H), 3.56-3.35 (m, 2H), 3.27 (d, J=13.6 Hz, 1H), 1.68 (m., 1H), 1.58 (m, 7H), 1.42-1.21 (m, 1H), 0.98 (d, J=12.8 Hz, 1H); LCMS (M+H)=500.3; HPLC RT=7.29 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=9.86 min (Column: Chiralcel OD-H 250×4.6 mm, 5 μm particles; Mobile Phase: 75/25 CO$_2$/MeOH; Flow: 2 mL/min); $[α]_D^{20}$=−99.55 (c=0.14, CHCl$_3$). Enantiomer B: $^1$H NMR (400 MHz, DMSO-$d_6$) δ 8.59 (s, 1H), 8.56-8.46 (bs, 1H), 8.15 (d, J=8.4 Hz, 1H), 8.03-8.11 (m, 2H), 7.73 (dd, J=8.6, 5.5 Hz, 2H), 7.48 (d, J=8.6 Hz, 1H), 7.18 (t, J=8.8 Hz, 2H), 5.83 (d, J=11.2 Hz, 1H), 5.22 (s, 1H), 4.14 (s, 3H), 4.01-3.84 (m, 1H), 3.81-3.66 (m, 1H), 3.49 (s, 2H), 3.30-3.18 (m, 1H), 1.82-1.65 (m, 1H), 1.58 (m, 7H, overlapping 2CH3 and 1CH), 1.40-1.21 (m, 1H), 1.10-0.89 (m, 1H); LCMS (M+H)=500.3; HPLC RT=7.28 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=12.09 min (Column: Chiralcel OD-H 250×4.6 mm, 5 μm particles; Mobile Phase: 75/25 CO$_2$/MeOH; Flow: 2 mL/min); $[α]_D^{20}$=+98.84 (c=0.14, CHCl$_3$).

Example 69

2-[5-Benzyl-3-(dimethyl-1H-1,2,3-triazol-5-yl)-5H-pyrido[3,2-b]indol-7-yl]propan-2-ol

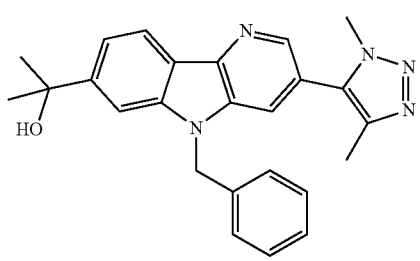 [SMILES: Cc1nnn(C)c1-c1cnc2c3ccc(C(C)(C)O)cc3n(Cc3ccccc3)c2c1]

Following procedures analogous to those described in Example 46, methyl 3-(1,4-dimethyl-1H-1,2,3-triazol-5-yl)-5H-pyrido[3,2-b]indole-7-carboxylate (Step 3 of Example 54, 58 mg, 0.18 mmol) was converted to the title compound (57 mg, 78% over 2 steps). $^1$H NMR (500 MHz, CDCl$_3$) δ 8.49 (d, J=1.8 Hz, 1H), 8.40 (d, J=8.2 Hz, 1H), 7.78 (d, J=0.9 Hz, 1H), 7.48 (dd, J=8.2, 1.5 Hz, 1H), 7.42 (d, J=1.8 Hz, 1H), 7.35-7.29 (m, 3H), 7.16 (dd, J=0.7, 1.8 Hz, 2H), 5.59 (s, 2H), 3.89 (s, 3H), 2.29 (s, 3H), 1.87 (s, 1H), 1.71 (s, 6H); LCMS (M+H)=412.4; HPLC RT=2.33 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 70 & 71

2-[3-(Dimethyl-1H-1,2,3-triazol-5-yl)-6-fluoro-5-[oxan-4-yl(phenyl)methyl]-5H-pyrido[3,2-b]indol-7-yl]propan-2-ol Enantiomer A, Example 70

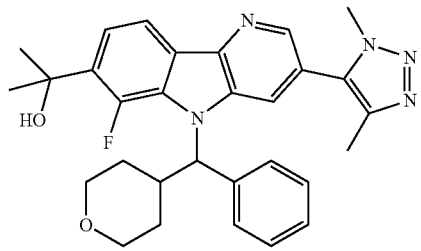

Enantiomer B, Example 71

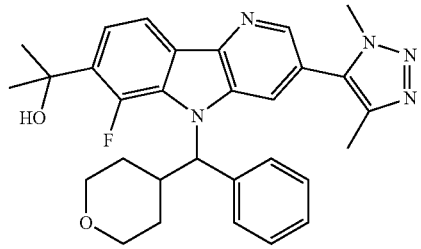

Step 1: Methyl 3-((2-chloro-5-(1,4-dimethyl-1H-1,2,3-triazol-5-yl)pyridin-3-yl)amino)-2-fluorobenzoate To a 70 mL pressure vial containing 2-chloro-5-(1,4-dimethyl-1H-1,2,3-triazol-5-yl)pyridin-3-amine (Step 1 of Example 54, 500 mg, 2.24 mmol), methyl 3-bromo-2-fluorobenzoate (Oakwood, 781 mg, 3.35 mmol) and Cs$_2$CO$_3$ (728 mg, 2.24 mmol) in dioxane (10 mL) was added 1,1'-bis(diphenylphosphino)ferrocene (62.0 mg, 0.11 mmol), Pd(OAc)$_2$ (85 mg, 0.38 mmol) and Xantphos (65 mg, 0.11 mmol). N$_2$ was bubbled through the reaction mixture for 2 min. The vial was sealed and heated to 100° C. for 24 h. BrettPhos precatalyst (100 mg, 0.12 mmol) and additional methyl 3-bromo-2-fluorobenzoate (781 mg, 3.35 mmol) were added. N$_2$ was bubbled through the reaction mixture for 2 min, and then heating was continued at 110° C. for 24 h. Additional BrettPhos precatalyst (100 mg, 012 mmol) was added and stirring was continued at 120° C. for 5 h. BrettPhos precatalyst (100 mg, 0.12 mmol) was again added and the reaction mixture was heated at 120° C. for 5 h. After cooling to room temperature, the mixture was diluted with CHCl₃ and filtered through Celite® rinsing with CHCl₃. The filtrate was concentrated and purified using ISCO silica gel chromatography (40 g column, gradient from 0% to 100% EtOAc/CH₂Cl₂) to give the title compound (140 mg, 17%) as a white solid. ¹H NMR (400 MHz, CDCl₃) δ 7.90 (d, J=2.1 Hz, 1H), 7.74 (ddd, J=8.0, 6.5, 1.7 Hz, 1H), 7.52-7.44 (m, 1H), 7.24 (d, J=0.9 Hz, 1H), 7.17 (t, J=2.0 Hz, 1H), 6.34 (s, 1H), 3.97 (d, J=0.7 Hz, 6H), 2.32 (s, 3H); LCMS (M+H)=376.3; HPLC RT=2.23 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-[3-(Dimethyl-1H-1,2,3-triazol-5-yl)-6-fluoro-5-[oxan-4-yl)phenyl)methyl]-5H-pyrido[3,2-b]indol-7-yl]propan-2-ol Following procedures analogous to those described in Steps 3, 4 and 5 of Example 1, methyl 3-((2-chloro-5-(1,4-dimethyl-1H-1,2,3-triazol-5-yl)pyridin-3-yl)amino)-2-fluorobenzoate (139 mg, 0.37 mmol) was converted to racemic 2-[3-(dimethyl-1H-1,2,3-triazol-5-yl)-6-fluoro-5-[oxan-4-yl(phenyl)methyl]-5H-pyrido[3,2-b]indol-7-yl]propan-2-ol, which was separated by chiral prep SFC to give Enantiomer A (28 mg, 15% over 3 steps) and Enantiomer B (27 mg, 14% over 3 steps). Enantiomer A: ¹H NMR (500 MHz, CDCl₃) δ 8.44 (d, J=1.7 Hz, 1H), 8.15 (d, J=8.2 Hz, 1H), 7.63 (dd, J=8.2, 6.7 Hz, 1H), 7.54-7.47 (m, 3H), 7.40-7.34 (m, 2H), 7.31 (d, J=7.3 Hz, 1H), 6.15 (br. s., 1H), 4.06 (dd, J=11.6, 2.3 Hz, 1H), 3.89 (dd, J=11.5, 2.1 Hz, 1H), 3.81 (s, 3H), 3.56 (td, J=11.9, 2.1 Hz, 1H), 3.39-3.28 (m, 1H), 3.03 (d, J=7.0 Hz, 1H), 2.26 (s, 3H), 2.23 (d, J=2.4 Hz, 1H), 2.11-2.03 (m, 1H), 1.85 (d, J=2.7 Hz, 6H), 1.68-1.60 (m, 1H), 1.53-1.47 (m, 1H), 1.02 (d, J=13.3 Hz, 1H); LCMS (M+H)=514.4; HPLC RT=2.84 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=9.50 min (Column: Chiralcel OD-H 250×4.6 mm, 5 μm; Mobile Phase: 75/25 CO₂/MeOH; Flow: 2 mL/min); $[\alpha]_D^{20}$=−142.33 (c=0.08, CHCl₃). Enantiomer B: ¹H NMR (500 MHz, CDCl₃) δ 8.44 (d, J=1.7 Hz, 1H), 8.15 (d, J=8.2 Hz, 1H), 7.63 (dd, J=8.2, 6.7 Hz, 1H), 7.54-7.47 (m, 3H), 7.40-7.34 (m, 2H), 7.31 (d, J=7.3 Hz, 1H), 6.15 (br. s., 1H), 4.06 (dd, J=11.6, 2.3 Hz, 1H), 3.89 (dd, J=11.5, 2.1 Hz, 1H), 3.81 (s, 3H), 3.56 (td, J=11.9, 2.1 Hz, 1H), 3.39-3.28 (m, 1H), 3.03 (d, J=7.0 Hz, 1H), 2.26 (s, 3H), 2.23 (d, J=2.4 Hz, 1H), 2.11-2.03 (m, 1H), 1.85 (d, J=2.7 Hz, 6H), 1.68-1.60 (m, 1H), 1.53-1.47 (m, 1H), 1.02 (d, J=13.3 Hz, 1H); LCMS (M+H)=514.4; HPLC RT=2.84 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.86 min (Column: Chiralcel OD-H 250×4.6 mm, 5 μm; Mobile Phase: 75/25 CO₂/MeOH; Flow: 2 mL/min); $[\alpha]_D^{20}$=+92.61 (c=0.10, CHCl₃).

Examples 72-77

The compounds in Table 4 were prepared according to the procedures described for Example 70:

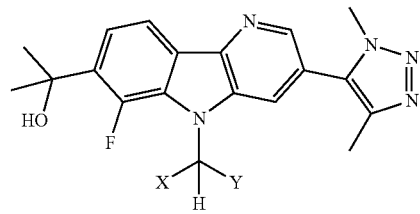

TABLE 4

| Example | X | Y | HPLC RT (min) | LCMS (M + H) | Optical Rotation $[\alpha]_D^{20}$ | HPLC Method |
|---|---|---|---|---|---|---|
| 72 Enantiomer A | tetrahydropyran-4-yl | 4-fluorophenyl | 11.65 | 532.4 | +89.59 (c = 0.08, CHCl₃) | A |
| 73 Enantiomer B | tetrahydropyran-4-yl | 4-fluorophenyl | 13.56 | 532.4 | N/A | A |
| 74 | CF₃CH₂CH₂− | −CH₂CH₂CF₃ | 2.93 | 546.4 | N/A | B |
| 75 | propyl | propyl | 3.12 | 438.5 | N/A | B |

TABLE 4-continued

| Example | X | Y | HPLC RT (min) | LCMS (M + H) | Optical Rotation $[\alpha]_D^{20}$ | HPLC Method |
|---|---|---|---|---|---|---|
| 76 Enantiomer A | tetrahydropyran-4-yl | 2-fluorophenyl | 5.86 | 532.4 | −145.77 (c = 1.45, CHCl$_3$) | C |
| 77 Enantiomer B | tetrahydropyran-4-yl | 2-fluorophenyl | 7.12 | 532.4 | +147.40 (c = 2.02, CHCl$_3$) | C |

HPLC Conditions for Table 4:
Method A:
Column: Phenomenex Lux Cellulose 2, 250×4.6 mm, 5 μm particles; Mobile Phase: 75/25 CO$_2$/MeOH; Flow: 2 mL/min; Detection UV at 220 nm.
Method B:
Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min; Detection: UV at 220 nm.
Method C:
Column: Chiralcel OD-H 250×4.6 mm, 5 μm particles; Mobile Phase: 80/20 CO$_2$/MeOH; Flow: 2 mL/min; Detection UV at 220 nm.

Example 78 & 79

2-[3-(Dimethyl-1H-1,2,3-triazol-5-yl)-8-fluoro-5-[(4-fluorophenyl)(oxan-4-yl)methyl]-5H-pyrido[3,2-b]indol-7-yl]propan-2-ol

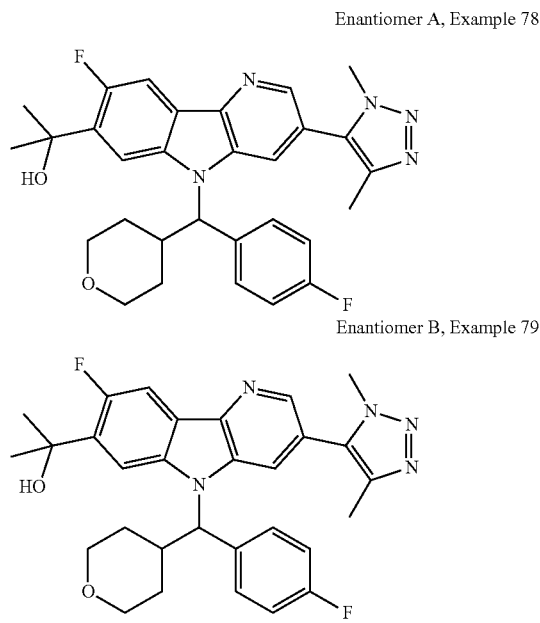

Enantiomer A, Example 78

Enantiomer B, Example 79

Step 1: Methyl 4-(5-bromo-3-nitropyridin-2-yl)-2-fluorobenzoate

Following a procedure analogous to that described for Step 1 of Example 40, 2,5-dibromo-3-nitropyridine (2.28 g, 8.08 mmol) and (3-fluoro-4-(methoxycarbonyl)phenyl)boronic acid (1.60 g, 8.08 mmol) were converted the title compound (1.8 g, 63%). $^1$H NMR (400 MHz, CDCl$_3$) δ 8.97 (d, J=2.1 Hz, 1H), 8.39 (d, J=2.0 Hz, 1H), 8.05 (t, J=7.7 Hz, 1H), 7.73-7.71 (m, 1H), 7.40 (dd, J=10.9, 1.7 Hz, 1H), 7.35 (dd, J=8.1, 1.7 Hz, 1H), 3.99 (s, 3H); LCMS (M+H)=355.2; HPLC RT=2.58 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 3-bromo-6-fluoro-5H-pyrido[3,2-b]indole-7-carboxylate

Methyl 3-bromo-8-fluoro-5H-pyrido[3,2-b]indole-7-carboxylate

Following a procedure analogous to that described for Step 2 of Example 40, conversion of methyl 4-(5-bromo-3-nitropyridin-2-yl)-2-fluorobenzoate (1.80 g, 5.07 mmol) generated a mixture of the title compounds, which were separated using ISCO silica gel chromatography (120 g column, gradient from 50% to 70% EtOAc/hexanes) to give methyl 3-bromo-6-fluoro-5H-pyrido[3,2-b]indole-7-carboxylate (200 mg, 12%) and methyl 3-bromo-8-fluoro-5H-pyrido[3,2-b]indole-7-carboxylate (240 mg, 15%) as white solids. Methyl 3-bromo-6-fluoro-5H-pyrido[3,2-b]indole-7-carboxylate: $^1$H NMR (400 MHz, DMSO-d$_6$) δ 12.43 (br. s., 1H), 8.64 (d, J=2.0 Hz, 1H), 8.18 (d, J=2.0 Hz, 1H), 8.06 (d, J=8.1 Hz, 1H), 7.71 (dd, J=8.3, 6.1 Hz, 1H), 3.92 (s, 3H); LCMS (M+H)=323.1; HPLC RT=2.62 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min). Methyl 3-bromo-8-fluoro-5H-pyrido[3,2-b]indole-7-carboxylate: $^1$H NMR (400 MHz, DMSO-d$_6$) δ 11.81 (s, 1H), 8.59 (d, J=2.0 Hz, 1H), 8.29 (d, J=2.0 Hz, 1H), 8.11 (d, J=5.9 Hz, 1H), 8.02 (d, J=10.6 Hz, 1H), 3.91 (s, 3H); LCMS (M+H)=323.1; HPLC RT=2.56 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: Methyl 3-(1,4-dimethyl-1H-1,2,3-triazol-5-yl)-8-fluoro-5H-pyrido[3,2-b]indole-7-carboxylate Following a procedure analogous to that described for Step 1 of Example 66, methyl 3-bromo-8-fluoro-5H-pyrido[3,2-b]indole-7-carboxylate (240 mg, 0.74 mmol) and 1,4-dimethyl-5-(tributylstannyl)-1H-1,2,3-triazole (344 mg, 0.89 mmol) [Seefeld, M. A. et al. PCT Int. Appl., 2008, WO2008098104] were converted to the title compound (115 mg, 46%). $^1$H NMR (400 MHz, CD$_3$OD) δ 8.58 (d, J=1.7 Hz, 1H), 8.19 (d, J=5.5 Hz, 1H), 8.12 (d, J=10.8 Hz, 1H), 8.09 (d, J=1.8 Hz, 1H), 4.08 (s, 3H), 4.01 (s, 3H), 2.38 (s, 3H); LCMS (M+H)=340.2; HPLC RT=2.13 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 2-[3-(Dimethyl-1H-1,2,3-triazol-5-yl)-8-fluoro-5-[(4-fluorophenyl)(oxan-4-yl)methyl]-5H-pyrido[3,2-b]indol-7-yl]propan-2-ol Following procedures analogous to those described in Steps 4 and 5 of Example 1, methyl 3-(1,4-dimethyl-1H-1,2,3-triazol-5-yl)-8-fluoro-5H-pyrido[3,2-b]indole-7-carboxylate (115 mg, 0.34 mmol) and (4-fluorophenyl)(tetrahydro-2H-pyran-4-yl)methanol (Step 1 of Example 25, 143 mg, 0.68 mmol) were converted to racemic 2-[3-(dimethyl-1H-1,2,3-triazol-5-yl)-8-fluoro-5-[(4-fluorophenyl)(oxan-4-yl)methyl]-5H-pyrido[3,2-b]indol-7-yl]propan-2-ol, which was separated by chiral prep SFC to give Enantiomer A (10 mg, 11%) and Enantiomer B (10 mg, 11%). Enantiomer A: $^1$H NMR (400 MHz, CDCl$_3$) δ 8.46 (d, J=1.7 Hz, 1H), 8.03 (d, J=11.4 Hz, 1H), 7.99 (d, J=6.1 Hz, 1H), 7.58 (d, J=1.6 Hz, 1H), 7.43 (dd, J=8.7, 5.1 Hz, 2H), 7.10-7.02 (m, 2H), 5.53 (d, J=10.5 Hz, 1H), 4.07 (dd, J=11.7, 2.7 Hz, 1H), 3.94 (s, 3H), 3.89 (dd, J=11.7, 2.8 Hz, 1H), 3.60-3.49 (m, 1H), 3.36 (td, J=11.9, 1.9 Hz, 1H), 3.12-2.98 (m, 1H), 2.32 (s, 3H), 2.26 (d, J=2.0 Hz, 1H), 1.99 (d, J=13.4 Hz, 1H), 1.81 (s, 6H), 1.69-1.55 (m, 1H), 1.48-1.35 (m, 1H), 1.11 (d, J=12.8 Hz, 1H); LCMS (M+H)=532.4; HPLC RT=10.52 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=6.71 min (Column: Chiralcel OD-H 250×4.6 mm, 5 μm particles; Mobile Phase: 75/25 CO$_2$/MeOH; Flow: 2 mL/min). $[α]_D^{20}$=−100.86 (c=0.68, CHCl$_3$). Enantiomer B: $^1$H NMR (400 MHz, CDCl$_3$) δ 8.46 (d, J=1.7 Hz, 1H), 8.03 (d, J=11.4 Hz, 1H), 7.99 (d, J=6.1 Hz, 1H), 7.58 (d, J=1.6 Hz, 1H), 7.43 (dd, J=8.7, 5.1 Hz, 2H), 7.11-7.02 (m, 2H), 5.53 (d, J=10.5 Hz, 1H), 4.07 (dd, J=11.7, 2.8 Hz, 1H), 3.94 (s, 3H), 3.89 (dd, J=11.9, 2.8 Hz, 1H), 3.60-3.51 (m, 1H), 3.36 (td, J=11.9, 1.9 Hz, 1H), 3.12-2.99 (m, 1H), 2.32 (s, 3H), 2.28 (d, J=2.1 Hz, 1H), 1.99 (d, J=13.7 Hz, 1H), 1.81 (s, 6H), 1.68-1.55 (m, 1H), 1.49-1.36 (m, 1H), 1.11 (d, J=12.6 Hz, 1H); LCMS (M+H)=499.3; HPLC RT=10.54 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm); SFC RT=8.09 min (Column: Chiralcel OD-H 250×4.6 mm, 5 μm particles; Mobile Phase: 75/25 CO$_2$/MeOH; Flow: 2 mL/min). $[α]_D^{20}$=91.50 (c=1.58, CHCl$_3$).

Example 80 & 81

2-[3-(Dimethyl-1,2-oxazol-4-yl)-6-fluoro-5-[(4-fluorophenyl)(oxan-4-yl)methyl]-5H-pyrido[3,2-b]indol-7-yl]propan-2-ol Enantiomer A, Example 80

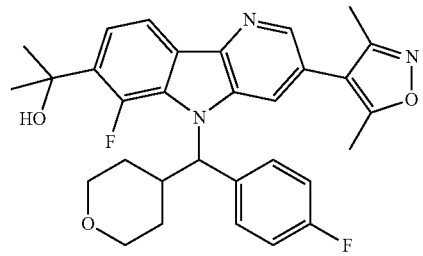

Enantiomer B, Example 81

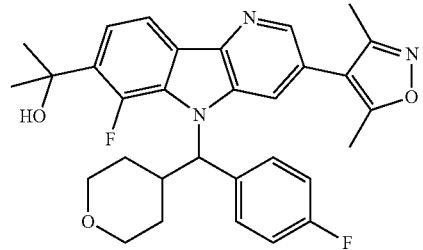

Racemic 2-[3-(dimethyl-1,2-oxazol-4-yl)-6-fluoro-5-[(4-fluorophenyl)(oxan-4-yl)methyl]-5H-pyrido[3,2-b]indol-7-yl]propan-2-ol, was prepared following procedures analogous to those described for Example 70, substituting 2-chloro-5-(3,5-dimethylisoxazol-4-yl)pyridin-3-amine (Step 1 of Example 1) for 2-chloro-5-(1,4-dimethyl-1H-1,2,3-triazol-5-yl)pyridin-3-amine in Step 1. Separation by chiral prep SFC gave Enantiomers A and B. Enantiomer A: $^1$H NMR (400 MHz, DMSO-d$_6$) δ 8.47 (br s, 1H), 7.97 (d, J=8.1 Hz, 1H), 7.53-7.81 (m, 3H), 7.12-7.23 (m, 3H), 5.94 (d, J=11.0 Hz, 1H), 3.88 (d, J=11.9 Hz, 1H), 3.75 (dd, J=10.5, 3.2 Hz, 1H), 3.44-3.53 (m, 1H), 3.26 (dd, J=11.8, 10.0 Hz, 2H), 2.42 (br s, 3H), 2.24 (br s, 3H), 1.78 (d, J=12.1 Hz, 1H), 1.67 (br s, 6H), 1.25-1.40 (m, 1H), 0.98-1.09 (m, 1H); LCMS (M+H)=532.4; HPLC RT=9.36 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). SFC RT=15.16 min (Column: Phenomenex Lux Cellulose 4, 250×4.6 mm, 5 μm particles; Mobile Phase: 75/25 CO$_2$/MeOH; Flow: 2 mL/min). Enantiomer B: $^1$H NMR (400

MHz, DMSO-d$_6$) δ 8.47 (br s, 1H), 7.97 (d, J=8.1 Hz, 1H), 7.54-7.77 (m, 3H), 7.17 (t, J=7.7 Hz, 2H), 5.94 (d, J=10.6 Hz, 1H), 3.88 (d, J=9.2 Hz, 1H), 3.72-3.79 (m, 1H), 3.49 (dd, J=11.6, 10.0 Hz, 1H), 3.21-3.31 (m, 1H), 2.42 (br s, 3H), 2.24 (br s, 3H), 1.78 (d, J=12.3 Hz, 1H), 1.67 (br s, 6H), 1.30 (d, J=9.7 Hz, 1H), 1.03 (d, J=12.5 Hz, 1H); LCMS (M+H)=532.4; HPLC RT=9.36 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min); SFC RT=18.88 min (Column: Phenomenex Lux Cellulose 4, 250×4.6 mm, 5 μm particles; Mobile Phase: 75/25 CO$_2$/MeOH; Flow: 2 mL/min).

Examples 82-87

The compounds in Table 5 were prepared according to the procedure described for Example 80:

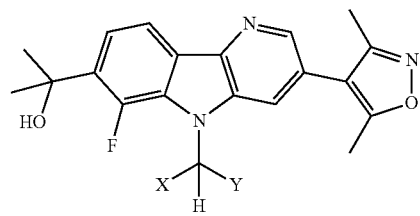

TABLE 5

| Example | X | Y | HPLC RT (min) | LCMS (M + H) | Optical Rotation [α]$_D^{20}$ | HPLC Method |
|---|---|---|---|---|---|---|
| 82 | propyl | propyl | 10.18 | 438.3 | N/A | A |
| 83 | CH$_2$CH$_2$CF$_3$ | CH$_2$CH$_2$CF$_3$ | 10.16 | 546.3 | N/A | A |
| 84 Enantiomer A | CH$_2$CH$_2$CF$_3$ | 2-(CF$_3$)phenyl | 3.70 | 594.4 | −74.05 (c = 0.14, CHCl$_3$) | B |
| 85 Enantiomer B | CH$_2$CH$_2$CF$_3$ | 2-(CF$_3$)phenyl | 4.26 | 594.4 | +72.70 (c = 0.20, CHCl$_3$) | B |
| 86 Enantiomer A | CH$_2$CH$_2$CF$_3$ | 2-Cl-phenyl | 6.30 | 560.4 | −181.90 (c = 0.08, CHCl$_3$) | B |
| 87 Enantiomer B | CH$_2$CH$_2$CF$_3$ | 2-Cl-phenyl | 7.53 | 560.4 | +165.57 (c = 0.10, CHCl$_3$) | B |

N/A: Not Applicable/Available

HPLC Conditions for Table 5:
Method A:
Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm.
Method B:
Column: Chiralpak IC, 250×4.6 mm, 5 μm particles; Mobile Phase: 70/30 CO₂/MeOH; Flow: 2 mL/min; Detection UV at 220 nm.

Example 88

(S)-2-(3-(4-(Hydroxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol

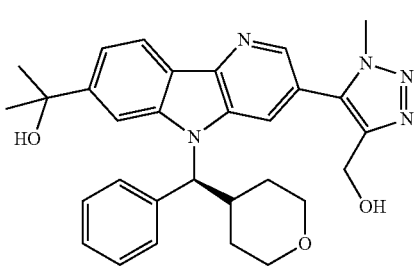 [SMILES: Cn1nnc(CO)c1-c1cnc2c3ccc(C(C)(C)O)cc3n([C@H](c3ccccc3)C3CCOCC3)c2c1]

Step 1: 4-(((tert-Butyldimethylsilyl)oxy)methyl)-5-iodo-1-((trimethylsilyl)methyl)-1H-1,2,3-triazole A mixture of tert-butyldimethyl(prop-2-yn-1-yloxy)silane (Aldrich, 0.85 mL, 4.19 mmol), (azidomethyl)trimethylsilane (TCI, 0.560 g, 4.61 mmol), copper (I) iodide (0.88 g, 4.61 mmol), 1-bromopyrrolidine-2,5-dione (Aldrich, 0.90 g, 5.03 mmol) and DIEA (0.73 mL, 4.19 mmol) in THF (35.0 mL) was stirred at room temperature overnight and then concentrated in vacuo. The residue was dissolved in EtOAc, washed with 10/90 conc. NH₄OH/sat. NH₄Cl solution, water and sat. NaCl and then dried over Na₂SO₄. Filtration and concentration provided a crude oil which was purified using ISCO silica gel chromatography (80 g column, gradient from 0% to 50% EtOAc/hexanes) to give the title compound (0.40 g, 22%) as an amber oil. LCMS (M+H)=426.2; $^1$H NMR (400 MHz, CDCl₃) δ 4.77 (s, 2H), 3.84 (s, 2H), 1.00-0.86 (m, 9H), 0.25-0.19 (m, 9H), 0.16-0.11 (m, 6H).

Step 2: (S)-Methyl 3-bromo-5-(phenyl(tetrahydro-2H-pyran-4-yl)methyl)-5H-pyrido[3,2-b]indole-7-carboxylate Following a procedure analogous to that described for Step 4 of Example 1, methyl 3-bromo-5H-pyrido[3,2-b]indole-7-carboxylate (Step 2 of Example 40, 1.00 g, 3.28 mmol) and (R)-phenyl(tetrahydro-2H-pyran-4-yl)methanol (1.26 g, 6.55 mmol) [obtained after chiral SFC of racemic phenyl(tetrahydro-2H-pyran-4-yl)methanol prepared according to Orjales, A. et al. *J. Med. Chem.* 2003, 46, 5512-5532] were converted to the title compound (2.06 g) as an impure mixture, which was carried on to the subsequent step without further purification. LCMS (M+H)=481.2.

Step 3: (S)-Methyl 5-(phenyl(tetrahydro-2H-pyran-4-yl)methyl)-3-(4,4,5,5-tetramethyl-1,3,2-dioxaborolan-2-yl)-5H-pyrido[3,2-b]indole-7-carboxylate Following a procedure analogous to that described for Step 4 of Example 40, (5)-methyl 3-bromo-5-(phenyl(tetrahydro-2H-pyran-4-yl)methyl)-5H-pyrido[3,2-b]indole-7-carboxylate (800 mg, 1.67 mmol) was converted to the title compound (365 mg, 42%). LCMS (M+H)=445.4 (boronic acid).

Step 4: (S)-Methyl 3-(4-(((tert-butyldimethylsilyl)oxy)methyl)-1-((trimethylsilyl)methyl)-1H-1,2,3-triazol-5-yl)-5-(phenyl(tetrahydro-2H-pyran-4-yl)methyl)-5H-pyrido[3,2-b]indole-7-carboxylate A vial containing a mixture of (5)-methyl 5-(phenyl(tetrahydro-2H-pyran-4-yl)methyl)-3-(4,4,5,5-tetramethyl-1,3,2-dioxaborolan-2-yl)-5H-pyrido[3,2-b]indole-7-carboxylate (360 mg, 0.68 mmol), 4-(((tert-butyldimethylsilyl)oxy)methyl)-5-iodo-1-((trimethylsilyl)methyl)-1H-1,2,3-triazole (393 mg, 0.92 mmol) PdCl₂dppf (25 mg, 0.034 mmol) and aq. potassium phosphate tribasic (3M, 0.68 mL, 2.05 mmol) in THF (5 mL) was vacuum purged with N₂ (3×). The resulting mixture was warmed to 80° C., stirred for 1 h and then cooled to room temperature. The mixture was diluted with EtOAc, transferred to a reparatory funnel, washed with water and sat. NaCl, and dried over Na₂SO₄. Filtration and concentration provided a crude oil which was purified using ISCO silica gel chromatography (40 g column, gradient from 0% to 100% EtOAc/hexanes) to give the title compound (277 mg, 58%). LCMS (M+H)=698.6.

Step 5: (S)-2-(3-(4-(((tert-Butyldimethylsilyl)oxy)methyl)-1-((trimethylsilyl)methyl)-1H-1,2,3-triazol-5-yl)-5-(phenyl(tetrahydro-2H-pyran-4-yl)methyl)-5H-pyrido[3,2-b]indol-7-yl)propan-2-ol Following a procedure analogous to that described for Step 5 of Example 1, (5)-methyl 3-(4-4(tert-butyldimethylsilyl)oxy)methyl)-1-((trimethylsilyl)methyl)-1H-1,2,3-triazol-5-yl)-5-(phenyl(tetrahydro-2H-pyran-4-yl)methyl)-5H-pyrido[3,2-b]indole-7-carboxylate (270 mg, 0.39 mmol) was converted to the title compound (212 mg, 79%). LCMS (M+H)=698.7.

Step 6: (S)-2-(3-(4-(Hydroxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol TBAF (1M in THF, 0.74 mL, 0.74 mmol) was added to a 0° C. solution of (S)-2-(3-(44(tert-butyldimethylsilyl)oxy)methyl)-1-((trimethylsilyl)methyl)-1H-1,2,3-triazol-5-yl)-5-(phenyl(tetrahydro-2H-pyran-4-yl)methyl)-5H-pyrido[3,2-b]indol-7-yl)propan-2-ol, (208 mg, 0.30 mmol) in THF (3.0 mL) and water (11 μL, 0.60 mmol). The resulting reaction mixture was stirred at 0° C. for 30 min. Additional TBAF (1M in THF, 0.74 mL, 0.74 mmol) was added and stirring was continued at room temperature for 1 h. TBAF (1M in THF, 0.74 mL, 0.74 mmol) was again added, and after stirring for 1 h the reaction mixture was quenched with sat. NH₄Cl and transferred to a separatory funnel. The aqueous layer was extracted with EtOAc (2×). The combined extracts were washed with sat. NH₄Cl, water and sat. NaCl, and then dried over Na₂SO₄. Filtration and concentration gave a residue which was purified using ISCO silica gel chromatography (24 g column, gradient from 0% to 10% MeOH/

CH₂Cl₂) to give the title compound (128 mg, 78%). ¹H NMR (400 MHz, DMSO-d₆) δ 8.64 (d, J=1.8 Hz, 1H), 8.54 (br s, 1H), 8.15 (d, J=8.4 Hz, 2H), 7.67 (d, J=7.3 Hz, 2H), 7.53-7.45 (m, 1H), 7.39-7.30 (m, 2H), 7.26 (d, J=7.3 Hz, 1H), 5.79 (d, J=11.2 Hz, 1H), 5.37 (t, J=5.2 Hz, 1H), 5.23 (s, 1H), 4.54 (t, J=4.6 Hz, 2H), 4.07 (s, 3H), 3.89 (br s, 1H), 3.74 (br s, 1H), 3.45 (d, J=13.0 Hz, 2H), 3.29 (br s, 1H), 1.67 (br s, 1H), 1.59 (m, 7H), 1.40-1.20 (m, 1H), 1.05 (br s, 1H); LCMS (M+H)=512.4; HPLC: RT=6.08 min (Column: Sunfire C18 3.5 µm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min).

Example 89

2-{3-[4-(Methoxymethyl)-1-methyl-1H-1,2,3-triazol-5-yl]-5-[(S)-oxan-4-yl(phenyl)methyl]-5H-pyrido[3,2-b]indol-7-yl}propan-2-ol

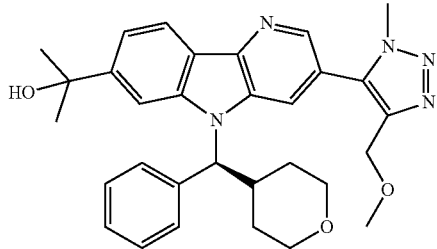 [SMILES: COCc1nnn(C)c1-c1cnc2c3ccc(C(C)(C)O)cc3n([C@H](c3ccccc3)C3CCOCC3)c2c1]

Step 1: Methyl 3-(4-(hydroxymethyl)-1-methyl-1H-1,2,3-triazol-5-yl)-5-(phenyl(tetrahydro-2H-pyran-4-yl)methyl)-5H-pyrido[3,2-b]indole-7-carboxylate Tetrabutylammonium fluoride (1M in THF, 16.1 mL, 16.1 mmol) was added to a room-temperature solution of (5)-methyl 3-(4-(((tert-butyldimethylsilyl)oxy)methyl)-1-((trimethylsilyl)methyl)-1H-1,2,3-triazol-5-yl)-5-(phenyl (tetrahydro-2H-pyran-4-yl)methyl)-5H-pyrido[3,2-b] indole-7-carboxylate, prepared in Example 88, Step 4 (750 mg, 1.07 mmol) in THF (10 mL). The resulting mixture was stirred for 15 min. The reaction was quenched with sat. aq. NH₄Cl solution, transferred to a separatory funnel, and extracted with ethyl acetate. The extracts were combined, washed with sat. aq. NH₄Cl solution, water and brine, dried over anhydrous sodium sulfate, filtered, and concentrated to provide a clear-yellow oil. The crude product was purified using ISCO silica gel chromatography (40 g column, 0% to 100% ethyl acetate/dichloromethane) to give (S)-methyl 3-(4-(hydroxymethyl)-1-methyl-1H-1,2,3-triazol-5-yl)-5-(phenyl(tetrahydro-2H-pyran-4-yl)methyl)-5H-pyrido[3,2-b]indole-7-carboxylate (500 mg, 0.977 mmol, 91%). Analytical Chiral SFC indicated 93% chiral purity. The compound was submitted to preparative chiral SFC separation to give (S)-methyl 3-(4-(hydroxymethyl)-1-methyl-1H-1,2,3-triazol-5-yl)-5-(phenyl(tetrahydro-2H-pyran-4-yl) methyl)-5H-pyrido[3,2-b]indole-7-carboxylate (400 mg, 0.782 mmol, 73% yield, >99.% chiral purity as determined by analytical chiral SFC. LCMS (M+H)=512.3.

Step 2: (S)-Methyl 3-(4-(methoxymethyl)-1-methyl-1H-1,2,3-triazol-5-yl)-5-(phenyl(tetrahydro-2H-pyran-4-yl)methyl)-5H-pyrido[3,2-b]indole-7-carboxylate Sodium hydride (60% in oil, 8.44 mg, 0.211 mmol) was added to a vial containing a 0° C. solution of (S)-methyl 3-(4-(hydroxymethyl)-1-methyl-1H-1,2,3-triazol-5-yl)-5-(phenyl(tetrahydro-2H-pyran-4-yl)methyl)-5H-pyrido[3,2-b]indole-7-carboxylate (54.0 mg, 0.106 mmol) in DMF (1 mL). Gas evolution occurred and the reaction was stirred for 10 min before adding iodomethane (0.0130 mL, 0.211 mmol). After 10 min, more sodium hydride (60% in oil, 8.44 mg, 0.211 mmol) and iodomethane (0.0130 mL, 0.211 mmol) were added. The reaction was quenched with sat. aq. NH₄Cl, diluted with ethyl acetate, transferred to a separatory funnel, washed with 10% LiCl solution, water and brine, dried over anhydrous sodium sulfate, filtered, and concentrated to provide crude (S)-methyl 3-(4-(methoxymethyl)-1-methyl-1H-1,2,3-triazol-5-yl)-5-(phenyl(tetrahydro-2H-pyran-4-yl)methyl)-5H-pyrido[3,2-b]indole-7-carboxylate (72.0 mg, 0.137 mmol, 130%) as a yellow oil. LCMS (M+H)=525.0. The product was used without further purification.

Step 3: (S)-2-(3-(4-(Methoxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol Methylmagnesium bromide (3M in Et₂O, 0.533 mL, 1.60 mmol) was added to a 0° C. solution of (S)-methyl 3-(4-(methoxymethyl)-1-methyl-1H-1,2,3-triazol-5-yl)-5-(phenyl(tetrahydro-2H-pyran-4-yl)methyl)-5H-pyrido[3,2-b]indole-7-carboxylate (56.0 mg, 0.107 mmol) in THF (1 mL). After 15 min, the reaction was quenched cautiously with sat. aq. ammonium chloride solution, transferred to a separatory funnel, diluted with ethyl acetate, washed with water and brine, dried over anhydrous sodium sulfate, filtered, and concentrated to provide a clear oil. The oil was dissolved in a minimum of dichloromethane and purified on an ISCO companion chromatography system (12 g silica cartridge, eluting with 0-10% methanol/dichloromethane, 30 mL/min) to provide impure (S)-2-(3-(4-(methoxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol (41.4 mg, 0.0790 mmol, 74%). LCMS (M+H)=526.4. HPLC: RT=3.02 min (Column: Sunfire C18 3.5 µm, 3.0×150 mm; Mobile Phase A: 10:90 methanol:water with 0.1% TFA; Mobile Phase B: 90:10 methanol:water with 0.1% TFA; Gradient 0-100% B over 5 min; Flow: 1.0 mL/min). The product was further purified by preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 17-57% B over 25 min, then a 5-min hold at 100% B; Flow: 20 mL/min. Fractions containing the desired product were combined and dried via centrifugal evaporation to provide (S)-2-(3-(4-(methoxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol (32.4 mg, 0.0620 mmol, 58%), and its estimated purity by LCMS analysis was 100%. Two analytical LC/MS injections were used to determine the final purity. HPLC (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220.) RT: 1.59 min. LCMS (M+H)=526.3 nm. HPLC (Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.11 mL/min; Detection: UV at 220 nm); HPLC RT: 1.39. LCMS (M+H)=526.3. $^1$H NMR (500 MHz, DMSO-d$_6$) δ 8.57 (s, 1H), 8.49 (br. s., 1H), 8.16 (m 2H), 7.66 (d, J=7.4 Hz, 2H), 7.49 (d, J=8.1 Hz, 1H), 7.38-7.30 (m, 2H), 7.29-7.20 (m, 1H), 5.80 (d, J=11.1 Hz, 1H), 4.47 (s, 2H), 4.07 (br. s., 3H), 3.91 (d, J=6.1 Hz, 1H), 3.75 (d, J=9.1 Hz, 1H), 3.32-3.21 (m, 4H), 2.51 (br. s., 2H), 1.70 (d, J=12.5 Hz, 1H), 1.59 (m 7H), 1.40-1.25 (m, 1H), 1.11-0.93 (m, 1H).

Examples 90 & 91

2-[3-(Dimethyl-1H-1,2,3-triazol-5-yl)-5-[(S)-oxan-4-yl)phenyl)($^2$H)methyl]-5H-pyrido[3,2-b]indol-7-yl] propan-2-ol Enantiomer A, Example 90

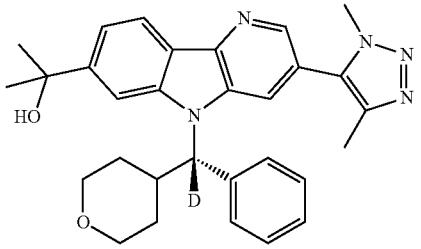

Enantiomer B, Example 91

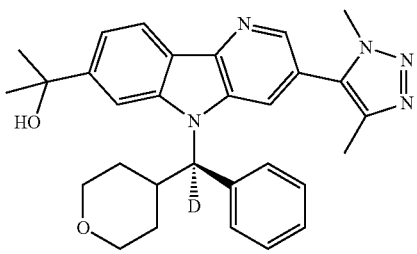

Step 1: N-Methoxy-N-methyloxane-4-carboxamide

In a 1 L RB flask, a solution of tetrahydro-2H-pyran-4-carboxylic acid (46.0 g, 353 mmol) in dichloromethane (250 mL) was treated with 1,1'-carbonyldiimidazole (63.0 g, 389 mmol) portion-wise—caution bubbling. After the addition was complete the mixture was stirred at room temperature for 2 h and then treated portion wise with N,O-dimethylhydroxylamine, HCl (37.9 g, 389 mmol) and then stirred overnight at room temperature. Washed with water and brine, dried over MgSO$_4$, filtered, and concentrated to give N-methoxy-N-methyloxane-4-carboxamide (55.0 g, 302 mmol, 85%) as light amber oil. $^1$H NMR (400 MHz, CDCl$_3$) δ 4.02 (ddd, J=11.4, 4.2, 2.1 Hz, 2H), 3.71 (s, 3H), 3.46 (td, J=11.8, 2.2 Hz, 2H), 3.19 (s, 3H), 1.93-1.80 (m, 2H), 1.69-1.62 (m, 2H).

Step 2: 4-Benzoyloxane

A solution of N-methoxy-N-methyloxane-4-carboxamide (5.00 g, 28.9 mmol) in Tetrahydrofuran (50 mL) in a RB flask was cooled to −78° C. in a dry-ice/acetone bath under nitrogen. The solution was treated via syringe with phenyl-lithium 1.8 M in dibutylether (24.1 mL, 43.3 mmol) slowly over 10 min. The resulting dark mixture was stirred in the bath for 2 h before it was poured into ice/sat. aq. ammonium chloride and extracted into ethyl acetate. The organics were washed with water and brine and concentrated. The light yellow oil was purified by silica gel column chromatography on an ISCO Companion (120 g silica gel column) and eluted with an EtOAc/hexane gradient (10-50%). The fractions containing product were collected, and the volatiles were removed to give 4-benzoyloxane (4.30 g, 22.6 mmol, 78%) as an almost colorless oil. LCMS: Waters Acquity SDS. Column: BEH C18 2.1×50 mm 1.7 u (1.6 min grad) 2-98% B. Flow Rate=0.8 mL/min. Solvent A: H$_2$O-0.1% TFA. Solvent B: Acetonitrile-0.1% TFA. RT=0.78 min; (ES): m/z (M+H)$^+$=191.1. HPLC: Chromolith ODS S5 4.6×50 mm (4 min grad) 0-100% B. Flow Rate=4 mL/min. Inj. Vol.=10 uL. Wavelength=220. Oven Temp.=40° C. Solvent A: 10% MeOH-90% H$_2$O-0.1% TFA. Solvent B: 90% MeOH-10% H$_2$O-0.1% TFA. HPLC: RT=1.65 min.

Step 3: Oxan-4-yl(phenyl)($^2$H)methanol

A solution of 4-benzoyloxane (300 mg, 1.58 mmol) in methanol (3 mL) in a scintillation vial was treated slowly portion-wise with sodium borodeuteride 98% D (99.0 mg, 2.37 mmol)—immediate bubbling occurs. After the addition was complete, the mixture was stirred at room temperature for 1 h. The mixture was diluted with water and extracted into ethyl acetate. The organics were washed with water and brine and concentrated to give oxan-4-yl(phenyl)($^2$H)methanol (300 mg, 98%) as a thick oil. This was used without further purification. HPLC: Chromolith ODS S5 4.6×50 mm (4 min grad) 0-100% B. Flow Rate=4 mL/min. Inj. Vol.=10 uL. Wavelength=220. Oven Temp.=40° C. Solvent A: 10% MeOH-90% H$_2$O-0.1% TFA. Solvent B: 90% MeOH-10% H$_2$O-0.1% TFA. HPLC: RT=1.443 min; LCMS: Waters Acquity SDS. Column: BEH C18 2.1×50 mm 1.7 u (1.6 min grad) 2-98% B. Flow Rate=0.8 mL/min. Solvent A: H$_2$O-0.1% TFA. Solvent B: Acetonitrile-0.1% TFA. LCMS: RT=0.77 min; (ES): m/z (M+H-H$_2$O)$^+$=176.1.

Step 4: Methyl 3-(1,4-dimethyl-1H-1,2,3-triazol-5-yl)-5-(phenyl(tetrahydro-2H-pyran-4-yl)($^2$H) methyl)-5H-pyrido[3,2-b]indole-7-carboxylate A suspension of methyl 3-(1,4-dimethyl-1H-1,2,3-triazol-5-yl)-5H-pyrido[3,2-b]indole-7-carboxylate (249 mg, 0.776 mmol), phenyl(tetrahydro-2H-pyran-4-yl)($^2$H)methanol (300 mg, 1.55 mmol), and triphenylphosphine (407 mg, 1.55 mmol) in dichloromethane (5 mL) was stirred in a RB flask and treated drop wise with DIAD (0.302 mL, 1.55 mmol). The mixture was stirred at room temperature for 16 h. The reaction mixture was added directly onto a silica gel column and was purified using silica gel column chromatography with an ISCO Companion (40 g silica gel column) and eluted with ethyl acetate. The fractions containing product were collected, and the volatiles were removed to give methyl 3-(1,4-dimethyl-1H-1,2,3-triazol-5-yl)-5-(phenyl (tetrahydro-2H-pyran-4-yl)($^2$H)methyl)-5H-pyrido[3,2-b] indole-7-carboxylate (190 mg, 0.383 mmol, 49%) as a white solid. LCMS: Waters Acquity SDS. Column: BEH C18 2.1×50 mm 1.7 u (1.6 min grad) 2-98% B. Flow Rate=0.8 mL/min. Solvent A: H$_2$O-0.1% TFA. Solvent B: Acetonitrile-0.1% TFA. LCMS: RT=0.89 min; (ES): m/z (M+H)$^+$=497.2.

Step 5: 2-[3-(Dimethyl-1H-1,2,3-triazol-5-yl)-5-[oxan-4-yl(phenyl)($^2$H)methyl]-5H-pyrido[3,2-b] indol-7-yl]propan-2-ol In a RB flask, a solution of methyl 3-(1,4-dimethyl-1H-1,2,3-triazol-5-yl)-5-(phenyl(tetrahydro-2H-pyran-4-yl)

($^2$H)methyl)-5H-pyrido[3,2-b]indole-7-carboxylate (190 mg, 0.383 mmol) in tetrahydrofuran (10 mL) was cooled in an ice bath under nitrogen and treated with methylmagnesium bromide (3M in ether, 3.06 mL, 9.20 mmol). After 2 h the reaction was quenched with sat. aq. ammonium chloride and extracted into ethyl acetate. The organics were washed with water, and the volatiles were concentrated to give 120 mg of a white solid. The material was purified using silica gel column chromatography on an ISCO Companion (40 g silica gel column) and eluted with (90:9:1 CH$_2$Cl$_2$:MeOH: NH$_4$OH)/CH$_2$Cl$_2$ gradient (0-100%). The fractions containing the product were collected, and the volatiles were removed to give 150 mg of the racemate, which was separated by chiral prep SFC (Column: Chiral OD-H 25×3 cm, 5 μm; Mobile Phase: 70/30 CO$_2$/MeOH; Flow: 85 mL/min) to give 2-[3-(dimethyl-1H-1,2,3-triazol-5-yl)-5-[(S)-oxan-4-yl(phenyl)($^2$H)methyl]-5H-pyrido[3,2-b]indol-7-yl]propan-2-ol Enantiomer A (50.0 mg, 26%) and 2-[3-(dimethyl-1H-1,2,3-triazol-5-yl)-5-[(R)-oxan-4-yl(phenyl)($^2$H)methyl]-5H-pyrido[3,2-b]indol-7-yl]propan-2-ol Enantiomer B (50.0 mg, 26%). Enantiomer A: 1H NMR (400 MHz, CDCl$_3$) δ 8.42 (d, J=1.8 Hz, 1H), 8.35 (dd, J=8.3, 0.5 Hz, 1H), 7.97 (d, J=0.7 Hz, 1H), 7.55 (d, J=1.7 Hz, 1H), 7.48-7.40 (m, 3H), 7.37-7.27 (m, 3H), 4.05 (dd, J=11.2, 3.3 Hz, 1H), 3.89-3.81 (m, 4H), 3.54 (td, J=11.9, 2.0 Hz, 1H), 3.34 (td, J=11.9, 2.1 Hz, 1H), 3.13-3.03 (m, 1H), 2.29 (s, 3H), 2.06-1.97 (m, 2H), 1.74 (s, 6H), 1.69-1.60 (m, 1H), 1.48-1.35 (m, 1H), 1.11 (d, J=12.2 Hz, 1H). LCMS: RT=0.76 min; (ES): m/z (M+H)$^+$=497.3 (Waters Acquity SDS. Column: BEH C18 2.1×50 mm 1.7 u (1.6 min grad) 2-98% B. Flow Rate=0.8 mL/min. Solvent A: H$_2$O-0.1% TFA. Solvent B: Acetonitrile-0.1% TFA). HPLC: RT=8.148 min; (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). Chiral SFC RT=1.06 min (Column: Chiralcel OD-H 250×4.6 mm, 5 μm; Mobile Phase: 50/50 CO$_2$/(1:1 MeOH/CH$_3$CN); Flow: 2 mL/min). Enantiomer B: Chiral SFC RT=2.83 min (Column: Chiralcel OD-H 250×4.6 mm, 5 μm; Mobile Phase: 50/50 CO$_2$/MeOH Flow: 2 mL/min).

Examples 92 & 93

2-[3-(Dimethyl-1H-1,2,3-triazol-5-yl)-5-[(S)-oxan-4-yl(2-fluorophenyl)($^2$H)methyl]-5H-pyrido[3,2-b]indol-7-yl]propan-2-ol Enantiomer A, Example 92

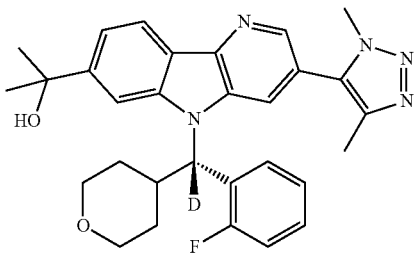

Enantiomer B, Example 93

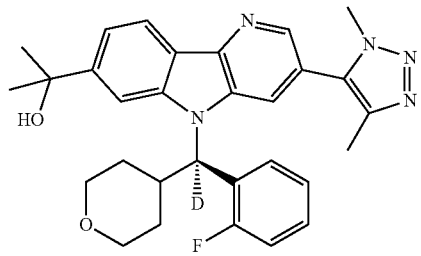

Step 1: 4-(2-Fluorobenzoyl)oxane

A solution of 1-bromo-2-fluorobenzene (10.1 g, 57.7 mmol) in tetrahydrofuran (50 mL) in a RB flask was cooled to −78° C. in a dry ice and acetone bath and treated slowly via syringe with nBuLi, 2.5 M in hexanes (23.1 mL, 57.7 mmol), and the resulting amber solution stirred for 35 min in bath. The mixture was treated with a solution N-methoxy-N-methyloxane-4-carboxamide (5.00 g, 28.9 mmol) in 10 mL of tetrahydrofuran via syringe to give a dark solution. After 2 h, the mixture was quenched with sat. aq. NH$_4$Cl and extracted into ethyl acetate. The organics were washed with water and brine, and the volatiles were concentrated to give a dark-yellow oil. The material purified using silica gel column chromatography on an ISCO Companion (120 g silica gel column) and eluted with an EtOAc/hexane hexane gradient (10-40%). The fractions containing product were collected, and the volatiles were removed were collected, and the volatiles were removed to give 4-(2-fluorobenzoyl)oxane (4.50 g, 21.6 mmol, 75%) as a light-amber oil. LCMS: Waters Acquity SDS. Column: BEH C18 2.1×50 mm 1.7 u (1.6 min grad) 2-98% B. Flow Rate=0.8 mL/min. Solvent A: H$_2$O-0.1% TFA. Solvent B: Acetonitrile-0.1% TFA. LCMS: RT=0.81 min; (ES): m/z (M+H)$^+$=209.1. HPLC: Chromolith ODS S5 4.6×50 mm (4 min grad) 0-100% B. Flow Rate=4 mL/min. Inj. Vol.=10 uL. Wavelength=220. Oven Temp.=40° C. Solvent A: 10% MeOH-90% H$_2$O-0.1% TFA. Solvent B: 90% MeOH-10% H$_2$O-0.1% TFA. HPLC: RT=1.797 min.

Step 2: 2-Fluorophenyl(oxan-4-yl)($^2$H)methanol

A solution of (2-fluorophenyl)(tetrahydro-2H-pyran-4-yl)methanone (300 mg, 1.44 mmol) in methanol (3 mL) in a scintillation vial was treated slowly portion-wise with sodium borodeuteride (90.0 mg, 2.16 mmol)—immediate bubbling occurs. After addition was complete, the mixture was stirred at room temperature 1.5 h. The mixture was diluted with water and extracted into ethyl acetate. The organics were washed with water and brine, and the volatiles were concentrated to give 2-fluorophenyl(oxan-4-yl)($^2$H) methanol (304 mg, 100%) as a colorless oil. HPLC: Chromolith ODS S5 4.6×50 mm (4 min grad) 0-100% B. Flow Rate=4 mL/min. Inj. Vol.=10 uL. Wavelength=220. Oven Temp.=40° C. Solvent A: 10% MeOH-90% H$_2$O-0.1% TFA. Solvent B: 90% MeOH-10% H$_2$O-0.1% TFA. HPLC: RT=1.557 min.

Step 3: 2-[3-(Dimethyl-1H-1,2,3-triazol-5-yl)-5-[(S)-oxan-4-yl(2-fluorophenyl)($^2$H)methyl]-5H-pyrido[3,2-b]indol-7-yl]propan-2-ol and 2-[3-(dimethyl-1H-1,2,3-triazol-5-yl)-5-[(R)-oxan-4-yl(2-fluorophenyl)($^2$H)methyl]-5H-pyrido[3,2-b]indol-7-yl]propan-2-ol Following a procedure analogous to that described for the synthesis of 2-[3-(dimethyl-1H-1,2,3-triazol-5-yl)-5-[(S)-oxan-4-yl(phenyl)($^2$H)methyl]-5H-pyrido[3,2-b]indol-7-yl]propan-2-ol, methyl 3-(1,4-dimethyl-1H-1,2,3-triazol-5-yl)-5H-pyrido[3,2-b]indole-7-carboxylate (228 mg, 0.710 mmol) and (2-fluorophenyl)(tetrahydro-2H-pyran-4-yl)($^2$H)methanol (300 mg, 1.42 mmol) were converted to 150 mg of racemic 2-[3-(dimethyl-1H-1,2,3-triazol-5-yl)-5-[(S)-oxan-4-yl(2-fluorophenyl)($^2$H)methyl]-5H-pyrido[3,2-b]indol-7-yl]propan-2-ol, which was separated by chiral prep SFC (Column: Chiral OD-H 25×3 cm, 5 μm; Mobile Phase: 70/30 CO$_2$/MeOH; Flow: 85 mL/min) to give 2-[3-(dimethyl-1H-1,2,3-triazol-5-yl)-5-[(S)-oxan-4-yl(2-fluorophenyl)($^2$H)methyl]-5H-pyrido[3,2-b]indol-7-yl]propan-2-ol Enantiomer A (70.0 mg, 35%) and 2-[3-(dimethyl-1H-1,2,3-triazol-5-yl)-5-[(R)-oxan-4-yl(2-fluorophenyl)($^2$H)methyl]-5H-pyrido[3,2-b]indol-7-yl]propan-2-ol Enantiomer B (50.0 mg, 25%). Enantiomer A: 1H NMR (400 MHz, CDCl$_3$) δ 8.46 (d, J=1.7 Hz, 1H), 8.36-8.30 (m, 1H), 8.01 (s, 1H), 7.82-7.72 (m, 2H), 7.45 (dd, J=8.3, 1.4 Hz, 1H), 7.37-7.28 (m, 1H), 7.25-7.18 (m, 1H), 7.04 (ddd, J=10.5, 8.2, 1.2 Hz, 1H), 4.05 (dd, J=10.6, 3.4 Hz, 1H), 4.00 (s, 3H), 3.87 (dd, J=11.7, 2.4 Hz, 1H), 3.57-3.48 (m, 1H), 3.33 (td, J=11.9, 2.0 Hz, 1H), 3.16 (t, J=11.3 Hz, 1H), 2.37 (s, 3H), 1.95 (s, 1H), 1.88 (d, J=12.3 Hz, 1H), 1.73 (d, J=2.9 Hz, 6H), 1.63 (m, 1H), 1.47-1.34 (m, 1H), 1.12 (d, J=12.6 Hz, 1H). LCMS: RT=0.78 min; (ES): m/z (M+H)$^+$=515.3 (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). HPLC: RT=8.133 min (Column: Sunfire C18 3.5 μm, 3.0× 150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). Chiral SFC RT=4.335 min (Column: Chiralcel OD-H 250×4.6 mm, 5 μm; Mobile Phase: 70/30 CO$_2$/MeOH; Flow: 2 mL/min). Enantiomer B: Chiral SFC RT=7.569 min (Column: Chiralcel OD-H 250× 4.6 mm, 5 μm; Mobile Phase: 70/30 CO$_2$/MeOH; Flow: 2 mL/min).

Examples 94 & 95

2-{5-[(2,3-Difluorophenyl)(oxan-4-yl)methyl]-3-(dimethyl-1H-1,2,3-triazol-5-yl)-5H-pyrido[3,2-b]indol-7-yl}propan-2-ol Enantiomer A, Example 94

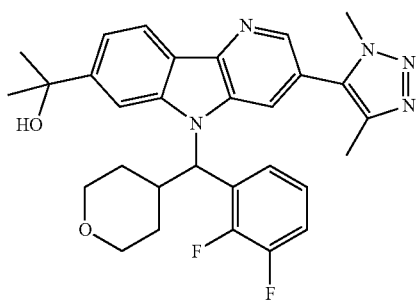

Enantiomer B, Example 95

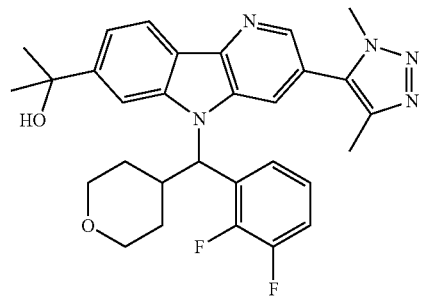

Step 1: 4-(2,3-Difluorobenzoyl)oxane

A solution of 4-bromo-1,2-difluorobenzene (2.40 g, 12.4 mmol) in tetrahydrofuran (20 mL) in a RB flask was cooled to −78° C. in a dry ice and acetone bath and treated slowly drop wise via syringe with nBuLi, 2.5 M in hexanes (4.97 mL, 12.4 mmol) and stirred for 20 min in bath. The mixture was then treated with a solution of N-methoxy-N-methyl-oxane-4-carboxamide (0.718 g, 4.15 mmol) in 2 mL of tetrahydrofuran via syringe to give a light-brown solution. After 1 h, the mixture was quenched with sat. aq. NH$_4$Cl and extracted into ethyl acetate. The organics were washed with water and brine, and the volatiles were concentrated to give an oil. Analysis by LCMS shows 2 isomeric products formed. The material was purified by silica gel column chromatography on an ISCO Companion (40 g silica gel column) and eluted with an EtOAc/hexane hexane gradient (0-50%). The fractions containing the major isomer were collected, and the volatiles were removed to give 4-(2,3-difluorobenzoyl)oxane (350 mg, 37%) as a colorless oil. $^1$H NMR (400 MHz, CDCl$_3$) δ 7.54 (ddt, J=7.9, 6.1, 1.7 Hz, 1H), 7.37 (dtd, J=9.5, 8.0, 1.7 Hz, 1H), 7.20 (tdd, J=8.1, 4.6, 1.4 Hz, 1H), 4.05 (dt, J=11.4, 3.5 Hz, 2H), 3.55 (td, J=11.3, 2.9 Hz, 2H), 3.42-3.30 (m, 1H), 1.93-1.74 (m, 4H). The fractions containing the minor isomer were collected, and the volatiles were removed to give 4-(3,4-difluorobenzoyl)oxane (130 mg, 14%) as a colorless oil. $^1$H NMR (400 MHz, CDCl$_3$) δ 7.83-7.70 (m, 2H), 7.33-7.22 (m, 1H), 4.11-4.01 (m, 2H), 3.56 (td, J=11.6, 2.5 Hz, 2H), 3.43 (tt, J=11.0, 4.0 Hz, 1H), 1.95-1.82 (m, 2H), 1.81-1.71 (m, 2H).

Step 2: (2,3-Difluorophenyl)(oxan-4-yl)methanol

A solution of 4-(2,3-difluorobenzoyl)oxane (350 mg, 1.55 mmol) in methanol (10 mL) was treated slowly portion wise with NaBH4 (88.0 mg, 2.32 mmol)—immediate bubbling. After addition was complete, the mixture was stirred at room temperature. The volatiles were removed, and the residue was partitioned between sat. aq. NH$_4$Cl and ethyl acetate. The organics were washed with water, and the volatiles were concentrated to give (2,3-difluorophenyl)(oxan4-yl)methanol (350 mg, 99%) as a colorless oil. LCMS: Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA. LCMS: RT=0.74 min; (ES): m/z (M+H-H$_2$O)$^+$=211. $^1$H NMR (400 MHz, CDCl$_3$) δ 7.26-7.17 (m, 1H), 7.14-7.06 (m, 2H), 4.80 (dd, J=7.2, 4.3 Hz, 1H), 4.03 (dd, J=11.4, 3.8 Hz, 1H), 3.95 (dd, J=10.9, 4.1 Hz, 1H), 3.42-3.26 (m, 2H), 2.12 (d, J=4.4 Hz, 1H), 1.97-1.89 (m, 1H), 1.89-1.80 (m, 1H), 1.56-1.39 (m, 2H), 1.31-1.23 (m, 1H).

Step 3: 2-{5-[(2,3-Difluorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described for the synthesis of 2-[3-(dimethyl-1H-1,2,3-triazol-5-yl)-5-[(S)-oxan-4-yl(phenyl)($^2$H)methyl]-5H-pyrido[3,2-b]indol-7-yl]propan-2-ol and 2-[3-(dimethyl-1H-1,2,3-triazol-5-yl)-5-[(R)-oxan-4-yl(phenyl)($^2$H)methyl]-5H-pyrido[3,2-b]indol-7-yl]propan-2-ol, 3-(1,4-dimethyl-1H-1,2,3-triazol-5-yl)-5H-pyrido[3,2-b]indole-7-carboxylate (150 mg, 0.467 mmol) and (2,3-difluorophenyl)(tetrahydro-2H-pyran-4-yl)methanol (213 mg, 0.934 mmol) were converted to 140 mg of racemic 2-{5-[(2,3-difluorophenyl)(oxan-4-yl)methyl]-3-(dimethyl-1H-1,2,3-triazol-5-yl)-5H-pyrido[3,2-b]indol-7-yl}propan-2-ol as a white solid, which was separated by chiral prep SFC (Column: Chiral OD-H 25×3 cm, 5 µm; Mobile Phase: 75/25 CO$_2$/MeOH; Flow: 85 mL/min) to give Enantiomer A (50 mg, 23%) and Enantiomer B (40 mg, 22%). Enantiomer A: $^1$H NMR (400 MHz, CDCl$_3$) δ 8.49 (d, J=1.7 Hz, 1H), 8.36 (d, J=8.2 Hz, 1H), 8.00 (s, 1H), 7.80 (s, 1H), 7.58-7.51 (m, 1H), 7.46 (dd, J=8.3, 1.3 Hz, 1H), 7.23-7.11 (m, 2H), 5.77 (d, J=11.6 Hz, 1H), 4.12-4.05 (m, 1H), 4.03 (s, 3H), 3.88 (dd, J=11.9, 2.6 Hz, 1H), 3.59-3.47 (m, 1H), 3.34 (td, J=11.9, 2.1 Hz, 1H), 3.24-3.11 (m, 1H), 2.39 (s, 3H), 2.00 (s, 1H), 1.88 (d, J=12.7 Hz, 1H), 1.74 (d, J=4.9 Hz, 6H), 1.67-1.53 (m, 1H), 1.49-1.33 (m, 1H), 1.14 (d, J=11.7 Hz, 1H). LCMS: RT=0.78 min; (ES): m/z (M+H)$^+$=532.4 (Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). HPLC RT=9.133 min (Column: Sunfire C18 3.5 µm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 0.5 mL/min; Detection: UV at 220 nm). Chiral SFC RT=6.660 min (Column: Chiralcel OD-H 250×4.6 mm, 5 µm; Mobile Phase: 75/25 CO$_2$/MeOH; Flow: 2 mL/min). Enantiomer B: Chiral SFC RT=11.635 min (Column: Chiralcel OD-H 250×4.6 mm, 5 µm; Mobile Phase: 75/25 CO$_2$/MeOH; Flow: 2 mL/min).

Examples 96 & 97

2-{5-[(3,4-Difluorophenyl)(oxan-4-yl)methyl]-3-(dimethyl-1H-1,2,3-triazol-5-yl)-5H-pyrido[3,2-b]indol-7-yl}propan-2-ol Enantiomer A, Example 96

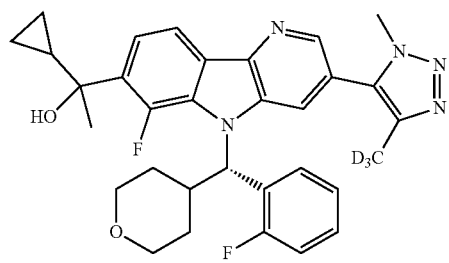

Enantiomer B, Example 97

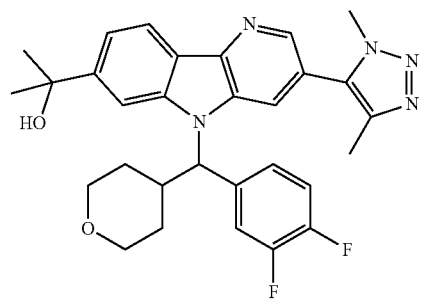

Step 1: 4-(3,4-Difluorobenzoyl)oxane

To a solution of 4-bromo-1,2-difluorobenzene (1.18 mL, 10.4 mmol) in dry THF (50 mL) was added isopropylmagnesium chloride (5.21 mL, 10.4 mmol) via syringe and then stirred at room temperature for 2 h. A etheral solution of N-methoxy-N-methyloxane-4-carboxamide (1.64 g, 9.47 mmol) was added, and the reaction mixture was stirred at room temperature for 16 h. The reaction mixture was quenched with water (20 mL) and extracted with ethyl acetate. The combined organic layers were washed with brine, dried over Na$_2$SO$_4$, and concentrated. The crude residue was also purified (24 g combiflash column/compound absorbed on silica, eluted at 10-5% EA in petroleum ether) to obtain 4-(3,4-difluorobenzoyl)oxane (700 mg, 32%) as a colorless oil. $^1$H NMR (400 MHz, CDCl$_3$) δ 7.83-7.70 (m, 2H), 7.33-7.22 (m, 1H), 4.11-4.01 (m, 2H), 3.56 (td, J=11.6, 2.5 Hz, 2H), 3.43 (tt, J=11.0, 4.0 Hz, 1H), 1.95-1.82 (m, 2H), 1.81-1.71 (m, 2H).

Step 2: (3,4-Difluorophenyl)(oxan-4-yl)methanol

To a stirred solution of 4-(3,4-difluorobenzoyl)oxane (2.80 g, 12.4 mmol) in MeOH (60 mL) was added NaBH$_4$ (0.937 g, 24.8 mmol) portion wise over the period of 2 min and then stirred at room temperature for 2 h. Methanol was evaporated, and the residue was quenched with ice water (55 mL) and extracted with EtOAc(2×100 mL). The EtOAc extract was dried over Na$_2$SO$_4$, filtered, and concentrated to give (3,4-difluorophenyl)(oxan-4-yl)methanol (2.50 g, 11.0 mmol, 88%) as a colorless liquid. $^1$H NMR (400 MHz, CDCl$_3$) δ 7.23-7.10 (m, 2H), 7.03 (ddd, J=1.8, 4.1, 8.2 Hz, 1H), 4.38 (dd, J=2.8, 7.3 Hz, 1H), 4.08-3.88 (m, 2H), 3.42-3.23 (m, 2H), 1.97 (s, 1H), 1.91-1.72 (m, 2H), 1.50-1.29 (m, 2H), 1.24-1.13 (m, 1H).

Step 3: 2-{5-[(3,4-Difluorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described for the synthesis of 2-{5-[(2,3-difluorophenyl)(oxan-4-yl)methyl]-3-(dimethyl-1H-1,2,3-triazol-5-yl)-5H-pyrido[3,2-b]indol-7-yl}propan-2-ol, (3,4-difluorophenyl)(tetrahydro-2H-pyran-4-yl)methanol (355 mg, 1.56 mmol) was converted to 114 mg of racemic 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol as a white solid which was separated by chiral prep HPLC (Column: Lux Cellulose 4 25×2.1 cm, 5 µm; Mobile Phase: 70/30 0.2% DEA in hexane/methanol; Flow: 18 mL/min) to give Enantiomer A (20.0 mg, 8%) and Enantiomer B (40 mg, 16%). Enantiomer A: $^1$H NMR (400 MHz, CD$_3$OD) δ 8.47 (d, J=2.0 Hz, 1H), 8.31 (d, J=8.0 Hz, 2H), 8.08 (s, 1H), 7.63 (ddd, J=2.3, 7.8, 11.5 Hz, 1H), 7.53-7.49 (m, 1H), 7.47-7.41 (m, 1H), 7.24 (td, J=8.5, 10.5 Hz, 1H), 5.75 (d, J=11.0 Hz, 1H), 4.04 (s, 3H), 4.00 (dd, J=2.8, 11.8 Hz, 1H), 3.82 (dd, J=2.8, 11.8 Hz, 1H), 3.60 (dt, J=2.0, 11.8 Hz, 1H), 3.45-3.34 (m, 2H), 2.34 (s, 3H), 1.89 (d, J=12.5 Hz, 1H), 1.68 (d, J=4.0 Hz, 7H), 1.65-1.57 (m, 1H), 1.44-1.38 (m, 1H), 1.13 (d, J=12.0 Hz, 1H). LCMS: RT=1.852 min; MS (ES): m/z=532.5 [M+H]$^+$ (ACN/H$_2$O with HCOONH$_4$, Ascentis Express C18 2.7 μm (50×2.1) mm, gradient=4 min, wavelength=220 nm); HPLC RT=13.127 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 30 min; Flow: 1 mL/min; Detection: UV at 220 nm). Chiral HPLC RT=15.105 min (Column: Lux Cellulose 4, 250×4.6 mm, 5 μm; Mobile Phase: 70/30 0.2% DEA in Hexane/Methanol; Flow: 1 mL/min). Enantiomer B: Chiral HPLC RT=18.032 min (Column: Lux Cellulose 4, 250×4.6 mm, 5 μm; Mobile Phase: 70/30 0.2% DEA in Hexane/Methanol; Flow: 1 mL/min).

60/40 CO$_2$/(0.25% DEA in methanol); Flow: 60 mL/min) to give Enantiomer A (14.0 mg, 8%) and Enantiomer B (14.0 mg, 8%). Enantiomer A: $^1$H NMR (400 MHz, CD$_3$OD) δ 8.47 (d, J=1.5 Hz, 1H), 8.30 (d, J=8.0 Hz, 2H), 8.08 (s, 1H), 7.51 (dd, J=1.3, 8.3 Hz, 1H), 7.36-7.23 (m, 2H), 6.93-6.84 (m, 1H), 5.76 (d, J=11.0 Hz, 1H), 4.08-3.94 (m, 4H), 3.86-3.77 (m, 1H), 3.64-3.54 (m, 1H), 3.44-3.33 (m, 2H), 2.33 (s, 3H), 1.92-1.83 (m, 1H), 1.73-1.57 (m, 7H), 1.45-1.36 (m, 1H), 1.14 (d, J=13.6 Hz, 1H). LCMS: RT=2.423 min; MS (ES): m/z=532.2, [M+H]$^+$ (ACN/H$_2$O with HCOONH$_4$, Ascentis Express C18 2.7 μm (50×2.1) mm, gradient=4 min, wavelength=220 nm); HPLC RT=8.633 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.58 min (Column: Lux Cellulose 4, 250×4.6 mm, 5 μm; Mobile Phase: 60/40 CO$_2$/(0.25% DEA in methanol; Flow: 4 mL/min). Enantiomer B: Chiral SFC RT=4.69 min (Column: Lux Cellulose 4, 250×4.6 mm, 5 μm; Mobile Phase: 60/40 CO$_2$/(0.25% DEA in methanol; Flow: 4 mL/min).

Examples 98 & 99

2-{5-[(3,5-Difluorophenyl)(oxan-4-yl)methyl]-3-(dimethyl-1H-1,2,3-triazol-5-yl)-5H-pyrido[3,2-b]indol-7-yl}propan-2-ol Examples 100 & 101

2-[3-(Dimethyl-1H-1,2,3-triazol-5-yl)-5-[(3-fluorophenyl)(oxan-4-yl)methyl]-5H-pyrido[3,2-b]indol-7-yl]propan-2-ol Enantiomer A, Example 98

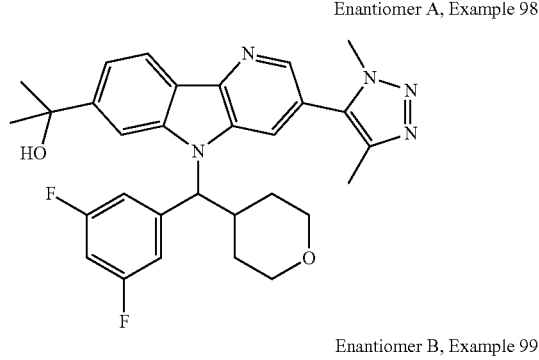

Enantiomer A, Example 100

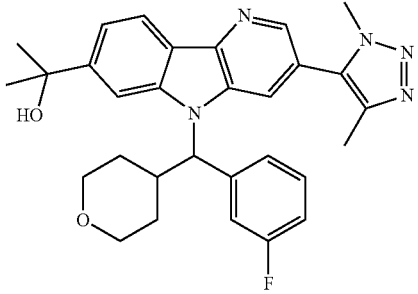

Enantiomer B, Example 99

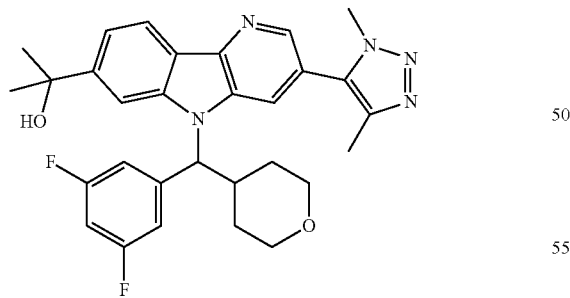

Enantiomer B, Example 101

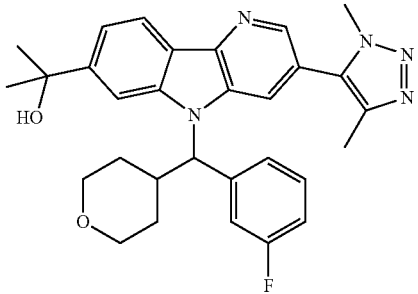

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (3,5-difluorophenyl)(tetrahydro-2H-pyran-4-yl)methanol was converted to 40 mg of racemic 2-{5-[(3,5-difluorophenyl)(oxan-4-yl)methyl]-3-(dimethyl-1H-1,2,3-triazol-5-yl)-5H-pyrido[3,2-b]indol-7-yl}propan-2-ol as a white solid which was separated by chiral prep SFC (Column: Lux Cellulose-4, 25×2.1 cm, 5 μm; Mobile Phase:

Following a procedure analogous to that described for the synthesis of 2-{5-[(3,5-difluorophenyl)(oxan-4-yl)methyl]-3-(dimethyl-1H-1,2,3-triazol-5-yl)-5H-pyrido[3,2-b]indol-7-yl}propan-2-ol, (3-fluorophenyl)(tetrahydro-2H-pyran-4-yl)methanol (355 mg, 1.56 mmol) was converted to 120 mg of racemic 2-[3-(dimethyl-1H-1,2,3-triazol-5-yl)-5-[(3-fluorophenyl)(oxan-4-yl)methyl]-5H-pyrido[3,2-b]indol-7-yl]propan-2-ol as a white solid, which was separated by chiral prep SFC (Column: Chiral OD-H 25×2.1 cm, 5 μm; Mobile Phase: 60/40 CO$_2$/(0.25% DEA in MeOH); Flow: 70 mL/min) to give Enantiomer A (48.0 mg, 19%) and Enantiomer B (47.0 mg, 18%). Enantiomer A: $^1$H NMR (400 MHz, CD$_3$OD) δ 8.46 (d, J=1.5 Hz, 1H), 8.32-8.27 (m, 2H), 8.11 (s, 1H), 7.53-7.48 (m, 1H), 7.46-7.40 (m, 2H), 7.39-7.32 (m, 1H), 7.06-6.98 (m, 1H), 5.78 (d, J=11.5 Hz, 1H), 4.02 (s, 3H), 3.98 (d, J=3.0 Hz, 1H), 3.82 (dd, J=2.5, 11.5 Hz, 1H), 3.60 (dt, J=2.3, 11.9 Hz, 1H), 3.43-3.33 (m, 2H), 2.33 (s, 3H), 1.92 (d, J=13.1 Hz, 1H), 1.71-1.66 (m, 7H), 1.48-1.33 (m, 1H), 1.13 (d, J=12.0 Hz, 1H). LCMS: RT=1.822 min; MS (ES): m/z=514 [M+H]$^+$ (ACN/H$_2$O with HCOONH$_4$, Ascentis Express C18 2.7 µm (50×2.1) mm, gradient=4 min, wavelength=220 nm); HPLC RT=8.155 min (Column: Sunfire C18 3.5 µm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=6.16 min (Column: Chiralcel OD-H 250×4.6 mm, 5 µm; Mobile Phase: 70/30 CO$_2$/(0.25% DEA in MeOH); Flow: 3 mL/min). Enantiomer B: Chiral SFC RT=3.81 min (Column: Chiralcel OD-H 250×4.6 mm, 5 µm; Mobile Phase: 70/30 CO$_2$/(0.25% DEA in MeOH); Flow: 3 mL/min).

Examples 102 & 103

2-[3-(Dimethyl-1H-1,2,3-triazol-5-yl)-5-[oxan-4-yl(2,4,6-trifluorophenyl)methyl]-5H-pyrido[3,2-b]indol-7-yl]propan-2-ol

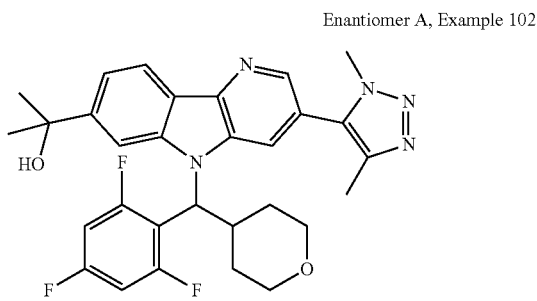

Enantiomer A, Example 102

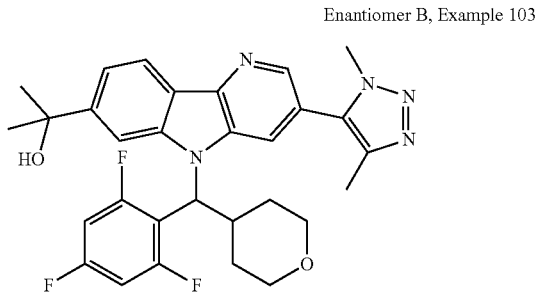

Enantiomer B, Example 103

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,4,6-trifluorophenyl)(tetrahydro-2H-pyran-4-yl)methanol was converted to 40 mg of racemic 2-[3-(dimethyl-1H-1,2,3-triazol-5-yl)-5-[oxan-4-yl(2,4,6-trifluorophenyl)methyl]-5H-pyrido[3,2-b]indol-7-yl]propan-2-ol as a white solid, which was separated by chiral prep SFC (Column: Chiralpak OJ-H 25×2.1 cm, 5 µm; Mobile Phase: 80/20 CO$_2$/(0.25% DEA in MeOH); Flow: 60 mL/min) to give Enantiomer A (12.0 mg, 6%) and Enantiomer B (11.0 mg, 6%). Enantiomer A: $^1$H NMR (400 MHz, CD$_3$OD) δ 8.50 (d, J=2.0 Hz, 1H), 8.37 (br. s., 1H), 8.33-8.27 (m, 1H), 8.10-8.03 (m, 1H), 7.52 (dd, J=1.5, 8.5 Hz, 1H), 7.02-6.92 (m, 2H), 6.04 (d, J=12.0 Hz, 1H), 4.15-4.07 (m, 3H), 4.06-3.98 (m, 1H), 3.80 (d, J=11.5 Hz, 1H), 3.60-3.51 (m, 1H), 3.46-3.34 (m, 2H), 2.42-2.37 (m, 3H), 1.79 (d, J=11.5 Hz, 1H), 1.71-1.55 (m, 7H), 1.40 (d, J=8.0 Hz, 1H), 1.09 (br. s., 1H). LCMS: RT=2.394 min; MS (ES): m/z=550.2 [M+H]$^+$ (ACN/H$_2$O with HCOONH$_4$, Ascentis Express C18 2.7 µm (50×2.1) mm, gradient=4 min, wavelength=220 nm); HPLC RT=8.445 min (Column: Sunfire C18 3.5 µm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.94 min (Column: Chiralpak OJ-H 250×4.6 mm, 5 µm; Mobile Phase: 80/20 CO$_2$/(0.25% DEA in MeOH); Flow: 3 mL/min). Enantiomer B: Chiral SFC RT=4.29 min (Column: Chiralpak OJ-H 250×4.6 mm, 5 µm; Mobile Phase: 80/20 CO$_2$/(0.25% DEA in MeOH); Flow: 3 mL/min).

Examples 104 & 105

2-[3-(Dimethyl-1H-1,2,3-triazol-5-yl)-9-fluoro-5-[oxan-4-yl(2,4,6-trifluorophenyl)methyl]-5H-pyrido[3,2-b]indol-7-yl]propan-2-ol

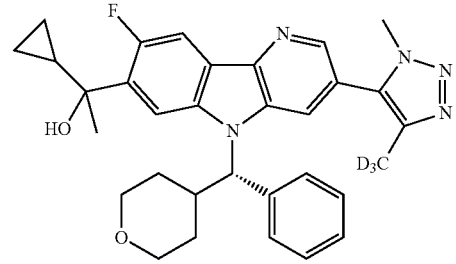

Enantiomer A, Example 104

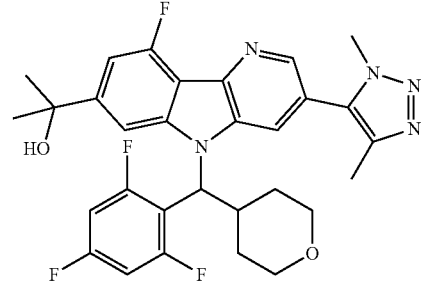

Enantiomer B, Example 105

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,4,6-trifluorophenyl)(oxan-4-yl)methanol and methyl 3-(dimethyl-1H-1,2,3-triazol-5-yl)-9-fluoro-5H-pyrido[3,2-b]indole-7-carboxylate were converted to racemic 2-[3-(dimethyl-1H-1,2,3-triazol-5-yl)-9-fluoro-5-[oxan-4-yl(2,4,6-trifluorophenyl)methyl]-5H-pyrido[3,2-b]indol-7-yl]propan-2-ol, which was separated by chiral prep SFC (Column: Lux Cellulose-2, 25×2.1 cm, 5 µm; Mobile Phase: 60/40 CO$_2$/(0.25% DEA in MeOH); Flow: 60 mL/min) to give Enantiomer A (17.0 mg, 33%) and Enantiomer B (19.0 mg, 37%). Enantiomer A: ¹H NMR (400 MHz, CD₃OD) δ 8.53 (d, J=1.5 Hz, 1H), 8.43 (br. s., 1H), 7.85 (s, 1H), 7.27-7.21 (m, 1H), 7.04-6.95 (m, 2H), 6.07 (d, J=11.5 Hz, 1H), 4.11 (s, 3H), 4.03 (d, J=14.6 Hz, 1H), 3.85-3.77 (m, 1H), 3.59-3.51 (m, 1H), 3.43-3.35 (m, 2H), 2.40 (s, 3H), 1.78 (d, J=11.5 Hz, 1H), 1.69-1.61 (m, 7H), 1.42 (m, 1H), 1.07 (d, J=11.5 Hz, 1H). LCMS: RT=1.859 min; MS (ES): m/z=568.2 [M+H]⁺ (ACN/H₂O with HCOONH₄, Ascentis Express C18 2.7 μm (50×2.1) mm, gradient=4 min, wavelength=220 nm); HPLC RT=9.155 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=8.15 min (Column: Lux Cellulose-2, 250×4.6 mm, 5 μm; Mobile Phase: 60/40 CO₂/(0.25% DEA in MeOH); Flow: 3 mL/min). Enantiomer B: Chiral SFC RT=9.58 min (Column: Lux Cellulose-2, 250×4.6 mm, 5 μm; Mobile Phase: 60/40 CO₂/(0.25% DEA in MeOH); Flow: 3 mL/min).

Examples 106 & 107

2-{5-[(2,5-Difluorophenyl)(oxan-4-yl)methyl]-3-(dimethyl-1H-1,2,3-triazol-5-yl)-9-fluoro-5H-pyrido[3,2-b]indol-7-yl}propan-2-ol Enantiomer A, Example 106

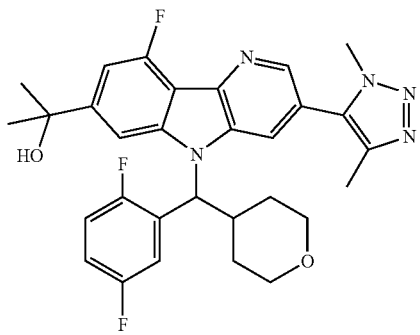

Enantiomer B, Example 107

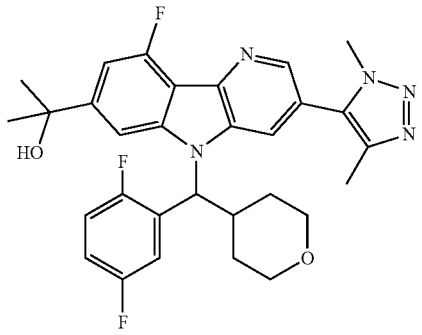

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,5-difluorophenyl)(oxan-4-yl)methanol and methyl 3-(dimethyl-1H-1,2,3-triazol-5-yl)-9-fluoro-5H-pyrido[3,2-b]indole-7-carboxylate were converted to racemic 2-{5-[(2,5-difluorophenyl)(oxan-4-yl)methyl]-3-(dimethyl-1H-1,2,3-triazol-5-yl)-9-fluoro-5H-pyrido[3,2-b] indol-7-yl}propan-2-ol, which was separated by chiral prep SFC (Column: Chiralcel OD-H, 25×2.1 cm, 5 μm; Mobile Phase: 80/20 CO₂/(0.25% DEA in MeOH); Flow: 60 mL/min) to give Enantiomer A (22.0 mg, 44%) and Enantiomer B (25.0 mg, 48%). Enantiomer A: ¹H NMR (400 MHz, CD₃OD) δ 8.49 (d, J=2.0 Hz, 1H), 8.39 (br. s., 1H), 7.99-7.90 (m, 1H), 7.83 (br. s., 1H), 7.21 (d, J=12.5 Hz, 1H), 7.14-7.04 (m, 2H), 5.99 (d, J=11.5 Hz, 1H), 4.05 (s, 3H), 4.02-3.95 (m, 1H), 3.81 (dd, J=2.8, 11.8 Hz, 1H), 3.65-3.56 (m, 1H), 3.42-3.34 (m, 2H), 2.35 (s, 3H), 1.97-1.86 (m, 1H), 1.72-1.59 (m, 7H), 1.45-1.40 (m, 1H), 0.98 (d, J=13.1 Hz, 1H). LCMS: RT=1.85 min; MS (ES): m/z=550.2 [M+H]⁺ (ACN/H₂O with HCOONH₄, Ascentis Express C18 2.7 μm (50×2.1) mm, gradient=4 min, wavelength=220 nm); HPLC RT=8.838 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=8.39 min (Column: Chiralcel OD-H, 250×4.6 mm, 5 μm; Mobile Phase: 75/25 CO₂/(0.25% DEA in MeOH); Flow: 3 mL/min). Enantiomer B: Chiral SFC RT=10.10 min (Column: Chiralcel OD-H, 250×4.6 mm, 5 μm; Mobile Phase: 75/25 CO₂/(0.25% DEA in MeOH); Flow: 3 mL/min).

Examples 108 & 109

2-{5-[(2,3-Difluorophenyl)(oxan-4-yl)methyl]-3-(dimethyl-1H-1,2,3-triazol-5-yl)-9-fluoro-5H-pyrido[3,2-b]indol-7-yl}propan-2-ol Enantiomer A, Example 108

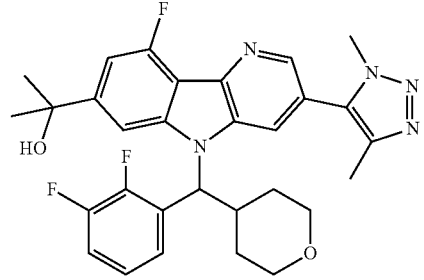

Enantiomer B, Example 109

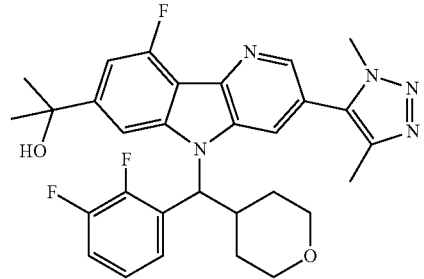

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,3-difluorophenyl)(oxan-4-yl)methanol and methyl 3-(dimethyl-1H-1,2,3-triazol-5-yl)-9-fluoro-5H-pyrido[3,2-b]indole-7-carboxylate were converted to racemic 2-{5-[(2,3-difluorophenyl)(oxan-4-yl)methyl]-3-(dimethyl-1H-1,2,3-triazol-5-yl)-9-fluoro-5H-pyrido[3,2-b]

indol-7-yl}propan-2-ol, which was separated by chiral prep SFC (Column: Chiralcel OD-H, 25×2.1 cm, 5 μm; Mobile Phase: 65/35 CO$_2$/(0.25% DEA in MeOH); Flow: 75 mL/min) to give Enantiomer A (22.0 mg, 44%) and Enantiomer B (15.0 mg, 30%). Enantiomer A: $^1$H NMR (400 MHz, CD$_3$OD) δ 8.52 (d, J=1.5 Hz, 1H), 8.39 (br. s., 1H), 7.97-7.82 (m, 2H), 7.39-7.19 (m, 3H), 6.07 (d, J=11.5 Hz, 1H), 4.12-3.99 (m, 4H), 3.83 (dd, J=3.0, 11.5 Hz, 1H), 3.67-3.56 (m, 1H), 3.46-3.37 (m, 2H), 2.37 (s, 3H), 1.93 (d, J=13.6 Hz, 1H), 1.76-1.61 (m, 7H), 1.49-1.40 (m, 1H), 0.99 (d, J=12.5 Hz, 1H). LCMS: RT=1.85 min; MS (ES): m/z=550.2 [M+H]$^+$ (ACN/H$_2$O with HCOONH$_4$, Ascentis Express C18 2.7 μm (50×2.1) mm, gradient=4 min, wavelength=220 nm); HPLC RT=8.918 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.609 min (Column: Chiralcel OD-H, 250×4.6 mm, 5 μm; Mobile Phase: 70/30 CO$_2$/(0.25% DEA in MeOH); Flow: 3 mL/min). Enantiomer B: Chiral SFC RT 4.36 min (Column: Chiralcel OD-H, 250×4.6 mm, 5 μm; Mobile Phase: 70/30 CO$_2$/(0.25% DEA in MeOH); Flow: 3 mL/min).

Examples 110 & 111

2-{5-[(2,4-Difluorophenyl)(oxan-4-yl)methyl]-3-(dimethyl-1H-1,2,3-triazol-5-yl)-9-fluoro-5H-pyrido[3,2-b]indol-7-yl}propan-2-ol indol-7-yl}propan-2-ol, which was separated by chiral prep SFC (Column: Chiralpak IC, 25×2.1 cm, 5 μm; Mobile Phase: 60/40 CO$_2$/(0.25% DEA in MeOH); Flow: 60 mL/min) to give Enantiomer A (12.0 mg, 21%) and Enantiomer B (10.0 mg, 17%). Enantiomer A: $^1$H NMR (400 MHz, CD$_3$OD) δ 8.50 (d, J=1.5 Hz, 1H), 8.37 (br. s., 1H), 8.19-8.10 (m, 1H), 7.80 (br. s., 1H), 7.24-7.07 (m, 2H), 6.95 (ddd, J=2.5, 8.7, 10.9 Hz, 1H), 5.97 (d, J=11.5 Hz, 1H), 4.09-3.97 (m, 4H), 3.81 (d, J=9.0 Hz, 1H), 3.64-3.55 (m, 1H), 3.42-3.35 (m, 2H), 2.36 (s, 3H), 1.90 (t, J=5.8 Hz, 2H), 1.70-1.60 (m, 7H), 1.45-1.39 (m, 1H), 0.96 (d, J=14.6 Hz, 1H). LCMS: RT=1.86 min; MS (ES): m/z=550.2 [M+H]$^+$ (ACN/H$_2$O with HCOONH$_4$, Ascentis Express C18 2.7 μm (50×2.1) mm, gradient=4 min, wavelength=220 nm); HPLC RT=9.112 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=10.61 min (Column: Chiralpak IC, 250×4.6 mm, 5 μm; Mobile Phase: 60/40 CO$_2$/(0.25% DEA in MeOH); Flow: 4 mL/min). Enantiomer B: Chiral SFC RT=12.94 min (Column: Chiralpak IC, 250×4.6 mm, 5 μm; Mobile Phase: 60/40 CO$_2$/(0.25% DEA in MeOH); Flow: 4 mL/min).

Examples 112 & 113

2-[3-(Dimethyl-1H-1,2,3-triazol-5-yl)-9-fluoro-5-[(3-fluorophenyl)(oxan-4-yl)methyl]-5H-pyrido[3,2-b]indol-7-yl]propan-2-ol

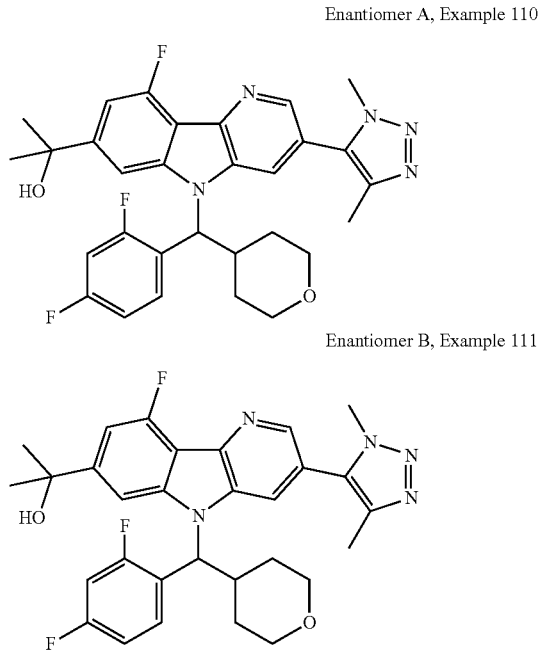

Enantiomer A, Example 110

Enantiomer B, Example 111

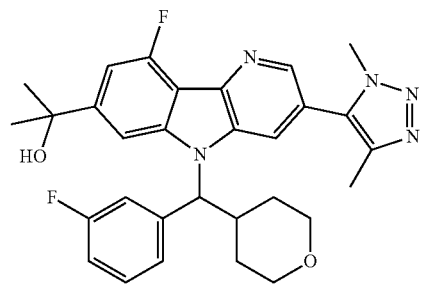

Enantiomer A, Example 112

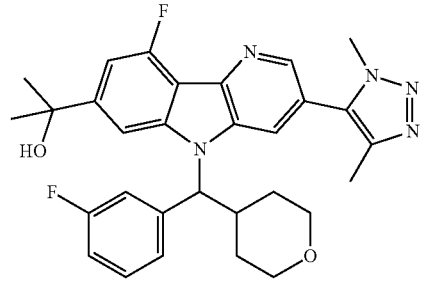

Enantiomer B, Example 113

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,4-difluorophenyl)(oxan-4-yl)methanol and methyl 3-(dimethyl-1H-1,2,3-triazol-5-yl)-9-fluoro-5H-pyrido[3,2-b]indole-7-carboxylate were converted to racemic 2-{5-[(2,4-difluorophenyl)(oxan-4-yl)methyl]-3-(dimethyl-1H-1,2,3-triazol-5-yl)-9-fluoro-5H-pyrido[3,2-b]

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (3-fluorophenyl)(oxan-4-yl)methanol and methyl 3-(dimethyl-1H-1,2,3-triazol-5-yl)-9-fluoro-5H-pyrido[3,2-b]indole-7-carboxylate were converted to racemic 2-[3-(dimethyl-1H-1,2,3-triazol-5-yl)-9-fluoro-5-[(3-fluorophenyl)(oxan-4-yl)methyl]-5H-pyrido[3,2-b]indol-7- yl]propan-2-ol, which was separated by chiral prep SFC (Column: Chiralcel OD-H, 25×2.1 cm, 5 µm; Mobile Phase: 60/40 CO$_2$/(0.25% DEA in MeOH); Flow: 75 mL/min) to give Enantiomer A (5.00 mg, 9%) and Enantiomer B (15.0 mg, 29%). Enantiomer A: $^1$H NMR (400 MHz, CD$_3$OD) δ 8.40 (d, J=2.0 Hz, 1H), 8.2 (br. s., 1H), 7.81 (s, 1H), 7.34-7.26 (m, 3H), 7.18 (m, 1H), 6.91 (m, 1H), 5.70 (d, J=11.5 Hz, 1H), 3.92 (s, 3H), 3.90 (d, J=3.0 Hz, 1H), 3.72 (d, J=3.0 Hz, 1H), 3.51 (m, 1H), 3.40-3.37 (m, 2H), 2.23 (s, 3H), 1.93 (d, J=13.6 Hz, 1H), 1.76-1.61 (m, 7H), 1.49-1.40 (m, 1H), 0.99 (d, J=12.5 Hz, 1H). LCMS: RT=1.85 min; MS (ES): m/z=532.2 [M+H]$^+$ (ACN/H$_2$O with HCOONH$_4$, Ascentis Express C18 2.7 µm (50×2.1) mm, gradient=4 min, wavelength=220 nm). HPLC RT=8.907 min (Column: Sunfire C18 3.5 µm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.09 min (Column: Chiralcel OD-H, 250× 4.6 mm, 5 µm; Mobile Phase: 60/40 CO$_2$/(0.25% DEA in MeOH); Flow: 4 mL/min). Enantiomer B: Chiral SFC RT 3.00 min (Column: Chiralcel OD-H, 250×4.6 mm, 5 µm; Mobile Phase: 60/40 CO$_2$/(0.25% DEA in MeOH); Flow: 4 mL/min).

Example 114

2-[3-(Dimethyl-1H-1,2,3-triazol-5-yl)-9-fluoro-5-[(S)-(2-fluorophenyl)(oxan-4-yl)methyl]-5H-pyrido[3,2-b]indol-7-yl]propan-2-ol

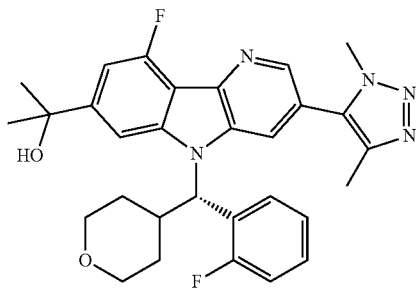 [SMILES: Cc1nnn(C)c1-c1cnc2c3c(F)cc(C(C)(C)O)cc3n([C@H](c3ccccc3F)C3CCOCC3)c2c1]

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (R)-(2-fluorophenyl)(oxan-4-yl)methanol and methyl 3-(dimethyl-1H-1,2,3-triazol-5-yl)-9-fluoro-5H-pyrido[3,2-b]indole-7-carboxylate were converted to 2-[3-(dimethyl-1H-1,2,3-triazol-5-yl)-9-fluoro-5-[(S)-(2-fluorophenyl)(oxan-4-yl)methyl]-5H-pyrido[3,2-b]indol-7-yl]propan-2-ol. LCMS: RT=1.617 min; (ES): m/z (M+H)$^+$=532.2; (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). $^1$H NMR (500 MHz, DMSO-d$_6$) δ 8.57 (br. s., 1H), 8.23 (br. s., 1H), 7.96 (s, 1H), 7.46-7.26 (m, 3H), 7.22 (d, J=11.4 Hz, 1H), 7.18-7.05 (m, 1H), 6.05 (d, J=11.4 Hz, 1H), 4.01 (br. s., 3H), 3.94-3.86 (m, 1H), 3.73 (d, J=9.4 Hz, 1H), 3.49 (br. s., 1H), 3.22 (t, J=11.4 Hz, 1H), 2.30 (br. s., 3H), 1.75 (d, J=11.1 Hz, 1H), 1.69-1.60 (m, 2H), 1.55 (br. s., 6H), 1.36 (d, J=9.1 Hz, 1H).

Examples 115 & 116

5-{5-[(2-Fluorophenyl)(oxan-4-yl)methyl]-9-methanesulfonyl-5H-pyrido[3,2-b]indol-3-yl}-1,4-dimethyl-1H-1,2,3-triazole Enantiomer A, Example 115

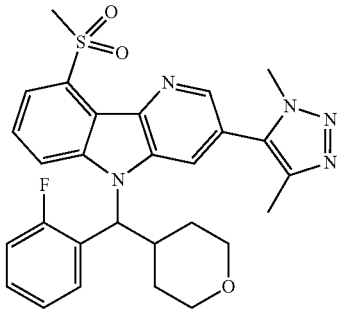

Enantiomer B, Example 116

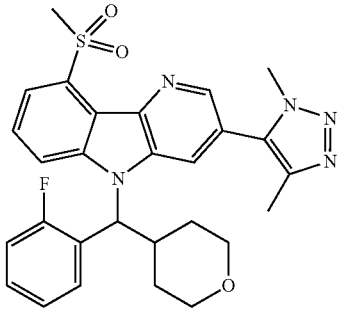

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2-fluorophenyl)(oxan-4-yl)methanol and methyl 3-(dimethyl-1H-1,2,3-triazol-5-yl)-9-methanesulfonyl-5H-pyrido[3,2-b]indole-7-carboxylate were converted to racemic 5-{5-[(2-fluorophenyl)(oxan-4-yl)methyl]-9-methanesulfonyl-5H-pyrido[3,2-b]indol-3-yl}-1,4-dimethyl-1H-1,2,3-triazole, which was separated by chiral prep SFC (Column: Chiralcel OD-H, 25×2.1 cm, 5 µm; Mobile Phase: 60/40 CO$_2$/(0.25% DEA in MeOH); Flow: 75 mL/min) to give Enantiomer A (14.0 mg, 9%) and Enantiomer B (15.0 mg, 9%). Enantiomer A: $^1$H NMR (400 MHz, CD$_3$OD) δ 8.71 (d, J=2.0 Hz, 1H), 8.42 (br. s., 2H), 8.21-8.14 (m, 1H), 8.08 (d, J=7.5 Hz, 1H), 7.84 (br. s., 1H), 7.43-7.33 (m, 2H), 7.12-7.03 (m, 1H), 6.16 (d, J=11.5 Hz, 1H), 4.10-3.98 (m, 4H), 3.85-3.77 (m, 4H), 3.63 (dd, J=10.0, 11.5 Hz, 1H), 3.49-3.36 (m, 2H), 2.37 (s, 3H), 2.03-1.94 (m, 1H), 1.76-1.62 (m, 1H), 1.45 (dt, J=7.8, 12.4 Hz, 1H), 0.92 (d, J=14.1 Hz, 1H). LCMS: RT=1.863 min; MS (ES): m/z=534.2 [M+H]$^+$ (ACN/H$_2$O with HCOONH$_4$, Ascentis Express C18 2.7 µm (50×2.1) mm, gradient=4 min, wavelength=220 nm). HPLC RT=9.004 min (Column: Sunfire C18 3.5 µm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.58 min (Column: Chiralcel OD-H, 250×4.6 mm, 5 µm; Mobile Phase: 60/40 CO$_2$/(0.25% DEA in MeOH); Flow: 4 mL/min). Enantiomer B: Chiral SFC RT 6.18 min

Examples 117 & 118

5-{9-Methanesulfonyl-5-[oxan-4-yl(2,4,6-trifluorophenyl)methyl]-5H-pyrido[3,2-b]indol-3-yl}-1,4-dimethyl-1H-1,2,3-triazole Enantiomer A, Example 117

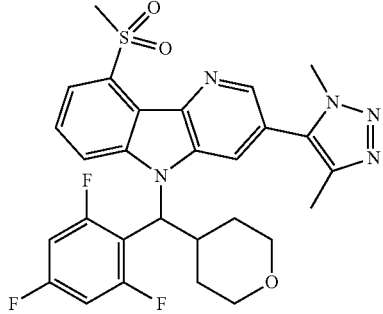

Enantiomer B, Example 118

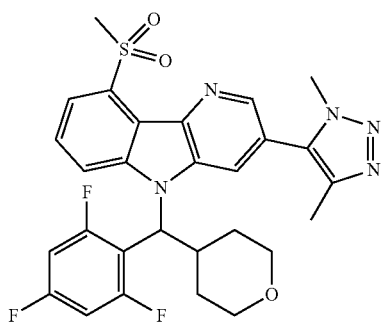

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,4,6-trifluorophenyl)(oxan-4-yl)methanol and methyl 3-(dimethyl-1H-1,2,3-triazol-5-yl)-9-methanesulfonyl-5H-pyrido[3,2-b]indole-7-carboxylate were converted to racemic 5-{9-methanesulfonyl-5-[oxan-4-yl(2,4,6-trifluorophenyl)methyl]-5H-pyrido[3,2-b]indol-3-yl}-1,4-dimethyl-1H-1,2,3-triazole, which was separated by chiral prep SFC (Column: Chiralcel OD-H, 25×2.1 cm, 5 μm; Mobile Phase: 60/40 CO$_2$/(0.25% DEA in MeOH); Flow: 75 mL/min) to give Enantiomer A (13.0 mg, 8%) and Enantiomer B (13.0 mg, 8%). Enantiomer A: $^1$H NMR (400 MHz, CD$_3$OD) δ 8.76 (d, J=1.5 Hz, 1H), 8.47 (br. s., 1H), 8.34 (br. s., 1H), 8.11 (d, J=7.0 Hz, 1H), 7.93-7.82 (m, 1H), 7.02 (t, J=9.0 Hz, 2H), 6.22 (d, J=11.5 Hz, 1H), 4.14 (s, 3H), 4.05 (d, J=11.5 Hz, 1H), 3.86-3.76 (m, 4H), 3.61-3.52 (m, 1H), 3.46-3.36 (m, 2H), 2.42 (s, 3H), 1.83 (d, J=12.0 Hz, 1H), 1.77-1.63 (m, 1H), 1.50-1.39 (m, 1H), 1.01 (d, J=12.5 Hz, 1H). LCMS: RT=1.898 min; MS (ES): m/z=570.2 [M+H]$^+$ (ACN/H$_2$O with HCOONH$_4$, Ascentis Express C18 2.7 μm (50×2.1) mm, gradient=4 min, wavelength=220 nm). HPLC RT=9.683 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.18 min (Column: Chiralcel OD-H, 250×4.6 mm, 5 μm; Mobile Phase: 60/40 CO$_2$/(0.25% DEA in MeOH); Flow: 4 mL/min). Enantiomer B: Chiral SFC RT 4.78 min (Column: Chiralcel OD-H, 250×4.6 mm, 5 μm; Mobile Phase: 60/40 CO$_2$/(0.25% DEA in MeOH); Flow: 4 mL/min).

Examples 119 & 120

2-[3-(Dimethyl-1H-1,2,3-triazol-5-yl)-5-[(2-fluoro-4-methoxyphenyl)(oxan-4-yl)methyl]-5H-pyrido[3, 2-b]indol-7-yl]propan-2-ol Enantiomer A, Example 119

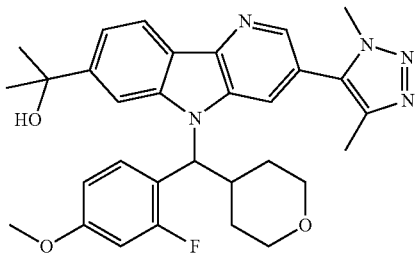

Enantiomer B, Example 120

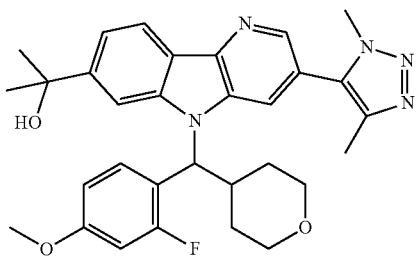

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2-fluoro-4-methoxyphenyl)(tetrahydro-2H-pyran-4-yl)methanol was converted to racemin 2-[3-(dimethyl-1H-1,2,3-triazol-5-yl)-5-[(2-fluoro-4-methoxyphenyl)(oxan-4-yl)methyl]-5H-pyrido[3,2-b]indol-7-yl]propan-2-ol, which was separated using chiral prep SFC (Column: Chiral OD-H 25×2.1 cm, 5 μm; Mobile Phase: 60/40 CO$_2$/(0.25% DEA in MeOH); Flow: 70 mL/min) to give 2 enantiomers. Enantiomer A: $^1$H NMR (400 MHz, CD$_3$OD) δ 8.47 (d, J=1.5 Hz, 1H), 8.30 (d, J=8.0 Hz, 2H), 8.06 (s, 1H), 7.98 (t, J=8.8 Hz, 1H), 7.53-7.47 (m, 1H), 6.89 (dd, J=2.0, 8.5 Hz, 1H), 6.68 (dd, J=2.5, 12.5 Hz, 1H), 5.92 (d, J=11.5 Hz, 1H), 4.10-3.97 (m, 4H), 3.86-3.75 (m, 4H), 3.66-3.57 (m, 1H), 3.43-3.36 (m, 2H), 2.42-2.34 (m, 3H), 1.95 (d, J=9.5 Hz, 1H), 1.72-1.60 (m, 7H), 1.43 (dq, J=4.5, 12.4 Hz, 1H), 0.98 (d, J=12.0 Hz, 1H). LCMS: RT=1.831 min; MS (ES): m/z=544.4 [M+H]$^+$ (ACN/H$_2$O with HCOONH$_4$, Ascentis Express C18 2.7 μm (50×2.1) mm, gradient=4 min, wavelength=220 nm); HPLC RT=8.114 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.20 min (Column: Chiralcel OD-H 250×4.6 mm, 5 μm; Mobile Phase: 60/40 CO$_2$/(0.25% DEA in MeOH); Flow: 4 mL/min). Enantiomer B: Chiral SFC RT=3.40 min (Column: Chiralcel OD-H 250×4.6 mm, 5 μm; Mobile Phase: 60/40 CO$_2$/(0.25% DEA in MeOH); Flow: 4 mL/min).

Examples 121 & 122

2-{5-[(2,3-Difluoro-4-methoxyphenyl)(oxan-4-yl)methyl]-3-(dimethyl-1H-1,2,3-triazol-5-yl)-5H-pyrido[3,2-b]indol-7-yl}propan-2-ol Enantiomer A, Example 121

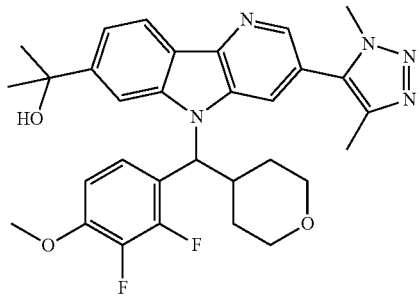

Enantiomer B, Example 122

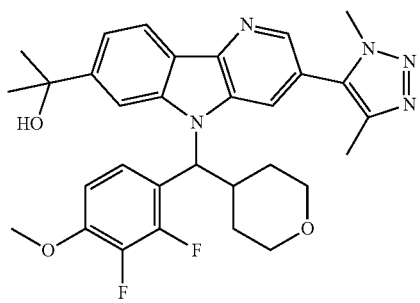

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,3-difluoro-4-methoxyphenyl)(tetrahydro-2H-pyran-4-yl)methanol was converted to racemic 2-{5-[(2,3-difluoro-4-methoxyphenyl)(oxan-4-yl)methyl]-3-(dimethyl-1H-1,2,3-triazol-5-yl)-5H-pyrido[3,2-b]indol-7-yl}propan-2-ol, which was separated using chiral prep SFC (Column: Chiral OD-H 25×2.1 cm, 5 μm; Mobile Phase: 60/40 CO$_2$/(0.25% DEA in MeOH); Flow: 70 mL/min) to give 2 enantiomers. Enantiomer A: $^1$H NMR (400 MHz, CD$_3$OD) δ ppm 8.46 (d, J=1.51 Hz, 1H) 8.29 (d, J=8.53 Hz, 2H) 8.02 (s, 1H) 7.78 (t, J=7.28 Hz, 1H) 7.48 (d, J=8.03 Hz, 1H) 7.03 (t, J=7.28 Hz, 1H) 5.92 (d, J=11.04 Hz, 1H) 4.05 (s, 3H) 3.99 (d, J=9.04 Hz, 1H) 3.88 (s, 3H) 3.79 (d, J=10.04 Hz, 1H) 3.58 (t, J=11.04 Hz, 1H) 3.34-3.40 (m, 2H) 2.35 (s, 3H) 1.91 (d, J=11.55 Hz, 1H) 1.57-1.70 (m, 7H) 1.37-1.46 (m, 1H) 0.95 (d, J=14.06 Hz, 1H). LCMS: RT=2.38 min; MS (ES): m/z=560 [M–H]— (ACN/H$_2$O with HCOONH$_4$, Ascentis Express C18 2.7 μm (50×2.1) mm, gradient=4 min, wavelength=220 nm); HPLC RT=7.953 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.19 min (Column: Chiralcel OD-H 250×4.6 mm, 5 μm; Mobile Phase: 60/40 CO$_2$/(0.25% DEA in MeOH); Flow: 4 mL/min). Enantiomer B: Chiral SFC RT=3.27 min (Column: Chiralcel OD-H 250×4.6 mm, 5 μm; Mobile Phase: 60/40 CO$_2$/(0.25% DEA in MeOH); Flow: 4 mL/min).

Examples 123 & 124

2-{5-[(2,5-Difluoro-4-methoxyphenyl)(oxan-4-yl)methyl]-3-(dimethyl-1H-1,2,3-triazol-5-yl)-5H-pyrido[3,2-b]indol-7-yl}propan-2-ol Enantiomer A, Example 123

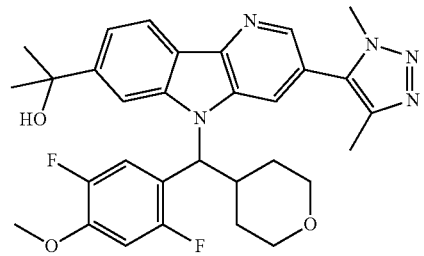

Enantiomer B, Example 124

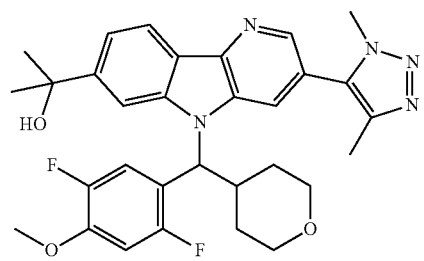

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, (2,5-difluoro-4-methoxyphenyl)(tetrahydro-2H-pyran-4-yl)methanol was converted to racemic 2-{5-[(2,5-difluoro-4-methoxyphenyl)(oxan-4-yl)methyl]-3-(dimethyl-1H-1,2,3-triazol-5-yl)-5H-pyrido[3,2-b]indol-7-yl}propan-2-ol, which was separated using chiral prep SFC (Column: Lux Cellulose –4, 25×2.1 cm, 5 μm; Mobile Phase: 60/40 CO$_2$/(0.25% DEA in methanol); Flow: 75 mL/min) to give 2 enantiomers. Enantiomer A: $^1$H NMR (400 MHz, CD$_3$OD) δ ppm 8.46 (d, J=1.51 Hz, 1H) 8.34 (br. s., 1H) 8.28 (d, J=8.03 Hz, 1H) 8.03 (s, 1H) 7.89 (dd, J=12.05, 7.03 Hz, 1H) 7.49 (dd, J=8.28, 1.25 Hz, 1H) 6.89 (dd, J=11.55, 7.03 Hz, 1H) 5.91 (d, J=11.55 Hz, 1H) 4.06 (s, 3H) 4.00 (d, J=7.03 Hz, 1H) 3.76-3.84 (m, 4H) 3.60 (t, J=10.79 Hz, 1H) 3.35-3.41 (m, 2H) 2.36 (s, 3H) 1.83-1.93 (m, 1H) 1.58-1.69 (m, 7H) 1.43 (br. s., 1H) 0.99 (d, J=13.05 Hz, 1H). LCMS: RT=1.83 min; MS (ES): m/z=562 [M+H]$^+$ (ACN/H$_2$O with HCOONH$_4$, Ascentis Express C18 2.7 μm (50×2.1) mm, gradient=4 min, wavelength=220 nm); HPLC RT=7.953 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=6.70 min (Column: Lux Cellulose –4, 250×21 mm, 5 μm; Mobile Phase: 60/40 CO$_2$/(0.25% DEA in methanol); Flow: 4 mL/min). Enantiomer B: Chiral SFC RT=12.06 min (Column: Lux Cellulose –4, 250×21 mm, 5 μm; Mobile Phase: 60/40 CO$_2$/(0.25% DEA in methanol); Flow: 4 mL/min).

Examples 125 & 126

2-{5-[(2,4-Difluorophenyl)(oxan-4-yl)methyl]-3-(dimethyl-1,2-oxazol-4-yl)-5H-pyrido[3,2-b]indol-7-yl}propan-2-ol Enantiomer A, Example 125

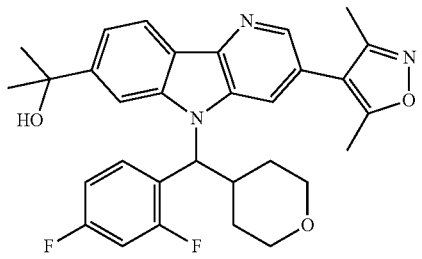

Enantiomer B, Example 126

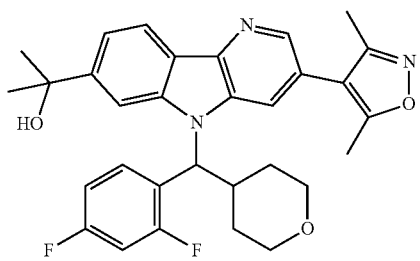

Examples 127 & 128

2-[3-(Dimethyl-1,2-oxazol-4-yl)-5-[oxan-4-yl(2,4,6-trifluorophenyl)methyl]-5H-pyrido[3,2-b]indol-7-yl]propan-2-ol Enantiomer A, Example 127

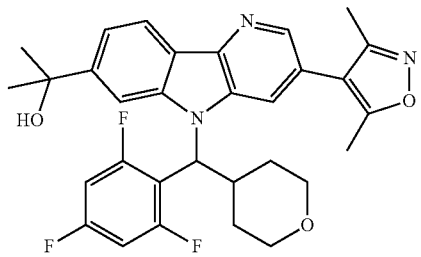

Enantiomer B, Example 128

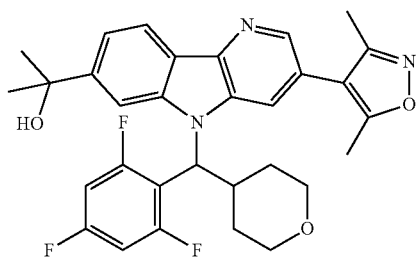

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, 3-(3,5-dimethylisoxazol-4-yl)-5H-pyrido[3,2-b]indole-7-carboxylate and (2,4-difluorophenyl)(tetrahydro-2H-pyran-4-yl)methanol were converted to racemic 2-{5-[(2,4-difluorophenyl)(oxan-4-yl)methyl]-3-(dimethyl-1,2-oxazol-4-yl)-5H-pyrido[3,2-b]indol-7-yl}propan-2-ol, which was separated using chrial prep SFC (Column: Chiral OD-H 25×2.1 cm, 5 μm; Mobile Phase: 75/25 CO$_2$/(0.25% DEA in MeOH); Flow: 70 mL/min) to give 2 enantiomers. Enantiomer A: $^1$H NMR (400 MHz, d4-MeOH) δ 8.39 (m, 1H), 8.28-8.12 (m, 3H), 8.02 (m, 1H), 7.47 (d, J=9.6 Hz, 1H), 7.12 (m, 1H), 6.96 (m, 1H), 5.95 (d, J=11.2 Hz, 1H), 4.03 (m, 1H), 3.81 (m, 1H), 3.61 (m, 1H), 3.33 (m, 3H), 2.51 (s, 3H), 2.35 (s, 3H), 1.91 (m, 1H), 1.68 (s, 6H), 1.64 (m, 1H), 1.43 (m, 1H), 0.99 (m, 1H). LCMS: RT=2.00 min; MS (ES): m/z=532.5 [M+H]$^+$ (ACN/H$_2$O with HCOONH$_4$, Ascentis Express C18 2.7 μm (50×2.1) mm, gradient=4 min, wavelength=220 nm); HPLC RT=8.530 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=4.06 min (Column: Chiralcel OD-H 250×4.6 mm, 5 μm; Mobile Phase: 75/25 CO$_2$/(0.25% DEA in MeOH); Flow: 3 mL/min). Enantiomer B: Chiral SFC RT=4.87 min (Column: Chiralcel OD-H 250×4.6 mm, 5 μm; Mobile Phase: 75/25 CO$_2$/(0.25% DEA in MeOH); Flow: 3 mL/min).

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, methyl 3-(3,5-dimethylisoxazol-4-yl)-5H-pyrido[3,2-b]indole-7-carboxylate and (2,4,6-trifluorophenyl)(tetrahydro-2H-pyran-4-yl)methanol were converted to racemic 2-[3-(dimethyl-1,2-oxazol-4-yl)-5-[oxan-4-yl(2,4,6-trifluorophenyl)methyl]-5H-pyrido[3,2-b]indol-7-yl]propan-2-ol, which was separated using chiral prep SFC (Column: Lux Cellulose –2, 25×2.1 cm, 5 μm; Mobile Phase: 75/25 CO$_2$/(0.25% DEA in methanol); Flow: 60 mL/min) to give 2 enantiomers. Enantiomer A: $^1$H NMR (400 MHz, d4-MeOH) δ 8.42 (m, 1H), 8.28 (m, 2H), 8.06 (m, 1H), 7.52 (m, 1H), 6.99 (t, J=8.0 Hz, 2H), 6.05 (d, J=11.6 Hz, 1H), 4.04 (m, 1H), 3.83 (m, 1H), 3.66 (m, 1H), 3.57 (m, 1H), 2.54 (s, 3H), 2.39 (s, 3H), 1.81 (m, 1H), 1.67 (m, 8H), 1.41 (m, 1H), 1.16 (m, 1H). LCMS: RT=2.01 min; MS (ES): m/z=550.5 [M+H]$^+$ (ACN/H$_2$O with HCOONH$_4$, Ascentis Express C18 2.7 μm (50×2.1) mm, gradient=4 min, wavelength=220 nm); HPLC RT=8.529 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=7.40 min (Column: Lux Cellulose –2, 250×4.6 mm, 5 μm; Mobile Phase: 70/30 CO$_2$/(0.25% DEA in methanol); Flow: 3 mL/min). Enantiomer B: Chiral SFC RT=8.59 min (Column: Lux Cellulose –2, 250×4.6 mm, 5 μm; Mobile Phase: 70/30 CO$_2$/(0.25% DEA in MeOH); Flow: 3 mL/min).

Examples 129 & 130

2-{5-[(3,5-Difluorophenyl)(oxan-4-yl)methyl]-3-(dimethyl-1,2-oxazol-4-yl)-5H-pyrido[3,2-b]indol-7-yl}propan-2-ol Enantiomer A, Example 129

Enantiomer B, Example 130

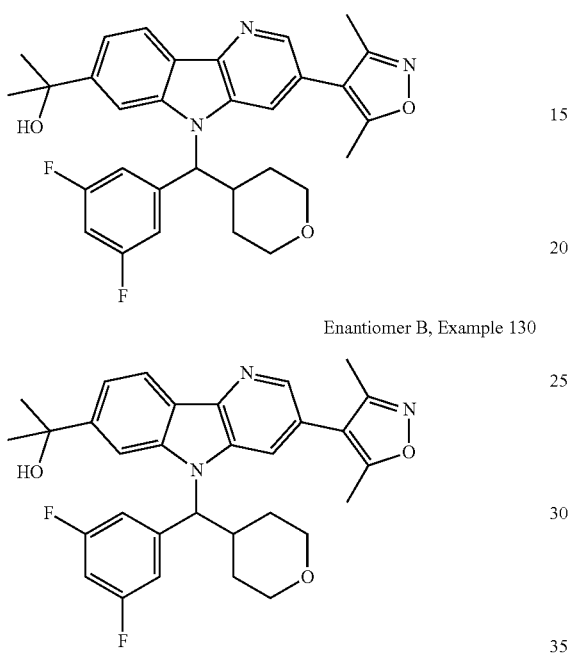

Following a procedure analogous to that described for the synthesis of 2-{5-[(3,4-difluorophenyl)(oxan-4-yl)methyl]-3-(dimethyl-1H-1,2,3-triazol-5-yl)-5H-pyrido[3,2-b]indol-7-yl}propan-2-ol, methyl 3-(3,5-dimethylisoxazol-4-yl)-5H-pyrido[3,2-b]indole-7-carboxylate and (3,5-difluorophenyl)(tetrahydro-2H-pyran-4-yl)methanol were converted to racemic 2-{5-[(3,5-difluorophenyl)(oxan-4-yl)methyl]-3-(dimethyl-1,2-oxazol-4-yl)-5H-pyrido[3,2-b]indol-7-yl}propan-2-ol, which was separated using chiral prep SFC (Column: Lux Cellulose -2, 25×2.1 cm, 5 μm; Mobile Phase: 65/35 CO$_2$/(0.25% DEA in methanol); Flow: 60 mL/min) to give 2 enantiomers. Enantiomer A: $^1$H NMR (400 MHz, CD$_3$OD) δ 8.43-8.38 (m, 1H), 8.30 (d, J=8.5 Hz, 1H), 8.19 (s, 1H), 8.09 (s, 1H), 7.54-7.48 (m, 1H), 7.30 (d, J=6.5 Hz, 2H), 6.96-6.87 (m, 1H), 5.77 (d, J=11.0 Hz, 1H), 4.02 (d, J=12.0 Hz, 1H), 3.84 (d, J=11.5 Hz, 1H), 3.69-3.58 (m, 1H), 3.48-3.36 (m, 2H), 2.49 (s, 3H), 2.33 (s, 3H), 1.92 (d, J=12.5 Hz, 1H), 1.70 (d, J=4.0 Hz, 6H), 1.67 (m, 1H), 1.43 (m, 1H), 1.16 (d, J=12.5 Hz, 1H). LCMS: RT=2.26 min; MS (ES): m/z=532.2 [M+H]$^+$ (ACN/H$_2$O with HCOONH$_4$, Ascentis Express C18 2.7 μm (50×2.1) mm, gradient=4 min, wavelength=220 nm); HPLC RT=8.948 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.79 min (Column: Lux Cellulose -2, 250×4.6 mm, 5 μm; Mobile Phase: 70/30 CO$_2$/(0.25% DEA in methanol); Flow: 3 mL/min). Enantiomer B: Chiral SFC RT=4.67 min (Column: Lux Cellulose -2, 250×4.6 mm, 5 μm; Mobile Phase: 70/30 CO$_2$/(0.25% DEA in MeOH); Flow: 3 mL/min).

Examples 131 & 132

2-{5-[(2,5-Difluorophenyl)(oxan-4-yl)methyl]-3-(dimethyl-1H-1,2,3-triazol-5-yl)-5H-pyrido[3,2-b]indol-7-yl}propan-2-ol Enantiomer A, Example 131

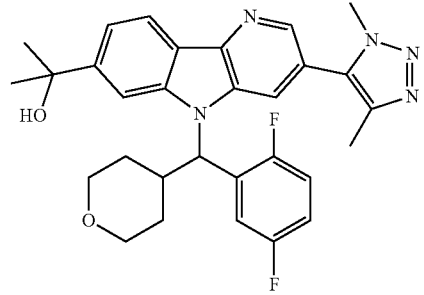

Enantiomer B, Example 132

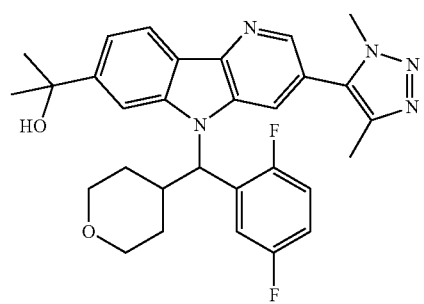

Step 1: Methyl 3-bromo-5-((2,5-difluorophenyl)(tetrahydro-2H-pyran-4-yl)methyl)-5H-pyrido[3,2-b]indole-7-carboxylate A mixture of methyl 3-bromo-5H-pyrido[3,2-b]indole-7-carboxylate (300 mg, 0.983 mmol) and (2,5-difluorophenyl)(tetrahydro-2H-pyran-4-yl)methanol (449 mg, 1.97 mmol) in DCM (18 mL) was added triphenylphosphine (516 mg, 1.97 mmol) and DIAD (0.382 mL, 1.97 mmol) drop wise over the period of 2 min at 25° C., and the resulting mixture was stirred at room temperature for 16 h. The mixture was purified using silica gel column chromatography on an ISCO Companion (24 g silica gel flash column) using a gradient of 0 to 1% MeOH/CHCl$_3$ over 30 min. Fractions containing product were combined and concentrated, and the solid obtained was triturated with diethyl ether (10 mL) to give methyl 3-bromo-5-((2,5-difluorophenyl)(tetrahydro-2H-pyran-4-yl)methyl)-5H-pyrido[3,2-b]indole-7-carboxylate (200 mg, 37%) as a white solid. LCMS: HPLC: RT=1.21 min, MS (ES): m/z=515, 517 [M+H]$^+$; (ACN/H$_2$O with NH$_4$OAc, Acquity BEH C18 1.7 μm (50×2.1) mm, gradient=3 min, wavelength=220 nm).

Step 2: Methyl 5-((2,5-difluorophenyl)(tetrahydro-2H-pyran-4-yl)methyl)-3-(1,4-dimethyl-1H-1,2,3-triazol-5-yl)-5H-pyrido[3,2-b]indole-7-carboxylate A stirred solution of methyl 3-bromo-5-((2,5-difluorophenyl)(tetrahydro-2H-pyran-4-yl)methyl)-5H-pyrido[3,2-b]indole-7-carboxylate (0.400 g, 0.287 mmol) and 1,4-dimethyl-5-(tributylstannyl)-1H-1,2,3-triazole (0.122 g, 0.316 mmol) in DMF (1.5 ml) was purged under a stream of nitrogen for several min. To the mixture was added tetrakis(triphenylphosphine) palladium (0.022 g, 0.0190 mmol), copper(I) iodide (8.20 mg, 0.0430 mmol), and $Et_3N$ (0.0800 mL, 0.574 mmol), and the mixture was heated to 95° C. for 2 h in a microwave. The mixture was diluted with water (20 mL) and extracted with EtOAc (30 mL×2), and the extracts concentrated. The residue was purified using silica gel column chromatography (ISCO, Silica adsorbed, 12 g flash column, 0 to 1.5% $MeOH/CHCl_3$ over 30 min). Fractions containing the product were concentrated to give methyl 5-((2,5-difluorophenyl)(tetrahydro-2H-pyran-4-yl)methyl)-3-(1,4-dimethyl-1H-1,2,3-triazol-5-yl)-5H-pyrido[3,2-b]indole-7-carboxylate (0.100 g, 0.188 mmol, 66%) as a white solid. LCMS: HPLC: RT=1.04 min, MS (ES): m/z=532 $[M+H]^+$; ($ACN/H_2O$ with $NH_4OAc$, Acquity BEH C18 1.7 μm (50×2.1) mm, gradient=3 min, wavelength=220 nm).

Step 3: 2-{5-[(2,5-Difluorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described in Step 2 for the synthesis of 2-[3-(dimethyl-1H-1,2,3-triazol-5-yl)-5-[(S)-oxan-4-yl(phenyl)($^2$H)methyl]-5H-pyrido[3,2-b]indol-7-yl]propan-2-ol, methyl 5-((2,5-difluorophenyl)(tetrahydro-2H-pyran-4-yl)methyl)-3-(1,4-dimethyl-1H-1,2,3-triazol-5-yl)-5H-pyrido[3,2-b]indole-7-carboxylate was converted to racemic 2-{5-[(2,5-difluorophenyl)(oxan-4-yl)methyl]-3-(dimethyl-1H-1,2,3-triazol-5-yl)-5H-pyrido[3,2-b]indol-7-yl}propan-2-ol as a white solid, which was separated by chiral prep SFC (Column: Chiral OD-H 25×2.1 cm, 5 μm; Mobile Phase: 80/20 $CO_2$/(0.25% DEA in MeOH); Flow: 70 mL/min) to give Enantiomer A (20.0 mg, 20%) and Enantiomer B (16.0 mg, 16%). Enantiomer A: $^1$H NMR (400 MHz, $CD_3OD$) δ 8.47 (d, J=2.0 Hz, 1H), 8.37 (br. s., 1H), 8.30 (s, 1H), 8.04 (s, 1H), 7.98-7.88 (m, 1H), 7.54-7.46 (m, 1H), 7.14-7.05 (m, 2H), 5.98 (d, J=11.0 Hz, 1H), 4.06 (s, 3H), 4.00 (d, J=8.5 Hz, 1H), 3.81 (br. s., 1H), 3.66-3.57 (m, 1H), 3.43-3.34 (m, 2H), 2.36 (s, 3H), 1.90 (d, J=13.1 Hz, 1H), 1.70-1.61 (m, 7H), 1.43 (dt, J=7.8, 12.4 Hz, 1H), 1.00 (d, J=13.6 Hz, 1H). LCMS: RT=1.822 min; MS (ES): m/z=532.5 $[M+H]^+$ ($ACN/H_2O$ with $HCOONH_4$, Ascentis Express C18 2.7 μm (50×2.1) mm, gradient=4 min, wavelength=220 nm); HPLC RT=8.178 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=8.76 min (Column: Chiralcel OD-H 250×4.6 mm, 5 μm; Mobile Phase: 80/20 $CO_2$/(0.25% DEA in MeOH); Flow: 3 mL/min). Enantiomer B: Chiral SFC RT=8.17 min (Column: Chiralcel OD-H 250×4.6 mm, 5 μm; Mobile Phase: 80/20 $CO_2$/(0.25% DEA in MeOH); Flow: 3 mL/min).

Examples 133 & 134

2-{5-[(2,6-Difluorophenyl)(oxan-4-yl)methyl]-3-(dimethyl-1H-1,2,3-triazol-5-yl)-5H-pyrido[3,2-b]indol-7-yl}propan-2-ol

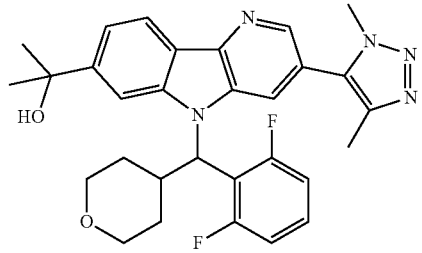

Enantiomer A, Example 133

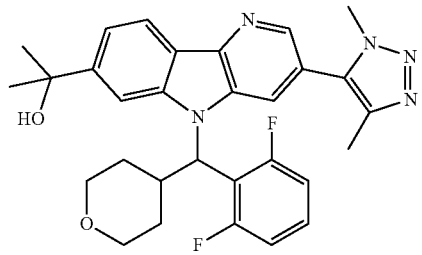

Enantiomer B, Example 134

Following a procedure analogous to that described for the synthesis of 2-{5-[(2,5-difluorophenyl)(oxan-4-yl)methyl]-3-(dimethyl-1H-1,2,3-triazol-5-yl)-5H-pyrido[3,2-b]indol-7-yl}propan-2-ol, (2,6-difluorophenyl)(tetrahydro-2H-pyran-4-yl)methanol was converted to racemic 2-{5-[(2,6-difluorophenyl)(oxan-4-yl)methyl]-3-(dimethyl-1H-1,2,3-triazol-5-yl)-5H-pyrido[3,2-b]indol-7-yl}propan-2-ol, which was separated by chiral prep SFC (Column: Chiral OD-H 25×2.1 cm, 5 μm; Mobile Phase: 70/30 $CO_2$/(0.25% DEA in MeOH); Flow: 60 mL/min) to give Enantiomer A (30.0 mg, 22%) and Enantiomer B (30.0 mg, 22%). Enantiomer A: $^1$H NMR (400 MHz, $CD_3OD$): δ 8.50-8.51 (m, 1H), 8.41 (s, 1H), 8.32 (d, J=8.00 Hz, 1H), 7.54-7.56 (m, 1H), 7.40-7.44 (m, 1H), 7.39-7.43 (m, 1H), 7.05-7.09 (m, 2H), 6.09-6.12 (m, 1H), 4.12 (s, 3H), 4.03-4.06 (m, 1H), 3.81-3.84 (m, 1H), 3.54-3.62 (m, 1H), 3.45-3.51 (m, 1H), 2.41 (s, 3H), 1.82-1.85 (m, 1H), 1.70 (s, 6H), 1.31-1.46 (m, 2H), 1.23-1.31 (m, 1H), 1.08-1.12 (m, 1H). LCMS: RT=2.43 min; MS (ES): m/z=532.2 $[M+H]^+$ ($ACN/H_2O$ with $HCOONH_4$, Ascentis Express C18 2.7 μm (50×2.1) mm, gradient=4 min, wavelength=220 nm); HPLC RT=8.053 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=7.83 min (Column: Lux Cellulose 2, 250×4.6 mm, 5 μm; Mobile Phase: 60/40 $CO_2$/(0.25% DEA in MeOH); Flow: 4 mL/min). Enantiomer B: Chiral SFC RT=9.03 min (Column: Lux Cellulose 2, 250×4.6 mm, 5 μm; Mobile Phase: 60/40 $CO_2$/(0.25% DEA in MeOH); Flow: 4 mL/min).

Examples 135 & 136

2-{5-[(2,4-Difluorophenyl)(oxan-4-yl)methyl]-3-(dimethyl-1H-1,2,3-triazol-5-yl)-5H-pyrido[3,2-b]indol-7-yl}propan-2-ol

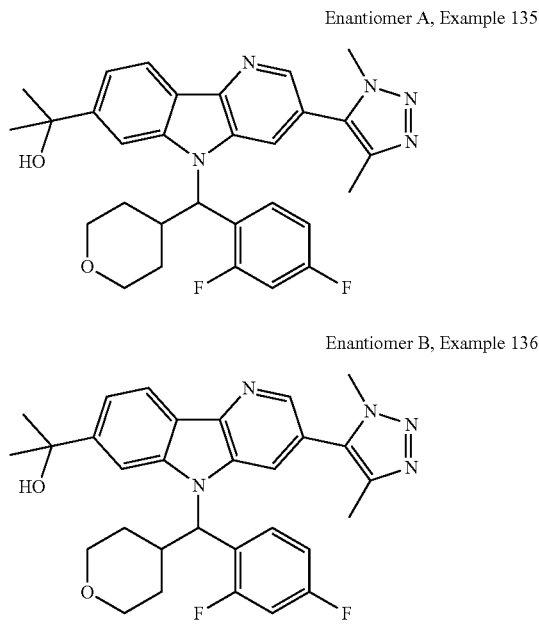

Enantiomer A, Example 135

Enantiomer B, Example 136

Following a procedure analogous to that described for the synthesis of 2-{5-[(2,5-difluorophenyl)(oxan-4-yl)methyl]-3-(dimethyl-1H-1,2,3-triazol-5-yl)-5H-pyrido[3,2-b]indol-7-yl}propan-2-ol, (2,4-difluorophenyl)(tetrahydro-2H-pyran-4-yl)methanol was converted to racemic 2-{5-[(2,4-difluorophenyl)(oxan-4-yl)methyl]-3-(dimethyl-1H-1,2,3-triazol-5-yl)-5H-pyrido[3,2-b]indol-7-yl}propan-2-ol, which was separated by chiral prep SFC (Column: Lux Cellulose 4, 250×21.5 mm, 5 μm; Mobile Phase: 65/35 CO$_2$/(0.25% DEA in MeOH); Flow: 70 mL/min)) to give Enantiomer A (26.0 mg, 8%) and Enantiomer B (20.0 mg, 6%). Enantiomer A: $^1$H NMR (400 MHz, CD$_3$OD): δ 8.46 (m, 1H), 8.32-8.27 (m, 2H), 8.14 (m, 1H), 8.01 (m, 1H), 7.48 (dd, J=8.0, 0.8 Hz, 1H), 7.10 (m, 1H), 6.93 (m, 1H), 5.95 (d, J 11.2 Hz, 1H), 4.05 (s, 3H), 3.99 (m, 1H), 3.79 (m, 1H), 3.58 (m, 1H), 3.36 (m, 2H), 2.35 (s, 3H), 1.89 (m, 1H), 1.66 (s, 3H), 1.64 (s, 3H), 1.61 (m, 1H), 1.41 (m, 1H), 0.95 (m, 1H). LCMS: RT=1.84 min; MS (ES): m/z=532.2 [M+H]$^+$ (ACN/H$_2$O with HCOONH$_4$, Ascentis Express C18 2.7 μm (50×2.1) mm, gradient=4 min, wavelength=220 nm); HPLC RT=8.301 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=4.32 min (Column: Lux Cellulose 4, 250×4.6 mm, 5 μm; Mobile Phase: 65/35 CO$_2$/(0.25% DEA in MeOH); Flow: 4 mL/min). Enantiomer B: Chiral SFC RT=9.15 min (Column: Lux Cellulose 4, 250×4.6 mm, 5 μm; Mobile Phase: 65/35 CO$_2$/(0.25% DEA in MeOH); Flow: 4 mL/min).

Examples 137 & 138

2-[3-(Dimethyl-1H-1,2,3-triazol-5-yl)-5-[(2-fluorophenyl)(oxan-4-yl)methyl]-9-methoxy-5H-pyrido[3,2-b]indol-7-yl]propan-2-ol

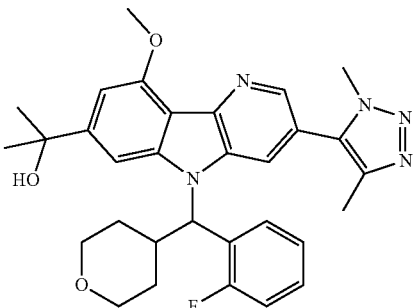

Enantiomer A, Example 137

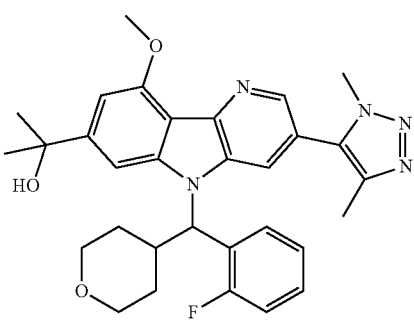

Enantiomer B, Example 138

Following a procedure analogous to that described for the synthesis of 2-{5-[(2,5-difluorophenyl)(oxan-4-yl)methyl]-3-(dimethyl-1H-1,2,3-triazol-5-yl)-5H-pyrido[3,2-b]indol-7-yl}propan-2-ol, (2-fluorophenyl)(oxan-4-yl)methanol and methyl 3-bromo-9-methoxyl-5H-pyrido[3,2-b]indole-7-carboxylate were converted to racemic 2-[3-(dimethyl-1H-1,2,3-triazol-5-yl)-5-[(2-fluorophenyl)(oxan-4-yl)methyl]-9-methoxy-5H-pyrido[3,2-b]indol-7-yl]propan-2-ol, which was separated by chiral prep SFC (Column: Chiral OD-H 25×2.1 cm, 5 μm; Mobile Phase: 60/40 CO$_2$/(0.25% DEA in MeOH); Flow: 60 mL/min) to give Enantiomer A (30.0 mg, 22%) and Enantiomer B (30.0 mg, 22%). Enantiomer A: $^1$H NMR (400 MHz, CD$_3$OD) δ 8.4 (s, 1H), 8.3 (br. s., 1H), 8.1 (td, J=7.5, 2.0 Hz, 1H), 7.6 (s, 1H), 7.3-7.4 (m, 2H), 7.0-7.1 (m, 2H), 6.0 (d, J=11.5 Hz, 1H), 4.1 (s, 3H), 4.0-4.1 (m, 4H), 3.8 (dd, J=11.5, 3.0 Hz, 1H), 3.6-3.7 (m, 1H), 3.4 (d, J=12.0 Hz, 2H), 2.4 (s, 3H), 1.9 (d, J=13.1 Hz, 1H), 1.6-1.7 (m, 7H), 1.4 (qd, J=12.3, 4.3 Hz, 1H), 1.0 (d, J=13.1 Hz, 1H). LCMS: RT=1.76 min; MS (ES): m/z=544.4 [M+H]$^+$ (ACN/H$_2$O with HCOONH$_4$, Ascentis Express C18 2.7 μm (50×2.1) mm, gradient=4 min, wavelength=220 nm); HPLC RT=7.960 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=1.90 min (Column: Chiral OD-H 250×4.6 mm, 5 μm; Mobile Phase: 60/40 CO$_2$/(0.25% DEA in MeOH); Flow: 4 mL/min). Enantiomer B: Chiral SFC RT=2.90 min (Column: Chiral OD-H 250×4.6 mm, 5 μm; Mobile Phase: 60/40 CO$_2$/(0.25% DEA in MeOH); Flow: 4 mL/min).

Examples 139 & 140

2-{5-[(2,5-Difluorophenyl)(oxan-4-yl)methyl]-3-(dimethyl-1,2-oxazol-4-yl)-5H-pyrido[3,2-b]indol-7-yl}propan-2-ol

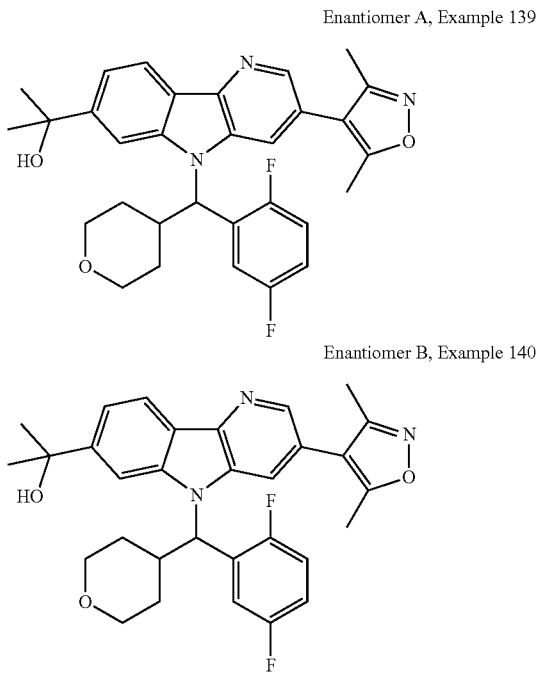

Enantiomer A, Example 139

Enantiomer B, Example 140

Step 1: Methyl 3-bromo-5-((2,5-difluorophenyl)(tetrahydro-2H-pyran-4-yl)methyl)-5H-pyrido[3,2-b]indole-7-carboxylate To a mixture of methyl 3-bromo-5H-pyrido[3,2-b]indole-7-carboxylate (300 mg, 0.983 mmol) and (2,5-difluorophenyl)(tetrahydro-2H-pyran-4-yl)methanol (449 mg, 1.97 mmol) in DCM (18 mL) was added triphenylphosphine (516 mg, 1.97 mmol) and DIAD (0.382 mL, 1.97 mmol) drop wise over the period of 2 min at 25° C., and the resulting mixture stirred at room temperature for 16 h. The mixture was purified using silica gel column chromatography on an ISCO Companion (24 g silica gel flash column, 0 to 1% MeOH/CHCl$_3$ over 30 min). Fractions containing product were combined and concentrated, and the solid obtained was triturated with diethyl ether (10 mL) to give methyl 3-bromo-5-((2,5-difluorophenyl)(tetrahydro-2H-pyran-4-yl)methyl)-5H-pyrido[3,2-b]indole-7-carboxylate (250 mg, 49%) as a white solid. LCMS: HPLC: RT=1.19 min, MS (ES): m/z=515, 517 [M+H]$^+$; (ACN/H$_2$O with NH$_4$OAc, Acquity BEH C18 1.7 μm (50×2.1) mm, gradient=3 min, wavelength=220 nm).

Step 2: Methyl 5-((2,5-difluorophenyl)(tetrahydro-2H-pyran-4-yl)methyl)-3-(3,5-dimethylisoxazol-4-yl)-5H-pyrido[3,2-b]indole-7-carboxylate A mixture of methyl 3-bromo-5-((2,5-difluorophenyl)(tetrahydro-2H-pyran-4-yl)methyl)-5H-pyrido[3,2-b]indole-7-carboxylate (200 mg, 0.388 mmol), 3,5-dimethyl-4-(4,4,5,5-tetramethyl-1,3,2-dioxaborolan-2-yl)isoxazole (130 mg, 0.582 mmol), K$_2$CO$_3$ (161 mg, 1.16 mmol), PdCl$_2$(dppf)-CH$_2$Cl$_2$ adduct (31.7 mg, 0.0390 mmol), 1,4-dioxane (6.5 mL), and water (1.3 mL) in a vial was purged with a stream of argon for 5 min. The vial was capped with a septum, evacuated and filled with argon, and then was heated to 100° C. for 1 h. The mixture was diluted with 30 mL of water and extracted with EtOAc (45 mL×2), dried over Na$_2$SO$_4$, filtered, concentrated, and crude product was purified using silica gel column chromatography using an ISCO (Silica gel, 12 g flash column, 0 to 2% MeOH/CHCl$_3$ over 30 min) to give methyl 5-((2,5-difluorophenyl)(tetrahydro-2H-pyran-4-yl)methyl)-3-(3,5-dimethylisoxazol-4-yl)-5H-pyrido[3,2-b]indole-7-carboxylate (200 mg, 0.376 mmol, 97%) as a yellow liquid. LCMS: RT=0.96 min; MS (ES): m/z=532 [M+1]$^+$ (ACN/H$_2$O with NH$_4$OAc, Acquity BEH C18 1.7 μm (50×2.1) mm, gradient=3 min, wavelength=220 nm).

Step 3: 2-{5-[(2,5-Difluorophenyl)(oxan-4-yl)methyl]-3-(dimethyl-1,2-oxazol-4-yl)-5H-pyrido[3,2-b]indol-7-yl}propan-2-ol A stirred solution of methyl 5-((2,5-difluorophenyl)(tetrahydro-2H-pyran-4-yl)methyl)-3-(3,5-dimethylisoxazol-4-yl)-5H-pyrido[3,2-b]indole-7-carboxylate (150 mg, 0.282 mmol) in tetrahydrofuran (1 mL) was cooled to −20° C. and treated with methylmagnesium bromide (3M in THF, 0.470 mL, 1.41 mmol) via syringe, and after addition was complete the reaction mixture was slowly warmed to room temperature over a period of 5 h. The mixture was cooled in an ice bath, quenched with sat. aq. NH$_4$Cl (20 mL), and the aqueous layer was extracted with EtOAc (30 mL×2). The extract was dried over Na$_2$SO$_4$, filtered, concentrated, and the residue purified by prep HPLC (Column: Sunfire C18 (250×30*7 u) Mobile Phase A: 10 mm NH$_4$OAc in water, Mobile Phase B: ACN Solubility: MEOH+THF, Flow: 30 mL/min) to give racemic 2-{5-((2,5-difluorophenyl)(tetrahydro-2H-pyran-4-yl)methyl]-3-(3,5-dimethylisoxazol-4-yl)-5H-pyrido[3,2-b]indol-7-yl}propan-2-ol (100 mg, 0.184 mmol, 65%) as a white solid, which was separated by chiral prep SFC (Column: Chiral OD-H 25×2.1 cm, 5 μm; Mobile Phase: 85/15 CO$_2$/(0.25% DEA in MeOH); Flow: 60 mL/min) to give Enantiomer A (40 mg, 26%) and Enantiomer B (40 mg, 26%). Enantiomer A: $^1$H NMR (400 MHz, CD$_3$OD) δ 8.38 (d, J=1.8 Hz, 1H), 8.25 (d, J=8.3 Hz, 1H), 8.20 (br. s., 1H), 8.02 (s, 1H), 7.93 (d, J=7.3 Hz, 1H), 7.47 (dd, J=1.3, 8.3 Hz, 1H), 7.13-7.05 (m, 2H), 5.95 (d, J=11.5 Hz, 1H), 4.00 (dd, J=2.8, 11.5 Hz, 1H), 3.80 (dd, J=3.0, 11.8 Hz, 1H), 3.67-3.56 (m, 1H), 3.43-3.34 (m, 2H), 2.49 (s, 3H), 2.33 (s, 3H), 1.92 (d, J=13.3 Hz, 1H), 1.66 (d, J=3.8 Hz, 7H), 1.42 (dd, J=4.3, 12.5 Hz, 1H), 0.98 (d, J=13.3 Hz, 1H). LCMS: RT=1.99 min; MS (ES): m/z=532.4 [M+H]$^+$ (ACN/H$_2$O with HCOONH$_4$, Ascentis Express C18 2.7 μm (50×2.1) mm, gradient=4 min, wavelength=220 nm); HPLC RT=8.487 min (Column: Sunfire C18 3.5 μm, 4.6× 150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.67 min (Column: Chiralcel OD-H 250×4.6 mm, 5 μm; Mobile Phase: 70/30 CO$_2$/(0.25% DEA in MeOH); Flow: 3 mL/min). Enantiomer B: Chiral SFC RT=4.38 min (Column: Chiralcel OD-H 250×4.6 mm, 5 μm; Mobile Phase: 70/30 CO$_2$/(0.25% DEA in MeOH); Flow: 3 mL/min).

Examples 141 & 142

2-{5-[(3,4-Difluorophenyl)(oxan-4-yl)methyl]-3-(dimethyl-1,2-oxazol-4-yl)-5H-pyrido[3,2-b]indol-7-yl}propan-2-ol

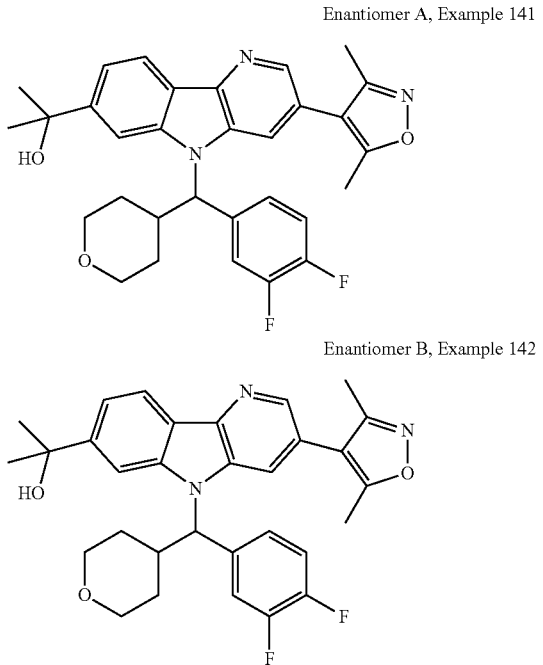

Enantiomer A, Example 141

Enantiomer B, Example 142

Examples 143 & 144

2-{5-[(2,6-Difluorophenyl)(oxan-4-yl)methyl]-3-(dimethyl-1,2-oxazol-4-yl)-5H-pyrido[3,2-b]indol-7-yl}propan-2-ol

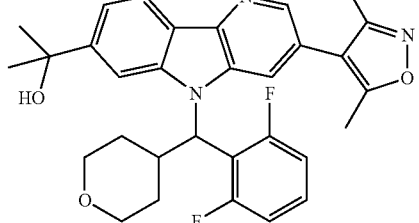

Enantiomer A, Example 143

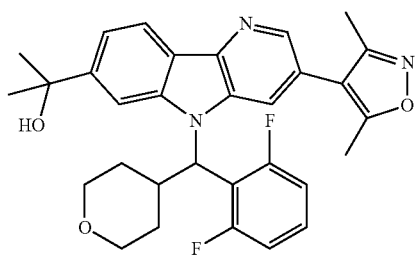

Enantiomer B, Example 144

Following a procedure analogous to that described for the synthesis of 2-{5-[(2,5-difluorophenyl)(tetrahydro-2H-pyran-4-yl)methyl]-3-(3,5-dimethylisoxazol-4-yl)-5H-pyrido[3,2-b]indol-7-yl}propan-2-ol, (3,4-difluorophenyl)(tetrahydro-2H-pyran-4-yl)methanol was converted to racemic 2-{5-[(3,4-difluorophenyl)(oxan-4-yl)methyl]-3-(dimethyl-1,2-oxazol-4-yl)-5H-pyrido[3,2-b]indol-7-yl}propan-2-ol (90.0 mg, 49%), which was separated by chiral prep SFC (Column: Lux Cellulose 4, 25×2.1 cm, 5 μm; Mobile Phase: 65/35 $CO_2$/(0.25% DEA in MeOH); Flow: 60 mL/min) to give Enantiomer A (25.0 mg, 14%) and Enantiomer B (23.0 mg, 13%). Enantiomer A: $^1$H NMR (400 MHz, $CD_3OD$) δ 8.37 (d, J=2.0 Hz, 1H), 8.27 (d, J=8.5 Hz, 1H), 8.15 (s, 1H), 8.05 (s, 1H), 7.68-7.57 (m, 1H), 7.52-7.39 (m, 2H), 7.24 (td, J=8.5, 10.5 Hz, 1H), 5.75 (s, 1H), 4.06-3.95 (m, 1H), 3.89-3.78 (m, 1H), 3.66-3.55 (m, 1H), 3.40 (m, 2H), 2.49 (s, 3H), 2.33 (s, 3H), 1.92 (d, J=13.3 Hz, 1H), 1.68 (d, J=3.5 Hz, 6H), 1.65-1.58 (m, 1H), 1.45-1.34 (m, 1H), 1.16-1.07 (d, J=13.3 Hz, 1H). LCMS: RT=2.05 min; MS (ES): m/z=532.4 [M+H]$^+$ (ACN/$H_2O$ with HCOONH$_4$, Ascentis Express C18 2.7 μm (50×2.1) mm, gradient=4 min, wavelength=220 nm); HPLC RT=8.911 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.36 min (Column: Lux Cellulose 4, 250×4.6 mm, 5 μm; Mobile Phase: 55/45 $CO_2$/(0.25% DEA in MeOH); Flow: 3 mL/min). Enantiomer B: Chiral SFC RT=3.89 min (Column: Lux Cellulose 4, 250×4.6 mm, 5 μm; Mobile Phase: 55/45 $CO_2$/(0.25% DEA in MeOH); Flow: 3 mL/min).

Following a procedure analogous to that described for the synthesis of 2-{5-[(2,5-difluorophenyl)(tetrahydro-2H-pyran-4-yl)methyl]-3-(3,5-dimethylisoxazol-4-yl)-5H-pyrido[3,2-b]indol-7-yl}propan-2-ol, (2,6-difluorophenyl)(tetrahydro-2H-pyran-4-yl)methanol was converted to racemic 2-{5-[(2,6-difluorophenyl)(oxan-4-yl)methyl]-3-(dimethyl-1,2-oxazol-4-yl)-5H-pyrido[3,2-b]indol-7-yl}propan-2-ol, which was separated by chiral prep SFC (Column: Chiralcel OD-H, 25×2.1 cm, 5 μm; Mobile Phase: 60/40 $CO_2$/(0.25% DEA in MeOH); Flow: 70 mL/min) to give Enantiomer A (7.00 mg, 9%) and Enantiomer B (6.00 mg, 7%). Enantiomer A: $^1$H NMR (400 MHz, $CD_3OD$) δ 8.40 (d, J=1.5 Hz, 1H), 8.29-8.20 (m, 2H), 8.08 (s, 1H), 7.55-7.50 (m, 1H), 7.45-7.35 (m, 1H), 7.09-7.02 (m, 2H), 6.07 (d, J=11.5 Hz, 1H), 4.03 (d, J=9.0 Hz, 1H), 3.81 (d, J=11.5 Hz, 1H), 3.61-3.50 (m, 1H), 3.45-3.35 (m, 2H), 2.53 (s, 3H), 2.37 (s, 3H), 1.83 (d, J=14.1 Hz, 1H), 1.66 (s, 6H), 1.72-1.62 (m, 1H), 1.42 (m, 1H), 1.06 (d, J=13.1 Hz, 1H). LCMS: RT=1.85 min; MS (ES): m/z=532.4 [M+H]$^+$ (ACN/$H_2O$ with HCOONH$_4$, Ascentis Express C18 2.7 μm (50×2.1) mm, gradient=4 min, wavelength=220 nm); HPLC RT=8.403 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.62 min (Column: Chiralcel OD-H, 250×4.6 mm, 5 μm; Mobile Phase: 55/45 $CO_2$/(0.25% DEA in MeOH); Flow: 3 mL/min). Enantiomer B: Chiral SFC RT=3.66 min (Column: Chiralcel OD-H, 250×4.6 mm, 5 μm; Mobile Phase: 55/45 $CO_2$/(0.25% DEA in MeOH); Flow: 3 mL/min).

Examples 145 & 146

2-{5-[(2,3-Difluorophenyl)(oxan-4-yl)methyl]-3-(dimethyl-1,2-oxazol-4-yl)-5H-pyrido[3,2-b]indol-7-yl}propan-2-ol

Examples 147 & 148

2-[3-(Dimethyl-1,2-oxazol-4-yl)-5-[(3-fluorophenyl)(oxan-4-yl)methyl]-5H-pyrido[3,2-b]indol-7-yl]propan-2-ol Enantiomer A, Example 145

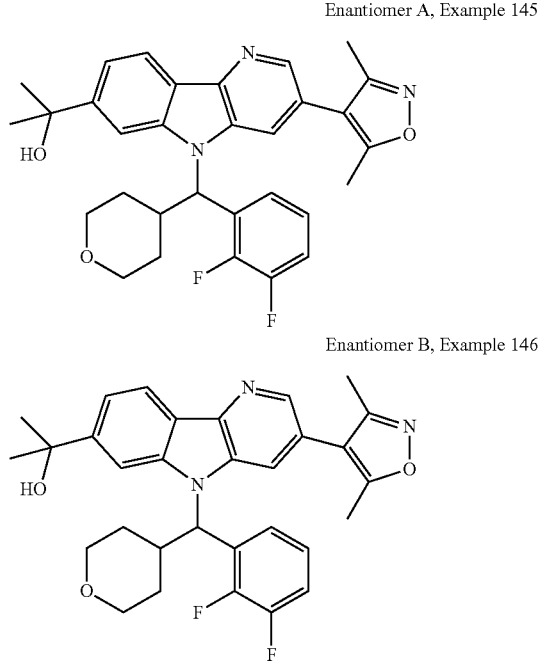

Enantiomer B, Example 146

Enantiomer A, Example 147

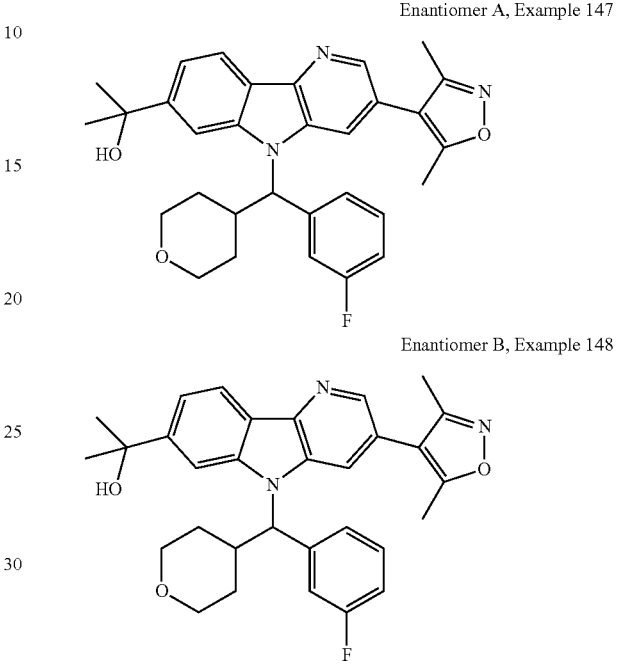

Enantiomer B, Example 148

Following a procedure analogous to that described for the synthesis of 2-{5-[(2,5-difluorophenyl)(tetrahydro-2H-pyran-4-yl)methyl]-3-(3,5-dimethylisoxazol-4-yl)-5H-pyrido[3,2-b]indol-7-yl}propan-2-ol, (2,3-difluorophenyl)(tetrahydro-2H-pyran-4-yl)methanol was converted to racemic 2-{5-[(2,3-difluorophenyl)(oxan-4-yl)methyl]-3-(dimethyl-1,2-oxazol-4-yl)-5H-pyrido[3,2-b]indol-7-yl}propan-2-ol, which was separated by chiral prep SFC (Column: Chiralcel OD-H, 25×2.1 cm, 5 μm; Mobile Phase: 60/40 $CO_2$/(0.25% DEA in MeOH); Flow: 70 mL/min) to give Enantiomer A (52.0 mg, 30%) and Enantiomer B (54.0 mg, 31%). Enantiomer A: $^1$H NMR (400 MHz, $CD_3OD$) δ 8.38 (d, J=1.60 Hz, 1H), 8.26 (d, J=8.40 Hz, 1H), 8.20 (s, 1H), 8.02 (s, 1H), 7.89 (t, J=7.60 Hz, 1H), 7.47 (d, J=8.00 Hz, 1H), 7.20-7.32 (m, 2H), 6.00 (d, J=12.00 Hz, 1H), 3.99 (dd, J=3.20, 11.00 Hz, 1H), 3.80 (dd, J=2.80, 11.40 Hz, 1H), 3.60 (dt, J=11.60, Hz, 1H), 3.33-3.40 (m, 2H), 2.48 (s, 3H), 2.32 (s, 3H), 1.89-2.04 (m, 1H), 1.60-1.70 (m, 7H), 1.37-1.47 (m, 1H), 0.97 (d, J=12.80 Hz, 1H). LCMS: RT=2.013 min; MS (ES): m/z=532.5 [M+H]$^+$ (ACN/$H_2O$ with $HCOONH_4$, Ascentis Express C18 2.7 μm (50×2.1) mm, gradient=4 min, wavelength=220 nm); HPLC RT=8.534 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.38 min (Column: Chiralcel OD-H, 250×4.6 mm, 5 μm; Mobile Phase: 55/45 $CO_2$/(0.25% DEA in MeOH); Flow: 4 mL/min). Enantiomer B: Chiral SFC RT=2.96 min (Column: Chiralcel OD-H, 250×4.6 mm, 5 μm; Mobile Phase: 55/45 $CO_2$/(0.25% DEA in MeOH); Flow: 4 mL/min).

Following a procedure analogous to that described for the synthesis of 2-{5-[(2,5-difluorophenyl)(tetrahydro-2H-pyran-4-yl)methyl]-3-(3,5-dimethylisoxazol-4-yl)-5H-pyrido[3,2-b]indol-7-yl}propan-2-ol, (3-fluorophenyl)(tetrahydro-2H-pyran-4-yl)methanol was converted to racemic 2-[3-(dimethyl-1,2-oxazol-4-yl)-5-[(3-fluorophenyl)(oxan-4-yl)methyl]-5H-pyrido[3,2-b]indol-7-yl]propan-2-ol (110 mg, 48%), which was separated by chiral prep SFC (Column: Chiralcel OD-H, 25×2.1 cm, 5 μm; Mobile Phase: 65/35 $CO_2$/(0.25% DEA in MeOH); Flow: 60 mL/min) to give Enantiomer A (30.0 mg, 13%) and Enantiomer B (30.0 mg, 13%). Enantiomer A: $^1$H NMR (400 MHz, $CD_3OD$) δ 8.36 (d, J=1.5 Hz, 1H), 8.27 (d, J=8.5 Hz, 1H), 8.13 (s, 1H), 8.08 (s, 1H), 7.51-7.31 (m, 4H), 7.06-6.98 (m, 1H), 5.77 (s, 1H), 4.04-3.97 (m, 1H), 3.82 (dd, J=2.5, 11.5 Hz, 1H), 3.66-3.56 (m, 1H), 3.47-3.40 (m, 2H), 2.49 (s, 3H), 2.33 (s, 3H), 1.94 (d, J=13.1 Hz, 1H), 1.68 (d, J=3.0 Hz, 6H), 1.65-1.59 (m, 1H), 1.46-1.38 (m, 1H), 1.16-1.08 (m, 1H). LCMS: RT=2.02 min; MS (ES): m/z=514.4 [M+H]$^+$ (ACN/$H_2O$ with $HCOONH_4$, Ascentis Express C18 2.7 μm (50×2.1) mm, gradient=4 min, wavelength=220 nm); HPLC RT=8.511 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=3.28 min (Column: Chiralcel OD-H, 250×4.6 mm, 5 μm; Mobile Phase: 65/35 $CO_2$/(0.25% DEA in MeOH); Flow: 3 mL/min). Enantiomer B: Chiral SFC RT=5.06 min (Column: Chiralcel OD-H, 250×4.6 mm, 5 μm; Mobile Phase: 65/35 $CO_2$/(0.25% DEA in MeOH); Flow: 3 mL/min).

Examples 149 & 150

2-[3-(Dimethyl-1,2-oxazol-4-yl)-5-[(2-fluorophenyl)(oxan-4-yl)methyl]-5H-pyrido[3,2-b]indol-7-yl]propan-2-ol

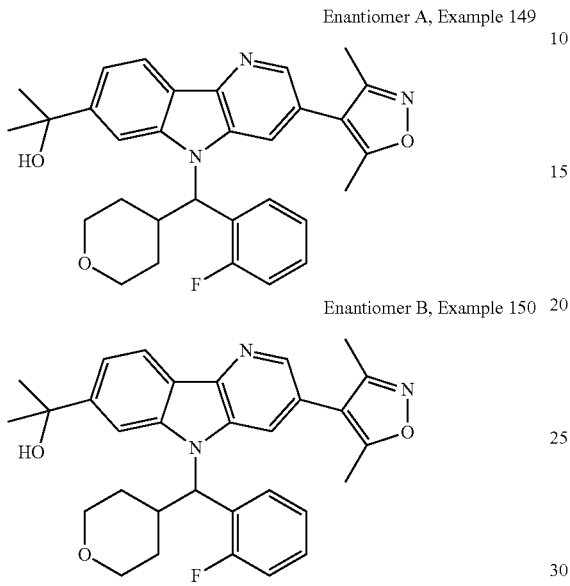

Enantiomer A, Example 149

Enantiomer B, Example 150

Following a procedure analogous to that described for the synthesis of 2-{5-[(2,5-difluorophenyl)(tetrahydro-2H-pyran-4-yl)methyl]-3-(3,5-dimethylisoxazol-4-yl)-5H-pyrido[3,2-b]indol-7-yl}propan-2-ol, (2-fluorophenyl)(tetrahydro-2H-pyran-4-yl)methanol was converted to racemic 2-[3-(dimethyl-1,2-oxazol-4-yl)-5-[(2-fluorophenyl)(oxan-4-yl)methyl]-5H-pyrido[3,2-b]indol-7-yl]propan-2-ol (70.0 mg, 70%), which was separated by chiral prep SFC (Column: Chiralcel OD-H, 25×2.1 cm, 5 μm; Mobile Phase: 60/40 CO$_2$/(0.25% DEA in MeOH); Flow: 70 mL/min) to give Enantiomer A (35.0 mg, 34%) and Enantiomer B (35.0 mg, 34%). Enantiomer A: $^1$H NMR (400 MHz, CD$_3$OD) δ 8.34-8.35 (m, 1H), 8.24 (d, J=8.00 Hz, 1H), 8.16 (s, 1H), 8.02-8.09 (m, 2H), 7.43-7.46 (m, 1H), 7.28-7.36 (m, 2H), 7.03-7.08 (m, 1H), 5.94-5.97 (m, 1H), 3.97-3.98 (m, 1H), 3.77-3.81 (m, 1H), 3.56-3.62 (m, 1H), 3.30-3.39 (m, 2H), 2.47 (s, 3H), 2.31 (s, 3H), 1.88-1.93 (m, 1H), 1.60-1.68 (m, 7H), 1.39-1.43 (m, 1H), 0.95-0.98 (m, 1H). LCMS: RT=2.28 min; MS (ES): m/z=514.2 [M+H]$^+$ (ACN/H$_2$O with HCOONH$_4$, Ascentis Express C18 2.7 μm (50×2.1) mm, gradient=4 min, wavelength=220 nm); HPLC RT=8.068 min (Column: Sunfire C18 3.5 μm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.25 min (Column: Chiralcel OD-H, 250×4.6 mm, 5 μm; Mobile Phase: 55/45 CO$_2$/(0.25% DEA in MeOH); Flow: 3 mL/min). Enantiomer B: Chiral SFC RT=3.59 min (Column: Chiralcel OD-H, 250×4.6 mm, 5 μm; Mobile Phase: 55/45 CO$_2$/(0.25% DEA in MeOH); Flow: 3 mL/min).

Example 151

N-Cyclopropyl-3-(dimethyl-1H-1,2,3-triazol-5-yl)-5-[(S)-oxan-4-yl(phenyl)methyl]-5H-pyrido[3,2-b]indole-9-carboxamide

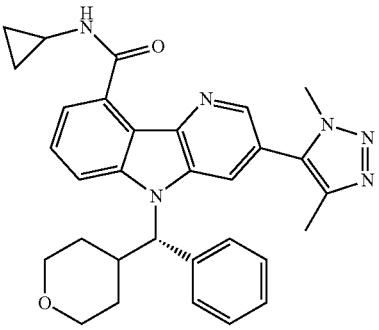 [SMILES: Cc1nnn(C)c1-c1cnc2c3c(C(=O)NC4CC4)cccc3n([C@H](c3ccccc3)C3CCOCC3)c2c1]

Step 1: Methyl 2-(5-bromo-3-nitropyridin-2-yl)benzoate

In a 40 ml, vial was added a mixture of 2,5-dibromo-3-nitropyridine (2.00 g, 7.09 mmol), (2-(methoxycarbonyl)phenyl)boronic acid (1.41 g, 7.80 mmol), and 2 M aqueous tripotassium phosphate (7.09 mL, 14.2 mmol) in tetrahydrofuran (20 mL), and the reaction mixture was purged under a stream of nitrogen for several min. The mixture was then treated with PdCl$_2$(dppf)-CH$_2$Cl$_2$ adduct (0.290 g, 0.355 mmol), capped with a septum, evacuated, and purged with nitrogen 3 times. The reaction mixture was then heated in a heating block at 80° C. for 3 h. The reaction mixture was diluted with water and extracted into ethyl acetate. The organics were washed with water, and the volatiles were removed under reduced pressure to give a dark residue. The material was purified using silica gel column chromatography with an ISCO Companion (80 g silica gel column) and eluted with an EtOAc/hexane gradient (10-50%) to give methyl 2-(5-bromo-3-nitropyridin-2-yl)benzoate (1.10 g, 3.26 mmol, 46%) as a light-yellow residue that slowly solidified. LCMS: Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA; LCMS: RT=0.92 min; (ES): m/z (M+H)$^+$=337.0, 339.0.

Step 2: 3-Bromo-5H-pyrido[3,2-b]indole-9-carboxylate

A solution of methyl 2-(5-bromo-3-nitropyridin-2-yl)benzoate (1.00 g, 2.97 mmol) and 1,3-bis(diphenylphosphino)propane (1.35 g, 3.26 mmol) in 1,2-dichlorobenzene (10 mL) was sealed in a large 20 mL vial and heated in a heating block at 155° C. overnight. The solvent was removed under high vacuum to give a dark residue, which was purified using silica gel column chromatography with an ISCO Companion (80 g silica gel column) and eluted with a EtOAc/hexane gradient (20-50%) to give methyl 3-bromo-5H-pyrido[3,2-b]indole-9-carboxylate (220 mg, 0.721 mmol, 24%). LCMS: Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA. LCMS: RT=0.60 min; (ES): m/z (M+H)$^+$=305.0, 307.0. 1H NMR (400 MHz, CDCl$_3$) δ 8.71 (d, J=2.0 Hz, 1H), 8.40 (br. s., 1H), 7.90 (s, 1H), 7.75 (dd, J=7.2, 1.2 Hz, 1H), 7.66-7.54 (m, 2H), 4.12 (s, 3H).

Step 3: Methyl 3-(1,4-dimethyl-1H-1,2,3-triazol-5-yl)-5H-pyrido[3,2-b]indole-9-carboxylate A solution of methyl 3-bromo-5H-pyrido[3,2-b]indole-9-carboxylate (220 mg, 0.721 mmol), 1,4-dimethyl-5-(tributylstannyl)-1H-1,2,3-triazole (334 mg, 0.865 mmol), copper (I) iodide (27.5 mg, 0.144 mmol), Pd(Ph$_3$P)$_4$ (83.0 mg, 0.0720 mmol), TEA (0.201 mL, 1.44 mmol), and DMF (5 mL) in a 20 mL vial was capped and heated in a heating block at 95° C. overnight. The reaction mixture was diluted with NH$_4$OH (aq) and water and extracted into ethyl acetate. The organics were washed with water and brine and concentrated. The residue was purified using silica gel column chromatography with an ISCO Companion (40 g silica gel column) and eluted with a MeOH/CH$_2$Cl$_2$ gradient (0-10%) to give methyl 3-(1,4-dimethyl-1H-1,2,3-triazol-5-yl)-5H-pyrido[3,2-b]indole-9-carboxylate (70.0 mg, 0.218 mmol, 30%). LCMS: Waters Acquity SDS. Column: BEH C18 2.1×50 mm 1.7 u (1.6 min grad) 2-98% B. Flow Rate=0.8 mL/min. Solvent A: H$_2$O –0.1% TFA. Solvent B: Acetonitrile–0.1% TFA. LCMS: RT=0.56 min; (ES): m/z (M+H)$^+$=322.2.

Step 4. (S)-Methyl 3-(1,4-dimethyl-1H-1,2,3-triazol-5-yl)-5-(phenyl(tetrahydro-2H-pyran-4-yl)methyl)-5H-pyrido[3,2-b]indole-9-carboxylate A solution of methyl 3-(1,4-dimethyl-1H-1,2,3-triazol-5-yl)-5H-pyrido[3,2-b]indole-9-carboxylate (70.0 mg, 0.218 mmol), (R)-phenyl(tetrahydro-2H-pyran-4-yl)methanol (84.0 mg, 0.436 mmol), and triphenylphosphine (114 mg, 0.436 mmol) in dichloromethane (4 mL) was treated drop wise with DIAD (0.0850 mL, 0.436 mmol), and the mixture was stirred at room temperature overnight. The mixture was directed loaded onto a silica gel column. The material was purified using silica gel column chromatography using an ISCO Companion (40 g silica gel column) and eluted with a MeOH/CH$_2$Cl$_2$ gradient (0-10%). The fractions that contained product were collected, and the volatiles were removed to give a yellow oil, which was purified a second time on an ISCO Companion (24 g silica gel column) and eluted with ethyl acetate to give (S)-methyl 3-(1,4-dimethyl-1H-1,2,3-triazol-5-yl)-5-(phenyl(tetrahydro-2H-pyran-4-yl)methyl)-5H-pyrido[3,2-b]indole-9-carboxylate (35.0 mg, 35%). LCMS: Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA; LCMS: RT=0.74 min; (ES): m/z (M+H)$^+$=496.3. $^1$H NMR (500 MHz, DMSO-d$_6$) δ 8.58 (s, 1H), 8.33 (br. s., 1H), 7.96 (s, 1H), 7.67 (d, J=7.4 Hz, 3H), 7.45 (d, J=7.4 Hz, 1H), 7.37-7.30 (m, 2H), 7.28-7.21 (m, 1H), 5.90 (d, J=11.1 Hz, 1H), 4.02 (br. s., 2H), 3.95 (s, 3H), 3.91 (d, J=9.4 Hz, 1H), 3.72 (d, J=9.4 Hz, 1H), 3.52-3.38 (m, 2H), 3.27 (t, J=11.3 Hz, 1H), 2.30 (br. s., 3H), 1.73 (d, J=13.1 Hz, 1H), 1.61-1.51 (m, 1H), 1.36-1.25 (m, 1H), 0.97 (d, J=12.5 Hz, 1H).

Step 5: N-Cyclopropyl-3-(dimethyl-1H-1,2,3-triazol-5-yl)-5-[(S)-oxan-4-yl(phenyl)methyl]-5H-pyrido[3,2-b]indole-9-carboxamide A solution of (S)-methyl 3-(1,4-dimethyl-1H-1,2,3-triazol-5-yl)-5-(phenyl(tetrahydro-2H-pyran-4-yl)methyl)-5H-pyrido[3,2-b]indole-9-carboxylate (35.0 mg, 0.0710 mmol) in methanol (2 mL) was treated with 1 N NaOH (0.706 mL, 0.706 mmol), and the light-yellow solution was stirred at room temperature. The mixture was concentrated on a rotary evaporator to obtain a solid residue. This was treated with 1 N HCl and dissolved in 2 mL of methanol, and the solution was concentrated on a rotary evaporator to give of (S)-3-(1,4-dimethyl-1H-1,2,3-triazol-5-yl)-5-(phenyl(tetrahydro-2H-pyran-4-yl)methyl)-5H-pyrido[3,2-b]indole-9-carboxylic acid (34.0 mg, 0.0710 mmol) as a white solid, which was used without purification. LCMS: Waters Acquity SDS. Column: BEH C18 2.1×50 mm 1.7 u (1.6 min grad) 2-98% B. Flow Rate=0.8 ml/min. Solvent A: H$_2$O–0.1% TFA. Solvent B: Acetonitrile–0.1% TFA. LCMS: RT=0.80 min; (ES): m/z (M+H)$^+$=482.3.

A solution of (S)-3-(1,4-dimethyl-1H-1,2,3-triazol-5-yl)-5-(phenyl(tetrahydro-2H-pyran-4-yl)methyl)-5H-pyrido[3,2-b]indole-9-carboxylic acid (34.0 mg, 0.0710 mmol) in DMF (2 mL) was treated with EDC (27.1 mg, 0.141 mmol), HOBT (21.6 mg, 0.141 mmol), and then with cyclopropylamine (20.2 mg, 0.353 mmol), and the mixture was stirred at room temperature overnight. The reaction mixture was diluted with water and 1 N HCl. The aqueous layer was extracted with ethyl acetate, and the organics were washed with water and concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min, then a 5-min hold at 55% B; Flow: 20 mL/min. Fractions containing the desired product were combined and dried via centrifugal evaporation to give N-cyclopropyl-3-(dimethyl-1H-1,2,3-triazol-5-yl)-5-[(S)-oxan-4-yl(phenyl)methyl]-5H-pyrido[3,2-b]indole-9-carboxamide (6.00 mg, 16%). LCMS: RT=1.72 min; (ES): m/z (M+H)$^+$=521.3 (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). $^1$H NMR (500 MHz, DMSO-d$_6$) δ 12.17 (d, J=3.7 Hz, 1H), 8.68 (br. s., 1H), 8.64-8.36 (m, 1H), 8.15 (d, J=6.1 Hz, 1H), 7.96 (s, 1H), 7.76 (br. s., 1H), 7.67 (d, J=7.7 Hz, 2H), 7.40-7.30 (m, 2H), 7.29-7.21 (m, 1H), 5.99 (d, J=11.1 Hz, 1H), 4.03 (br. s., 3H), 3.90 (d, J=8.8 Hz, 1H), 3.71 (d, J=9.1 Hz, 1H), 3.49 (d, J=11.1 Hz, 1H), 3.42-3.35 (m, 1H), 3.25 (t, J=11.4 Hz, 1H), 3.07 (td, J=7.2, 3.9 Hz, 1H), 2.31 (br. s., 3H), 1.76 (d, J=11.4 Hz, 1H), 1.66-1.52 (m, 1H), 1.36-1.24 (m, 1H), 0.91 (d, J=10.1 Hz, 1H), 0.83 (d, J=7.1 Hz, 2H), 0.73 (br. s., 2H).

Example 152

[3-(Dimethyl-1H-1,2,3-triazol-5-yl)-9-fluoro-5-[(S)-oxan-4-yl(phenyl)methyl]-5H-pyrido[3,2-b]indol-6-yl]methanol

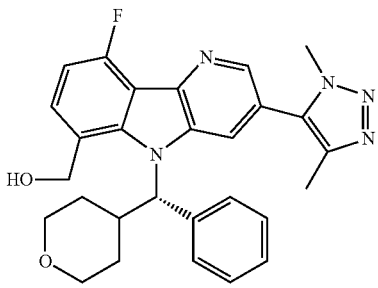 [SMILES: Cc1nnn(C)c1-c1cnc2c3c(F)ccc(CO)c3n([C@H](c3ccccc3)C3CCOCC3)c2c1]

Step 1: Methyl 3-(5-bromo-3-nitropyridin-2-yl)-4-fluorobenzoate

A mixture of 2,5-dibromo-3-nitropyridine (705 mg, 2.50 mmol) and (2-fluoro-5-(methoxycarbonyl)phenyl)boronic acid (495 mg, 2.50 mmol) in tetrahydrofuran (10 mL) in a 20 mL vial was purged under a stream of nitrogen and then treated with 2 M aqueous tripotassium phosphate (3.75 mL, 7.50 mmol) (solids formed) and then with $PdCl_2$(dppf)-$CH_2Cl_2$ adduct (204 mg, 0.250 mmol). The vial was capped with a septum, evacuated, and purged with nitrogen 3 times before the reaction mixture was heated in a heating block to 80° C. Note—the solids gradually dissolved on heating. After 3 h, the mixture was cooled to room temperature, diluted with water, and extracted into ethyl acetate. The organics were washed with water, and the volatiles were removed under reduced pressure to give a dark residue. The material was purified using silica gel column chromatography with an ISCO Companion (80 g silica gel column) and eluted with EtOAc/hexane gradient (10-40%) to give methyl 3-(5-bromo-3-nitropyridin-2-yl)-4-fluorobenzoate (507 mg, 1.43 mmol, 57%) as a white crystalline solid. LCMS: Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA. LCMS: RT=0.99 min; (ES): m/z (M+H)$^+$=355.0, 356.9. $^1$H NMR (400 MHz, $CDCl_3$) δ 8.99 (d, J=2.1 Hz, 1H), 8.52 (d, J=2.1 Hz, 1H), 8.39 (dd, J=7.0, 2.2 Hz, 1H), 8.18 (ddd, J=8.7, 5.1, 2.3 Hz, 1H), 7.18 (dd, J=9.7, 8.8 Hz, 1H), 3.94 (s, 3H).

Step 2: Methyl 3-bromo-9-fluoro-5H-pyrido[3,2-b]indole-6-carboxylate

A mixture of methyl 3-(5-bromo-3-nitropyridin-2-yl)-4-fluorobenzoate (500 mg, 1.41 mmol) and 1,2-bis(diphenylphosphino)ethane (701 mg, 1.76 mmol) in 1,2-dichlorobenzene (5 mL) was capped in a 20 mL vial and heated in a heating block at 170° C. for 5 h. The reaction mixture was removed from the heating block, and the dark mixture was transferred to a RB flask and concentrated under high vacuum. The resulting black residue was dissolved in DCM and purified using silica gel column chromatography with an ISCO Companion (40 g silica gel column) and eluted with EtOAc/hexane gradient (15-50%) to give methyl 3-bromo-9-fluoro-5H-pyrido[3,2-b]indole-6-carboxylate (170 mg, 0.526 mmol, 37%) as a white solid. LCMS: Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA. LCMS: RT=0.93 min; (ES): m/z (M+H)$^1$=323.0, 325.0.

Step 3: Methyl 3-(1,4-dimethyl-1H-1,2,3-triazol-5-yl)-9-fluoro-5H-pyrido[3,2-b]indole-6-carboxylate In a 20 mL vial was added a mixture of 1,4-dimethyl-5-(tributylstannyl)-1H-1,2,3-triazole (264 mg, 0.684 mmol), methyl 3-bromo-9-fluoro-5H-pyrido[3,2-b]indole-6-carboxylate (170 mg, 0.526 mmol), copper(I) iodide (20.0 mg, 0.105 mmol), and TEA (0.147 mL, 1.05 mmol) in DMF (5 mL), and the mixture was purged under a stream of nitrogen. Then was added Pd(Ph$_3$P)$_4$ (60.8 mg, 0.0530 mmol) and capped with a septum. The vial was evacuated and purged with nitrogen 3 times and then the reaction mixture was heated in a heating block at 95° C. for 3 h. The mixture was cooled to room temperature, diluted with water and aqueous ammonium hydroxide, and extracted into ethyl acetate. The organics were washed with water and brine, and the volatiles were removed. The resulting residue was dissolved in DCM and purified using silica gel column chromatography with an ISCO Companion (24 g silica gel column) and eluted with ethyl acetate to give methyl 3-(1,4-dimethyl-1H-1,2,3-triazol-5-yl)-9-fluoro-5H-pyrido[3,2-b]indole-6-carboxylate (160 mg, 0.292 mmol, 56%) as an off-white solid. LCMS: Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA. LCMS: RT=0.75 min; (ES): m/z (M+H)$^+$=340.1.

Step 4. (S)-Methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-6-carboxylate In a 20 mL vial was added methyl 3-(1,4-dimethyl-1H-1,2,3-triazol-5-yl)-9-fluoro-5H-pyrido[3,2-b]indole-6-carboxylate (160 mg, 0.472 mmol), (R)-phenyl(tetrahydro-2H-pyran-4-yl)methanol (181 mg, 0.943 mmol) and dichloromethane (6 mL), and the reaction mixture was then treated with triphenylphosphine (247 mg, 0.943 mmol) and was treated drop wise with DIAD (0.183 mL, 0.943 mmol). The reaction mixture was stirred at room temperature overnight. The crude reaction mixture was directly loaded onto a silica gel column and was purified using an ISCO Companion (40 g silica gel column) with ethyl acetate to give (S)-methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-6-carboxylate (150 mg, 60%) as a white solid. LCMS4: Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA. LCMS: RT=0.92 min; (ES): m/z (M+H)$^+$=514.2.

Step 5: [3-(Dimethyl-1H-1,2,3-triazol-5-yl)-9-fluoro-5-[(S)-oxan-4-yl)phenyl)methyl]-5H-pyrido[3,2-b]indol-6-yl]methanol A solution of (S)-methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-6-carboxylate (40.0 mg, 0.0780 mmol) in tetrahydrofuran (5 mL) in a 20 mL vial was cooled in an ice bath and treated with solid LiAlH$_4$ (5.91 mg, 0.156 mmol), and the mixture was stirred in the bath. After 1 h, more LiAlH$_4$ (5.91 mg, 0.156 mmol) was added. After 2 h the mixture was quenched with sat. aq. ammonium chloride and extracted into ethyl acetate. The organics were washed with water, and the volatiles were removed under reduced pressure to give a white solid. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min, then a 5-min hold at 55% B; Flow: 20 mL/min. Fractions containing the desired product were combined and dried via centrifugal evaporation to give [3-(dimethyl-1H-1,2,3-triazol-5-yl)-9-fluoro-5-[(S)-oxan-4-yl(phenyl)methyl]-5H-pyrido[3,2-b]indol-6-yl]methanol (8.00 mg, 20%). LCMS: RT 1.39 min; (ES): m/z (M+H)$^+$ =486.2 (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). $^1$H NMR (500 MHz, DMSO-d$_6$) δ 8.57 (s, 1H), 7.96 (s, 1H), 7.67 (d, J=7.7 Hz, 2H), 7.64-7.58 (m, 1H), 7.36-7.31 (m, 2H), 7.28-7.22 (m, 1H), 7.11 (t, J=8.8 Hz, 1H), 6.41 (d, J=11.1 Hz, 1H), 5.10-5.04 (m, 2H), 3.92-3.87 (m, 1H), 3.84 (s, 3H), 3.71 (d, J=8.4 Hz, 1H), 3.55-3.40 (m, 2H), 3.23 (t, J=11.4 Hz, 1H), 2.16 (s, 3H), 1.92 (m, 1H), 1.60-1.44 (m, 2H), 0.70 (d, J=12.8 Hz, 1H).

Example 153

4-[3-(Dimethyl-1H-1,2,3-triazol-5-yl)-5-[(S)-oxan-4-yl)phenyl)methyl]-5H-pyrido[3,2-b]indol-8-yl]-2-methylbutan-2-ol

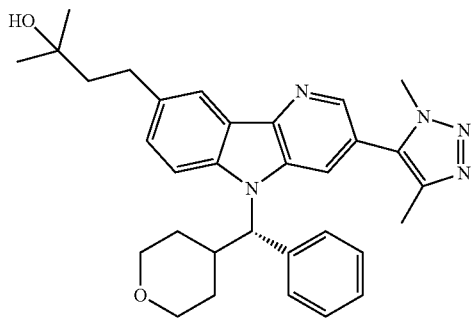 [SMILES: Cc1nnn(C)c1-c1cnc2c3cc(CCC(C)(C)O)ccc3n([C@H](c3ccccc3)C3CCOCC3)c2c1]

Step 1: Methyl 3-(3-(5-bromo-3-nitropyridin-2-yl)phenyl)propanoate

Following a procedure analogous to that described for the synthesis of methyl 3-(5-bromo-3-nitropyridin-2-yl)-4-fluorobenzoate, 2,5-dibromo-3-nitropyridine (1084 mg, 3.85 mmol) and (3-(3-methoxy-3-oxopropyl)phenyl)boronic acid (800 mg, 3.85 mmol) were converted to methyl 3-(3-(5-bromo-3-nitropyridin-2-yl)phenyl)propanoate (700 mg, 1.92 mmol, 50%) as a light-yellow, thick oil. LCMS: RT=1.00 min; (ES): m/z (M+H)$^+$=365.0, 367.0. (LCMS: Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). $^1$H NMR (400 MHz, CDCl$_3$) δ 8.91 (d, J=2.0 Hz, 1H), 8.28 (d, J=2.0 Hz, 1H), 7.45-7.31 (m, 4H), 3.69 (s, 3H), 3.02 (t, J=7.7 Hz, 2H), 2.67 (t, J=7.8 Hz, 2H).

Step 2: Methyl 3-(3-bromo-5H-pyrido[3,2-b]indol-6-yl)propanoate

Following a procedure analogous to that described for the synthesis of methyl 3-bromo-9-fluoro-5H-pyrido[3,2-b]indole-6-carboxylate, methyl 3-(3-(5-bromo-3-nitropyridin-2-yl)phenyl)propanoate (700 mg, 1.92 mmol) was converted to methyl 3-(3-bromo-5H-pyrido[3,2-b]indol-6-yl)propanoate (280 mg, 0.840 mmol, 44%) as white solid. LCMS: RT=0.83 min; (ES): m/z (M+H)$^+$=333.0, 335.0 (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). $^1$H NMR (400 MHz, CDCl$_3$) δ 9.21 (br. s., 1H), 8.60 (d, J=2.0 Hz, 1H), 8.22 (d, J=7.5 Hz, 1H), 7.96 (d, J=2.0 Hz, 1H), 7.38-7.34 (m, 1H), 7.30 (d, J=7.6 Hz, 1H), 3.69 (s, 3H), 3.32-3.22 (m, 2H), 2.88-2.78 (m, 2H). Also obtained from the reaction was the isomeric methyl 3-(3-bromo-5H-pyrido[3,2-b]indol-8-yl)propanoate (210 mg, 0.630 mmol, 33%) as a white solid. $^1$H NMR (400 MHz, CDCl$_3$) δ 8.60 (d, J=2.0 Hz, 1H), 8.18-8.16 (m, 1H), 8.06 (br. s., 1H), 7.88 (d, J=2.0 Hz, 1H), 7.44-7.39 (m, 2H), 3.69 (s, 3H), 3.17 (t, J=7.8 Hz, 2H), 2.81-2.71 (m, 2H). LCMS: RT=0.79 min; (ES): m/z (M+H)$^+$=333.0, 335.0 (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA).

Step 3: (S)-Methyl 3-(3-(1,4-dimethyl-1H-1,2,3-triazol-5-yl)-5-(phenyl(tetrahydro-2H-pyran-4-yl)methyl)-5H-pyrido[3,2-b]indol-8-yl)propanoate Following a procedure analogous to that described in steps 3 and 4 for the synthesis of (S)-methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-6-carboxylate, methyl 3-(3-bromo-5H-pyrido[3,2-b]indol-8-yl)propanoate (210 mg, 0.630 mmol) was converted to (S)-methyl 3-(3-(1,4-dimethyl-1H-1,2,3-triazol-5-yl)-5-(phenyl(tetrahydro-2H-pyran-4-yl)methyl)-5H-pyrido[3,2-b]indol-8-yl)propanoate (33.0 mg, 18%). LCMS: RT=0.86 min; (ES): m/z (M+H)$^+$=524.3 (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). 1H NMR (500 MHz, DMSO-d6) δ 8.51 (s, 1H), 8.07 (m, 2H), 7.95 (s, 1H), 7.66 (d, J=7.4 Hz, 2H), 7.50 (d, J=7.4 Hz, 1H), 7.37-7.27 (m, 2H), 7.27-7.17 (m, 1H), 5.77 (d, J=11.4 Hz, 1H), 4.01 (br. s., 3H), 3.88 (d, J=13.8 Hz, 1H), 3.72 (d, J=8.8 Hz, 1H), 3.58 (s, 3H), 3.48-3.34 (m, 2H), 3.27 (t, J=11.3 Hz, 1H), 3.05 (t, J=7.4 Hz, 2H), 2.80-2.68 (m, 2H), 2.30 (s, 3H), 1.67 (d, J=12.5 Hz, 1H), 1.60-1.45 (m, 1H), 1.37-1.19 (m, 1H), 1.00 (d, J=12.5 Hz, 1H).

Step 4: 4-[3-(Dimethyl-1H-1,2,3-triazol-5-yl)-5-[(S)-oxan-4-yl(phenyl)methyl]-5H-pyrido[3,2-b]indol-8-yl]-2-methylbutan-2-ol Following a procedure analogous to that described for the synthesis of (S)-2-[3-(dimethyl-1H-1,2,3-triazol-5-yl)-5-[oxan-4-yl(phenyl)methyl]-5H-pyrido[3,2-b]indol-7-yl]propan-2-ol, (S)-methyl 3-(3-(1,4-dimethyl-1H-1,2,3-triazol-5-yl)-5-(phenyl(tetrahydro-2H-pyran-4-yl)methyl)-5H-pyrido[3,2-b]indol-8-yl)propanoate was converted to 4-[3-

(dimethyl-1H-1,2,3-triazol-5-yl)-5-[(S)-oxan-4-yl(phenyl)methyl]-5H-pyrido[3,2-b]indol-8-yl]-2-methylbutan-2-ol. $^1$H NMR (500 MHz, DMSO-d6) δ 8.50 (s, 1H), 8.04 (s, 2H), 7.94 (s, 1H), 7.66 (d, J=7.7 Hz, 2H), 7.47 (d, J=7.4 Hz, 1H), 7.37-7.27 (m, 2H), 7.27-7.17 (m, 1H), 5.76 (d, J=11.1 Hz, 1H), 4.01 (br. s., 3H), 3.88 (d, J=13.5 Hz, 1H), 3.72 (d, J=9.4 Hz, 1H), 3.55-3.36 (m, 2H), 3.27 (t, J=11.3 Hz, 1H), 2.85-2.76 (m, 2H), 2.30 (s, 3H), 1.79-1.71 (m, 2H), 1.67 (d, J=12.5 Hz, 1H), 1.58-1.46 (m, 1H), 1.35-1.24 (m, 1H), 1.18 (s, 6H), 1.01 (d, J=12.1 Hz, 1H). LCMS: RT=1.75 min; (ES): m/z (M+H)$^+$=524.35 (LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min).

Examples 154 & 155

4-{5-[(4,4-Difluorocyclohexyl)(phenyl)methyl]-7-methanesulfonyl-5H-pyrido[3,2-b]indol-3-yl}-3,5-dimethyl-1,2-oxazole Enantiomer A, Example 154

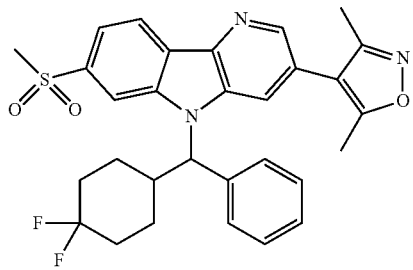

Enantiomer B, Example 155

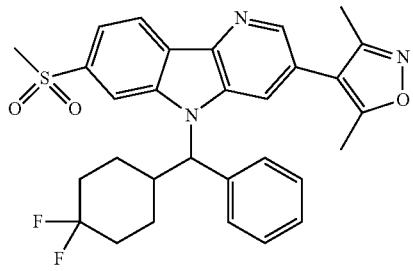

Step 1: 3-Bromo-5-((4,4-difluorocyclohexyl)(phenyl)methyl)-7-(methylsulfonyl)-5H-pyrido[3,2-b]indole In a 20 mL vial was added a mixture of 3-bromo-7-(methylsulfonyl)-5H-pyrido[3,2-b]indole (300 mg, 0.923 mmol), (4,4-difluorocyclohexyl)(phenyl)methanol (417 mg, 1.85 mmol), and triphenylphosphine (484 mg, 1.85 mmol), and dichloromethane (10 mL), and the mixture was stirred at room temperature while treated drop wise with DIAD (0.359 mL, 1.85 mmol), and then stirred at room temperature. The suspension gradually became a solution during the addition. After 5 h, the mixture was loaded onto a silica gel column and purified using silica gel column chromatography, using an ISCO Companion (120 g silica gel column) and eluted with a EtOAc/hexane gradient (20-0%) to give 3-bromo-5-((4,4-difluorocyclohexyl)(phenyl)methyl)-7-(methylsulfonyl)-5H-pyrido[3,2-b]indole (492 mg, 0.922 mmol, 100%). LCMS: RT=1.06 min; (ES): m/z (M+H)$^+$=533.0, 535.0. (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA).

Step 2: 4-{5-[(4,4-Difluorocyclohexyl)(phenyl)methyl]-7-methanesulfonyl-5H-pyrido[3,2-b]indol-3-yl}-3,5-dimethyl-1,2-oxazole In a 2 dram vial was added a mixture of 3-bromo-5-((4,4-difluorocyclohexyl)(phenyl)methyl)-7-(methylsulfonyl)-5H-pyrido[3,2-b]indole (150 mg, 0.281 mmol), 3,5-dimethyl-4-(4,4,5,5-tetramethyl-1,3,2-dioxaborolan-2-yl)isoxazole (94.0 mg, 0.422 mmol), PdCl$_2$(dppf)-CH$_2$Cl$_2$ adduct (34.4 mg, 0.0420 mmol), 2 M aqueous tripotassium phosphate (0.422 mL, 0.844 mmol), and tetrahydrofuran (3 mL). The mixture was purged with a nitrogen stream. The vial was capped and heated in a heating block at 90° C. 3 h. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 min, then a 5-min hold at 100% B; Flow: 20 mL/min. Fractions containing the desired product were combined and dried via centrifugal evaporation to give racemic 4-{5-[(4,4-difluorocyclohexyl)(phenyl)methyl]-7-methanesulfonyl-5H-pyrido[3,2-b]indol-3-yl}-3,5-dimethyl-1,2-oxazole, which was separated by chiral prep HPLC (Chiralcel OD 20×250 mm 20 mL/min 15% EtOH/0.5% DEA in Heptane) to give Enantiomer A (5.00 mg, 3%) and Enantiomer B (4.00 mg, 3%). Enantiomer A: $^1$H NMR (500 MHz, DMSO-d$_6$) δ 8.76 (br. s., 1H), 8.59 (s, 1H), 8.46 (d, J=8.2 Hz, 1H), 8.38 (br. s., 1H), 7.85 (d, J=8.2 Hz, 1H), 7.66 (d, J=7.7 Hz, 2H), 7.38-7.31 (m, 2H), 7.30-7.22 (m, 1H), 6.05 (d, J=11.3 Hz, 1H), 3.39 (s, 3H), 2.49 (s, 3H), 2.31 (s, 3H), 2.17-1.97 (m, 3H), 1.92 (br. s., 2H), 1.84-1.68 (m, 1H), 1.64 (br. s., 1H), 1.37 (d, J=13.4 Hz, 1H), 1.28-1.13 (m, 1H). LCMS: RT=1.98 min; (ES): m/z (M+H)$^+$=550.1. (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). Chiral HPLC: RT=11.761 min (Column: Chiralcel OD 250×4.6 mm, 5 μm; Mobile Phase: 20% Ethanol (0.1% DEA) in Heptane (0.1 5 DEA); Flow: 1 mL/min). Enantiomer A: Chiral HPLC: RT=13.669 min(Column: Chiralcel OD 250×4.6 mm, 5 μm; Mobile Phase: 20% Ethanol (0.1% DEA) in heptane (0.1 5 DEA); Flow: 1 mL/min).

Examples 156 & 157

5-{5-[(4,4-Difluorocyclohexyl)(phenyl)methyl]-7-methanesulfonyl-5H-pyrido[3,2-b]indol-3-yl}-1,4-dimethyl-1H-1,2,3-triazole

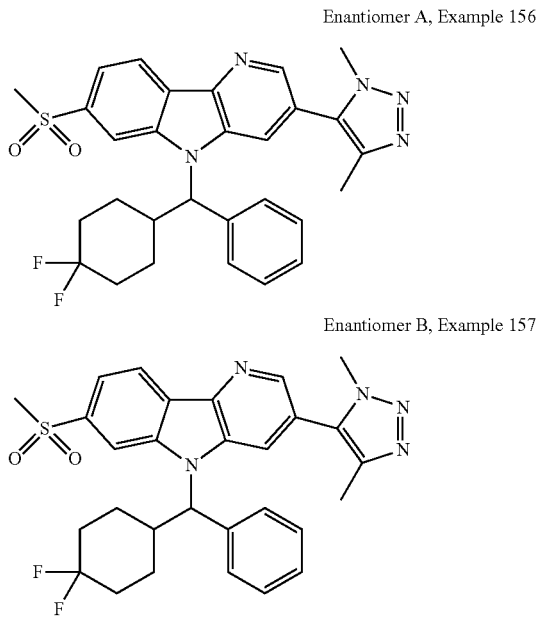

Enantiomer A, Example 156

Enantiomer B, Example 157

In a 2 dram vial was added a mixture of 3-bromo-5-((4,4-difluorocyclohexyl)(phenyl)methyl)-7-(methylsulfonyl)-5H-pyrido[3,2-b]indole (150 mg, 0.281 mmol), 1,4-dimethyl-5-(tributylstannyl)-1H-1,2,3-triazole (163 mg, 0.422 mmol), copper(I) iodide (10.7 mg, 0.0560 mmol), Pd(Ph$_3$P)$_4$ (32.5 mg, 0.0280 mmol), and DMF (2 mL). The mixture was treated with Et$_3$N (0.118 mL, 0.844 mmol) and purged with a nitrogen stream. The vial was capped and heated in a heating block at 90° C. for 4 h and was filtered through a 0.45 um nylon membrane filter, and the crude material was purified via preparative LC/MS with the following conditions: Column: Waters XBridge C18, 19×200 mm, 5-µm; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation. The material was further purified on chiral prep SFC (Column: Chiral ID 25×3 cm, 5 µm; Mobile Phase: 70/30 CO$_2$/MeOH; Flow: 85 mL/min) to give 5-{5-[(4,4-difluorocyclohexyl)(phenyl)methyl]-7-methanesulfonyl-5H-pyrido[3,2-b]indol-3-yl}-1,4-dimethyl-1H-1,2,3-triazole Enantiomer A (20.0 mg, 13%) and Enantiomer B (20.0 mg 13%). Enantiomer A: $^1$H NMR (500 MHz, DMSO-d$_6$) δ 8.79 (br. s., 1H), 8.67 (s, 1H), 8.58-8.53 (m, 1H), 8.50 (d, J=8.2 Hz, 1H), 7.87 (d, J=8.2 Hz, 1H), 7.67 (d, J=7.6 Hz, 2H), 7.41-7.31 (m, 2H), 7.30-7.22 (m, 1H), 6.06 (d, J=11.0 Hz, 1H), 4.02 (s, 3H), 3.39 (br. s., 3H), 2.30 (s, 3H), 2.16-1.98 (m, 2H), 1.91 (br. s., 2H), 1.83-1.53 (m, 3H), 1.38 (d, J=11.9 Hz, 1H), 1.23 (br. s., 1H). LCMS: RT=1.742 min; (ES): m/z (M+H)$^+$=550.15 (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). Chiral SFC RT=7.50 min (Column: Chiralcel ID 250×4.6 mm, 5 µm; Mobile Phase: 70/30 CO$_2$/MeOH; Flow: 2 mL/min). Enantiomer B: Chiral SFC RT=8.50 min (Column: Chiralcel ID 250×4.6 mm, 5 µm; Mobile Phase: 70/30 CO$_2$/MeOH; Flow: 2 mL/min).

Examples 158 & 159

5-{5-[(4,4-Difluorocyclohexyl)(phenyl)methyl]-7-methanesulfonyl-5H-pyrido[3,2-b]indol-3-yl}-4-($^2$H$_3$)methyl-1-methyl-1H-1,2,3-triazole

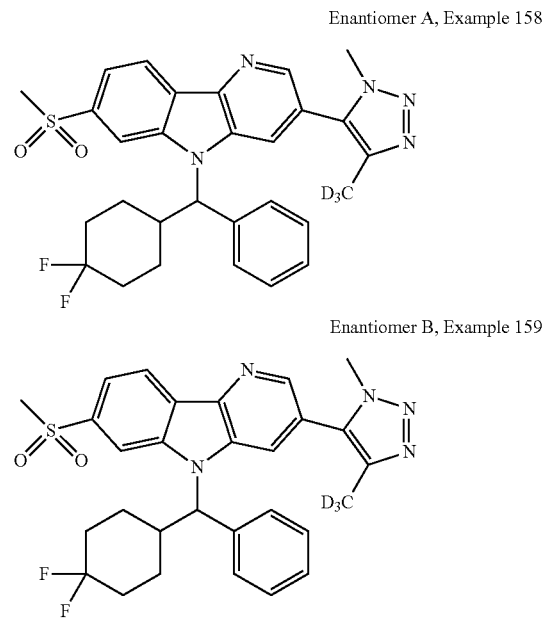

Enantiomer A, Example 158

Enantiomer B, Example 159

Following a procedure analogous to that described for the synthesis of 5-{5-[(4,4-difluoro cyclohexyl)(phenyl)methyl]-7-methanesulfonyl-5H-pyrido[3,2-b]indol-3-yl}-1,4-dimethyl-1H-1,2,3-triazole, 4-($^2$H$_3$)methyl-1-methyl-5-(tributylstannyl)-1H-1,2,3-triazole and 3-bromo-5-((4,4-difluorocyclohexyl)(phenyl)methyl)-7-(methylsulfonyl)-5H-pyrido[3,2-b]indole were converted, after chiral prep SFC (Column: Chiral ID 25×3 cm, 5 µm; Mobile Phase: 70/30 CO$_2$/MeOH; Flow: 85 mL/min), to 5-{5-[(4,4-difluoro cyclohexyl)(phenyl)methyl]-7-methanesulfonyl-5H-pyrido[3,2-b]indol-3-yl}-4-($^2$H$_3$)methyl-1-methyl-1H-1,2,3-triazole Enantiomer A (16.0 mg, 10%) and Enantiomer B (17.0 mg 11%). Enantiomer A: $^1$H NMR (500 MHz, DMSO-d$_6$) δ 8.77 (br. s., 1H), 8.67 (s, 1H), 8.59-8.52 (m, 1H), 8.50 (d, J=8.2 Hz, 1H), 7.87 (d, J=8.2 Hz, 1H), 7.66 (d, J=7.6 Hz, 2H), 7.42-7.31 (m, 2H), 7.31-7.22 (m, 1H), 6.06 (d, J=11.3 Hz, 1H), 4.02 (s, 3H), 3.39 (s, 3H), 2.16-1.98 (m, 3H), 1.91 (br. s., 2H), 1.83-1.67 (m, 1H), 1.65-1.52 (m, 1H), 1.38 (d, J=12.0 Hz, 1H), 1.23 (br. s., 1H). LCMS: RT=1.736 min; (ES): m/z (M+H)$^+$=553.10 (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). Chiral SFC RT=7.50 min (Column: Chiralcel ID 250×4.6

Example 160

5-{6,7-Difluoro-9-methanesulfonyl-5-[(S)-oxan-4-yl(phenyl)methyl]-5H-pyrido[3,2-b]indol-3-yl}-1,4-dimethyl-1H-1,2,3-triazole

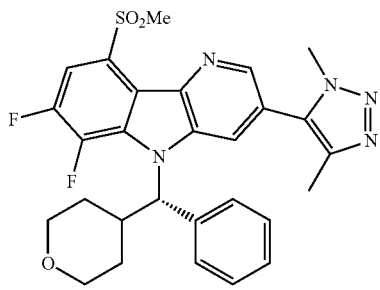 [SMILES: Cc1nnn(C)c1-c1cnc2c3c(S(C)(=O)=O)cc(F)c(F)c3n([C@H](c3ccccc3)C3CCOCC3)c2c1]

Step 1:
(2-Bromo-4,5-difluorophenyl)(methyl)sulfane

In a 40 mL vial, a solution of 1-bromo-2,4,5-trifluorobenzene (2.00 g, 9.48 mmol) in DMSO (15 mL) was treated with NaSMe (3.32 g, 47.4 mmol), and the resulting suspension stirred at room temperature for 4 h. The reaction mixture was diluted with DCM, and the organics were washed with water and brine. The volatiles were concentrated to give (2-bromo-4,5-difluorophenyl)(methyl)sulfane (2.20 g, 98%), which was used without further purification in next reaction. $^1$H NMR (400 MHz, CDCl$_3$) δ 7.23 (dd, J=8.7, 5.7 Hz, 1H), 6.98 (dd, J=8.5, 6.4 Hz, 1H), 2.46 (s, 3H). HPLC: RT=2.756 min; (Chromolith ODS S5 4.6×50 mm (4 min grad) 0-100% B. Flow Rate=4 ml/min. Inj. Vol.=10 uL. Wavelength=220. Oven Temp.=40° C. Solvent A: 10% MeOH–90% H$_2$O–0.1% TFA. Solvent B: 90% MeOH–10% H$_2$O–0.1% TFA).

Step 2:
1-Bromo-4,5-difluoro-2-(methylsulfonyl)benzene

A solution of (2-bromo-4,5-difluorophenyl)(methyl)sulfane (2.20 g, 9.20 mmol) in 2-propanol (50 mL) in a RB flask was treated with Oxone (11.3 g, 18.4 mmol), and the suspension was stirred vigorously and diluted with some water to dissolve some of the Oxone solids to give a white milky suspension, which was stirred at room temperature and stirred overnight. The mixture was diluted with water and extracted into DCM, and the combined organics were concentrated to give 1-bromo-4,5-difluoro-2-(methylsulfonyl)benzene (2.40 g, 8.85 mmol, 96%) as a white solid. HPLC: RT=1.362 min; (Chromolith ODS S5 4.6×50 mm (4 min grad) 0-100% B. Flow Rate=4 ml/min. Inj. Vol.=10 uL. Wavelength=220. Oven Temp.=40° C. Solvent A: 10% MeOH–90% H$_2$O–0.1% TFA. Solvent B: 90% MeOH–10% H$_2$O–0.1% TFA). LCMS: RT=0.79 min; (ES): m/z (M+H)$^+$=270.8, 272.9. (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). $^1$H NMR (400 MHz, CDCl$_3$) δ 7.76 (dd, J=7.1, 5.7 Hz, 1H), 7.55 (dd, J=8.4, 5.0 Hz, 1H), 3.25 (d, J=0.6 Hz, 3H).

Step 3: 2-(4,5-Difluoro-2-(methylsulfonyl)phenyl)-4,4,5,5-tetramethyl-1,3,2-dioxaborolane In a large 40 mL vial was added a mixture of 1-bromo-4,5-difluoro-2-(methylsulfonyl)benzene (2.40 g, 8.85 mmol), 4,4,4',4',5,5,5',5'-octamethyl-2,2'-bi(1,3,2-dioxaborolane) (2.70 g, 10.6 mmol), potassium acetate (2.61 g, 26.6 mmol), and PdCl$_2$ (dppf)-CH$_2$Cl$_2$ adduct (0.362 g, 0.443 mmol) in dioxane (20 mL). The vial was capped and heated in heating block at 90° C. overnight. Diluted with water and extracted into ethyl acetate. The organics were washed with water, and the volatiles were removed under reduced pressure and the resulting black residue was dissolve in DCM and purified using silica gel column chromatography with an ISCO Companion 40 g silica gel column and eluted with an EtOAc/hexane gradient (50-100%) to give 2-(4,5-difluoro-2-(methylsulfonyl)phenyl)-4,4,5,5-tetramethyl-1,3,2-dioxaborolane (2.1 g, 6.60 mmol, 74.6%) as a yellow slowly solidifying residue. $^1$H NMR (400 MHz, CDCl$_3$) δ 7.69-7.58 (m, 2H), 3.25 (d, J=0.6 Hz, 3H), 1.41-1.37 (m, 12H). LCMS: RT=0.54 min; (ES): m/z (M+H)$^+$=237.1 (boronic acid) (Waters Acquity SDS. Column: BEH C18 2.1×50 mm 1.7 u (1.6 min grad) 2-98% B. Flow Rate=0.8 ml/min. Solvent A: H$_2$O–0.1% TFA. Solvent B: Acetonitrile–0.1% TFA).

Step 4: 5-Bromo-2-(4,5-difluoro-2-(methylsulfonyl)phenyl)-3-nitropyridine

In a 40 ml vial was added a mixture of 2,5-dibromo-3-nitropyridine (1.861 g, 6.60 mmol), 2-(4,5-difluoro-2-(methylsulfonyl)phenyl)-4,4,5,5-tetramethyl-1,3,2-dioxaborolane (2.1 g, 6.60 mmol), PdCl$_2$(dppf)-CH$_2$Cl$_2$ adduct (0.404 g, 0.495 mmol), and 2 Molar aqueous tripotassium phosphate (9.90 mL, 19.8 mmol), and the mixture was purged under a stream of nitrogen. The vial was capped and heated in a heating block at 80° C. for 3 h. Diluted with water and extracted into ethyl acetate. The organics were washed with water and brine and concentrated to give a black residue that was purified using silica gel column chromatography with an ISCO Companion 120 g silica gel column and eluted with CH$_2$Cl$_2$/EtOAc gradient (0-50%) to give 5-bromo-2-(4,5-difluoro-2-(methylsulfonyl)phenyl)-3-nitropyridine (1.2 g, 3.05 mmol, 46.2%) as a light-yellow solid. LCMS: RT=0.90 min; (ES): m/z (M+H)$^+$=392.7, 394.7. (Waters Acquity SDS. Column: BEH C18 2.1×50 mm 1.7 u (1.6 min grad) 2-98% B. Flow Rate=0.8 ml/min. Solvent A: H$_2$O–0.1% TFA. Solvent B: Acetonitrile–0.1% TFA) $^1$H NMR (400 MHz, CDCl$_3$) δ 9.04 (d, J=2.0 Hz, 1H), 8.61 (d, J=2.1 Hz, 1H), 7.76 (dd, J=8.6, 5.3 Hz, 1H), 7.63 (dd, J=9.2, 5.1 Hz, 1H), 3.32 (d, J=0.5 Hz, 3H).

Step 5: 3-Bromo-6,7-difluoro-9-(methylsulfonyl)-5H-pyrido[3,2-b]indole

A solution of 5-bromo-2-(4,5-difluoro-2-(methylsulfonyl)phenyl)-3-nitropyridine (1.2 g, 3.05 mmol) and 1,2-bis(diphenylphosphino)ethane (1.459 g, 3.66 mmol) in 1,2-dichlorobenzene (15 mL) in a 40 mL vial was capped and heated in a heating block at 170° C. for 5 h. The solvents were evaporated on a rotary evaporator with heating under high vacuum, and the residue was purified using silica gel column chromatography with an ISCO Companion (120 g silica gel column) and eluted with an $CH_2Cl_2$/EtOAc gradient (20-70%) to give 3-bromo-6,7-difluoro-9-(methylsulfonyl)-5H-pyrido[3,2-b]indole (230 mg, 0.637 mmol, 21%) as a light-yellow solid. LCMS: RT=0.81 min; (ES): m/z $(M+H)^+$=360.9, 362.9. (Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA). $^1$H NMR (400 MHz, $CDCl_3$) δ 8.70 (d, J=2.0 Hz, 1H), 8.09 (d, J=2.1 Hz, 1H), 7.44 (dd, J=8.8, 4.2 Hz, 1H), 3.33 (s, 3H).

Step 6: (S)-3-Bromo-6,7-difluoro-9-(methylsulfonyl)-5-(phenyl(tetrahydro-2H-pyran-4-yl)methyl)-5H-pyrido[3,2-b]indole In a RB flask was added a suspension of 3-bromo-6,7-difluoro-9-(methylsulfonyl)-5H-pyrido[3,2-b]indole (230 mg, 0.637 mmol) and (R)-phenyl(tetrahydro-2H-pyran-4-yl)methanol (245 mg, 1.27 mmol) in dichloromethane (6 mL), and the resulting reaction mixture was treated with triphenylphosphine (334 mg, 1.27 mmol) before the drop wise addition of DIAD (0.248 mL, 1.27 mmol) at room temperature. The mixture was stirred at room temperature overnight. The material was purified using silica gel column chromatography with an ISCO Companion (80 g silica gel column) and eluted with an $CH_2Cl_2$/EtOAc gradient (0-100%) to give (S)-3-bromo-6,7-difluoro-9-(methylsulfonyl)-5-(phenyl(tetrahydro-2H-pyran-4-yl)methyl)-5H-pyrido[3,2-b]indole (315 mg, 0.588 mmol, 92%) as a light-yellow solid. LCMS: RT=1.01 min; (ES): m/z $(M+H)^+$=534.9, 536.9. (Waters Acquity SDS. Column: BEH C18 2.1×50 mm 1.7 u (1.6 min grad) 2-98% B. Flow Rate=0.8 mL/min. Solvent A: $H_2O$–0.1% TFA. Solvent B: Acetonitrile–0.1% TFA).

Step 7: 5-{6,7-Difluoro-9-methanesulfonyl-5-[(S)-oxan-4-yl(phenyl)methyl]-5H-pyrido[3,2-b]indol-3-yl}-1,4-dimethyl-1H-1,2,3-triazole In a 2 dram vial was added a mixture of (S)-3-bromo-6,7-difluoro-9-(methylsulfonyl)-5-(phenyl(tetrahydro-2H-pyran-4-yl)methyl)-5H-pyrido[3,2-b]indole (30.0 mg, 0.0560 mmol), 1,4-dimethyl-5-(tributylstannyl)-1H-1,2,3-triazole (32.5 mg, 0.0840 mmol), copper(I) iodide (2.13 mg, 0.0110 mmol), $Pd(Ph_3P)_4$ (6.47 mg, 5.60 µmol), and TEA (0.0230 mL, 0.168 mmol) in DMF (1 mL). The vial was capped and heated in a heating block at 80° C. overnight. The reaction mixture was then diluted with ammonium hydroxide and water and extracted into ethyl acetate. The organics were washed with water and brine, and the organics were concentrated. The material was purified using silica gel column chromatography with an ISCO Companion (24 g silica gel column) and eluted with ethyl acetate. The fractions containing product were collected, and the volatiles were removed to give 15.0 mg of a white solid. This material was further purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 5-{6,7-difluoro-9-methanesulfonyl-5-[(S)-oxan-4-yl(phenyl)methyl]-5H-pyrido[3,2-b]indol-3-yl}-1,4-dimethyl-1H-1,2,3-triazole (5.10 mg, 16%). LCMS: RT=1.605 min; (ES): m/z $(M+H)^+$=552.10; (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min) $^1$H NMR (500 MHz, DMSO-$d_6$) δ 8.74 (br. s., 1H), 8.34 (br. s., 1H), 7.69 (br. s., 2H), 7.51 (br. s., 1H), 7.38 (br. s., 2H), 7.31 (d, J=6.9 Hz, 1H), 5.97 (br. s., 1H), 3.97-3.86 (m, 4H), 3.76 (d, J=9.6 Hz, 1H), 3.63-3.45 (m, 5H), 3.28 (t, J=10.6 Hz, 1H), 2.22 (br. s., 3H), 1.83 (br. s., 1H), 1.39 (br. s., 2H), 1.04 (d, J=12.2 Hz, 1H).

Example 161

5-{6,7-Difluoro-9-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole

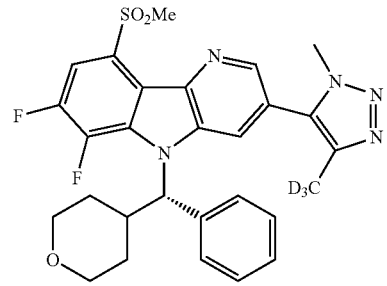 [SMILES: [2H]C([2H])([2H])c1nnn(C)c1-c1cnc2c3c(S(C)(=O)=O)cc(F)c(F)c3n([C@H](c3ccccc3)C3CCOCC3)c2c1]

Following a procedure analogous to that described for the synthesis of 5-{6,7-difluoro-9-methanesulfonyl-5-[(S)-oxan-4-yl(phenyl)methyl]-5H-pyrido[3,2-b]indol-3-yl}-1,4-dimethyl-1H-1,2,3-triazole, (S)-3-bromo-6,7-difluoro-9-(methylsulfonyl)-5-(phenyl(tetrahydro-2H-pyran-4-yl)methyl)-5H-pyrido[3,2-b]indole and 4-($^2H_3$)methyl-1-methyl-5-(tributylstannyl)-1H-1,2,3-triazole were converted to 5-{6,7-difluoro-9-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole. LCMS: RT=1.634 min; (ES): m/z $(M+H)^+$=555.10; (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). $^1$H NMR (500 MHz, DMSO-$d_6$) δ 8.76 (br. s., 1H), 8.37 (br. s., 1H), 7.71 (br. s., 2H), 7.52 (br. s., 1H), 7.38 (br. s., 2H), 7.32 (d, J=7.1 Hz, 1H), 5.98 (br. s., 1H), 4.01-3.85 (m, 4H), 3.77 (d, J=10.3 Hz, 1H), 3.60-3.41 (m, 5H), 3.34-3.22 (m, 1H), 1.81 (br. s., 1H), 1.40 (br. s., 2H), 1.05 (d, J=12.3 Hz, 1H).

Example 162

5-{9-Methanesulfonyl-6,7-dimethoxy-5-[(S)-oxan-4-yl(phenyl)methyl]-5H-pyrido[3,2-b]indol-3-yl}-4-($^2$H$_3$)methyl-1-methyl-1H-1,2,3-triazole

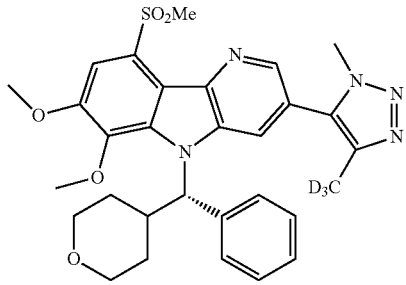 [SMILES: [2H]C([2H])([2H])c1nnn(C)c1-c1cnc2c3c(S(C)(=O)=O)cc(OC)c(OC)c3n([C@H](c3ccccc3)C3CCOCC3)c2c1]

In a 2 dram vial, a mixture of 5-{6,7-difluoro-9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (10.0 mg, 0.0180 mmol) and KOtBu (10.1 mg, 0.0900 mmol) in methanol (1 mL) was heated in a heating block at 90° C. overnight. The crude material was purified via preparative LC/MS with the following conditions: Column: Waters XBridge Shield RP18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 min, then a 5-min hold at 100% B; Flow: 20 mL/min. Fractions containing the product were combined and dried via centrifugal evaporation to give 5-{9-methanesulfonyl-6,7-dimethoxy-5-[(S)-oxan-4-yl(phenyl)methyl]-5H-pyrido[3,2-b]indol-3-yl}-4-($^2$H$_3$)methyl-1-methyl-1H-1,2,3-triazole (4.40 mg, 40%). LCMS: RT=1.605 min; (ES): m/z (M+H)$^+$=579.2. (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min). LCMS: RT=0.81 min; (ES): m/z (M+H)$^+$=579.2 (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). $^1$H NMR (500 MHz, DMSO-d$_6$) δ 8.64 (s, 1H), 8.14 (br. s., 1H), 7.61 (d, J=7.5 Hz, 2H), 7.36-7.29 (m, 2H), 7.26 (d, J=7.6 Hz, 2H), 6.26 (d, J=10.9 Hz, 1H), 4.16 (s, 3H), 4.06 (s, 3H), 3.94-3.84 (m, 4H), 3.77 (d, J=9.3 Hz, 1H), 3.47 (br. s., 5H), 3.34 (t, J=11.3 Hz, 1H), 1.80 (d, J=12.5 Hz, 1H), 1.45 (d, J=12.1 Hz, 2H), 1.11 (d, J=12.1 Hz, 1H).

Example 163

5-{7-Fluoro-9-methanesulfonyl-6-methoxy-5-[(S)-oxan-4-yl(phenyl)methyl]-5H-pyrido[3,2-b]indol-3-yl}-4-($^2$H$_3$)methyl-1-methyl-1H-1,2,3-triazole

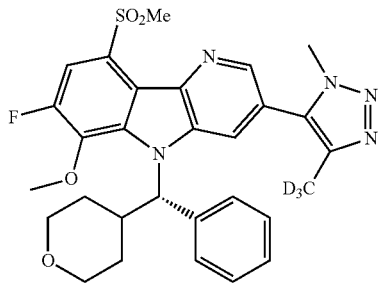 [SMILES: [2H]C([2H])([2H])c1nnn(C)c1-c1cnc2c3c(S(C)(=O)=O)cc(F)c(OC)c3n([C@H](c3ccccc3)C3CCOCC3)c2c1]

In a 2 dram vial, a mixture of 5-{6,7-difluoro-9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (13.0 mg, 0.0230 mmol) and KOtBu (22.0 mg, 0.200 mmol) in methanol (2 mL) was stirred at room temperature for 11 days. The resulting white suspension was diluted with water and HCl and extracted into ethyl acetate. The organics were washed with water, and the volatiles were removed under reduced pressure to give a white solid. The material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 5 min, then a 20-min hold at 100% B; Flow: 20 mL/min. Fractions containing the desired product were combined and dried via centrifugal evaporation to give 5-{7-fluoro-9-methanesulfonyl-6-methoxy-5-[(S)-oxan-4-yl(phenyl)methyl]-5H-pyrido[3,2-b]indol-3-yl}-4-($^2$H$_3$)methyl-1-methyl-1H-1,2,3-triazole (8.50 mg, 44%). $^1$H NMR (500 MHz, DMSO-d$_6$) δ 8.68 (s, 1H), 8.18 (s, 1H), 7.62 (d, J=7.7 Hz, 2H), 7.53 (d, J=8.9 Hz, 1H), 7.39-7.29 (m, 2H), 7.29-7.19 (m, 1H), 6.24 (d, J=10.9 Hz, 1H), 4.19 (s, 3H), 3.93-3.83 (m, 4H), 3.76 (d, J=9.9 Hz, 1H), 3.66-3.52 (m, 2H), 3.49 (s, 3H), 3.33 (t, J=11.1 Hz, 1H), 1.80 (d, J=12.4 Hz, 1H), 1.50-1.36 (m, J=12.1, 12.1 Hz, 2H), 1.10 (d, J=12.5 Hz, 1H). LCMS: RT=1.696 min; (ES): m/z (M+H)$^+$=567.1 (Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min).

Example 164

5-{5-[(4,4-Difluorocyclohexyl)(phenyl)methyl]-6,7-difluoro-9-methanesulfonyl-5H-pyrido[3,2-b]indol-3-yl}-4-($^2$H$_3$)methyl-1-methyl-1H-1,2,3-triazole (Enantiomer A)

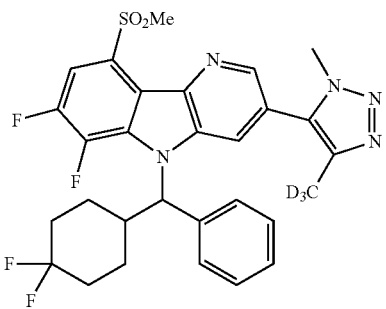 [SMILES: [2H]C([2H])([2H])c1nnn(C)c1-c1cnc2c3c(S(C)(=O)=O)cc(F)c(F)c3n(C(c3ccccc3)C3CCC(F)(F)CC3)c2c1]

Step 1: 3-Bromo-5-((4,4-difluorocyclohexyl)(phenyl)methyl)-6,7,9-trifluoro-5H-pyrido[3,2-b]indole In a 20 mL vial was added a suspension of 3-bromo-6,7,9-trifluoro-5H-pyrido[3,2-b]indole (400 mg, 1.33 mmol), (4,4-difluorocyclohexyl)(phenyl)methanol (601 mg, 2.66 mmol), and triphenylphosphine (697 mg, 2.66 mmol), and dichloromethane (6 mL). The mixture was stirred during drop-wise addition of DIAD (0.517 mL, 2.66 mmol), and the mixture was stirred at room temperature overnight. The reaction mixture was loaded onto a silica gel column and purified using silica gel column chromatography with an ISCO Companion (80 g silica gel column) and eluted with an EtOAc/hexane gradient (10-50%) to give 3-bromo-5-((4,4-difluorocyclohexyl)(phenyl)methyl)-6,7,9-trifluoro-5H-pyrido[3,2-b]indole (300 mg, 0.589 mmol, 44%) as a white solid. LCMS: RT=1.22 min; (ES): m/z (M+H)$^+$=509.0, 511.0. (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA).

Step 2: 5-{-[(4,4-Diflurocyclohexyl)(phenyl) methyl]-6,7,9-trifluoro-5H-pyrido[3,2-b]indol-3-yl}- 4-($^2$H$_3$)methyl-1-methyl-1H-1,2,3-triazole In a 20 mL vial was added a mixture of 3-bromo-5-((4,4-difluorocyclohexyl)(phenyl)methyl)-6,7,9-trifluoro-5H-pyrido[3,2-b]indole (300 mg, 0.589 mmol), 4-($^2$H$_3$)methyl-1-methyl-5-(tributylstannyl)-1H-1,2,3-triazole (344 mg, 0.884 mmol), copper(I) iodide (22.4 mg, 0.118 mmol), and Pd(Ph$_3$P)$_4$ (68.1 mg, 0.0590 mmol) in DMF (6 mL). The mixture was purged under a stream of nitrogen for a few min and then was added Et$_3$N (0.246 mL, 1.767 mmol), and the vial was capped and heated in a heating block at 90° C. for 3 h. The reaction mixture was cooled to room temperature and diluted with aq. ammonium hydroxide and water and extracted into ethyl acetate. The organics were washed with water and brine and concentrated. The material was purified using silica gel column chromatography with an ISCO Companion (40 g silica gel column) and eluted with an EtOAc/hexane gradient (50-100%) to give 5-{-[(4,4-difluorocyclohexyl)(phenyl)methyl]-6,7,9-trifluoro-5H-pyrido[3,2-b]indol-3-yl}-4-($^2$H$_3$)methyl-1-methyl-1H-1,2,3-triazole (230 mg, 0.435 mmol, 74%) as a white solid, which was separated by chiral prep SFC (Column Whelk-O R,R 25×3 cm, 5 μm; Mobile Phase: 85/15 CO$_2$/MeOH; Flow: 85 mL/min) to give Enantiomer A (110 mg, 34%) and Enantiomer B (106 mg, 33%). Enantiomer A: $^1$H NMR (400 MHz, CDCl$_3$) δ 8.55 (d, J=1.7 Hz, 1H), 7.54 (s, 1H), 7.50-7.45 (m, 2H), 7.43-7.31 (m, 3H), 6.98 (ddd, J=10.5, 9.0, 5.3 Hz, 1H), 6.02 (br. s., 1H), 3.82 (s, 3H), 2.95-2.82 (m, J=8.4 Hz, 1H), 2.22 (d, J=11.6 Hz, 2H), 2.11-2.01 (m, 1H), 2.00-1.82 (m, 1H), 1.76-1.62 (m, 1H), 1.51 (d, J=12.7 Hz, 1H), 1.27 (br. s., 1H), 0.91-0.84 (m, 1H). LCMS: RT=1.09 min; (ES): m/z (M+H)$^+$=529.2; (Waters Acquity SDS. Column: BEH C18 2.1×50 mm 1.7 u (1.6 min grad) 2-98% B. Flow Rate=0.8 mL/min. Solvent A: H$_2$O–0.1% TFA. Solvent B: Acetonitrile–0.1% TFA). HPLC: RT=3.468 min; (Chromolith ODS S5 4.6×50 mm (4 min grad) 0-100% B. Flow Rate=4 mL/min. Inj. Vol.=10 uL. Wavelength=220. Oven Temp.=40° C. Solvent A: 10% MeOH–90% H$_2$O– 0.1% TFA. Solvent B: 90% MeOH–10% H$_2$O–0.1% TFA). HPLC: RT=14.067 min; (Sunfire C18 3.5 μm, 3.0×150 mm: 95/5 to 5/95 H$_2$O/CH$_3$CN/0.05% TFA, flow=5 mL/min, gradient=15 min, at 220 nm). Chiral SFC RT=12.219 min (Column: Whelk-O R,R, 250×21 mm, 5 μm; Mobile Phase: 80/20 CO$_2$/methanol; Flow: 2 mL/min). Enantiomer B: Chiral SFC RT=14.392 min (Column: Whelk-O R,R, 250× 21 mm, 5 μm; Mobile Phase: 80/20 CO$_2$/Methanol; Flow: 2 mL/min).

Step 3: 5-{-[(4,4-Difluorocyclohexyl)(phenyl) methyl]-6,7,-difluoro-9-methanesulfonyl-5H-pyrido [3,2-b]indol-3-yl}-4-($^2$H$_3$)methyl-1-methyl-1H-1,2, 3-triazole Enantiomer A In a 2 dram vial was added a mixture of 5-{-[(4,4-difluorocyclohexyl)(phenyl)methyl]-6,7,9-trifluoro-5H-pyrido[3,2-b]indol-3-yl}-4-($^2$H$_3$)methyl-1-methyl-1H-1,2,3-triazole Enantiomer A (20.0 mg, 0.0380 mmol) and sodium methanesulfinate (38.0 mg, 0.372 mmol) in DMSO (1 mL), and the vial was capped and heated in a heating block at 90° C. overnight. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 min, then a 5-min hold at 100% B; Flow: 20 mL/min. Fractions containing the desired product were combined and dried via centrifugal evaporation to give 5-{-[(4,4-difluorocyclohexyl)(phenyl)methyl]-6,7,-difluoro-9-methanesulfonyl-5H-pyrido[3,2-b]indol-3-yl}-4-($^2$H$_3$)methyl-1-methyl-1H-1,2,3-triazole Enantiomer A. (6.80 mg, 30%). $^1$H NMR (500 MHz, DMSO-d6) δ 8.75 (br. s., 1H), 8.31 (br. s., 1H), 7.67 (br. s., 2H), 7.51 (br. s., 1H), 7.41-7.26 (m, 3H), 5.97 (br. s., 1H), 3.93 (br. s., 3H), 3.56 (br. s., 3H), 2.14-1.89 (m, 5H), 1.87-1.67 (m, 1H), 1.48-1.26 (m, 3H). LCMS: RT=1.93 min; (ES): m/z (M+H)$^+$=589.1; (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min).

Examples 165 and 166

2-[3-(Dimethyl-1H-1,2,3-triazol-5-yl)-5-[oxan-4-yl (phenyl)methyl]-5H-pyrido[3,2-b]indol-7-yl]propan-2-amine Enantiomer A, Example 165

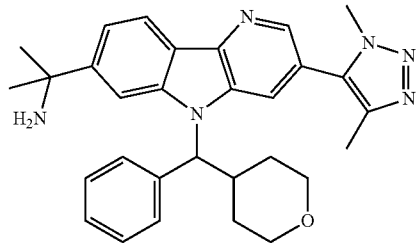

Enantiomer B, Example 166

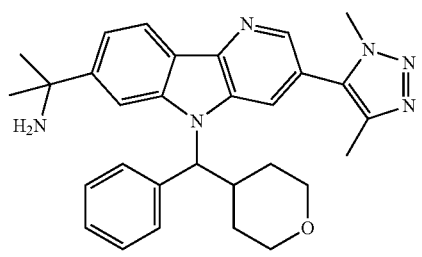

Step 1: 7-(2-Azidopropan-2-yl)-3-(1,4-dimethyl-1H-1,2,3-triazol-5-yl)-5-(phenyl(tetrahydro-2H-pyran-4-yl)methyl)-5H-pyrido[3,2-b]indole A mixture of 2-(3-(1,4-dimethyl-1H-1,2,3-triazol-5-yl)-5-(phenyl(tetrahydro-2H-pyran-4-yl)methyl)-5H-pyrido[3,2-b]indol-7-yl)propan-2-ol (600 mg, 0.847 mmol) and TMS-N3 (0.281 mL, 2.12 mmol) in DCM (20 mL) was cooled to 0° C. and treated with $BF_3 \cdot OEt_2$ (0.537 mL, 4.24 mmol) drop wise over the period of 2 min. The mixture was slowly brought to room temperature over the period of 2 h and then stirred at room temperature overnight. The mixture was quenched with 25 mL of water followed by 25 mL of 10% $NaHCO_3$ solution and extracted with DCM (50 mL×2). The organics were dried over $Na_2SO_4$, filtered, and concentrated, and the residue was purified using silica gel column chromatography to give 7-(2-azidopropan-2-yl)-3-(1,4-dimethyl-1H-1,2,3-triazol-5-yl)-5-(phenyl(tetrahydro-2H-pyran-4-yl)methyl)-5H-pyrido[3,2-b]indole (430 mg, 0.826 mmol, 84%) as a white solid. LCMS: HPLC: RT=1.10 min; MS (ES): m/z=521 [M+1]$^+$ (ACN/$H_2O$ with $NH_4OAc$, Acquity BEH C18 1.7 µm (50×2.1) mm, gradient=3 min, wavelength=220 nm).

Step 2: 2-[3-(Dimethyl-1H-1,2,3-triazol-5-yl)-5-[oxan-4-yl(phenyl)methyl]-5H-pyrido[3,2-b]indol-7-yl]propan-2-amine A stirred suspension of 7-(2-azidopropan-2-yl)-3-(1,4-dimethyl-1H-1,2,3-triazol-5-yl)-5-(phenyl(tetrahydro-2H-pyran-4-yl)methyl)-5H-pyrido[3,2-b]indole (0.400 g, 0.768 mmol), MeOH (10 mL), and Pd/C (10% on Carbon, 0.0400 g, 0.376 mmol) was hydrogenated at room temperature under a balloon of hydrogen gas for 3 h. The mixture was filtered through Celite and washed with methanol (50 mL), and the filtrate was concentrated to give racemic 2-[3-(dimethyl-1H-1,2,3-triazol-5-yl)-5-[oxan-4-yl(phenyl)methyl]-5H-pyrido[3,2-b]indol-7-yl]propan-2-amine (0.300 g, 0.607 mmol, 86%) as a white solid, which was separated by chiral prep SFC (Column: Chiral OD-H 25×2.1 cm, 5 µm; Mobile Phase: 70/30 $CO_2$/(0.25% DEA in MeOH); Flow: 75 mL/min) to give Enantiomer A and Enantiomer B. Enantiomer A: $^1$H NMR (400 MHz, $CD_3OD$) δ 8.43 (d, J=1.5 Hz, 1H), 8.34-8.29 (m, 1H), 8.22 (s, 1H), 8.09 (s, 1H), 7.64 (d, J=7.5 Hz, 2H), 7.54 (dd, J=1.5, 8.0 Hz, 1H), 7.39-7.32 (m, 2H), 7.30-7.22 (m, 1H), 5.82 (d, J=10.5 Hz, 1H), 4.03-3.96 (m, 4H), 3.82 (dd, J=3.0, 11.5 Hz, 1H), 3.66-3.57 (m, 1H), 3.45-3.35 (m, 2H), 2.33-2.29 (m, 3H), 1.98 (d, J=13.6 Hz, 1H), 1.69-1.62 (m, 7H), 1.45 (dd, J=4.0, 13.1 Hz, 1H), 1.07 (d, J=12.0 Hz, 1H). LCMS: HPLC: RT=1.73 min MS (ES): m/z=495.5 [M+H]$^+$ (ACN/$H_2O$ with $HCOONH_4$, Ascentis Express C18 2.7 µm (5×2.1) mm, gradient=4 min, wavelength=220 nm). HPLC RT=5.81 min (Column: Sunfire C18 3.5 µm, 4.6×150 mm; Mobile Phase A: 5:95 acetonitrile:water with 0.05% TFA; Mobile Phase B: 95:5 acetonitrile:water with 0.05% TFA; Gradient 10-100% B over 15 min; Flow: 1 mL/min; Detection: UV at 220 nm). Chiral SFC RT=2.41 min (Column: Chiralcel OD-H 250×4.6 mm, 5 µm; Mobile Phase: 70/30 $CO_2$/(0.25% DEA in MeOH); Flow: 4 mL/min). Enantiomer B: Chiral SFC RT=3.65 min (Column: Chiralcel OD-H 250×4.6 mm, 5 µm; Mobile Phase: 70/30 $CO_2$/(0.25% DEA in MeOH); Flow: 4 mL/min).

Examples 167 & 168

N-{2-[3-(Dimethyl-1H-1,2,3-triazol-5-yl)-5-[oxan-4-yl(phenyl)methyl]-5H-pyrido[3,2-b]indol-7-yl]propan-2-yl}-2-(dimethylamino)acetamide

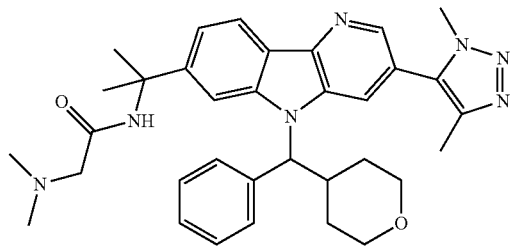

Enantiomer A, Example 167

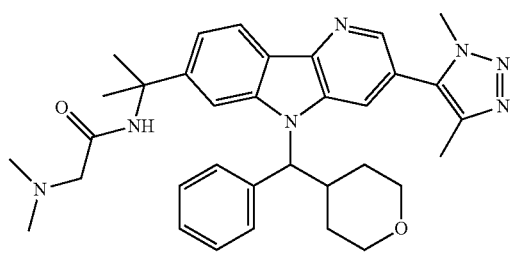

Enantiomer B, Example 168

A solution of 2-[3-(dimethyl-1H-1,2,3-triazol-5-yl)-5-[oxan-4-yl(phenyl)methyl]-5H-pyrido[3,2-b]indol-7-yl]propan-2-amine (50.0 mg, 0.101 mmol) in DMF (1 mL) was treated with 2-(dimethylamino)acetic acid (13.6 mg, 0.131 mmol), $Et_3N$ (0.0420 mL, 0.303 mmol), and HATU (50.0 mg, 0.131 mmol), and the reaction mixture was stirred at room temperature for 16 h. The mixture was quenched with 10 mL of water and extracted with EtOAc (25 mL×2), dried over $Na_2SO_4$, filtered, and concentrated and the residue purified by prep HPLC (Column: X bridge C18 (250×19, 5µ), Mobile phase A=Buffer:10 mm Ammonium Acetate in $H_2O$, Mobile phase B=ACN, Flow: 17 mL/min, Grad:T % B:0/30, 10/60) to give racemic N-{2-[3-(dimethyl-1H-1,2,3-triazol-5-yl)-5-[oxan-4-yl(phenyl)methyl]-5H-pyrido[3,2-b]indol-7-yl]propan-2-yl}-2-(dimethylamino)acetamide (35.0 mg, 0.0590 mmol, 49%) as a white color solid, which was separated by chiral prep SFC (Column: Chiral OD-H 250×4.6 mm, 5 µm; Mobile Phase: 60/40 $CO_2$/(0.25% DEA in MeOH); Flow: 4 mL/min) to give Enantiomer A and Enantiomer B. Enantiomer A: $^1$H NMR (400 MHz, $CD_3OD$): δ 8.44 (d, J=1.60 Hz, 1H), 8.30 (s, 1H), 8.28 (s, 1H), 8.20 (s, 1H), 7.58-7.60 (m, 2H), 7.45 (dd, J=8.40, Hz, 1H), 7.33-7.37 (m, 2H), 7.25-7.29 (m, 1H), 5.77 (d, J=10.80 Hz, 1H), 3.90-4.00 (m, 1H), 3.90 (s, 3H), 3.81 (dd, J=8.40, Hz, 1H), 3.58-3.61 (m, 1H), 3.39-3.40 (m, 2H), 3.00 (s, 2H), 2.37 (s, 6H), 2.30 (s, 3H), 1.89-1.98 (m, 1H), 1.67-1.82 (m, 6H), 1.58-1.67 (m, 1H), 1.41-1.44 (m, 1H), 1.09 (d, J=12.00 Hz, 1H). LCMS: RT=1.98 min, MS (ES): m/z=580.4 [M+H]$^+$ (ACN/$H_2O$ with $HCOONH_4$, Ascentis Express C18 2.7 µm (50×2.1) mm, gradient=4 min, wavelength=220 nm); HPLC RT=5.96 min (Sunfire C18 (4.6×150) mm, 3.5 micron, Mobile Phase A:0.05% TFA in water:Acetonitrile (95:5), Mobile Phase B:Acetonitrile:0.05% TFA in water (95:5), FLOW: 1 mL/min, wavelength=220 nm); Chiral SFC RT=2.31 (Chiral OD-H 250×4.6 mm, 5 µm; Mobile Phase: 60/40 $CO_2$/(0.25% DEA in MeOH); Flow: 4 mL/min).

Enantiomer B: Chiral SFC RT=4.86 (Chiral OD-H 250×4.6 mm, 5 μm; Mobile Phase: 60/40 CO$_2$/(0.25% DEA in MeOH); Flow: 4 mL/min).

Examples 169 and 170

4-[7-(2-Hydroxypropan-2-yl)-5-[oxan-4-yl(phenyl) methyl]-5H-pyrido[3,2-b]indol-3-yl]-3,5-dimethyl-2, 3-dihydro-1,3-thiazol-2-one Enantiomer A, Example 169

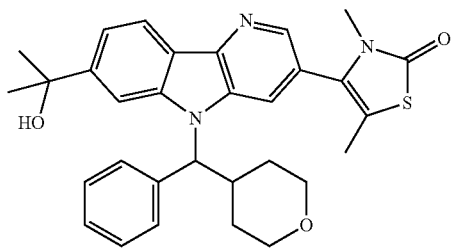

Enantiomer B, Example 170

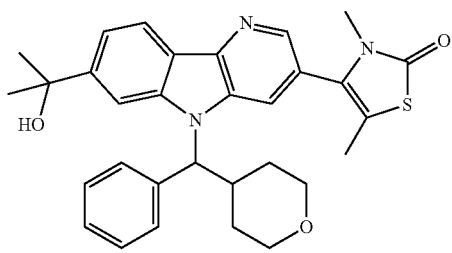

Step 1: Methyl 3-(5-formyl-3-methyl-2-oxo-2,3-dihydrothiazol-4-yl)-5-(phenyl(tetrahydro-2H-pyran-4-yl)methyl)-5H-pyrido[3,2-b]indole-7-carboxylate A mixture of methyl 5-(phenyl(tetrahydro-2H-pyran-4-yl)methyl)-3-(4,4,5,5-tetramethyl-1,3,2-dioxaborolan-2-yl)-5H-pyrido[3,2-b]indole-7-carboxylate (489 mg, 0.929 mmol), 4-chloro-3-methyl-2-oxo-2,3-dihydrothiazole-5-carbaldehyde (150 mg, 0.845 mmol), and tripotassium phosphate (2M in water, 1.27 ml, 2.53 mmol) in THF (10 mL) was purged under a stream of argon for 5 min. PdCl$_2$(dppf)-CH$_2$Cl$_2$ adduct (69.0 mg, 0.0850 mmol) was added, and the vial was capped with a septum, evacuated, purged with argon 3 times, and then heated to 80° C. for 2 h in a microwave. The reaction was quenched with water (50 mL) and extracted with EtOAc (75 mL×2), dried over Na$_2$SO$_4$, concentrated, and the residue was purified using silica gel column chromatography (ISCO 40 g flash column, 0-2% MeOH/CHCl$_3$ over 45 min) to give methyl 3-(5-formyl-3-methyl-2-oxo-2,3-dihydrothiazol-4-yl)-5-(phenyl(tetrahydro-2H-pyran-4-yl)methyl)-5H-pyrido[3,2-b]indole-7-carboxylate. LCMS: RT=1.17 min MS (ES): m/z=542 [M+1]$^+$ (ACN/H$_2$O with NH$_4$OAc, Acquity BEH C18 1.7 μm (50×2.1) mm, gradient=3 min, wavelength=220 nm).

Step 2: Methyl 3-(5-(hydroxymethyl)-3-methyl-2-oxo-2,3-dihydrothiazol-4-yl)-5-(phenyl(tetrahydro-2H-pyran-4-yl)methyl)-5H-pyrido[3,2-b]indole-7-carboxylate A stirred solution of methyl 3-(5-formyl-3-methyl-2-oxo-2,3-dihydrothiazol-4-yl)-5-(phenyl(tetrahydro-2H-pyran-4-yl)methyl)-5H-pyrido[3,2-b]indole-7-carboxylate (200 mg, 0.369 mmol) in MeOH (10 mL) was treated with NaBH$_4$ (18.2 mg, 0.480 mmol) and stirred at room temperature for 45 min. The mixture was quenched with sat.aq. NH$_4$Cl (30 mL) and extracted with DCM (50 mL×2), dried over Na$_2$SO$_4$, filtered, and concentrated to give methyl 3-(5-(hydroxymethyl)-3-methyl-2-oxo-2,3-dihydrothiazol-4-yl)-5-(phenyl(tetrahydro-2H-pyran-4-yl)methyl)-5H-pyrido[3,2-b]indole-7-carboxylate (180 mg, 0.331 mmol, 90%) as a yellow solid. LCMS: HPLC: RT=1.03 min; MS (ES): m/z=544 [M+1]$^+$ (ACN/H$_2$O with NH$_4$OAc, Acquity BEH C18 1.7 μm (50×2.1) mm, gradient=3 min, wavelength=220 nm).

Step 3: Methyl 3-(3,5-dimethyl-2-oxo-2,3-dihydrothiazol-4-yl)-5-(phenyl(tetrahydro-2H-pyran-4-yl)methyl)-5H-pyrido[3,2-b]indole-7-carboxylate To a stirred solution of methyl 3-(5-(hydroxymethyl)-3-methyl-2-oxo-2,3-dihydrothiazol-4-yl)-5-(phenyl(tetrahydro-2H-pyran-4-yl)methyl)-5H-pyrido[3,2-b]indole-7-carboxylate (100 mg, 0.184 mmol) in DCM (10 mL) under N$_2$ (g) was added triethylsilane (0.147 ml, 0.920 mmol) followed by TFA (10.0 mL, 130 mmol), and the reaction was heated to reflux for 16 h. The solvents were removed under vacuum, the residue was quenched with ice water, basified with aq.NaHCO$_3$ (15 mL), and extracted with DCM (30 mL×2). The extract was dried over Na$_2$SO$_4$, filtered, concentrated, and the residue was purified using silica gel column chromatography (ISCO Silica gel 12 g flash column, 0-2% MeOH/CHCl$_3$ over 45 min) to give methyl 3-(3,5-dimethyl-2-oxo-2,3-dihydrothiazol-4-yl)-5-(phenyl(tetrahydro-2H-pyran-4-yl)methyl)-5H-pyrido[3,2-b]indole-7-carboxylate (90.0 mg, 0.171 mmol, 93%) as a yellow solid. LCMS: HPLC: RT=1.15 min; MS (ES): m/z=528 [M+1]$^+$ (ACN/H$_2$O with NH$_4$OAc, Acquity BEH C18 1.7 μm (50×2.1) mm, gradient=3 min, wavelength=220 nm).

Step 4: 4-[7-(2-Hydroxypropan-2-yl)-5-[oxan-4-yl (phenyl)methyl]-5H-pyrido[3,2-b]indol-3-yl]-3,5-dimethyl-2,3-dihydro-1,3-thiazol-2-one A stirred solution of methyl 3-(3,5-dimethyl-2-oxo-2,3-dihydrothiazol-4-yl)-5-(phenyl(tetrahydro-2H-pyran-4-yl) methyl)-5H-pyrido[3,2-b]indole-7-carboxylate (100 mg, 0.191 mmol) in tetrahydrofuran (0.7 mL) was cooled to −20° C. and treated with methylmagnesium bromide (3M in THF, 0.316 mL, 0.948 mmol). The reaction mixture was slowly allowed to warm to room temperature over the period of 5 h. The reaction was quenched with sat. aq. NH$_4$Cl (30 mL) and extracted with EtOAc (50 mL×2), dried over Na$_2$SO$_4$, filtered, and concentrated. The crude product was purified by prep. HPLC (Column: phenyl X bridge(250×19.5μ),M. Phase A: 10 mm ammonium acetate in water, M. Phase B: ACN, Flow: 17 mL/min, isocratic 0/30,10/60) to give racemic 4-[7-(2-hydroxypropan-2-yl)-5-[oxan-4-yl(phenyl)methyl]-5H-pyrido[3,2-b]indol-3-yl]-3,5-dimethyl-2,3-dihydro-1,3-thiazol-2-one (45.0 mg, 0.0840 mmol, 37%) as a white solid, which was separated by prep chiral SFC (Column: Chiral OD-H 250×30 mm, 5 μm; Mobile Phase: 60/40 CO$_2$/(0.25% DEA in MeOH); Flow: 80 mL/min) to give Enantiomer A (18.0 mg, 0.0330 mmol, 17%) and Enantiomer B (17.0 mg, 0.0320 mmol, 16%). Enantiomer A: $^1$H NMR (400 MHz, CD$_3$OD) δ 8.37 (d, J=1.5 Hz, 1H), 8.29 (d, J=8.5 Hz, 1H), 8.20 (s, 1H), 8.11 (s, 1H), 7.62 (d, J=7.5 Hz, 2H), 7.48 (dd, J=1.3, 8.3 Hz, 1H), 7.38-7.31 (m, 2H), 7.29-7.23 (m, 1H), 5.74 (d, J=11.0 Hz, 1H), 4.00 (d, J=11.5 Hz, 1H), 3.83 (d, J=8.0 Hz, 1H), 3.66-3.57 (m, 1H), 3.50-3.38 (m, 2H), 3.06 (s, 3H), 2.09-2.04 (m, 3H), 1.95 (d, J=10.0 Hz, 1H), 1.70-1.60 (m, 7H), 1.47-1.40 (m, 1H), 1.13 (d, J=13.1 Hz, 1H). LCMS: RT=2.00 min MS (ES): m/z=528 [M+H]$^+$ (ACN/H$_2$O with HCOONH$_4$, Ascentis Express C18 2.7 μm (50×2.1) mm, gradient=4 min, wavelength=220 nm). HPLC-RT=8.67 min Sunfire C18 (4.6× 150) mm, 3.5 micron, Mobile Phase A:0.05% TFA in water:Acetonitrile (95:5), Mobile Phase B:Acetonitrile: 0.05% TFA in water (95:5), Flow: 1 mL/min, wavelength=220 nm). Chiral SFC RT=2.92 (Chiral OD-H 250× 4.6 mm, 5 μm; Mobile Phase: 60/40 CO$_2$/(0.25% DEA in MeOH); Flow: 4 mL/min). Enantiomer B: Chiral SFC RT=10.04 (Chiral OD-H 250×4.6 mm, 5 μm; Mobile Phase: 60/40 CO$_2$/(0.25% DEA in MeOH); Flow: 4 mL/min).

Example 171

4-{7-Methanesulfonyl-5-[(S)-oxan-4-yl)phenyl)methyl]-5H-pyrido[3,2-b]indol-3-yl}-3,5-dimethyl-1,2-oxazole

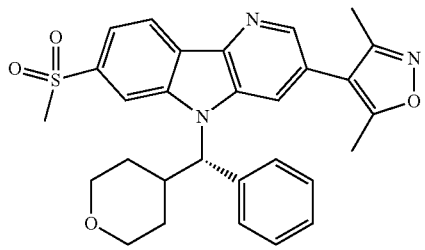 [SMILES: Cc1noc(C)c1-c1cnc2c3ccc(S(C)(=O)=O)cc3n([C@H](c3ccccc3)C3CCOCC3)c2c1]

Following procedures analogous to those described in (S)-methyl 3-(1,4-dimethyl-1 H-1,2,3-triazol-5-yl)-5-(phenyl(tetrahydro-2H-pyran-4-yl)methyl)-5H-pyrido[3,2-b]indole-7-carboxylate, the intermediate 4-(7-(methylsulfonyl)-5H-pyrido[3,2-b]indol-3-yl)-3,5-dimethyl-1,2-oxazole (30.0 mg, 0.0880 mmol) was converted to the title compound (18.5 mg, 37%). $^1$H NMR (500 MHz, CDCl$_3$) δ 8.57 (d, J=8.2 Hz, 1H), 8.53 (d, J=1.7 Hz, 1H), 8.33 (s, 1H), 7.90 (dd, J=8.2, 1.3 Hz, 1H), 7.66 (d, J=1.5 Hz, 1H), 7.45 (d, J=7.5 Hz, 2H), 7.40-7.34 (m, 2H), 7.34-7.29 (m, 1H), 5.58 (d, J=10.5 Hz, 1H), 4.07 (dd, J=11.7, 2.8 Hz, 1H), 3.87 (dd, J=11.7, 2.7 Hz, 1H), 3.55 (td, J=11.9, 1.8 Hz, 1H), 3.36 (td, J=11.9, 1.8 Hz, 1H), 3.19 (s, 3H), 3.17-3.04 (m, 1H), 2.41 (s, 3H), 2.25 (s, 3H), 2.03 (d, J=13.7 Hz, 1H), 1.67-1.59 (m, 1H), 1.45-1.34 (m, 1H), 1.07 (d, J=13.1 Hz, 1H); LCMS (M+H)$^+$=516; HPLC RT=2.593 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 172

4-{5-[(S)-(4-Fluorophenyl)(oxan-4-yl)methyl]-7-methanesulfonyl-5H-pyrido[3,2-b]indol-3-yl}-3,5-dimethyl-1,2-oxazole

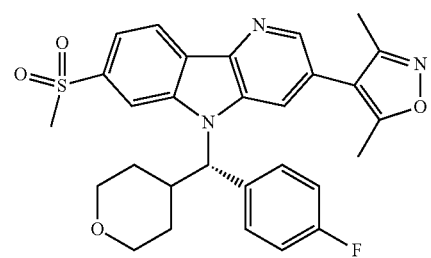 [SMILES: Cc1noc(C)c1-c1cnc2c3ccc(S(C)(=O)=O)cc3n([C@H](c3ccc(F)cc3)C3CCOCC3)c2c1]

The enantiomers of (4-fluorophenyl)(oxan-4-yl)methanol (1.10 g, 5.23 mmol) were separated on preparative SFC. (Column: Chiralpak AD-H 5×25 cm, 5 μm; Mobile Phase: 80/20 CO$_2$/MeOH; Flow: 150 mL/min; Temperature 40° C.). The fractions containing the separated peaks were concentrated and dried under vacuum to give white solids. Enantiomer A: (S)-(4-fluorophenyl)(oxan-4-yl)methanol (496 mg, 45%) SFC RT=2.30 min (Column: Chiralpac AD 250×4.6 mm, 5 μm; Mobile Phase: 80/20 CO$_2$/MeOH; Flow: 3 mL/min); Temperature 35° C. Enantiomer B: (R)-(4-fluorophenyl)(oxan-4-yl)methanol (530 mg, 48%) SFC RT=3.17 min (Column: Chiralpac AD 250×4.6 mm, 5 μm; Mobile Phase: 80/20 CO$_2$/MeOH; Flow: 3 mL/min); Temperature 35° C.

Following procedures analogous to those described in 4-{7-methanesulfonyl-5-[(S)-oxan-4-yl(phenyl)methyl]-5H-pyrido[3,2-b]indol-3-yl}-3,5-dimethyl-1,2-oxazole, the intermediate 4-(7-(methylsulfonyl)-5H-pyrido[3,2-b]indol-3-yl)-3,5-dimethyl-1,2-oxazole (30.0 mg, 0.0880 mmol) and (R)-(4-fluorophenyl)(oxan-4-yl)methanol (37 mg, 0.176 mmol) were converted to the title compound (13.9 mg, 29%). $^1$H NMR (500 MHz, CDCl$_3$) δ 8.57 (d, J=8.2 Hz, 1H), 8.54 (d, J=1.7 Hz, 1H), 8.30 (s, 1H), 7.91 (dd, J=8.2, 1.3 Hz, 1H), 7.63 (s, 1H), 7.44 (dd, J=8.6, 5.1 Hz, 2H), 7.10-7.02 (m, 2H), 5.55 (d, J=10.7 Hz, 1H), 4.08 (dd, J=11.6, 2.7 Hz, 1H), 3.87 (dd, J=11.8, 2.7 Hz, 1H), 3.55 (td, J=11.9, 1.8 Hz, 1H), 3.39-3.30 (m, 1H), 3.20 (s, 3H), 3.12-3.02 (m, 1H), 2.44 (s, 3H), 2.28 (s, 3H), 1.99 (d, J=13.6 Hz, 1H), 1.67-1.59 (m, 1H), 1.45-1.34 (m, 1H), 1.08 (d, J=13.1 Hz, 1H); LCMS (M+H)$^+$=534.4; HPLC RT=2.645 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 173-174

The compounds in Table 6 were prepared according to the procedure described for 4-{7-methanesulfonyl-5-[(S)-oxan-4-yl(phenyl)methyl]-5H-pyrido[3,2-b]indol-3-yl}-3,5-dimethyl-1,2-oxazole:

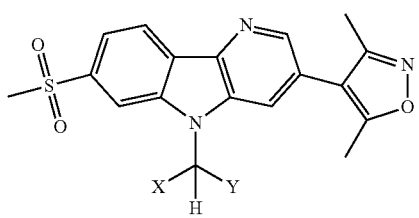

TABLE 6

| Example | X | Y | HPLC RT (min) | LCMS (M + H) | HPLC Method |
|---|---|---|---|---|---|
| 173 Enantiomer | tetrahydropyran-4-yl | 2-fluorophenyl | 8.69 | 534.4 | A |
| 174 Enantiomer | tetrahydropyran-4-yl | 2-fluorophenyl | 10.64 | 534.4 | A |

N/A: Not Applicable/Available

HPLC Conditions for Table 6: Method A: Column: Chiral IB, 250×4.6 mm, 5 µm particles; Mobile Phase: 80/20 $CO_2$/MeOH; Flow: 2 mL/min; Detection UV at 220 nm.

Example 175

2-[3-(Dimethyl-1H-1,2,3-triazol-5-yl)-5-[(S)-oxan-4-yl)phenyl)methyl]-5H-pyrido[3,2-b]indol-8-yl]propan-2-ol

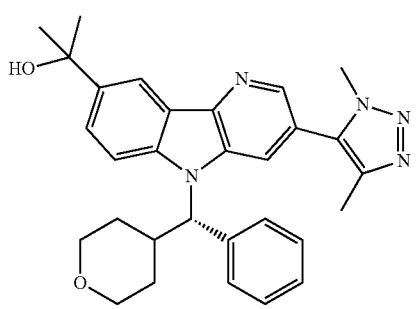 [SMILES: Cc1nnn(C)c1-c1cnc2c3cc(C(C)(C)O)ccc3n([C@H](c3ccccc3)C3CCOCC3)c2c1]

Step 1: Methyl 4-((2-chloro-5-(1,4-dimethyl-1H-1,2,3-triazol-5-yl)pyridin-3-yl)amino)benzoate Following procedures analogous to those described for methyl 3-((2-chloro-5-(1,4-dimethyl-1H-1,2,3-triazol-5-yl) pyridin-3-yl)amino)benzoate, 2-chloro-5-(3,5-dimethylisoxazol-4-yl)pyridin-3-amine (200 mg, 0.894 mmol) and 4-(methoxycarbonyl)phenyl)boronic acid (322 mg, 1.79 mmol) were converted to the title compound (122 mg, 38%). LCMS (M+H)=358.2; HPLC RT=2.268 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 4-(1,4-dimethyl-1H-1,2,3-triazol-5-yl)-5H-pyrido[3,2-b]indole-7-carboxylate Following procedures analogous to those described for methyl 3-(1,4-dimethyl-1H-1,2,3-triazol-5-yl)-5H-pyrido[3,2-b]indole-7-carboxylate, methyl 4-((2-chloro-5-(1,4-dimethyl-1H-1,2,3-triazol-5-yl)pyridin-3-yl)amino)benzoate (121 mg, 0.340 mmol) was converted to the title compound (96.0 mg, 88%). $^1$H NMR (400 MHz, CDCl$_3$) δ 9.24-9.08 (m, 1H), 8.61 (s, 1H), 8.58 (d, J=1.8 Hz, 1H), 8.32 (dd, J=8.6, 1.7 Hz, 1H), 7.73 (d, J=1.8 Hz, 1H), 7.57 (d, J=8.6 Hz, 1H), 4.04 (s, 3H), 4.00 (s, 3H), 2.40 (s, 3H); LCMS (M+H)=322.3; HPLC RT=1.895 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: (S)-Methyl 4-(1,4-dimethyl-1H-1,2,3-triazol-5-yl)-5-(phenyl(tetrahydro-2H-pyran-4-yl)methyl)-5H-pyrido[3,2-b]indole-7-carboxylate Following procedures analogous to those described for (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate, methyl 4-(1,4-dimethyl-1H-1,2,3-triazol-5-yl)-5H-pyrido[3,2-b]indole-7-carboxylate (30.0 mg, 0.0930 mmol) was converted to the title compound (19.6 mg, 42%). LCMS (M+H)=496; HPLC RT=2.836 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 2-[3-(Dimethyl-1H-1,2,3-triazol-5-yl)-5-[(S)-oxan-4-yl(phenyl)methyl]-5H-pyrido[3,2-b]indol-8-yl]propan-2-ol Following procedures analogous to those described for (S)-2-[3-(dimethyl-1H-1,2,3-triazol-5-yl)-5-[oxan-4-yl(phenyl)methyl]-5H-pyrido[3,2-b]indol-7-yl]propan-2-ol, (S)-methyl 4-(1,4-dimethyl-1H-1,2,3-triazol-5-yl)-5-(phenyl(tetrahydro-2H-pyran-4-yl)methyl)-5H-pyrido[3,2-b]indole-7-carboxylate (19.6 mg, 0.0400 mmol) was converted to the title compound (19.6 mg, 100%). $^1$H NMR (500 MHz, CDCl$_3$) δ 8.50 (d, J=1.5 Hz, 1H), 8.45 (d, J=1.7 Hz, 1H), 7.90 (dd, J=8.7, 2.0 Hz, 1H), 7.71 (d, J=8.7 Hz, 1H), 7.59 (d, J=1.8 Hz, 1H), 7.45 (d, J=7.2 Hz, 2H), 7.38-7.32 (m, 2H), 7.31-7.28 (m, 1H), 5.50 (d, J=10.7 Hz, 1H), 4.06 (dd, J=11.8, 2.8 Hz, 1H), 3.94-3.84 (m, 4H), 3.54 (td, J=11.9, 2.0 Hz, 1H), 3.36 (td, J=11.9, 2.0 Hz, 1H), 3.10 (qt, J=11.1, 3.5 Hz, 1H), 2.31 (s, 3H), 2.01 (d, J=13.4 Hz, 1H), 1.87 (s, 1H), 1.75 (d, J=1.5 Hz, 6H), 1.65-1.59 (m, 1H), 1.47-1.36 (m, 1H), 1.19-1.11 (m, 1H); LCMS (M+H)=496.4; HPLC RT=2.535 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 176

2-[3-(Dimethyl-1H-1,2,3-triazol-5-yl)-5-[(S)-(4-fluorophenyl)(oxan-4-yl)methyl]-5H-pyrido[3,2-b]indol-8-yl]propan-2-ol

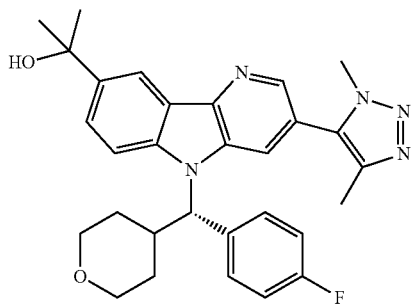 [SMILES: Cc1nnn(C)c1-c1cnc2c3cc(C(C)(C)O)ccc3n([C@H](c3ccc(F)cc3)C3CCOCC3)c2c1]

Step 1: (S)-Methyl 4-(1,4-dimethyl-1H-1,2,3-triazol-5-yl)-5-(4-fluorophenyl(tetrahydro-2H-pyran-4-yl)methyl)-5H-pyrido[3,2-b]indole-7-carboxylate Following procedures analogous to those described for (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate, methyl 4-(1,4-dimethyl-1H-1,2,3-triazol-5-yl)-5H-pyrido[3,2-b]indole-7-carboxylate (30.0 mg, 0.0930 mmol) and (R)-(4-fluorophenyl)(oxan-4-yl)methanol (36.6 mg, 0.174 mmol) were converted to the title compound (19.6 mg, 42%). LCMS (M+H)=496; HPLC RT=2.836 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-[3-(Dimethyl-1H-1,2,3-triazol-5-yl)-5-[(S)-(4-fluorophenyl)(oxan-4-yl)methyl]-5H-pyrido[3,2-b]indol-8-yl]propan-2-ol Following procedures analogous to those described 2-[3-(dimethyl-1H-1,2,3-triazol-5-yl)-5-[(S)-oxan-4-yl(phenyl)methyl]-5H-pyrido[3,2-b]indol-8-yl]propan-2-ol, (S)-methyl 4-(1,4-dimethyl-1H-1,2,3-triazol-5-yl)-5-((4-fluorophenyl(tetrahydro-2H-pyran-4-yl)methyl)-5H-pyrido[3,2-b]indole-7-carboxylate (15.3 mg, 0.0300 mmol) was converted to the title compound (14.8 mg, 95%). $^1$H NMR (500 MHz, CDCl$_3$) δ 8.50 (d, J=1.4 Hz, 1H), 8.47 (d, J=1.7 Hz, 1H), 7.89 (dd, J=8.7, 2.0 Hz, 1H), 7.67 (d, J=8.9 Hz, 1H), 7.58 (d, J=1.5 Hz, 1H), 7.46-7.39 (m, 2H), 7.07-7.01 (m, 2H), 5.46 (d, J=10.7 Hz, 1H), 4.06 (dd, J=11.6, 2.6 Hz, 1H), 3.95 (s, 3H), 3.87 (dd, J=11.7, 2.9 Hz, 1H), 3.54 (td, J=11.9, 2.1 Hz, 1H), 3.36 (td, J=11.9, 2.0 Hz, 1H), 3.11-3.01 (m, 1H), 2.33 (s, 3H), 1.96 (d, J=13.0 Hz, 1H), 1.86 (s, 1H), 1.74 (s, 6H), 1.65-1.59 (m, 1H), 1.45-1.36 (m, 1H), 1.20-1.13 (m, 1H); LCMS (M+H)=514.4; HPLC RT=2.577 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 177

5-{7-Methanesulfonyl-5-[(S)-oxan-4-yl(phenyl)methyl]-5H-pyrido[3,2-b]indol-3-yl}-1,4-dimethyl-1H-1,2,3-triazole

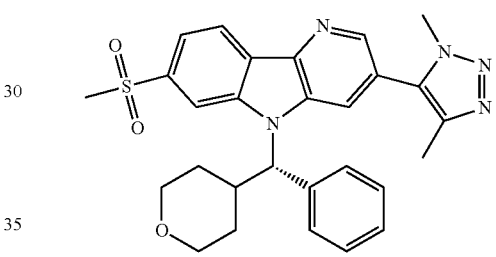

Step 1: 2-Chloro-5-(1,4-dimethyl-1H-1,2,3-triazole)-N-(3-(methylsulfonyl)phenyl)pyridin-3-amine Following procedures analogous to those described for methyl 3-((2-chloro-5-(1,4-dimethyl-1H-1,2,3-triazol-5-yl)pyridin-3-yl)amino)benzoate, 2-chloro-5-(dimethyl-1H-1,2,3-triazol-5-yl)pyridin-3-amine (500 mg, 2.24 mmol) and (3-(methylsulfonyl)phenyl)boronic acid (939 mg, 4.69 mmol) were converted to the title compound (287 mg, 34%). LCMS (M+H)=378.2; HPLC RT=1.700 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 5-(7-(Methylsulfonyl)-5H-pyrido[3,2-b]indol-3-yl)-1,4-dimethyl-1H-1,2,3-triazole Following procedures analogous to those described for methyl 3-(1,4-dimethyl-1H-1,2,3-triazol-5-yl)-5H-pyrido[3,2-b]indole-7-carboxylate, 2-chloro-5-(1,4-dimethyl-1H-1,2,3-triazole)-N-(3-(methylsulfonyl)phenyl)pyridin-3-amine (287 mg, 0.760 mmol) was converted to the title compound (111 mg, 43%). $^1$H NMR (500 MHz, CDCl$_3$) δ 8.83 (s, 1H), 8.63 (d, J=1.8 Hz, 1H), 8.60 (d, J=8.2 Hz, 1H), 8.22 (d, J=0.9 Hz, 1H), 7.94 (dd, J=8.2, 1.5 Hz, 1H), 7.82 (d, J=1.8 Hz, 1H), 4.06 (s, 3H), 3.19 (s, 3H), 2.41 (s, 3H); LCMS (M+H)=322.3; HPLC RT=1.512 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 5-{7-Methanesulfonyl-5-[(S)-oxan-4-yl(phenyl)methyl]-5H-pyrido[3,2-b]indol-3-yl}-1,4-dimethyl-1H-1,2,3-triazole Following procedures analogous to those described for 4-{7-methanesulfonyl-5-[(S)-oxan-4-yl(phenyl)methyl]-5H-pyrido[3,2-b]indol-3-yl}-3,5-dimethyl-1,2-oxazole, 5-(7-(methylsulfonyl)-5H-pyrido[3,2-b]indol-3-yl)-1,4-dimethyl-1H-1,2,3-triazole (30.0 mg, 0.0880 mmol) was converted to the title compound (18.8 mg, 41%). $^1$H NMR (500 MHz, CDCl$_3$) δ 8.60 (d, J=8.2 Hz, 1H), 8.57 (d, J=1.7 Hz, 1H), 8.37 (s, 1H), 7.93 (dd, J=8.2, 1.3 Hz, 1H), 7.70 (d, J=1.5 Hz, 1H), 7.47-7.42 (m, 2H), 7.41-7.35 (m, 2H), 7.35-7.31 (m, 1H), 5.61 (d, J=10.5 Hz, 1H), 4.07 (dd, J=11.6, 2.9 Hz, 1H), 3.91 (s, 3H), 3.88 (dd, J=11.8, 2.8 Hz, 1H), 3.56 (td, J=12.0, 1.8 Hz, 1H), 3.36 (td, J=11.9, 1.8 Hz, 1H), 3.21 (s, 3H), 3.16-3.06 (m, 1H), 2.34-2.29 (m, 3H), 2.04 (d, J=14.5 Hz, 1H), 1.68-1.60 (m, 1H), 1.47-1.36 (m, 1H), 1.07 (d, J=13.0 Hz, 1H); LCMS (M+H)=516.4; HPLC RT=2.362 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 178

5-{5-[(S)-(4-Fluorophenyl)(oxan-4-yl)methyl]-7-methanesulfonyl-5H-pyrido[3,2-b]indol-3-yl}-1,4-dimethyl-1H-1,2,3-triazole

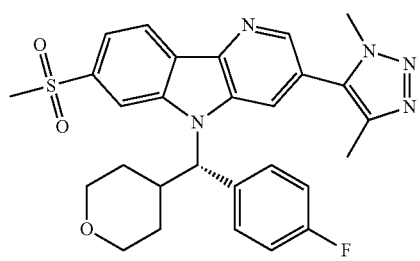 [SMILES: Cc1nnn(C)c1-c1cnc2c3ccc(S(C)(=O)=O)cc3n([C@H](c3ccc(F)cc3)C3CCOCC3)c2c1]

Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 5-(7-(methylsulfonyl)-5H-pyrido[3,2-b]indol-3-yl)-1,4-dimethyl-1H-1,2,3-triazole (30.0 mg, 0.0880 mmol) was converted to the title compound (16.4 mg, 34%). $^1$H NMR (500 MHz, CDCl$_3$) δ 8.61 (d, J=8.2 Hz, 1H), 8.58 (d, J=1.7 Hz, 1H), 8.34 (s, 1H), 7.94 (dd, J=8.2, 1.2 Hz, 1H), 7.69 (s, 1H), 7.43 (dd, J=8.5, 5.0 Hz, 2H), 7.07 (t, J=8.5 Hz, 2H), 5.57 (d, J=10.7 Hz, 1H), 4.08 (dd, J=11.7, 2.9 Hz, 1H), 3.96 (s, 3H), 3.88 (dd, J=11.7, 2.7 Hz, 1H), 3.55 (td, J=11.9, 1.7 Hz, 1H), 3.39-3.32 (m, 1H), 3.21 (s, 3H), 3.12-3.02 (m, 1H), 2.33 (s, 3H), 1.99 (d, J=13.3 Hz, 1H), 1.67-1.60 (m, 1H), 1.40 (qd, J=12.3, 4.5 Hz, 1H), 1.08 (d, J=13.0 Hz, 1H); LCMS (M+H)=534.4; HPLC RT=2.408 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 179

(5-{7-Methanesulfonyl-5-[(S)-oxan-4-yl(phenyl)methyl]-5H-pyrido[3,2-b]indol-3-yl}-1-methyl-1H-1,2,3-triazol-4-yl)methanol

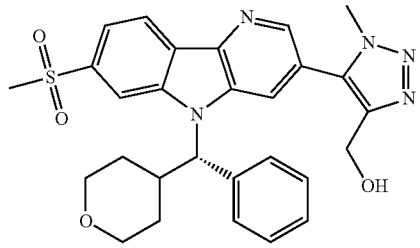 [SMILES: Cn1nnc(CO)c1-c1cnc2c3ccc(S(C)(=O)=O)cc3n([C@H](c3ccccc3)C3CCOCC3)c2c1]

Step 1: 5-Bromo-2-(4-methanesulfonylphenyl)-3-nitropyridine

Following procedures analogous to those described for methyl 4-(5-bromo-3-nitropyridin-2-yl)benzoate, (3-(methylsulfonyl)phenyl)boronic acid (114 mg, 0.568 mmol) was converted to the title compound (185 mg, 91%). LCMS (M+H)=357; HPLC RT=1.798 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 3-Bromo-7-methanesulfonyl-5H-pyrido[3,2-b]indole

Following procedures analogous to those described for methyl 3-bromo-5H-pyrido[3,2-b]indole-7-carboxylate, 5-bromo-2-(4-methanesulfonylphenyl)-3-nitropyridine (185 mg, 0.520 mmol) was converted to the title compound (74.8 mg, 44%). $^1$H NMR (500 MHz, CDCl$_3$) δ 8.71 (d, J=2.0 Hz, 1H), 8.52 (d, J=8.2 Hz, 1H), 8.48 (br. s., 1H), 8.16-8.13 (m, 1H), 8.02 (d, J=2.0 Hz, 1H), 7.90 (dd, J=8.2, 1.5 Hz, 1H), 3.16 (s, 3H); LCMS (M+H)=325; HPLC RT=1.945 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 3-Bromo-7-methanesulfonyl-5-[(S)-oxan-4-yl(phenyl)methyl]-5H-pyrido[3,2-b]indole Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 3-bromo-7-methanesulfonyl-5H-pyrido[3,2-b]indole (74.0 mg, 0.230 mmol) was converted to the title compound (57.0 mg, 50%). $^1$H NMR (500 MHz, CDCl$_3$) δ 8.66 (d, J=1.8 Hz, 1H), 8.51 (d, J=8.1 Hz, 1H), 8.26 (d, J=0.8 Hz, 1H), 8.07 (d, J=1.8 Hz, 1H), 7.86 (dd, J=8.2, 1.4 Hz, 1H), 7.50-7.44 (m, 2H), 7.42-7.35 (m, 2H), 7.34-7.29 (m, 1H), 5.45 (d, J=11.0 Hz, 1H), 4.07 (dd, J=11.8, 3.0 Hz, 1H), 3.87 (dd, J=11.8, 3.0 Hz, 1H), 3.56 (td, J=11.9, 2.1 Hz, 1H), 3.38 (td, J=11.9, 2.1 Hz, 1H), 3.19-3.07 (m, 4H), 1.98 (d, J=13.1 Hz, 1H), 1.65-1.57 (m, 1H), 1.43-1.32 (m, 1H), 1.03 (dd, J=13.4, 1.3 Hz, 1H); LCMS (M+H)=499; HPLC RT=2.828 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: (5-{7-Methanesulfonyl-5-[(S)-oxan-4-yl(phenyl)methyl]-5H-pyrido[3,2-b]indol-3-yl}-1-methyl-1H-1,2,3-triazol-4-yl)methanol Following procedures analogous to those described for methyl 3-(1,4-dimethyl-1H-1,2,3-triazol-5-yl)-5H-pyrido[3,2-b]indole-7-carboxylate, 3-bromo-7-methanesulfonyl-5-[(S)-oxan-4-yl(phenyl)methyl]-5H-pyrido[3,2-b]indole (57.0 mg, 0.114 mmol) and 4-{[(tert-butyldimethylsilyl)oxy]methyl}-5-(tributylstannyl)-1-[(trimethylsilyl)methyl]-1H-1,2,3-triazole (101 mg, 0.171 mmol) were converted, after desilylation with 1M TBAF in THF (1.70 mL, 1.70 mmol), to the title compound (61.0 mg, 99%). $^1$H NMR (500 MHz, CDCl$_3$) δ 8.68 (d, J=1.7 Hz, 1H), 8.60 (d, J=8.2 Hz, 1H), 8.39 (s, 1H), 8.25 (d, J=1.8 Hz, 1H), 7.92 (dd, J=8.2, 1.4 Hz, 1H), 7.56-7.50 (m, 2H), 7.40-7.35 (m, 2H), 7.34-7.29 (m, 1H), 5.58 (d, J=10.8 Hz, 1H), 4.80-4.74 (m, 1H), 4.72-4.66 (m, 1H), 4.09 (s, 3H), 4.06 (dd, J=11.8, 2.8 Hz, 1H), 3.87 (dd, J=11.7, 2.9 Hz, 1H), 3.55 (td, J=11.9, 1.9 Hz, 1H), 3.41 (td, J=11.9, 2.0 Hz, 1H), 3.30-3.22 (m, 1H), 3.21 (s, 3H), 2.36 (t, J=6.3 Hz, 1H), 1.97 (d, J=13.4 Hz, 1H), 1.64-1.59 (m, 1H), 1.46-1.36 (m, 1H), 1.10 (d, J=12.5 Hz, 1H); LCMS (M+H)=532; HPLC RT=2.107 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 180

4-(Fluoromethyl)-5-{7-methanesulfonyl-5-[(S)-oxan-4-yl(phenyl)methyl]-5H-pyrido[3,2-b]indol-3-yl}-1-methyl-1H-1,2,3-triazole

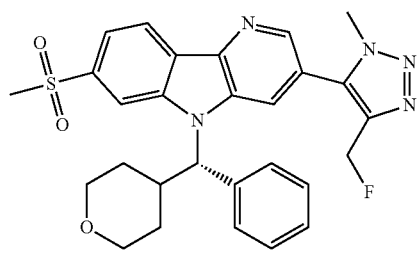 [SMILES: Cn1nnc(CF)c1-c1cnc2c3ccc(S(C)(=O)=O)cc3n([C@H](c3ccccc3)C3CCOCC3)c2c1]

In a 20 mL flask containing (5-{7-methanesulfonyl-5-[(S)-oxan-4-yl(phenyl)methyl]-5H-pyrido[3,2-b]indol-3-yl}-1-methyl-1H-1,2,3-triazol-4-yl)methanol (47.0 mg, 0.0880 mmol) cooled in a −78° C. bath was added DAST (53.0 uL, 0.398 mmol). The reaction mixture was stirred for 1 h in the −78° C. bath then sat. aq. NaHCO$_3$ was added, and the reaction was allowed to warm to room temperature. The reaction mixture was then diluted with 10% aq. LiCl and extracted twice with CHCl$_3$. The combined organic layers were dried over MgSO$_4$, filtered, and concentrated. The crude residue was purified on a silica gel column (40 g) and eluted with a gradient from 100% CH$_2$Cl$_2$ to 4% MeOH/CH$_2$Cl$_2$. The tubes with product were collected and concentrated to give the title compound (33.7 mg, 71%). $^1$H NMR (400 MHz, CDCl$_3$) δ 8.66 (d, J=1.8 Hz, 1H), 8.61 (d, J=8.4 Hz, 1H), 8.40 (s, 1H), 8.06 (d, J=1.5 Hz, 1H), 7.94 (dd, J=8.4, 1.3 Hz, 1H), 7.48 (d, J=7.3 Hz, 2H), 7.41-7.34 (m, 2H), 7.34-7.29 (m, 1H), 5.58 (d, J=10.8 Hz, 1H), 5.53-5.45 (m, 1H), 5.40-5.33 (m, 1H), 4.09 (s, 3H), 4.08-4.02 (m, 1H), 3.87 (dd, J=12.0, 2.8 Hz, 1H), 3.60-3.50 (m, 1H), 3.38 (td, J=11.9, 2.0 Hz, 1H), 3.21 (s, 3H), 3.20-3.12 (m, 1H), 1.97 (d, J=12.8 Hz, 1H), 1.65-1.57 (m, 1H), 1.47-1.35 (m, 1H), 1.09 (d, J=12.8 Hz, 1H); LCMS (M+H)=534; HPLC RT=2.375 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 181

5-{9-Fluoro-6-methanesulfonyl-5-[(S)-oxan-4-yl)phenyl)methyl]-5H-pyrido[3,2-b]indol-3-yl}-1,4-dimethyl-1H-1,2,3-triazole

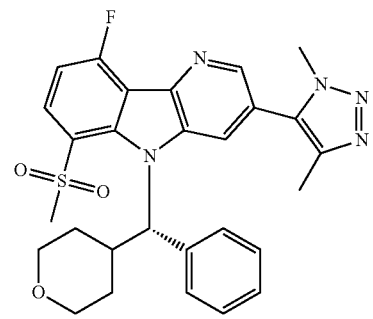 [SMILES: Cc1nnn(C)c1-c1cnc2c3c(F)ccc(S(C)(=O)=O)c3n([C@H](c3ccccc3)C3CCOCC3)c2c1]

Step 1: 5-Bromo-2-(2-fluoro-5-methanesulfonylphenyl)-3-nitropyridine

Following procedures analogous to those described for methyl 4-(5-bromo-3-nitropyridin-2-yl)benzoate, 2-(2-fluoro-5-methanesulfonylphenyl)-4,4,5,5-tetramethyl-1,3,2-dioxaborolane (500 mg, 1.66 mmol) was converted to the title compound (325 mg, 52%). $^1$H NMR (500 MHz, CDCl$_3$) δ 9.02 (d, J=2.0 Hz, 1H), 8.58 (d, J=2.0 Hz, 1H), 8.34 (dd, J=6.5, 2.4 Hz, 1H), 8.10 (ddd, J=8.7, 4.7, 2.4 Hz, 1H), 7.34 (dd, J=9.4, 8.8 Hz, 1H), 3.15 (s, 3H); LCMS (M+H)=375; HPLC RT=1.977 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 3-Bromo-9-fluoro-6-methanesulfonyl-5H-pyrido[3,2-b]indole

Following procedures analogous to those described for methyl 3-bromo-5H-pyrido[3,2-b]indole-7-carboxylate, 5-bromo-2-(2-fluoro-5-methanesulfonylphenyl)-3-nitropyridine (325 mg, 0.866 mmol) was converted to the title compound (173 mg, 58%). $^1$H NMR (500 MHz, DMSO-d$_6$) δ 11.99 (s, 1H), 8.68 (d, J=2.1 Hz, 1H), 8.30 (d, J=2.1 Hz, 1H), 8.05 (dd, J=8.5, 4.9 Hz, 1H), 7.31 (dd, J=9.8, 8.7 Hz, 1H), 3.38 (s, 3H); LCMS (M+H)=343; HPLC RT=1.998 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 3-Bromo-9-fluoro-6-methanesulfonyl-5-[(S)-oxan-4-yl(phenyl)methyl]-5H-pyrido[3,2-b]indole Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 3-bromo-9-fluoro-6-methanesulfonyl-5H-pyrido[3,2-b]indole (100 mg, 0.290 mmol) was converted to the title compound (121 mg, 81%). $^1$H NMR (500 MHz, CDCl$_3$) δ 8.71 (d, J=1.5 Hz, 1H), 8.36 (dd, J=8.8, 5.3 Hz, 1H), 7.78 (d, J=1.5 Hz, 1H), 7.51 (d, J=7.6 Hz, 2H), 7.44-7.31 (m, 3H), 7.18 (t, J=8.6 Hz, 1H), 6.96 (d, J=9.8 Hz, 1H), 4.06 (d, J=8.9 Hz, 1H), 3.86-3.70 (m, 1H), 3.53 (t, J=11.2 Hz, 1H), 3.34-3.15 (m, 4H), 2.92 (q, J=11.0 Hz, 1H), 2.11 (d, J=13.4 Hz, 1H), 1.97-1.79 (m, 1H), 1.54-1.44 (m, 1H), 0.37 (d, J=12.4 Hz, 1H); LCMS (M+H)=517; HPLC RT=2.913 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 5-{9-Fluoro-6-methanesulfonyl-5-[(S)-oxan-4-yl(phenyl)methyl]-5H-pyrido[3,2-b]indol-3-yl}-1,4-dimethyl-1H-1,2,3-triazole Following procedures analogous to those described for methyl 3-(1,4-dimethyl-1H-1,2,3-triazol-5-yl)-5H-pyrido[3,2-b]indole-7-carboxylate, 3-bromo-9-fluoro-6-methanesulfonyl-5-[(S)-oxan-4-yl(phenyl)methyl]-5H-pyrido[3,2-b]indole (60.0 mg, 0.116 mmol) was converted to the title compound (21.8 mg, 33%). $^1$H NMR (500 MHz, CDCl$_3$) δ 8.64 (d, J=1.7 Hz, 1H), 8.40 (dd, J=8.9, 5.3 Hz, 1H), 7.52 (d, J=7.9 Hz, 2H), 7.46 (d, J=1.8 Hz, 1H), 7.43-7.37 (m, 2H), 7.37-7.32 (m, 1H), 7.24 (t, J=8.7 Hz, 1H), 7.00 (d, J=9.8 Hz, 1H), 4.07 (dd, J=11.6, 2.6 Hz, 1H), 3.78 (dd, J=11.7, 3.1 Hz, 1H), 3.72 (s, 3H), 3.57-3.50 (m, 1H), 3.37 (s, 3H), 3.21 (td, J=12.0, 2.0 Hz, 1H), 3.00-2.87 (m, 1H), 2.20 (br. s., 1H), 2.18 (s, 3H), 2.03-1.93 (m, 1H), 1.68-1.58 (m, 1H), 0.38 (d, J=12.7 Hz, 1H); LCMS (M+H)=534; HPLC RT=2.463 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 182

5-{6-Methanesulfonyl-9-methoxy-5-[(S)-oxan-4-yl(phenyl)methyl]-5H-pyrido[3,2-b]indol-3-yl}-1,4-dimethyl-1H-1,2,3-triazole

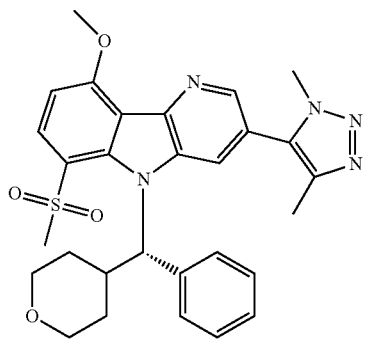 [SMILES: COc1ccc(S(C)(=O)=O)c2c1c1ncc(-c3c(C)nnn3C)cc1n2[C@H](c1ccccc1)C1CCOCC1]

To an 8 mL vial containing 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole (50.0 mg, 0.0940 mmol) in DMSO (2 mL) was added NaOMe (101 mg, 1.87 mmol). The reaction mixture was stirred at room temperature for 20 min then diluted with water, cooled with ice, and neutralized with aq. 1M citric acid. The white precipitate that formed was collected by filtration and purified on prep HPLC (Column: Phen Luna C18, 30×100 mm, 5 μm particles; Mobile Phase A: 5:95 acetonitrile:water with 0.1% TFA; Mobile Phase B: 95:5 acetonitrile:water with 0.1% TFA; Gradient: 10-100% B over 12 min, then a 3-min hold at 100% B; Flow: 40 mL/min). The tubes containing product were basified with sat aq. K$_2$CO$_3$ and concentrated to remove acetonitrile. A white precipitate formed while concentrating and was filtered with water rinses and dried under vacuum to give the title compound (27.1 mg, 52%). $^1$H NMR (500 MHz, CDCl$_3$) δ 8.63 (d, J=1.7 Hz, 1H), 8.40 (d, J=8.9 Hz, 1H), 7.51 (d, J=7.9 Hz, 2H), 7.42 (d, J=1.7 Hz, 1H), 7.40-7.35 (m, 2H), 7.35-7.30 (m, 1H), 7.04-6.93 (m, 2H), 4.30 (s, 3H), 4.06 (d, J=9.2 Hz, 1H), 3.75 (dd, J=11.3, 2.9 Hz, 1H), 3.70 (s, 3H), 3.52 (t, J=11.1 Hz, 1H), 3.32 (s, 3H), 3.23-3.13 (m, 1H), 2.98-2.85 (m, 1H), 2.22-2.14 (m, 4H), 2.03-1.91 (m, 1H), 1.63-1.58 (m, 1H), 0.36 (d, J=12.8 Hz, 1H); LCMS (M+H)=546; HPLC RT=2.325 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 183

5-{6-Methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole

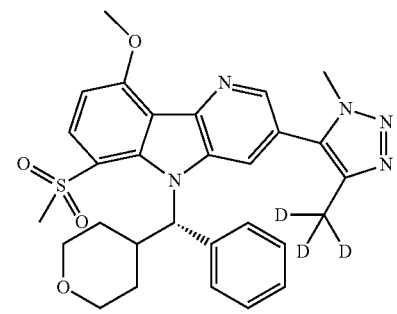 [SMILES: [2H]C([2H])([2H])c1nnn(C)c1-c1cnc2c3c(OC)ccc(S(C)(=O)=O)c3n([C@H](c3ccccc3)C3CCOCC3)c2c1]

Step 1: 5-Bromo-2-(5-methanesulfonyl-2-methoxyphenyl)-3-nitropyridine

Following procedures analogous to those described for methyl 4-(5-bromo-3-nitropyridin-2-yl)benzoate, 2-(5-methanesulfonyl-2-methoxyphenyl)-4,4,5,5-tetramethyl-1,3,2-dioxaborolane (1.00 g, 3.20 mmol) was converted to the title compound (789 mg, 63%). $^1$H NMR (400 MHz, CDCl$_3$) δ 8.96 (d, J=2.0 Hz, 1H), 8.43 (d, J=2.1 Hz, 1H), 8.25 (d, J=2.3 Hz, 1H), 8.05 (dd, J=8.7, 2.4 Hz, 1H), 7.06 (d, J=8.8 Hz, 1H), 3.82 (s, 3H), 3.12 (s, 3H); LCMS (M+H)=387; HPLC RT=1.952 min (Column: Chromolith ODS S5 4.6×50 mm; Mobile Phase A: 10:90 MeOH:water with 0.1% TFA;

Mobile Phase B: 90:10 MeOH:water with 0.1% TFA; Temperature: 40° C.; Gradient: 0-100% B over 4 min; Flow: 4 mL/min).

Step 2: 3-Bromo-6-methanesulfonyl-9-methoxy-5H-pyrido[3,2-b]indole

Following procedures analogous to those described for methyl 3-bromo-5H-pyrido[3,2-b]indole-7-carboxylate, 5-bromo-2-(5-methanesulfonyl-2-methoxyphenyl)-3-nitropyridine (788 mg, 2.03 mmol) was converted to the title compound (321 mg, 44%). $^1$H NMR (400 MHz, DMSO-$d_6$) δ 11.65 (s, 1H), 8.60 (d, J=2.2 Hz, 1H), 8.22 (d, J=2.0 Hz, 1H), 7.97 (d, J=8.6 Hz, 1H), 7.04 (d, J=8.8 Hz, 1H), 4.10 (s, 3H), 3.30 (s, 3H); LCMS (M+H)=355; HPLC RT=1.635 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 3-Bromo-6-methanesulfonyl-9-methoxy-5-[(S)-oxan-4-yl(phenyl)methyl]-5H-pyrido[3,2-b]indole Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 3-bromo-6-methanesulfonyl-9-methoxy-5H-pyrido[3,2-b]indole (166 mg, 0.470 mmol) was converted to the title compound (172 mg, 69%). $^1$H NMR (400 MHz, CDCl$_3$) δ 8.70 (d, J=2.0 Hz, 1H), 8.36 (d, J=8.8 Hz, 1H), 7.74 (d, J=2.0 Hz, 1H), 7.51 (d, J=7.8 Hz, 2H), 7.44-7.36 (m, 2H), 7.35-7.30 (m, 1H), 6.98-6.91 (m, 2H), 4.25 (s, 3H), 4.05 (d, J=11.2 Hz, 1H), 3.74 (dd, J=11.9, 2.7 Hz, 1H), 3.51 (t, J=10.9 Hz, 1H), 3.27-3.15 (m, 4H), 2.98-2.83 (m, 1H), 2.10 (d, J=13.3 Hz, 1H), 1.97-1.83 (m, 1H), 1.51-1.42 (m, 1H), 0.35 (d, J=12.6 Hz, 1H); LCMS (M+H)=529; HPLC RT=2.766 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 5-{6-Methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole In a 4 mL vial was combined 3-bromo-6-methanesulfonyl-9-methoxy-5-[(S)-oxan-4-yl(phenyl)methyl]-5H-pyrido[3,2-b]indole (30.0 mg, 0.0570 mmol), 4-($^2$H$_3$)methyl-1-[(trimethylsilyl)methyl]-1H-1,2,3-triazole (19.5 mg, 0.113 mmol), and tetrabutylammonium acetate (34.2 mg, 0.113 mmol) in NMP (0.1 mL). To the mixture was added tris(dibenzylideneacetone)dipalladium-chloroform adduct (5.80 mg, 0.00500 mmol), the vial was sealed under N$_2$ (g) and heated on a 100° C. heating block for 3 h. The reaction mixture was cooled to room temperature, and a 1M solution of TBAF in THF (0.560 mL, 0.560 mmol) was added. After stirring for 10 min, sat. aq. NH$_4$OH was added, and then the mixture was concentrated to remove THF. The residue was diluted with 10% aq. LiCl, and the resulting precipitate was collected by filtration. The crude solid was purified on prep HPLC (Column: Phen Luna C18, 30×100 mm, 5 μm particles; Mobile Phase A: 5:95 acetonitrile:water with 0.1% TFA; Mobile Phase B: 95:5 acetonitrile:water with 0.1% TFA; Gradient: 10-100% B over 12 min, then a 3-min hold at 100% B; Flow: 40 mL/min). The tubes containing product were basified with sat. aq. K$_2$CO$_3$ and concentrated to remove acetonitrile. A white precipitate formed while concentrating and was filtered with water rinses and dried under vacuum to give the title compound (11.7 mg, 37%). $^1$H NMR (500 MHz, CDCl$_3$) δ 8.63 (d, J=1.8 Hz, 1H), 8.41 (d, J=8.9 Hz, 1H), 7.51 (d, J=7.9 Hz, 2H), 7.42 (d, J=1.8 Hz, 1H), 7.40-7.35 (m, 2H), 7.35-7.30 (m, 1H), 7.02-6.95 (m, 2H), 4.30 (s, 3H), 4.06 (dd, J=11.7, 2.7 Hz, 1H), 3.75 (dd, J=11.3, 3.1 Hz, 1H), 3.70 (s, 3H), 3.52 (t, J=10.8 Hz, 1H), 3.32 (s, 3H), 3.18 (td, J=12.0, 1.8 Hz, 1H), 2.99-2.87 (m, 1H), 2.24-2.14 (m, 1H), 2.04-1.92 (m, 1H), 1.63-1.57 (m, 1H), 0.36 (d, J=13.0 Hz, 1H); LCMS (M+H)=549; HPLC RT=2.292 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 184

5-[6-($^2$H$_3$)Methanesulfonyl-9-($^2$H$_3$)methoxy-5-[(S)-oxan-4-yl)phenyl)methyl]-5H-pyrido[3,2-b]indol-3-yl]-1,4-dimethyl-1H-1,2,3-triazole

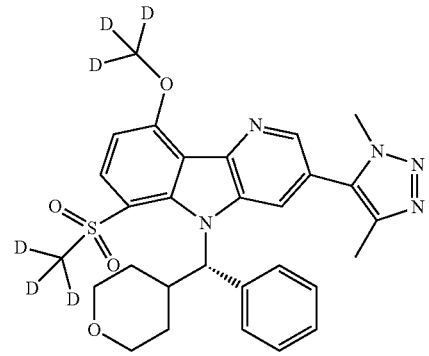 [SMILES: [2H]C([2H])([2H])Oc1ccc(S(=O)(=O)C([2H])([2H])[2H])c2c1c1ncc(-c3c(C)nnn3C)cc1n2[C@H](c1ccccc1)C1CCOCC1]

In a 4 mL vial containing a solution of KOtBu (56.8 mg, 0.510 mmol) in CD$_3$OD (0.750 mL) was added (5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole (27.0 mg, 0.0510 mmol) to give a white suspension. The reaction mixture was diluted with DMSO (0.4 mL) and the solid dissolved. After stirring for 30 min at room temperature, the reaction was neutralized with 1M aq. citric acid and then concentrated. The mixture was diluted with water, and the resulting white precipitate was collected by filtration to give the title compound (23.3 mg, 83%). $^1$H NMR (500 MHz, CDCl$_3$) δ 8.63 (d, J=1.8 Hz, 1H), 8.40 (d, J=9.0 Hz, 1H), 7.51 (d, J=7.8 Hz, 2H), 7.42 (d, J=1.8 Hz, 1H), 7.40-7.35 (m, 2H), 7.35-7.30 (m, 1H), 7.02-6.92 (m, 2H), 4.05 (dd, J=11.8, 2.7 Hz, 1H), 3.75 (dd, J=11.6, 3.1 Hz, 1H), 3.70 (s, 3H), 3.55-3.47 (m, 1H), 3.22-3.13 (m, 1H), 2.98-2.86 (m, 1H), 2.24-2.13 (m, 4H), 2.03-1.92 (m, 1H), 1.57-1.50 (m, 1H), 0.36 (d, J=12.8 Hz, 1H); LCMS (M+H)=552; HPLC RT=2.325 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 185

4-{6-Methanesulfonyl-9-methoxy-5-[(S)-oxan-4-yl(phenyl)methyl]-5H-pyrido[3,2-b]indol-3-yl}-3,5-dimethyl-1,2-oxazole

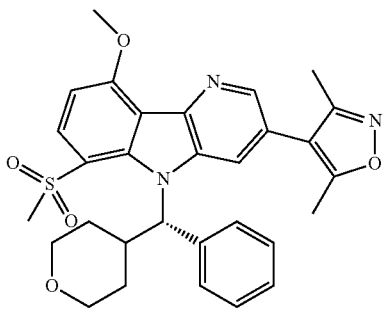 [SMILES: COc1ccc(S(C)(=O)=O)c2c1c1ncc(-c3c(C)noc3C)cc1n2[C@H](c1ccccc1)C1CCOCC1]

Step 1: 4-{9-Fluoro-6-methanesulfonyl-5-[(S)-oxan-4-yl(phenyl)methyl]-5H-pyrido[3,2-b]indol-3-yl}-3,5-dimethyl-1,2-oxazole Following procedures analogous to those described for 2-chloro-5-(3,5-dimethylisoxazol-4-yl)pyridin-3-amine, 3-bromo-9-fluoro-6-methanesulfonyl-5-[(S)-oxan-4-yl(phenyl)methyl]-5H-pyrido[3,2-b]indole (60.0 mg, 0.116 mmol) was converted to the title compound (55.0 mg, 88%). $^1$H NMR (500 MHz, CDCl$_3$) δ 8.60 (d, J=1.7 Hz, 1H), 8.36 (dd, J=8.9, 5.3 Hz, 1H), 7.52 (d, J=8.1 Hz, 2H), 7.43-7.37 (m, 3H), 7.36-7.30 (m, 1H), 7.21 (t, J=8.7 Hz, 1H), 6.99 (d, J=9.8 Hz, 1H), 4.06 (dd, J=11.6, 2.7 Hz, 1H), 3.77 (dd, J=11.7, 3.1 Hz, 1H), 3.52 (td, J=11.9, 1.8 Hz, 1H), 3.34 (s, 3H), 3.21 (td, J=12.0, 2.0 Hz, 1H), 3.01-2.87 (m, 1H), 2.25 (s, 3H), 2.22-2.14 (m, 1H), 2.08 (s, 3H), 2.02-1.90 (m, 1H), 1.63-1.57 (m, 1H), 0.38 (d, J=12.8 Hz, 1H); LCMS (M+H)=534; HPLC RT=2.731 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 4-{6-Methanesulfonyl-9-methoxy-5-[(S)-oxan-4-yl(phenyl)methyl]-5H-pyrido[3,2-b]indol-3-yl}-3,5-dimethyl-1,2-oxazole Following procedures analogous to those described for 5-{6-methanesulfonyl-9-methoxy-5-[(S)-oxan-4-yl(phenyl)methyl]-5H-pyrido[3,2-b]indol-3-yl}-1,4-dimethyl-1H-1,2,3-triazole, 4-{9-fluoro-6-methanesulfonyl-5-[(S)-oxan-4-yl(phenyl)methyl]-5H-pyrido[3,2-b]indol-3-yl}-3,5-dimethyl-1,2-oxazole (55.0 mg, 0.100 mmol) was converted to the title compound (21.7 mg, 38%). $^1$H NMR (400 MHz, CDCl$_3$) δ 8.59 (d, J=1.6 Hz, 1H), 8.37 (d, J=8.9 Hz, 1H), 7.52 (d, J=7.6 Hz, 2H), 7.43-7.35 (m, 3H), 7.32 (d, J=7.2 Hz, 1H), 7.02-6.93 (m, 2H), 4.28 (s, 3H), 4.05 (d, J=8.8 Hz, 1H), 3.80-3.68 (m, 1H), 3.50 (t, J=11.2 Hz, 1H), 3.28 (s, 3H), 3.17 (t, J=10.9 Hz, 1H), 2.99-2.85 (m, 1H), 2.24 (s, 3H), 2.17 (d, J=14.1 Hz, 1H), 2.07 (s, 3H), 2.03-1.91 (m, 1H), 1.51 (br. s., 1H), 0.36 (d, J=12.5 Hz, 1H); LCMS (M+H)=546; HPLC RT=2.428 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 186

4-{5-[(S)-(2-Fluorophenyl)(oxan-4-yl)methyl]-6-methanesulfonyl-9-methoxy-5H-pyrido[3,2-b]indol-3-yl}-3,5-dimethyl-1,2-oxazole

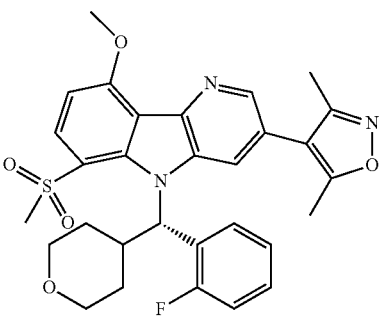 [SMILES: COc1ccc(S(C)(=O)=O)c2c1c1ncc(-c3c(C)noc3C)cc1n2[C@H](c1ccccc1F)C1CCOCC1]

Step 1: 3-Bromo-5-[(S)-(2-fluorophenyl)(oxan-4-yl)methyl]-6-methanesulfonyl-9-methoxy-5H-pyrido[3,2-b]indole Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 3-bromo-6-methanesulfonyl-9-methoxy-5H-pyrido[3,2-b]indole (75.0 mg, 0.210 mmol) and (R)-(2-fluorophenyl)(oxan-4-yl)methanol (89.0 mg, 0.422 mmol) were converted to the title compound (96.3 mg, 83%). LCMS (M+H)=547; HPLC RT=2.668 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 4-{5-[(S)-(2-Fluorophenyl)(oxan-4-yl)methyl]-6-methanesulfonyl-9-methoxy-5H-pyrido[3,2-b]indol-3-yl}-3,5-dimethyl-1,2-oxazole Following procedures analogous to those described for 4-{9-fluoro-6-methanesulfonyl-5-[(S)-oxan-4-yl(phenyl)methyl]-5H-pyrido[3,2-b]indol-3-yl}-3,5-dimethyl-1,2-oxazole, 3-bromo-5-[(S)-(2-fluorophenyl)(oxan-4-yl)methyl]-6-methanesulfonyl-9-methoxy-5H-pyrido[3,2-b]indole (30.0 mg, 0.0550 mmol) was converted to the title compound (21.7 mg, 66%). $^1$H NMR (500 MHz, CDCl$_3$) δ 8.56 (d, J=1.7 Hz, 1H), 8.45 (d, J=9.0 Hz, 1H), 7.75 (t, J=7.6 Hz, 1H), 7.46 (d, J=1.7 Hz, 1H), 7.36-7.28 (m, 2H), 7.23 (d, J=9.9 Hz, 1H), 7.01-6.94 (m, 2H), 4.27 (s, 3H), 4.11-4.04 (m, 1H), 3.84 (dd, J=11.5, 3.1 Hz, 1H), 3.58-3.47 (m, 1H), 3.35 (s, 3H), 3.29-3.21 (m, 1H), 3.05 (q, J=11.1 Hz, 1H), 2.27 (s, 3H), 2.15-2.04 (m, 4H), 2.00-1.89 (m, 2H), 0.58 (d, J=12.7 Hz, 1H); LCMS (M+H)=564; HPLC RT=2.280 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 187

4-{5-[(S)-(4-Fluorophenyl)(oxan-4-yl)methyl]-6-methanesulfonyl-9-methoxy-5H-pyrido[3,2-b]indol-3-yl}-3,5-dimethyl-1,2-oxazole

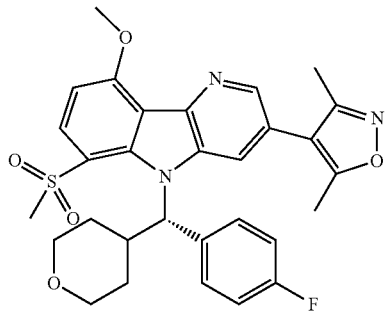 [SMILES: COc1ccc(S(C)(=O)=O)c2c1c1ncc(-c3c(C)noc3C)cc1n2[C@H](c1ccc(F)cc1)C1CCOCC1]

Following procedures analogous to those described for 4-{9-fluoro-6-methanesulfonyl-5-[(S)-oxan-4-yl(phenyl)methyl]-5H-pyrido[3,2-b]indol-3-yl}-3,5-dimethyl-1,2-oxazole, 3-bromo-5-[(S)-(4-fluorophenyl)(oxan-4-yl)methyl]-6-methanesulfonyl-9-methoxy-5H-pyrido[3,2-b]indole (32.5 mg, 0.0590 mmol) was converted to the title compound (28.5 mg, 83%). $^1$H NMR (500 MHz, CDCl$_3$) δ 8.60 (d, J=1.7 Hz, 1H), 8.32 (d, J=9.0 Hz, 1H), 7.55 (dd, J=8.5, 5.1 Hz, 2H), 7.37 (d, J=1.8 Hz, 1H), 7.11-7.04 (m, 2H), 6.96 (d, J=9.0 Hz, 1H), 6.92 (d, J=9.8 Hz, 1H), 4.28 (s, 3H), 4.05 (d, J=9.2 Hz, 1H), 3.73 (dd, J=11.6, 2.9 Hz, 1H), 3.49 (t, J=11.1 Hz, 1H), 3.31 (s, 3H), 3.20-3.11 (m, 1H), 2.93-2.82 (m, 1H), 2.29 (s, 3H), 2.17-2.08 (m, 4H), 1.97-1.85 (m, 1H), 1.51-1.40 (m, 1H), 0.33 (d, J=13.4 Hz, 1H); LCMS (M+H)=564; HPLC RT=2.473 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 188

5-{5-[(S)-(2-Fluorophenyl)(oxan-4-yl)methyl]-6-methanesulfonyl-9-methoxy-5H-pyrido[3,2-b]indol-3-yl}-1,4-dimethyl-1H-1,2,3-triazole

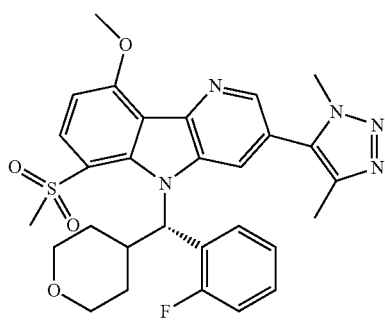 [SMILES: COc1ccc(S(C)(=O)=O)c2c1c1ncc(-c3c(C)nnn3C)cc1n2[C@H](c1ccccc1F)C1CCOCC1]

Following procedures analogous to those described for 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole, 3-bromo-5-[(S)-(2-fluorophenyl)(oxan-4-yl)methyl]-6-methanesulfonyl-9-methoxy-5H-pyrido[3,2-b]indole (30.0 mg, 0.0550 mmol) was converted to the title compound (13.5 mg, 43%). $^1$H NMR (500 MHz, CDCl$_3$) δ 8.59 (br. s., 1H), 8.50 (d, J=8.9 Hz, 1H), 7.75 (t, J=7.7 Hz, 1H), 7.51 (br. s., 1H), 7.39-7.28 (m, 2H), 7.03-6.87 (m, 2H), 4.28 (s, 3H), 4.12-4.02 (m, 1H), 3.85 (d, J=8.5 Hz, 1H), 3.76 (br. s., 3H), 3.53 (t, J=11.1 Hz, 1H), 3.37 (s, 3H), 3.26 (t, J=11.4 Hz, 1H), 3.04 (d, J=10.7 Hz, 1H), 2.24-1.90 (m, 6H), 0.59 (d, J=13.0 Hz, 1H); LCMS (M+H)=564; HPLC RT=2.243 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 189

5-{5-[(S)-(2-Fluorophenyl)(oxan-4-yl)methyl]-6-methanesulfonyl-9-methoxy-5H-pyrido[3,2-b]indol-3-yl}-4-($^2$H$_3$)methyl-1-methyl-1H-1,2,3-triazole

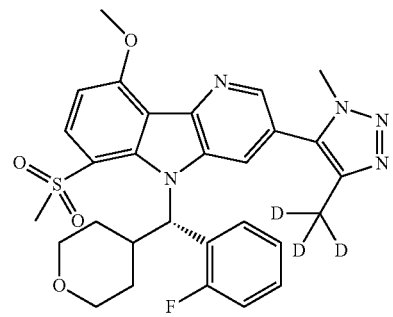 [SMILES: [2H]C([2H])([2H])c1nnn(C)c1-c1cnc2c3c(OC)ccc(S(C)(=O)=O)c3n([C@H](c3ccccc3F)C3CCOCC3)c2c1]

Following procedures analogous to those described for 5-{6-methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole, 3-bromo-5-[(S)-(2-fluorophenyl)(oxan-4-yl)methyl]-6-methanesulfonyl-9-methoxy-5H-pyrido[3,2-b]indole (30.0 mg, 0.0550 mmol) was converted to the title compound (6.70 mg, 21%). $^1$H NMR (500 MHz, CDCl$_3$) δ 8.60 (d, J=1.8 Hz, 1H), 8.49 (d, J=8.9 Hz, 1H), 7.75 (t, J=7.6 Hz, 1H), 7.51 (d, J=1.8 Hz, 1H), 7.37-7.31 (m, 1H), 7.31-7.28 (m, 1H), 7.24 (s, 1H), 7.02-6.94 (m, 2H), 4.28 (s, 3H), 4.10-4.06 (m, 1H), 3.85 (dd, J=11.9, 3.1 Hz, 1H), 3.76 (s, 3H), 3.57-3.49 (m, 1H), 3.37 (s, 3H), 3.26 (td, J=12.0, 1.8 Hz, 1H), 3.10-2.99 (m, 1H), 2.18-1.93 (m, 3H), 0.59 (d, J=12.2 Hz, 1H); LCMS (M+H)=567; HPLC RT=2.237 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 190

5-{5-[(S)-(4-Fluorophenyl)(oxan-4-yl)methyl]-6-methanesulfonyl-9-methoxy-5H-pyrido[3,2-b]indol-3-yl}-1,4-dimethyl-1H-1,2,3-triazole

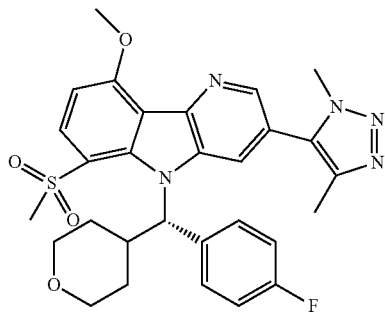 [SMILES: COc1ccc(S(C)(=O)=O)c2c1c1ncc(-c3c(C)nnn3C)cc1n2[C@H](c1ccc(F)cc1)C1CCOCC1]

Following procedures analogous to those described for 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole, 3-bromo-5-[(S)-(4-fluorophenyl)(oxan-4-yl)methyl]-6-methanesulfonyl-9-methoxy-5H-pyrido[3,2-b]indole (32.5 mg, 0.0590 mmol) was converted to the title compound (26.0 mg, 77%). $^1$H NMR (500 MHz, CDCl$_3$) δ 8.64 (d, J=1.8 Hz, 1H), 8.36 (d, J=8.9 Hz, 1H), 7.54 (dd, J=8.5, 5.2 Hz, 2H), 7.43 (d, J=1.8 Hz, 1H), 7.12-7.04 (m, 2H), 6.99 (d, J=9.0 Hz, 1H), 6.94 (d, J=9.9 Hz, 1H), 4.29 (s, 3H), 4.05 (dd, J=11.5, 2.8 Hz, 1H), 3.80 (s, 3H), 3.75 (dd, J=11.7, 3.1 Hz, 1H), 3.54-3.46 (m, 1H), 3.34 (s, 3H), 3.16 (td, J=11.9, 1.8 Hz, 1H), 2.94-2.82 (m, 1H), 2.20 (s, 3H), 2.12 (d, J=13.6 Hz, 1H), 1.99-1.86 (m, 1H), 1.53-1.45 (m, 1H), 0.34 (d, J=12.5 Hz, 1H); LCMS (M+H)=564; HPLC RT=2.405 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 191

5-{5-[(S)-(4-Fluorophenyl)(oxan-4-yl)methyl]-6-methanesulfonyl-9-methoxy-5H-pyrido[3,2-b]indol-3-yl}-4-($^2$H$_3$)methyl-1-methyl-1H-1,2,3-triazole

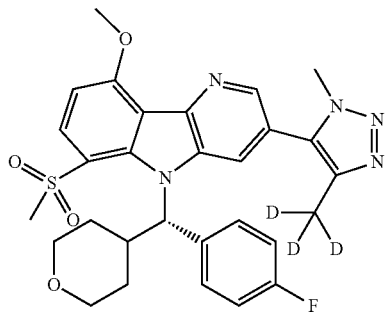 [SMILES: [2H]C([2H])([2H])c1nnn(C)c1-c1cnc2c3c(OC)ccc(S(C)(=O)=O)c3n([C@H](c3ccc(F)cc3)C3CCOCC3)c2c1]

Following procedures analogous to those described for 5-{6-methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole, 3-bromo-5-[(S)-(4-fluorophenyl)(oxan-4-yl)methyl]-6-methanesulfonyl-9-methoxy-5H-pyrido[3,2-b]indole (28.5 mg, 0.0520 mmol) was converted to the title compound (2.80 mg, 9.4%). $^1$H NMR (500 MHz, CDCl$_3$) δ 8.64 (d, J=1.8 Hz, 1H), 8.36 (d, J=8.9 Hz, 1H), 7.54 (dd, J=8.3, 5.1 Hz, 2H), 7.43 (d, J=1.8 Hz, 1H), 7.10-7.05 (m, 2H), 6.99 (d, J=9.0 Hz, 1H), 6.94 (d, J=9.5 Hz, 1H), 4.29 (s, 3H), 4.05 (d, J=9.2 Hz, 1H), 3.80 (s, 3H), 3.75 (d, J=12.1 Hz, 1H), 3.50 (t, J=11.0 Hz, 1H), 3.34 (s, 3H), 3.21-3.11 (m, 1H), 2.95-2.82 (m, 1H), 2.12 (d, J=13.1 Hz, 1H), 1.98-1.86 (m, 1H), 1.50 (d, J=4.6 Hz, 1H), 0.34 (d, J=12.7 Hz, 1H); LCMS (M+H)=567; HPLC RT=2.392 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 192

2-{3-[5-($^2$H$_3$)Methyl-3-methyl-1,2-oxazol-4-yl]-5-[(S)-oxan-4-yl(phenyl)methyl]-5H-pyrido[3,2-b]indol-7-yl}propan-2-ol

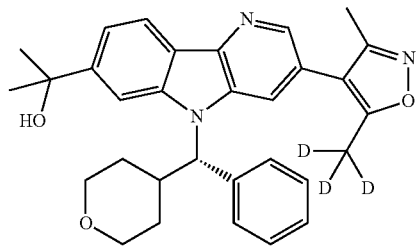 [SMILES: [2H]C([2H])([2H])c1onc(C)c1-c1cnc2c3ccc(C(C)(C)O)cc3n([C@H](c3ccccc3)C3CCOCC3)c2c1]

In a 4 mL vial containing 2-[3-(dimethyl-1,2-oxazol-4-yl)-5-[(S)-oxan-4-yl(phenyl)methyl]-5H-pyrido[3,2-b]indol-7-yl]propan-2-ol (20.0 mg, 0.0400 mmol) in CD$_3$OD (1.5 mL) was added KOtBu (20.4 mg, 0.182 mmol). The mixture was heated on an 80° C. heating block for 23 h, then at room temperature sat. aq. NaHCO$_3$ was added, and the mixture was concentrated to remove CD$_3$OD. The mixture was diluted with water, and the resulting white precipitate was collected by filtration to give the title compound (18.1 mg, 89%). $^1$H NMR (500 MHz, CDCl$_3$) δ 8.39 (d, J=1.7 Hz, 1H), 8.33 (d, J=8.2 Hz, 1H), 7.94 (s, 1H), 7.52 (d, J=1.7 Hz, 1H), 7.46 (d, J=7.3 Hz, 2H), 7.42 (dd, J=8.2, 1.4 Hz, 1H), 7.37-7.31 (m, 2H), 7.30-7.28 (m, 1H), 5.56 (d, J=10.7 Hz, 1H), 4.06 (dd, J=11.7, 2.6 Hz, 1H), 3.86 (dd, J=11.7, 2.8 Hz, 1H), 3.55 (td, J=11.9, 1.8 Hz, 1H), 3.35 (td, J=11.9, 2.0 Hz, 1H), 3.16-3.04 (m, 1H), 2.23 (s, 3H), 2.03 (d, J=13.4 Hz, 1H), 1.93 (s, 1H), 1.74 (s, 6H), 1.68-1.59 (m, 1H), 1.47-1.36 (m, 1H), 1.11 (d, J=13.6 Hz, 1H); LCMS (M+H)=499; HPLC RT=2.422 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 193

4-[6-($^2H_3$)Methanesulfonyl-9-methoxy-5-[(S)-oxan-4-yl(phenyl)methyl]-5H-pyrido[3,2-b]indol-3-yl]-5-($^2H_3$)methyl-3-methyl-1,2-oxazole

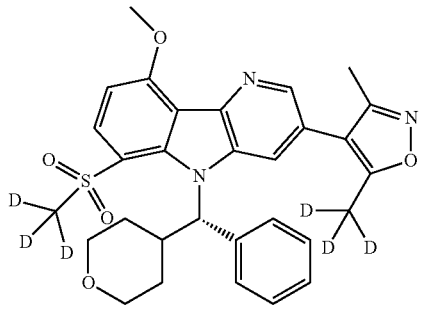 [SMILES: [2H]C([2H])([2H])c1onc(C)c1-c1cnc2c3c(OC)ccc(S(=O)(=O)C([2H])([2H])[2H])c3n([C@H](c3ccccc3)C3CCOCC3)c2c1]

Following procedures analogous to those described for 2-{3-[5-($^2H_3$)methyl-3-methyl-1,2-oxazol-4-yl]-5-[(S)-oxan-4-yl(phenyl)methyl]-5H-pyrido[3,2-b]indol-7-yl}propan-2-ol, 4-{6-methanesulfonyl-9-methoxy-5-[(S)-oxan-4-yl(phenyl)methyl]-5H-pyrido[3,2-b]indol-3-yl}-3,5-dimethyl-1,2-oxazole (11.0 mg, 0.0200 mmol) was converted to the title compound (9.00 mg, 80%). $^1$H NMR (500 MHz, CDCl$_3$) δ 8.59 (d, J=1.8 Hz, 1H), 8.36 (d, J=8.9 Hz, 1H), 7.52 (d, J=8.1 Hz, 2H), 7.41-7.35 (m, 3H), 7.34-7.29 (m, 1H), 6.99-6.93 (m, 2H), 4.28 (s, 3H), 4.05 (dd, J=11.5, 2.7 Hz, 1H), 3.74 (dd, J=11.6, 3.2 Hz, 1H), 3.51 (td, J=11.9, 1.8 Hz, 1H), 3.18 (td, J=11.9, 1.9 Hz, 1H), 3.00-2.87 (m, 1H), 2.17 (d, J=13.7 Hz, 1H), 2.07 (s, 3H), 2.03-1.92 (m, 1H), 1.53 (dd, J=12.8, 4.4 Hz, 1H), 0.35 (d, J=13.0 Hz, 1H); LCMS (M+H)=552; HPLC RT=2.392 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 194

5-{9-Fluoro-7-methanesulfonyl-5-[(S)-oxan-4-yl(phenyl)methyl]-5H-pyrido[3,2-b]indol-3-yl}-1,4-dimethyl-1H-1,2,3-triazole

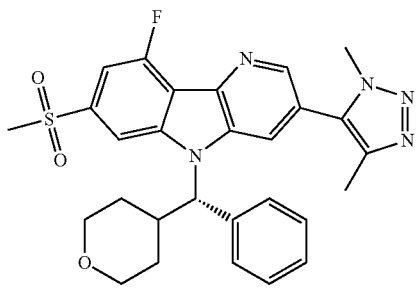 [SMILES: Cc1nnn(C)c1-c1cnc2c3c(F)cc(S(C)(=O)=O)cc3n([C@H](c3ccccc3)C3CCOCC3)c2c1]

Step 1: 5-Bromo-2-(2-fluoro-4-methanesulfonylphenyl)-3-nitropyridine

Following procedures analogous to those described for methyl 4-(5-bromo-3-nitropyridin-2-yl)benzoate, 2-(2-fluoro-4-methanesulfonylphenyl)-4,4,5,5-tetramethyl-1,3,2-dioxaborolane (2.96 g, 9.86 mmol) was converted to the title compound (469 mg, 13%). $^1$H NMR (400 MHz, CDCl$_3$) δ 9.03 (d, J=2.0 Hz, 1H), 8.59 (d, J=2.1 Hz, 1H), 8.02-7.86 (m, 2H), 7.73 (dd, J=9.2, 1.5 Hz, 1H), 3.14 (s, 3H); HPLC RT=1.973 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 3-Bromo-9-fluoro-7-methanesulfonyl-5H-pyrido[3,2-b]indole

Following procedures analogous to those described for methyl 3-bromo-5H-pyrido[3,2-b]indole-7-carboxylate, 5-bromo-2-(2-fluoro-4-methanesulfonylphenyl)-3-nitropyridine (469 mg, 1.25 mmol) was converted to the title compound (136 mg, 32%). $^1$H NMR (500 MHz, DMSO-d$_6$) δ 12.34 (br. s., 1H), 8.69 (br. s., 1H), 8.39 (s, 1H), 8.01 (s, 1H), 7.60 (d, J=9.5 Hz, 1H), 3.34 (br. s., 3H); LCMS (M+H)=343; HPLC RT=1.940 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 3-Bromo-9-fluoro-7-methanesulfonyl-5-[(S)-oxan-4-yl(phenyl)methyl]-5H-pyrido[3,2-b]indole Following procedures analogous to those described for 5-{7-methanesulfonyl-5-[(S)-oxan-4-yl(phenyl)methyl]-5H-pyrido[3,2-b]indol-3-yl}-1,4-dimethyl-1H-1,2,3-triazole, 3-bromo-9-fluoro-7-methanesulfonyl-5H-pyrido[3,2-b]indole (136 mg, 0.400 mmol) was converted to the title compound (76.0 mg, 37%). $^1$H NMR (500 MHz, CDCl$_3$) δ 8.75 (d, J=1.8 Hz, 1H), 8.09 (d, J=1.8 Hz, 1H), 8.06 (s, 1H), 7.54 (dd, J=8.9, 0.9 Hz, 1H), 7.45 (d, J=7.5 Hz, 2H), 7.41-7.36 (m, 2H), 7.35-7.31 (m, 1H), 5.46 (d, J=11.0 Hz, 1H), 4.07 (dd, J=11.7, 2.9 Hz, 1H), 3.88 (dd, J=11.8, 3.0 Hz, 1H), 3.57 (td, J=11.9, 2.0 Hz, 1H), 3.38 (td, J=11.9, 2.1 Hz, 1H), 3.15-3.05 (m, 4H), 2.00 (d, J=13.3 Hz, 1H), 1.64-1.57 (m, 1H), 1.42-1.32 (m, 1H), 1.00 (d, J=12.2 Hz, 1H); LCMS (M+H)=517; HPLC RT=2.761 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 5-{9-Fluoro-7-methanesulfonyl-5-[(S)-oxan-4-yl(phenyl)methyl]-5H-pyrido[3,2-b]indol-3-yl}-1,4-dimethyl-1H-1,2,3-triazole Following procedures analogous to those described for methyl 3-(1,4-dimethyl-1H-1,2,3-triazol-5-yl)-5H-pyrido[3,2-b]indole-7-carboxylate, 3-bromo-9-fluoro-7-methanesulfonyl-5-[(S)-oxan-4-yl(phenyl)methyl]-5H-pyrido[3,2-b]indole (38.0 mg, 0.0730 mmol) was converted to the title compound (28.2 mg, 71%). $^1$H NMR (500 MHz, CDCl$_3$) δ 8.66 (d, J=1.7 Hz, 1H), 8.18 (s, 1H), 7.71 (d, J=1.5 Hz, 1H), 7.64-7.59 (m, 1H), 7.46-7.42 (m, 2H), 7.41-7.37 (m, 2H), 7.36-7.32 (m, 1H), 5.61 (d, J=10.5 Hz, 1H), 4.08 (dd, J=11.7, 2.8 Hz, 1H), 3.95-3.84 (m, 4H), 3.56 (td, J=11.9, 1.8 Hz, 1H), 3.36 (td, J=11.9, 1.8 Hz, 1H), 3.21 (s, 3H), 3.15-3.04 (m, 1H), 2.31 (s, 3H), 2.06 (d, J=13.3 Hz, 1H), 1.63 (dd, J=13.4, 4.0 Hz, 1H), 1.46-1.34 (m, 1H), 1.04 (d, J=13.0 Hz, 1H); LCMS (M+H)=534; HPLC RT=2.363 min (Column:

Example 195

5-{9-Fluoro-7-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole

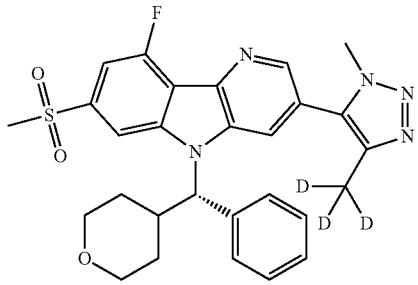 [SMILES: [2H]C([2H])([2H])c1nnn(C)c1-c1cnc2c3c(F)cc(S(C)(=O)=O)cc3n([C@H](c3ccccc3)C3CCOCC3)c2c1]

Following procedures analogous to those described for 5-{6-methanesulfonyl-9-methoxy-5-[(S)-oxan-4-yl(phenyl)methyl]-5H-pyrido[3,2-b]indol-3-yl}-4-($^2H_3$)methyl-1-methyl-1H-1,2,3-triazole, 3-bromo-9-fluoro-7-methanesulfonyl-5-[(S)-oxan-4-yl(phenyl)methyl]-5H-pyrido[3,2-b]indole (38.0 mg, 0.0730 mmol) was converted to the title compound (18.0 mg, 45%). $^1$H NMR (500 MHz, CDCl$_3$) δ 8.66 (d, J=1.7 Hz, 1H), 8.18 (s, 1H), 7.71 (d, J=1.7 Hz, 1H), 7.62 (dd, J=8.7, 0.9 Hz, 1H), 7.46-7.42 (m, 2H), 7.41-7.37 (m, 2H), 7.37-7.32 (m, 1H), 5.61 (d, J=10.5 Hz, 1H), 4.08 (dd, J=11.8, 2.8 Hz, 1H), 3.94-3.85 (m, 4H), 3.56 (td, J=11.9, 1.8 Hz, 1H), 3.36 (td, J=11.9, 1.9 Hz, 1H), 3.21 (s, 3H), 3.15-3.05 (m, 1H), 2.06 (d, J=13.3 Hz, 1H), 1.68-1.59 (m, 1H), 1.41 (qd, J=12.4, 4.4 Hz, 1H), 1.04 (d, J=13.0 Hz, 1H); LCMS (M+H)=537; HPLC RT=2.362 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 196

5-{9-Fluoro-5-[(S)-(2-fluorophenyl)(oxan-4-yl)methyl]-7-methanesulfonyl-5H-pyrido[3,2-b]indol-3-yl}-4-($^2H_3$)methyl-1-methyl-1H-1,2,3-triazole

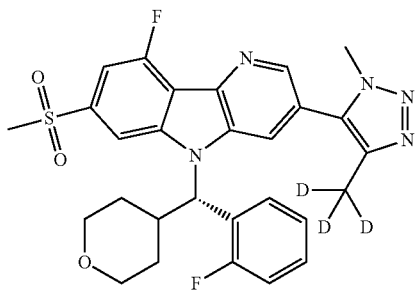 [SMILES: [2H]C([2H])([2H])c1nnn(C)c1-c1cnc2c3c(F)cc(S(C)(=O)=O)cc3n([C@H](c3ccccc3F)C3CCOCC3)c2c1]

Following procedures analogous to those described for 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole, 3-bromo-9-fluoro-5-[(S)-(2-fluorophenyl)(oxan-4-yl)methyl]-7-methanesulfonyl-5H-pyrido[3,2-b]indole (150 mg, 0.280 mmol) and 4-($^2H_3$)methyl-5-(tributylstannyl)-1-[(trimethylsilyl)methyl]-1H-1,2,3-triazole (194 mg, 0.420 mmol) were converted to the title compound (68.7 mg, 44%). $^1$H NMR (500 MHz, CDCl$_3$) δ 8.68 (d, J=1.5 Hz, 1H), 8.20 (s, 1H), 7.91 (s, 1H), 7.80 (br t, J=7.2 Hz, 1H), 7.59 (d, J=8.5 Hz, 1H), 7.41-7.34 (m, 1H), 7.33-7.28 (m, 1H), 7.11-7.03 (m, 1H), 5.78 (br d, J=11.4 Hz, 1H), 4.07 (br dd, J=11.8, 2.8 Hz, 1H), 4.01 (s, 3H), 3.88 (br dd, J=11.7, 2.9 Hz, 1H), 3.59-3.51 (m, 1H), 3.38-3.29 (m, 1H), 3.23-3.11 (m, 4H), 1.95 (br d, J=13.3 Hz, 1H), 1.66-1.60 (m, 1H), 1.39 (qd, J=12.3, 4.4 Hz, 1H), 0.99 (br d, J=12.8 Hz, 1H); LCMS (M+H)=555; HPLC RT=2.367 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 197

5-{7-Methanesulfonyl-9-methoxy-5-[(S)-oxan-4-yl(phenyl)methyl]-5H-pyrido[3,2-b]indol-3-yl}-4-($^2H_3$)methyl-1-methyl-1H-1,2,3-triazole

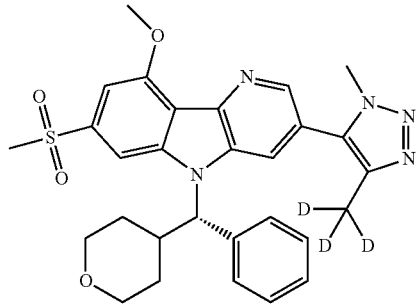 [SMILES: [2H]C([2H])([2H])c1nnn(C)c1-c1cnc2c3c(OC)cc(S(C)(=O)=O)cc3n([C@H](c3ccccc3)C3CCOCC3)c2c1]

In an 8 mL vial was added 5-{9-fluoro-7-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole (20.0 mg, 0.0370 mmol) in MeOH (2 mL). To the mixture was added KOtBu (20.6 mg, 0.184 mmol), and the reaction was heated on an 80° C. heating block. After heating for 17 h, the reaction was cooled to room temperature and neutralized with 1M aq. citric acid. The mixture was concentrated to remove MeOH and diluted with water, then sat. aq. K$_2$CO$_3$ was added, and the white precipitate was collected by filtration to give the title compound (16.4 mg, 78%). $^1$H NMR (500 MHz, CDCl$_3$) δ 8.65 (d, J=1.8 Hz, 1H), 7.99 (s, 1H), 7.66 (s, 1H), 7.46-7.40 (m, 2H), 7.40-7.30 (m, 4H), 5.60 (d, J=10.5 Hz, 1H), 4.27 (s, 3H), 4.07 (br dd, J=11.7, 2.8 Hz, 1H), 3.91-3.82 (m, 4H), 3.60-3.51 (m, 1H), 3.39-3.30 (m, 1H), 3.21 (s, 3H), 3.15-3.04 (m, 1H), 2.06 (br d, J=14.2 Hz, 1H), 1.69-1.60 (m, 1H), 1.45-1.33 (m, 1H), 1.01 (br d, J=13.0 Hz, 1H); LCMS (M+H)=549; HPLC RT=2.273 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 198

5-{5-[(S)-(2-Fluorophenyl)(oxan-4-yl)methyl]-7-methanesulfonyl-9-methoxy-5H-pyrido[3,2-b]indol-3-yl}-4-($^2H_3$)methyl-1-methyl-1H-1,2,3-triazole

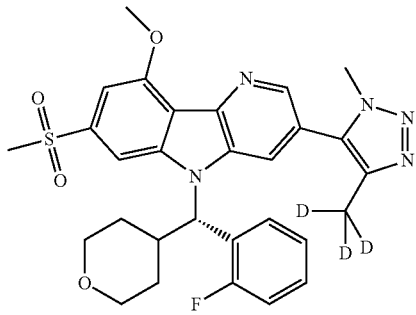 [SMILES: [2H]C([2H])([2H])c1nnn(C)c1-c1cnc2c3c(OC)cc(S(C)(=O)=O)cc3n([C@H](c3ccccc3F)C3CCOCC3)c2c1]

Following procedures analogous to those described for 5-{7-methanesulfonyl-9-methoxy-5-[(S)-oxan-4-yl(phenyl)methyl]-5H-pyrido[3,2-b]indol-3-yl}-4-($^2H_3$)methyl-1-methyl-1H-1,2,3-triazole, 5-{9-fluoro-5-[(S)-(2-fluorophenyl)(oxan-4-yl)methyl]-7-methanesulfonyl-5H-pyrido[3,2-b]indol-3-yl}-4-($^2H_3$)methyl-1-methyl-1H-1,2,3-triazole (20.0 mg, 0.0360 mmol) was converted to the title compound (14.3 mg, 66%). $^1$H NMR (500 MHz, CDCl$_3$) δ 8.68 (d, J=1.7 Hz, 1H), 8.22-7.98 (m, 1H), 7.93-7.74 (m, 2H), 7.39-7.29 (m, 3H), 7.08-7.00 (m, 1H), 5.76 (br d, J=11.0 Hz, 1H), 4.25 (s, 3H), 4.09-4.04 (m, 1H), 4.03-3.95 (m, 3H), 3.89-3.81 (m, 1H), 3.58-3.51 (m, 1H), 3.37-3.29 (m, 1H), 3.17 (s, 4H), 1.94 (br d, J=13.0 Hz, 1H), 1.43-1.33 (m, 1H), 0.97 (br d, J=14.2 Hz, 1H); LCMS (M+H)=567; HPLC RT=2.297 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 199 & 200

5-{5-[(4,4-Difluorocyclohexyl)(phenyl)methyl]-9-fluoro-7-methanesulfonyl-5H-pyrido[3,2-b]indol-3-yl}-4-($^2H_3$)methyl-1-methyl-1H-1,2,3-triazole Enantiomer A, Example 199

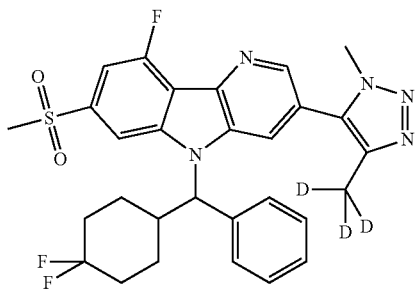

Enantiomer B, Example 200

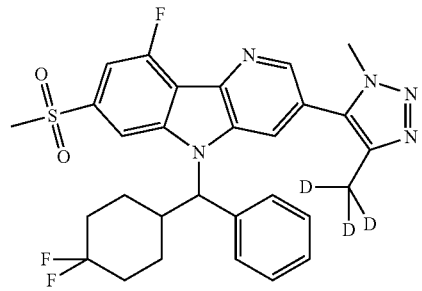

Step 1: 3-Bromo-5-[(4,4-difluorocyclohexyl)(phenyl)methyl]-9-fluoro-7-methanesulfonyl-5H-pyrido[3,2-b]indole Following procedures analogous to those described for 3-bromo-5-[(4,4-difluorocyclohexyl)(phenyl)methyl]-7-methanesulfonyl-5H-pyrido[3,2-b]indole, 3-bromo-9-fluoro-7-methanesulfonyl-5H-pyrido[3,2-b]indole (50.0 mg, 0.148 mmol) was converted to the title compound (71.0 mg, 88%). LCMS (M+H)=551; HPLC RT=3.045 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 5-{5-[(4,4-Difluorocyclohexyl)(phenyl)methyl]-9-fluoro-7-methanesulfonyl-5H-pyrido[3,2-b]indol-3-yl}-4-($^2H_3$)methyl-1-methyl-1H-1,2,3-triazole Following procedures analogous to those described for 5-{5-[(4,4-difluorocyclohexyl)(phenyl)methyl]-7-methanesulfonyl-5H-pyrido[3,2-b]indol-3-yl}-4-($^2H_3$)methyl-1-methyl-1H-1,2,3-triazole, 3-bromo-5-[(4,4-difluorocyclohexyl)(phenyl)methyl]-9-fluoro-7-methanesulfonyl-5H-pyrido[3,2-b]indole (80.0 mg, 0.145 mmol) was converted to racemic 5-{5-[(4,4-difluorocyclohexyl)(phenyl)methyl]-9-fluoro-7-methanesulfonyl-5H-pyrido[3,2-b]indol-3-yl}-4-($^2H_3$)methyl-1-methyl-1H-1,2,3-triazole, which was separated on chiral prep SFC to give enantiomer A (19.1 mg, 22%) and enantiomer B (20.7 mg, 24%). Enantiomer A: $^1$H NMR (500 MHz, CDCl$_3$) δ 8.67 (d, J=1.7 Hz, 1H), 8.17 (s, 1H), 7.72 (s, 1H), 7.62 (dd, J=8.7, 0.9 Hz, 1H), 7.45-7.32 (m, 5H), 5.61 (d, J=10.5 Hz, 1H), 3.92 (s, 3H), 3.21 (s, 3H), 2.95 (q, J=11.2 Hz, 1H), 2.23 (br d, J=12.5 Hz, 2H), 2.08-1.84 (m, 2H), 1.77-1.62 (m, 2H), 1.39 (qd, J=12.9, 3.5 Hz, 1H), 1.27 (br d, J=10.2 Hz, 1H); LCMS (M+H)=571; HPLC RT=2.587 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=15.4 min (Column: Chiralpak IC, 250×4.6 mm, 5 μm; Mobile Phase: 55/45 CO$_2$/MeOH; Flow: 2 mL/min). Enantiomer B: $^1$H NMR (500 MHz, CDCl$_3$) δ 8.67 (d, J=1.8 Hz, 1H), 8.17 (s, 1H), 7.70 (d, J=1.7 Hz, 1H), 7.62 (dd, J=8.7, 0.9 Hz, 1H), 7.45-7.32 (m, 5H), 5.61 (d, J=10.7 Hz, 1H), 3.91 (s, 3H), 3.21 (s, 3H), 2.95 (q, J=11.0 Hz, 1H), 2.23 (br d, J=12.7 Hz, 2H), 2.10-1.84 (m, 2H), 1.76-1.59 (m, 2H), 1.44-1.34 (m, 1H), 1.28 (br s, 1H); LCMS (M+H)=571; HPLC RT=2.583 min (Column: Chromolith ODS S5 4.6×50 mm; Mobile Phase A: 10:90 MeOH:water with 0.1% TFA;

Mobile Phase B: 90:10 MeOH:water with 0.1% TFA; Temperature: 40° C.; Gradient: 0-100% B over 4 min; Flow: 4 mL/min); SFC RT=17.5 min (Column: Chiralpak IC, 250× 4.6 mm, 5 μm; Mobile Phase: 55/45 CO₂/MeOH; Flow: 2 mL/min).

Example 201

5-{9-Fluoro-5-[(S)-(4-fluorophenyl)(oxan-4-yl) methyl]-7-methanesulfonyl-5H-pyrido[3,2-b]indol-3-yl}-4-(²H₃)methyl-1-methyl-1H-1,2,3-triazole

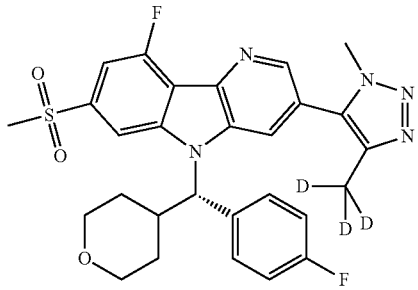 [SMILES: [2H]C([2H])([2H])c1nnn(C)c1-c1cnc2c3c(F)cc(S(C)(=O)=O)cc3n([C@H](c3ccc(F)cc3)C3CCOCC3)c2c1]

Following procedures analogous to those described for 5-{9-fluoro-6-methanesulfonyl-5-[(S)-oxan-4-yl(phenyl) methyl]-5H-pyrido[3,2-b]indol-3-yl}-1,4-dimethyl-1H-1,2,3-triazole, 3-bromo-9-fluoro-5-[(S)-(4-fluorophenyl)(oxan-4-yl)methyl]-7-methanesulfonyl-5H-pyrido[3,2-b]indole (72.7 mg, 0.136 mmol) and 4-(²H₃)methyl-5-(tributylstannyl)-1-[(trimethylsilyl)methyl]-1H-1,2,3-triazole (79.0 mg, 0.200 mmol) were converted to the title compound (40.5 mg, 53%). ¹H NMR (400 MHz, CDCl₃) δ 8.68 (d, J=1.7 Hz, 1H), 8.14 (s, 1H), 7.70 (d, J=1.7 Hz, 1H), 7.62 (dd, J=8.7, 1.0 Hz, 1H), 7.43 (dd, J=8.8, 5.0 Hz, 2H), 7.13-7.04 (m, 2H), 5.57 (d, J=10.6 Hz, 1H), 4.08 (br dd, J=12.2, 2.5 Hz, 1H), 3.96 (s, 3H), 3.89 (br dd, J=11.9, 2.7 Hz, 1H), 3.60-3.50 (m, 1H), 3.41-3.30 (m, 1H), 3.21 (s, 3H), 3.12-3.00 (m, 1H), 2.01 (br d, J=12.3 Hz, 1H), 1.64-1.60 (m, 1H), 1.46-1.34 (m, 1H), 1.05 (br d, J=12.2 Hz, 1H); LCMS (M+H)=555; HPLC RT=2.492 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 202

5-{5-[(S)-(4-Fluorophenyl)(oxan-4-yl)methyl]-7-methanesulfonyl-9-methoxy-5H-pyrido[3,2-b]indol-3-yl}-4-(²H₃)methyl-1-methyl-1H-1,2,3-triazole

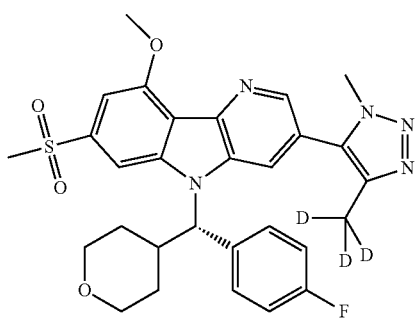 [SMILES: [2H]C([2H])([2H])c1nnn(C)c1-c1cnc2c3c(OC)cc(S(C)(=O)=O)cc3n([C@H](c3ccc(F)cc3)C3CCOCC3)c2c1]

Following procedures analogous to those described for 5-{7-methanesulfonyl-9-methoxy-5-[(S)-oxan-4-yl(phenyl) methyl]-5H-pyrido[3,2-b]indol-3-yl}-4-(²H₃)methyl-1-methyl-1H-1,2,3-triazole, 5-{9-fluoro-5-[(S)-(4-fluorophenyl)(oxan-4-yl)methyl]-7-methanesulfonyl-5H-pyrido[3,2-b]indol-3-yl}-4-(²H₃)methyl-1-methyl-1H-1,2,3-triazole (30.0 mg, 0.0540 mmol) was converted to the title compound (25.6 mg, 80%). ¹H NMR (400 MHz, CDCl₃) δ 8.67 (d, J=1.8 Hz, 1H), 7.95 (s, 1H), 7.65 (s, 1H), 7.42 (dd, J=8.6, 5.1 Hz, 2H), 7.34 (s, 1H), 7.07 (t, J=8.5 Hz, 2H), 5.56 (br d, J=10.5 Hz, 1H), 4.27 (s, 3H), 4.07 (br dd, J=11.7, 2.6 Hz, 1H), 3.94 (s, 3H), 3.87 (br dd, J=11.6, 3.4 Hz, 1H), 3.54 (br td, J=11.7, 1.6 Hz, 1H), 3.34 (td, J=11.9, 1.9 Hz, 1H), 3.21 (s, 3H), 3.12-2.99 (m, 1H), 2.01 (br d, J=13.7 Hz, 1H), 1.68-1.60 (m, 1H), 1.38 (qd, J=12.4, 4.7 Hz, 1H), 1.02 (br d, J=12.7 Hz, 1H); LCMS (M+H)=567; HPLC RT=2.443 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Examples 203 & 204

2-{5-[(4,4-Difluorocyclohexyl)(phenyl)methyl]-3-[4-(²H₃)methyl-1-methyl-1H-1,2,3-triazol-5-yl]-5H-pyrido[3,2-b]indol-7-yl}propan-2-ol Enantiomer A, Example 203

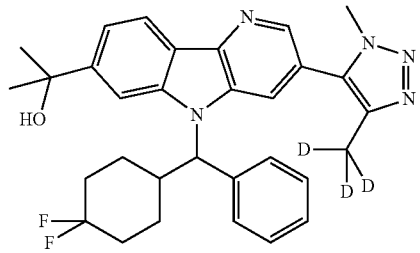

Enantiomer B, Example 204

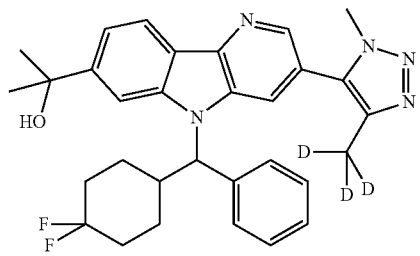

Step 1: Methyl 3-bromo-5-[(S)-(4,4-difluorocyclohexyl)(phenyl)methyl]-5H-pyrido[3,2-b]indole-7-carboxylate Following procedures analogous to those described for 3-bromo-5-[(4,4-difluorocyclohexyl)(phenyl)methyl]-7-methanesulfonyl-5H-pyrido[3,2-b]indole, methyl 3-bromo-5H-pyrido[3,2-b]indole-7-carboxylate (45.0 mg, 0.147 mmol) was converted to the title compound and was used without purification in the next step without purification. LCMS (M+H)=513; HPLC RT=3.520 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: Methyl 5-[(4,4-Difluorocyclohexyl)(phenyl)methyl]-3-[4-($^2$H$_3$)methyl-1-methyl-1H-1,2,3-triazol-5-yl]-5H-pyrido[3,2-b]indole-7-carboxylate Following procedures analogous to those described for 5-{5-[(4,4-difluorocyclohexyl)(phenyl)methyl]-7-methanesulfonyl-5H-pyrido[3,2-b]indol-3-yl}-4-($^2$H$_3$)methyl-1-methyl-1H-1,2,3-triazole, methyl 3-bromo-5-[(S)-(4,4-difluorocyclohexyl)(phenyl)methyl]-5H-pyrido[3,2-b]indole-7-carboxylate was converted to the title compound (25.4 mg, 32%). LCMS (M+H)=533; HPLC RT=3.128 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 2-{5-[(4,4-Difluorocyclohexyl)(phenyl)methyl]-3-[4-($^2$H$_3$)methyl-1-methyl-1H-1,2,3-triazol-5-yl]-5H-pyrido[3,2-b]indol-7-yl}propan-2-ol Following procedures analogous to those described for (S)-2-[3-(dimethyl-1H-1,2,3-triazol-5-yl)-5-[oxan-4-yl(phenyl)methyl]-5H-pyrido[3,2-b]indol-7-yl]propan-2-ol, methyl 5-[(4,4-difluorocyclohexyl)(phenyl)methyl]-3-[4-($^2$H$_3$)methyl-1-methyl-1H-1,2,3-triazol-5-yl]-5H-pyrido[3,2-b]indole-7-carboxylate (25.4 mg, 0.0480 mmol) was converted to the racemic 2-{5-[(4,4-difluorocyclohexyl)(phenyl)methyl]-3-[4-($^2$H$_3$)methyl-1-methyl-1H-1,2,3-triazol-5-yl]-5H-pyrido[3,2-b]indol-7-yl}propan-2-ol, which was separated on chiral prep SFC to give enantiomer A (11.1 mg, 42%) and enantiomer B (10.7 mg, 41%). Enantiomer A: $^1$H NMR (500 MHz, CDCl$_3$) δ 8.45 (d, J=1.7 Hz, 2H), 8.00 (s, 1H), 7.60 (br s, 1H), 7.49-7.41 (m, 3H), 7.38-7.34 (m, 2H), 7.33-7.29 (m, 1H), 5.61 (br d, J=10.5 Hz, 1H), 3.88 (s, 3H), 2.99-2.86 (m, 1H), 2.22 (br d, J=10.8 Hz, 2H), 2.06-1.83 (m, 3H), 1.75 (d, J=2.7 Hz, 6H), 1.72-1.69 (m, 1H), 1.45-1.31 (m, 2H); LCMS (M+H)=533; HPLC RT=2.783 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.4 min (Column: Chiral IB, 250×4.6 mm, 5 μm; Mobile Phase: 80/20 CO$_2$/MeOH; Flow: 2 mL/min). Enantiomer B: $^1$H NMR (500 MHz, CDCl$_3$) δ 8.44 (d, J=1.8 Hz, 1H), 8.35 (d, J=8.2 Hz, 1H), 7.97 (s, 1H), 7.54 (d, J=1.8 Hz, 1H), 7.47-7.41 (m, 3H), 7.37-7.32 (m, 2H), 7.32-7.28 (m, 1H), 5.59 (d, J=10.5 Hz, 1H), 3.88 (s, 3H), 2.99-2.89 (m, 1H), 2.21 (br d, J=12.7 Hz, 2H), 2.05-1.96 (m, 1H), 1.96-1.83 (m, 2H), 1.75 (d, J=2.6 Hz, 6H), 1.62 (br s, 1H), 1.45-1.32 (m, 2H); LCMS (M+H)=533; HPLC RT=2.781 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.0 min (Column: Chiral IB, 250×4.6 mm, 5 μm; Mobile Phase: 80/20 CO$_2$/MeOH; Flow: 2 mL/min).

Examples 205 & 206

2-{5-[(S)-(4,4-Difluorocyclohexyl)(phenyl)methyl]-3-(dimethyl-1H-1,2,3-triazol-5-yl)-5H-pyrido[3,2-b]indol-7-yl}propan-2-ol Enantiomer A, Example 205

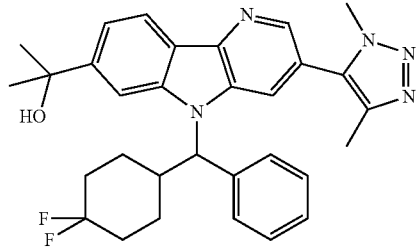

Enantiomer B, Example 206

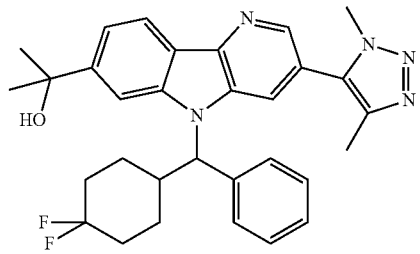

Step 1: Methyl 5-[(4,4-difluorocyclohexyl)(phenyl)methyl]-3-(dimethyl-1H-1,2,3-triazol-5-yl)-5H-pyrido[3,2-b]indole-7-carboxylate Following procedures analogous to those described for methyl 3-(1,4-dimethyl-1H-1,2,3-triazol-5-yl)-5H-pyrido[3,2-b]indole-7-carboxylate, methyl 3-bromo-5-[(S)-(4,4-difluorocyclohexyl)(phenyl)methyl]-5H-pyrido[3,2-b]indole-7-carboxylate (38.0 mg, 0.0740 mmol) was converted to the title compound (19.8 mg, 50%). LCMS (M+H)=530; HPLC RT=3.128 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-{5-[(S)-(4,4-Difluorocyclohexyl)(phenyl)methyl]-3-(dimethyl-1H-1,2,3-triazol-5-yl)-5H-pyrido[3,2-b]indol-7-yl}propan-2-ol Following procedures analogous to those described for (S)-2-[3-(dimethyl-1H-1,2,3-triazol-5-yl)-5-[oxan-4-yl(phenyl)methyl]-5H-pyrido[3,2-b]indol-7-yl]propan-2-ol, methyl 5-[(4,4-difluorocyclohexyl)(phenyl)methyl]-3-(dimethyl-1H-1,2,3-triazol-5-yl)-5H-pyrido[3,2-b]indole-7-carboxylate (19.8 mg, 0.0370 mmol) was converted to racemic 2-{5-[(S)-(4,4-difluorocyclohexyl)(phenyl)methyl]-3-(dimethyl-1H-1,2,3-triazol-5-yl)-5H-pyrido[3,2-b]indol-7-yl}propan-2-ol, which was separated on chiral prep SFC to give enantiomer A (7.90 mg, 39%) and enantiomer B (8.20 mg, 40%). Enantiomer A: $^1$H NMR (500 MHz, CDCl$_3$) δ 8.44 (d, J=1.7 Hz, 1H), 8.36 (d, J=8.2 Hz, 1H), 7.97 (s, 1H), 7.54 (d, J=1.8 Hz, 1H), 7.47-7.41 (m, 3H), 7.37-7.33 (m, 2H), 7.32-7.29 (m, 1H), 5.59 (d, J=10.5 Hz, 1H), 3.88 (s, 3H), 2.99-2.89 (m, 1H), 2.30 (s, 3H), 2.21 (br d, J=12.2 Hz, 2H), 2.06-1.96 (m, 1H), 1.96-1.83 (m, 2H), 1.75 (d, J=2.7 Hz, 6H), 1.62 (br s, 1H), 1.45-1.33 (m, 2H); LCMS (M+H)=530; HPLC RT=2.785 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.4 min (Column: Chiral IB, 250×4.6 mm, 5 µm; Mobile Phase: 80/20 CO$_2$/MeOH; Flow: 2 mL/min). Enantiomer B: $^1$H NMR (500 MHz, CDCl$_3$) δ 8.44 (d, J=1.8 Hz, 1H), 8.36 (d, J=7.9 Hz, 1H), 7.97 (s, 1H), 7.54 (d, J=1.7 Hz, 1H), 7.47-7.42 (m, 3H), 7.37-7.33 (m, 2H), 7.32-7.29 (m, 1H), 5.59 (d, J=10.5 Hz, 1H), 3.88 (s, 3H), 2.94 (br q, J=11.0 Hz, 1H), 2.30 (s, 3H), 2.27-2.17 (m, 2H), 2.05-1.96 (m, 1H), 1.96-1.83 (m, 2H), 1.75 (d, J=2.6 Hz, 6H), 1.64-1.59 (m, 1H), 1.44-1.32 (m, 2H); LCMS (M+H)=530; HPLC RT=2.786 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.0 min (Column: Chiral IB, 250×4.6 mm, 5 µm; Mobile Phase: 80/20 CO$_2$/MeOH; Flow: 2 mL/min).

Examples 207 & 208

3-Fluoro-2-[{7-methanesulfonyl-9-methoxy-3-[4-($^2$H$_3$)methyl-1-methyl-1H-1,2,3-triazol-5-yl]-5H-pyrido[3,2-b]indol-5-yl}(oxan-4-yl)methyl]pyridine Enantiomer A, Example 207

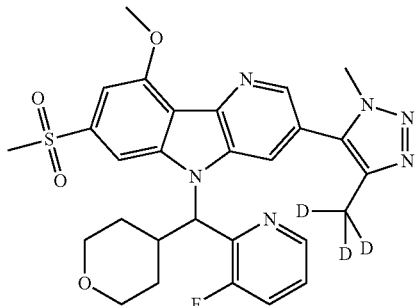

Enantiomer B, Example 208

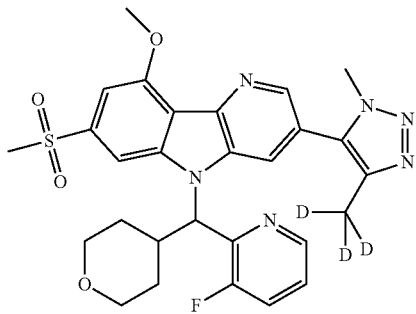

Following procedures analogous to those described for 5-{7-methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole, 3-fluoro-2-({9-fluoro-7-methanesulfonyl-3-[4-($^2$H$_3$)methyl-1-methyl-1H-1,2,3-triazol-5-yl]-5H-pyrido[3,2-b]indol-5-yl}(oxan-4-yl)methyl)pyridine (53.0 mg, 0.0930 mmol) was converted to the racemic 3-fluoro-2-[{7-methanesulfonyl-9-methoxy-3-[4-($^2$H$_3$)methyl-1-methyl-1H-1,2,3-triazol-5-yl]-5H-pyrido[3,2-b]indol-5-yl}(oxan-4-yl)methyl]pyridine, which was separated on chiral prep SFC to give enantiomer A (4.00 mg, 7%) and enantiomer B (4.0 mg, 7%). Enantiomer A: $^1$H NMR (500 MHz, CDCl$_3$) δ 8.68 (d, J=1.7 Hz, 1H), 8.52 (br s, 1H), 8.28-8.04 (m, 1H), 7.45-7.39 (m, 1H), 7.37-7.31 (m, 2H), 5.86 (br d, J=8.7 Hz, 1H), 4.25 (s, 3H), 4.06 (s, 3H), 4.00 (br dd, J=11.7, 2.8 Hz, 1H), 3.83 (br dd, J=11.8, 3.0 Hz, 1H), 3.51 (br t, J=11.1 Hz, 2H), 3.30 (br t, J=11.6 Hz, 1H), 3.21 (br s, 3H), 1.71 (br d, J=10.4 Hz, 1H), 1.49 (qd, J=11.9, 4.0 Hz, 1H), 1.40-1.28 (m, 1H), 0.86 (br d, J=12.1 Hz, 1H); LCMS (M+H)=568; HPLC RT=2.213 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=5.1 min (Column: Chiral OJ-H, 250×4.6 mm, 5 µm; Mobile Phase: 80/20 CO$_2$/MeOH; Flow: 2 mL/min). Enantiomer B: $^1$H NMR (500 MHz, CDCl$_3$) δ 8.68 (d, J=1.5 Hz, 1H), 8.52 (br s, 1H), 8.27-8.06 (m, 1H), 7.45-7.40 (m, 1H), 7.37-7.31 (m, 2H), 5.86 (br d, J=7.5 Hz, 1H), 4.25 (s, 3H), 4.06 (s, 3H), 4.00 (br dd, J=11.7, 3.0 Hz, 1H), 3.83 (br dd, J=11.8, 3.0 Hz, 1H), 3.51 (br t, J=11.4 Hz, 2H), 3.30 (br t, J=11.4 Hz, 1H), 3.21 (br s, 3H), 1.71 (br d, J=11.3 Hz, 1H), 1.53-1.44 (m, 1H), 1.39-1.29 (m, 1H), 0.91-0.82 (m, 1H); LCMS (M+H)=568; HPLC RT=2.208 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=6.9 min (Column: Chiral OJ-H, 250×4.6 mm, 5 µm; Mobile Phase: 80/20 CO$_2$/MeOH; Flow: 2 mL/min).

Examples 209 & 210

5-{5-[(S)-(4,4-Difluorocyclohexyl)(phenyl)methyl]-9-ethoxy-7-methanesulfonyl-5H-pyrido[3,2-b]indol-3-yl}-4-($^2$H$_3$)methyl-1-methyl-1H-1,2,3-triazole Enantiomer A, Example 209

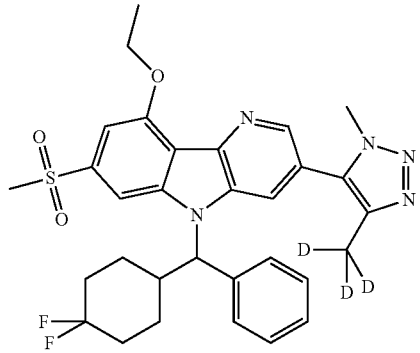

195
-continued

Enantiomer B, Example 210

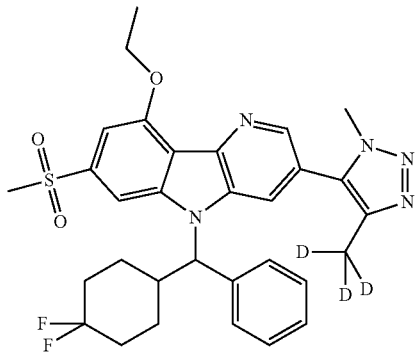

To a 20 mL vial containing KOtBu (72.4 mg, 0.645 mmol) in EtOH (3 mL) was added racemic 5-{5-[(4,4-difluorocyclohexyl)(phenyl)methyl]-9-fluoro-7-methanesulfonyl-5H-pyrido[3,2-b]indol-3-yl}-4-($^2$H$_3$)methyl-1-methyl-1H-1,2,3-triazole (36.6 mg, 0.0640 mmol), and the reaction mixture was heated on an 80° C. heating block for 2 h. After cooling to room temperature, the reaction was neutralized with 1M aq. citric acid and concentrated to remove EtOH. Water was added to the mixture, and the resulting white precipitate was collected by filtration to give racemic 5-{5-[(S)-(4,4-difluorocyclohexyl)(phenyl)methyl]-9-ethoxy-7-methanesulfonyl-5H-pyrido[3,2-b]indol-3-yl}-4-($^2$H$_3$)methyl-1-methyl-1H-1,2,3-triazole, which was separated on chiral prep SFC to give enantiomer A (15.9 mg, 41%) and enantiomer B (15.6 mg, 40%). Enantiomer A: $^1$H NMR (500 MHz, CDCl$_3$) δ 8.64 (d, J=1.8 Hz, 1H), 7.93 (s, 1H), 7.62 (d, J=1.4 Hz, 1H), 7.43-7.39 (m, 2H), 7.38-7.34 (m, 2H), 7.34-7.31 (m, 2H), 5.59 (d, J=10.5 Hz, 1H), 4.55 (q, J=7.0 Hz, 2H), 3.87 (s, 3H), 3.20 (s, 3H), 2.93 (q, J=10.7 Hz, 1H), 2.24 (br d, J=11.0 Hz, 2H), 2.05-1.84 (m, 2H), 1.68 (t, J=7.0 Hz, 4H), 1.62 (br s, 1H), 1.41-1.31 (m, 1H), 1.28-1.20 (m, 1H); LCMS (M+H)=597; HPLC RT=2.760 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.57 min (Column: Chiral OD-H, 250×4.6 mm, 5 μm; Mobile Phase: 80/20 CO$_2$/MeOH; Flow: 2 mL/min). Enantiomer B: $^1$H NMR (500 MHz, CDCl$_3$) δ 8.64 (d, J=1.8 Hz, 1H), 7.93 (s, 1H), 7.62 (d, J=1.4 Hz, 1H), 7.42-7.39 (m, 2H), 7.38-7.34 (m, 2H), 7.34-7.30 (m, 2H), 5.59 (d, J=10.5 Hz, 1H), 4.55 (q, J=7.0 Hz, 2H), 3.87 (s, 3H), 3.20 (s, 3H), 2.93 (q, J=10.8 Hz, 1H), 2.24 (br d, J=11.6 Hz, 2H), 2.05-1.82 (m, 2H), 1.74-1.61 (m, 5H), 1.42-1.31 (m, 1H), 1.28-1.20 (m, 1H); LCMS (M+H)=597; HPLC RT=2.765 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=8.96 min (Column: Chiral OD-H, 250×4.6 mm, 5 μm; Mobile Phase: 80/20 CO$_2$/MeOH; Flow: 2 mL/min).

196

Examples 211 & 212

2-[(4,4-Difluorocyclohexyl)({9-fluoro-7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine Enantiomer A, Example 211

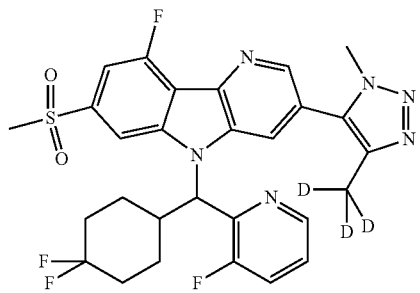

Enantiomer B, Example 212

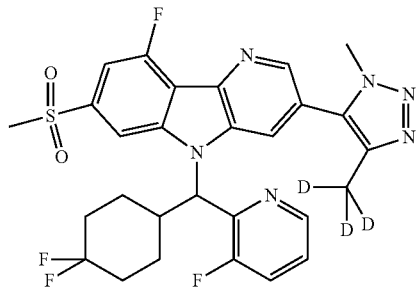

Step 1: 2-({3-Bromo-9-fluoro-7-methanesulfonyl-5H-pyrido[3,2-b]indol-5-yl}(4,4-difluorocyclohexyl)methyl)-3-fluoropyridine Following procedures analogous to those described for 2-({3-bromo-9-fluoro-6-methanesulfonyl-5H-pyrido[3,2-b]indol-5-yl}(4,4-difluorocyclohexyl)methyl)-3-fluoropyridine, 3-bromo-9-fluoro-7-methanesulfonyl-5H-pyrido[3,2-b]indole (60.0 mg, 0.175 mmol) was converted to the title compound and was used without purification in the next step. LCMS (M+H)=570; HPLC RT=3.011 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-[(4,4-Difluorocyclohexyl)({9-fluoro-7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine Following procedures analogous to those described for 5-{5-[(4,4-difluorocyclohexyl)(phenyl)methyl]-7-methanesulfonyl-5H-pyrido[3,2-b]indol-3-yl}-4-($^2$H$_3$)methyl-1-methyl-1H-1,2,3-triazole, 2-({3-bromo-9-fluoro-7-methanesulfonyl-5H-pyrido[3,2-b]indol-5-yl}(4,4-difluorocyclohexyl)methyl)-3-fluoropyridine was converted to racemic 2-[(4,4-difluorocyclohexyl)({9-fluoro-7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine (75.1 mg, 72% over 2 steps). Chiral separation was performed on the racemic compound (37.0 mg, 0.0630 mmol) using chiral prep SFC to give enantiomer A (17.4 mg, 46%) and enantiomer B (17.4 mg, 46%). Enantiomer A: $^1$H NMR (400 MHz, CDCl$_3$) δ 8.70 (d, J=1.7 Hz, 1H), 8.59-8.35 (m, 2H), 7.61 (d, J=8.3 Hz, 1H), 7.48-7.41 (m, 1H), 7.39-7.33 (m, 1H), 5.88 (br d, J=10.5 Hz, 1H), 4.08 (s, 3H), 3.38 (br s, 1H), 3.21 (s, 3H), 2.16 (br s, 1H), 1.97 (br d, J=3.9 Hz, 1H), 1.88 (br d, J=14.7 Hz, 2H), 1.72-1.61 (m, 1H), 1.49 (br d, J=11.4 Hz, 1H), 1.42-1.27 (m, 2H), 1.12 (br d, J=13.0 Hz, 1H); LCMS (M+H)=590; HPLC RT=2.608 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.7 min (Column: Chiral AS, 250×4.6 mm, 5 μm; Mobile Phase: 90/10 CO$_2$/MeOH; Flow: 2 mL/min). Enantiomer B: $^1$H NMR (400 MHz, CDCl$_3$) δ 8.70 (d, J=1.7 Hz, 1H), 8.60-8.33 (m, 2H), 7.61 (d, J=8.3 Hz, 1H), 7.49-7.41 (m, 1H), 7.40-7.34 (m, 1H), 5.87 (br d, J=10.6 Hz, 1H), 4.08 (s, 3H), 3.38 (br s, 1H), 3.21 (s, 3H), 2.23-2.11 (m, 1H), 2.05-1.80 (m, 3H), 1.72-1.61 (m, 1H), 1.52-1.43 (m, 1H), 1.42-1.24 (m, 2H), 1.12 (br d, J=12.2 Hz, 1H); LCMS (M+H)=590; HPLC RT=2.606 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=9.6 min (Column: Chiral AS, 250×4.6 mm, 5 μm; Mobile Phase: 90/10 CO$_2$/MeOH; Flow: 2 mL/min).

Examples 213 & 214

2-[(4,4-Difluorocyclohexyl)({7-methanesulfonyl-9-methoxy-3-[4-($^2$H$_3$)methyl-1-methyl-1H-1,2,3-triazol-5-yl]-5H-pyrido[3,2-b]indol-5-yl})methyl]-3-fluoropyridine Enantiomer A, Example 213

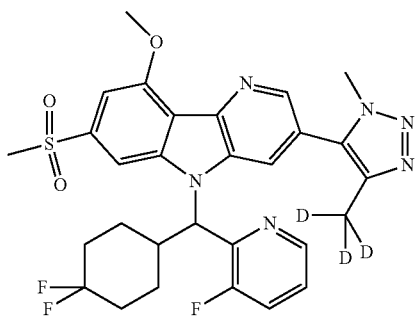

Enantiomer B, Example 214

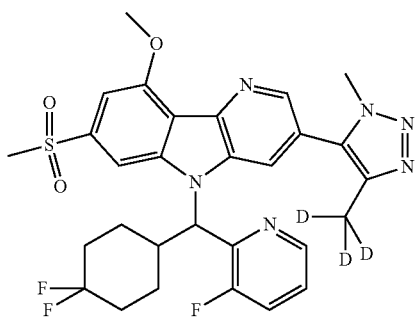

Following procedures analogous to those described for 5-{7-methanesulfonyl-9-methoxy-5-[(S)-oxan-4-yl(phenyl)methyl]-5H-pyrido[3,2-b]indol-3-yl}-4-($^2$H$_3$)methyl-1-methyl-1H-1,2,3-triazole, racemic 2-[(4,4-difluorocyclohexyl)({9-fluoro-7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine (37.0 mg, 0.0630 mmol) was converted to the racemic 2-[(4,4-difluorocyclohexyl)({7-methanesulfonyl-9-methoxy-3-[4-($^2$H$_3$)methyl-1-methyl-1H-1,2,3-triazol-5-yl]-5H-pyrido[3,2-b]indol-5-yl})methyl]-3-fluoropyridine, which was separated on chiral prep SFC to give enantiomer A (15.5 mg, 40%) and enantiomer B (17.0 mg, 44%). Enantiomer A: $^1$H NMR (400 MHz, CDCl$_3$) δ 8.69 (d, J=1.7 Hz, 1H), 8.53 (br s, 1H), 8.19 (br s, 1H), 7.46-7.39 (m, 1H), 7.38-7.31 (m, 2H), 5.86 (br d, J=9.9 Hz, 1H), 4.25 (s, 3H), 4.05 (s, 3H), 3.37 (br s, 1H), 3.21 (s, 3H), 2.14 (br s, 1H), 2.02-1.79 (m, 3H), 1.70-1.59 (m, 1H), 1.51-1.44 (m, 1H), 1.39-1.25 (m, 2H), 1.07 (br d, J=11.2 Hz, 1H); LCMS (M+H)=602; HPLC RT=2.575 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.8 min (Column: Chiral AS, 250×4.6 mm, 5 μm; Mobile Phase: 85/15 CO$_2$/MeOH; Flow: 2 mL/min). Enantiomer B: $^1$H NMR (400 MHz, CDCl$_3$) δ 8.69 (d, J=1.7 Hz, 1H), 8.53 (br s, 1H), 8.19 (br s, 1H), 7.46-7.39 (m, 1H), 7.38-7.32 (m, 2H), 5.86 (br d, J=11.1 Hz, 1H), 4.25 (s, 3H), 4.05 (s, 3H), 3.38 (br s, 1H), 3.25-3.17 (m, 3H), 2.21-2.10 (m, 1H), 2.03-1.80 (m, 3H), 1.71-1.60 (m, 1H), 1.48 (br d, J=14.2 Hz, 1H), 1.39-1.23 (m, 2H), 1.08 (br d, J=11.7 Hz, 1H); LCMS (M+H)=602; HPLC RT=2.582 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=10.0 min (Column: Chiral AS, 250×4.6 mm, 5 μm; Mobile Phase: 85/15 CO$_2$/MeOH; Flow: 2 mL/min).

Example 216

N-[3-(dimethyl-1H-1,2,3-triazol-5-yl)-6-methanesulfonyl-5-[(S)-oxan-4-yl(phenyl)methyl]-5H-pyrido[3,2-b]indol-9-yl]methanesulfonamide

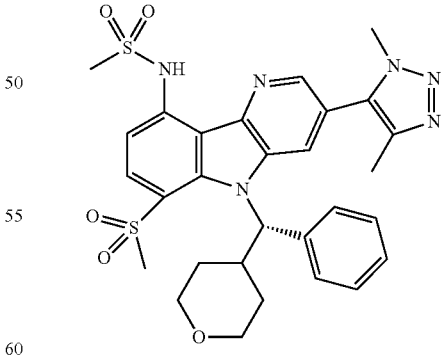

To a stirred solution of 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole (15.0 mg, 0.0280 mmol) and methanesulfonamide (15 mg, 0.158 mmol) in NMP (0.15 mL) was added t-BuOK (11.0 mg, 0.0980 mmol). This mixture was heated at 65° C. for 24 h and cooled to room temperature. The mixture was diluted with 10% LiCl solution and extracted with EtOAc (2×). The organics were dried over MgSO$_4$, filtered, and concentrated. The resulting residue was purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 20 min; Flow: 20 mL/min. Fractions containing the desired product were combined and dried via centrifugal evaporation to give the title compound (1.6 mg, 9%). $^1$H NMR (500 MHz, DMSO-d6) δ 8.58 (br s, 1H), 8.27 (br s, 1H), 7.80 (br s, 1H), 7.55 (br d, J=7.7 Hz, 2H), 7.43 (br d, J=7.4 Hz, 1H), 7.36-7.27 (m, 3H), 7.25-7.20 (m, 1H), 6.71 (br d, J=10.4 Hz, 1H), 3.84 (br d, J=8.8 Hz, 1H), 3.73 (s, 3H), 3.62 (br s, 1H), 3.58 (br s, 3H), 3.46 (br t, J=11.3 Hz, 1H), 3.27 (br d, J=10.4 Hz, 1H), 3.18 (br t, J=11.8 Hz, 1H), 2.54 (s, 3H), 2.00 (s, 3H), 1.93 (br s, 1H), 1.66-1.50 (m, 2H), 0.44 (br d, J=11.8 Hz, 1H). LCMS: RT=1.64 min; (ES): m/z (M+H)$^+$=609.4; LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 100%.

Examples 217-219

The compounds in Table 7 were prepared according to the procedure described above (Example 216):

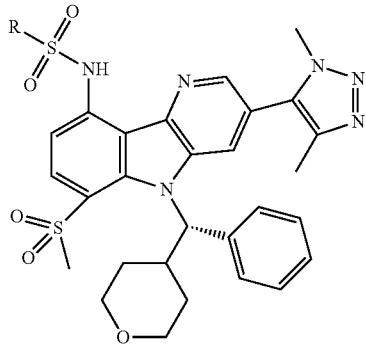

TABLE 7

| Example | R | HPLC RT (min) | LCMS (M + H) | HPLC Method |
|---|---|---|---|---|
| 217 | Me⌇ | 1.53 | 623.0 | B |
| 218 | ▽⌇ | 1.72 | 635.2 | B |
| 219 | △⌇ | 1.83 | 649.4 | B |

HPLC Conditions for Table 7: Method B: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm.

Example 221

5-{9-Fluoro-6-methanesulfonyl-5-[(S)-oxan-4-yl (phenyl)methyl]-5H-pyrido[3,2-b]indol-3-yl}-4-($^2$H$_3$)methyl-1-methyl-1H-1,2,3-triazole

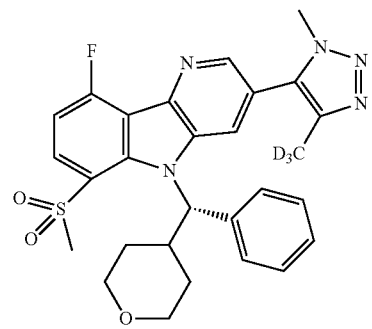 [SMILES: [2H]C([2H])([2H])c1nnn(C)c1-c1cnc2c3c(F)ccc(S(C)(=O)=O)c3n([C@H](c3ccccc3)C3CCOCC3)c2c1]

In a 4 mL vial, (S)-3-bromo-9-fluoro-6-(methylsulfonyl)-5-(phenyl(tetrahydro-2H-pyran-4-yl)methyl)-5H-pyrido[3,2-b]indole (150 mg, 0.290 mmol), 4-($^2$H$_3$)methyl-5-(tributylstannyl)-1-[(trimethylsilyl)methyl]-1H-1,2,3-triazole (241 mg, 0.522 mmol), and tetrakis(triphenylphosphine)palladium (0) (40.2 mg, 0.0350 mmol) were dissolved in DMF (1.00 mL) to give an orange suspension. Copper (I) iodide (8.28 mg, 0.0430 mmol) and Et$_3$N (0.0890 mL, 0.638 mmol) were added. The reaction mixture was purged with nitrogen for 5 min and then heated at 95° C. for 40 min. The mixture was cooled to room temperature and combined with 1M nBu$_4$NF in THF (1.16 mL, 1.16 mmol). The resulting mixture was stirred at room temperature for 30 min, and diluted with EtOAc. The mixture was washed with 10% aq. LiCl solution and brine. The organic layer was dried (MgSO$_4$), filtered, and concentrated to give the crude mixture. This mixture was purified by silica gel column chromatography (Teledyne ISCO CombiFlash 0% to 100% solvent A/B=hexane/EtOAc, RediSep SiO$_2$ 80 g, detecting at 254 nM, and monitoring at 220 nM). Concentration of appropriate fractions provided 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (156 mg, 65%). 1H NMR $^1$H NMR (500 MHz, DMSO-d$_6$) δ 8.68 (s, 1H), 8.38 (dd, J=8.8, 5.0 Hz, 1H), 7.88 (s, 1H), 7.62 (br d, J=7.7 Hz, 2H), 7.41 (t, J=8.9 Hz, 1H), 7.37-7.31 (m, 2H), 7.29-7.23 (m, 1H), 6.79 (br d, J=10.4 Hz, 1H), 3.93-3.82 (m, 1H), 3.76 (s, 3H), 3.71 (s, 3H), 3.65 (br d, J=8.8 Hz, 1H), 3.54-3.46 (m, 1H), 3.40 (br s, 1H), 3.24-3.13 (m, 1H), 1.96 (br d, J=13.1 Hz, 1H), 1.77-1.56 (m, 2H), 0.46 (br d, J=12.5 Hz, 1H).). LCMS: RT=1.572 min; (ES): m/z (M+H)$^+$=537.10; LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 99%.

Example 222

N-{6-Methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}cyclopropanesulfonamide

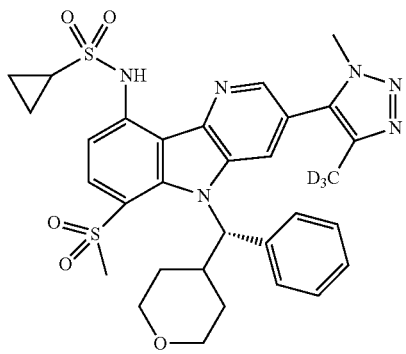 [SMILES: [2H]C([2H])([2H])c1nnn(C)c1-c1cnc2c3c(NS(=O)(=O)C4CC4)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (25.0 mg, 0.0500 mmol) and cyclopropanesulfonamide (22.6 mg, 0.190 mmol) in NMP (0.25 mL) was added t-BuOK (18.3 mg, 0.160 mmol). This mixture was heated at 65° C. for 17 h before it was cooled to room temperature. The mixture was then diluted with 10% aq. LiCl solution and extracted with EtOAc. Combined EtOAc extracts were dried (MgSO$_4$), filtered, and concentrated to give the crude mixture. It was purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give N-{6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}cyclopropanesulfonamide (14.7 mg, 50%). $^1$H NMR (500 MHz, DMSO-d$_6$) δ 8.70 (s, 1H), 8.34 (d, J=8.8 Hz, 1H), 7.95-7.91 (m, 1H), 7.63 (br d, J=7.7 Hz, 2H), 7.53 (d, J=8.8 Hz, 1H), 7.37-7.31 (m, 2H), 7.30-7.22 (m, 1H), 6.76 (s, 1H), 3.88 (br d, J=16.2 Hz, 1H), 3.79 (s, 3H), 3.68 (br s, 1H), 3.64 (s, 3H), 3.51 (br d, J=12.1 Hz, 1H), 3.43 (br d, J=10.1 Hz, 1H), 3.25-3.20 (m, 1H), 3.15 (br d, J=4.4 Hz, 1H), 2.54 (s, 1H), 1.95 (br d, J=12.5 Hz, 1H), 1.64 (br d, J=8.4 Hz, 2H), 1.21 (br s, 2H), 1.10 (br d, J=8.1 Hz, 2H), 0.51 (br d, J=12.1 Hz, 1H). LCMS: RT=1.792 min; (ES): m/z (M+H)$^+$=638.15; LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 98%.

Example 223

The compound in Table 8 was prepared according to the procedure described above (Example 222):

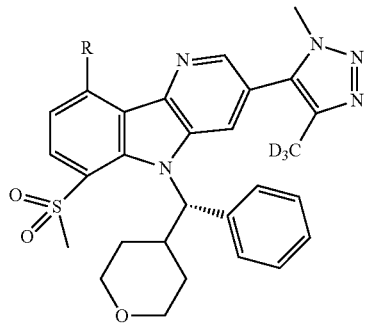

TABLE 8

| Example | R | HPLC RT (min) | LCMS (M + H) | HPLC Method |
|---|---|---|---|---|
| 223 | ![structure] | 1.75 | 626.1 | B |

HPLC Conditions for Table 8: Method B: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm.

Example 225

4-({6-Methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}amino)butanoic acid

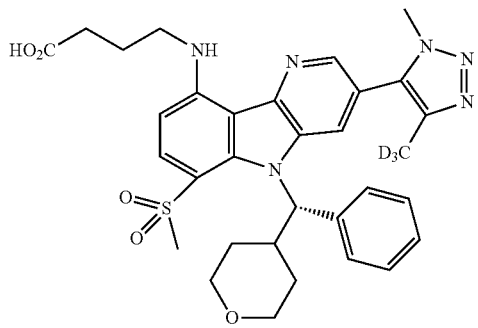 [SMILES: [2H]C([2H])([2H])c1nnn(C)c1-c1cnc2c3c(NCCCC(=O)O)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (20.0 mg, 0.0400 mmol) and pyrrolidin-2-one (0.100 mL, 0.0400 mmol) in NMP (0.10 mL) was added t-BuOK (20.0 mg, 0.180 mmol). This mixture was heated at 95° C. for 2 h and cooled to room temperature. The mixture was diluted with MeOH and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 4-({6-methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-yl}amino)butanoic acid (5.80 mg, 25%). $^1$H NMR (500 MHz, DMSO-$d_6$) δ 8.55 (s, 1H), 8.20 (br s, 1H), 8.10 (br d, J=8.8 Hz, 1H), 7.76 (s, 1H), 7.57 (br d, J=7.4 Hz, 2H), 7.37-7.27 (m, 2H), 7.27-7.22 (m, 1H), 6.77-6.69 (m, 2H), 3.87 (br d, J=9.8 Hz, 1H), 3.75 (s, 3H), 3.67 (br d, J=10.4 Hz, 1H), 3.52 (br s, 1H), 3.46 (s, 1H), 3.36 (br s, 1H), 3.20 (br t, J=11.8 Hz, 1H), 2.54 (s, 5H), 2.40 (br t, J=7.1 Hz, 2H), 1.98-1.88 (m, 3H), 1.72-1.53 (m, 2H), 0.53 (br d, J=11.8 Hz, 1H). LCMS: RT=1.328 min; (ES): m/z (M+H)$^+$=620.10. LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 98%.

Example 226

N-(2-Amino-2-methylpropyl)-6-methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-amine

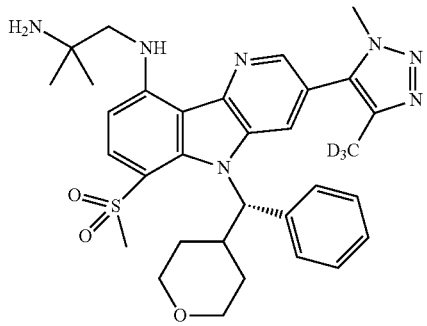 [SMILES: [2H]C([2H])([2H])c1nnn(C)c1-c1cnc2c3c(NCC(C)(C)N)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole (22.0 mg, 0.0410 mmol) and 3,3-dimethyl-1,2,5-thiadiazolidine-1,1-dione (44.1 mg, 0.290 mmol) in NMP (0.10 mL) was added t-BuOK (32.0 mg, 0.280 mmol). This mixture was gradually heated to 95° C. for 3 h and cooled to room temperature. The mixture was diluted with MeOH and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give N-(2-amino-2-methylpropyl)-6-methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-amine (8.60 mg, 35%). $^1$H NMR (500 MHz, DMSO-$d_6$) δ 8.51 (s, 1H), 8.42 (br t, J=6.1 Hz, 1H), 8.04 (d, J=9.1 Hz, 1H), 7.66 (s, 1H), 7.54 (br d, J=7.7 Hz, 2H), 7.35-7.29 (m, 2H), 7.26-7.19 (m, 1H), 6.75 (d, J=9.1 Hz, 1H), 6.70 (br d, J=10.1 Hz, 1H), 3.85 (br d, J=14.5 Hz, 1H), 3.71 (br s, 2H), 3.65 (br s, 3H), 3.60 (br d, J=6.7 Hz, 1H), 3.51-3.45 (m, 1H), 3.42 (s, 2H), 3.30 (br d, J=9.4 Hz, 1H), 3.19 (br t, J=11.8 Hz, 1H), 2.54 (s, 3H), 1.95 (br d, J=12.1 Hz, 1H), 1.72-1.63 (m, 1H), 1.60 (br d, J=12.1 Hz, 1H), 1.27 (s, 6H), 0.51 (br d, J=12.5 Hz, 1H). LCMS: RT=1.299 min; (ES): m/z (M+H)$^+$=605.15; LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 100%.

Example 227

6-Methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-amine

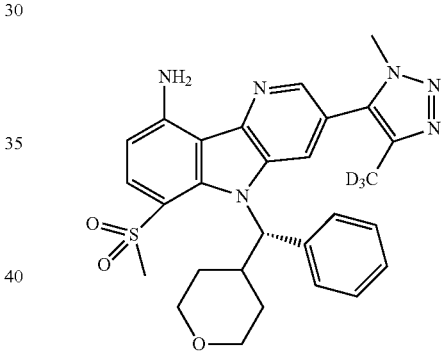

5-{9-Fluoro-6-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole (8.00 mg, 0.0200 mmol) was mixed with 0.5 M NH$_3$ in dioxane (0.200 mL, 0.100 mmol). This mixture was heated to 95° C. for 7 h and cooled to room temperature. To this mixture was then added 0.5 M NH$_3$ in dioxane (0.500 mL, 0.250 mmol) and heated at 125° C. for 14 h in a pressurized, sealed vial. The mixture was cooled to room temperature and diluted with MeOH. It was purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 6-methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-amine (4.60 mg, 57%). $^1$H NMR (500 MHz, DMSO-$d_6$) δ 8.52 (s, 1H), 8.01 (d, J=8.8 Hz, 1H), 7.74 (s, 1H), 7.57 (br d, J=7.7 Hz, 2H), 7.50 (s, 2H), 7.35-7.28 (m, 2H), 7.27-7.21 (m, 1H), 6.73 (br d, J=10.1 Hz, 1H), 6.64 (s, 1H), 3.87 (br d, J=9.1 Hz, 1H), 3.75 (s, 3H), 3.68 (br d, J=8.4 Hz, 1H), 3.55-3.47 (m, 1H), 3.46-3.41 (m, 1H), 3.21 (br t, J=11.6 Hz, 1H), 2.54 (s, 3H), 1.94 (br d, J=13.5 Hz, 1H), 1.73-1.56 (m, 2H), 0.55 (br d, J=12.5 Hz, 1H). LCMS: RT=1.586 min; (ES): m/z (M+H)$^+$=534.10, LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 99%.

Example 228

2,2,2-Trifluoro-N-{6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}ethane-1-sulfonamide

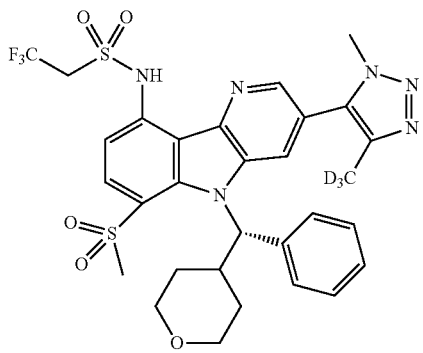 [SMILES: [2H]C([2H])([2H])c1nnn(C)c1-c1cnc2c3c(NS(=O)(=O)CC(F)(F)F)ccc(S(C)(=O)=O)c3n([C@H](c3ccccc3)C3CCOCC3)c2c1]

To a stirred solution of 6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-amine (41.2 mg, 0.0800 mmol) in DCE (1.00 mL) was added DIEA (0.200 mL, 1.15 mmol) and 2,2,2-trifluoroethanesulfonyl chloride (0.0500 mL, 0.450 mmol). The mixture was stirred at room temperature for 45 min and diluted with EtOAc. The resulting mixture was washed with saturated aq. NaHCO$_3$ solution and brine. The EtOAc layer was dried (MgSO$_4$), filtered, and concentrated. The crude product was purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 2,2,2-trifluoro-N-{6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}ethane-1-sulfonamide (2.19 mg, 3%). $^1$H NMR (500 MHz, DMSO-d$_6$) δ 8.72 (s, 1H), 8.35 (br d, J=8.8 Hz, 1H), 7.98 (s, 1H), 7.63 (br d, J=7.7 Hz, 2H), 7.53 (br d, J=8.7 Hz, 1H), 7.34 (br t, J=7.4 Hz, 2H), 7.29-7.22 (m, 1H), 6.77 (br d, J=10.4 Hz, 1H), 5.14 (br d, J=9.5 Hz, 2H), 3.87 (br d, J=6.6 Hz, 1H), 3.79 (s, 3H), 3.75 (br s, 1H), 3.66-3.61 (m, 1H), 3.50 (br t, J=10.6 Hz, 1H), 3.40 (br d, J=18.8 Hz, 1H), 3.21 (br t, J=11.6 Hz, 1H), 2.54 (s, 3H), 1.94 (br d, J=11.9 Hz, 1H), 1.70-1.58 (m, 2H), 0.50 (br d, J=12.1 Hz, 1H). LCMS: RT=1.791 min; (ES): m/z (M+H)$^+$=680.10. LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 99%.

Example 229

5-[9-(2,2-Difluoroethoxy)-6-methanesulfonyl-5-[(S)-oxan-4-yl(phenyl)methyl]-5H-pyrido[3,2-b]indol-3-yl]-4-($^2$H$_3$)methyl-1-methyl-1H-1,2,3-triazole

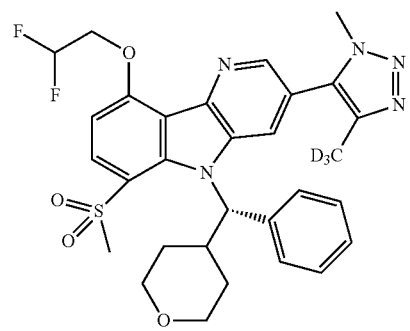 [SMILES: [2H]C([2H])([2H])c1nnn(C)c1-c1cnc2c3c(OCC(F)F)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (28.0 mg, 0.0500 mmol) and 2,2-difluoroethanol (37.0 mg, 0.450 mmol) in NMP (0.30 mL) was added t-BuOK (112 mg, 0.210 mmol). This mixture was heated at 65° C. for 5 h and cooled to room temperature. The mixture was diluted with MeOH and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 5-[9-(2,2-difluoroethoxy)-6-methanesulfonyl-5-[(S)-oxan-4-yl(phenyl)methyl]-5H-pyrido[3,2-b]indol-3-yl]-4-($^2$H$_3$)methyl-1-methyl-1H-1,2,3-triazole (6.50 mg. 20%). $^1$H NMR (500 MHz, DMSO-d$_6$) δ 8.61 (s, 1H), 8.29 (d, J=9.1 Hz, 1H), 7.76 (s, 1H), 7.56 (br d, J=7.7 Hz, 2H), 7.38-7.29 (m, 2H), 7.28-7.22 (m, 1H), 7.20 (d, J=9.1 Hz, 1H), 6.75 (br d, J=10.1 Hz, 1H), 6.69-6.39 (m, 1H), 4.78-4.67 (m, 2H), 3.85 (br d, J=9.1 Hz, 1H), 3.74 (s, 3H), 3.62 (br s, 1H), 3.49 (br t, J=11.4 Hz, 1H), 3.34 (br d, J=10.8 Hz, 1H), 3.18 (br t, J=11.8 Hz, 1H), 2.54 (s, 3H), 1.96 (br d, J=12.5 Hz, 1H), 1.77-1.66 (m, 1H), 1.63-1.51 (m, 1H), 0.42 (br d, J=12.1 Hz, 1H) LCMS: RT=1.594 min; (ES): m/z (M+H)$^+$=599.05, LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 95%.

Example 230

5-[9-(2,2-Difluoropropoxy)-6-methanesulfonyl-5-[(S)-oxan-4-yl(phenyl)methyl]-5H-pyrido[3,2-b]indol-3-yl]-4-($^2$H$_3$)methyl-1-methyl-1H-1,2,3-triazole

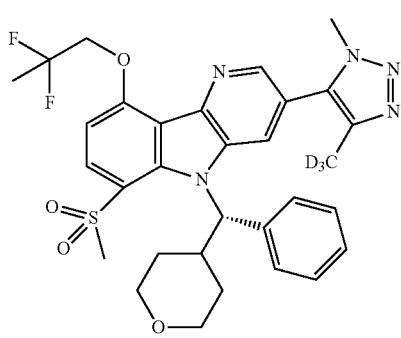 [SMILES: [2H]C([2H])([2H])c1nnn(C)c1-c1cnc2c3c(OCC(C)(F)F)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (31.0 mg, 0.0600 mmol) and 2,2-difluoropropan-2-ol (27.8 mg, 0.290 mmol) in NMP (0.30 mL) was added t-BuOK (25.9 mg, 0.230 mmol). This mixture was heated at 65° C. for 1 h and cooled to room temperature. The mixture was diluted with MeOH and purified via preparative LC/MS with the following conditions: Column: Waters XBridge Phenyl, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 5-[9-(2,2-difluoropropoxy)-6-methanesulfonyl-5-[(S)-oxan-4-yl(phenyl)methyl]-5H-pyrido[3,2-b]indol-3-yl]-4-($^2$H$_3$)methyl-1-methyl-1H-1,2,3-triazole (13.8 mg, 37%). $^1$H NMR (500 MHz, DMSO-d$_6$) δ 8.60 (s, 1H), 8.29 (d, J=8.8 Hz, 1H), 7.74 (s, 1H), 7.56 (br d, J=7.7 Hz, 2H), 7.36-7.29 (m, 2H), 7.28-7.22 (m, 1H), 7.18 (d, J=8.9 Hz, 1H), 6.74 (s, 1H), 4.67 (br t, J=12.0 Hz, 2H), 3.86 (br d, J=15.1 Hz, 1H), 3.73 (s, 3H), 3.60-3.55 (m, 1H), 3.49 (br t, J=11.5 Hz, 1H), 3.33 (br d, J=11.8 Hz, 1H), 3.23-3.16 (m, 1H), 2.54 (s, 3H), 1.95 (br t, J=19.4 Hz, 3H), 1.69 (br d, J=10.8 Hz, 1H), 1.62-1.50 (m, 1H), 1.22 (br d, J=8.8 Hz, 1H), 0.43 (br d, J=12.0 Hz, 1H). LCMS: RT=1.731 min; (ES): m/z (M+H)$^+$=613.15, LCMS: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 95%.

Example 231

5-{9-Fluoro-5-[(S)-(2-fluorophenyl)(oxan-4-yl)methyl]-6-methanesulfonyl-5H-pyrido[3,2-b]indol-3-yl}-4-($^2$H$_3$)methyl-1-methyl-1H-1,2,3-triazole

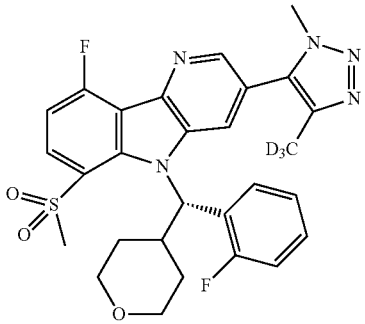 [SMILES: [2H]C([2H])([2H])c1nnn(C)c1-c1cnc2c3c(F)ccc(S(C)(=O)=O)c3n([C@H](c3ccccc3F)C3CCOCC3)c2c1]

Step 1: (S)-3-Bromo-9-fluoro-5-((2-fluorophenyl)(tetrahydro-2H-pyran-4-yl)methyl)-6-(methylsulfonyl)-5H-pyrido[3,2-b]indole To a stirred solution of 3-bromo-9-fluoro-6-(methylsulfonyl)-5H-pyrido[3,2-b]indole (100 mg, 0.290 mmol) and (R)-(2-fluorophenyl)(tetrahydro-2H-pyran-4-yl)methanol (123 mg, 0.580 mmol) in toluene (2.0 mL) was added triphenylphosphine (153 mg, 0.580 mmol) and DIAD (0.110 mL, 0.580 mmol). The mixture was stirred at room temperature for 2 h and was then directly purified by silica gel column chromatography (Teledyne ISCO CombiFlash 0% to 100% solvent A/B=hexane/EtOAc, RediSep SiO$_2$ 24 g, detecting at 254 nM, and monitoring at 220 nM). Concentration of appropriate fractions provided (S)-3-bromo-9-fluoro-5-[(S)-2-fluorophenyl)(oxan-4-yl)methyl]-6-methanesulfonyl-5H-pyrido[3,2-b]indole (156 mg) in a quantitative yield. $^1$H NMR (400 MHz, DMSO-d$_6$) δ 8.86 (s, 1H), 8.64 (d, J=1.8 Hz, 1H), 8.42 (dd, J=8.9, 5.4 Hz, 1H), 8.17-8.12 (m, 1H), 8.11 (d, J=1.8 Hz, 1H), 7.40 (t, J=8.9 Hz, 1H), 7.37-7.31 (m, 1H), 7.07-6.99 (m, 1H), 6.96 (d, J=10.4 Hz, 1H), 4.77 (dt, J=12.3, 6.2 Hz, 1H), 3.89 (br d, J=10.5 Hz, 1H), 3.73 (br dd, J=11.0, 2.9 Hz, 1H), 3.64-3.58 (m, 1H), 3.56 (s, 3H), 3.40-3.33 (m, 1H), 1.93-1.66 (m, 3H), 0.70 (br d, J=11.9 Hz, 1H). HPLC: RT=2.771 min (Chromolith ODS 4.6×50 mm (4 min grad) eluting with 10-90% aqueous MeOH over 4 min containing 0.1% TFA, 4 mL/min, monitoring at 220 nm); MS (ES): m/z=535, 537 (Br pattern) [M+H]$^+$.

Step 2: 5-{9-Fluoro-5-[(S)-(2-fluorophenyl)(oxan-4-yl)methyl]-6-methanesulfonyl-5H-pyrido[3,2-b]indol-3-yl}-4-($^2$H$_3$)methyl-1-methyl-1H-1,2,3-triazole To a stirred solution of (S)-3-bromo-9-fluoro-5-((2-fluorophenyl)(tetrahydro-2H-pyran-4-yl)methyl)-6-(methylsulfonyl)-5H-pyrido[3,2-b]indole (216 mg, 0.400 mmol) and 4-($^2$H$_3$)methyl-1-methyl-5-(tributylstannyl)-1-H-1,2,3-triazole (283 mg, 0.730 mmol) in DMF (4.0 mL) was added Et$_3$N (0.120 mL, 0.880 mmol), and the mixture was purged with nitrogen. While purging, copper (I) iodide (11.5 mg, 0.0600 mmol) and tetrakis(triphenylphosphine) palladium (0) (55.9 mg, 0.0500 mmol) were added. The reaction mixture was purged with nitrogen for another 5 min and then heated at 95° C. for 40 min. The mixture was cooled to room temperature, diluted with MeOH, and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 5-{9-fluoro-5-[(S)-(2-fluorophenyl) (oxan-4-yl)methyl]-6-methanesulfonyl-5H-pyrido[3,2-b]indol-3-yl}-4-($^2H_3$)methyl-1-methyl-1H-1,2,3-triazole (9.50 mg, 4%). $^1$H NMR (500 MHz, DMSO-$d_6$) δ 8.63 (s, 1H), 8.42 (dd, J=8.8, 5.3 Hz, 1H), 8.14-8.07 (m, 1H), 7.98 (s, 1H), 7.41 (t, J=8.8 Hz, 1H), 7.36-7.29 (m, 2H), 7.05-6.99 (m, 1H), 6.96 (br d, J=10.4 Hz, 1H), 3.88 (br d, J=9.8 Hz, 1H), 3.75 (s, 3H), 3.71 (br s, 1H), 3.57 (br s, 2H), 3.27 (br t, J=11.3 Hz, 1H), 2.54 (s, 3H), 1.95-1.84 (m, 1H), 1.83-1.69 (m, 2H), 0.74 (br d, J=12.3 Hz, 1H). LCMS: RT=1.577 min; (ES): m/z (M+H)+=555.15. LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 97%. LCMS: RT=1.577 min; (ES): m/z (M+H)+=555.15.

Example 233

5-{9-Fluoro-5-[(S)-(4-fluorophenyl)(oxan-4-yl) methyl]-6-methanesulfonyl-5H-pyrido[3,2-b]indol-3-yl}-4-($^2H_3$)methyl-1-methyl-1H-1,2,3-triazole

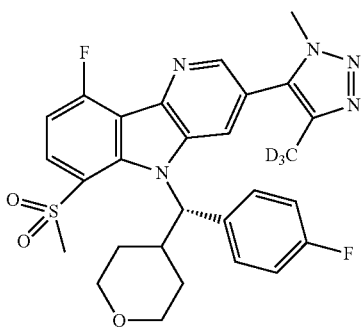 [SMILES: [2H]C([2H])([2H])c1nnn(C)c1-c1cnc2c3c(F)ccc(S(C)(=O)=O)c3n([C@H](c3ccc(F)cc3)C3CCOCC3)c2c1]

Step 1: 3-Bromo-9-fluoro-5-[(S)-(4-fluorophenyl) (oxan-4-yl)methyl]-6-methanesulfonyl-5H-pyrido[3, 2-b]indole To a stirred solution of 3-bromo-9-fluoro-6-methanesulfonyl-5H-pyrido[3,2-b]indole (100 mg, 0.290 mmol) and (R)-(4-fluorophenyl)(tetrahydor-2H-pyran-4-yl)methanol (123 mg, 0.580 mmol) in toluene (2.0 mL) was added triphenylphosphine (153 mg, 0.580 mmol) and DIAD (0.110 mL, 0.580 mmol). The mixture was stirred at room temperature for 3 h and was then directly purified by silica gel column chromatography (Teledyne ISCO CombiFlash 0% to 100% solvent A/B=hexane/EtOAc, RediSep SiO₂ 24 g, detecting at 254 nM, and monitoring at 220 nM). Concentration of appropriate fractions provided 3-bromo-9-fluoro-5-[(S)-(4-fluorophenyl)(oxan-4-yl)methyl]-6-methanesulfonyl-5H-pyrido[3,2-b]indole (156 mg) in a quantitative yield. $^1$H NMR (400 MHz, DMSO-$d_6$) δ 8.86 (s, 1H), 8.66 (d, J=1.8 Hz, 1H), 8.36 (dd, J=8.9, 5.3 Hz, 1H), 7.97 (d, J=1.8 Hz, 1H), 7.71 (dd, J=8.6, 5.4 Hz, 1H), 7.39 (t, J=8.9 Hz, 1H), 7.19 (t, J=8.9 Hz, 1H), 6.71 (d, J=10.4 Hz, 1H), 4.77 (dt, J=12.4, 6.2 Hz, 1H), 3.86 (br dd, J=11.0, 2.7 Hz, 1H), 3.71 (s, 3H), 3.63 (br dd, J=11.1, 3.2 Hz, 1H), 3.55 (br t, J=11.0 Hz, 1H), 3.35 (br s, 1H), 3.26-3.15 (m, 1H), 1.91 (br d, J=13.4 Hz, 1H), 1.71-1.47 (m, 1H), 1.23 (br d, J=3.4 Hz, 1H), 0.36 (br d, J=11.9 Hz, 1H). HPLC: RT=2.935 min (Chromolith ODS 4.6×50 mm (4 min grad) eluting with 10-90% aqueous MeOH over 4 min containing 0.1% TFA, 4 mL/min, monitoring at 220 nm); MS (ES): m/z=535, 537 (Br pattern) [M+H]+.

Step 2: 5-{9-Fluoro-5-[(S)-(4-fluorophenyl)(oxan-4-yl)methyl]-6-methanesulfonyl-5H-pyrido[3,2-b]indol-3-yl}-4-($^2H_3$)methyl-1-methyl-1H-1,2,3-triazole To a stirred solution of 3-bromo-9-fluoro-5-[(S)-(4-fluorophenyl)(oxan-4-yl)methyl]-6-methanesulfonyl-5H-pyrido[3,2-b]indole (233 mg, 0.430 mmol) in DMF (4.0 mL) was added Et₃N (0.140 mL, 0.960 mmol), and the mixture was purged with nitrogen. While purging, copper (I) iodide (12.4 mg, 0.0700 mmol) and tetrakis(triphenylphosphine) palladium (0) (60.3 mg, 0.0500 mmol) were added. The reaction mixture was purged with nitrogen for another 5 min and then heated at 95° C. for 15 h. The mixture was cooled to room temperature, diluted with MeOH, and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 5-{9-fluoro-5-[(S)-(4-fluorophenyl) (oxan-4-yl)methyl]-6-methanesulfonyl-5H-pyrido[3,2-b]indol-3-yl}-4-($^2H_3$)methyl-1-methyl-1H-1,2,3-triazole (50.3 mg, 21%). $^1$H NMR (500 MHz, DMSO-$d_6$) δ 8.68 (s, 1H), 8.37 (br dd, J=8.6, 5.0 Hz, 1H), 7.89 (s, 1H), 7.70-7.64 (m, 2H), 7.40 (br t, J=8.7 Hz, 1H), 7.17 (br t, J=8.6 Hz, 2H), 6.75 (br d, J=10.2 Hz, 1H), 3.86 (br d, J=9.5 Hz, 1H), 3.82 (s, 3H), 3.64 (br d, J=8.8 Hz, 1H), 3.53-3.51 (m, 1H), 3.37 (br s, 1H), 3.18 (br t, J=11.4 Hz, 1H), 2.54 (s, 3H), 1.90 (br s, 1H), 1.69-1.54 (m, 2H), 0.46 (br d, J=12.0 Hz, 1H). LCMS: RT=1.604 min; (ES): m/z (M+H)+=555.15, LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 min, then a 0.75-min hold at 100% B; Flow: 1.11 mL/min. HPLC Purity at 220 nm: 99%.

Examples 235 & 236

3-Fluoro-2-({9-fluoro-6-methanesulfonyl-3-[4-($^2$H$_3$)methyl-1-methyl-1H-1,2,3-triazol-5-yl]-5H-pyrido[3,2-b]indol-5-yl}(oxan-4-yl)methyl)pyridine Enantiomer A, Example 235

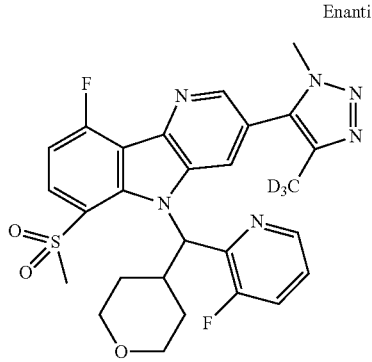

Enantiomer B, Example 236

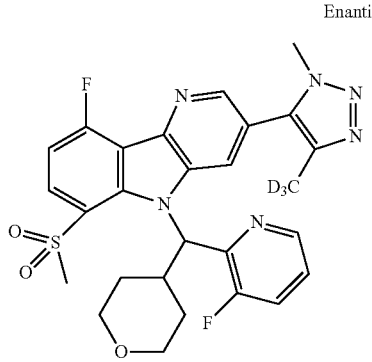

Step 1: 5-(9-Fluoro-6-methanesulfonyl-5H-pyrido[3,2-b]indol-3-yl)-4-($^2$H$_3$)methyl-1-methyl-1H-1,2,3-trizole To a stirred solution of 3-bromo-9-fluoro-6-methanesulfonyl-5H-pyrido[3,2-b]indole (50.0 mg, 0.150 mmol) and 4-($^2$H$_3$)methyl-1-methyl-5-(tributylstannyl)-1-H-1,2,3-triazole (102 mg, 0.260 mmol) in DMF (1.00 mL) was added Et$_3$N (0.0500 mL, 0.320 mmol). While purging with nitrogen, the mixture was combined with copper (I) iodide (4.16 mg, 0.0200 mmol) and tetrakis(triphenylphosphine) palladium (0) (20.2 mg, 0.0200 mmol). The mixture was heated at 95° C. for 7 h. The reaction mixture was cooled to room temperature. To this cooled mixture was added 4-($^2$H$_3$)methyl-1-methyl-5-(tributylstannyl)-1-H-1,2,3-triazole (102 mg, 0.260 mmol), Et$_3$N (0.0500 mL, 0.320 mmol), copper (I) iodide (4.16 mg, 0.0200 mmol) and tetrakis(triphenylphosphine) palladium (0) (20.2 mg, 0.0200 mmol) under nitrogen. The mixture was then heated at 95° C. for 14 h and cooled to room temperature. The mixture was diluted with 10% aq. LiCl solution and extracted with EtOAc. Combined EtOAc extracts were washed with brine, dried (MgSO$_4$), filtered, and concentrated to give the crude mixture. The crude product was purified by silica gel column chromatography (Teledyne ISCO CombiFlash 0% to 100% solvent A/B=DCM/10% MeOH in DCM, RediSep SiO$_2$ 24 g, detecting at 254 nM, and monitoring at 220 nM). Concentration of appropriate fractions provided 5-(9-fluoro-6-methanesulfonyl-5H-pyrido[3,2-b]indol-3-yl)-4-($^2$H$_3$)methyl-1-methyl-1H-1,2,3-trizole (25.0 mg, 47%). $^1$H NMR (400 MHz, CDCl$_3$) δ 10.99 (br s, 1H), 8.64 (s, 1H), 8.08 (dd, J=8.6, 4.6 Hz, 1H), 7.98 (d, J=1.6 Hz, 1H), 7.20 (t, J=8.9 Hz, 1H), 4.05 (s, 3H), 3.25 (s, 3H), HPLC: RT=0.65 min (Chromolith ODS 4.6×50 mm (4 min grad) eluting with 10-90% aqueous MeOH over 4 min containing 0.1% TFA, 4 mL/min, monitoring at 220 nm); MS (ES): m/z=363.1 [M+H]$^+$.

Step 2: 3-Fluoro-2-({9-fluoro-6-methanesulfonyl-3-[4-($^2$H$_3$)methyl-1-methyl-1H-1,2,3-triazol-5-yl]-5H-pyrido[3,2-b]indol-5-yl}(oxan-4-yl)methyl)pyridine To a stirred solution of 5-(9-fluoro-6-methanesulfonyl-5H-pyrido[3,2-b]indol-3-yl)-4-($^2$H$_3$)methyl-1-methyl-1H-1,2,3-trizole 1 (25.0 mg, 0.0700 mmol) and (3-fluoropyridin-2-yl)(tetrahydro-2H-pyran-4-yl)methanol (29.1 mg, 0.140 mmol) in toluene (0.5 mL) was added triphenylphosphine (36.2 mg, 0.140 mmol) and DIAD (0.0270 mL, 0.140 mmol). The mixture was stirred at room temperature was monitored by LCMS until the reaction was complete. The reaction mixture was then directly purified by silica gel column chromatography (Teledyne ISCO CombiFlash 0% to 100% solvent A/B=DCM/EtOAc, RediSep SiO$_2$ 12 g, detecting at 254 nM, and monitoring at 220 nM). Concentration of appropriate fractions provided racemic 3-fluoro-2-({9-fluoro-6-methanesulfonyl-3-[4-($^2$H3)methyl-1-methyl-1H-1,2,3-triazol-5-yl]-5H-pyrido[3,2-b]indol-5-yl}(oxan-4-yl)methyl)pyridine (14.0 mg). This racemic mixture was separated by chiral prep SFC (Berger SFC MGII, Column: Chiral OD-H 25×3 cm ID, 5 μm Flow rate:85.0 mL/min. Mobile Phase:70/30 CO$_2$/MeOH Detector Wavelength: 220 nm) to give Enantiomer A (5.20 mg, 14%) and Enantiomer B (4.00 mg, 10%). Enantiomer A: $^1$H NMR (400 MHz, CDCl$_3$) δ 8.64 (d, J=1.8 Hz, 1H), 8.49 (dt, J=4.2, 1.6 Hz, 1H), 8.45 (dd, J=8.9, 5.4 Hz, 1H), 8.12 (d, J=1.8 Hz, 1H), 7.42-7.33 (m, 2H), 7.30-7.29 (m, 1H), 7.25-7.18 (m, 1H), 4.06-3.98 (m, 1H), 3.96 (s, 3H), 3.83 (br dd, J=11.6, 3.4 Hz, 1H), 3.48 (td, J=11.4, 3.1 Hz, 1H), 3.42 (s, 3H), 3.23-3.22 (m, 1H), 3.22 (td, J=11.9, 2.0 Hz, 1H), 1.96-1.88 (m, 1H), 1.84-1.74 (m, 2H), 0.56 (br d, J=11.4 Hz, 1H). LCMS (M+H)=556.2; SFC RT=6.457 min (Column: Chiralcel OD-H 250×4.6 mm, 5 μm; Mobile Phase: 70/30 CO$_2$/MeOH; Flow: 2 mL/min); Enantiomer B: $^1$H NMR (400 MHz, CDCl$_3$) δ 8.64 (d, J=1.8 Hz, 1H), 8.49 (dt, J=4.2, 1.6 Hz, 1H), 8.45 (dd, J=8.9, 5.4 Hz, 1H), 8.12 (d, J=1.8 Hz, 1H), 7.42-7.33 (m, 2H), 7.30-7.29 (m, 1H), 7.25-7.18 (m, 1H), 4.06-3.98 (m, 1H), 3.96 (s, 3H), 3.83 (br dd, J=11.6, 3.4 Hz, 1H), 3.48 (td, J=11.4, 3.1 Hz, 1H), 3.42 (s, 3H), 3.23-3.22 (m, 1H), 3.22 (td, J=11.9, 2.0 Hz, 1H), 1.96-1.88 (m, 1H), 1.84-1.74 (m, 2H), 0.56 (br d, J=11.4 Hz, 1H) LCMS (M+H)=556.2; SFC RT=8.286 min (Column: Chiralcel OD-H 250×4.6 mm, 5 μm; Mobile Phase: 70/30 CO$_2$/MeOH; Flow: 2 mL/min).

Examples 239 & 240

2-[(4,4-Difluorocyclohexyl)({7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine Enantiomer A, Example 239

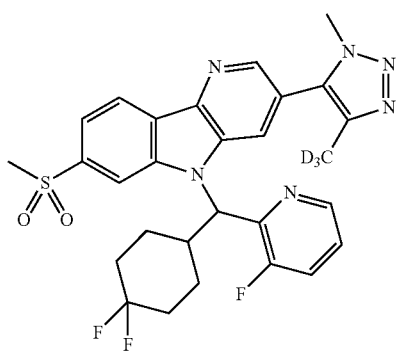

Enantiomer B, Example 240

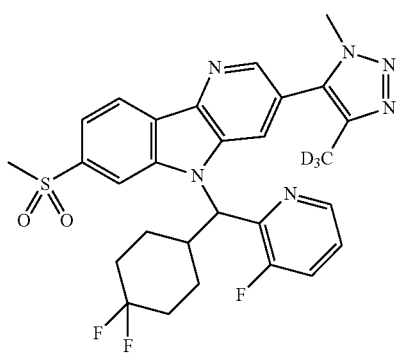

Step 1: 4,4-Difluorocyclohexyl)(3-fluoropyridin-2-yl)methanone

To a stirred solution of 2-bromo-3-fluoropyridine (2.00 g, 11.4 mmol) in THF (20 mL) under nitrogen in an acetone-dry ice bath was added nBuLi (2.5M in hexane, 5.00 mL, 12.5 mmol) slowly over 15 min through the side of the reaction flask. The mixture was stirred at −78° C. under nitrogen for 95 min. At that time, a solution of 4,4-difluoro-N-methoxy-N-methylcyclohexanecarboxamide (2.35 g, 11.4 mmol) in THF (4 mL) was added over 5 min. The mixture was stirred at −78° C. for 10 min and at room temperature for 15 min. The mixture was quenched with saturated aq. NH$_4$Cl solution and extracted with EtOAc. The EtOAc extract was washed with brine, dried (MgSO$_4$), filtered, and concentrated. The crude mixture was purified by silica gel column chromatography (Teledyne ISCO CombiFlash 0% to 30% solvent A/B=DCM/EtOAc, RediSep SiO$_2$ 40 g, detecting at 254 nM, and monitoring at 220 nM). Concentration of appropriate fractions provided 4,4-difluorocyclohexyl)(3-fluoropyridin-2-yl)methanone (722 mg, 2.97 mmol, 26%). $^1$H NMR (400 MHz, CDCl$_3$) δ 8.48 (dt, J=4.1, 1.5 Hz, 1H), 7.59-7.42 (m, 2H), 3.83-3.72 (m, 1H), 2.27-2.10 (m, 2H), 2.00 (br dd, J=7.2, 3.1 Hz, 2H), 1.92-1.78 (m, 4H). HPLC: RT=1.937 min (Chromolith ODS 4.6×50 mm (4 min grad) eluting with 10-90% aqueous MeOH over 4 min containing 0.1% TFA, 4 mL/min, monitoring at 220 nm); MS (ES): m/z=244.1 [M+H]$^+$.

Step 2: (4,4-Difluorocyclohexyl)(phenyl)methanol

To a stirred solution of (4,4-difluorocyclohexyl)(3-fluoropyridin-2-yl)methanone (0.920 g, 3.78 mmol) in MeOH (10.0 mL) at 0° C. was added NaBH$_4$ (0.215 g, 5.67 mmol) portionwise over 5 min. The mixture was stirred in the ice water bath for 20 min and quenched with water. The resulting mixture was extracted with EtOAc. Combined EtOAc extracts were washed with saturated aq. NaHCO$_3$ solution and brine. The organic layer was dried (MgSO$_4$), filtered, and concentrated to give (4,4-difluorocyclohexyl)(phenyl)methanol (0.860 g, 93%), $^1$H NMR (400 MHz, DMSO-d$_6$) δ 8.42 (dt, J=4.6, 1.5 Hz, 1H), 7.68 (ddd, J=10.4, 8.4, 1.3 Hz, 1H), 7.40 (dt, J=8.4, 4.3 Hz, 1H), 5.30 (d, J=6.4 Hz, 1H), 4.62-4.52 (m, 1H), 2.09-1.87 (m, 3H), 1.84-1.57 (m, 2H), 1.40-1.08 (m, 4H). HPLC: RT=0.72 min (Chromolith ODS 4.6×50 mm (4 min grad) eluting with 10-90% aqueous MeOH over 4 min containing 0.1% TFA, 4 mL/min, monitoring at 220 nm); MS (ES): m/z=246.1 [M+H]$^+$.

Step 3: 5-((4,4-Difluorocyclohexyl)(4-fluoropyridin-3-yl)methyl)-7-(methylsulfonyl)-5H-pyrido[3,2-b]indole To a stirred solution of 3-bromo-7-(methylsulfonyl)-5H-pyrido[3,2-b]indole (60.0 mg, 0.185 mmol) and (4,4-difluorocyclohexyl)(3-fluoropyridin-2-yl)methanol (91.0 mg, 0.369 mmol) in toluene (2.0 mL) was added triphenylphosphine (97.0 mg, 0.369 mmol) and DIAD (0.0720 mL, 0.369 mmol). The mixture was stirred at room temperature for 1.5 h and was then directly purified by silica gel column chromatography (Teledyne ISCO CombiFlash 0% to 100% solvent A/B=DCM/EtOAc, RediSep SiO$_2$ 24 g, detecting at 254 nM, and monitoring at 220 nM). Concentration of appropriate fractions provided 5-((4,4-difluorocyclohexyl)(4-fluoropyridin-3-yl)methyl)-7-(methylsulfonyl)-5H-pyrido[3,2-b]indole (102 mg) in quantitative yield. $^1$H NMR (400 MHz, DMSO-d$_6$) δ 8.86 (d, J=1.8 Hz, 1H), 8.67 (s, 1H), 8.62 (br d, J=4.6 Hz, 1H), 8.41 (d, J=8.2 Hz, 1H), 7.82 (br d, J=8.2 Hz, 1H), 7.74-7.64 (m, 1H), 7.51 (dt, J=8.6, 4.4 Hz, 1H), 7.46-7.30 (m, 1H), 6.32 (br d, J=11.1 Hz, 1H), 5.48-5.23 (m, 1H), 4.87 (dd, J=12.6, 6.4 Hz, 1H), 4.78 (ddd, J=18.6, 12.4, 6.3 Hz, 1H), 4.45-4.20 (m, 1H), 3.29 (br s, 3H), 1.45-1.34 (m, 1H), 1.23 (br d, J=3.5 Hz, 2H), 1.21-1.12 (m, 2H). HPLC: RT=3.036 min (Chromolith ODS 4.6×50 mm (4 min gradiant) eluting with 10-90% aqueous MeOH over 4 min containing 0.1% TFA, 4 mL/min, monitoring at 220 nm); MS (ES): m/z=552.0 [M+H]$^+$.

Step 4: 2-[(4,4-Difluorocyclohexyl)({7-methanesulfonyl-3-[4-($^2$H$_3$)methyl-1-methyl-1H-1,2,3-triazol-5-yl]-5H-pyrido[3,2-b]indol-5-yl})methyl]-3-fluoropyridine To a stirred solution of 3-bromo-5-((4,4-difluorocyclohexyl)(4-fluoropyridin-3-yl)methyl)-7-(methylsulfonyl)-5H-pyrido[3,2-b]indole (77.4 mg, 0.140 mmol) and 4-($^2$H$_3$)methyl-1-methyl-5-(tributylstannyl)-1-H-1,2,3-triazole (98.0 mg, 0.252 mmol) in DMF (1.0 mL) was added Et$_3$N (0.0430 mL, 0.308 mmol), and the mixture was purged with nitrogen. While purging, copper (I) iodide (4.00 mg, 0.0210 mmol) and tetrakis(triphenylphosphine) palladium (0) (19.4 mg, 0.0170 mmol) were added. The reaction mixture was purged with nitrogen for another 5 min and then heated at 95° C. for 2 h. The mixture was cooled to room temperature and diluted with 10% aq. LiCl solution. The mixture was extracted with EtOAc. Combined EtOAc extracts were washed with brine, dried (MgSO₄), filtered, and concentrated to give the crude mixture. The crude product was then purified by silica gel column chromatography (Teledyne ISCO CombiFlash 0% to 100% solvent A/B=DCM/10% MeOH in DCM, RediSep SiO₂ 24 g, detecting at 254 nM, and monitoring at 220 nM). Concentration of appropriate fractions provided racemic 2-[(4,4-difluorocyclohexyl)({7-methanesulfonyl-3-[4-($^2$H₃)methyl-1-methyl-1H-1,2,3-triazol-5-yl]-5H-pyrido[3,2-b]indol-5-yl})methyl]-3-fluoropyridine (125 mg). This racemic mixture was separated by chiral prep SFC (Berger SFC MGII, Column: Chiral AD-H 25×3 cm ID, 5 μm Flow rate: 85.0 mL/min, Mobile Phase: 85/15 CO₂/MeOH Detector Wavelength: 220 nm) to give Enantiomers A (11.8 mg, 14%) and B (12.6 mg, 15%). Enantiomer A: $^1$H NMR (400 MHz, CDCl₃) δ 8.59 (d, J=1.7 Hz, 2H), 8.56 (s, 1H), 8.53 (br d, J=3.9 Hz, 1H), 7.93 (dd, J=8.3, 1.3 Hz, 1H), 7.46-7.39 (m, 1H), 7.37-7.31 (m, 2H), 5.89 (br d, J=10.6 Hz, 1H), 4.07 (s, 3H), 3.20 (s, 3H), 2.15 (br s, 1H), 1.99-1.91 (m, 1H), 1.86 (br s, 1H), 1.55-1.44 (m, 1H), 1.39-1.24 (m, 2H), 1.12 (br d, J=12.6 Hz, 1H), 1.03-0.94 (m, 2H); LCMS (M+H)=572.3, SFC RT=7.453 min (Column: Chiralcel AD 250×4.6 mm, 5 μm; Mobile Phase: 85/15 CO₂/MeOH; Flow: 2 mL/min); Enantiomer B: $^1$H NMR (400 MHz, CDCl₃) δ 8.59 (d, J=1.7 Hz, 2H), 8.57 (d, J=8.2 Hz, 1H), 8.53 (br d, J=3.9 Hz, 1H), 7.93 (dd, J=8.2, 1.2 Hz, 1H), 7.46-7.39 (m, 1H), 7.37-7.31 (m, 2H), 5.89 (br d, J=10.8 Hz, 1H), 4.07 (s, 3H), 3.20 (s, 3H), 2.15 (br s, 1H), 1.95 (br d, J=13.3 Hz, 1H), 1.88 (br d, J=14.8 Hz, 1H), 1.55-1.44 (m, 1H), 1.42-1.22 (m, 2H), 1.12 (br d, J=12.1 Hz, 1H). LCMS (M+H)=572.3; SFC RT=8.218 min (Column: Chiralcel AD 250×4.6 mm, 5 μm; Mobile Phase: 85/15 CO₂/MeOH; Flow: 2 mL/min).

Example 243

3-[3-(Dimethyl-1H-1,2,3-triazol-5-yl)-5-[(S)-(4-fluorophenyl)(oxan-4-yl)methyl]-5H-pyrido[3,2-b]indol-7-yl]oxetan-3-ol

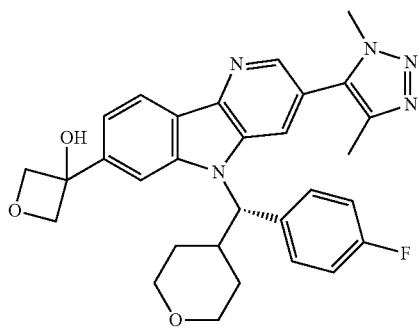 [SMILES: Cc1nnn(C)c1-c1cnc2c3ccc(C4(O)COC4)cc3n([C@H](c3ccc(F)cc3)C3CCOCC3)c2c1]

Step 1: ((3-(4-Bromophenyl)oxetan-3-yl)oxy)(tert-butyl)dimethylsilane

To a stirred reaction solution of 3-(4-bromophenyl)oxetan-3-ol (6.24 g, 27.2 mmol; WO2011/159760; (2011); (A1)), tert-butylchlorodimethylsilane (7.39 g, 49.0 mmol) and imidazole (3.71 g, 54.5 mmol) in DMF (50.0 mL) was added 4-dimethylaminopyridine (3.33 g, 27.2 mmol). The mixture was stirred at room temperature for 67 h and then diluted with ether. The resulting mixture was washed with 10% aq. LiCl solution and brine. The organic layer was dried (MgSO₄), filtered, and concentrated to give the crude mixture. The crude product was purified by silica gel column chromatography (Teledyne ISCO CombiFlash 0% to 100% solvent A/B=hexane/EtOAc, RediSep SiO₂ 120 g, detecting at 254 nM, and monitoring at 220 nM). Concentration of appropriate fractions provided ((3-(4-bromophenyl)oxetan-3-yl)oxy)(tert-butyl)dimethylsilane (7.11 g, 76%). $^1$H NMR (400 MHz, CDCl₃) δ 7.57-7.44 (m, 4H), 5.04-4.95 (m, 2H), 4.80-4.72 (m, 2H), 0.96 (s, 9H), 0.04 (s, 6H); HPLC: RT=1.27 min (Chromolith ODS 4.6×50 mm (4 min grad) eluting with 10-90% aqueous MeOH over 4 min containing 0.1% TFA, 4 mL/min, monitoring at 220 nm).

Step 2: tert-Butyldimethyl((3-(4-(4,4,5,5-tetramethyl-1,3,2-dioxaborolan-2-yl)phenyl)oxetan-3-yl)oxy)silane To a stirred solution of ((3-(4-bromophenyl)oxetan-3-yl)oxy)(tert-butyl)dimethylsilane (100 mg, 0.291 mmol) under nitrogen in THF (2.00 mL) at −78° C. was added slowly nBuLi (2.5 M in hexanes, 0.128 mL, 0.320 mmol). The mixture was stirred at −78° C. for 15 min, at which time 4,4,4',4',5,5,5',5'-octamethyl-2,2'-bi(1,3,2-dioxaborolane) (74.0 mg, 0.291 mmol) was added. The mixture was warmed to room temperature and stirred for 16 h. The mixture was then quenched with saturated aq. NH₄Cl solution and extracted with EtOAc. Combined EtOAc extracts were washed with brine, dried (MgSO₄), filtered, and concentrated to give tert-butyldimethyl((3-(4-(4,4,5,5-tetramethyl-1,3,2-dioxaborolan-2-yl)phenyl)oxetan-3-yl)oxy)silane (105 mg, 92%). $^1$H NMR (400 MHz, CDCl₃) δ 7.72 (d, J=8.3 Hz, 2H), 7.27-7.24 (m, 2H), 4.87-4.84 (m, 2H), 4.73-4.68 (m, 2H), 1.23 (s, 9H), 1.14 (s, 12H), 0.82 (s, 6H); HPLC: RT=3.875 min (Chromolith ODS 4.6×50 mm (4 min grad) eluting with 10-90% aqueous MeOH over 4 min containing 0.1% TFA, 4 mL/min, monitoring at 220 nm).

Step 3: 5-Bromo-2-(4-(3-((tert-butyldimethylsilyl)oxy)oxetan-3-yl)phenyl)-3-nitropyridine tert-Butyldimethyl((3-(4-(4,4,5,5-tetramethyl-1,3,2-dioxaborolan-2-yl)phenyl)oxetan-3-yl)oxy)silane (1.25 g, 3.20 mmol) and 2,5-dibromo-3-nitropyridine (0.990 g, 3.51 mmol) were combined in dioxane (15 mL) under nitrogen. To this mixture was added 2 M aq. tripotassium phosphate (4.80 mL, 9.61 mmol), and it was purged with nitrogen. While purging, PdCl₂(dppf)-CH₂Cl₂ adduct (0.392 g, 0.480 mmol) was added. The mixture was heated at 85° C. for 3 h. The mixture was concentrated, diluted with water, and extracted with EtOAc. Combined EtOAc extracts were washed with brine, dried (MgSO₄), filtered, and concentrated to give the crude product. The crude product was purified by silica gel column chromatography (Teledyne ISCO CombiFlash 0% to 100% solvent A/B=hexane/EtOAc, RediSep SiO₂ 80 g, detecting at 254 nM, and monitoring at 220 nM). Concentration of appropriate fractions provided 5-bromo-2-(4-(3-((tert-butyldimethylsilyl)oxy)oxetan-3-yl)phenyl)-3-nitropyridine (0.570 g, 38%). $^1$H NMR (400 MHz, CDCl₃) δ 8.93 (d, J=2.1 Hz, 1H), 8.30 (d, J=2.1 Hz, 1H), 7.77-7.69 (m, 2H), 7.60 (d, J=8.6 Hz, 2H), 5.03 (d, J=7.1 Hz, 2H), 4.84 (d, J=7.2 Hz, 2H), 0.98 (s, 9H), 0.08 (s, 6H); HPLC: RT=3.711 min (Chromolith ODS 4.6×50 mm (4 min grad) eluting with 10-90% aqueous MeOH over 4 min containing 0.1% TFA, 4 mL/min, monitoring at 220 nm); MS (ES): m/z=465; 467.1 (Br pattern) [M+H]⁺.

Step 4: 3-Bromo-7-(3-((tert-butyldimethylsilyl)oxy)oxetan-3-yl)-5H-pyrido[3,2-b]indole 5-Bromo-2-(4-(3-((tert-butyldimethylsilyl)oxy)oxetan-3-yl)phenyl)-3-nitropyridine (1.67 g, 3.59 mmol) and 1,2-bis(diphenylphosphino)ethane (1.79 g, 4.49 mmol) were combined in 1,2-dichlorobenzene (35.0 mL) under nitrogen. The mixture was heated at 160° C. for 2 h and cooled to room temperature. The mixture was directly purified by silica gel column chromatography (Teledyne ISCO CombiFlash 0% to 100% solvent A/B=DCM/EtOAc, RediSep SiO$_2$ 120 g, detecting at 254 nM, and monitoring at 220 nM). Concentration of appropriate fractions provided 3-bromo-7-(3-((tert-butyldimethylsilyl)oxy)oxetan-3-yl)-5H-pyrido[3,2-b]indole (1.03 g, 66%). $^1$H NMR (400 MHz, CDCl$_3$) δ 8.62 (d, J=2.0 Hz, 1H), 8.35 (d, J=8.3 Hz, 1H), 8.17 (br. s., 1H), 7.90 (d, J=2.0 Hz, 1H), 7.70 (d, J=0.9 Hz, 1H), 7.64 (dd, J=8.3, 1.5 Hz, 1H), 5.08 (d, J=7.1 Hz, 2H), 4.92 (d, J=7.1 Hz, 2H), 0.99 (s, 9H), 0.01 (s, 6H); HPLC: RT=3.416 min (Chromolith ODS 4.6×50 mm (4 min grad) eluting with 10-90% aqueous MeOH over 4 min containing 0.1% TFA, 4 mL/min, monitoring at 220 nm); MS (ES): m/z=433.1; 435.1 (Br pattern) [M+H]$^+$.

Step 5: 7-(3-((tert-Butyldimethylsilyl)oxy)oxetan-3-yl)-3-(1,4-dimethyl-1H-1,2,3-triazol-5-yl)-5H-pyrido[3,2-b]indole A stirred mixture of 3-bromo-7-(3-((tert-butyldimethylsilyl)oxy)oxetan-3-yl)-5H-pyrido[3,2-b]indole (503 mg, 1.16 mmol), 1,4-dimethyl-5-(tributylstannyl)-1H-1,2,3-triazole (896 mg, 2.32 mmol), and Et$_3$N (0.485 mL, 3.48 mmol) in DMF (8.00 mL) was purged with nitrogen. While purging, the mixture was treated with copper(I) iodide (33.2 mg, 0.174 mmol) and Pd(Ph$_3$P)$_4$ (134 mg, 0.116 mmol), and the reaction mixture was then heated at 95° C. overnight. The cooled mixture was diluted with EtOAc and washed with 10% aq. LiCl solution and brine. The organic layer was dried (MgSO$_4$), filtered, and concentrated. The crude product was purified by silica gel column chromatography (Teledyne ISCO CombiFlash 0% to 100%; followed by 100% flash, solvent A/B=hexane/EtOAc, RediSep SiO$_2$ 24 g, detecting at 254 nM, and monitoring at 220 nM). Concentration of appropriate fractions provided 7-(3-((tert-butyldimethylsilyl)oxy)oxetan-3-yl)-3-(1,4-dimethyl-1H-1,2,3-triazol-5-yl)-5H-pyrido[3,2-b]indole (450 mg, 86%). $^1$H NMR (400 MHz, DMSO-d$_6$) δ 11.72 (s, 1H), 8.53 (d, J=2.0 Hz, 1H), 8.28 (d, J=8.2 Hz, 1H), 8.04 (d, J=1.8 Hz, 1H), 7.77 (s, 1H), 7.50 (dd, J=8.3, 1.5 Hz, 1H), 4.92 (s, 4H), 4.01 (s, 3H), 2.30 (s, 3H), 0.92 (s, 9H), −0.05 (s, 6H); HPLC: RT=3.048 min (Chromolith ODS 4.6×50 mm (4 min grad) eluting with 10-90% aqueous MeOH over 4 min containing 0.1% TFA, 4 mL/min, monitoring at 220 nm); MS (ES): m/z=450.2 [M+H]$^+$.

Step 6: (S)-7-(3-((tert-Butyldimethylsilyl)oxy)oxetan-3-yl)-3-(1,4-dimethyl-1H-1,2,3-triazol-5-yl)-5-((4-fluorophenyl)(tetrahydro-2H-pyran-4-yl)methyl)-5H-pyrido[3,2-b]indole To a stirred solution of 7-(3-((tert-butyldimethylsilyl)oxy)oxetan-3-yl)-3-(1,4-dimethyl-1H-1,2,3-triazol-5-yl)-5H-pyrido[3,2-b]indole (100 mg, 0.222 mmol) and ((R)-(4-fluorophenyl)(tetrahydro-2H-pyran-4-yl)methanol (94.0 mg, 0.445 mmol) in toluene (1.50 mL) in a cold water bath was added triphenylphosphine (117 mg, 0.445 mmol) and DIAD (0.0860 mL, 0.445 mmol). The mixture was stirred at room temperature for 4 h, at which time another batch of (R)-(4-fluorophenyl)(tetrahydro-2H-pyran-4-yl)methanol (94.0 mg, 0.445 mmol), triphenylphosphine (117 mg, 0.445 mmol), and DIAD (0.0860 mL, 0.445 mmol) were added. The mixture was stirred at room temperature for 15 h. The mixture was concentrated and purified by silica gel column chromatography (Teledyne ISCO CombiFlash 0% to 100% solvent A/B=DCM/EtOAc, RediSep SiO$_2$ 24 g, detecting at 254 nM, and monitoring at 220 nM). Concentration of appropriate fractions provided (S)-7-(3-((tert-butyldimethylsilyl)oxy)oxetan-3-yl)-3-(1,4-dimethyl-1H-1,2,3-triazol-5-yl)-5-((4-fluorophenyl)(tetrahydro-2H-pyran-4-yl)methyl)-5H-pyrido[3,2-b]indole (81.0 mg, 57%). HPLC: RT=3.578 min (Chromolith ODS 4.6×50 mm (4 min grad) eluting with 10-90% aqueous MeOH over 4 min containing 0.1% TFA, 4 mL/min, monitoring at 220 nm); MS (ES): m/z=642.3 [M+H]$^+$.

Step 7: 3-[3-(Dimethyl-1H-1,2,3-triazol-5-yl)-5-[(S)-(4-fluorophenyl)(oxan-4-yl)methyl]-5H-pyrido[3,2-b]indol-7-yl]oxetan-3-ol To a stirred solution of (S)-7-(3-((tert-butyldimethylsilyl)oxy)oxetan-3-yl)-3-(1,4-dimethyl-1H-1,2,3-triazol-5-yl)-5-((4-fluorophenyl)(tetrahydro-2H-pyran-4-yl)methyl)-5H-pyrido[3,2-b]indole (81.0 mg, 0.126 mmol) in THF (4.00 mL) was added 1M TBAF in THF (1.20 mL, 1.20 mmol). The mixture was stirred at room temperature for 10 min and concentrated. The crude product was dissolved in DMF and purified via preparative LC/MS with the following conditions: Column: Waters XBridge Phenyl, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 3-[3-(dimethyl-1H-1,2,3-triazol-5-yl)-5-[(S)-(4-fluorophenyl)(oxan-4-yl)methyl]-5H-pyrido[3,2-b]indol-7-yl]oxetan-3-ol (33.6 mg, 51%). $^1$H NMR (500 MHz, DMSO-d$_6$) δ 8.52 (s, 1H), 8.27 (d, J=8.1 Hz, 1H), 8.20 (br s, 1H), 7.93 (s, 1H), 7.71-7.66 (m, 3H), 7.59 (d, J=8.1 Hz, 1H), 7.15 (br t, J=8.6 Hz, 2H), 5.86 (br d, J=11.1 Hz, 1H), 4.88 (br s, 4H), 4.00 (br s, 3H), 3.88 (br d, J=9.4 Hz, 1H), 3.71 (br d, J=8.4 Hz, 1H), 3.47-3.41 (m, 1H), 3.23 (br t, J=11.3 Hz, 1H), 3.17-3.09 (m, 1H), 2.28 (s, 3H), 1.67 (br d, J=11.4 Hz, 1H), 1.56 (br d, J=8.8 Hz, 2H), 0.97 (br d, J=12.1 Hz, 1H).). LCMS: RT=1.30 min; (ES): m/z (M+H)$^+$=528.2, LCMS: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 100%.

Example 244

3-[3-(Dimethyl-1,2-oxazol-4-yl)-5-[(S)-oxan-4-yl(phenyl)methyl]-5H-pyrido[3,2-b]indol-7-yl]oxetan-3-ol

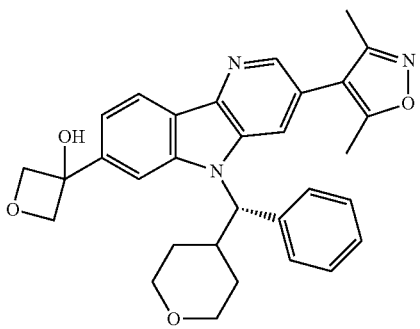 [SMILES: Cc1noc(C)c1-c1cnc2c3ccc(C4(O)COC4)cc3n([C@H](c3ccccc3)C3CCOCC3)c2c1]

Step 1: 4-(7-(3-((tert-Butyldimethylsilyl)oxy)oxetan-3-yl)-5H-pyrido[3,2-b]indol-3-yl)-3,5-dimethylisoxazole To a stirred solution of 3-bromo-7-(3-((tert-butyldimethylsilyl)oxy)oxetan-3-yl)-5H-pyrido[3,2-b]indole (418 mg, 0.964 mmol) and (3,5-dimethylisoxazol-4-yl)boronic acid (272 mg, 1.93 mmol) in THF (8.0 mL) was added tripotassium phosphate (2M in $H_2O$, 1.21 mL, 2.41 mmol). The reaction was degassed with bubbling nitrogen, then $PdCl_2$(dppf)-$CH_2Cl_2$ adduct (65.3 mg, 0.0800 mmol) was added and the reaction mixture was heated at 85° C. for 55 min. The cooled mixture was diluted with water and extracted with EtOAc. Combined EtOAc extracts were dried ($MgSO_4$), filtered, and concentrated to give the crude mixture. The crude product was purified by silica gel column chromatography (Teledyne ISCO CombiFlash 0% to 100% solvent A/B=DCM/EtOAc, RediSep $SiO_2$ 24 g, detecting at 254 nM, and monitoring at 220 nM). Concentration of appropriate fractions provided 4-(7-(3-((tert-butyldimethylsilyl)oxy)oxetan-3-yl)-5H-pyrido[3,2-b]indol-3-yl)-3,5-dimethylisoxazole (254 mg, 59%). $^1$H NMR (400 MHz, DMSO-$d_6$) δ 11.59 (s, 1H), 8.48 (d, J=1.8 Hz, 1H), 8.26 (d, J=8.3 Hz, 1H), 7.91 (d, J=2.0 Hz, 1H), 7.76 (d, J=1.0 Hz, 1H), 7.49 (dd, J=8.2, 1.5 Hz, 1H), 4.94 (s, 4H), 2.50 (s, 3H), 2.32 (s, 3H), 0.94 (s, 9H), −0.04 (s, 6H). HPLC: RT=2.983 min (Chromolith ODS 4.6×50 mm (4 min grad) eluting with 10-90% aqueous MeOH over 4 min containing 0.1% TFA, 4 mL/min, monitoring at 220 nm); MS (ES): m/z=450.2 [M+H]$^+$.

Step 2: (S)-4-(7-(3-((tert-Butyldimethylsilyl)oxy)oxetan-3-yl)-5-(phenyl(tetrahydro-2H-pyran-4-yl)methyl)-5H-pyrido[3,2-b]indol-3-yl)-3,5-dimethylisoxazole To a stirred solution of 4-(7-(3-((tert-butyldimethylsilyl)oxy)oxetan-3-yl)-5H-pyrido[3,2-b]indol-3-yl)-3,5-dimethylisoxazole (250 mg, 0.556 mmol) and ((R)-phenyl(tetrahydro-2H-pyran-4-yl)methanol (214 mg, 1.11 mmol) in toluene (4.50 mL) in a cold water bath was added triphenylphosphine (292 mg, 1.11 mmol) and DIAD (0.216 mL, 1.11 mmol). The mixture was stirred at room temperature for 2 h, at which time another batch of (R)-phenyl(tetrahydro-2H-pyran-4-yl)methanol (214 mg, 1.11 mmol), triphenylphosphine (292 mg, 1.11 mmol), and DIAD (0.216 mL, 1.112 mmol) were added. The mixture was stirred at room temperature for 14 h. The mixture was concentrated and purified by silica gel column chromatography (Teledyne ISCO CombiFlash 0% to 100% solvent A/B=DCM/EtOAc, RediSep $SiO_2$ 24 g, detecting at 254 nM, and monitoring at 220 nM). Concentration of appropriate fractions provided (S)-4-(7-(3-((tert-butyldimethylsilyl)oxy)oxetan-3-yl)-5-(phenyl(tetrahydro-2H-pyran-4-yl)methyl)-5H-pyrido[3,2-b]indol-3-yl)-3,5-dimethylisoxazole (400 mg, 0.641 mmol, 115%). HPLC: RT=3.573 min (Chromolith ODS 4.6×50 mm (4 min grad) eluting with 10-90% aqueous MeOH over 4 min containing 0.1% TFA, 4 mL/min, monitoring at 220 nm); MS (ES): m/z=624.3 [M+H]$^+$.

Step 3: 3-[3-(Dimethyl-1,2-oxazol-4-yl)-5-[(S)-oxan-4-yl(phenyl)methyl]-5H-pyrido[3,2-b]indol-7-yl]oxetan-3-ol To a stirred solution of (S)-4-(7-(3-((tert-butyldimethylsilyl)oxy)oxetan-3-yl)-5-(phenyl(tetrahydro-2H-pyran-4-yl)methyl)-5H-pyrido[3,2-b]indol-3-yl)-3,5-dimethylisoxazole (410 mg, 0.657 mmol) in THF (7.00 mL) was added 1M TBAF in THF (3.20 mL, 3.20 mmol). The mixture was stirred at room temperature for 15 min and concentrated. The crude product was dissolved in DMF and purified via preparative LC/MS with the following conditions: Column: Waters XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 min, then a 5-min hold at 100% B; Flow: 20 mL/min. Fractions containing the desired product were combined and dried via centrifugal evaporation to give 3-[3-(dimethyl-1,2-oxazol-4-yl)-5-[(S)-oxan-4-yl(phenyl)methyl]-5H-pyrido[3,2-b]indol-7-yl]oxetan-3-ol (16.5 mg, 5%) $^1$H NMR (500 MHz, DMSO-$d_6$) δ 8.48 (s, 1H), 8.27 (br d, J=8.4 Hz, 3H), 7.68 (br d, J=7.4 Hz, 2H), 7.61 (br d, J=8.1 Hz, 1H), 7.36 (br t, J=7.4 Hz, 2H), 7.31-7.23 (m, 1H), 6.59 (s, 1H), 5.88 (br d, J=11.1 Hz, 1H), 4.91 (br s, 4H), 3.97-3.89 (m, 1H), 3.76 (br d, J=8.4 Hz, 1H), 3.52 (br d, J=10.8 Hz, 1H), 3.42 (br s, 1H), 3.28 (br t, J=11.3 Hz, 1H), 2.54 (br s, 3H), 2.33 (br s, 3H), 1.76 (br d, J=12.5 Hz, 1H), 1.62 (br d, J=9.8 Hz, 1H), 1.35 (br d, J=8.8 Hz, 1H), 1.00 (br d, J=13.1 Hz, 1H). LCMS: RT=1.29 min; (ES): m/z (M+H)$^+$=510.2. LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min. HPLC Purity at 220 nm: 96%.

Examples 245 & 246

2-{[9-(2,2-Difluoroethoxy)-6-methanesulfonyl-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine Enantiomer A, Example 245

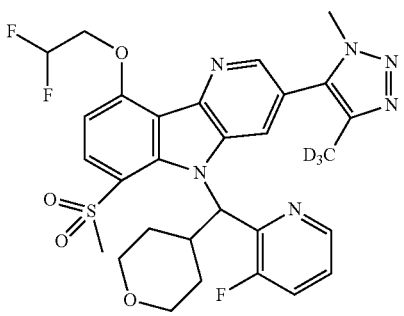

Enantiomer B, Example 246

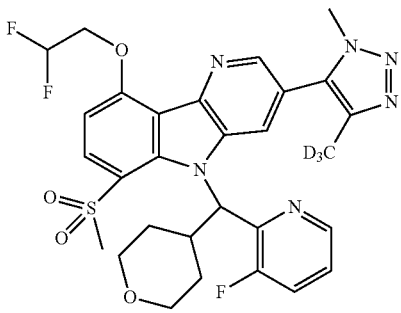

Step 1: 3-Bromo-9-(2,2-difluoroethoxy)-6-(methylsulfonyl)-5H-pyrido[3,2-b]indole To a stirred reaction mixture of 3-bromo-9-fluoro-6-(methylsulfonyl)-5H-pyrido[3,2-b]indole (50.0 mg, 0.146 mmol) and 2,2-difluoroethanol (120 mg, 1.46 mmol) in NMP (0.50 mL) was added t-BuOK (131 mg, 1.17 mmol). The mixture was heated at 65° C. for 17 h. The cooled mixture was diluted with EtOAc and washed with brine. The EtOAc layer was dried (MgSO$_4$), filtered, and concentrated to give the crude mixture. The crude product was purified by silica gel column chromatography (Teledyne ISCO CombiFlash 0% to 100% solvent A/B=DCM/10% MeOH in DCM, RediSep SiO$_2$ 12 g, detecting at 254 nM, and monitoring at 220 nM). Concentration of appropriate fractions provided 3-bromo-9-(2,2-difluoroethoxy)-6-(methylsulfonyl)-5H-pyrido[3,2-b]indole (64.0 mg, 108%). $^1$H NMR (400 MHz, DMSO-d$_6$) δ 11.75 (br s, 1H), 8.65 (d, J=2.1 Hz, 1H), 8.24 (d, J=2.1 Hz, 1H), 7.95 (s, 1H), 7.13 (d, J=8.7 Hz, 1H), 4.72 (td, J=14.4, 3.7 Hz, 2H), 3.33-3.32 (m, 1H), 2.69 (s, 3H). HPLC: RT=2.067 min (Chromolith ODS 4.6×50 mm (4 min grad) eluting with 10-90% aqueous MeOH over 4 min containing 0.1% TFA, 4 mL/min, monitoring at 220 nm); MS (ES): m/z=405.1; 407 (Br pattern) [M+H]$^+$.

Step 2: 5-[9-(2,2-Difluoroethoxy)-6-methanesulfonyl-5Hpyrido[3,2-b]indol-3-yl]-4-($^2$H$_3$)methyl-1-methyl-1H-1,2,3-triazole A stirred solution of 3-bromo-9-(2,2-difluoroethoxy)-6-(methylsulfonyl)-5H-pyrido[3,2-b]indole (62.3 mg, 0.154 mmol) and 4-($^2$H$_3$)methyl-1-methyl-5-(tributylstannyl)-1-H-1,2,3-triazole (108 mg, 0.277 mmol) in DMF (0.80 mL) and Et$_3$N (0.0470 mL, 0.338 mmol) was purged with nitrogen. While purging with nitrogen, to this mixture was added Pd(PPh$_3$)$_4$ (21.3 mg, 0.0180 mmol) and copper (I) iodide (4.39 mg, 0.0230 mmol). The reaction mixture was heated at 95° C. for 5 h. The cooled mixture was diluted with 10% aq. LiCl solution and extracted with EtOAc. Combined EtOAc extracts were washed with brine, dried (MgSO$_4$), filtered, and concentrated to give the crude mixture. The crude product was purified by silica gel column chromatography (Teledyne ISCO CombiFlash 0% to 100% solvent A/B=DCM/10% MeOH in DCM, RediSep SiO$_2$ 12 g, detecting at 254 nM, and monitoring at 220 nM). Concentration of appropriate fractions provided 5-[9-(2,2-difluoroethoxy)-6-methanesulfonyl-5H-pyrido[3,2-b]indol-3-yl]-4-($^2$H$_3$)methyl-1-methyl-1H-1,2,3-triazole (24.3 mg, 37%). $^1$H NMR (400 MHz, CD$_3$OD) δ 8.58 (d, J=2.0 Hz, 1H), 8.07 (d, J=8.7 Hz, 2H), 8.02 (d, J=2.0 Hz, 1H), 7.00 (s, 1H), 4.68 (td, J=13.0, 4.2 Hz, 3H), 4.06 (s, 3H), 3.25 (s, 3H). HPLC: RT=1.750 min (Chromolith ODS 4.6×50 mm (4 min grad) eluting with 10-90% aqueous MeOH over 4 min containing 0.1% TFA, 4 mL/min, monitoring at 220 nm); MS (ES): m/z=425.2 [M+H]$^+$.

Step 3: 2-{[9-(2,2-Difluoroethoxy)-6-methanesulfonyl-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine 5-[9-(2,2-Difluoroethoxy)-6-methanesulfonyl-5H-pyrido[3,2-b]indol-3-yl]-4-($^2$H$_3$)methyl-1-methyl-1H-1,2,3-triazole (22.0 mg, 0.0520 mmol) and (3-fluoropyridin-2-yl)(tetrahydro-2H-pyran-4-yl)methanol (21.9 mg, 0.104 mmol) were combined in Toluene (0.50) in a cold water bath. To this mixture was added triphenylphosphine (27.2 mg, 0.104 mmol) and DIAD (0.0200 mL, 0.104 mmol). The mixture was stirred at room temperature for 4.5 h and purified by silica gel column chromatography (Teledyne ISCO CombiFlash 0% to 100% solvent A/B=DCM/10% MeOH in DCM, RediSep SiO$_2$ 12 g, detecting at 254 nM, and monitoring at 220 nM). Concentration of appropriate fractions provided racemic 2-{[9-(2,2-difluoroethoxy)-6-methanesulfonyl-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine (105 mg). This racemic mixture was separated by chiral prep SFC (Berger SFC MGII, Column: Chiral IB 25×2.1 cm ID, 5 μm Flow rate: 50.0 mL/min. Mobile Phase: 78/22 CO$_2$/MeOH Detector Wavelength: 220 nm) to give Enantiomers A (1.10 mg, 3%) and B (1.00 mg, 3%). Enantiomer A: $^1$H NMR (500 MHz, DMSO-d$_6$) δ 8.66 (s, 1H), 8.51 (br d, J=4.4 Hz, 1H), 8.30 (d, J=9.0 Hz, 1H), 8.07 (s, 1H), 7.63 (br t, J=9.5 Hz, 1H), 7.46 (dt, J=8.3, 4.2 Hz, 1H), 7.23 (d, J=8.9 Hz, 1H), 6.96 (br d, J=10.2 Hz, 1H), 6.69-6.42 (m, 1H), 4.73 (td, J=14.3, 3.2 Hz, 2H), 3.89 (s, 3H), 3.83 (br d, J=10.9 Hz, 1H), 3.62 (br d, J=7.8 Hz, 1H), 3.58-3.53 (m, 1H), 3.36-3.28 (m, 1H), 3.12 (br t, J=11.7 Hz, 1H), 2.54 (s, 3H), 1.79-1.64 (m, 2H), 1.63-1.51 (m, 1H), 0.42 (br d, J=12.2 Hz, 1H). LCMS (M+H)=618.3; SFC RT=5.019 min (Column: Chiralcel IB 250×4.6 mm, 5 μm; Mobile Phase: 70/30 CO$_2$/MeOH; Flow: 2 mL/min); Enantiomer B: $^1$H NMR (500 MHz, DMSO-d$_6$) δ 8.67 (s, 1H), 8.52 (br d, J=4.5 Hz, 1H), 8.30 (d, J=8.9 Hz, 1H), 8.08 (s, 1H), 7.68-7.57 (m, 1H), 7.52-7.41 (m, 1H), 7.24 (d, J=9.0 Hz, 1H), 6.96 (br d, J=10.1 Hz, 1H), 6.71-6.38 (m, 1H), 4.74 (td, J=14.3, 3.2 Hz, 2H), 3.93-3.88 (m, 3H), 3.84 (br d, J=9.8 Hz, 1H), 3.63 (br d, J=9.2 Hz, 1H), 3.54 (s, 1H), 3.36-3.26 (m, 1H), 3.12 (br t, J=11.7 Hz, 1H), 2.54 (s, 3H), 1.79-1.65 (m, 2H), 1.63-1.50 (m, 1H), 0.42 (br d, J=12.0 Hz, 1H). LCMS (M+H)=618.3. SFC RT=6.211 min (Column: Chiralcel OD-H 250×4.6 mm, 5 μm; Mobile Phase: 70/30 $CO_2$/MeOH; Flow: 2 mL/min).

Examples 247 & 248

2-{[9-(2,2-Difluoropropoxy)-6-methanesulfonyl-3-[4-($^2H_3$)methyl-1-methyl-1H-1,2,3-triazol-5-yl]-5H-pyrido[3,2-b]indol-5-yl](oxan-4-yl)methyl}-3-fluoropyridine Enantiomer A, Example 247

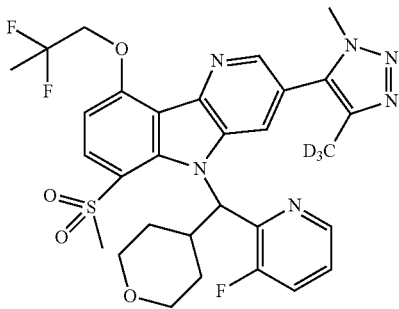

Enantiomer B, Example 248

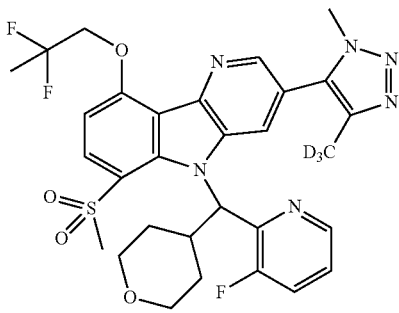

Step 1: 3-Bromo-9-(2,2-difluoroethoxy)-6-(methylsulfonyl)-5H-pyrido[3,2-b]indole To a stirred reaction mixture of 3-bromo-9-fluoro-6-(methylsulfonyl)-5H-pyrido[3,2-b]indole (50.0 mg, 0.146 mmol) and 2,2-difluoropropan-1-ol (140 mg, 1.46 mmol) in NMP (0.50 mL) was added t-BuOK (131 mg, 1.17 mmol). The mixture was heated at 65° C. for 2 h. The cooled mixture was diluted with EtOAc and washed with water and brine. The EtOAc layer was dried ($MgSO_4$), filtered, and concentrated to give the crude mixture. The crude product was purified by silica gel column chromatography (Teledyne ISCO CombiFlash 0% to 100% solvent A/B=DCM/10% MeOH in DCM, RediSep $SiO_2$ 12 g, detecting at 254 nM, and monitoring at 220 nM). Concentration of appropriate fractions provided 3-bromo-9-(2,2-difluoroethoxy)-6-(methylsulfonyl)-5H-pyrido[3,2-b]indole (61.0 mg, 100%). $^1$H NMR (400 MHz, DMSO-$d_6$) δ 11.73 (br s, 1H), 8.64 (d, J=2.1 Hz, 1H), 8.24 (s, 1H), 7.96 (d, J=8.7 Hz, 1H), 7.12 (d, J=8.7 Hz, 1H), 4.67 (t, J=12.2 Hz, 2H), 3.32-3.27 (m, 3H), 2.69 (s, 3H). HPLC: RT=2.392 min (Chromolith ODS 4.6×50 mm (4 min grad) eluting with 10-90% aqueous MeOH over 4 min containing 0.1% TFA, 4 mL/min, monitoring at 220 nm); MS (ES): m/z=419; 421 (Br pattern) [M+H]$^+$.

Step 2

5-[9-(2,2-Difluoropropoxy)-6-methanesulfonyl-5H-pyrido[3,2-b]indol-3-yl]-4-($^2H_3$)methyl-1-methyl-1H-1,2,3-triazole A stirred solution of 3-bromo-9-(2,2-difluoropropoxy)-6-(methylsulfonyl)-5H-pyrido[3,2-b]indole (60.3 mg, 0.144 mmol) and 4-($^2H_3$)methyl-1-methyl-5-(tributylstannyl)-1-H-1,2,3-triazole (101 mg, 0.259 mmol) in DMF (0.80 mL) and $Et_3N$ (0.044 mL, 0.316 mmol) was purged with nitrogen. While purging with nitrogen, to this mixture was added Pd(PPh$_3$)$_4$ (19.9 mg, 0.0170 mmol) and copper (I) iodide (4.11 mg, 0.0220 mmol). The reaction mixture was heated at 95° C. for 1.5 h. The cooled mixture was diluted with 10% aq. LiCl solution and extracted with EtOAc. Combined EtOAc extracts were washed with brine, dried (MgSO$_4$), filtered, and concentrated to give the crude mixture. The crude product was purified by silica gel column chromatography (Teledyne ISCO CombiFlash 0% to 100% solvent A/B=DCM/10% MeOH in DCM, RediSep $SiO_2$ 12 g, detecting at 254 nM, and monitoring at 220 nM). Concentration of appropriate fractions provided 5-[9-(2,2-difluoropropoxy)-6-methanesulfonyl-5H-pyrido[3,2-b]indol-3-yl]-4-($^2H_3$)methyl-1-methyl-1H-1,2,3-triazole (40.0 mg, 63%). $^1$H NMR (400 MHz, DMSO-$d_6$) δ 11.79 (s, 1H), 8.68 (d, J=2.0 Hz, 1H), 8.13 (d, J=2.1 Hz, 1H), 7.98 (d, J=8.6 Hz, 1H), 7.14 (d, J=8.7 Hz, 1H), 4.70 (t, J=12.1 Hz, 2H), 4.01 (s, 3H), 3.34 (s, 3H), 2.04-1.90 (m, 3H). HPLC: RT=1.995 min (Chromolith ODS 4.6×50 mm (4 min grad) eluting with 10-90% aqueous MeOH over 4 min containing 0.1% TFA, 4 mL/min, monitoring at 220 nm); MS (ES): m/z=439.2 [M+H]$^+$.

Step 3: 2-{[9-(2,2-Difluoropropoxy)-6-methanesulfonyl-3-[4-($^2H_3$)methyl-1-methyl-1H-1,2,3-triazol-5-yl]-5H-pyrido[3,2-b]indol-5-yl](oxan-4-yl)methyl}-3-fluoropyridine 5-[9-(2,2-Difluoropropoxy)-6-methanesulfonyl-5H-pyrido[3,2-b]indol-3-yl]-4-($^2H_3$)methyl-1-methyl-1H-1,2,3-triazole (38.0 mg, 0.0870 mmol) and (3-fluoropyridin-2-yl)(tetrahydro-2H-pyran-4-yl)methanol (36.6 mg, 0.173 mmol) were dissolved in toluene (1.00 mL) in a cold water bath. To this mixture was added triphenylphosphine (45.5 mg, 0.173 mmol) and DIAD (0.0340 mL, 0.173 mmol). The mixture was stirred at room temperature for 4.5 h and purified by silica gel column chromatography (Teledyne ISCO CombiFlash 0% to 100% solvent A/B=DCM/10% MeOH in DCM, RediSep $SiO_2$ 12 g, detecting at 254 nM, and monitoring at 220 nM). Concentration of appropriate fractions provided racemic 2-{[9-(2,2-difluoropropoxy)-6-methanesulfonyl-3-[4-($^2H_3$)methyl-1-methyl-1H-1,2,3-triazol-5-yl]-5H-pyrido[3,2-b]indol-5-yl](oxan-4-yl)methyl}-3-fluoropyridine (164 mg). This racemic mixture was separated by chiral prep SFC (Berger SFC MGII, Column: Chiral IB 25×2.1 cm IB, 5 μm Flow rate: 50.0 mL/min. Mobile Phase: 78/22 $CO_2$/MeOH Detector Wavelength: 220 nm) to give Enantiomers A (4.30 mg, 8%) and B (4.30 mg, 8%). Enantiomer A: $^1$H NMR (500 MHz, DMSO-$d_6$) δ 8.66 (s, 1H), 8.52 (br d, J=4.4 Hz, 1H), 8.30 (d, J=8.8 Hz, 1H), 8.04 (s, 1H), 7.63 (br t, J=9.6 Hz, 1H), 7.47 (dt, J=8.3, 4.2 Hz, 1H), 7.22 (d, J=9.0 Hz, 1H), 6.98 (br d, J=10.2 Hz, 1H), 4.68 (br t, J=11.9 Hz, 2H), 3.89 (s, 3H), 3.84 (br d, J=9.4 Hz, 1H), 3.63 (br d, J=8.3 Hz, 1H), 3.56-3.50 (m, 1H), 3.34 (br t, J=10.9 Hz, 1H), 3.13 (br t, J=11.3 Hz, 1H), 2.54 (s, 3H), 1.97 (br t, J=19.4 Hz, 3H), 1.80-1.66 (m, 2H), 1.64-1.52 (m, 1H), 0.44 (br d, J=11.8 Hz, 1H) LCMS (M+H)=632.3; SFC RT=6.376 min (Column: Chiralcel IB 250×4.6 mm, 5 µm; Mobile Phase: 75/25 CO₂/MeOH; Flow: 2 mL/min). Enantiomer B: ¹H NMR (500 MHz, DMSO-d₆) δ 8.66 (s, 1H), 8.52 (br d, J=4.5 Hz, 1H), 8.30 (d, J=8.9 Hz, 1H), 8.04 (s, 1H), 7.63 (br t, J=9.6 Hz, 1H), 7.47 (dt, J=8.3, 4.2 Hz, 1H), 7.22 (d, J=9.0 Hz, 1H), 6.98 (br d, J=10.1 Hz, 1H), 4.68 (br t, J=11.9 Hz, 2H), 3.89 (s, 3H), 3.83 (br s, 1H), 3.63 (br d, J=8.4 Hz, 1H), 3.55-3.49 (m, 1H), 3.37-3.27 (m, 1H), 3.13 (br t, J=11.2 Hz, 1H), 2.54 (s, 3H), 1.97 (br t, J=19.4 Hz, 3H), 1.80-1.65 (m, 2H), 1.63-1.52 (m, 1H), 0.44 (br d, J=11.4 Hz, 1H). LCMS (M+H)=632.2; SFC RT=7.707 min (Column: Chiralcel OD-H 250×4.6 mm, 5 µm; Mobile Phase: 70/30 CO₂/MeOH; Flow: 2 mL/min).

Examples 249 & 250

2-[3-(Dimethyl-1H-1,2,3-triazol-5-yl)-5-[(4-methoxyphenyl)(oxan-4-yl)methyl]-5H-pyrido[3,2-b]indol-7-yl]propan-2-ol Enantiomer A, Example 249

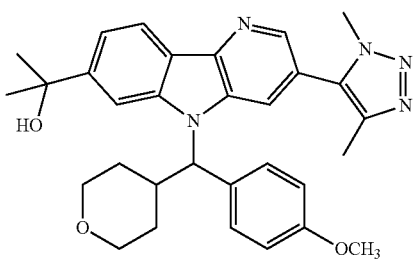

Enantiomer B, Example 250

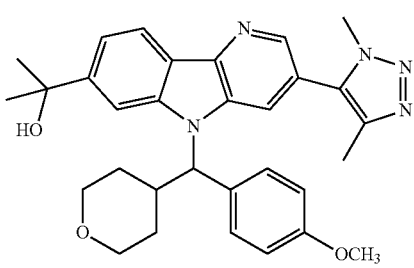

Step 1: N-Methoxy-N-methyloxane-4-carboxamide

To a 500 mL round bottom flask containing a solution of oxane-4-carboxylic acid (8.00 g, 61.5 mmol) in CH₂Cl₂ (100 mL), 1,1'-carbonyldiimidazole (12.0 g, 73.8 mmol) was added in portions. The reaction solution was stirred at room temperature for 2 h. N,O-Dimethylhydroxylamine hydrochloride (6.60 g, 67.6 mmol) then was added in one portion. The reaction was stirred at room temperature for 16 h. The reaction mixture was quenched with saturated aq. ammonium chloride and separated. The organic layer was washed with saturated aq. NaHCO₃, dried with sodium sulfate, filtered, and concentrated to give the title compound (9.50 g, 89%), which was used as without purification. ¹H NMR (400 MHz, CD₃OD) δ 3.99 (ddd, J=11.5, 4.2, 2.1 Hz, 2H), 3.77 (s, 3H), 3.51 (td, J=11.8, 2.4 Hz, 2H), 1.7 Hz, 1H), 3.21 (s, 3H), 3.06 (br. s., 1H), 1.88-1.52 (m, 4H); LCMS (M+H)=174.2; HPLC RT=1.39 min (Column: Waters Sunfire C18, 2.1×50 mm, 3.5-µm particles; Mobile Phase A: 10:90 MeOH:water with 0.1% TFA; Mobile Phase B: 90:10 MeOH:water with 0.1% TFA; Temperature: 40° C.; Gradient: 0-100% B over 4 min, then a 1.00 min hold at 100% B; Flow: 4 mL/min; Detection: UV at 220 nm).

Step 2: 4-(4-Methoxybenzoyl)oxane

To a 100 mL round bottom flask containing a solution of 1-bromo-4-methoxybenzene (3.24 g, 17.3 mmol) in THF (10 mL) cooled to −78° C., 1.6 M nBuLi in hexanes (10.8 mL, 17.3 mmol) was added dropwise. The reaction solution became cloudy and was stirred at −78° C. for 10 min, then at room temperature for 10 min to give a clear solution. The reaction was then cooled back down to −78° C. and treated with a solution of N-methoxy-N-methyloxane-4-carboxamide (1.00 g, 5.77 mmol) in 5 mL of THF to give a very dark solution. The solution was stirred at −78° C. for 1 h. The reaction was quenched by pouring it into a mixture of ice and saturated aq. NH₄Cl and extracting the product into ethyl acetate. The organic phase was washed with water and concentrated to give an off-white solid. The crude product mixture was purified using ISCO silica gel chromatography (40 g column, gradient from 0% to 25% EtOAc/DCM in 10 min) to give the title compound (1.02 g, 80%). ¹H NMR (400 MHz, CDCl₃) δ 8.07-7.86 (m, 2H), 7.06-6.91 (m, 2H), 4.15-4.00 (m, 2H), 3.94-3.86 (m, 3H), 3.66-3.31 (m, 3H), 2.06-1.69 (m, 4H); LCMS (M+H)=221.0; HPLC RT=0.80 min (Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 1.5 min, then a 0.2-min hold at 100% B; Flow: 0.8 mL/min; Detection: UV at 220 nm).

Step 3: (4-Methoxyphenyl)(oxan-4-yl)methanol

A 100 mL round bottomed flask was charged with a solution of 4-(4-methoxybenzoyl)oxane (1000 mg, 4.54 mmol) in MeOH (10 mL). The reaction solution was cooled in an ice bath. Solid NaBH₄ (258 mg, 6.81 mmol) was added slowly in small batches to the reaction solution. The reaction was stirred in an ice/water bath for 1 h. The reaction was quenched with water, and the reaction solution concentrated in vacuo. The solution was acidified with citric acid to pH 4, and extracted with DCM (2×). The organic phase was washed with brine, dried, and concentrated. The crude product mixture was purified using ISCO silica gel chromatography (40 g column, gradient from 0% to 25% EtOAc/DCM in 15 min) to give the title compound (0.910 g, 90%). ¹H NMR (400 MHz, CDCl₃) δ 7.28-7.21 (m, 2H), 7.35-7.17 (m, 7H), 6.91 (d, J=8.8 Hz, 2H), 4.48-3.85 (m, 4H), 3.83 (s, 3H), 3.69-3.17 (m, 2H), 1.79 (d, J=2.9 Hz, 3H), 1.57-0.97 (m, 14H); LCMS (M-18)=205; HPLC RT=0.70 min (Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 1.5 min, then a 0.2-min hold at 100% B; Flow: 0.8 mL/min; Detection: UV at 220 nm).

Step 4: Methyl 3-(dimethyl-1H-1,2,3-triazol-5-yl)-5-((4-methoxyphenyl)(oxan-4-yl)methyl)-5H-pyrido[3,2-b]indole-7-carboxylate To a 25 mL round bottomed flask containing a solution of methyl 3-(dimethyl-1H-1,2,3-triazol-5-yl)-5H-pyrido[3,2-b]

indole-7-carboxylate (85.0 mg, 0.265 mmol) and 4-methoxyphenyl)(oxan-4-yl)methanol (118 mg, 0.529 mmol) in DCM (10 mL) at 0° C. was added solid triphenylphosphine (139 mg, 0.529 mmol) and DIAD (0.103 mL, 0.529 mmol). The resulting suspension was stirred at room temperature overnight and then concentrated. The crude product mixture was purified using ISCO silica gel chromatography (40 g column, gradient from 0% to 100% EtOAc/CH$_2$Cl$_2$ in 15 min) to give the title compound (75.0 mg, 54%). LCMS (M+H)=526; HPLC RT=0.93 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 1.5 min, then a 0.2-min hold at 100% B; Flow: 0.8 mL/min; Detection: UV at 220 nm).

Step 5: 2-[3-(Dimethyl-1H-1,2,3-triazol-5-yl)-5-[(4-methoxyphenyl)(oxan-4-yl)methyl]-5H-pyrido[3,2-b]indol-7-yl]propan-2-ol A 25 mL round-bottomed flask containing methyl 3-(dimethyl-1H-1,2,3-triazol-5-yl)-5-((4-methoxyphenyl)(oxan-4-yl)methyl)-5H-pyrido[3,2-b]indole-7-carboxylate (75.0 mg, 0.143 mmol) in THF (8 mL) was cooled in an ice/MeOH bath. A solution of methylmagnesium bromide (3M in Et$_2$O, 0.381 mL, 1.14 mmol) was added slowly dropwise. The reaction was stirred in the ice/MeOH bath for 15 min then let warm to room temperature for 10 min. The reaction was re-cooled in an ice/MeOH bath, and another portion of methylmagnesium bromide (3M in Et$_2$O, 0.381 mL, 1.14 mmol) was added. After 15 min, the reaction was warmed to room temperature for 10 min. The reaction was re-cooled in the ice/MeOH bath and quenched with saturated aq. NH$_4$Cl solution and diluted with 10% aq. LiCl solution. The aqueous layer was extracted with CHCl$_3$ (2×), and the organic layer was dried over Na$_2$SO$_4$, filtered, and concentrated. The crude product mixture was purified using ISCO silica gel chromatography (24 g column, gradient from 0% to 100% EtOAc/CH$_2$Cl$_2$ in 15 min) to give the racemic title compound, which was separated using chiral prep SFC (Column: Chiralpak IB, 25×2 cm, 5 μm; Mobile Phase: 75/25 CO$_2$/MeOH; Flow: 50 mL/min). The faster eluting peak was assigned as Enantiomer A (16.0 mg, 20%). $^1$H NMR (400 MHz, CD$_3$OD) δ 8.44 (s, 1H), 8.31 (d, J=8.1 Hz, 1H), 8.22 (s, 1H), 8.13 (s, 1H), 7.59-7.38 (m, 3H), 6.90 (d, J=8.6 Hz, 2H), 5.73 (d, J=11.0 Hz, 1H), 4.08-3.94 (m, 4H), 3.82 (dd, J=11.3, 3.0 Hz, 1H), 3.74 (s, 2H), 3.65-3.49 (m, 1H), 3.48-3.35 (m, 1H), 2.44-2.23 (m, 2H), 1.98 (d, J=13.2 Hz, 1H), 1.81-1.50 (m, 7H), 1.51-1.02 (m, 3H LCMS (M+H)=526.5; HPLC RT=8.08 min (Column: Sunfire C18 3.5 μm, 3.0×150 mm; Mobile Phase A: 5:95 acetonitrile:water with 0.05% TFA; Mobile Phase B: 95:5 acetonitrile:water with 0.05% TFA; Gradient 0-100% B over 15 min; Flow: 1.0 mL/min; Detection: UV at 220 nm); Chiral HPLC RT=8.778 min (Column: Chiralpak IB, 250×4.6 mm, 5um particle; Mobile Phase: 75/25 CO$_2$/MeOH; Flow rate: 2.0 mL/min; Detection: UV at 220 nm). The slower eluting peak was assigned as Enantiomer B (14.3 mg, 19%). $^1$H NMR (500 MHz, DMSO-d$_6$) δ 8.56-8.22 (m, 1H), 8.22-8.01 (m, 1H), 7.57 (d, J=8.8 Hz, 1H), 7.46 (d, J=8.1 Hz, 1H), 6.86 (d, J=8.8 Hz, 2H), 5.73 (d, J=11.1 Hz, 1H), 4.00 (br. s., 2H), 3.89 (d, J=9.1 Hz, 1H), 3.72 (d, J=8.8 Hz, 1H), 3.67-3.54 (m, 2H), 3.46 (t, J=11.4 Hz, 1H), 3.39-3.15 (m, 2H), 2.29 (s, 3H), 1.70 (d, J=12.5 Hz, 1H), 1.65-1.40 (m, 6H), 1.30 (d, J=9.1 Hz, 1H), 0.99 (d, J=11.4 Hz, 1H) LCMS (M+H) =526.5; HPLC RT=1.608 min Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm; Chiral HPLC RT=12.020 min (Column: Chiralpak IB, 250×4.6 mm, 5 μm particle; Mobile Phase: 75/25 CO$_2$/MeOH; Flow rate: 2.0 mL/min; Detection: UV at 220 nm).

Example 251

2-{5-[Cyclobutyl(4-fluorophenyl)methyl]-3-(dimethyl-1H-1,2,3-triazol-5-yl)-5H-pyrido[3,2-b]indol-7-yl}propan-2-ol

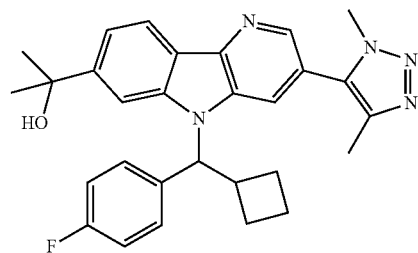 [SMILES: Cc1nnn(C)c1-c1cnc2c3ccc(C(C)(C)O)cc3n(C(c3ccc(F)cc3)C3CCC3)c2c1]

Step 1: Cyclobutyl(4-fluorophenyl)methanol

A mixture of magnesium (0.783 g, 32.2 mmol), bromocyclobutane (4.35 g, 32.2 mmol), and 2 drops of dibromoethane in THF (40.3 ml) was sonicated for 2 min and then refluxed for 1 h. The mixture was cooled to 0° C. followed by a slow addition of a solution of 4-fluorobenzaldehyde (2.00 g, 16.1 mmol) in THF (5 mL). The reaction was stirred at 0° C. for 2 h. The reaction was quenched with NH$_4$Cl, and the mixture was extracted with EtOAc (3×). The organic layer was separated, concentrated, and the residue was purified by silica gel chromatography (40 g column, gradient from 0% to 50% EtOAc/hexanes) to give the title compound (1.50 g, 52%) as a colorless oil. $^1$H NMR (400 MHz, CDCl$_3$) δ 7.30 (dd, J=8.6, 5.7 Hz, 2H), 7.03 (t, J=8.7 Hz, 2H), 4.58 (dd, J=7.9, 3.3 Hz, 1H), 2.72-2.53 (m, 1H), 2.17-2.07 (m, 1H), 2.05-1.95 (m, 1H), 1.91 (d, J=3.3 Hz, 1H), 1.89-1.75 (m, 4H); LCMS (M+H—H$_2$O)=163.1; HPLC RT=0.87 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: 2-{5-[Cyclobutyl(4-fluorophenyl)methyl]-3-(dimethyl-1H-1,2,3-triazol-5-yl)-5H-pyrido[3,2-b]indol-7-yl}propan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, methyl 3-(1,4-dimethyl-1H-1,2,3-triazol-5-yl)-5H-pyrido[3,2-b]indole-7-carboxylate (75.0 mg, 0.230 mmol) and cyclobutyl(4-fluorophenyl)methanol (84.0 mg, 0.480 mmol) were converted to racemic 2-{5-[cyclobutyl(4-fluorophenyl)methyl]-3-(dimethyl-1H-1,2,3-triazol-5-yl)-5H-pyrido[3,2-b]indol-7-yl}propan-2-ol, which was separated by chiral prep SFC to give the title compound (15.0 mg, 19%). $^1$H NMR (400 MHz, CD$_3$OD) δ 8.45 (d, J=1.6 Hz, 1H), 8.33 (d, J=8.3 Hz, 1H), 7.94 (br. s., 2H), 7.53-7.48 (m, 2H), 7.38-7.32 (m, 3H), 7.07 (t, J=8.7 Hz, 2H), 6.13 (d, J=11.0 Hz, 1H), 3.96 (s, 3H), 3.70 (s, 2H), 3.66 (s, 2H), 2.28 (s, 3H), 2.08-1.98 (m, 2H), 1.86-1.76 (m, 2H), 1.65 (d, J=1.7 Hz, 6H); LCMS (M+H)=484.5; HPLC RT=0.85 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min); SFC RT=13.03 min (Column: Chiralcel OJ-H 250×4.6 mm, 5 μm; Mobile Phase: 89/11 CO$_2$/MeOH; Flow: 2 mL/min).

Example 252

1-[3-(Dimethyl-1,2-oxazol-4-yl)-5-[(S)-oxan-4-yl(phenyl)methyl]-5H-pyrido[3,2-b]indol-7-yl]-2-methylpropan-2-ol

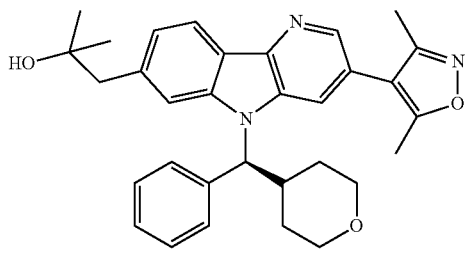 [SMILES: Cc1noc(C)c1-c1cnc2c3ccc(CC(C)(C)O)cc3n([C@H](c3ccccc3)C3CCOCC3)c2c1]

Step 1: Ethyl 2-(4-(4,4,5,5-tetramethyl-1,3,2-dioxaborolan-2-yl)phenyl)acetate

A suspension of ethyl 2-(4-bromophenyl)acetate (500 mg, 2.06 mmol), bis(pinacolato)diboron (1.05 mg, 4.11 mmol), and potassium acetate (606 mg, 6.17 mmol) in dioxane (4 mL) was degassed with bubbling nitrogen. PdCl$_2$(dppf)-CH$_2$Cl$_2$ adduct (84.0 mg, 0.100 mmol) was added, and the reaction was heated to 85° C. for 4 h. The reaction was diluted with ethyl acetate (30 mL) and filtered through Celite. The organic layer was washed with brine, separated, and dried with sodium sulfate. The solvent was evaporated, and the residue was purified by column chromatography on silica gel (40 g column, gradient from 0% to 20% EtOAc/hexanes) to give the title compound (471 mg, 79%) as a colorless oil. $^1$H NMR (400 MHz, CDCl$_3$) δ 7.79 (d, J=7.9 Hz, 2H), 7.32 (d, J=7.9 Hz, 2H), 4.16 (q, J=7.1 Hz, 2H), 3.64 (s, 2H), 1.36 (s, 12H), 1.26 (t, J=7.2 Hz, 3H); LCMS (M+H)=291.3; HPLC RT=1.03 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: Ethyl 2-(4-(5-bromo-3-nitropyridin-2-yl)phenyl)acetate

To a solution of ethyl 2-(4-(4,4,5,5-tetramethyl-1,3,2-dioxaborolan-2-yl)phenyl)acetate (460 mg, 1.59 mmol) and 2,5-dibromo-3-nitropyridine (447 mg, 1.59 mmol) in THF (5 mL) was added tripotassium phosphate (2M) (1.50 mL, 3.17 mmol). The reaction was degassed with bubbling nitrogen followed by the addition of PdCl$_2$(dppf)-CH$_2$Cl$_2$ adduct (64.7 mg, 0.0790 mmol). The reaction was heated to 70° C. for 4 h. The reaction mixture was transferred to a reparatory funnel containing saturated aqueous NaHCO$_3$ solution (25 mL). The aqueous layer was extracted with ethyl acetate (3×20 mL). The combined organic layers were washed with brine (20 mL), dried over MgSO$_4$, filtered, and concentrated. The residue was purified by column chromatography on silica gel (24 g column, gradient from 0% to 20% EtOAc/hexanes) to give the title compound (265 mg, 46%) as a colorless oil. LCMS (M+H)=365.2; HPLC RT=0.98 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 3: Ethyl 2-(3-bromo-5H-pyrido[3,2-b]indol-7-yl)acetate

A solution of ethyl 2-(4-(5-bromo-3-nitropyridin-2-yl)phenyl)acetate (260 mg, 0.710 mmol) and DPPE (355 mg, 0.890 mmol) in o-dichlorobenzene (2.4 mL) was heated to 170° C. for 2 h. The solvent was evaporated, and the residue was purified by column chromatography on silica gel (24 g column, gradient from 0% to 30% EtOAc/hexanes) to give the title compound (155 mg, 65%). $^1$H NMR (400 MHz, CDCl$_3$) δ 8.61 (d, J=2.0 Hz, 1H), 8.28 (d, J=8.1 Hz, 1H), 8.10 (br. s., 1H), 7.88 (d, J=2.0 Hz, 1H), 7.43 (s, 1H), 4.21 (q, J=7.1 Hz, 2H), 3.82 (s, 2H), 1.30 (t, J=7.1 Hz, 3H); LCMS (M+H)=334.9; HPLC RT=0.84 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 4: Ethyl 2-(3-(3,5-dimethylisoxazol-4-yl)-5H-pyrido[3,2-b]indol-7-yl)acetate To a suspension of ethyl 2-(3-bromo-5H-pyrido[3,2-b]indol-7-yl)acetate (150 mg, 0.450 mmol) and (3,5-dimethylisoxazol-4-yl)boronic acid (127 mg, 0.900 mmol) in DMF (2 mL), tripotassium phosphate (3M in H$_2$O) (675 μl, 1.35 mmol) was added. The solution was degassed with nitrogen. PdCl$_2$(dppf) (16.5 mg, 0.0230 mmol) was added, and the mixture was heated in a pressure vial at 80° C. for 3 h. The reaction mixture was transferred to a separatory funnel containing saturated aqueous NaHCO$_3$ solution (25 mL). The aqueous layer was extracted with ethyl acetate (3×25 mL). The combined organic layers were washed with brine (25 mL), dried over MgSO$_4$, filtered, and concentrated. The residue was purified by column chromatography on silica gel (24 g column, gradient from 0% to 5% MeOH/DCM) to give the title compound (82.0 mg, 52%). $^1$H NMR (400 MHz, CDCl$_3$) δ 8.94 (s, 1H), 8.44 (d, J=1.8 Hz, 1H), 8.26 (d, J=8.1 Hz, 1H), 7.56 (d, J=1.7 Hz, 1H), 7.44 (s, 1H), 7.24 (dd, J=8.1, 1.1 Hz, 1H), 4.22 (q, J=7.2 Hz, 2H), 3.83 (s, 2H), 2.47 (s, 3H), 2.32 (s, 3H), 1.30 (t, J=7.1 Hz, 3H); LCMS (M+H)=350.3; HPLC RT=0.68 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 5: 1-[3-(Dimethyl-1,2-oxazol-4-yl)-5-[(S)-oxan-4-yl(phenyl)methyl]-5H-pyrido[3,2-b]indol-7-yl]-2-methylpropan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, ethyl 2-(3-(3,5-dimethylisoxazol-4-yl)-5H-pyrido[3,2-b]indol-7-yl)acetate (30.0 mg, 0.0900 mmol) and (R)-phenyl(tetrahydro-2H-pyran-4-yl)methanol (33.0 mg, 0.170 mmol) were converted to the title compound (9.50 mg, 47%). $^1$H NMR (400 MHz, CD₃OD) δ 8.56 (d, J=1.5 Hz, 1H), 8.53 (br. s., 1H), 8.31 (d, J=8.2 Hz, 1H), 7.98 (s, 1H), 7.66 (d, J=7.3 Hz, 2H), 7.40-7.34 (m, 3H), 7.33-7.27 (m, 1H), 5.86 (d, J=11.0 Hz, 1H), 4.01 (dd, J=11.6, 2.8 Hz, 1H), 3.84 (dd, J=11.4, 2.8 Hz, 1H), 3.62 (td, J=11.8, 1.9 Hz, 1H), 3.49-3.39 (m, 2H), 3.07 (s, 2H), 2.48 (s, 3H), 2.31 (s, 3H), 1.74-1.57 (m, 1H), 1.51-1.38 (m, 1H), 1.27 (d, J=12.2 Hz, 6H), 1.14 (d, J=12.7 Hz, 1H); LCMS (M+H)=510.4; HPLC RT=0.81 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Examples 253 & 254

2-[3-(Dimethyl-1H-1,2,3-triazol-5-yl)-5-[4,4,4-trifluoro-1-(pyridin-2-yl)butyl]-5H-pyrido[3,2-b]indol-7-yl]propan-2-ol Enantiomer A, Example 253

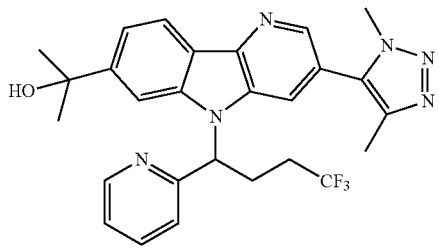

Enantiomer B, Example 254

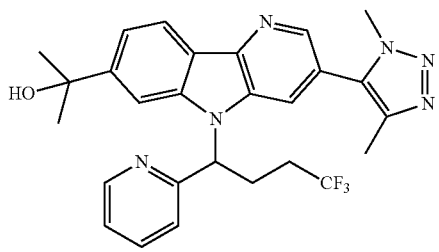

Step 1: 4,4,4-Trifluoro-1-(pyridin-2-yl)butan-1-ol

To a mixture of magnesium (0.340 g, 14.0 mmol) and dibromoethane (2 drops) in THF (23.3 ml), 3-bromo-1,1,1-trifluoropropane (2.45 g, 14.0 mmol) was added. The mixture was heated to 60° C. for 40 min. The reaction was cooled to 0° C. followed by a slow addition of picolinaldehyde (1.00 g, 9.34 mmol). The reaction was stirred at 0° C. for 1 h. The reaction was quenched with 2 mL NH₄Cl solution and diluted with water. The aqueous layer was extracted with EtOAc (2×). The organic layer was separated, concentrated, and dried to afford the title compound (1.10 g, 57%) as a tan solid. ¹H NMR (400 MHz, CD₃OD) δ 8.52-8.42 (m, 1H), 7.86 (td, J=7.8, 1.7 Hz, 1H), 7.63-7.53 (m, 1H), 7.32 (ddd, J=7.5, 4.9, 1.0 Hz, 1H), 4.76 (dd, J=8.3, 4.3 Hz, 1H), 2.36-2.19 (m, 2H), 2.14-2.00 (m, 1H), 1.96-1.85 (m, 1H); LCMS (M+H)=206.2; HPLC RT=0.49 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: 2-(3-(1,4-Dimethyl-1H-1,2,3-triazol-5-yl)-5-(4,4,4-trifluoro-1-(pyridin-2-yl)butyl)-5H-pyrido[3,2-b]indol-7-yl)propan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, methyl 3-(1,4-dimethyl-1H-1,2,3-triazol-5-yl)-5H-pyrido[3,2-b]indole-7-carboxylate (100 mg, 0.310 mmol) and 4,4,4-trifluoro-1-(pyridin-2-yl)butan-1-ol (128 mg, 0.620 mmol) were converted to racemic 2-(3-(1,4-dimethyl-1H-1,2,3-triazol-5-yl)-5-(4,4,4-trifluoro-1-(pyridin-2-yl)butyl)-5H-pyrido[3,2-b]indol-7-yl)propan-2-ol, which was separated by chiral prep SFC to give Enantiomers A and B. Enantiomer A: ¹H NMR (400 MHz, CD₃OD) δ 8.67 (dd, J=4.8, 0.8 Hz, 1H), 8.51 (d, J=1.7 Hz, 1H), 8.36 (d, J=8.3 Hz, 1H), 8.08 (d, J=1.6 Hz, 1H), 7.88 (s, 1H), 7.74 (td, J=7.7, 1.8 Hz, 1H), 7.56 (dd, J=8.4, 1.3 Hz, 1H), 7.35 (dd, J=7.2, 5.3 Hz, 1H), 7.28 (d, J=7.9 Hz, 1H), 6.32 (dd, J=10.0, 5.7 Hz, 1H), 4.01 (s, 3H), 3.17-3.03 (m, 1H), 2.99-2.85 (m, 1H), 2.43 (dt, J=14.7, 5.5 Hz, 1H), 2.31 (s, 3H), 1.98-1.80 (m, 1H), 1.64 (s, 6H); LCMS (M+H)=509.3; HPLC RT=0.79 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min); SFC RT=5.41 (Column: Chiralcel OD-H 250×4.6 mm, 5 μm; Mobile Phase: 80/20 CO₂/MeOH; Flow: 2 mL/min). Enantiomer B: ¹H NMR (400 MHz, CD₃OD) δ 8.67 (dd, J=4.8, 0.8 Hz, 1H), 8.51 (d, J=1.7 Hz, 1H), 8.36 (d, J=8.3 Hz, 1H), 8.08 (d, J=1.6 Hz, 1H), 7.88 (s, 1H), 7.74 (td, J=7.8, 1.8 Hz, 1H), 7.56 (dd, J=8.4, 1.3 Hz, 1H), 7.35 (dd, J=7.2, 5.3 Hz, 1H), 7.28 (d, J=7.9 Hz, 1H), 6.32 (dd, J=10.1, 5.6 Hz, 1H), 4.01 (s, 3H), 3.16-3.04 (m, 1H), 2.99-2.85 (m, 1H), 2.42 (s, 1H), 2.31 (s, 3H), 1.97-1.83 (m, 1H), 1.64 (s, 6H); LCMS (M+H)=509.4; HPLC RT=0.79 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min); SFC RT=6.68 (Column: Chiralcel OD-H 250×4.6 mm, 5 μm; Mobile Phase: 80/20 CO₂/MeOH; Flow: 2 mL/min).

Example 255

1-[3-(Dimethyl-1H-1,2,3-triazol-5-yl)-5-[(S)-oxan-4-yl)phenyl)methyl]-5H-pyrido[3,2-b]indol-8-yl]-2-methylpropan-2-ol

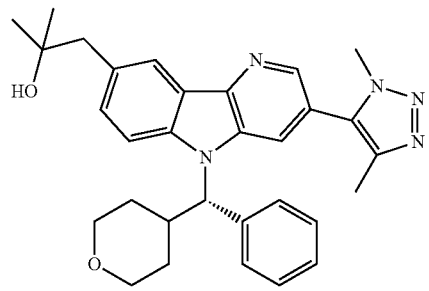 [SMILES: Cc1nnn(C)c1-c1cnc2c3cc(CC(C)(C)O)ccc3n([C@H](c3ccccc3)C3CCOCC3)c2c1]

Step 1: Methyl 2-(3-(4,4,5,5-tetramethyl-1,3,2-dioxaborolan-2-yl)phenyl)acetate

A suspension of methyl 2-(3-bromophenyl)acetate (5.00 g, 21.8 mmol), bis(pinacolato)diboron (11.1 g, 43.7 mmol)

and potassium acetate (6.43 g, 65.5 mmol) in dioxane (43.7 ml) was degassed with bubbling nitrogen. PdCl₂(dppf)-CH₂Cl₂ adduct (0.446 g, 0.546 mmol) was added, and the reaction was heated to 85° C. for 4 h. The reaction was diluted with ethyl acetate (30 mL) and filtered through Celite. The organic layer was washed with brine, separated, and dried with sodium sulfate. The solvent was evaporated, and the residue was purified by column chromatography on silica gel (220 g column, gradient from 0% to 40% EtOAc/hexanes) to give the title compound (6.00 g, 100%) as a colorless oil. $^1$H NMR (400 MHz, CDCl₃) δ 7.74 (s, 1H), 7.72 (s, 1H), 7.40 (t, J=1.7 Hz, 1H), 7.38-7.33 (m, 1H), 3.70 (s, 3H), 3.65 (s, 2H), 1.36 (s, 12H); LCMS (M+H)=277.3; HPLC RT=0.99 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: Methyl 2-(3-(5-bromo-3-nitropyridin-2-yl)phenyl)acetate

Following a procedure analogous to that described for ethyl 2-(4-(5-bromo-3-nitropyridin-2-yl)phenyl)acetate, methyl 2-(3-(4,4,5,5-tetramethyl-1,3,2-dioxaborolan-2-yl)phenyl)acetate (5.00 g, 18.1 mmol) and 2,5-dibromo-3-nitropyridine (5.10 g, 18.1 mmol) were converted to the title compound (4.20 g, 66%). $^1$H NMR (400 MHz, DMSO-d₆) δ 9.10 (d, J=2.1 Hz, 1H), 8.82 (d, J=2.0 Hz, 1H), 7.49 (s, 1H), 7.44 (d, J=1.6 Hz, 1H), 7.42-7.41 (m, 1H), 3.78 (s, 2H), 3.64 (s, 3H); LCMS (M+H)=351.1; HPLC RT=0.93 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 3: Methyl 2-(3-bromo-5H-pyrido[3,2-b]indol-8-yl)acetate

Following a procedure analogous to that described for ethyl 2-(3-bromo-5H-pyrido[3,2-b]indol-7-yl)acetate, methyl 2-(3-(5-bromo-3-nitropyridin-2-yl)phenyl)acetate (4.00 g, 11.4 mmol) and DPPE (5.67 g, 14.2 mmol) were converted to the title compound (1.05 g, 29%). $^1$H NMR (400 MHz, DMSO-d₆) δ 11.57 (s, 1H), 8.51 (d, J=2.0 Hz, 1H), 8.14 (d, J=2.0 Hz, 1H), 8.07 (s, 1H), 7.56-7.52 (m, 1H), 7.45 (dd, J=8.3, 1.7 Hz, 1H), 3.86 (s, 2H), 3.64 (s, 3H); LCMS (M+H)=319.1; HPLC RT=0.78 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 4: Methyl 2-(3-(1,4-dimethyl-1H-1,2,3-triazol-5-yl)-5H-pyrido[3,2-b]indol-8-yl)acetate A solution of methyl 2-(3-bromo-5H-pyrido[3,2-b]indol-8-yl)acetate (100 mg, 0.313 mmol), 1,4-dimethyl-5-(tributylstannyl)-1H-1,2,3-triazole (242 mg, 0.627 mmol), triethylamine (87.0 μl, 0.627 mmol), and copper(I) iodide (8.95 mg, 0.0470 mmol) in DMF (2089 μl) was degassed with bubbling nitrogen.
Tetrakis(triphenylphosphine)palladium(0) (36.2 mg, 0.0310 mmol) was added, and the reaction was heated to 90° C. for 4 h. The reaction was cooled, diluted with water, then extracted twice with EtOAc (2×). The organic layer was washed with ammonium hydroxide, brine, separated, and dried over sodium sulfate. The solvent was concentrated, and the residue was purified by column chromatography on silica gel (24 g column, gradient from 0% to 5% MeOH/DCM) to afford the title compound (32.0 mg, 31%). $^1$H NMR (400 MHz, DMSO-d₆) δ 9.08 (s, 1H), 8.47 (d, J=1.8 Hz, 1H), 8.27 (s, 1H), 7.66 (d, J=1.7 Hz, 1H), 7.54-7.49 (m, 1H), 7.48-7.43 (m, 1H), 4.03 (s, 3H), 3.86 (s, 2H), 3.75 (s, 3H), 2.39 (s, 3H); LCMS (M+H)=336.2; HPLC RT=0.59 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 5: 1-[3-(Dimethyl-1H-1,2,3-triazol-5-yl)-5-[(S)-oxan-4-yl(phenyl)methyl]-5H-pyrido[3,2-b]indol-8-yl]-2-methylpropan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, methyl 2-(3-(1,4-dimethyl-1H-1,2,3-triazol-5-yl)-5H-pyrido[3,2-b]indol-8-yl)acetate (57.0 mg, 0.170 mmol) and (R)-phenyl(tetrahydro-2H-pyran-4-yl)methanol (66.0 mg, 0.340 mmol) were converted to the title compound (16.0 mg, 19%). $^1$H NMR (400 MHz, CD₃OD) δ 8.45 (d, J=1.7 Hz, 1H), 8.27 (s, 1H), 8.24 (d, J=1.3 Hz, 1H), 7.94 (d, J=8.6 Hz, 1H), 7.64 (d, J=7.5 Hz, 2H), 7.61 (d, J=1.5 Hz, 1H), 7.39-7.33 (m, 2H), 7.30-7.25 (m, 1H), 5.75 (d, J=11.0 Hz, 1H), 4.01 (s, 3H), 3.99 (br. s., 1H), 3.84 (dd, J=11.1, 2.6 Hz, 1H), 3.64-3.56 (m, 1H), 3.46-3.36 (m, 3H), 2.99 (s, 2H), 2.34 (s, 3H), 1.63 (dd, J=12.6, 3.9 Hz, 1H), 1.49-1.36 (m, 1H), 1.27 (s, 6H); LCMS (M+H)=510.4; HPLC RT=0.80 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 256

1-[3-(Dimethyl-1H-1,2,3-triazol-5-yl)-5-[(S)-(4-fluorophenyl)(oxan-4-yl)methyl]-5H-pyrido[3,2-b]indol-7-yl]-2-methylpropan-2-ol

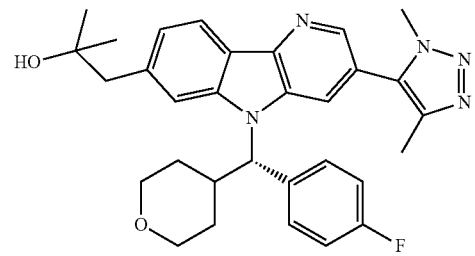 [SMILES: Cc1nnn(C)c1-c1cnc2c3ccc(CC(C)(C)O)cc3n([C@H](c3ccc(F)cc3)C3CCOCC3)c2c1]

Step 1: Ethyl 2-(3-(1,4-dimethyl-1H-1,2,3-triazol-5-yl)-5H-pyrido[3,2-b]indol-7-yl)acetate Following a procedure analogous to that described for methyl 2-(3-(1,4-dimethyl-1H-1,2,3-triazol-5-yl)-5H-pyrido[3,2-b]indol-8-yl)acetate, ethyl 2-(3-bromo-5H-pyrido[3,2-b]indol-7-yl)acetate (200 mg, 0.600 mmol) and 1,4-dimethyl-5-(tributylstannyl)-1H-1,2,3-triazole (464 mg, 1.20 mmol) were converted to the title compound (111 mg, 53%). LCMS (M+H)=350.2; HPLC RT=0.66 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: 1-[3-(Dimethyl-1H-1,2,3-triazol-5-yl)-5-[(S)-(4-fluorophenyl)(oxan-4-yl)methyl]-5H-pyrido[3,2-b]indol-7-yl]-2-methylpropan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, ethyl 2-(3-(1,4-dimethyl-1H-1,2,3-triazol-5-yl)-5H-pyrido[3,2-b]indol-7-yl)acetate (55.0 mg, 0.160 mmol) and (R)-(4-fluorophenyl)(tetrahydro-2H-pyran-4-yl)methanol (66.2 mg, 0.320 mmol) were converted to the title compound (3.20 mg, 4%). $^1$H NMR (500 MHz, DMSO-$d_6$) δ 8.50 (s, 1H), 8.11 (d, J=8.1 Hz, 1H), 7.92 (br. s., 1H), 7.73 (dd, J=8.2, 5.6 Hz, 2H), 7.20 (d, J=7.7 Hz, 1H), 7.14 (t, J=8.8 Hz, 2H), 5.77 (d, J=11.1 Hz, 1H), 4.03 (br. s., 2H), 3.90 (d, J=7.4 Hz, 1H), 3.73 (d, J=9.1 Hz, 1H), 3.53-3.35 (m, 1H), 3.26 (t, J=11.1 Hz, 1H), 2.92 (br. s., 1H), 2.31 (br. s., 3H), 1.77 (s, 1H), 1.65 (d, J=12.5 Hz, 1H), 1.56-1.46 (m, 1H), 1.35-1.22 (m, 1H), 1.20 (d, J=6.1 Hz, 1H), 1.16-1.07 (m, 6H), 1.05 (d, J=12.5 Hz, 1H), 0.99 (d, J=6.1 Hz, 1H); LCMS (M+H)=528.3; HPLC RT=0.79 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 257

5-{5-[(S)-(4-Fluorophenyl)(oxan-4-yl)methyl]-9-methanesulfonyl-5H-pyrido[3,2-b]indol-3-yl}-1,4-dimethyl-1H-1,2,3-triazole

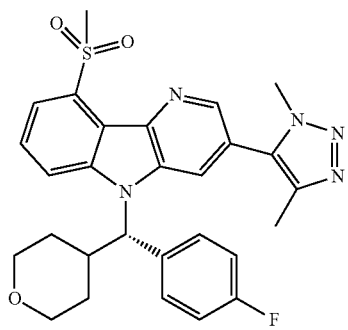 [SMILES: Cc1nnn(C)c1-c1cnc2c3c(S(C)(=O)=O)cccc3n([C@H](c3ccc(F)cc3)C3CCOCC3)c2c1]

Step 1: 4,4,5,5-Tetramethyl-2-(2-(methylsulfonyl)phenyl)-1,3,2-dioxaborolane A suspension of 1-bromo-2-(methylsulfonyl)benzene (800 mg, 3.40 mmol), bis(pinacolato)diboron (1040 mg, 4.08 mmol) and potassium acetate (668 mg, 6.81 mmol) in dioxane (4 ml) was degassed with bubbling nitrogen. $PdCl_2$(dppf)-$CH_2Cl_2$ adduct (139 mg, 0.170 mmol) was added, and the reaction was heated to 95° C. for 2 h. The reaction was diluted with EtOAc (30 mL) and filtered through Celite. The organic layer was washed with brine and dried with sodium sulfate. The solvent was evaporated, and the residue was purified by column chromatography on silica gel (40 g column, gradient from 0% to 40% EtOAc/hexanes) to give the title compound (626 mg, 65%) as a colorless oil. $^1$H NMR (400 MHz, CDCl$_3$) δ 8.03 (dd, J=7.6, 1.2 Hz, 1H), 7.72-7.67 (m, 1H), 7.61 (dtd, J=18.6, 7.4, 1.5 Hz, 2H), 5.32 (s, 1H), 3.24 (s, 3H), 1.43 (s, 12H); LCMS (M+H)=283.2; HPLC RT=0.89 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: 5-Bromo-2-(2-(methylsulfonyl)phenyl)-3-nitropyridine

Following a procedure analogous to that described for ethyl 2-(4-(5-bromo-3-nitropyridin-2-yl)phenyl)acetate, 4,4,5,5-tetramethyl-2-(3-(methylsulfonyl)phenyl)-1,3,2-dioxaborolane (620 mg, 2.20 mmol) and 2,5-dibromo-3-nitropyridine (650 mg, 2.31 mmol) were converted to the title compound (554 mg, 71%). LCMS (M+H)=359.0; HPLC RT=0.81 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 3: 3-Bromo-9-(methylsulfonyl)-5H-pyrido[3,2-b]indole

Following a procedure analogous to that described for ethyl 2-(3-bromo-5H-pyrido[3,2-b]indol-7-yl)acetate, 5-bromo-2-(2-(methylsulfonyl)phenyl)-3-nitropyridine (550 mg, 1.54 mmol) and DPPE (767 mg, 1.93 mmol) were converted to the title compound (201 mg, 40%). $^1$H NMR (400 MHz, DMSO-$d_6$) δ 12.28 (s, 1H), 8.71 (d, J=2.1 Hz, 1H), 8.36 (d, J=2.1 Hz, 1H), 8.00 (dd, J=8.3, 0.8 Hz, 1H), 7.90 (dd, J=7.5, 0.9 Hz, 1H), 7.82-7.72 (m, 1H), 3.75 (s, 3H); LCMS (M+H)=327.0; HPLC RT=0.76 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 4: 3-(1,4-Dimethyl-1H-1,2,3-triazol-5-yl)-9-(methylsulfonyl)-5H-pyrido[3,2-b]indole Following a procedure analogous to that described for 2-(3-(1,4-dimethyl-1H-1,2,3-triazol-5-yl)-5H-pyrido[3,2-b]indol-8-yl)acetate, 3-bromo-9-(methylsulfonyl)-5H-pyrido[3,2-b]indole (200 mg, 0.615 mmol) and 1,4-dimethyl-5-(tributylstannyl)-1H-1,2,3-triazole (475 mg, 1.23 mmol) were converted to the title compound (195 mg, 93%). $^1$H NMR (400 MHz, DMSO-$d_6$) δ 12.37 (s, 1H), 8.74 (d, J=1.8 Hz, 1H), 8.22 (d, J=2.0 Hz, 1H), 8.06-8.00 (m, 1H), 7.93 (dd, J=7.5, 0.7 Hz, 1H), 7.82-7.75 (m, 1H), 4.04 (s, 3H), 3.83 (s, 3H), 2.33 (s, 3H); LCMS (M+H)=342.1; HPLC RT=0.60 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 5: 5-{5-[(S)-(4-Fluorophenyl)(oxan-4-yl)methyl]-9-methanesulfonyl-5H-pyrido[3,2-b]indol-3-yl}-1,4-dimethyl-1H-1,2,3-triazole To a suspension of 3-(1,4-dimethyl-1H-1,2,3-triazol-5-yl)-9-(methylsulfonyl)-5H-pyrido[3,2-b]indole (50.0 mg, 0.146 mmol), (R)-(4-fluorophenyl)(tetrahydro-2H-pyran-4-yl)methanol (61.6 mg, 0.293 mmol), and triphenylphosphine (77.0 mg, 0.293 mmol) in THF (1.5 mL) cooled in an ice bath was added DIAD (57.0 µl, 0.293 mmol). The resulting suspension was stirred at room temperature overnight and then concentrated. The residue was purified by reverse phase HPLC (Column: Waters XBridge Phenyl, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient:

20-55% B over 25 min, then a 5-min hold at 55% B; Flow: 20 mL/min) to give the title compound (18.6 mg, 24%). ¹H NMR (500 MHz, DMSO-$d_6$) δ 8.77 (br. s., 1H), 7.96 (s, 2H), 7.88 (br. s., 1H), 7.75 (dd, J=8.1, 5.4 Hz, 2H), 7.18 (t, J=8.6 Hz, 2H), 6.04 (d, J=11.1 Hz, 1H), 4.05 (br. s., 3H), 3.91 (d, J=5.7 Hz, 1H), 3.81 (s, 3H), 3.72 (d, J=9.8 Hz, 1H), 3.49 (d, J=10.8 Hz, 1H), 3.25 (t, J=11.6 Hz, 1H), 2.33 (br. s., 3H), 1.72 (d, J=11.8 Hz, 1H), 1.58 (d, J=9.4 Hz, 1H), 1.29 (d, J=9.4 Hz, 1H), 0.94 (br. s., 1H); LCMS (M+H)=534.2; HPLC RT=0.83 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 258

2-{1-[3-(Dimethyl-1H-1,2,3-triazol-5-yl)-9-methanesulfonyl-5H-pyrido[3,2-b]indol-5-yl]-4,4,4-trifluorobutyl}pyridine

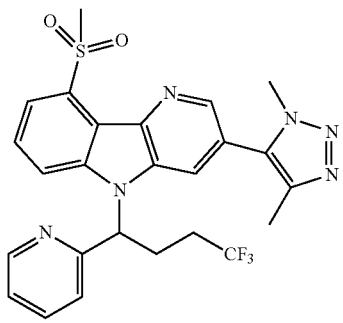 [SMILES: Cc1nnn(C)c1-c1cnc2c3c(S(C)(=O)=O)cccc3n(C(CCC(F)(F)F)c3ccccn3)c2c1]

Following a procedure analogous to that described for 5-{5-[(S)-(4-fluorophenyl)(oxan-4-yl)methyl]-9-methanesulfonyl-5H-pyrido[3,2-b]indol-3-yl}-1,4-dimethyl-1H-1,2,3-triazole, 3-(1,4-dimethyl-1H-1,2,3-triazol-5-yl)-9-(methylsulfonyl)-5H-pyrido[3,2-b]indole (50.0 mg, 0.150 mmol) and 4,4,4-trifluoro-1-(pyridin-2-yl)butan-1-ol (60.1 mg, 0.290 mmol) were converted to racemic 2-{1-[3-(dimethyl-1H-1,2,3-triazol-5-yl)-9-methanesulfonyl-5H-pyrido[3,2-b]indol-5-yl]-4,4,4-trifluorobutyl}pyridine, which was separated using chiral prep SFC (Column: Chiral OD-H 25×3 cm, 5 µm; Mobile Phase: 77/23 $CO_2$/MeOH; Flow: 85 mL/min). The slower eluting peak was concentrated to give 11.2 mg (15%). ¹H NMR (400 MHz, $CD_3OD$) δ 8.72 (d, J=1.8 Hz, 1H), 8.64 (d, J=5.6 Hz, 1H), 8.22-8.15 (m, 2H), 8.10 (d, J=7.2 Hz, 1H), 7.85-7.78 (m, 1H), 7.74 (td, J=0.7, 1.8 Hz, 1H), 7.35 (dd, J=7.1, 5.0 Hz, 1H), 7.30 (d, J=7.7 Hz, 1H), 6.44 (dd, J=10.3, 6.0 Hz, 1H), 4.01 (s, 3H), 3.80 (s, 3H), 3.16-3.06 (m, 1H), 2.99-2.86 (m, 1H), 2.49-2.36 (m, 1H), 2.30 (s, 3H), 1.97-1.83 (m, 1H); LCMS (M+H)=529.3; HPLC RT=0.85 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 259

5-{9-Methanesulfonyl-5-[(S)-oxan-4-yl(phenyl) methyl]-5H-pyrido[3,2-b]indol-3-yl}-1,4-dimethyl-1H-1,2,3-triazole

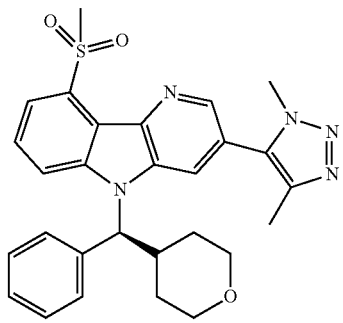 [SMILES: Cc1nnn(C)c1-c1cnc2c3c(S(C)(=O)=O)cccc3n([C@H](c3ccccc3)C3CCOCC3)c2c1]

Following a procedure analogous to that described for 5-{5-[(S)-(4-fluorophenyl)(oxan-4-yl)methyl]-9-methanesulfonyl-5H-pyrido[3,2-b]indol-3-yl}-1,4-dimethyl-1H-1,2,3-triazole, 3-(1,4-dimethyl-1H-1,2,3-triazol-5-yl)-9-(methylsulfonyl)-5H-pyrido[3,2-b]indole (50.0 mg, 0.150 mmol) and (R)-phenyl(tetrahydro-2H-pyran-4-yl)methanol (56.3 mg, 0.290 mmol) were converted to the title compound (15.0 mg, 20%). ¹H NMR (500 MHz, DMSO-$d_6$) δ 8.96 (d, J=1.3 Hz, 1H), 8.84 (d, J=8.4 Hz, 1H), 8.77 (br. s., 1H), 8.69 (s, 1H), 8.16 (d, J=7.7 Hz, 1H), 7.98-7.93 (m, 2H), 7.86 (br. s., 1H), 7.28-7.22 (m, 1H), 6.03 (d, J=11.1 Hz, 1H), 5.36 (quin, J=6.2 Hz, 1H), 4.09 (s, 3H), 3.91 (br. s., 1H), 3.81 (s, 3H), 3.72 (d, J=9.1 Hz, 1H), 3.50 (d, J=11.8 Hz, 1H), 3.26 (t, J=11.6 Hz, 1H), 2.36 (s, 3H), 1.76 (d, J=12.8 Hz, 1H), 1.63-1.56 (m, 1H), 1.31 (d, J=9.8 Hz, 1H), 0.93 (d, J=10.8 Hz, 1H); LCMS (M+H)=516.3; HPLC RT=0.83 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 260

2-[3-(Dimethyl-1H-1,2,3-triazol-5-yl)-9-methoxy-5-[(S)-oxan-4-yl(phenyl)methyl]-5H-pyrido[3,2-b] indol-7-yl]propan-2-ol

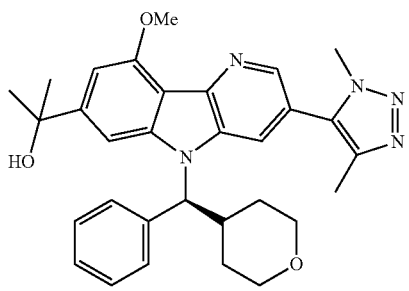 [SMILES: COc1cc(C(C)(C)O)cc2c1c1ncc(-c3c(C)nnn3C)cc1n2[C@H](c1ccccc1)C1CCOCC1]

Step 1: Methyl 3-methoxy-5-(4,4,5,5-tetramethyl-1,3,2-dioxaborolan-2-yl)benzoate Following a procedure analogous to that described for 4,4,5,5-tetramethyl-2-(2-(methylsulfonyl)phenyl)-1,3,2-dioxaborolane, methyl 4-bromo-3-methoxybenzoate (1.30 g, 5.30 mmol) and bis(pinacolato)diboron (1.62 g, 6.37 mmol) were converted to the title compound (820 mg, 53%). LCMS (M+H)=293.2; HPLC RT=0.97 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 2: Methyl 4-(5-bromo-3-nitropyridin-2-yl)-3-methoxybenzoate

Following a procedure analogous to that described for ethyl 2-(4-(5-bromo-3-nitropyridin-2-yl)phenyl)acetate, methyl 3-methoxy-5-(4,4,5,5-tetramethyl-1,3,2-dioxaborolan-2-yl)benzoate (820 mg, 2.81 mmol) and 2,5-dibromo-3-nitropyridine (831 mg, 2.95 mmol) were converted to the title compound (705 mg, 68%). LCMS (M+H)=367.0; HPLC RT=0.98 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 3: Methyl 3-bromo-9-methoxy-5H-pyrido[3,2-b]indole-7-carboxylate

Following a procedure analogous to that described for ethyl 2-(3-bromo-5H-pyrido[3,2-b]indol-7-yl)acetate, methyl 4-(5-bromo-3-nitropyridin-2-yl)-3-methoxybenzoate (620 mg, 1.69 mmol) and DPPE (841 mg, 2.11 mmol) were converted to the title compound (238 mg, 42%). $^1$H NMR (400 MHz, CD$_3$OD) δ 8.54 (d, J=2.0 Hz, 1H), 8.10 (d, J=2.0 Hz, 1H), 7.85 (d, J=1.1 Hz, 1H), 7.42 (d, J=1.0 Hz, 1H), 4.14 (s, 3H), 3.99 (s, 3H); LCMS (M+H)=335.1; HPLC RT=0.74 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 4: Methyl 3-(1,4-dimethyl-1H-1,2,3-triazol-5-yl)-9-methoxy-5H-pyrido[3,2-b]indole-7-carboxylate Following a procedure analogous to that described for 2-(3-(1,4-dimethyl-1H-1,2,3-triazol-5-yl)-5H-pyrido[3,2-b]indol-8-yl)acetate, methyl 3-bromo-9-methoxy-5H-pyrido[3,2-b]indole-7-carboxylate (235 mg, 0.700 mmol) and 1,4-dimethyl-5-(tributylstannyl)-1H-1,2,3-triazole (542 mg, 1.40 mmol) were converted to the title compound (151 mg, 61%). $^1$H NMR (400 MHz, CDCl$_3$) δ 11.76 (br. s., 1H), 8.56 (s, 1H), 7.90 (s, 1H), 7.80 (d, J=6.8 Hz, 1H), 7.42 (s, 1H), 4.19 (s, 3H), 3.95 (s, 3H), 3.91 (s, 3H), 2.30 (s, 3H); LCMS (M+H)=352.2; HPLC RT=0.61 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Step 5: 2-[3-(Dimethyl-1H-1,2,3-triazol-5-yl)-9-methoxy-5-[(S)-oxan-4-yl(phenyl)methyl]-5H-pyrido[3,2-b]indol-7-yl]propan-2-ol Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, methyl 3-(1,4-dimethyl-1H-1,2,3-triazol-5-yl)-9-methoxy-5H-pyrido[3,2-b]indole-7-carboxylate (150 mg, 0.430 mmol) and (R)-phenyl(tetrahydro-2H-pyran-4-yl)methanol (123 mg, 0.640 mmol) were converted to the title compound (7.90 mg, 4%). $^1$H NMR (400 MHz, CDCl$_3$) δ 8.54 (d, J=1.7 Hz, 1H), 7.53-7.50 (m, 2H), 7.44 (d, J=7.2 Hz, 2H), 7.37-7.31 (m, 2H), 6.95 (s, 1H), 6.37 (br. s., 2H), 5.58 (d, J=10.5 Hz, 1H), 4.21 (s, 3H), 4.07 (dd, J=12.0, 2.7 Hz, 1H), 3.86 (s, 3H), 3.61-3.51 (m, 1H), 3.40-3.30 (m, 1H), 3.08 (d, J=10.9 Hz, 1H), 2.28 (s, 3H), 2.09-2.00 (m, 2H), 1.76 (d, J=3.4 Hz, 6H), 1.66 (td, J=12.4, 4.0 Hz, 2H), 1.41 (dd, J=12.8, 4.2 Hz, 1H); LCMS (M+H)=526.5; HPLC RT=0.71 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 261

1-[3-(Dimethyl-1H-1,2,3-triazol-5-yl)-5-[(S)-oxan-4-yl(phenyl)methyl]-5H-pyrido[3,2-b]indol-7-yl]-2-methylpropan-2-ol

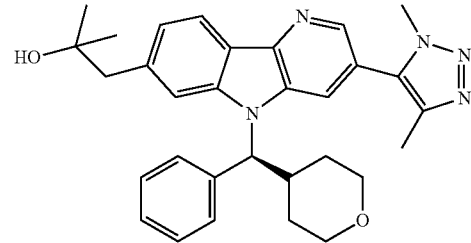 [SMILES: Cc1nnn(C)c1-c1cnc2c3ccc(CC(C)(C)O)cc3n([C@H](c3ccccc3)C3CCOCC3)c2c1]

Following procedures analogous to those described in Steps 4 and 5 of 2-[3-(dimethyl-1,2-oxazol-4-yl)-5-[oxan-4-yl(phenyl)methyl]-5H-pyrido[3,2-b]indol-7-yl]propan-2-ol, ethyl 2-(3-(1,4-dimethyl-1H-1,2,3-triazol-5-yl)-5H-pyrido[3,2-b]indol-7-yl)acetate (55.0 mg, 0.160 mmol) and (R)-phenyl(tetrahydro-2H-pyran-4-yl)methanol (60.5 mg, 0.320 mmol) were converted to the title compound (3.20 mg, 4%). $^1$H NMR (500 MHz, DMSO-d$_6$) δ 8.56 (s, 2H), 8.15 (d, J=8.1 Hz, 1H), 7.95 (s, 1H), 7.69 (d, J=7.7 Hz, 2H), 7.35-7.28 (m, 2H), 7.24 (t, J=7.7 Hz, 2H), 5.79 (d, J=11.1 Hz, 1H), 4.02 (br. s., 3H), 3.89 (d, J=7.1 Hz, 1H), 3.73 (d, J=10.1 Hz, 1H), 3.52-3.38 (m, 2H), 3.27 (t, J=11.4 Hz, 1H), 2.94 (s, 2H), 2.31 (s, 3H), 1.68 (d, J=12.8 Hz, 1H), 1.53 (d, J=9.1 Hz, 1H), 1.35-1.25 (m, 1H), 1.12 (d, J=10.4 Hz, 6H); LCMS (M+H)=510.3; HPLC RT=0.78 min (Column: BEH C18 2.1×50 mm; Mobile Phase A: Water with 0.05% TFA; Mobile Phase B: Acetonitrile with 0.05% TFA; Gradient: 2-98% B over 1.6 min; Flow: 0.8 mL/min).

Example 262

2-{3-[4-($^2$H$_3$)Methyl-1-methyl-1H-1,2,3-triazol-5-yl]-5-[(S)-oxan-4-yl(phenyl)methyl]-5H-pyrido[3,2-b]indol-7-yl}propan-2-ol

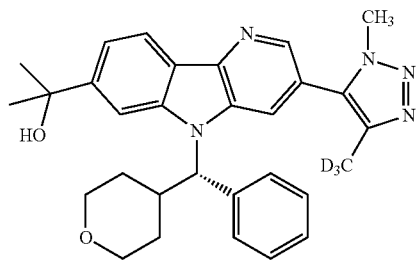 [SMILES: [2H]C([2H])([2H])c1nnn(C)c1-c1cnc2c3ccc(C(C)(C)O)cc3n([C@H](c3ccccc3)C3CCOCC3)c2c1]

Step 1: 4-($^2$H$_3$)Methyl-1-((trimethylsilyl)methyl)-1H-1,2,3-triazole

A solution of sodium ascorbate (344 mg, 1.74 mmol) in water (2170 μL) was added to a stirred solution of trimethyl ($^2$H$_3$-prop-1-yn-1-yl)silane (prepared according to PCT Int. Appl., 2007112352, 4 Oct. 2007, 200 mg, 1.74 mmol) and (azidomethyl)trimethylsilane (294 mg, 1.91 mmol) in t-BuOH (4340 μL) at ambient temperature. Copper (II) sulfate pentahydrate (87.0 mg, 0.347 mmol) in water (2170 μL) was subsequently added in a drop wise fashion. The reaction was stirred at ambient temperature for 16 h before it was diluted with water (10 mL) and ethyl acetate (20 mL). The 2 layers were separated, and the aqueous layer was washed with additional ethyl acetate (2×20 mL). The combined organics were dried over sodium sulfate, the solids were filtered away, and the volatiles were removed under reduced pressure. The crude material was purified using silica gel column chromatography with a gradient of ethyl acetate in hexanes (0-60%). 4-($^2$H$_3$)Methyl-1-((trimethylsilyl)methyl)-1H-1,2,3-triazole (125 mg, 0.725 mmol, 42%) was isolated as a colorless oil. $^1$H NMR (500 MHz, CDCl$_3$) δ 7.16 (br. s., 1H), 3.89 (s, 2H), 0.15 (s, 9H); LC/MS (M+H)=173.2; LC/MS RT=1.20 min (Column: Phenomenex Luna 30×2.0 mm 3 u; Mobile Phase A: 10:90 acetonitrile: water with 0.1% TFA; Mobile Phase B: 90:10 acetonitrile: water with 0.1% TFA; Temperature: 40° C.; Gradient: 0-100% B over 2 min; Flow: 1 mL/min).

Step 2: Methyl 3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate (S)-Methyl 3-bromo-5-(phenyl(tetrahydro-2H-pyran-4-yl)methyl)-5H-pyrido[3,2-b]indole-7-carboxylate (174 mg, 0.363 mmol), 4-($^2$H$_3$)methyl-1-((trimethylsilyl)methyl)-1H-1,2,3-triazole (125 mg, 0.725 mmol), bis(triphenylphosphine) palladium(II) chloride (25.5 mg, 0.0360 mmol), and tetramethylammonium acetate (72.5 mg, 0.544 mmol) were stirred in NMP (1810 μL) at 90° C. under N$_2$ (g) for 16 h. The reaction mixture was subsequently allowed to cool to ambient temperature before additional portions of bis(triphenylphosphine) palladium (II) chloride (25.5 mg, 0.0360 mmol) and tetramethylammonium acetate (72.5 mg, 0.544 mmol) were added. The reaction vessel was purged with N$_2$ (g) and heated for an additional 24 h. The volatiles were removed under reduced pressure, and the crude material was purified using silica gel column chromatography with a gradient of ethyl acetate in hexanes (0-100%) to afford methyl 3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate (51.0 mg, 0.102 mmol, 28%). $^1$H NMR (DMSO-d$_6$) δ: 8.73 (br. s., 1H), 8.64 (s, 1H), 8.53 (br. s, 1H), 8.37 (d, J=8.4 Hz, 1H), 7.93 (d, J=8.4 Hz, 1H), 7.67 (d, J=7.3 Hz, 2H), 7.32-7.37 (m, 2H), 7.24-7.28 (m, 1H), 6.00 (d, J=11.4 Hz, 1H), 4.02 (s, 3H), 3.97 (s, 3H), 3.86-3.93 (m, 1H), 3.72 (d, J=8.8 Hz, 1H), 3.35-3.52 (m, 2H), 3.25 (t, J=11.6 Hz, 1H), 1.59-1.77 (m, 2H), 1.27-1.40 (m, 1H), 0.96 (d, J=13.9 Hz, 1H); LC/MS (M+H)=499.3; LC/MS RT=1.10 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 3: 2-{3-[4-($^2$H$_3$)Methyl-1-methyl-1H-1,2,3-triazol-5-yl]-5-[(S)-oxan-4-yl(phenyl)methyl]-5H-pyrido[3,2-b]indol-7-yl}propan-2-ol Methyllithium (251 μl, 0.401 mmol) in Et$_2$O was added to a stirred solution of methyl 3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate (50.0 mg, 0.100 mmol) in THF (1000 μL) under N$_2$ (g) at −78° C. The reaction was stirred at that temperature for 1 h. The reaction mixture was quenched with saturated aqueous ammonium chloride (8 mL) and diluted with ethyl acetate (20 mL) while still at −78° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-100% B over 5 min, then a 20-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min. Fractions containing the desired product were combined and dried via centrifugal evaporation to afford 2-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol (6.70 mg, 0.0130 mmol, 13%). $^1$H NMR (500 MHz, DMSO-d$_6$) δ 8.50 (s, 1H), 8.41 (br. s., 1H), 8.15 (d, J=8.1 Hz, 2H), 7.67 (d, J=7.3 Hz, 2H), 7.48 (d, J=8.4 Hz, 1H), 7.36-7.29 (m, 2H), 7.28-7.21 (m, 1H), 5.82 (d, J=11.0 Hz, 1H), 5.26 (s, 1H), 4.01 (s, 3H), 3.90 (d, J=10.3 Hz, 1H), 3.75 (d, J=9.2 Hz, 1H), 3.53-3.36 (m, 2H), 3.27 (t, J=11.0 Hz, 1H), 1.72 (d, J=12.5 Hz, 1H), 1.59 (s, 7H), 1.40-1.25 (m, 1H), 1.02 (d, J=12.1 Hz, 1H);); LC/MS (M+H)=499.3; LC/MS RT=0.92 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Example 263

5-{7-Methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole

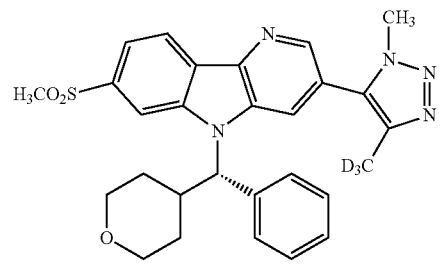

Step 1: 4-($^2$H$_3$)Methyl-1-methyl-1H-1,2,3-triazole

TBAF (60.9 ml, 60.9 mmol) was added drop wise to a stirred solution of 4-($^2$H$_3$)methyl-1-((trimethylsilyl)methyl)-

1H-1,2,3-triazole (prepared in route to methyl 3-[4-($^2$H$_3$) methyl-1-methyl-1H-1,2,3-triazol-5-yl]-5-[(S)-oxan-4-yl (phenyl)methyl]-5H-pyrido[3,2-b]indole-7-carboxylate, 8.75 g, 50.8 mmol) and water (1.83 mL, 102 mmol) in THF (203 mL) at 0° C. The reaction was stirred at that temperature for 1 h before it was removed from the cold bath and allowed to warm to ambient temperature. The reaction mixture was stirred at ambient temperature for 16 h. The volatiles were removed from the aqueous layer under reduced pressure. The resulting oil was purified using silica gel column chromatography with a gradient of methanol in ethyl acetate (0-20%). 1-Methyl-4-($^2$H$_3$)methyl-1H-1,2,3-triazole (4.67 g, 46.6 mmol, 92%) was isolated as a yellow oil. $^1$H NMR (500 MHz, DMSO-d$_6$) δ 7.76 (s, 1H), 3.98 (s, 3H); LC/MS (M+H)=101.2; LC/MS RT=0.57 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 2: 4-($^2$H$_3$)Methyl-1-methyl-5-(tributylstannyl)-1H-1,2,3-triazole n-BuLi (9.59 mL, 24.0 mmol) in hexanes was added drop wise to a stirred solution of 1-methyl-4-($^2$H$_3$)methyl-1H-1,2,3-triazole (2.00 g, 20.0 mmol) in THF (49.9 mL) at −78° C. under N$_2$ (g). A white precipitate formed upon addition. The reaction was stirred at that temperature for 30 min before tributyltin chloride (5.96 mL, 22.0 mmol) was added drop wise. The reaction was stirred for an additional 10 min before the cold bath was removed, and the reaction was allowed to warm to ambient temperature over 30 min. The reaction mixture was quenched with saturated aqueous ammonium chloride (20 mL) and diluted with 10% aqueous LiCl (20 mL). The layers were separated and the aqueous layer was washed with diethyl ether (3×30 mL). The combined organics were dried over sodium sulfate, the solids were filtered away, and the volatiles were removed under reduced pressure. The crude material was purified using silica gel column chromatography with a gradient of ethyl acetate in hexanes (0-50%). 1-Methyl-5-(tributylstannyl)-4-($^2$H$_3$)methyl-1H-1,2,3-triazole (6.02 g, 15.5 mmol, 77%) was isolated as a colorless oil. $^1$H NMR (500 MHz, DMSO-d$_6$) δ 3.97 (s, 3H), 1.62-1.39 (m, 6H), 1.35-1.25 (m, 6H), 1.24-1.10 (m, 6H), 0.91-0.83 (m, 9H).

Step 3: 5-{7-Methanesulfonyl-5-[(S)-oxan-4-yl(phenyl)methyl]-5H-pyrido[3,2-b]indol-3-yl}-4-($^2$H$_3$) methyl-1-methyl-1H-1,2,3-triazole A solution of (S)-3-bromo-7-(methylsulfonyl)-5-(phenyl (tetrahydro-2H-pyran-4-yl)methyl)-5H-pyrido[3,2-b]indole (139 mg, 0.278 mmol), 1-methyl-5-(tributylstannyl)-4-($^2$H$_3$) methyl-1H-1,2,3-triazole (119 mg, 0.306 mmol), tetrakis (triphenylphosphine)palladium(0) (32.2 mg, 0.0280 mmol), copper (I) iodide (10.6 mg, 0.0560 mmol), and triethylamine (46.6 μL, 0.334 mmol) in DMF (2783 μL) was degassed using N$_2$ (g) for 3 min. The reaction mixture was then heated to 80° C. for 16 h. The volatiles were removed under reduced pressure, and the crude material was purified using silica gel column chromatography with a gradient of methanol in ethyl acetate (0-20%). 5-{7-Methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (114.0 mg, 0.215 mmol, 77%) was isolated as a white solid. $^1$H NMR (500 MHz, DMSO-d$_6$) δ 8.78 (br. s., 1H), 8.68 (d, J=1.3 Hz, 1H), 8.56 (br. s., 1H), 8.49 (d, J=8.2 Hz, 1H), 7.88 (d, J=9.1 Hz, 1H), 7.70 (d, J=7.7 Hz, 2H), 7.38-7.33 (m, 2H), 7.30-7.24 (m, 1H), 6.03 (d, J=11.3 Hz, 1H), 4.02 (s, 3H), 3.91 (d, J=7.9 Hz, 1H), 3.74 (d, J=8.5 Hz, 1H), 3.54-3.44 (m, 2H), 3.41 (s, 3H), 3.31-3.23 (m, 1H), 1.73 (d, J=13.1 Hz, 1H), 1.68-1.56 (m, 1H), 1.44-1.30 (m, 1H), 0.97 (d, J=11.7 Hz, 1H); LC/MS (M+H)=519.3; LC/MS RT=1.41 min (Column: Phenomenex Luna 30×2.0 mm 3 u; Mobile Phase A: 10:90 acetonitrile: water with 0.1% TFA; Mobile Phase B: 90:10 acetonitrile: water with 0.1% TFA; Temperature: 40° C.; Gradient: 0-100% B over 2 min; Flow: 1 mL/min).

Examples 264-267

The compounds in Table 9 were prepared according to the procedures described for 5-{7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. Conversion of methyl ester intermediates into final compounds was carried out according to the procedure described for 2-{3-[4-($^2$H$_3$) methyl-1-methyl-1H-1,2,3-triazol-5-yl]-5-[(S)-oxan-4-yl (phenyl)methyl]-5H-pyrido[3,2-b]indol-7-yl}propan-2-ol (Step 3):

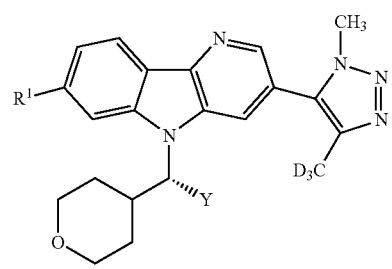

TABLE 9

| Example | R$^1$ | Y | LC/MS RT (min) | LC/MS (M+H) | LC/MS Method |
|---|---|---|---|---|---|
| 264 | CH$_3$O$_2$S— | 2-F-phenyl | 1.46 | 537.2 | A |
| 265 | CH$_3$O$_2$S— | 4-F-phenyl | 1.88 | 537.2 | B |
| 266 | HO(CH$_3$)$_2$C— | 2-F-phenyl | 1.39 | 517.3 | A |
| 267 | HO(CH$_3$)$_2$C— | 4-F-phenyl | 1.49 | 517.3 | A |

HPLC Conditions for Table 9: Method A: Column: Phenomenex Luna 30×2.0 mm 3 u; Mobile Phase A: 10:90

Example 268

5-{9-Methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole

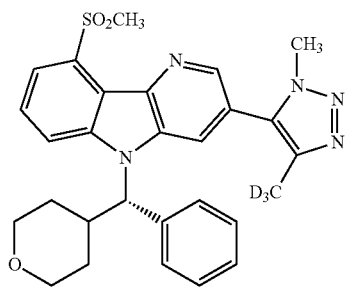 [SMILES: [2H]C([2H])([2H])c1nnn(C)c1-c1cnc2c3c(S(C)(=O)=O)cccc3n([C@H](c3ccccc3)C3CCOCC3)c2c1]

Step 1: 5-{9-Methanesulfonyl-5H-pyrido[3,2-b]indol-3-yl}-4-($^2$H$_3$)methyl-1-methyl-1H-1,2,3-triazole A solution of 3-bromo-9-methanesulfonyl-5H-pyrido[3,2-b]indole (prepared in route to 5-{5-[(2-fluorophenyl)(oxan-4-yl)methyl]-9-methanesulfonyl-5H-pyrido[3,2-b]indol-3-yl}-1,4-dimethyl-1H-1,2,3-triazole, 300 mg, 0.923 mmol), 4-($^2$H$_3$)methyl-1-methyl-5-(tributylstannyl)-1H-1,2,3-triazole (395 mg, 1.02 mmol), tetrakis(triphenylphosphine)palladium(0) (107 mg, 0.0920 mmol), copper (I) iodide (35.1 mg, 0.185 mmol), and Et$_3$N (154 μL, 1.11 mmol) in DMF (9230 μL) was degassed using N$_2$ (g) for 3 min. The reaction mixture was then heated to 80° C. for 16 h. The crude reaction mixture was purified using silica gel column chromatography with a gradient of methanol in ethyl acetate (0-5%). 5-{9-Methanesulfonyl-5H-pyrido[3,2-b]indol-3-yl}-4-($^2$H$_3$)methyl-1-methyl-1H-1,2,3-triazole (121 mg, 0.352 mmol, 38%) was isolated as a gummy solid. $^1$H NMR (500 MHz, DMSO-d$_6$) δ 12.37 (s, 1H), 8.75 (d, J=1.9 Hz, 1H), 8.23 (d, J=1.9 Hz, 1H), 8.03 (dd, J=8.2, 0.9 Hz, 1H), 7.93 (dd, J=7.5, 0.9 Hz, 1H), 7.79 (t, J=7.9 Hz, 1H), 4.05 (s, 3H), 3.83 (s, 3H); LC/MS (M+H)=345.2; LC/MS RT=1.04 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min. Method B: Column: Phenomenex Luna 30×2.0 mm 3 u; Mobile Phase A: 10:90 MeOH:water with 0.1% TFA; Mobile Phase B: 90:10 MeOH:water with 0.1% TFA; Temperature: 40° C.; Gradient: 0-100% B over 2 min; Flow: 1 mL/min.

Step 2: (R)-Cyclohexyl(phenyl)methyl methanesulfonate

Methanesulfonyl chloride (24.3 μL, 0.312 mmol) was added drop wise to a stirred solution of (R)-cyclohexyl(phenyl)methanol (prepared in route to (S)-2-[3-(dimethyl-1H-1,2,3-triazol-5-yl)-5-[oxan-4-yl(phenyl)methyl]-5H-pyrido[3,2-b]indol-7-yl]propan-2-ol, 40.0 mg, 0.208 mmol) and Et$_3$N (58.0 μL, 0.416 mmol) in DCM (2080 μL) at 0° C. under N$_2$ (g). The reaction was stirred for 15 min before the reaction vessel was removed from the cold bath, and the reaction mixture was allowed to warm to ambient temperature over 1 h. The reaction mixture was quenched with saturated aqueous NaHCO$_3$ (5 mL). The layers were separated, and the aqueous layer was washed with diethyl ether (2×7 mL). The combined organics were dried over sodium sulfate, the solids were filtered away, and the volatiles were removed under reduced pressure. The product was used without additional purification.

Step 3: 5-{9-Methanesulfonyl-5-[(S)-oxan-4-yl)phenyl)methyl]-5H-pyrido[3,2-b]indol-3-yl}-4-($^2$H$_3$)methyl-1-methyl-1H-1,2,3-triazole 5-{9-Methanesulfonyl-5H-pyrido[3,2-b]indol-3-yl}-4-($^2$H$_3$)methyl-1-methyl-1H-1,2,3-triazole (40.0 mg, 0.116 mmol), (R)-cyclohexyl(phenyl)methyl methanesulfonate (62.8 mg, 0.232 mmol), and cesium carbonate (151 mg, 0.465 mmol) were stirred in DMF (581 μL) at 60° C. under N$_2$ (g) for 16 h. The volatiles were removed under reduced pressure, and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 min, then a 5-min hold at 100% B; Flow: 20 mL/min. Fractions containing the desired product were combined and dried via centrifugal evaporation to afford 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (12.7 mg, 0.0240 mmol, 21%). $^1$H NMR (500 MHz, DMSO-d$_6$) δ 8.86-8.34 (m, 3H), 7.96 (d, J=7.0 Hz, 1H), 7.92-7.77 (m, 1H), 7.69 (d, J=7.7 Hz, 2H), 7.37-7.31 (m, 2H), 7.30-7.23 (m, 1H), 6.02 (d, J=11.0 Hz, 1H), 4.04 (br. s., 3H), 3.91 (d, J=10.6 Hz, 1H), 3.80 (s, 3H), 3.72 (d, J=8.8 Hz, 1H), 3.53-3.45 (m, 1H), 3.40 (br. s., 1H), 3.27 (t, J=11.4 Hz, 1H), 1.75 (d, J=11.4 Hz, 1H), 1.65-1.53 (m, 1H), 1.37-1.23 (m, 1H), 0.94 (d, J=11.7 Hz, 1H); LC/MS (M+H)=519.3; LC/MS RT=1.46 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 269 & 270

The compounds in Table 10 were prepared according to the procedures described for 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole:

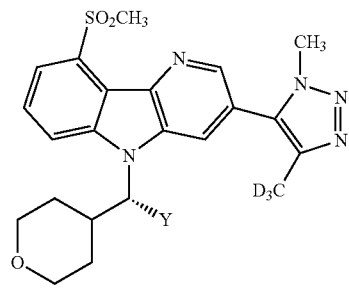

TABLE 10

| Example | Y | LC/MS RT (min) | LC/MS (M + H) | LC/MS Method |
|---|---|---|---|---|
| 269 | ![2-fluorophenyl] | 1.06 | 537.1 | A |
| 270 | ![4-fluorophenyl] | 1.49 | 537.3 | B |

HPLC Conditions for Table 10: Method A: Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min. Method B: Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min.

Example 271

2-{6-Fluoro-5-[(S)-(4-fluorophenyl)(oxan-4-yl)methyl]-3-[4-($^2H_3$)methyl-1-methyl-1H-1,2,3-triazol-5-yl]-5H-pyrido[3,2-b]indol-7-yl}propan-2-ol

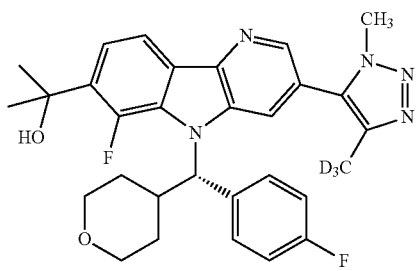 [SMILES: [2H]C([2H])([2H])c1nnn(C)c1-c1cnc2c3ccc(C(C)(C)O)c(F)c3n([C@H](c3ccc(F)cc3)C3CCOCC3)c2c1]

Step 1: Methyl 6-fluoro-5-[(S)-(4-fluorophenyl)(oxan-4-yl)methyl]-3-[4-($^2H_3$)methyl-1-methyl-1H-1,2,3-triazol-5-yl]-5H-pyrido[3,2-b]indole-7-carboxylate Methyl 6-fluoro-3-[4-($^2H_3$)methyl-1-methyl-1H-1,2,3-triazol-5-yl]-5H-pyrido[3,2-b]indole-7-carboxylate (prepared in route to (1R)-1-cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol, 12.5 mg, 0.0370 mmol), (R)-(4-fluorophenyl)(tetrahydro-2H-pyran-4-yl)methyl methanesulfonate (prepared according to Step 2 in route to 5-{9-methanesulfonyl-5-[(S)-oxan-4-yl(phenyl)methyl]-5H-pyrido[3,2-b]indol-3-yl}-4-($^2H_3$)methyl-1-methyl-1H-1,2,3-triazole, 15.8 mg, 0.0550 mmol), and cesium carbonate (29.7 mg, 0.0910 mmol) were stirred in DMF (183 µL) at 60° C. under $N_2$ (g) for 16 h. A second portion of (R)-(4-fluorophenyl)(tetrahydro-2H-pyran-4-yl)methyl methanesulfonate (15.8 mg, 0.0550 mmol) and cesium carbonate (29.7 mg, 0.0910 mmol) were added. The reaction was heated to 60° C. for an additional 16 h. The volatiles were removed under reduced pressure, and the material was used without additional purification. LC/MS (M+H)=535.4; LC/MS RT=1.66 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 2-{6-Fluoro-5-[(S)-(4-fluorophenyl)(oxan-4-yl)methyl]-3-[4-($^2H_3$)methyl-1-methyl-1H-1,2,3-triazol-5-yl]-5H-pyrido[3,2-b]indol-7-yl}propan-2-ol Methylmagnesium bromide (355 µL, 1.07 mmol, 3 M) was added to a stirred solution of methyl 6-fluoro-5-[(S)-(4-fluorophenyl)(oxan-4-yl)methyl]-3-[4-($^2H_3$)methyl-1-methyl-1H-1,2,3-triazol-5-yl]-5H-pyrido[3,2-b]indole-7-carboxylate (19.0 mg, 0.0360 mmol) in THF (355 µL) under $N_2$ (g) at −20° C. The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10 mM ammonium acetate; Gradient: 30-70% B over 15 min, then a 5-min hold at 100% B; Flow: 20 mL/min. Fractions containing the desired product were combined and dried via centrifugal evaporation to afford 2-{6-fluoro-5-[(S)-(4-fluorophenyl)(oxan-4-yl)methyl]-3-[4-($^2H_3$)methyl-1-methyl-1H-1,2,3-triazol-5-yl]-5H-pyrido[3,2-b]indol-7-yl}propan-2-ol (1.30 mg, 2.47 µmol, 7%). LC/MS (M+H)=535.4; LC/MS RT=1.49 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 272

2-{6-Fluoro-5-[(S)-(2-fluorophenyl)(oxan-4-yl)methyl]-3-[4-($^2H_3$)methyl-1-methyl-1H-1,2,3-triazol-5-yl]-5H-pyrido[3,2-b]indol-7-yl}propan-2-ol

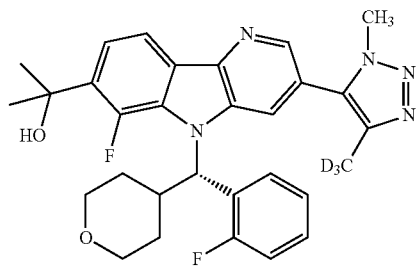 [SMILES: [2H]C([2H])([2H])c1nnn(C)c1-c1cnc2c3ccc(C(C)(C)O)c(F)c3n([C@H](c3ccccc3F)C3CCOCC3)c2c1]

2-{6-Fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol (3.60 mg, 6.73 μmol, 19%) was prepared according to the procedures described for 2-{6-fluoro-5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. LC/MS (M+H)=535.4; LC/MS RT=1.44 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 273

2-{9-Methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol

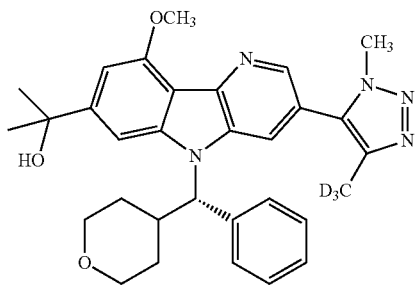 [SMILES: [2H]C([2H])([2H])c1nnn(C)c1-c1cnc2c3c(OC)cc(C(C)(C)O)cc3n([C@H](c3ccccc3)C3CCOCC3)c2c1]

Step 1: Methyl 9-methoxy-3-[4-($^2$H$_3$)methyl-1-methyl-1H-1,2,3-triazol-5-yl]-5H-pyrido[3,2-b]indole-7-carboxylate A solution of methyl 3-bromo-9-methoxy-5H-pyrido[3,2-b]indole-7-carboxylate (prepared in route to 2-[3-(dimethyl-1H-1,2,3-triazol-5-yl)-5-[(2-fluorophenyl)(oxan-4-yl)methyl]-9-methoxy-5H-pyrido[3,2-b]indol-7-yl]propan-2-ol, 300 mg, 0.895 mmol), 1-methyl-5-(tributylstannyl)-4-($^2$H$_3$)methyl-1H-1,2,3-triazole (prepared in route to 5-{7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 383 mg, 0.985 mmol), tetrakis(triphenylphosphine)palladium(0) (103 mg, 0.0900 mmol), copper (I) iodide (34.1 mg, 0.179 mmol), and Et$_3$N (150 μL, 1.07 mmol) in DMF (8950 μL) was degassed using N$_2$ (g) for 3 min. The reaction mixture was then heated to 80° C. for 16 h. The crude reaction mixture was purified using silica gel column chromatography with a gradient of methanol in ethyl acetate (0-10%). Methyl 9-methoxy-3-[4-($^2$H$_3$)methyl-1-methyl-1H-1,2,3-triazol-5-yl]-5H-pyrido[3,2-b]indole-7-carboxylate was isolated as a yellow crystalline solid (239 mg, 0.673 mmol, 75%). $^1$H NMR (400 MHz, DMSO-d$_6$) δ 11.98 (s, 1H), 8.59 (s, 1H), 8.09 (d, J=1.5 Hz, 1H), 7.85 (s, 1H), 7.32 (s, 1H), 4.08 (s, 3H), 4.01 (s, 3H), 3.93 (s, 3H); LC/MS (M+H)=555.3; LC/MS RT=1.03 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: Methyl 9-methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate Methyl 9-methoxy-3-[4-($^2$H$_3$)methyl-1-methyl-1H-1,2,3-triazol-5-yl]-5H-pyrido[3,2-b]indole-7-carboxylate (40.0 mg, 0.113 mmol), (R)-phenyl(tetrahydro-2H-pyran-4-yl)methyl methanesulfonate (prepared in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 61.0 mg, 0.226 mmol), and cesium carbonate (147 mg, 0.451 mmol) were stirred in DMF (564 μL) at 60° C. under N$_2$ (g) for 16 h. The volatiles were removed under reduced pressure, and the material was used without additional purification. LC/MS (M+H)=529.5; LC/MS RT=1.39 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 2-{9-Methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol Methylmagnesium bromide (1120 μL, 3.35 mmol) was added to a stirred solution of methyl 9-methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate (59.0 mg, 0.112 mmol) in THF (1120 μL) under N$_2$ (g) at −20° C. The reaction was stirred at that temperature for 1 h. The reaction mixture was quenched with saturated aqueous ammonium chloride (8 mL) and diluted with ethyl acetate (20 mL) while still at −20° C. The reaction mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 30-70% B over 30 min, then a 5-min hold at 100% B; Flow: 20 mL/min. Fractions containing the desired product were combined and dried via centrifugal evaporation to afford 2-{9-methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol (20.4 mg, 0.0370 mmol, 33%). $^1$H NMR (500 MHz, DMSO-d$_6$) δ 8.47 (s, 1H), 8.38-8.22 (m, 1H), 7.74-7.59 (m, 3H), 7.36-7.28 (m, 2H), 7.28-7.21 (m, 1H), 7.01 (s, 1H), 5.78 (d, J=11.4 Hz, 1H), 4.03-3.95 (m, 6H), 3.89 (d, J=12.1 Hz, 1H), 3.74 (d, J=10.6 Hz, 1H), 3.51-3.45 (m, 2H), 3.25 (t, J=11.4 Hz, 1H), 1.73 (d, J=13.6 Hz, 1H), 1.59 (d, J=6.6 Hz, 7H), 1.35-1.20 (m, 1H), 0.97 (d, J=13.2 Hz, 1H); LC/MS (M+H)=529.5; LC/MS RT=1.18 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 274 & 275

The compounds in Table 11 were prepared according to the procedures described for 2-{9-methoxy-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol:

251

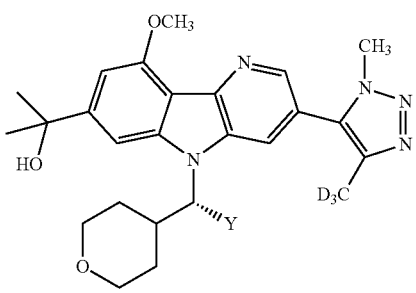

TABLE 11

| Example | Y | LC/MS RT (min) | LC/MS (M + H) | LC/MS Method |
|---|---|---|---|---|
| 274 | 2-fluorophenyl | 1.19 | 547.8 | A |
| 275 | 4-fluorophenyl | 1.21 | 547.5 | A |

HPLC Conditions for Table 11: Method A: Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min.

Example 276

2-{8-Fluoro-5-[(S)-(2-fluorophenyl)(oxan-4-yl) methyl]-3-[4-($^2$H$_3$)methyl-1-methyl-1H-1,2,3-triazol-5-yl]-5H-pyrido[3,2-b]indol-7-yl}propan-2-ol

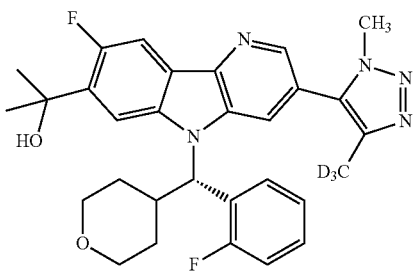 [SMILES: [2H]C([2H])([2H])c1nnn(C)c1-c1cnc2c3cc(F)c(C(C)(C)O)cc3n([C@H](c3ccccc3F)C3CCOCC3)c2c1]

Step 1: Methyl 8-fluoro-5-[(S)-(2-fluorophenyl) (oxan-4-yl)methyl]-3-[4-($^2$H$_3$)methyl-1-methyl-1H-1,2,3-triazol-5-yl]-5H-pyrido[3,2-b]indole-7-carboxylate Methyl 8-fluoro-3-[4-($^2$H$_3$)methyl-1-methyl-1H-1,2,3-triazol-5-yl]-5H-pyrido[3,2-b]indole-7-carboxylate (prepared in route to 2-[3-(dimethyl-1H-1,2,3-triazol-5-yl)-8-

252 fluoro-5-[(4-fluorophenyl)(oxan-4-yl)methyl]-5H-pyrido[3,2-b]indol-7-yl]propan-2-ol, 105 mg, 0.307 mmol), (R)-(2-fluorophenyl)(tetrahydro-2H-pyran-4-yl)methyl methanesulfonate (prepared similarly to Step 2 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole, 221 mg, 0.767 mmol), and cesium carbonate (400 mg, 1.23 mmol) were stirred in DMF (1530 µL) at 60° C. under N$_2$ (g) for 16 h. The volatiles were removed under reduced pressure, and methyl 8-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate was used without additional purification. LC/MS (M+H)=535.3; LC/MS RT=2.48 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 2-{8-Fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol Methylmagnesium bromide (2990 µL, 8.98 mmol) was added to a stirred solution of methyl 8-fluoro-5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate (160 mg, 0.299 mmol) in THF (2990 µL) under N$_2$ (g) at −20° C. The reaction was stirred at that temperature for 1 h. The reaction mixture was quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10 mM ammonium acetate; Gradient: 25-65% B over 15 min, then a 5-min hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 40-80% B over 20 min, then a 5-min hold at 100% B; Flow: 20 mL/min. Fractions containing the desired product were combined and dried via centrifugal evaporation to afford 2-{8-fluoro-5-[(S)-(2-fluorophenyl)(oxan-4-yl) methyl]-3-[4-($^2$H$_3$)methyl-1-methyl-1H-1,2,3-triazol-5-yl]-5H-pyrido[3,2-b]indol-7-yl}propan-2-ol (16.3 mg, 0.0290 mmol, 10%). $^1$H NMR (500 MHz, DMSO-d$_6$) δ 8.54 (s, 1H), 8.42 (br. s., 1H), 8.14 (br. s., 2H), 7.88 (d, J=11.0 Hz, 1H), 7.43-7.28 (m, 2H), 7.17-7.10 (m, 1H), 5.94 (br. s., 1H), 5.55 (s, 1H), 4.00 (br. s., 3H), 3.90 (d, J=9.2 Hz, 1H), 3.72 (d, J=11.0 Hz, 1H), 3.54-3.44 (m, 1H), 3.40 (br. s., 1H), 3.26-3.11 (m, 1H), 1.74 (d, J=11.7 Hz, 1H), 1.64-1.48 (m, 7H), 1.32 (d, J=11.7 Hz, 1H), 0.79 (br. s., 1H); LC/MS (M+H)=535.3; LC/MS RT=2.23 min (Column: Phenomenex Luna 30×2.0 mm 3 u; Mobile Phase A: 10:90 acetonitrile: water with 0.1% TFA; Mobile Phase B: 90:10 acetonitrile:

water with 0.1% TFA; Temperature: 40° C.; Gradient: 0-100% B over 2 min; Flow: 1 mL/min).

Example 277

2-{8-Fluoro-5-[(S)-(4-fluorophenyl)(oxan-4-yl)methyl]-3-[4-(²H₃)methyl-1-methyl-1H-1,2,3-triazol-5-yl]-5H-pyrido[3,2-b]indol-7-yl}propan-2-ol

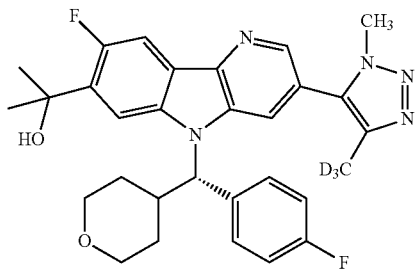 [SMILES: [2H]C([2H])([2H])c1nnn(C)c1-c1cnc2c3cc(F)c(C(C)(C)O)cc3n([C@H](c3ccc(F)cc3)C3CCOCC3)c2c1]

Step 1: 2-{8-Fluoro-5-[(S)-(4-fluorophenyl)(oxan-4-yl)methyl]-3-[4-(²H₃)methyl-1-methyl-1H-1,2,3-triazol-5-yl]-5H-pyrido[3,2-b]indol-7-yl}propan-2-ol 2-{8-Fluoro-5-[(S)-(4-fluorophenyl)(oxan-4-yl)methyl]-3-[4-(²H₃)methyl-1-methyl-1H-1,2,3-triazol-5-yl]-5H-pyrido[3,2-b]indol-7-yl}propan-2-ol (12.3 mg, 22.0 μmol, 7%) was prepared according to the procedures described for 2-{8-fluoro-5-[(S)-(2-fluorophenyl)(oxan-4-yl)methyl]-3-[4-(²H₃)methyl-1-methyl-1H-1,2,3-triazol-5-yl]-5H-pyrido[3,2-b]indol-7-yl}propan-2-ol. ¹H NMR (500 MHz, DMSO-d₆) δ 8.53 (s, 1H), 8.44 (br. s., 1H), 8.21 (br. s., 1H), 7.90 (d, J=11.0 Hz, 1H), 7.72-7.66 (m, 2H), 7.18 (t, J=8.8 Hz, 2H), 5.76 (d, J=10.6 Hz, 1H), 5.61 (s, 1H), 4.01 (s, 3H), 3.90 (d, J=8.8 Hz, 1H), 3.74 (d, J=9.2 Hz, 1H), 3.41-3.38 (m, 2H), 3.25 (t, J=11.2 Hz, 1H), 1.68 (d, J=13.2 Hz, 1H), 1.64-1.44 (m, 7H), 1.36-1.21 (m, 1H), 0.97 (d, J=12.8 Hz, 1H); LC/MS (M+H)=535.3; LC/MS RT=2.30 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 278

2-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}propan-2-ol

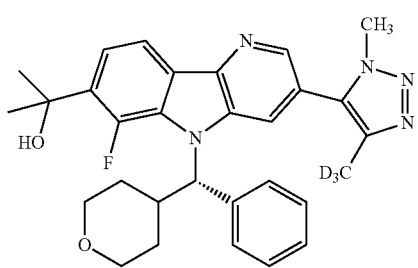 [SMILES: [2H]C([2H])([2H])c1nnn(C)c1-c1cnc2c3ccc(C(C)(C)O)c(F)c3n([C@H](c3ccccc3)C3CCOCC3)c2c1]

Step 1: 5-{7-Chloro-6-fluoro-5H-pyrido[3,2-b]indol-3-yl}-4-(²H₃)methyl-1-methyl-1H-1,2,3-triazole 5-{7-Chloro-6-fluoro-5H-pyrido[3,2-b]indol-3-yl}-4-(²H₃)methyl-1-methyl-1H-1,2,3-triazole (680 mg, 2.13 mmol, 85%) was prepared from 3-bromo-7-chloro-6-fluoro-5H-pyrido[3,2-b]indole (prepared in route to 1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol) according to Step 1 in route to 5-{9-methanesulfonyl-5-[(S)-oxan-4-yl(phenyl)methyl]-5H-pyrido[3,2-b]indol-3-yl}-4-(²H₃)methyl-1-methyl-1H-1,2,3-triazole. ¹H NMR (400 MHz, DMSO-d₆) δ 12.47 (s, 1H), 8.63 (d, J=2.0 Hz, 1H), 8.11-8.05 (m, 2H), 7.43 (dd, J=8.6, 6.4 Hz, 1H), 4.01 (s, 3H); LC/MS (M+H)=319.2; LC/MS RT=1.30 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 5-{7-Chloro-6-fluoro-5-[(S)-oxan-4-yl(phenyl)methyl]-5H-pyrido[3,2-b]indol-3-yl}-4-(²H₃)methyl-1-methyl-1H-1,2,3-triazole Di-tert-butyl azodicarboxylate (108 mg, 0.471 mmol) in THF (1 mL) was added drop wise to a stirred solution of triphenylphosphine (123 mg, 0.471 mmol) in THF (2350 μL) at 0° C. The reaction mixture was stirred for 10 min before (R)-oxan-4-yl(phenyl)methanol (prepared in route to (S)-2-[3-(dimethyl-1H-1,2,3-triazol-5-yl)-5-[oxan-4-yl(phenyl)methyl]-5H-pyrido[3,2-b]indol-7-yl]propan-2-ol, 90.0 mg, 0.471 mmol) was added in a single portion. The reaction was stirred for an additional 10 min before 3-bromo-7-chloro-6-fluoro-5H-pyrido[3,2-b]indole (75.0 mg, 0.235 mmol) in THF (1 mL) was added drop wise over an additional 10 min. The reaction mixture was allowed to warm to ambient temperature over 16 h. TFA (181 μL, 2.35 mmol) was added, and the reaction mixture was stirred for 10 min. Monobasic potassium phosphate (5 mL, 1.5 M) was added to the reaction mixture, followed by ethyl acetate (10 mL). The layers were separated, and the organics were dried over sodium sulfate. The aqueous layer was washed with ethyl acetate (2×10 mL), and the combined organics were dried over sodium sulfate. The solids were filtered away, and the volatiles were removed under reduced pressure. The crude material was purified using reverse phase preparatory HPLC (TFA/acetonitrile/water). 5-{7-Chloro-6-fluoro-5-[(S)-oxan-4-yl(phenyl)methyl]-5H-pyrido [3,2-b]indol-3-yl}-4-(²H₃)methyl-1-methyl-1H-1,2,3-triazole (116 mg, 0.235 mmol, 100%) was isolated as a yellow oil. LC/MS (M+H)=494.1; LC/MS RT=1.88 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 1-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}ethan-1-one A solution of 5-{7-chloro-6-fluoro-5-[(S)-oxan-4-yl(phenyl)methyl]-5H-pyrido[3,2-b]indol-3-yl}-4-(²H₃)methyl-1-

255 methyl-1H-1,2,3-triazole (116 mg, 0.235 mmol), tributyl(1-ethoxyvinyl)tin (170 mg, 0.471 mmol), Pd$_2$(dba)$_3$ (21.6 mg, 0.0240 mmol), tricyclohexylphosphine (13.2 mg, 0.0470 mmol), and cesium carbonate (153 mg, 0.471 mmol) in dioxane (2350 μL) was degassed with N$_2$ (g) for 3 min. The reaction mixture was subsequently stirred at 105° C. for 72 h. 1N Aqueous HCl (2 mL) was added drop wise, and the reaction mixture was stirred for 20 min. The reaction mixture was quenched with 1.5 M aqueous monobasic potassium phosphate (5 mL), and the layers were separated. The aqueous layer was washed with ethyl acetate (3×10 mL). The combined organics were dried over sodium sulfate. The solids were filtered away, and the volatiles were removed under reduced pressure. 1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-one was used without additional purification. LC/MS (M+H)=501.5; LC/MS RT=1.60 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: 2-{6-Fluoro-3-[4-($^2$H$_3$)methyl-1-methyl-1H-1,2,3-triazol-5-yl]-5-[(5)-oxan-4-yl(phenyl)methyl]-5H-pyrido[3,2-b]indol-7-yl}propan-2-ol Methylmagnesium bromide (2360 μL, 7.07 mmol) was added to a stirred solution of 1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-one (118 mg, 0.236 mmol) in THF (2360 μL) under N$_2$ (g) at −20° C. The reaction was stirred at that temperature for 1 h. The reaction mixture was quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 min, then a 5-min hold at 100% B; Flow: 20 mL/min. Fractions containing the desired product were combined and dried via centrifugal evaporation to afford 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol (11.1 mg, 0.0210 mmol, 9%). $^1$H NMR (DMSO-d$_6$) δ: 8.51 (br. s., 1H), 8.17 (br. s., 1H), 8.02 (d, J=8.1 Hz, 1H), 7.54-7.66 (m, 3H), 7.29-7.37 (m, 2H), 7.21-7.28 (m, 1H), 5.97 (br. s., 1H), 3.82-3.97 (m, 4H), 3.75 (d, J=7.7 Hz, 1H), 3.48 (t, J=11.0 Hz, 2H), 3.28 (t, J=11.6 Hz, 1H), 1.79 (d, J=11.7 Hz, 1H), 1.68 (s, 6H), 1.33 (d, J=10.6 Hz, 2H), 1.07 (d, J=12.1 Hz, 1H); LC/MS (M+H)=517.5; LC/MS RT=1.46 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

256

Example 279

2-{8-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol

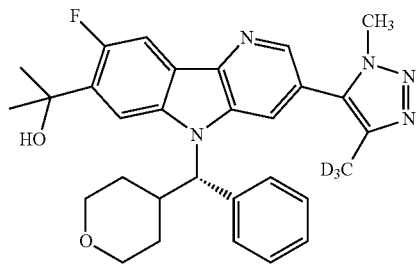 [SMILES: [2H]C([2H])([2H])c1nnn(C)c1-c1cnc2c3cc(F)c(C(C)(C)O)cc3n([C@H](c3ccccc3)C3CCOCC3)c2c1]

Step 1: 5-{7-Chloro-8-fluoro-5H-pyrido[3,2-b]indol-3-yl}-4-($^2$H$_3$)methyl-1-methyl-1H-1,2,3-triazole 5-{7-Chloro-8-fluoro-5H-pyrido[3,2-b]indol-3-yl}-4-($^2$H$_3$)methyl-1-methyl-1H-1, 2,3-triazole (334 mg, 1.05 mmol, 78%) was prepared from 3-bromo-7-chloro-8-fluoro-5H-pyrido[3,2-b]indole (prepared in route to 1-cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol) according to Step 1 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. $^1$H NMR (500 MHz, DMSO-d$_6$) δ 11.84 (s, 1H), 8.58 (d, J=1.9 Hz, 1H), 8.20 (d, J=9.0 Hz, 1H), 8.11 (d, J=1.9 Hz, 1H), 7.85 (d, J=6.0 Hz, 1H), 4.01 (s, 1H); LC/MS (M+H)=319.2; LC/MS RT=1.28 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 5-{7-Chloro-8-fluoro-5-[(S)-oxan-4-yl(phenyl)methyl]-5H-pyrido[3,2-b]indol-3-yl}-4-($^2$H$_3$)methyl-1-methyl-1H-1,2,3-triazole 5-{7-Chloro-8-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (60.7 mg, 0.123 mmol, 78%) was prepared from 5-{7-chloro-8-fluoro-5H-pyrido[3,2-b]indol-3-yl}-4-($^2$H$_3$)methyl-1-methyl-1H-1,2,3-triazole according to Step 2 in route to 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. LC/MS (M+H)=493.5; LC/MS RT=1.74 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 1-{8-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-one 1-{8-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-one was prepared from 5-{7-chloro-8-fluoro-5-[(S)-oxan-4-yl(phenyl)methyl]-5H-pyrido[3,2-b]

indol-3-yl}-4-($^2$H$_3$)methyl-1-methyl-1H-1,2,3-triazole according to Step 3 in route to 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. LC/MS (M+H)=501.3; LC/MS RT=1.15 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 4: 2-{8-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol 2-{8-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol (4.40 mg, 8.52 μmol, 17%) was prepared from 1-{8-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-one according to Step 4 in route to 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. $^1$H NMR (DMSO-d$_6$) δ: 8.53 (s, 1H), 8.38-8.49 (m, 1H), 8.20-8.27 (m, 1H), 7.89 (d, J=11.0 Hz, 1H), 7.66 (d, J=7.7 Hz, 2H), 7.31-7.39 (m, 2H), 7.23-7.30 (m, 1H), 5.74 (d, J=11.4 Hz, 1H), 4.01 (s, 3H), 3.90 (d, J=10.6 Hz, 1H), 3.74 (d, J=9.5 Hz, 1H), 3.46 (t, J=11.6 Hz, 1H), 3.32-3.39 (m, 1H), 3.26 (t, J=11.2 Hz, 1H), 1.71 (d, J=12.5 Hz, 1H), 1.48-1.65 (m, 7H), 1.31 (d, J=9.2 Hz, 1H), 0.98 (d, J=12.5 Hz, 1H); LC/MS (M+H)=517.3; LC/MS RT=1.45 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 280 & 281

2-{5-[(2,4-Difluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol

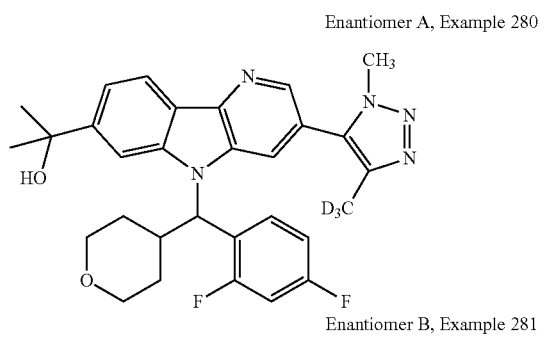

Enantiomer A, Example 280

Enantiomer B, Example 281

Step 1: Methyl 3-[4-($^2$H$_3$)methyl-1-methyl-1H-1,2,3-triazol-5-yl]-5H-pyrido[3,2-b]indole-7-carboxylate Methyl 3-[4-($^2$H$_3$)methyl-1-methyl-1H-1,2,3-triazol-5-yl]-5H-pyrido[3,2-b]indole-7-carboxylate (400 mg, 1.23 mmol, 100%) was prepared from methyl 3-bromo-5H-pyrido[3,2-b]indole-7-carboxylate according to Step 1 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. $^1$H NMR (500 MHz, DMSO-d$_6$) δ: 11.94 (s, 1H), 8.62 (d, J=1.7 Hz, 1H), 8.36 (d, J=8.2 Hz, 1H), 8.26 (dd, J=1.3, 0.7 Hz, 1H), 8.17 (d, J=1.9 Hz, 1H), 7.91 (dd, J=8.2, 1.4 Hz, 1H), 4.03 (s, 3H), 3.94 (s, 3H).

Step 2: Methyl 5-[(2,4-difluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate Methyl 5-[(2,4-difluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate was prepared from methyl 3-[4-($^2$H$_3$)methyl-1-methyl-1H-1,2,3-triazol-5-yl]-5H-pyrido[3,2-b]indole-7-carboxylate and (2,4-difluorophenyl)(oxan-4-yl)methanol (prepared in route to 2-{5-[(2,4-difluorophenyl)(oxan-4-yl)methyl]-3-(dimethyl-1,2-oxazol-4-yl)-5H-pyrido[3,2-b]indol-7-yl}propan-2-ol) according to Step 2 in route to 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. LC/MS (M+H)=535.1; LC/MS RT=1.15 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 3: 2-{5-[(2,4-Difluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol 2-{5-[(2,4-Difluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol was prepared from methyl 5-[(2,4-difluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate according to Step 2 in route to 2-{6-fluoro-5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. Enantiomers A and B were separated using chiral SFC (Column: Chiralcel OD-H preparative column, 30×250 mm, 5 μm; Mobile Phase: 15% methanol in CO$_2$, 150 bar; Flow: 70 mL/min; Temperature 35° C.). The first eluting enantiomer was defined as Enantiomer A (11.4 mg, 0.0210 mmol, 13%), and the second eluting enantiomer was defined as Enantiomer B (13.7 mg, 0.0250 mmol, 15%). $^1$H NMR (DMSO-d$_6$) δ: 8.35-8.72 (m, 2H), 8.28 (d, J=7.0 Hz, 1H), 8.15 (d, J=8.4 Hz, 1H), 7.98 (br. s, 1H), 7.47 (d, J=7.7 Hz, 1H), 7.12-7.24 (m, 2H), 5.99 (d, J=11.0 Hz, 1H), 4.02 (br. s., 3H), 3.85-3.94 (m, 1H), 3.72 (d, J=8.8 Hz, 1H), 3.34-3.54 (m, 2H), 3.14-3.25 (m, 2H), 1.66-1.78 (m, 1H), 1.45-1.66 (m, 6H), 1.28-1.42 (m, 1H), 0.74-0.89 (m, 1H); LC/MS (M+H)=535.6; LC/MS RT=1.32 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 282 & 283

2-{5-[(2,4-Difluorophenyl)(oxan-4-yl)methyl]-6-fluoro-3-[4-($^2$H$_3$)methyl-1-methyl-1H-1,2,3-triazol-5-yl]-5H-pyrido[3,2-b]indol-7-yl}propan-2-ol

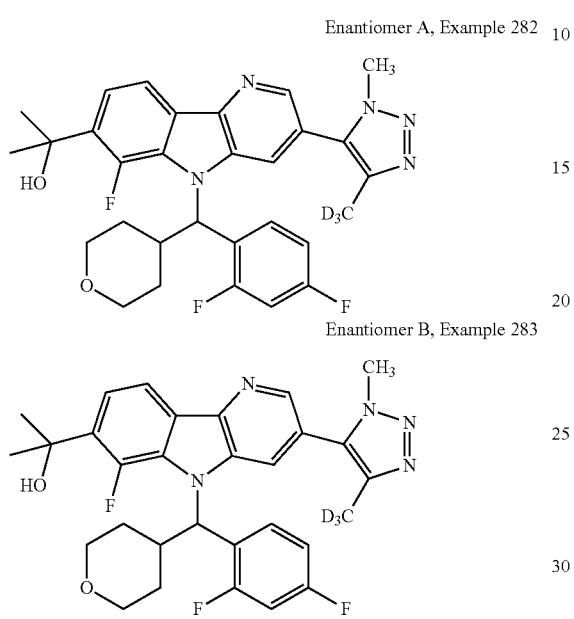

Enantiomer A, Example 282

Enantiomer B, Example 283

Step 1: 2-{5-[(2,4-Difluorophenyl)(oxan-4-yl)methyl]-6-fluoro-3-[4-($^2$H$_3$)methyl-1-methyl-1H-1,2,3-triazol-5-yl]-5H-pyrido[3,2-b]indol-7-yl}propan-2-ol 2-{5-[(2,4-Difluorophenyl)(oxan-4-yl)methyl]-6-fluoro-3-[4-($^2$H$_3$)methyl-1-methyl-1H-1,2,3-triazol-5-yl]-5H-pyrido[3,2-b]indol-7-yl}propan-2-ol was prepared from previously described starting materials following the route to 2-{5-[(2,4-difluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. Enantiomers A and B were separated using chiral preparatory HPLC (Column: Chiralpak OD 21×250 mm 10 u; Mobile Phase: 13% ethanol in heptane with 0.1% diethylamine; Flow: 15 mL/min). The first eluting enantiomer was defined as Enantiomer A (3.50 mg, 6.33 µmol, 6%), and the second eluting enantiomer was defined as Enantiomer B (3.70 mg, 6.70 µmol, 6%). $^1$H NMR (DMSO-d$_6$) δ: 8.49-8.56 (m, 1H), 8.22-8.33 (m, 1H), 8.07-8.14 (m, 1H), 8.00 (d, J=8.4 Hz, 1H), 7.58-7.68 (m, 1H), 7.10-7.24 (m, 2H), 6.17-6.30 (m, 1H), 3.85-3.95 (m, 4H), 3.71-3.83 (m, 1H), 3.25 (t, J=11.9 Hz, 1H), 3.17 (d, J=4.8 Hz, 2H), 1.74-1.81 (m, 1H), 1.66 (br. s., 6H), 1.31-1.43 (m, 2H), 0.99-1.09 (m, 1H); LC/MS (M+H)=553.3; LC/MS RT=1.50 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 284

2-{5-[(S)-(4-Fluorophenyl)(oxan-4-yl)methyl]-3-[5-($^2$H$_3$)methyl-3-methyl-1,2-oxazol-4-yl]-5H-pyrido[3,2-b]indol-7-yl}propan-2-ol

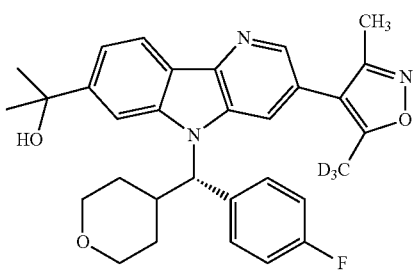 [SMILES: [2H]C([2H])([2H])c1onc(C)c1-c1cnc2c3ccc(C(C)(C)O)cc3n([C@H](c3ccc(F)cc3)C3CCOCC3)c2c1]

Step 1: Methyl 3-(dimethyl-1,2-oxazol-4-yl)-5-[(S)-(4-fluorophenyl)(oxan-4-yl)methyl]-5H-pyrido[3,2-b]indol-7-carboxylate Methyl 3-(dimethyl-1,2-oxazol-4-yl)-5-[(S)-(4-fluorophenyl)(oxan-4-yl)methyl]-5H-pyrido[3,2-b]indol-7-carboxylate was prepared from methyl 3-(dimethyl-1,2-oxazol-4-yl)-5H-pyrido[3,2-b]indol-7-carboxylate (prepared in route to 2-[3-(dimethyl-1,2-oxazol-4-yl)-5-[oxan-4-yl(phenyl)methyl]-5H-pyrido[3,2-b]indol-7-yl]propan-2-ol) and (R)-(4-fluorophenyl)(tetrahydro-2H-pyran-4-yl)methyl methanesulfonate according to Steps 2 and 3 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole). LC/MS (M+H)=514.3; LC/MS RT=1.71 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2

2-[3-(Dimethyl-1,2-oxazol-4-yl)-5-[(S)-(4-fluorophenyl)(oxan-4-yl)methyl]-5H-pyrido[3,2-b]indol-7-yl]propan-2-ol 2-[3-(Dimethyl-1,2-oxazol-4-yl)-5-[(S)-(4-fluorophenyl)(oxan-4-yl)methyl]-5H-pyrido[3,2-b]indol-7-yl]propan-2-ol (40.0 mg, 0.0780 mmol, 50%) was prepared from methyl 3-(dimethyl-1,2-oxazol-4-yl)-5-[(S)-(4-fluorophenyl)(oxan-4-yl)methyl]-5H-pyrido[3,2-b]indole-7-carboxylate according to Step 2 in route to 2-{6-fluoro-5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. LC/MS (M+H)=514.3; LC/MS RT=1.36 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 2-{5-[(S)-(4-Fluorophenyl)(oxan-4-yl)methyl]-3-[5-($^2$H$_3$)methyl-3-methyl-1,2-oxazol-4-yl]-5H-pyrido[3,2-b]indol-7-yl}propan-2-ol 2-[3-(Dimethyl-1,2-oxazol-4-yl)-5-[(S)-(4-fluorophenyl)(oxan-4-yl)methyl]-5H-pyrido[3,2-b]indol-7-yl]propan-2-ol (40.0 mg, 0.0780 mmol) and sodium tert-butoxide (44.9 mg, 0.467 mmol) were stirred in CD₃OD (779 μL) at 80° C. for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 min, then a 5-min hold at 100% B; Flow: 20 mL/min. Fractions containing the desired product were combined and dried via centrifugal evaporation to afford 2-{5-[(S)-(4-fluorophenyl)(oxan-4-yl)methyl]-3-[5-(²H₃)methyl-3-methyl-1,2-oxazol-4-yl]-5H-pyrido[3,2-b]indol-7-yl}propan-2-ol (8.40 mg, 0.0160 mmol, 20%). ¹H NMR (500 MHz, DMSO-d₆) δ 8.42 (s, 1H), 8.23 (br. s., 1H), 8.12 (d, J=8.1 Hz, 2H), 7.75-7.63 (m, 2H), 7.45 (d, J=8.1 Hz, 1H), 7.16 (t, J=8.6 Hz, 2H), 5.80 (d, J=11.0 Hz, 1H), 3.90 (d, J=5.1 Hz, 1H), 3.74 (d, J=11.0 Hz, 1H), 3.54-3.29 (m, 4H), 3.25 (t, J=11.6 Hz, 1H), 2.30 (s, 3H), 1.69 (d, J=12.5 Hz, 1H), 1.58 (s, 6H), 1.30 (d, J=8.8 Hz, 1H), 0.99 (d, J=12.5 Hz, 1H); LC/MS (M+H)=517.3; LC/MS RT=1.36 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 285

2-{5-[(S)-(2-Fluorophenyl)(oxan-4-yl)methyl]-3-[5-(²H₃)methyl-3-methyl-1,2-oxazol-4-yl]-5H-pyrido[3,2-b]indol-7-yl}propan-2-ol

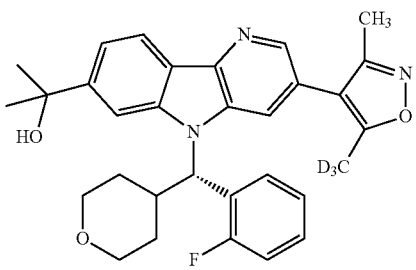 [SMILES: [2H]C([2H])([2H])c1onc(C)c1-c1cnc2c3ccc(C(C)(C)O)cc3n([C@H](c3ccccc3F)C3CCOCC3)c2c1]

2-{5-[(S)-(2-Fluorophenyl)(oxan-4-yl)methyl]-3-[5-(²H₃)methyl-3-methyl-1,2-oxazol-4-yl]-5H-pyrido[3,2-b]indol-7-yl}propan-2-ol (23.0, 0.0450 mmol, 38%) was prepared according to the procedures described for 2-{5-[(S)-(4-fluorophenyl)(oxan-4-yl)methyl]-3-[5-(²H₃)methyl-3-methyl-1,2-oxazol-4-yl]-5H-pyrido[3,2-b]indol-7-yl}propan-2-ol. ¹H NMR (500 MHz, DMSO-d₆) δ 8.42 (s, 1H), 8.30-8.07 (m, 3H), 7.95 (s, 1H), 7.44 (d, J=8.1 Hz, 1H), 7.39-7.26 (m, 2H), 7.11 (t, J=9.4 Hz, 1H), 5.98 (d, J=11.4 Hz, 1H), 3.90 (d, J=5.9 Hz, 1H), 3.72 (d, J=11.0 Hz, 1H), 3.55-3.32 (m, 3H), 3.27-3.14 (m, 1H), 2.29 (br. s., 3H), 1.74 (d, J=12.8 Hz, 1H), 1.67-1.43 (m, 7H), 1.43-1.25 (m, 1H), 0.81 (d, J=12.1 Hz, 1H); LC/MS (M+H)=517.4; LC/MS RT=1.37 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 286 & 287

2-[3-(Dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol Enantiomer A, Example 286

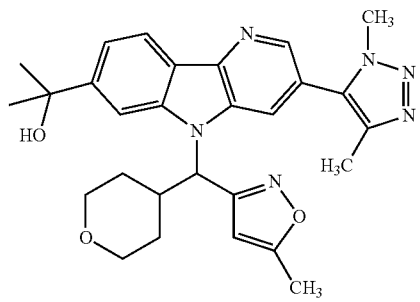

Enantiomer B, Example 287

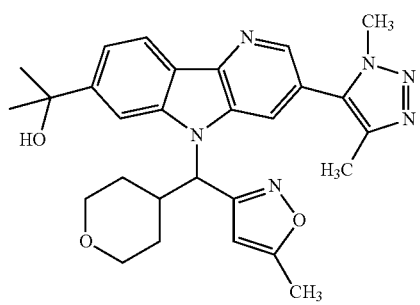

Step 1: (5-Methyl-1,2-oxazol-3-yl)(oxan-4-yl)methanol

4-Bromooxane (270 μL, 2.42 mmol) was added drop wise to a stirred suspension of magnesium (58.9 mg, 2.42 mmol) and one crystal of iodine in THF (1700 μL) at ambient temperature. The reaction mixture was stirred for 1 h before 5-methyl-1,2-oxazole-3-carbaldehyde (119 μL, 1.28 mmol) was added in a single portion. The reaction mixture was then stirred for 16 h. The reaction mixture was quenched with a minimum amount of saturated aqueous ammonium chloride (5 mL), and the volatiles were removed under reduced pressure. The crude reaction material was purified using reverse phase preparatory HPLC (TFA/acetonitrile/water). (5-Methyl-1,2-oxazol-3-yl)(oxan-4-yl)methanol (90.9 mg, 0.461 mmol, 36%) was isolated as a colorless oil. LC/MS (M+H)=198.2; LC/MS RT=0.84 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: (5-Methyl-1,2-oxazol-3-yl)(oxan-4-yl)methyl methanesulfonate (5-Methyl-1,2-oxazol-3-yl)(oxan-4-yl)methyl methanesulfonate (119 mg, 0.431 mmol, 94%) was prepared from (5-methyl-1,2-oxazol-3-yl)(oxan-4-yl)methanol according to Step 2 in route to 5-{9-methanesulfonyl-5-[(S)-oxan-4-yl(phenyl)methyl]-5H-pyrido[3,2-b]indol-3-yl}-4-(²H₃)methyl-1-methyl-1H-1,2,3-triazole. ¹H NMR (400 MHz, DMSO-d₆) δ 6.37 (s, 1H), 5.46 (d, J=7.8 Hz, 1H), 3.92-3.79 (m, 2H), 3.42-3.18 (m, 2H), 3.16 (s, 3H), 2.42 (s, 3H), 2.12 (dtd, J=11.5, 7.6, 3.9 Hz, 1H), 1.70 (d, J=11.8 Hz, 1H), 1.47-1.18 (m, 2H), 0.98 (br. s., 1H).

Step 3: Methyl 3-(dimethyl-1H-1,2,3-triazol-5-yl)-5-[(5-methyl-1,2-oxazol-3-yl)(oxan-4-yl)methyl]-5H-pyrido[3,2-b]indole-7-carboxylate Methyl 3-(dimethyl-1H-1,2,3-triazol-5-yl)-5-[(5-methyl-1,2-oxazol-3-yl)(oxan-4-yl)methyl]-5H-pyrido[3,2-b]indole-7-carboxylate was prepared from (5-methyl-1,2-oxazol-3-yl)(oxan-4-yl)methyl methanesulfonate and methyl 3-(dimethyl-1H-1,2,3-triazol-5-yl)-5H-pyrido[3,2-b]indole-7-carboxylate (prepared in route to 2-[3-(dimethyl-1H-1,2,3-triazol-5-yl)-5-[oxan-4-yl(phenyl)methyl]-5H-pyrido[3,2-b]indol-7-yl]propan-2-ol) according to Step 3 in route to 5-{9-methanesulfonyl-5-[(S)-oxan-4-yl(phenyl)methyl]-5H-pyrido[3,2-b]indol-3-yl}-4-($^2$H₃)methyl-1-methyl-1H-1,2,3-triazole. LC/MS (M+H)=501.3; LC/MS RT=1.42 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: 2-[3-(Dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol 2-[3-(Dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol was prepared from methyl 3-(dimethyl-1H-1,2,3-triazol-5-yl)-5-[(5-methyl-1,2-oxazol-3-yl)(oxan-4-yl)methyl]-5H-pyrido[3,2-b]indole-7-carboxylate according to Step 3 in route to 2-{3-[4-($^2$H₃)methyl-1-methyl-1H-1,2,3-triazol-5-yl]-5-[(S)-oxan-4-yl(phenyl)methyl]-5H-pyrido[3,2-b]indol-7-yl}propan-2-ol. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 30 min, then a 5-min hold at 100% B; Flow: 20 mL/min. Fractions containing the desired product were combined and dried via centrifugal evaporation to afford racemic 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol. Enantiomers A and B were separated using chiral preparatory HPLC (Column: Chiralpak OD 21×250 mm 10 u; Mobile Phase: 10% ethanol in heptane with 0.1% diethylamine; Flow: 15 mL/min). The first eluting enantiomer was defined as Enantiomer A (6.10 mg, 0.0120 mmol, 4%), and the second eluting enantiomer was defined as Enantiomer B (6.00 mg, 0.0120 mmol, 4%). ¹H NMR (500 MHz, DMSO-d₆) δ 8.56 (d, J=1.5 Hz, 1H), 8.34 (br. s., 1H), 8.17 (d, J=8.1 Hz, 1H), 8.04 (br. s., 1H), 7.50 (d, J=8.1 Hz, 1H), 6.30 (br. s., 1H), 5.97 (d, J=11.0 Hz, 1H), 4.04 (s, 3H), 3.92 (d, J=6.6 Hz, 1H), 3.69 (d, J=8.1 Hz, 1H), 3.41 (t, J=10.8 Hz, 1H), 3.19 (q, J=11.9 Hz, 2H), 2.35-2.28 (m, 6H), 1.71-1.59 (m, 1H), 1.56 (s, 6H), 1.33-1.15 (m, 2H), 0.86 (d, J=10.3 Hz, 1H); LC/MS (M+H)=501.3; LC/MS RT=1.19 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 288-307

The compounds in Table 12 were prepared from commercially available or previously described starting materials according to analogous procedures described for 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol, 2-{6-fluoro-3-[4-($^2$H₃)methyl-1-methyl-1H-1,2,3-triazol-5-yl]-5-[(S)-oxan-4-yl(phenyl)methyl]-5H-pyrido[3,2-b]indol-7-yl}propan-2-ol, or 2-{5-[(S)-(4-fluorophenyl)(oxan-4-yl)methyl]-3-[5-($^2$H₃)methyl-3-methyl-1,2-oxazol-4-yl]-5H-pyrido[3,2-b]indol-7-yl}propan-2-ol:

TABLE 12

| Example | Structure | HPLC RT (min) | HPLC Method | MS (M + H) |
|---|---|---|---|---|
| 288 Enantiomer A | 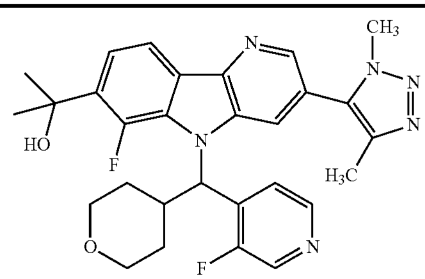 | 29.60 | A | 533.3 |
| 289 Enantiomer B | 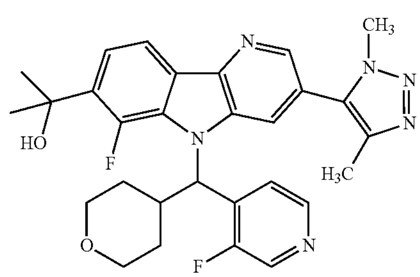 [SMILES: Cc1nnn(C)c1-c1cnc2c3ccc(C(C)(C)O)c(F)c3n(C(c3ccncc3F)C3CCOCC3)c2c1] | 36.73 | A | 533.3 |

TABLE 12-continued

| Example | Structure | HPLC RT (min) | HPLC Method | MS (M + H) |
|---|---|---|---|---|
| 290 Enantiomer B | 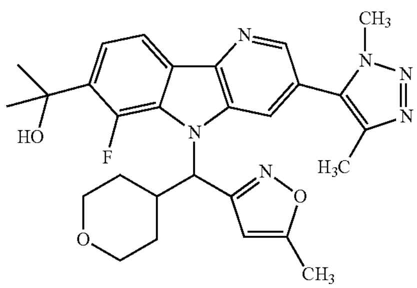 [SMILES: Cc1cc(C(C2CCOCC2)n2c3cc(-c4c(C)nnn4C)cnc3c3ccc(C(C)(C)O)c(F)c32)no1] | 22.68 | B | 519.3 |
| 291[A] | 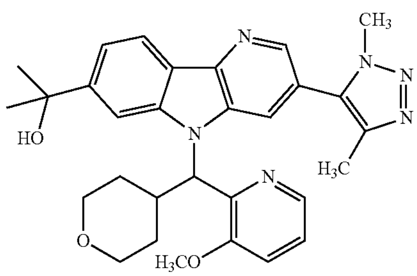 [SMILES: COc1cccnc1C(C1CCOCC1)n1c2cc(C(C)(C)O)ccc2c2ncc(-c3c(C)nnn3C)cc21] | 2.06 | C | 527.3 |
| 292[A] Enantiomer A | 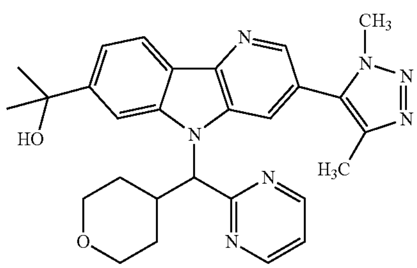 [SMILES: Cc1nnn(C)c1-c1cnc2c3ccc(C(C)(C)O)cc3n(C(c3ncccn3)C3CCOCC3)c2c1] | 1.88 | D | 498.3 |
| 293[A] Enantiomer A | 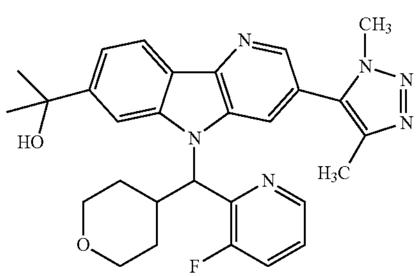 | 17.94 | E | 515.3 |
| 294[A] Enantiomer B | 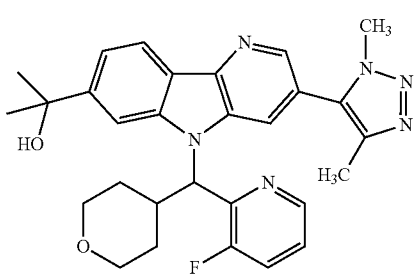 | 25.67 | E | 515.3 |

TABLE 12-continued

| Example | Structure | HPLC RT (min) | HPLC Method | MS (M + H) |
|---|---|---|---|---|
| 295[A] Enantiomer A | 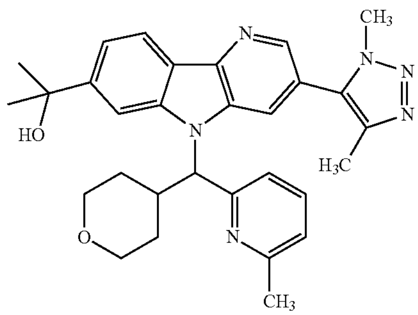 [SMILES: Cc1cccc(C(C2CCOCC2)n2c3cc(C(C)(C)O)ccc3c3ncc(-c4c(C)nnn4C)cc32)n1] | 15.41 | E | 511.3 |
| 296[A] Enantiomer A | 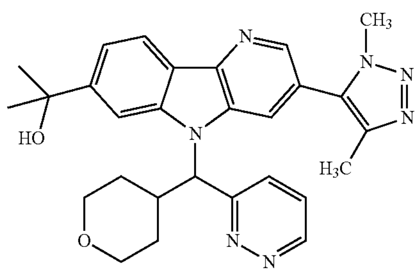 [SMILES: Cc1nnn(C)c1-c1cnc2c3ccc(C(C)(C)O)cc3n(C(c3cccnn3)C3CCOCC3)c2c1] | 19.86 | E | 498.4 |
| 297[A] Enantiomer A | 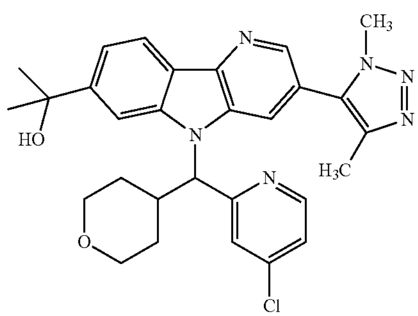 | 12.58 | F | 531.4 |
| 298[A] Enantiomer B | 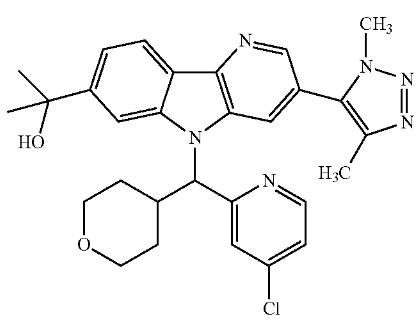 | 16.29 | F | 531.4 |
| 299[A,B] Enantiomer A | 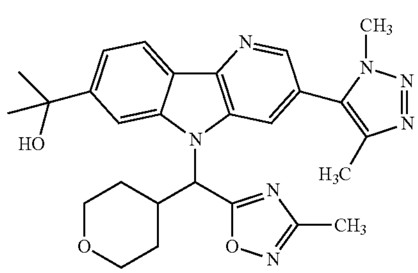 [SMILES: Cc1noc(C(C2CCOCC2)n2c3cc(C(C)(C)O)ccc3c3ncc(-c4c(C)nnn4C)cc32)n1] | 18.75 | G | 502.5 |

TABLE 12-continued

| Example | Structure | HPLC RT (min) | HPLC Method | MS (M + H) |
|---|---|---|---|---|
| 300[A,B] Enantiomer B | 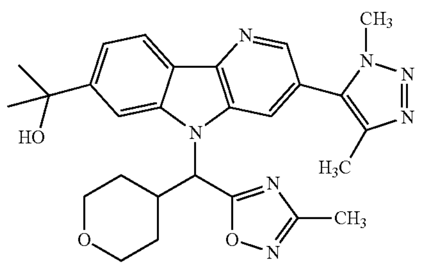 [SMILES: Cc1noc(C(C2CCOCC2)n2c3cc(C(C)(C)O)ccc3c3ncc(-c4c(C)nnn4C)cc32)n1] | 22.33 | G | 502.5 |
| 301[A] Enantiomer A | 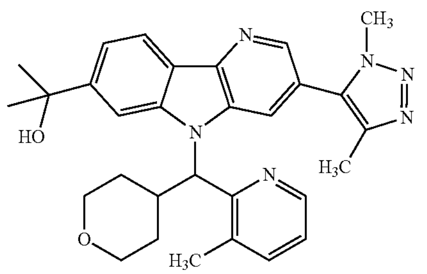 [SMILES: Cc1cccnc1C(C1CCOCC1)n1c2cc(C(C)(C)O)ccc2c2ncc(-c3c(C)nnn3C)cc21] | 12.25 | E | 511.5 |
| 302[A] Enantiomer B | 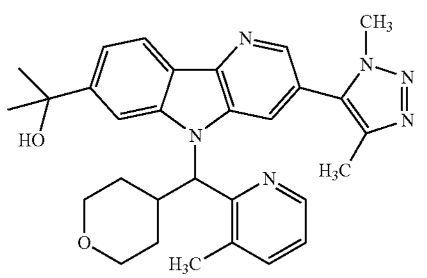 [SMILES: Cc1cccnc1C(C1CCOCC1)n1c2cc(C(C)(C)O)ccc2c2ncc(-c3c(C)nnn3C)cc21] | 16.01 | E | 511.5 |
| 303[A] Enantiomer A | 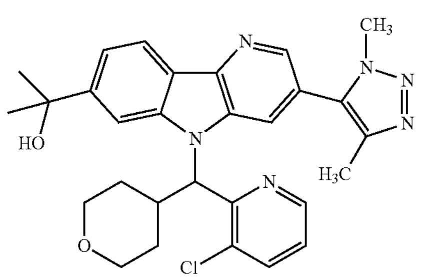 | 1.44 | H | 531.4 |
| 304[A] Enantiomer B | 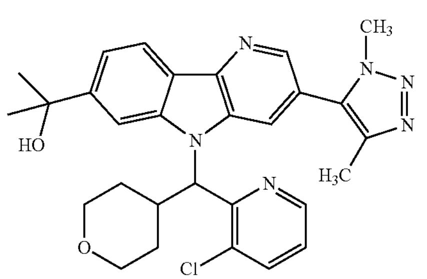 [SMILES: Cc1nnn(C)c1-c1cnc2c3ccc(C(C)(C)O)cc3n(C(c3ncccc3Cl)C3CCOCC3)c2c1] | 1.44 | H | 531.4 |

TABLE 12-continued

| Example | Structure | HPLC RT (min) | HPLC Method | MS (M + H) |
|---|---|---|---|---|
| 305[4] Enantiomer B | 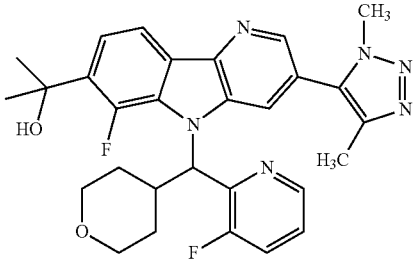 | 80.08 | I | 533.5 |
| 306 Enantiomer A | 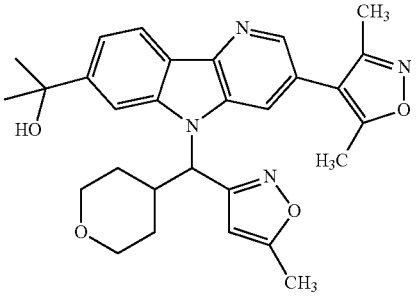 [SMILES: Cc1cc(C(C2CCOCC2)n2c3cc(C(C)(C)O)ccc3c3ncc(-c4c(C)noc4C)cc32)no1] | 34.43 | J | 501.5 |
| 307 Enantiomer B | 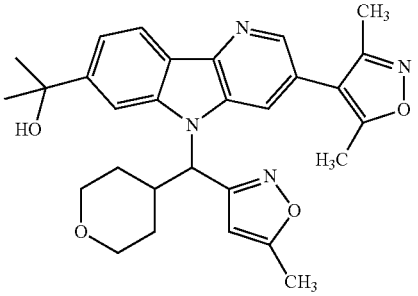 [SMILES: Cc1cc(C(C2CCOCC2)n2c3cc(C(C)(C)O)ccc3c3ncc(-c4c(C)noc4C)cc32)no1] | 39.51 | J | 501.5 |

Footnote A: Final compounds were prepared using methyllithium according to Step 3 in route to 2-{3-[4-($^{2}$H$_{3}$)methyl-1-methyl-1H-1,2,3-triazol-5-yl]-5-[(S)-oxan-4-yl(phenyl)methyl]-5H-pyrido[3,2-b]indol-7-yl}propan-2-ol. Footnote B: (3-Methyl-1,2,4-oxadiazol-5-yl)(oxan-4-yl)methanol prepared according to Amarasinghe, K. D. D.; et al. *Tetrahedron Lett.* 2006, 47, 3629-3631.

HPLC Conditions for Table 12: Method A: Column: Chiralcel OD 21×250 mm 10 μm; Mobile Phase: 20:80 ethanol:heptane with 0.1% diethylamine; Flow: 15 mL/min. Method B: Column: Chiralcel AD-H preparative column, 30×250 mm, 5 μm; Mobile Phase: 10% methanol in CO$_2$, 100 Bar; Flow: 70 mL/min. Method C: Column: Phenomenex Luna C18 50×2.0 MM 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 4 min; Flow: 0.8 mL/min. Method D: Column: Phenomenex Luna C18 50×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 4 min; Flow: 0.8 mL/min. Method E: Column: Chiralcel OD 21×250 mm 10 μm; Mobile Phase: 15:85 ethanol:heptane with 0.1% diethylamine; Flow: 15 mL/min. Method F: Column: Chiralcel OD-H preparative column, 30×250 mm, 5 μm; Mobile Phase: 20% methanol in CO$_2$, 150 Bar; Flow: 70 mL/min. Method G: Column: Chiralcel OD-H preparative column, 30×250 mm, 5 μm; Mobile Phase: 15% methanol in CO$_2$, 150 Bar; Flow: 70 mL/min. Method H: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 min, then a 0.5-min hold at 100% B; Flow: 1 mL/min. Method I: Column: Chiralpak AD 21×250 mm 10 μm; Mobile Phase: 12:78 ethanol:heptane with 0.1% diethylamine; Flow: 15 mL/min. Method J: Column: Chiralcel OD-H preparative column, 30×250 mm, 5 μm; Mobile Phase: 10% methanol in CO$_2$, 150 Bar; Flow: 70 mL/min.

Examples 308 & 309

2-{5-[(5-Methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol Enantiomer A, Example 308

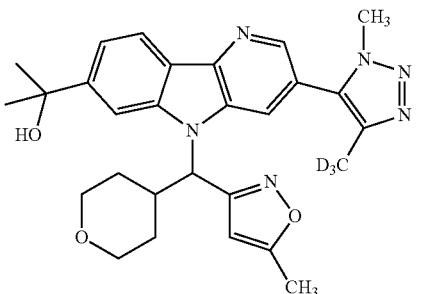

Enantiomer B, Example 309

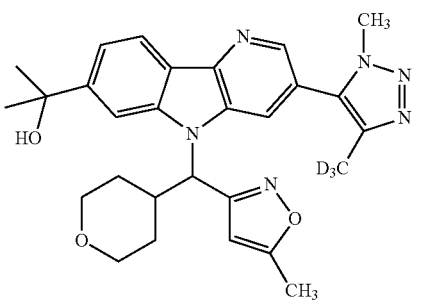

Step 1: Methyl 5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indole-7-carboxylate Methyl 5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indole-7-carboxylate was prepared from methyl 3-[4-($^2$H$_3$)methyl-1-methyl-1H-1,2,3-triazol-5-yl]-5H-pyrido[3,2-b]indole-7-carboxylate (prepared in route to 2-{5-[(2,4-difluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol) and (5-methyl-1,2-oxazol-3-yl)(oxan-4-yl) methanesulfonate (prepared in Step 2 in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol) according to Step 3 in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol. LC/MS (M+H)=504.3; LC/MS RT=1.43 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 2-{5-[(5-Methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol 2-{5-[(5-Methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol was prepared from methyl 5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indole-7-carboxylate according to the procedure described in Step 2 in route to methyl 6-fluoro-5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indole-7-carboxylate. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. Fractions containing the desired product were combined and dried via centrifugal evaporation to afford racemic 2-{5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. Enantiomers A and B were separated using chiral preparatory HPLC (Column: Chiralcel OD 21×250 mm 10 µm particles; Mobile Phase A: heptane with 0.1% diethylamine; Mobile Phase B: ethanol; Gradient: 12% B over 41 min; Flow: 15 mL/min). The first eluting enantiomer was defined as Enantiomer A (6.60 mg, 0.0130 mmol, 9%), and the second eluting enantiomer was defined as Enantiomer B (6.90 mg, 0.0140 mmol, 9%). $^1$H NMR (500 MHz, DMSO-d$_6$) δ 8.56 (s, 1H), 8.32 (br. s., 1H), 8.17 (d, J=8.1 Hz, 1H), 8.03 (br. s., 1H), 7.50 (d, J=8.1 Hz, 1H), 6.30 (br. s., 1H), 5.97 (d, J=11.0 Hz, 1H), 4.04 (s, 3H), 3.95-3.88 (m, 1H), 3.69 (d, J=9.5 Hz, 1H), 3.46-3.32 (m, 1H), 3.26-3.13 (m, 2H), 2.32 (s, 3H), 1.90 (d, J=11.7 Hz, 1H), 1.70-1.59 (m, 1H), 1.56 (s, 6H), 1.33-1.19 (m, 1H), 0.87 (d, J=11.0 Hz, 1H); LC/MS (M+H)=504.5; LC/MS RT=1.22 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 310-329

The compounds in Table 13 were prepared from commercially available or previously described starting materials according to analogous procedures described for 2-{5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol, 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol, 2-{8-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol, 2-{5-[(S)-(2-fluorophenyl)(oxan-4-yl)methyl]-3-[5-($^2$H$_3$)methyl-3-methyl-1,2-oxazol-4-yl]-5H-pyrido[3,2-b]indol-7-yl}propan-2-ol, or (1R)-1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol. All compounds are homochiral:

TABLE 13

| Example | Structure | HPLC RT (min) | HPLC Method | MS (M + H) |
|---|---|---|---|---|
| 310 Enantiomer A | 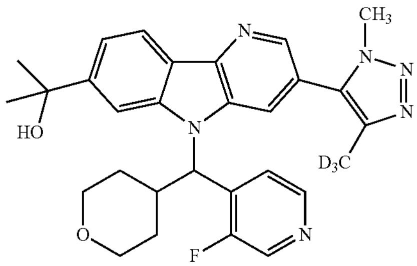 [SMILES: [2H]C([2H])([2H])c1nnn(C)c1-c1cnc2c3ccc(C(C)(C)O)cc3n(C(c3ccncc3F)C3CCOCC3)c2c1] | 3.41 | A | 518.3 |
| 311 Enantiomer B | 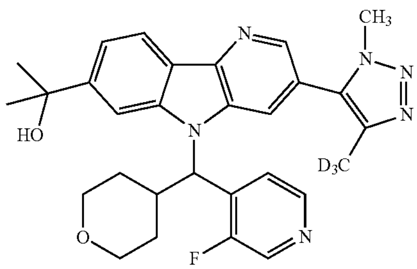 [SMILES: [2H]C([2H])([2H])c1nnn(C)c1-c1cnc2c3ccc(C(C)(C)O)cc3n(C(c3ccncc3F)C3CCOCC3)c2c1] | 5.71 | A | 518.3 |
| 312 Enantiomer B | 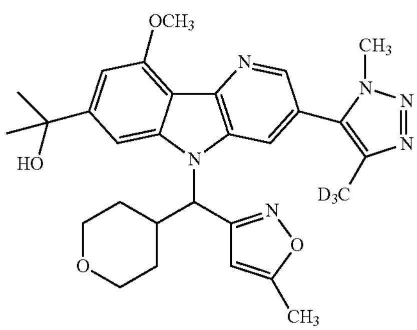 [SMILES: [2H]C([2H])([2H])c1nnn(C)c1-c1cnc2c3c(OC)cc(C(C)(C)O)cc3n(C(c3cc(C)on3)C3CCOCC3)c2c1] | 80.20 | B | 534.4 |
| 313 Enantiomer A | 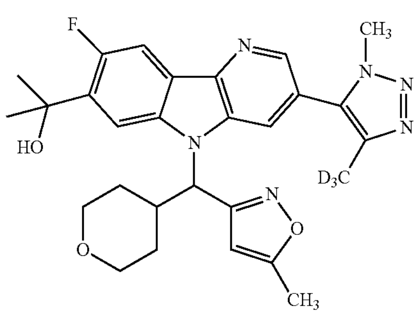 [SMILES: [2H]C([2H])([2H])c1nnn(C)c1-c1cnc2c3cc(F)c(C(C)(C)O)cc3n(C(c3cc(C)on3)C3CCOCC3)c2c1] | 14.09 | C | 522.4 |
| 314 Enantiomer B | 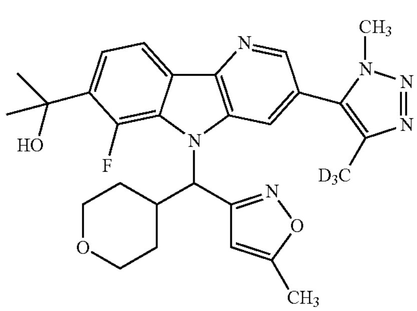 [SMILES: [2H]C([2H])([2H])c1nnn(C)c1-c1cnc2c3ccc(C(C)(C)O)c(F)c3n(C(c3cc(C)on3)C3CCOCC3)c2c1] | 23.94 | D | 522.4 |

TABLE 13-continued

| Example | Structure | HPLC RT (min) | HPLC Method | MS (M + H) |
|---|---|---|---|---|
| 315 Enantiomer A | 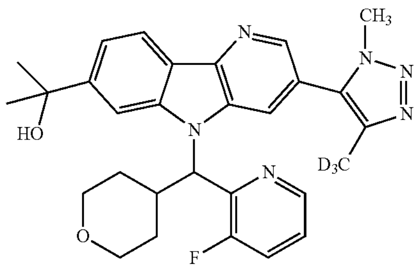 [SMILES: [2H]C([2H])([2H])c1nnn(C)c1-c1cnc2c3ccc(C(C)(C)O)cc3n(C(c3ncccc3F)C3CCOCC3)c2c1] | 18.76 | E | 518.5 |
| 316 Enantiomer B | 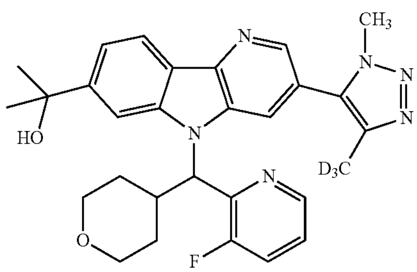 [SMILES: [2H]C([2H])([2H])c1nnn(C)c1-c1cnc2c3ccc(C(C)(C)O)cc3n(C(c3ncccc3F)C3CCOCC3)c2c1] | 25.62 | E | 518.5 |
| 317 Enantiomer B | 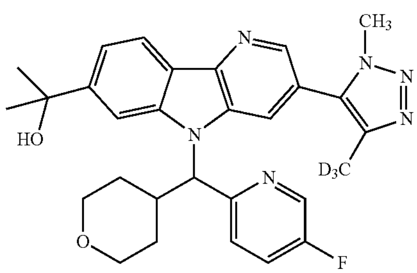 [SMILES: [2H]C([2H])([2H])c1nnn(C)c1-c1cnc2c3ccc(C(C)(C)O)cc3n(C(c3ccc(F)cn3)C3CCOCC3)c2c1] | 49.19 | F | 518.3 |
| 318 Enantiomer A | 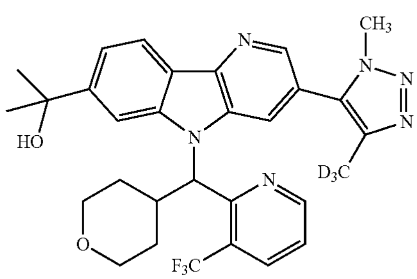 [SMILES: [2H]C([2H])([2H])c1nnn(C)c1-c1cnc2c3ccc(C(C)(C)O)cc3n(C(c3ncccc3C(F)(F)F)C3CCOCC3)c2c1] | 9.91 | G | 568.5 |
| 319 Enantiomer B | 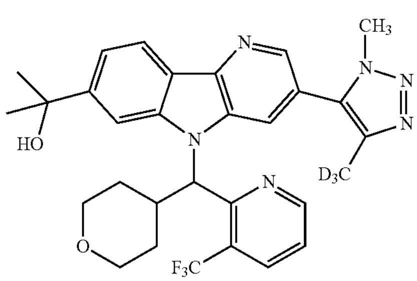 [SMILES: [2H]C([2H])([2H])c1nnn(C)c1-c1cnc2c3ccc(C(C)(C)O)cc3n(C(c3ncccc3C(F)(F)F)C3CCOCC3)c2c1] | 11.18 | G | 568.5 |

TABLE 13-continued

| Example | Structure | HPLC RT (min) | HPLC Method | MS (M + H) |
|---|---|---|---|---|
| 320 Enantiomer B | 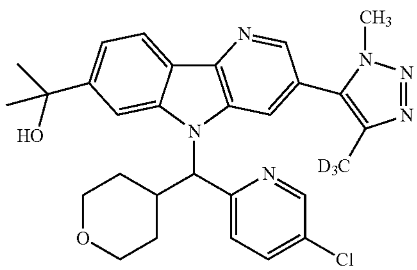 [SMILES: [2H]C([2H])([2H])c1nnn(C)c1-c1cnc2c3ccc(C(C)(C)O)cc3n(C(c3ccc(Cl)cn3)C3CCOCC3)c2c1] | 46.73 | F | 534.3 |
| 321 Enantiomer A | 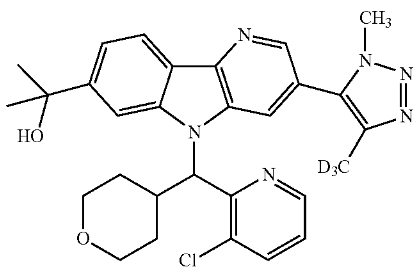 [SMILES: [2H]C([2H])([2H])c1nnn(C)c1-c1cnc2c3ccc(C(C)(C)O)cc3n(C(c3ncccc3Cl)C3CCOCC3)c2c1] | 81.38 | B | 534.5 |
| 322 Enantiomer B | 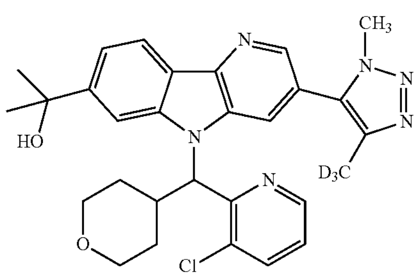 [SMILES: [2H]C([2H])([2H])c1nnn(C)c1-c1cnc2c3ccc(C(C)(C)O)cc3n(C(c3ncccc3Cl)C3CCOCC3)c2c1] | 118.13 | B | 534.5 |
| 323 Enantiomer B | 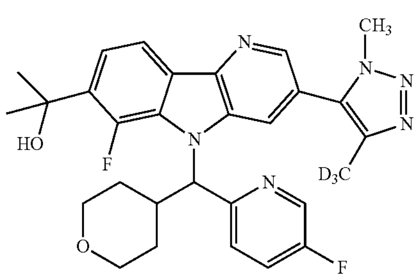 [SMILES: [2H]C([2H])([2H])c1nnn(C)c1-c1cnc2c3ccc(C(C)(C)O)c(F)c3n(C(c3ccc(F)cn3)C3CCOCC3)c2c1] | 25.91 | H | 536.6 |
| 324[A] Enantiomer A | 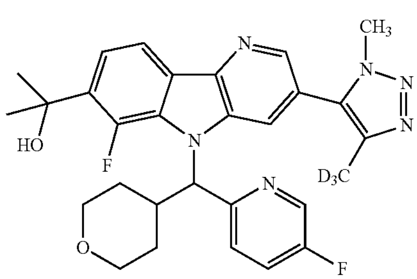 [SMILES: [2H]C([2H])([2H])c1nnn(C)c1-c1cnc2c3ccc(C(C)(C)O)c(F)c3n(C(c3ccc(F)cn3)C3CCOCC3)c2c1] | 29.18 | H | 536.6 |

TABLE 13-continued

| Example | Structure | HPLC RT (min) | HPLC Method | MS (M + H) |
|---|---|---|---|---|
| 325 Enantiomer A | 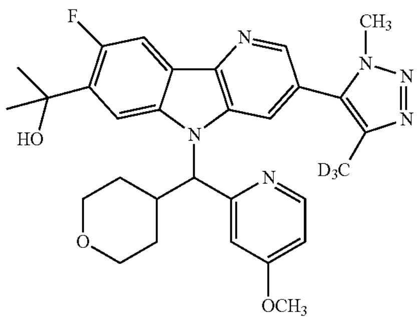 [SMILES: [2H]C([2H])([2H])c1nnn(C)c1-c1cnc2c3cc(F)c(C(C)(C)O)cc3n(C(c3cc(OC)ccn3)C3CCOCC3)c2c1] | 8.66 | I | 548.3 |
| 326 Enantiomer B | 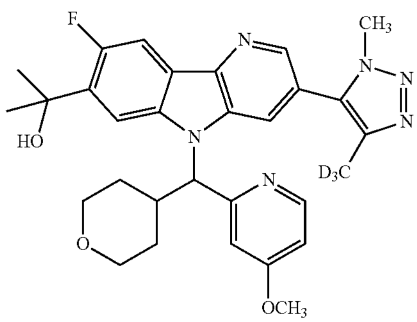 [SMILES: [2H]C([2H])([2H])c1nnn(C)c1-c1cnc2c3cc(F)c(C(C)(C)O)cc3n(C(c3cc(OC)ccn3)C3CCOCC3)c2c1] | 13.68 | I | 548.3 |
| 327 Enantiomer A | 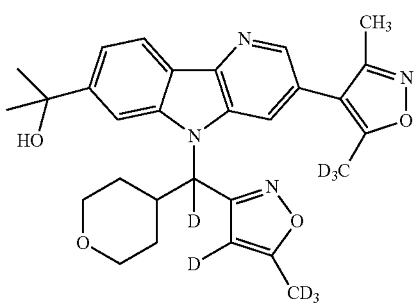 [SMILES: [2H]c1c(C([2H])(C2CCOCC2)n2c3cc(C(C)(C)O)ccc3c3ncc(-c4c(C)noc4C([2H])([2H])[2H])cc32)noc1C([2H])([2H])[2H]] | 11.88 | C | 508.7 |
| 328 Enantiomer B | 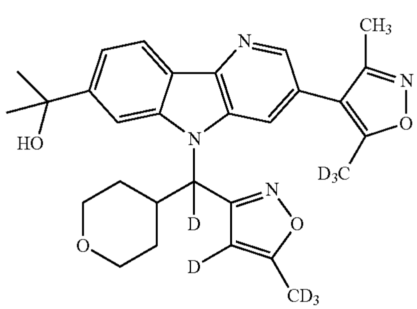 [SMILES: [2H]c1c(C([2H])(C2CCOCC2)n2c3cc(C(C)(C)O)ccc3c3ncc(-c4c(C)noc4C([2H])([2H])[2H])cc32)noc1C([2H])([2H])[2H]] | 13.47 | C | 508.7 |
| 329 Diastereomer D | 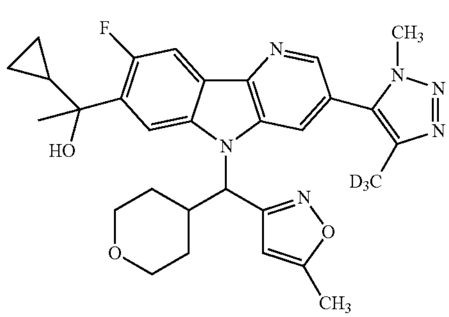 [SMILES: [2H]C([2H])([2H])c1nnn(C)c1-c1cnc2c3cc(F)c(C(C)(O)C4CC4)cc3n(C(c3cc(C)on3)C3CCOCC3)c2c1] | 40.44 | J | 548.7 |

Footnote A: Final compounds were prepared using methyllithium according to Step 3 in route to 2-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol.

HPLC Conditions for Table 13: Method A: Column: Chiralcel OJ-H preparative column, 30×250 mm, 5 μm; Mobile Phase: 30% methanol in CO$_2$, 140 Bar; Flow: 70 mL/min. Method B: Column: Chiralcel OJ 21×250 mm 10 μm; Mobile Phase: 10:90 ethanol:heptane with 0.1% diethylamine; Flow: 15 mL/min. Method C: Column: Chiralcel OD-H preparative column, 30×250 mm, 5 μm; Mobile Phase: 15% methanol in CO$_2$, 150 Bar; Flow: 70 mL/min. Method D: Column: Chiralcel AD-H preparative column, 30×250 mm, 5 μm; Mobile Phase: 10% ethanol in CO$_2$, 150 Bar; Flow: 70 mL/min. Method E: Column: Chiralcel OD 21×250 mm 10 μm; Mobile Phase: 15:85 ethanol:heptane with 0.1% diethylamine; Flow: 15 mL/min. Method F: Column: Chiralpak AD 21×250 mm 10 μm; Mobile Phase: 8:92 ethanol:heptane with 0.1% diethylamine; Flow: 15 mL/min. Method G: Column: Chiralcel OJ-H preparative column, 30×250 mm, 5 μm; Mobile Phase: 10% methanol in CO$_2$, 150 Bar; Flow: 70 mL/min. Method H: Column: Chiralpak IB preparative column, 30×250 mm, 5 μm; Mobile Phase: 10% methanol in CO$_2$, 150 Bar; Flow: 70 mL/min. Method I: Column: Chiralcel OD 21×250 mm 10 μm; Mobile Phase: 25:75 ethanol:heptane with 0.1% diethylamine; Flow: 15 mL/min. Method J: Column: Lux Cellulose-2 preparative column, 21×250 mm, 5 μm; Mobile Phase: 20% ethanol in CO$_2$, 150 Bar; Flow: 50 mL/min.

Examples 330 & 331

5-{7-Methanesulfonyl-5-[(5-methyl-1,2-oxazol-3-yl)(oxan-4-yl)methyl]-5H-pyrido[3,2-b]indol-3-yl}-4-($^2$H$_3$)methyl-1-methyl-1H-1,2,3-triazole Enantiomer A, Example 330

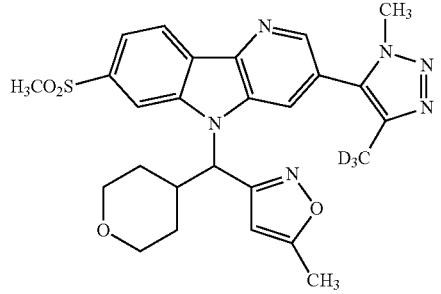

Enantiomer B, Example 331

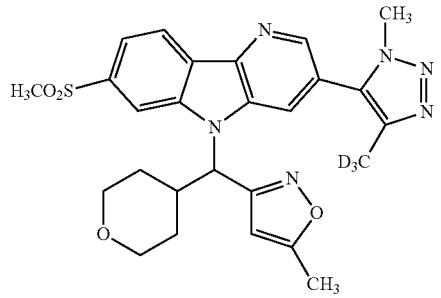

Step 1: 5-{7-Methanesulfonyl-5H-pyrido[3,2-b]indol-3-yl}-4-($^2$H$_3$)methyl-1-methyl-1H-1,2,3-triazole 5-{7-Methanesulfonyl-5H-pyrido[3,2-b]indol-3-yl}-4-($^2$H$_3$)methyl-1-methyl-1H-1,2,3-triazole (233 mg, 0.677 mmol, >100% yield) was prepared from 3-bromo-7-methanesulfonyl-5H-pyrido[3,2-b]indole and 4-($^2$H$_3$)methyl-1-methyl-5-(tributylstannyl)-1H-1,2,3-triazole (prepared in route to 5-{7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole) according to Step 1 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. $^1$H NMR (400 MHz, DMSO-d$_6$) δ 12.13 (s, 1H), 8.66 (d, J=1.5 Hz, 1H), 8.51-8.43 (m, 1H), 8.24-8.13 (m, 2H), 7.83 (dd, J=8.2, 1.1 Hz, 1H), 4.03 (s, 3H), 3.32 (s, 3H); LC/MS (M+H)=345.3; LC/MS RT=1.05 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 5-{7-Methanesulfonyl-5-[(5-methyl-1,2-oxazol-3-yl)(oxan-4-yl)methyl]-5H-pyrido[3,2-b]indol-3-yl}-4-($^2$H$_3$)methyl-1-methyl-1H-1,2,3-triazole 5-{7-Methanesulfonyl-5-[(5-methyl-1,2-oxazol-3-yl)(oxan-4-yl)methyl]-5H-pyrido[3,2-b]indol-3-yl}-4-($^2$H$_3$)methyl-1-methyl-1H-1,2,3-triazole was prepared from 5-{7-methanesulfonyl-5H-pyrido[3,2-b]indol-3-yl}-4-($^2$H$_3$)methyl-1-methyl-1H-1,2,3-triazole and (5-methyl-1,2-oxazol-3-yl)(oxan-4-yl)methyl methanesulfonate (prepared in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol) according to Step 3 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. The crude material was purified via preparative LC/MS with the following conditions: Column: Chiralcel OD 21×250 mm 10 μm particles; Mobile Phase A: heptane with 0.1% diethylamine; Mobile Phase B: ethanol; Gradient: 12% B over 41 min; Flow: 15 mL/min. Fractions containing the desired product were combined and dried via centrifugal evaporation to afford racemic 5-{7-methanesulfonyl-5-[(5-methyl-1,2-oxazol-3-yl)(oxan-4-yl)methyl]-5H-pyrido[3,2-b]indol-3-yl}-4-($^2$H$_3$)methyl-1-methyl-1H-1,2,3-triazole. Enantiomers A and B were separated using chiral SFC (Column: Chiralcel OJ-H preparative column, 30×250 mm, 5 μm; Mobile Phase: 20% methanol in CO$_2$, 150 Bar; Flow: 70 mL/min). The first eluting enantiomer was defined as Enantiomer A (12.1 mg, 0.0230 mmol, 10%), and the second eluting enantiomer was defined as Enantiomer B (12.6 mg, 0.0240 mmol, 10%). $^1$H NMR (500 MHz, DMSO-d$_6$) δ 8.79-8.58 (m, 2H), 8.52 (d, J=8.1 Hz, 2H), 7.90 (d, J=8.4 Hz, 1H), 6.38 (br. s., 1H), 6.18 (d, J=11.0 Hz, 1H), 4.06 (s, 3H), 3.92 (d, J=8.4 Hz, 1H), 3.68 (d, J=9.5 Hz, 1H), 3.42 (t, J=12.1 Hz, 1H), 3.29-3.12 (m, 2H), 2.33 (s, 3H), 1.87 (d, J=12.1 Hz, 1H), 1.68 (d, J=11.7 Hz, 1H), 1.37-1.21 (m, 1H), 0.88-0.76 (m, 1H); LC/MS (M+H)=524.4; LC/MS RT=1.28 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 332-340

The compounds in Table 14 were prepared from commercially available aldehydes according to the procedures described for 5-{7-methanesulfonyl-5-[(5-methyl-1,2-oxazol-3-yl)(oxan-4-yl)methyl]-5H-pyrido[3,2-b]indol-3-yl}-4-($^2H_3$)methyl-1-methyl-1H-1,2,3-triazole. All compounds are homochiral:

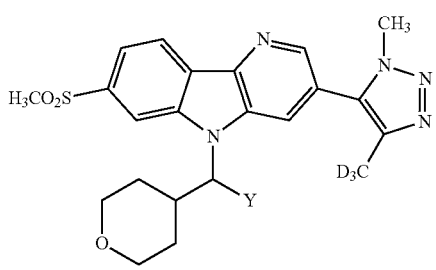

TABLE 14

| Example | Y | HPLC RT (min) | HPLC Method | MS (M + H) |
|---|---|---|---|---|
| 332 Enantiomer A | 3-F pyridin-2-yl | 35.36 | A | 538.5 |
| 333 Enantiomer B | 3-F pyridin-2-yl | 47.99 | A | 538.5 |
| 334 Enantiomer B | 5-Cl pyridin-2-yl | 20.22 | B | 554.5 |
| 335 Enantiomer A | 4-Cl pyridin-2-yl | 34.53 | C | 554.5 |
| 336 Enantiomer A | 4-OCH$_3$ pyridin-2-yl | 16.78 | D | 550.5 |
| 337 Enantiomer A | 4-CH$_3$ pyridin-2-yl | 67.13 | E | 534.0 |
| 338 Enantiomer B | 5-CH$_3$ pyridin-2-yl | 78.46 | F | 534.3 |
| 339 Enantiomer A | 3-Cl pyridin-2-yl | 51.77 | G | 554.5 |
| 340 Enantiomer B | 3-Cl pyridin-2-yl | 65.34 | G | 554.5 |

HPLC Conditions for Table 14: Method A: Column: Chiralpak AD 21×250 mm 10 μm; Mobile Phase: 18:82 ethanol:heptane with 0.1% diethylamine; Flow: 15 mL/min. Method B: Column: Chiralpak AD 21×250 mm 10 μm; Mobile Phase: 25:75 ethanol:heptane with 0.1% diethylamine; Flow: 15 mL/min. Method C: Column: Chiralpak AD-H preparative column, 30×250 mm, 5 μm; Mobile Phase: 10% methanol in CO$_2$, 100 Bar; Flow: 70 mL/min. Method D: Column: Chiralcel OD 21×250 mm 10 μm; Mobile Phase: 30:70 ethanol:heptane with 0.1% diethylamine; Flow: 15 mL/min. Method E: Column: Chiralpak AD 21×250 mm 10 μm; Mobile Phase: 10:90 ethanol:heptane with 0.1% diethylamine; Flow: 15 mL/min. Method F: Column: Chiralpak AD 21×250 mm 10 μm; Mobile Phase: 12:88 ethanol:heptane with 0.1% diethylamine; Flow: 15 mL/min. Method G: Column: Chiralpak AD 21×250 mm 10 μm; Mobile Phase: 15:85 ethanol:heptane with 0.1% diethylamine; Flow: 15 mL/min.

Examples 341 & 342

2-[3-(Dimethyl-1H-1,2,3-triazol-5-yl)-5-[(1,3-dimethyl-1H-pyrazol-5-yl)(oxan-4-yl)methyl]-5H-pyrido[3,2-b]indol-7-yl]propan-2-ol Enantiomer A, Example 341

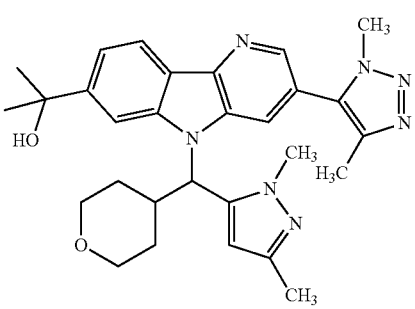

Enantiomer B, Example 342

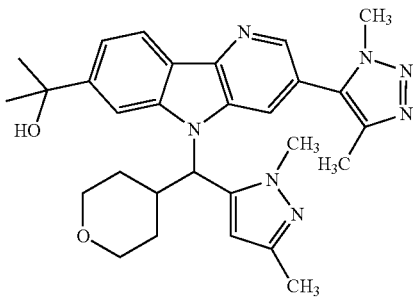

Step 1: (1,3-Dimethyl-1H-pyrazol-5-yl)(oxan-4-yl)methanol (1,3-Dimethyl-1H-pyrazol-5-yl)(oxan-4-yl)methanol was prepared according to Step 1 in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol. LC/MS (M+H)=211.2; LC/MS RT=0.92 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: Methyl 3-(dimethyl-1H-1,2,3-triazol-5-yl)-5-[(1,3-dimethyl-1H-pyrazol-5-yl)(oxan-4-yl)methyl]-5H-pyrido[3,2-b]indole-7-carboxylate Methyl 3-(dimethyl-1H-1,2,3-triazol-5-yl)-5H-pyrido[3,2-b]indole-7-carboxylate (prepared in route to 2-[3-(dimethyl-1H-1,2,3-triazol-5-yl)-5-[oxan-4-yl(phenyl)methyl]-5H-pyrido[3,2-b]indol-7-yl]propan-2-ol, 92.0 mg, 0.285 mmol), (1,3-dimethyl-1H-pyrazol-5-yl)(oxan-4-yl)methanol (90.0 mg, 0.428 mmol), and 2-(trimethylphosphoranylidene)acetonitrile (856 µL, 0.428 mmol) were stirred in toluene (2850 µL) at 85° C. under N$_2$ (g) for 16 h. The volatiles were removed under reduced pressure, and the reaction material was used without purification. LC/MS (M+H)=514.3; LC/MS RT=0.98 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 3: 2-[3-(Dimethyl-1H-1,2,3-triazol-5-yl)-5-[(1,3-dimethyl-1H-pyrazol-5-yl)(oxan-4-yl)methyl]-5H-pyrido[3,2-b]indol-7-yl]propan-2-ol 2-[3-(Dimethyl-1H-1,2,3-triazol-5-yl)-5-[(1,3-dimethyl-1H-pyrazol-5-yl)(oxan-4-yl)methyl]-5H-pyrido[3,2-b]indol-7-yl]propan-2-ol was prepared from methyl 3-(dimethyl-1H-1,2,3-triazol-5-yl)-5-[(1,3-dimethyl-1H-pyrazol-5-yl)(oxan-4-yl)methyl]-5H-pyrido[3,2-b]indole-7-carboxylate according to Step 3 in route to 2-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-45% B over 30 min, then a 5-min hold at 100% B; Flow: 20 mL/min. Fractions containing the desired product were combined and dried via centrifugal evaporation to afford racemic 2-[3-(dimethyl-1H-1,2,3-triazol-5-yl)-5-[(1,3-dimethyl-1H-pyrazol-5-yl)(oxan-4-yl)methyl]-5H-pyrido[3,2-b]indol-7-yl]propan-2-ol. Enantiomers A and B were separated using chiral SFC (Column: ChiralPak IC-H, 30×250 mm, 5 µm; Mobile Phase: 40% methanol in CO$_2$, 150 bar; Flow: 70 mL/min; Temperature 35° C.). The first eluting enantiomer was defined as Enantiomer A (2.10 mg, 3.43 µmol, 2%), and the second eluting enantiomer was defined as Enantiomer B (3.10 mg, 5.79 µmol, 3%). $^1$H NMR (500 MHz, DMSO-d$_6$) δ 8.54 (s, 1H), 8.41-8.01 (m, 2H), 7.52 (d, J=7.7 Hz, 1H), 7.39 (d, J=4.4 Hz, 1H), 6.84 (br. s., 1H), 5.96 (d, J=11.0 Hz, 1H), 4.01 (br. s., 3H), 3.91 (br. s., 1H), 3.68 (d, J=9.9 Hz, 1H), 3.43 (br. s., 1H), 3.21-3.05 (m, 2H), 2.30 (br. s., 3H), 2.14 (s, 3H), 1.97-1.82 (m, 1H), 1.72-1.46 (m, 7H), 1.31-1.21 (m, 3H), 0.89-0.77 (m, 1H), 0.72 (d, J=10.6 Hz, 1H); LC/MS (M+H)=514.3; LC/MS RT=0.87 min (Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Examples 343 & 344

2-{5-[(3-Fluoropyridin-4-yl)(oxan-4-yl)($^2$H)methyl]-3-[5-($^2$H$_3$)methyl-3-methyl-1,2-oxazol-4-yl]-5H-pyrido[3,2-b]indol-7-yl}propan-2-ol Enantiomer A, Example 343

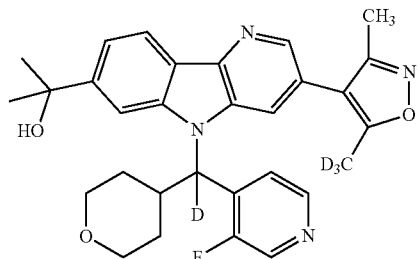

Enantiomer B, Example 344

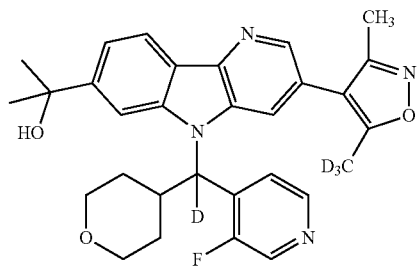

Step 1: (3-Fluoropyridin-4-yl)(oxan-4-yl)methanol (3-Fluoropyridin-4-yl)(oxan-4-yl)methanol (301 mg, 1.42 mmol, 47%) was prepared from 3-fluoropyridine-4-carbaldehyde according to Step 1 in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol. LC/MS (M+H)=212.2; LC/MS RT=0.40 min (Column: Phenomenex Luna 30×2.0 mm 3 u; Mobile Phase A: 10:90 acetonitrile:water with 0.1% TFA; Mobile Phase B: 90:10 acetonitrile:

water with 0.1% TFA; Temperature: 40° C.; Gradient: 0-100% B over 2 min; Flow: 1 mL/min).

Step 2: (3-Fluoropyridin-4-yl)(oxan-4-yl)methyl methanesulfonate (3-Fluoropyridin-4-yl)(oxan-4-yl)methyl methanesulfonate was prepared from (3-fluoropyridin-4-yl)(oxan-4-yl) methanol according to Step 2 in route to 2-[3-(dimethyl-1H-1,2,3-triazol-5-yl)-5-[(5-methyl-1,2-oxazol-3-yl)(oxan-4-yl)methyl]-5H-pyrido[3,2-b]indol-7-yl]propan-2-ol.

Step 3: Methyl 3-(dimethyl-1,2-oxazol-4-yl)-5-[(3-fluoropyridin-4-yl)(oxan-4-yl)methyl]-5H-pyrido[3,2-b]indole-7-carboxylate Methyl 3-(dimethyl-1,2-oxazol-4-yl)-5-[(3-fluoropyridin-4-yl)(oxan-4-yl)methyl]-5H-pyrido[3,2-b]indole-7-carboxylate was prepared from methyl 3-(dimethyl-1,2-oxazol-4-yl)-5H-pyrido[3,2-b]indole-7-carboxylate (prepared in route to 2-[3-(dimethyl-1,2-oxazol-4-yl)-5-[oxan-4-yl(phenyl)methyl]-5H-pyrido[3,2-b]indol-7-yl]propan-2-ol) and (3-fluoropyridin-4-yl)(oxan-4-yl)methyl methanesulfonate according to Step 3 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. LC/MS (M+H)=515.7; LC/MS RT=1.46 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: 3-(Dimethyl-1,2-oxazol-4-yl)-5-[(3-fluoropyridin-4-yl)(oxan-4-yl)methyl]-5H-pyrido[3,2-b]indol-7-yl]propan-2-ol 2-[3-(Dimethyl-1,2-oxazol-4-yl)-5-[(3-fluoropyridin-4-yl)(oxan-4-yl)methyl]-5H-pyrido[3,2-b]indol-7-yl]propan-2-ol was prepared from methyl 3-(dimethyl-1,2-oxazol-4-yl)-5-[(3-fluoropyridin-4-yl)(oxan-4-yl)methyl]-5H-pyrido[3,2-b]indole-7-carboxylate according to Step 3 in route to 2-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. LC/MS (M+H)=515.3; LC/MS RT=1.18 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 5: 2-{5-[(3-Fluoropyridin-4-yl)(oxan-4-yl)($^2$H) methyl]-3-[5-($^2$H$_3$)methyl-3-methyl-1,2-oxazol-4-yl]-5H-pyrido[3,2-b]indol-7-yl}propan-2-ol 2-{5-[(3-Fluoropyridin-4-yl)(oxan-4-yl)($^2$H)methyl]-3-[5-($^2$H$_3$)methyl-3-methyl-1,2-oxazol-4-yl]-5H-pyrido[3,2-b]indol-7-yl}propan-2-ol was prepared from 2-[3-(dimethyl-1,2-oxazol-4-yl)-5-[(3-fluoropyridin-4-yl)(oxan-4-yl)methyl]-5H-pyrido[3,2-b]indol-7-yl]propan-2-ol according to Step 3 in route to 2-{5-[(2,4-difluorophenyl)(oxan-4-yl)methyl]-6-fluoro-3-[4-($^2$H$_3$)methyl-1-methyl-1H-1,2,3-triazol-5-yl]-5H-pyrido[3,2-b]indol-7-yl}propan-2-ol. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min. Fractions containing the desired product were combined and dried via centrifugal evaporation to afford racemic 2-{5-[(3-fluoropyridin-4-yl)(oxan-4-yl)($^2$H) methyl]-3-[5-($^2$H$_3$)methyl-3-methyl-1,2-oxazol-4-yl]-5H-pyrido[3,2-b]indol-7-yl}propan-2-ol. Enantiomers A and B were separated using chiral SFC (Column: Chiralcel OD-H preparative column, 30×250 mm, Sum; Mobile Phase: 20% methanol in CO$_2$, 150 bar; Flow: 70 mL/min; Temperature 35° C.). The first eluting enantiomer was defined as Enantiomer A (1.90 mg, 3.66 µmol, 2%), and the second eluting enantiomer was defined as Enantiomer B (2.10 mg, 3.89 µmol, 2%). LC/MS (M+H)=519.3; LC/MS RT=1.18 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 345 & 346

2-[3-(Dimethyl-1,2-oxazol-4-yl)-5-[(3-fluoropyridin-2-yl)(oxan-4-yl)methyl]-5H-pyrido[3,2-b]indol-7-yl] propan-2-ol

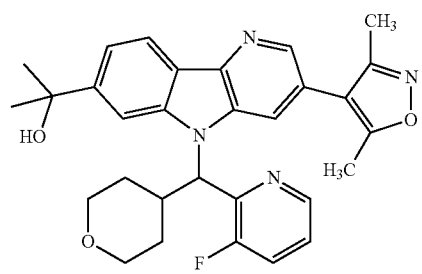

Enantiomer A, Example 345

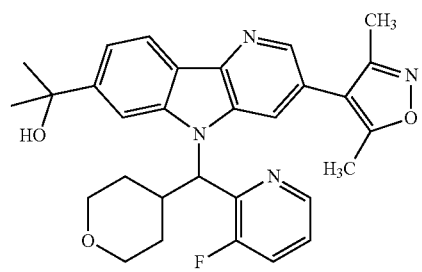

Enantiomer B, Example 346

Step 1: 2-[3-(Dimethyl-1,2-oxazol-4-yl)-5-[(3-fluoropyridin-2-yl)(oxan-4-yl)methyl]-5H-pyrido[3,2-b]indol-7-yl]propan-2-ol 2-[3-(Dimethyl-1,2-oxazol-4-yl)-5-[(3-fluoropyridin-2-yl)(oxan-4-yl)methyl]-5H-pyrido[3,2-b]indol-7-yl]propan-2-ol was analogously prepared according to Steps 1-4 in route to 2-{5-[(3-fluoropyridin-4-yl)(oxan-4-yl)($^2$H) methyl]-3-[5-($^2$H$_3$)methyl-3-methyl-1,2-oxazol-4-yl]-5H-pyrido[3,2-b]indol-7-yl}propan-2-ol. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 min, then a 5-min hold at 100% B; Flow: 20 mL/min. Fractions containing the desired product were combined and dried via centrifugal evaporation to afford racemic 2-{5-[(3-fluoropyridin-4-yl)(oxan-4-yl)($^2$H)methyl]-3-[5-($^2$H$_3$) methyl-3-methyl-1,2-oxazol-4-yl]-5H-pyrido[3,2-b]indol-7-yl}propan-2-ol. Enantiomers A and B were separated using chiral preparatory HPLC (Column: Chiralcel OJ 21×250 mm 10 μm particles; Mobile Phase A: heptane with 0.1% diethylamine; Mobile Phase B: ethanol; Gradient: 8% B over 110 min; Flow: 15 mL/min). The first eluting enantiomer was defined as Enantiomer A (10.9 mg, 0.0210 mmol, 21%), and the second eluting enantiomer was defined as Enantiomer B (9.00 mg, 0.0170 mmol, 17%). $^1$H NMR (DMSO-d$_6$) δ: 8.60 (br. s., 1H), 8.24-8.53 (m, 2H), 7.99-8.14 (m, 2H), 7.68 (d, J=8.8 Hz, 1H), 7.40-7.52 (m, 2H), 6.14 (d, J=10.6 Hz, 1H), 3.87 (d, J=10.3 Hz, 1H), 3.69 (d, J=10.3 Hz, 1H), 3.44-3.52 (m, 4H), 3.18 (t, J=11.7 Hz, 1H), 2.35 (br. s, 3H), 1.71 (br. s., 1H), 1.43-1.64 (m, 8H), 1.26-1.38 (m, 1H), 0.70 (d, J=12.8 Hz, 1H); LC/MS (M+H)=515.5; LC/MS RT=2.50 min (Column: Phenomenex Luna C18 50×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 4 min; Flow: 0.8 mL/min).

Examples 347 & 348

2-{5-[(3-Fluoropyridin-4-yl)(oxan-4-yl)methyl]-9-methoxy-3-[4-($^2$H$_3$)methyl-1-methyl-1H-1,2,3-triazol-5-yl]-5H-pyrido[3,2-b]indol-7-yl}propan-2-ol

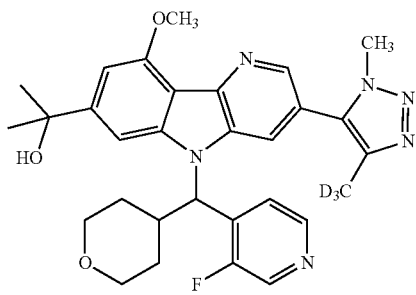

Enantiomer A, Example 347

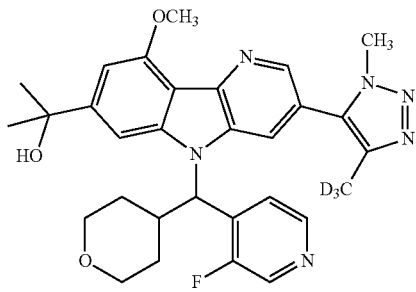

Enantiomer B, Example 348

Step 1: Methyl 3-bromo-5-[(3-fluoropyridin-4-yl)(oxan-4-yl)methyl]-9-methoxy-5H-pyrido[3,2-b]indole-7-carboxylate Methyl 3-bromo-5-[(3-fluoropyridin-4-yl)(oxan-4-yl)methyl]-9-methoxy-5H-pyrido[3,2-b]indole-7-carboxylate was prepared from methyl 3-bromo-9-methoxy-5H-pyrido[3,2-b]indole-7-carboxylate (prepared in route to 2-[3-(dimethyl-1H-1,2,3-triazol-5-yl)-5-[(2-fluorophenyl)(oxan-4-yl)methyl]-9-methoxy-5H-pyrido[3,2-b]indol-7-yl]propan-2-ol) and (3-fluoropyridin-4-yl)(oxan-4-yl)methyl methanesulfonate (prepared in route to 2-{5-[(3-fluoropyridin-4-yl)(oxan-4-yl)($^2$H)methyl]-3-[5-($^2$H$_3$)methyl-3-methyl-1,2-oxazol-4-yl]-5H-pyrido[3,2-b]indol-7-yl}propan-2-ol) according to Step 3 in route to 5-{9-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. LC/MS (M+H)=528.2; LC/MS RT=2.24 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 2-{3-Bromo-5-[(3-fluoropyridin-4-yl)(oxan-4-yl)methyl]-9-methoxy-5H-pyrido[3,2-b]indol-7-yl}propan-2-ol 2-{3-Bromo-5-[(3-fluoropyridin-4-yl)(oxan-4-yl)methyl]-9-methoxy-5H-pyrido[3, 2-b]indol-7-yl}propan-2-ol (22.3 mg, 0.0420 mmol, 12%) was prepared from methyl 3-bromo-5-[(3-fluoropyridin-4-yl)(oxan-4-yl)methyl]-9-methoxy-5H-pyrido[3,2-b]indole-7-carboxylate according to Step 2 in route to 2-{6-fluoro-5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol. LC/MS (M+H)=528.2; LC/MS RT=1.83 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 2-{5-[(3-Fluoropyridin-4-yl)(oxan-4-yl)methyl]-9-methoxy-3-[4-($^2$H$_3$)methyl-1-methyl-1H-1,2,3-triazol-5-yl]-5H-pyrido[3,2-b]indol-7-yl}propan-2-ol 2-{5-[(3-Fluoropyridin-4-yl)(oxan-4-yl)methyl]-9-methoxy-3-[4-($^2$H$_3$)methyl-1-methyl-1H-1,2,3-triazol-5-yl]-5H-pyrido[3,2-b]indol-7-yl}propan-2-ol was prepared according to Step 3 in route to 5-{7-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 min, then a 5-min hold at 100% B; Flow: 20 mL/min. Fractions containing the desired product were combined and dried via centrifugal evaporation to afford racemic 2-{5-[(3-fluoropyridin-4-yl)(oxan-4-yl)methyl]-9-methoxy-3-[4-($^2$H$_3$)methyl-1-methyl-1H-1,2,3-triazol-5-yl]-5H-pyrido[3, 2-b]indol-7-yl}propan-2-ol. Enantiomers A and B were separated using chiral preparatory HPLC (Column: Chiralcel OJ 21×250 mm 10 μm particles; Mobile Phase A: heptane with 0.1% diethylamine; Mobile Phase B: ethanol; Gradient: 30% B over 30 min; Flow: 15 mL/min). The first eluting enantiomer was defined as Enantiomer A (3.90 mg, 7.12 μmol, 17%), and the second eluting enantiomer was defined as Enantiomer B (4.00 mg, 7.30 μmol, 18%). LC/MS (M+H)=548.3; LC/MS RT=1.11 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 351

5-[7-(2-Fluoropropan-2-yl)-5-[(S)-oxan-4-yl(phenyl)methyl]-5H-pyrido[3,2-b]indol-3-yl]-1,4-dimethyl-1H-1,2,3-triazole

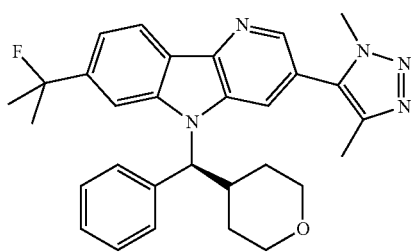 [SMILES: Cc1nnn(C)c1-c1cnc2c3ccc(C(C)(C)F)cc3n([C@H](c3ccccc3)C3CCOCC3)c2c1]

To a cold (−78° C.), stirred solution of (S)-2-(3-(1,4-dimethyl-1H-1,2,3-triazol-5-yl)-5-(phenyl(tetrahydro-2H-pyran-4-yl)methyl)-5H-pyrido[3,2-b]indol-7-yl)propan-2-ol (43.2 mg, 0.0870 mmol) in dichloromethane (9.7 mL) under N$_2$ was added diethylaminosulfur trifluoride (0.050 mL, 0.378 mmol), the reaction mixture was stirred for 3 h, warmed to 0° C., and stirred for 30 min. To the reaction was added sat. aq. NaHCO$_3$ (2 mL), and the reaction was warmed to room temperature. The mixture was diluted with DCM, washed with H$_2$O, dried (MgSO$_4$), filtered, and concentrated. The crude material was purified via preparative LC/MS (Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 min, then a 5-min hold at 100% B; Flow: 20 mL/min). Fractions containing the desired product were combined and dried via centrifugal evaporation to give (5-[7-(2-fluoropropan-2-yl)-5-[(S)-oxan-4-yl(phenyl)methyl]-5H-pyrido[3,2-b]indol-3-yl]-1,4-dimethyl-1H-1,2,3-triazole (17.7 mg, 40%): $^1$H NMR (500 MHz, DMSO-d$_6$) δ 8.53 (s, 1H), 8.43 (br. s., 1H), 8.22 (d, J=8.1 Hz, 1H), 8.09 (br. s., 1H), 7.66 (d, J=7.4 Hz, 2H), 7.40 (d, J=8.1 Hz, 1H), 7.28-7.36 (m, 2H), 7.21-7.27 (m, 1H), 5.89 (d, J=11.1 Hz, 1H), 4.00 (s, 3H), 3.84-3.93 (m, 1H), 3.73 (d, J=8.8 Hz, 1H), 3.48 (t, J=11.1 Hz, 1H), 3.37 (br. s., 1H), 3.25 (t, J=11.4 Hz, 1H), 2.29 (s, 3H), 1.75-1.88 (m, 6H), 1.70 (d, J=12.8 Hz, 1H), 1.52-1.65 (m, 1H), 1.25-1.40 (m, 1H), 0.98 (d, J=12.5 Hz, 1H); HPLC: RT=1.84 min (Column: Waters Acquity UPLC BEH C$_{18}$, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm); MS (ES): m/z=498 [M+1]$^+$.

Example 352

5-[6-Fluoro-7-(2-fluoropropan-2-yl)-5-[(S)-oxan-4-yl(phenyl)methyl]-5H-pyrido[3,2-b]indol-3-yl]-1,4-dimethyl-1H-1,2,3-triazole

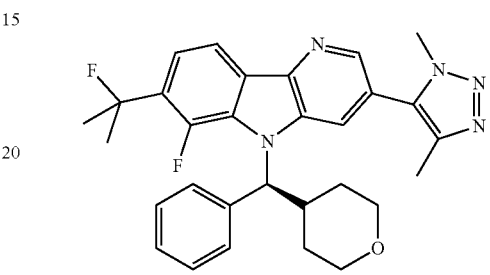

To a cold (−78° C.), stirred solution of (S)-2-(3-(1,4-dimethyl-1H-1,2,3-triazol-5-yl)-6-fluoro-5-(phenyl(tetrahydro-2H-pyran-4-yl)methyl)-5H-pyrido[3,2-b]indol-7-yl)propan-2-ol (50.4 mg, 0.0980 mmol) in dichloromethane (4.9 mL) under N$_2$ (g) was added diethylaminosulfur trifluoride (0.050 mL, 0.378 mmol). The reaction was stirred at −78° C. for 90 min. The reaction was placed in a 0° C. bath and stirred for 40 min. To the reaction was added sat. aq. NaHCO$_3$ (2 mL), and the reaction was warmed to room temperature. The mixture was diluted with DCM, washed with H$_2$O, dried (MgSO$_4$), filtered, and concentrated. The crude material was purified via preparative LC/MS (Column: Waters XBridge C$_{18}$, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-95% B over 20 min, then a 5-min hold at 100% B; Flow: 20 mL/min). Fractions containing the desired product were combined and dried via centrifugal evaporation to give (5-[6-fluoro-7-(2-fluoropropan-2-yl)-5-[(S)-oxan-4-yl(phenyl)methyl]-5H-pyrido[3,2-b]indol-3-yl]-1,4-dimethyl-1H-1,2,3-triazole (20.0 mg, 40%)): $^1$H NMR appears to be a mixture of atropisomers: $^1$H NMR (500 MHz, DMSO-d$_6$) δ 8.25 (br s, 1H), 8.08 (d, J=8.1 Hz, 2H), 7.94 (s, 1H), 7.64 (br s, 3H), 7.43 (br s, 2H), 7.34 (br s, 4H), 7.26 (br d, J=7.1 Hz, 2H), 6.00-5.89 (m, 2H), 4.00-3.82 (m, 7H), 3.76 (br d, J=9.1 Hz, 2H), 3.54-3.43 (m, 1H), 3.41 (br d, J=7.4 Hz, 1H), 3.27 (br t, J=11.3 Hz, 2H), 2.22 (br s, 6H), 2.01-1.69 (m, 14H), 1.34 (br d, J=10.4 Hz, 4H), 1.06 (br d, J=12.8 Hz, 2H); HPLC: RT=2.13 min (Column: Waters Acquity UPLC BEH C$_{18}$, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm); MS (ES): m/z=516 [M+1]$^+$.

Example 353

2-[3-(Dimethyl-1H-1,2,3-triazol-5-yl)-5-[(S)-(4-fluorophenyl)(oxan-4-yl)methyl]-8-methoxy-5H-pyrido[3,2-b]indol-7-yl]propan-2-ol

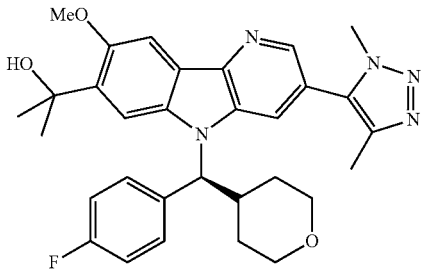 [SMILES: COc1cc2c3ncc(-c4c(C)nnn4C)cc3n([C@H](c3ccc(F)cc3)C3CCOCC3)c2cc1C(C)(C)O]

Step 1: Methyl 2-methoxy-4-(4,4,5,5-tetramethyl-1,3,2-dioxaborolan-2-yl)benzoate To a 100 mL round-bottomed flask equipped with a stir bar was added methyl 4-bromo-2-methoxybenzoate (1.79 g, 7.30 mmol), 4,4,4',4',5,5,5',5'-octamethyl-2,2'-bi(1,3,2-dioxaborolane) (2.78 g, 10.9 mmol), PdCl$_2$(dppf) (0.267 g, 0.365 mmol), and potassium acetate (2.15 g, 21.9 mmol) at ambient temperature. The flask was sealed with a septum, dioxane (36.5 ml) was added, and the atmosphere was purged with N$_2$ (g). The reaction was then heated to 90° C. with stirring for 3 h and cooled to room temperature. The reaction was concentrated, the residue was dissolved in EtOAc and washed with 1M aq. HCl and sat. aq. NaCl. The organics were dried (Na$_2$SO$_4$), filtered, and concentrated. The residue was purified by silica gel column chromatography (Teledyne ISCO CombiFlash Rf, gradient of 0% to 100% using solvent A/B=CH$_2$Cl$_2$/EtOAc over 15 column volumes, RediSep SiO$_2$ 80 g, loaded as DCM solution) to afford (methyl 2-methoxy-4-(4,4,5,5-tetramethyl-1,3,2-dioxaborolan-2-yl)benzoate (1.87 g, 88%) as a tan solid: $^1$H NMR (400 MHz, CDCl$_3$) δ 7.76 (d, J=7.7 Hz, 1H), 7.42 (dd, J=0.7, 0.9 Hz, 1H), 7.39 (s, 1H), 3.96 (s, 3H), 3.90 (s, 3H), 1.36 (s, 12H); HPLC: RT=1.284 min (Waters Acquity BEH C$_{18}$ 1.7 um 2.0×50 mm, CH$_3$CN/H$_2$O/0.1% TFA, 1.5 min gradient, wavelength=254 nm); MS (ES): m/z=293 [M+1]$^+$.

Step 2: Methyl 3-bromo-6-methoxy-5H-pyrido[3,2-b]indole-7-carboxylate and methyl 3-bromo-8-methoxy-5H-pyrido[3,2-b]indole-7-carboxylate To a stirred solution of methyl 2-methoxy-4-(4,4,5,5-tetramethyl-1,3,2-dioxaborolan-2-yl)benzoate (1.30 g, 4.43 mmol), 2,5-dibromo-3-nitropyridine (1.04 g, 3.69 mmol), and PdCl$_2$(dppf) (0.140 g, 0.191 mmol) in THF (37 mL) was added tripotassium phosphate (3M in H$_2$O, 3.7 mL, 11.1 mmol), purged with N$_2$ (g), and the reaction was heated to 75° C. with stirring for 30 min, cooled to room temperature, partially concentrated, diluted with EtOAc, washed with H$_2$O, sat. aq. NaCl, and dried over sodium sulfate. The solids were filtered away, and the volatiles were concentrated in vacuo. The residue was purified by silica gel column chromatography (Teledyne ISCO CombiFlash Rf, gradient of 0% to 100% using solvent A/B=CH$_2$Cl$_2$/EtOAc over 15 column volumes, RediSep SiO$_2$ 120 g, loaded as DCM solution) to afford a mixture of the mono- and bis-coupled products (1.04 g) as a pale-yellow solid: HPLC for major product: RT=1.212 min (Waters Acquity BEH C$_{18}$ 1.7 um 2.0×50 mm, CH$_3$CN/H$_2$O/0.1% TFA, 1.5 min gradient, wavelength=254 nm); MS (ES): m/z=367/369 Br$^{79}$/Br$^{81}$ [M+1]$^+$.

In a 100 mL RB flask was added the mixture above (1.04 g) and 1,2-bis(diphenylphosphino)ethane (1.27 g, 3.19 mmol) in 1,2-dichlorobenzene (12 mL), and the flask was heated in a pre-heated heating block at 170° C. for 90 min, then cooled to room temperature. The mixture was poured into 150 mL hexanes, the solid was collected by filtration, washed with hexanes, and air dried. The residue was purified by silica gel column chromatography (Teledyne ISCO CombiFlash Rf, gradient of 0% to 100% using solvent A/B=hexanes/EtOAc over 15 column volumes, RediSep SiO$_2$ 220 g Gold). The clean fractions were set aside, and the mixed fractions resubjected to flash chromatography (Teledyne ISCO CombiFlash Rf, gradient of 0% to 30% using solvent A/B=CH$_2$Cl$_2$/EtOAc over 19 column volumes, RediSep SiO$_2$ 12 g Gold). Two regioisomers were obtained: (methyl 3-bromo-6-methoxy-5H-pyrido[3,2-b]indole-7-carboxylate (339.7 mg, 36%)) as a cream solid: $^1$H NMR (400 MHz, DMSO-d$_6$) δ 12.04 (s, 1H), 8.59 (d, J=2.0 Hz, 1H), 8.12 (d, J=2.0 Hz, 1H), 7.98 (d, J=8.1 Hz, 1H), 7.61 (d, J=8.1 Hz, 1H), 4.01 (s, 3H), 3.90 (s, 3H); HPLC: RT=0.97 min (Waters Acquity BEH C18 1.7 um 2.0×50 mm, CH$_3$CN/H$_2$O/0.05% TFA, 1 min gradient, wavelength=220 nm); MS (ES): m/z=335/337 Br$^{79}$/Br$^{81}$ [M+1]$^+$ and (methyl 3-bromo-8-methoxy-5H-pyrido[3,2-b]indole-7-carboxylate (322 mg, 0.962 mmol, 34%)) as a yellow solid: $^1$H NMR (400 MHz, DMSO-d$_6$) δ 11.55 (s, 1H), 8.53 (d, J=2.0 Hz, 1H), 8.20 (d, J=2.0 Hz, 1H), 7.87 (s, 1H), 7.80 (s, 1H), 3.92 (s, 3H), 3.85 (s, 3H); HPLC: RT=0.90 min (Waters Acquity BEH C$_{18}$ 1.7 um 2.0×50 mm, CH$_3$CN/H$_2$O/0.05% TFA, 1 min gradient, wavelength=220 nm); MS (ES): m/z=335/337 Br$^{79}$/Br$^{81}$ [M+1]$^+$.

Step 3: Methyl 3-(1,4-dimethyl-1H-1,2,3-triazol-5-yl)-8-methoxy-5H-pyrido[3,2-b]indole-7-carboxylate In a 50 mL RB flask was added a mixture of methyl 3-bromo-8-methoxy-5H-pyrido[3,2-b]indole-7-carboxylate (322 mg, 0.962 mmol), 1,4-dimethyl-5-(tributylstannyl)-1H-1,2,3-triazole (533 mg, 1.38 mmol) and TEA (0.270 mL, 1.94 mmol) in DMF (19 mL), and the mixture was purged by bubbling nitrogen through the solution. While purging, copper(I) iodide (41.4 mg, 0.217 mmol) and Pd(Ph$_3$P)$_4$ (69.5 mg, 0.0600 mmol) were added, the flask fitted with a septum, and heated in a heating block at 95° C. with stirring overnight. The reaction cooled to room temperature and concentrated, the residue was dissolved in EtOAc, washed with H$_2$O, sat. aq. NaCl, dried over sodium sulfate, filtered, and concentrated in vacuo. The residue was dissolved in MeOH/acetone, SiO$_2$ (6 g) was added, and the volatiles removed in vacuo then dried under vacuum. The material was then purified by silica gel column chromatography (Teledyne ISCO CombiFlash Rf, gradient of 0% to 100% using solvent A/B=CH$_2$Cl$_2$/acetone over 15 column volumes, RediSep SiO$_2$ 40 g). Methyl 3-(1,4-dimethyl-1H-1,2,3-triazol-5-yl)-8-methoxy-5H-pyrido[3,2-b]indole-7-carboxylate (167.3 mg, 50%) was obtained as a yellow solid: $^1$H NMR (400 MHz, DMSO-d$_6$) δ 11.62 (s, 1H), 8.54 (d, J=1.8 Hz, 1H), 8.07 (d, J=2.0 Hz, 1H), 7.90 (s, 1H), 7.86 (s, 1H), 4.01 (s, 3H), 3.94 (s, 3H), 3.86 (s, 3H), 2.30 (s, 3H); HPLC: RT=0.917 min (Waters Acquity BEH C$_{18}$ 1.7 um 2.0×50 mm, CH₃CN/H₂O/0.1% TFA, 1.5 min gradient, wavelength=254 nm); MS (ES): m/z=352 [M+1]⁺.

Step 4: (S)-Methyl 3-(1,4-dimethyl-1H-1,2,3-triazol-5-yl)-5-((4-fluorophenyl)(tetrahydro-2H-pyran-4-yl)methyl)-8-methoxy-5H-pyrido[3,2-b]indole-7-carboxylate To a cool (0° C.), stirred suspension of methyl 3-(1,4-dimethyl-1H-1,2,3-triazol-5-yl)-8-methoxy-5H-pyrido[3,2-b]indole-7-carboxylate (89.6 mg, 0.255 mmol), (R)-(4-fluorophenyl)(tetrahydro-2H-pyran-4-yl)methanol (110 mg, 0.522 mmol) and triphenylphosphine (108 mg, 0.413 mmol) in toluene (5.2 mL) under N₂ (g) was added dropwise over 1 min via syringe DIAD (0.100 mL, 0.514 mmol), the solution stirred for 5 min, then removed from the ice bath and stirred at room temperature overnight. THF (5 mL) was added, and stirring continued overnight. The reaction was concentrated in vacuo and dried under vacuum. The residue was purified by silica gel column chromatography (Teledyne ISCO CombiFlash Rf, gradient of 0% to 30% using solvent A/B=CH₂Cl₂/MeOH over 20 column volumes, RediSep SiO₂ 40 g, loaded as DCM solution). The product was repurified by silica gel column chromatography (Teledyne ISCO CombiFlash Rf, gradient of 0% to 100% using solvent A/B=hexanes/EtOAc over 12 column volumes, RediSep SiO₂ 12 g, loaded as DCM solution, then solvents changed to CH₂Cl₂:MeOH, gradient of 0% to 10% over 12 column volumes. (S)-Methyl 3-(1,4-dimethyl-1H-1,2,3-triazol-5-yl)-5-((4-fluorophenyl)(tetrahydro-2H-pyran-4-yl)methyl)-8-methoxy-5H-pyrido[3,2-b]indole-7-carboxylate (36.0 mg, 26%) was obtained as a cream solid: ¹H NMR (400 MHz, CDCl₃) δ 8.47 (d, J=1.8 Hz, 1H), 8.14 (s, 1H), 7.96 (s, 1H), 7.58 (d, J=1.5 Hz, 1H), 7.42 (dd, J=5.2, 8.7 Hz, 2H), 7.05 (t, J=8.6 Hz, 2H), 5.46 (d, J=10.6 Hz, 1H), 4.06 (s, 3H), 4.03 (s, 3H), 3.99 (br dd, J=2.6, 3.7 Hz, 1H), 3.94 (s, 3H), 3.91-3.86 (m, 1H), 3.59-3.48 (m, 1H), 3.41-3.30 (m, 1H), 3.11-2.96 (m, 1H), 2.32 (s, 3H), 1.95 (br d, J=13.2 Hz, 1H), 1.67-1.58 (m, 1H), 1.50-1.36 (m, 1H), 1.13 (br d, J=12.8 Hz, 1H); HPLC: RT=1.125 min (Waters Acquity BEH C₁₈ 1.7 um 2.0×50 mm, CH₃CN/H₂O/0.1% TFA, 1.5 min gradient, wavelength=254 nm); MS (ES): m/z=544 [M+1]⁺.

Step 5: 2-[3-(Dimethyl-1H-1,2,3-triazol-5-yl)-5-[(S)-(4-fluorophenyl)(oxan-4-yl)methyl]-8-methoxy-5H-pyrido[3,2-b]indol-7-yl]propan-2-ol To a cold (−78° C.), stirred solution of (S)-methyl 3-(1,4-dimethyl-1H-1,2,3-triazol-5-yl)-5-((4-fluorophenyl)(tetrahydro-2H-pyran-4-yl)methyl)-8-methoxy-5H-pyrido[3,2-b]indole-7-carboxylate (36.0 mg, 0.0660 mmol) in THF (1.3 mL) under N₂ (g) was added methylmagnesium bromide (3M in Et₂O, 0.330 mL, 0.990 mmol). After 20 min, the reaction was warmed to −15° C. (ice/MeOH) for 10 min, then the reaction was quenched with sat. aq. NH₄Cl, diluted with EtOAc, the organic phase was separated, washed with sat. aq. NaCl then dried over sodium sulfate, filtered, and concentrated. The crude material was purified via preparative LC/MS (Column: Waters XBridge C₁₈, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-50% B over 25 min, then a 5-min hold at 50% B; Flow: 20 mL/min). Fractions containing the desired product were combined and dried via centrifugal evaporation to give 2-[3-(dimethyl-1H-1,2,3-triazol-5-yl)-5-[(S)-(4-fluorophenyl)(oxan-4-yl)methyl]-8-methoxy-5H-pyrido[3,2-b]indol-7-yl]propan-2-ol (22.8 mg, 60%): ¹H NMR (500 MHz, DMSO-d₆) δ 8.46 (s, 1H), 8.35 (br s, 2H), 8.19 (br s, 1H), 7.71 (s, 1H), 7.70-7.63 (m, 2H), 7.15 (br t, J=8.6 Hz, 2H), 5.67 (br d, J=11.1 Hz, 1H), 4.00 (br s, 3H), 3.92 (s, 3H), 3.88 (br d, J=7.7 Hz, 1H), 3.73 (br d, J=9.8 Hz, 1H), 3.50-3.37 (m, 1H), 3.25 (br t, J=11.1 Hz, 1H), 2.29 (s, 3H), 1.69-1.62 (m, 2H), 1.60 (br d, J=12.8 Hz, 5H), 1.54-1.43 (m, 1H), 1.35-1.20 (m, 1H), 0.98 (br d, J=12.5 Hz, 1H); HPLC: RT=1.52 min (Column: Waters Acquity UPLC BEH C₁₈, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm); MS (ES): m/z=544 [M+1]⁺.

Example 354

2-[3-(Dimethyl-1H-1,2,3-triazol-5-yl)-8-methoxy-5-[(S)-oxan-4-yl(phenyl)methyl]-5H-pyrido[3,2-b]indol-7-yl]propan-2-ol

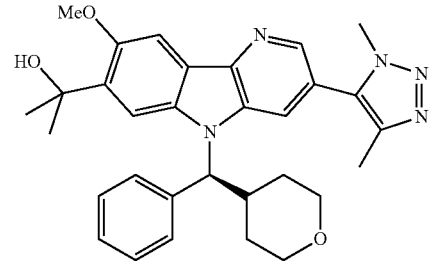 [SMILES: COc1cc2c3ncc(-c4c(C)nnn4C)cc3n([C@H](c3ccccc3)C3CCOCC3)c2cc1C(C)(C)O]

Step 1: (S)-Methyl 3-(1,4-dimethyl-1H-1,2,3-triazol-5-yl)-8-methoxy-5-(phenyl(tetrahydro-2H-pyran-4-yl)methyl)-5H-pyrido[3,2-b]indole-7-carboxylate To a cool (0° C.), stirred suspension of methyl 3-(1,4-dimethyl-1H-1,2,3-triazol-5-yl)-8-methoxy-5H-pyrido[3,2-b]indole-7-carboxylate (39.6 mg, 0.113 mmol), (R)-phenyl(tetrahydro-2H-pyran-4-yl)methanol (46.6 mg, 0.242 mmol), and triphenylphosphine (62.1 mg, 0.237 mmol) in THF (2.3 mL) under N₂ (g) was added dropwise over 1 min via syringe DIAD (0.0500 mL, 0.257 mmol). The suspension dissolved quickly, and the yellow solution was allowed to warm to room temperature and stirred overnight. The reaction was concentrated and dried under vacuum overnight. The residue was purified by silica gel column chromatography (Teledyne ISCO CombiFlash Rf, gradient of 0% to 7% using solvent A/B=CH₂Cl₂/MeOH over 30 column volumes, RediSep SiO₂ 24 g, loaded as DCM solution). (S)-Methyl 3-(1,4-dimethyl-1H-1,2,3-triazol-5-yl)-8-methoxy-5-(phenyl(tetrahydro-2H-pyran-4-yl)methyl)-5H-pyrido[3,2-b]indole-7-carboxylate (29.2 mg, 50%) was isolated as a pale yellow film. HPLC: RT=1.111 min (Waters Acquity BEH C₁₈ 1.7 um 2.0×50 mm, CH₃CN/H₂O/0.1% TFA, 1.5 min gradient, wavelength=254 nm); MS (ES): m/z=526 [M+1]⁺.

Step 2: 2-[3-(Dimethyl-1H-1,2,3-triazol-5-yl)-8-methoxy-5-[(S)-oxan-4-yl(phenyl)methyl]-5H-pyrido[3,2-b]indol-7-yl]propan-2-ol To a cold (−78° C.), stirred solution of (S)-methyl 3-(1, 4-dimethyl-1H-1,2,3-triazol-5-yl)-8-methoxy-5-(phenyl(tetrahydro-2H-pyran-4-yl)methyl)-5H-pyrido[3,2-b]indole-7-carboxylate (29.2 mg, 0.0560 mmol) in THF (1.1 mL) under N₂ (g) was added methylmagnesium bromide (3M in Et₂O, 296 μl, 0.889 mmol). After 15 min, the reaction was placed in an ice-water bath and stirred for 20 min. The reaction was quenched with sat. aq. NH₄Cl (5 mL), diluted with EtOAc, and the organic phase was separated and concentrated. The crude material was purified via preparative LC/MS (Column: XBridge C₁₈, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-85% B over 25 min, then a 5-min hold at 100% B; Flow: 20 mL/min). Fractions containing the desired product were combined and dried via centrifugal evaporation to give 2-[3-(dimethyl-1H-1,2,3-triazol-5-yl)-8-methoxy-5-[(5)-oxan-4-yl(phenyl)methyl]-5H-pyrido[3,2-b]indol-7-yl]propan-2-ol (14.3 mg, 49%): $^1$H NMR (500 MHz, DMSO-d₆) δ 8.45 (s, 1H), 8.37 (br s, 1H), 8.21 (s, 1H), 7.93 (s, 1H), 7.71 (s, 1H), 7.63 (br d, J=7.7 Hz, 2H), 7.36-7.29 (m, 2H), 7.27-7.20 (m, 1H), 5.65 (br d, J=11.1 Hz, 1H), 3.99 (s, 3H), 3.91 (s, 3H), 3.87 (br d, J=9.8 Hz, 1H), 3.72 (br d, J=8.8 Hz, 1H), 3.52 (br s, 1H), 3.44 (br t, J=11.3 Hz, 1H), 3.35 (br s, 1H), 3.26 (br t, J=11.3 Hz, 1H), 2.28 (s, 3H), 1.67 (br d, J=12.5 Hz, 1H), 1.60 (br d, J=14.1 Hz, 6H), 1.53-1.42 (m, 1H), 1.35-1.23 (m, 1H), 0.98 (br d, J=12.5 Hz, 1H); HPLC: RT=1.56 min (Column: Waters Acquity UPLC BEH C₁₈, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm); MS (ES): m/z=526 [M+1]⁺.

Example 355

2-[3-(Dimethyl-1H-1,2,3-triazol-5-yl)-6-methoxy-5-[(S)-oxan-4-yl(phenyl)methyl]-5H-pyrido[3,2-b]indol-7-yl]propan-2-ol

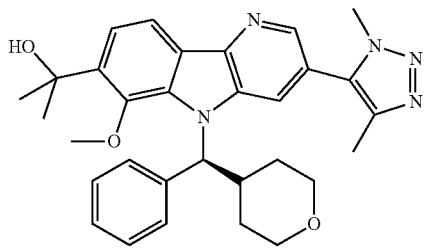 [SMILES: COc1c(C(C)(C)O)ccc2c3ncc(-c4c(C)nnn4C)cc3n([C@H](c3ccccc3)C3CCOCC3)c12]

Step 1: Methyl 3-(1,4-dimethyl-1H-1,2,3-triazol-5-yl)-6-methoxy-5H-pyrido[3,2-b]indole-7-carboxylate In a 50 mL RB Flask was added a mixture of methyl 3-bromo-6-methoxy-5H-pyrido[3,2-b]indole-7-carboxylate (340 mg, 1.01 mmol), 1,4-dimethyl-5-(tributylstannyl)-1H-1,2,3-triazole (603 mg, 1.56 mmol) and TEA (0.290 mL, 2.08 mmol) in DMF (21 mL), and the mixture was purged under a nitrogen stream. While purging, was added copper(I) iodide (39.0 mg, 0.205 mmol) and Pd(Ph₃P)₄ (75.1 mg, 0.0650 mmol), and the vial was capped and heated in a heating block at 95° C. with stirring for 40 h. The reaction was cooled to room temperature, SiO₂ (5 g) was added, the volatiles removed under reduced pressure. The material was then purified by silica gel column chromatography (Teledyne ISCO CombiFlash Rf, gradient of 0% to 100% using solvent A/B=CH₂Cl₂/acetone over 20 column volumes, RediSep SiO₂ 40 g). Methyl 3-(1,4-dimethyl-1H-1,2,3-triazol-5-yl)-6-methoxy-5H-pyrido[3,2-b]indole-7-carboxylate (304 mg, 85%) was isolated as a yellow solid: HPLC: RT=0.948 min (Waters Acquity BEH C₁₈ 1.7 um 2.0×50 mm, CH₃CN/H₂O/0.1% TFA, 1.5 min gradient, wavelength=254 nm); MS (ES): m/z=352 [M+1]⁺.

Step 2: (S)-Methyl 3-(1,4-dimethyl-1H-1,2,3-triazol-5-yl)-6-methoxy-5-(phenyl(tetrahydro-2H-pyran-4-yl)methyl)-5H-pyrido[3,2-b]indole-7-carboxylate To a cool, stirred suspension of methyl 3-(1,4-dimethyl-1H-1,2,3-triazol-5-yl)-6-methoxy-5H-pyrido[3,2-b]indole-7-carboxylate (40.5 mg, 0.115 mmol), (R)-phenyl(tetrahydro-2H-pyran-4-yl)methanol (47.1 mg, 0.245 mmol), and triphenylphosphine (60.2 mg, 0.230 mmol) in THF (2.4 mL) under N₂ (g) was added dropwise over 1 min via syringe DIAD (0.0500 mL, 0.257 mmol). The suspension dissolved quickly, and the yellow solution was allowed to warm to room temperature and stirred overnight. The reaction was concentrated and dried under vacuum overnight. The residue was purified by silica gel column chromatography (Teledyne ISCO CombiFlash Rf, gradient of 0% to 7% using solvent A/B=CH₂Cl₂/MeOH over 30 column volumes, RediSep SiO₂ 24 g, loaded as DCM solution). (S)-Methyl 3-(1,4-dimethyl-1H-1,2,3-triazol-5-yl)-6-methoxy-5-(phenyl(tetrahydro-2H-pyran-4-yl)methyl)-5H-pyrido[3,2-b]indole-7-carboxylate (53.0 mg, 87%) was isolated as a pale-yellow film: HPLC: RT=1.179 min (Waters Acquity BEH C₁₈ 1.7 um 2.0×50 mm, CH₃CN/H₂O/0.1% TFA, 1.5 min gradient, wavelength=254 nm); MS (ES): m/z=526 [M+1]⁺.

Step 3: 2-[3-(Dimethyl-1H-1,2,3-triazol-5-yl)-6-methoxy-5-[(S)-oxan-4-yl(phenyl)methyl]-5H-pyrido[3,2-b]indol-7-yl]propan-2-ol To a cold (−78° C.), stirred solution of (S)-methyl 3-(1,4-dimethyl-1H-1,2,3-triazol-5-yl)-6-methoxy-5-(phenyl(tetrahydro-2H-pyran-4-yl)methyl)-5H-pyrido[3,2-b]indole-7-carboxylate (53.0 mg, 0.101 mmol) in THF (2017 μl) under N₂ (g) was added methylmagnesium bromide (3M in Et₂O, 538 μl, 1.61 mmol), the reaction was stirred for 30 min before it was allowed to warm to 0° C., and stirred for 15 min before it was quenched with sat. aq. NH₄Cl (5 mL). The reaction mixture was diluted with EtOAc, the organic phase was separated, and the volatiles removed. The crude material was purified via preparative LC/MS (Column: Waters XBridge Shield RP₁₈, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 min, then a 5-min hold at 100% B; Flow: 20 mL/min). Fractions containing the desired product were combined and dried via centrifugal evaporation to give 2-[3-(dimethyl-1H-1,2,3-triazol-5-yl)-6-methoxy-5-[(S)-oxan-4-yl(phenyl)methyl]-5H-pyrido[3,2-b]indol-7-yl]propan-2-ol (8.90 mg, 17%): $^1$H NMR (500 MHz, DMSO-d₆) δ 8.50 (s, 1H), 8.17 (s, 1H), 7.95 (s, 1H), 7.90 (d, J=8.1 Hz, 1H), 7.64 (d, J=8.4 Hz, 1H), 7.51 (br d, J=7.4 Hz, 2H), 7.25-7.20 (m, 2H), 7.19-7.14 (m, 1H), 6.15 (br d, J=11.1 Hz, 1H), 3.96 (s, 3H), 3.95 (s, 3H), 3.83 (br t, J=12.3 Hz, 2H), 3.55-3.40 (m, 2H), 2.24 (s, 3H), 1.71 (s, 3H), 1.69 (s, 3H), 1.61 (br d, J=12.5 Hz, 1H), 1.54 (br d, J=9.4 Hz, 1H), 1.48-1.37 (m, 2H); HPLC: RT=1.56 min (Column: Waters Acquity UPLC BEH C$_{18}$, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.11 mL/min; Detection: UV at 220 nm); MS (ES): m/z=526 [M+1]$^1$.

Example 356

[3-(Dimethyl-1H-1,2,3-triazol-5-yl)-5-[(S)-oxan-4-yl(phenyl)methyl]-7-(prop-1-en-2-yl)-5H-pyrido[3,2-b]indol-6-yl]methanol

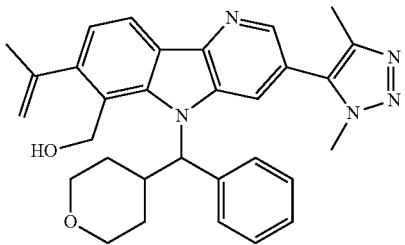 [SMILES: C=C(C)c1ccc2c3ncc(-c4c(C)nnn4C)cc3n(C(c3ccccc3)C3CCOCC3)c2c1CO]

Step 1: 5-(Tetramethyl-1,3,2-dioxaborolan-2-yl)-1,3-dihydro-2-benzofuran-1-one

In a 100 ml, round-bottomed flask was added 5-bromoisobenzofuran-1(3H)-one (1.00 g, 4.69 mmol), bis(pinacolato)diboron (1.31 g, 5.16 mmol), PdCl$_2$(dppf)-CH$_2$Cl$_2$ adduct (0.383 g, 0.469 mmol), and potassium acetate (1.15 g, 11.7 mmol) in dioxane (20 mL) to give a suspension. The flask was equipped with a reflux condenser and heated to 80° C. with stirring under nitrogen for 16 h. The reaction was partitioned between ethyl acetate (100 mL) and water (50 mL), and the organic layer was dried with Na$_2$SO$_4$, filtered, and concentrated. The reaction mixture was purified using ISCO silica gel chromatography (40 g column, gradient from 0% to 100% EtOAc/hexanes) to give the title compound (0.695 g, 57%). $^1$H NMR (400 MHz, DMSO-d$_6$) δ 7.97 (s, 1H), 7.85 (s, 2H), 5.43 (s, 2H), 1.33 (s, 12H) HPLC RT=0.76 min (Column: Waters Acquity BEH C182.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: 5-(5-Bromo-3-nitropyridin-2-yl)-1,3-dihydro-2-benzofuran-1-one

Following a procedure analogous to that described for methyl 4-(5-bromo-3-nitropyridin-2-yl)benzoate, 5-(tetramethyl-1,3,2-dioxaborolan-2-yl)-1,3-dihydro-2-benzofuran-1-one (695 mg, 2.67 mmol) was converted to the title compound, which was purified using ISCO silica gel chromatography (24 g column, gradient from 0% to 100% EtOAc/hexanes) to give 568 mg (70%). $^1$H NMR (400 MHz, DMSO-d$_6$) δ 9.17 (d, J=2.0 Hz, 1H), 8.91 (d, J=2.0 Hz, 1H), 7.97 (d, J=7.9 Hz, 1H), 7.90-7.86 (m, 1H), 7.75-7.69 (m, 1H), 5.50 (s, 2H). LCMS (M+H)=335; HPLC RT=1.12 min (Column: Waters Acquity BEH C182.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 3: 8-Bromo-1H-furo[3,4-g]pyrido[3,2-b]indol-3(10H)-one

Following a procedure analogous to that described for methyl 3-bromo-5H-pyrido[3,2-b]indole-7-carboxylate, 5-(5-bromo-3-nitropyridin-2-yl)-1,3-dihydro-2-benzofuran-1-one (568 mg, 1.70 mmol) was converted to the title compound, which was precipitated from the reaction mixture using DCM to give 287 mg (56%). $^1$H NMR (400 MHz, DMSO-d$_6$) δ 8.66 (d, J=2.0 Hz, 1H), 8.41 (d, J=2.0 Hz, 1H), 8.37 (d, J=8.1 Hz, 1H), 7.69 (d, J=8.1 Hz, 1H), 5.69 (s, 2H). LCMS (M+H)=303; HPLC RT=1.05 min (Column: Waters Acquity BEH C182.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 4: (S)-8-Bromo-10-(phenyl(tetrahydro-2H-pyran-4-yl)methyl)-1H-furo[3,4-g]pyrido[3,2-b]indol-3(10H)-one Following a procedure analogous to that described for methyl 3-(3,5-dimethylisoxazol-4-yl)-5-(phenyl(tetrahydro-2H-pyran-4-yl)methyl)-5H-pyrido[3,2-b]indole-7-carboxylate, 8-bromo-1H-furo[3,4-g]pyrido[3,2-b]indol-3(10H)-one (215 mg, 0.710 mmol) and phenyl(tetrahydro-2H-pyran-4-yl)methanol (363 mg, 0.890 mmol) were converted to the title compound (248 mg, 73%). $^1$H NMR (400 MHz, DMSO-d$_6$) δ 8.65 (s, 1H), 8.42 (d, J=8.1 Hz, 2H), 7.78 (d, J=7.9 Hz, 1H), 7.36 (d, J=8.8 Hz, 2H), 7.33-7.27 (m, 3H), 5.76 (s, 2H), 3.95-3.85 (m, 2H), 3.71 (d, J=11.0 Hz, 2H), 3.62-3.43 (m, 3H), 1.76 (br. s., 1H), 1.65-1.53 (m, 1H), 1.41-1.30 (m, 1H). LCMS (M+H)=477; HPLC RT=1.32 min (Column: Waters Acquity BEH C182.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 5: (S)-8-(1,4-Dimethyl-1H-1,2,3-triazol-5-yl)-10-(phenyl(tetrahydro-2H-pyran-4-yl)methyl)-1H-furo[3,4-g]pyrido[3,2-b]indol-3(10H)-one Following a procedure analogous to that described for the alternate synthesis of methyl 3-(1,4-dimethyl-1H-1,2,3-triazol-5-yl)-5H-pyrido[3,2-b]indole-7-carboxylate, (S)-8-bromo-10-(phenyl(tetrahydro-2H-pyran-4-yl)methyl)-1H-furo[3,4-g]pyrido[3,2-b]indol-3(10H)-one (248 mg, 0.520 mmol) was converted to the title compound (159 mg, 62%). $^1$H NMR (400 MHz, DMSO-d$_6$) δ 8.48 (d, J=8.1 Hz, 1H), 8.36 (br. s., 1H), 7.80 (d, J=8.1 Hz, 1H), 7.72 (d, J=7.0 Hz, 2H), 7.40-7.25 (m, 4H), 5.21 (d, J=11.2 Hz, 1H), 3.94 (s, 3H), 3.91 (br. s., 1H), 3.73 (d, J=9.2 Hz, 1H), 3.56-3.42 (m, 2H), 3.26 (t, J=10.8 Hz, 1H), 2.25 (s, 4H), 1.78 (d, J=13.2 Hz, 1H), 1.60 (d, J=8.4 Hz, 1H), 1.48-1.36 (m, 1H), 1.25 (d, J=2.4 Hz, 1H). LCMS (M+H)=494; HPLC RT=1.08 min (Column: Waters Acquity BEH C182.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 6: 2-[3-(Dimethyl-1H-1,2,3-triazol-5-yl)-6-(hydroxymethyl)-5-[(5)-oxan-4-yl(phenyl)methyl]-5H-pyrido[3,2-b]indol-7-yl]propan-2-ol Following a procedure analogous to that described for 2-[3-(dimethyl-1,2-oxazol-4-yl)-5-[oxan-4-yl(phenyl)methyl]-5H-pyrido[3,2-b]indol-7-yl]propan-2-ol, using (S)-8-(1,4-dimethyl-1H-1,2,3-triazol-5-yl)-10-(phenyl(tetrahydro-2H-pyran-4-yl)methyl)-1H-furo[3,4-g]pyrido[3,2-b]indol-3(10H)-one (15.0 mg, 0.0300 mmol) was converted to the title compound (3.10 mg, 20%). $^1$H NMR (500 MHz, DMSO-$d_6$) δ 8.46 (s, 1H), 8.14 (d, J=8.4 Hz, 1H), 7.89 (s, 1H), 7.63 (d, J=7.7 Hz, 2H), 7.52 (d, J=8.4 Hz, 1H), 7.31 (t, J=7.6 Hz, 2H), 7.25-7.17 (m, 1H), 6.65 (d, J=10.8 Hz, 1H), 5.52 (d, J=10.4 Hz, 1H), 5.48 (s, 1H), 5.35 (d, J=8.1 Hz, 1H), 5.26 (t, J=4.4 Hz, 1H), 3.90 (d, J=11.8 Hz, 1H), 3.82 (s, 3H), 3.70 (d, J=8.8 Hz, 1H), 3.50 (t, J=11.4 Hz, 1H), 3.43-3.32 (m, 1H), 3.22 (t, J=11.6 Hz, 1H), 2.15 (s, 3H), 1.90 (d, J=12.8 Hz, 1H), 1.75 (s, 6H), 1.62-1.42 (m, 2H), 0.69 (d, J=12.5 Hz, 1H). LCMS (M+H)=526; HPLC RT=1.01 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 7: [3-(Dimethyl-1H-1,2,3-triazol-5-yl)-5-[(S)-oxan-4-yl)phenyl)methyl]-7-(prop-1-en-2-yl)-5H-pyrido[3,2-b]indol-6-yl]methanol A solution of 2-[3-(dimethyl-1H-1,2,3-triazol-5-yl)-6-(hydroxymethyl)-5-[(S)-oxan-4-yl(phenyl)methyl]-5H-pyrido[3,2-b]indol-7-yl]propan-2-ol (122 mg, 0.230 mmol) was treated with conc. aq. $H_2SO_4$ (100 μl, 1.88 mmol) and heated to 50° C. for 60 min. The reaction was partitioned between ethyl acetate and sat. aq. $Na_2CO_3$. The organic phase was dried and evaporated under reduced pressure. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-55% B over 25 min, then a 5-min hold at 55% B; Flow: 20 mL/min. Fractions containing the desired product were combined and dried via centrifugal evaporation. The yield of the product was 7.10 mg. $^1$H NMR (500 MHz, DMSO-$d_6$) δ 8.52 (s, 1H), 8.23 (d, J=7.7 Hz, 1H), 8.17 (s, 1H), 7.63 (d, J=7.4 Hz, 2H), 7.39-7.33 (m, 2H), 7.30-7.21 (m, 2H), 5.77-5.70 (m, 1H), 5.68-5.62 (m, 1H), 5.14 (d, J=11.1 Hz, 1H), 3.94-3.84 (m, 4H), 3.74 (d, J=8.8 Hz, 1H), 3.24 (t, J=11.4 Hz, 1H), 2.22 (s, 3H), 1.77 (d, J=12.5 Hz, 1H), 1.58 (d, J=4.7 Hz, 6H), 1.52-1.42 (m, 2H), 1.32-1.18 (m, 2H), 0.88 (d, J=12.1 Hz, 1H). LCMS (M+H)=508; HPLC RT=1.16 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 357

2-[3-(Dimethyl-4H-1,2,4-triazol-4-yl)-5-[(R)-oxan-4-yl(phenyl)methyl]-5H-pyrido[3,2-b]indol-7-yl]propan-2-ol

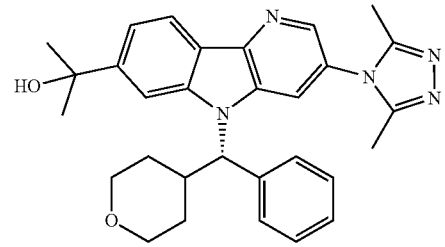 [SMILES: Cc1nnc(C)n1-c1cnc2c3ccc(C(C)(C)O)cc3n([C@H](c3ccccc3)C3CCOCC3)c2c1]

Step 1: Methyl 3-bromo-5-[(S)-oxan-4-yl(phenyl)methyl]-5H-pyrido[3,2-b]indol-7-carboxylate Following a procedure analogous to that described for methyl 3-(3,5-dimethylisoxazol-4-yl)-5-(phenyl(tetrahydro-2H-pyran-4-yl)methyl)-5H-pyrido[3,2-b]indole-7-carboxylate, methyl 3-bromo-5H-pyrido[3,2-b]indole-7-carboxylate (1.00 g, 3.28 mmol) and phenyl(tetrahydro-2H-pyran-4-yl)methanol (1.26 g, 6.55 mmol) were converted to the title compound (0.902 g, 57%). $^1$H NMR (400 MHz, DMSO-$d_6$) δ 8.62 (d, J=1.8 Hz, 1H), 8.33-8.27 (m, 1H), 7.89 (dd, J=8.1, 1.3 Hz, 1H), 7.63 (d, J=7.3 Hz, 2H), 7.40-7.33 (m, 2H), 7.31-7.22 (m, 1H), 5.93 (d, J=11.2 Hz, 1H), 3.94 (s, 3H), 3.92-3.85 (m, 1H), 3.71 (dd, J=11.1, 2.5 Hz, 1H), 3.57-3.47 (m, 1H), 3.31 (s, 3H), 3.29-3.22 (m, 1H), 1.78-1.70 (m, 1H), 1.69-1.54 (m, 1H), 1.31 (qd, J=12.4, 4.7 Hz, 1H), 0.85 (d, J=12.1 Hz, 1H). LCMS (M+H)=479; HPLC RT=1.42 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: Methyl 3-{[(2,4-dimethoxyphenyl)methyl]amino}-5-[(S)-oxan-4-yl(phenyl)methyl-5H-pyrido[3,2-b]indole-7-carboxylate A 25 mL screw top vial was charged with methyl 3-bromo-5-[(S)-oxan-4-yl(phenyl)methyl]-5H-pyrido[3,2-b]indole-7-carboxylate (800 mg, 1.67 mmol) and dioxane (15 mL). Nitrogen was then bubbled through the solution as 2,4-dimethoxybenzylamine (0.500 mL, 3.33 mmol), 4,5-bis(diphenylphosphino)-9,9-dimethylxanthene (97.0 mg, 0.167 mmol), and cesium carbonate (1090 mg, 3.34 mmol) were added, followed by addition of bis(dibenzylideneacetone)palladium (77.0 mg, 0.134 mmol). The vial was sealed and heated to 100° C. for 24 h. The reaction was filtered on Celite and the volatiles were removed under reduced pressure. The reaction mixture was purified using ISCO silica gel chromatography (80 g column, gradient from 0% to 100% EtOAc/hexanes) to give the title compound (0.394 g, 42%). $^1$H NMR (400 MHz, DMSO-$d_6$) δ 8.40 (br. s., 1H), 8.07 (d, J=2.2 Hz, 1H), 7.97 (d, J=8.1 Hz, 1H), 7.74 (d, J=8.1 Hz, 1H), 7.40 (d, J=7.5 Hz, 2H), 7.33-7.15 (m, 5H), 6.79 (br. s., 2H), 6.66 (d, J=2.2 Hz, 1H), 6.49 (dd, J=8.5, 2.3 Hz, 2H), 5.66 (d, J=11.0 Hz, 2H), 4.28 (d, J=5.7 Hz, 2H), 3.68-3.59 (m, 1H), 3.35 (t, J=11.0 Hz, 1H), 3.30 (s, 3H), 3.15-3.00 (m, 1H), 2.84 (br. s., 2H), 1.58 (br. s., 4H), 0.78 (d, J=12.3 Hz, 2H). LCMS (M+H)=566; HPLC RT=1.17 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 3: 2-[3-(Dimethyl-4H-1,2,4-triazol-4-yl)-5-[(R)-oxan-4-yl(phenyl)methyl]-5H-pyrido[3,2-b]indol-7-yl]propan-2-ol To a 20% solution of TFA in DCM was added methyl 3-{[(2,4-dimethoxyphenyl)methyl]amino}-5-[(S)-oxan-4-yl (phenyl)methyl]-5H-pyrido[3,2-b]indole-7-carboxylate (394 mg, 0.697 mmol) and the resulting solution was stirred at room temperature for 1 h. The reaction mixture was then partitioned between ethyl acetate and saturated $Na_2CO_3$. The organic phase was dried and evaporated under reduced pressure. To the crude mixture was added N-[1-(dimethyl-amino)ethylidene]-N,N-dimethyl-ethanehydrazonamide (205 mg, 1.20 mmol), and it was heated to 155° C. for 16 h. The reaction mixture was purified using ISCO silica gel chromatography (24 g column, gradient from 0% to 20% MeOH/DCM). The residue obtained was dissolved in THF (2 mL) and cooled to 0° C. Methylmagnesium bromide (3M in diethyl ether, 0.320 mL, 0.970 mmol) was added. The reaction mixture was warmed to room temperature and stirred at that temperature for 16 h. The reaction mixture was then partitioned between ethyl acetate and saturated aq. $Na_2CO_3$. The organic phase was dried and evaporated under reduced pressure. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 20 min, then a 0-min hold at 100% B; Flow: 20 mL/min. Fractions containing the desired product were combined and dried via centrifugal evaporation to give 12 mg (20%). $^1$H NMR (500 MHz, DMSO-$d_6$) δ 8.57 (br. s., 1H), 8.48 (s, 1H), 8.15 (d, J=8.1 Hz, 2H), 7.67 (d, J=7.7 Hz, 2H), 7.50 (d, J=8.1 Hz, 1H), 7.37-7.29 (m, 2H), 7.28-7.21 (m, 1H), 5.78 (d, J=11.1 Hz, 1H), 3.90 (d, J=11.4 Hz, 1H), 3.76 (d, J=9.8 Hz, 1H), 3.47 (t, J=11.1 Hz, 1H), 3.32-3.23 (m, 1H), 2.90 (s, 3H), 2.74 (s, 3H), 1.66 (d, J=12.1 Hz, 2H), 1.58 (s, 6H), 1.38-1.28 (m, 2H), 1.05 (d, J=12.5 Hz, 2H). LCMS (M+H)=496; HPLC RT=1.00 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 364

3,3,3-Trifluoropropyl N-[3-(dimethyl-1H-1,2,3-triazol-5-yl)-5-[(S)-oxan-4-yl(phenyl)methyl]-5H-pyrido[3,2-b]indol-7-yl]carbamate

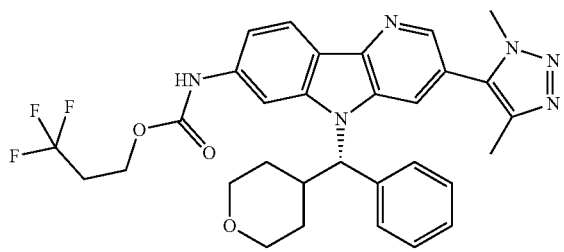 [SMILES: Cc1nnn(C)c1-c1cnc2c3ccc(NC(=O)OCCC(F)(F)F)cc3n([C@H](c3ccccc3)C3CCOCC3)c2c1]

Step 1: Methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate To a 200 mL round-bottomed flask containing methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate (1.23 g, 2.49 mmol) in THF (25 mL) was added sodium hydroxide (5M, 2.49 mL, 12.5 mmol), and the reaction mixture was heated to 60° C. After 16 h, 100 g of ice was added, and the volatiles were removed under reduced pressure. The pH was adjusted to pH 2 with concentrated aq. HCl and extracted with ethyl acetate (2×250 mL). The reaction mixture was purified using ISCO silica gel chromatography (80 g column, gradient from 0% to 10% MeOH/DCM) to give the title compound (1.15 g, 96%). $^1$H NMR (400 MHz, DMSO-$d_6$) δ 8.69-8.49 (m, 4H), 8.35-8.26 (m, 2H), 7.93 (d, J=7.9 Hz, 1H), 7.67 (s, 1H), 7.36-7.32 (m, 2H), 7.32-7.28 (m, 3H), 5.94 (d, J=11.2 Hz, 1H), 3.94-3.82 (m, 2H), 3.79-3.66 (m, 2H), 3.29-3.09 (m, 2H), 2.37-2.26 (m, 4H), 1.99 (s, 3H). LCMS (M+H)=482; HPLC RT=1.05 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: 5-{7-Isocyanato-5-[(S)-oxan-4-yl(phenyl)methyl]-5H-pyrido[3,2-b]indol-3-yl}-1,4-dimethyl-1H-1,2,3-triazole in 0.05M solution in dioxane To a 25 mL screw top vial containing (S)-3-(1,4-dimethyl-1H-1,2,3-triazol-5-yl)-5-(phenyl(tetrahydro-2H-pyran-4-yl)methyl)-5H-pyrido[3,2-b]indole-7-carboxylic acid (0.193 g, 0.400 mmol), diphenylphosphoryl azide (0.216 mL, 1.00 mmol), and TEA (0.139 mL, 1.00 mmol) was added dioxane (8 mL) to give a solution. This solution was heated to 60° C. for 2 h. The solution was cooled to room temperature and used without purification.

Step 3: 3,3,3-Trifluoropropyl N-[3-(dimethyl-1H-1,2,3-triazol-5-yl)-5-[(S)-oxan-4-yl(phenyl)methyl]-5H-pyrido[3,2-b]indol-7-yl]carbamate To 2 ml, of 0.05 M solution of 5-{7-isocyanato-5-[(S)-oxan-4-yl(phenyl)methyl]-5H-pyrido[3,2-b]indol-3-yl}-1,4-dimethyl-1H-1,2,3-triazole in dioxane was added 3,3,3-trifluoro-1-propanol (200 µL, 2.27 mmol), and the reaction mixture was heated to 80° C. for 16 h. The volatiles were removed under reduced pressure. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 min, then a 0-min hold at 100% B; Flow: 20 mL/min. Fractions containing the desired product were combined and dried via centrifugal evaporation to give 7.50 mg (16%). $^1$H NMR (500 MHz, DMSO-$d_6$) δ 10.09 (br. s., 1H), 8.48 (s, 2H), 8.26 (br. s., 1H), 8.14 (d, J=8.4 Hz, 1H), 7.64 (d, J=7.4 Hz, 2H), 7.43 (d, J=8.4 Hz, 1H), 7.38-7.31 (m, 2H), 7.29-7.21 (m, 1H), 5.64 (br. s., 1H), 4.41 (t, J=5.7 Hz, 2H), 4.02 (br. s., 3H), 3.90 (br. s., 1H), 3.75 (d, J=10.8 Hz, 1H), 3.45 (br. s., 1H), 3.27 (t, J=11.4 Hz, 1H), 2.84-2.70 (m, 3H), 2.30 (s, 3H), 1.69 (d, J=12.8 Hz, 1H), 1.50 (d, J=9.1 Hz, 1H), 1.35-1.21 (m, 1H), 1.07 (d, J=12.8 Hz, 1H). LCMS (M+H)=593; HPLC RT=0.89 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 365

Methyl N-[3-(dimethyl-1H-1,2,3-triazol-5-yl)-5-[(S)-oxan-4-yl)phenyl)methyl]-5H-pyrido[3,2-b]indol-7-yl]carbamate

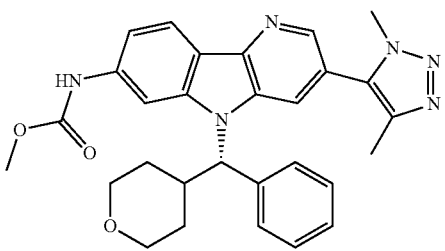 [SMILES: COC(=O)Nc1ccc2c3ncc(-c4c(C)nnn4C)cc3n([C@H](c3ccccc3)C3CCOCC3)c2c1]

The title compound was prepared using a procedure analogous to that described for 3,3,3-trifluoropropyl N-[3-(dimethyl-1H-1,2,3-triazol-5-yl)-5-[(S)-oxan-4-yl(phenyl)methyl]-5H-pyrido[3,2-b]indol-7-yl]carbamate, using MeOH (200 μL, 4.94 mmol) to give 7.90 mg (19%). $^1$H NMR (500 MHz, DMSO-d$_6$) δ 10.02 (br. s., 1H), 8.48 (s, 2H), 8.30 (br. s., 1H), 8.12 (d, J=8.8 Hz, 1H), 7.64 (d, J=7.4 Hz, 2H), 7.42-7.31 (m, 3H), 7.29-7.20 (m, 1H), 5.64 (br. s., 1H), 4.03 (br. s., 3H), 3.91 (s, 2H), 3.76 (s, 5H), 2.31 (s, 4H), 1.69 (d, J=12.5 Hz, 1H), 1.51 (d, J=8.8 Hz, 1H), 1.34-1.20 (m, 1H), 1.08 (d, J=11.8 Hz, 1H). LCMS (M+H)=511; HPLC RT=0.79 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 366

Ethyl N-[3-(dimethyl-1H-1,2,3-triazol-5-yl)-5-[(S)-oxan-4-yl(phenyl)methyl]-5H-pyrido[3,2-b]indol-7-yl]carbamate

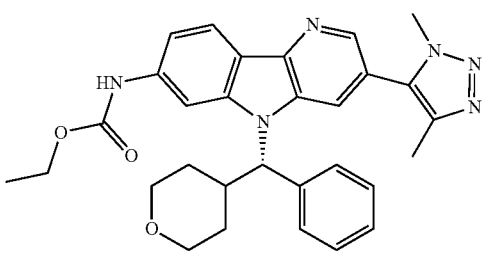 [SMILES: CCOC(=O)Nc1ccc2c3ncc(-c4c(C)nnn4C)cc3n([C@H](c3ccccc3)C3CCOCC3)c2c1]

The title compound was prepared using a procedure analogous to that described for 3,3,3-trifluoropropyl N-[3-(dimethyl-1H-1,2,3-triazol-5-yl)-5-[(S)-oxan-4-yl(phenyl)methyl]-5H-pyrido[3,2-b]indol-7-yl]carbamate, using EtOH (200 μL, 3.43 mmol) to give 8.70 mg (21%). $^1$H NMR (500 MHz, DMSO-d$_6$) δ 9.98 (br. s., 1H), 8.48 (s, 2H), 8.29 (br. s., 1H), 8.12 (d, J=8.4 Hz, 1H), 7.64 (d, J=7.7 Hz, 2H), 7.42-7.18 (m, 4H), 5.64 (br. s., 1H), 4.23 (q, J=7.1 Hz, 2H), 4.03 (br. s., 3H), 3.95-3.86 (m, 1H), 3.76 (d, J=10.4 Hz, 1H), 2.31 (s, 3H), 1.69 (d, J=12.1 Hz, 1H), 1.50 (d, J=12.1 Hz, 1H), 1.38-1.21 (m, 4H), 1.08 (d, J=11.8 Hz, 1H). LCMS (M+H)=525; HPLC RT=0.84 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 367

Propan-2-yl N-[3-(dimethyl-1H-1,2,3-triazol-5-yl)-5-[(S)-oxan-4-yl(phenyl)methyl]-5H-pyrido[3,2-b]indol-7-yl]carbamate

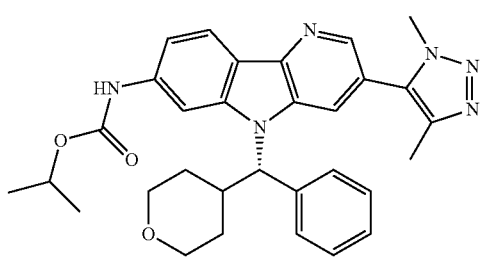 [SMILES: Cc1nnn(C)c1-c1cnc2c3ccc(NC(=O)OC(C)C)cc3n([C@H](c3ccccc3)C3CCOCC3)c2c1]

The title compound was prepared using a procedure analogous to that described for 3,3,3-trifluoropropyl N-[3-(dimethyl-1H-1,2,3-triazol-5-yl)-5-[(S)-oxan-4-yl(phenyl)methyl]-5H-pyrido[3,2-b]indol-7-yl]carbamate, using i-PrOH (200 μL, 2.60 mmol) to give 7.20 mg (17%). $^1$H NMR (500 MHz, DMSO-d$_6$) δ 9.91 (br. s., 1H), 8.47 (s, 1H), 8.27 (br. s., 1H), 8.11 (d, J=8.4 Hz, 1H), 7.64 (d, J=7.4 Hz, 2H), 7.48-7.14 (m, 4H), 5.63 (br. s., 1H), 5.07-4.89 (m, 1H), 4.02 (br. s., 3H), 3.91 (s, 1H), 3.75 (d, J=7.7 Hz, 1H), 3.48-3.35 (m, 2H), 3.28 (t, J=11.3 Hz, 2H), 2.31 (s, 3H), 1.68 (d, J=12.1 Hz, 1H), 1.50 (d, J=11.4 Hz, 1H), 1.38-1.21 (m, 7H), 1.08 (d, J=12.8 Hz, 1H). LCMS (M+H)=539; HPLC RT=0.88 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 369

2-[3-(Dimethyl-1H-1,2,3-triazol-5-yl)-9-fluoro-5-[(S)-oxan-4-yl)phenyl)methyl]-5H-pyrido[3,2-b]indol-7-yl]propan-2-ol

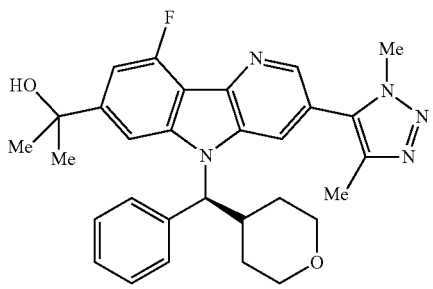 [SMILES: Cc1nnn(C)c1-c1cnc2c3c(F)cc(C(C)(C)O)cc3n([C@H](c3ccccc3)C3CCOCC3)c2c1]

Step 1: Methyl 4-(5-bromo-3-nitropyridin-2-yl)-3-fluorobenzoate

To a solution of (2-fluoro-4-(methoxycarbonyl)phenyl)boronic acid (0.500 g, 2.53 mmol) and 2,5-dibromo-3-nitropyridine (0.712 g, 2.53 mmol) in THF (8.42 mL) was added aq. tripotassium phosphate (2M, 2.53 ml, 5.05 mmol). The reaction was degassed with bubbling nitrogen, then PdCl$_2$(dppf)-CH$_2$Cl$_2$ adduct (0.124 g, 0.152 mmol) was added and the reaction was heated to 70° C. for 2 h. The reaction was cooled, diluted with water, and extracted 3 times with EtOAc. The combined organics were concentrated. The residue was purified via ISCO silica gel chromatography (40 g column; Hex/EtOAc; 0 to 100%) to give methyl 4-(5-bromo-3-nitropyridin-2-yl)-3-fluorobenzoate (0.610 g, 68%). $^1$H NMR (400 MHz, CDCl$_3$) δ 9.01 (d, J=2.1 Hz, 1H), 8.54 (d, J=2.1 Hz, 1H), 8.02 (dd, J=8.0, 1.5 Hz, 1H), 7.84-7.73 (m, 2H), 3.97 (s, 3H); LCMS (M+H)=355.1; HPLC RT=1.15 min. Analytical HPLC Method 1.

Step 2: Methyl 3-bromo-9-fluoro-5H-pyrido[3,2-b]indole-7-carboxylate

A solution of methyl 4-(5-bromo-3-nitropyridin-2-yl)-3-fluorobenzoate (0.610 g, 1.72 mmol) and DPPE (0.855 g, 2.15 mmol) in o-dichlorobenzene (5.73 mL) was heated to 170° C. After 1 h, the reaction was placed on the rotovap and concentrated. DCM and a small amount of hexanes were added to the residue, the solids were filtered off, and the solids were washed twice with DCM. The filtrate was concentrated, and the residue was purified via ISCO silica gel column chromatography (40 g column; Hex/EtOAc; 0 to 50% gradient). The solid from filtration was combined with the material obtained from the column to give methyl 3-bromo-9-fluoro-5H-pyrido[3,2-b]indole-7-carboxylate (0.380 g, 1.176 mmol, 68.5%). LCMS (M+H)=323.1; HPLC RT=0.88 min. Analytical HPLC Method 1.

Step 3: Methyl 3-(1,4-dimethyl-1H-1,2,3-triazol-5-yl)-9-fluoro-5H-pyrido[3,2-b]indole-7-carboxylate A solution of 1,4-dimethyl-5-(tributylstannyl)-1H-1,2,3-triazole (0.272 g, 0.706 mmol), methyl 3-bromo-9-fluoro-5H-pyrido[3,2-b]indole-7-carboxylate (0.190 g, 0.588 mmol), triethylamine (0.164 ml, 1.176 mmol), and copper(I) iodide (0.017 g, 0.088 mmol) in DMF (3.92 ml) was degassed with bubbling nitrogen. Tetrakis(triphenylphosphine)palladium(0) (0.068 g, 0.059 mmol) was added and the reaction was heated to 90° C. After, 4.5 h, triethylamine (0.164 ml, 1.176 mmol), 1,4-dimethyl-5-(tributylstannyl)-1H-1,2,3-triazole (0.272 g, 0.706 mmol), copper(I) iodide (0.017 g, 0.088 mmol), tetrakis(triphenylphosphine)palladium(0) (0.068 g, 0.059 mmol) and triethylamine (0.164 ml, 1.176 mmol) were added. After an additional 3 h, the reaction was cooled, diluted with water, then extracted twice with EtOAc. The organic layers were washed with ammonium hydroxide, then brine, then dried over sodium sulfate and concentrated. The residue was purified via ISCO silica gel column chromatography (via ISCO silica gel column chromatography (Hex/EtOAc; 0 to 100% gradient) to give methyl 3-(1,4-dimethyl-1H-1,2,3-triazol-5-yl)-9-fluoro-5H-pyrido[3,2-b]indole-7-carboxylate (0.030 g, 30.1%). $^1$H NMR (400 MHz, CDCl$_3$) δ 10.22 (s, 1H), 8.65 (d, J=1.8 Hz, 1H), 8.09 (d, J=1.0 Hz, 1H), 7.82 (d, J=1.8 Hz, 1H), 7.70 (dd, J=10.6, 1.0 Hz, 1H), 4.04 (s, 3H), 3.99 (s, 3H), 2.39 (s, 3H); LCMS (M+H)=340.3; HPLC RT=0.73 min. Analytical HPLC Method 1.

Step 4: (S)-2-(3-(1,4-Dimethyl-1H-1,2,3-triazol-5-yl)-9-fluoro-5-(phenyl(tetrahydro-2H-pyran-4-yl)methyl)-5H-pyrido[3,2-b]indol-7-yl)propan-2-ol A suspension of (R)-phenyl(tetrahydro-2H-pyran-4-yl)methanol (0.0850 g, 0.442 mmol), methyl 3-(1,4-dimethyl-1H-1,2,3-triazol-5-yl)-9-fluoro-5H-pyrido[3,2-b]indole-7-carboxylate (0.0600 g, 0.177 mmol), and triphenylphosphine (0.116 g, 0.442 mmol) in DCM (1.77 ml) was cooled in a water bath, and DIAD (0.0860 mL, 0.442 mmol) was added. The suspended material was dissolved upon addition. The reaction was stirred overnight, then the volatiles were removed under reduced pressure. The residue was purified via ISCO silica gel column chromatography (24 g column; DCM/EtOAc 0 to 100% gradient) to give partially pure (S)-methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-7-carboxylate. This material was dissolved in THF (1770 μL) and cooled in an ice bath. methylmagnesium bromide (3M in Et$_2$O, 472 μL, 1.42 mmol) was added. After 1.25 h, the reaction was quenched with sat. aq. NH$_4$Cl and extracted with EtOAc. The organic layer was washed with brine, dried with sodium sulfate, and concentrated. The residue was purified via ISCO silica gel column chromatography (12 g column; DCM/MeOH; 0 to 10% gradient). This material was further purified via preparative HPLC with the following conditions: Column: Luna C18, 30×100 mm, 5-μm particles; Mobile Phase A: 5:95 acetonitrile:water with 0.1% TFA; Mobile Phase B: 95:5 acetonitrile:water with 0.1% TFA; Gradient: 10-100% B over 15 min, then a 2-min hold at 100% B; Flow: 40 mL/min to give (S)-2-(3-(1,4-dimethyl-1H-1,2,3-triazol-5-yl)-9-fluoro-5-(phenyl(tetrahydro-2H-pyran-4-yl)methyl)-5H-pyrido[3,2-b]indol-7-yl)propan-2-ol (6.70 mg, 7%). $^1$H NMR (400 MHz, CD$_3$OD) δ 8.46 (d, J=1.7 Hz, 1H), 8.26 (s, 1H), 7.91 (s, 1H), 7.62 (d, J=7.3 Hz, 2H), 7.40-7.32 (m, 2H), 7.29 (d, J=7.2 Hz, 1H), 7.20 (d, J=11.7 Hz, 1H), 5.79 (d, J=11.1 Hz, 1H), 3.98 (s, 4H), 3.88-3.78 (m, 1H), 3.60 (s, 1H), 3.45-3.37 (m, 1H), 2.31 (s, 3H), 1.97 (d, J=12.8 Hz, 1H), 1.66 (s, 6H), 1.62 (d, J=3.3 Hz, 2H), 1.43 (dd, J=13.0, 4.6 Hz, 1H), 1.08 (d, J=12.7 Hz, 1H); LCMS (M+H)=514.4; HPLC RT=0.81 min. Analytical HPLC Method 1

Example 370

2-[3-(Dimethyl-1,2-oxazol-4-yl)-9-fluoro-5-[(S)-oxan-4-yl(phenyl)methyl]-5H-pyrido[3,2-b]indol-7-yl]propan-2-ol

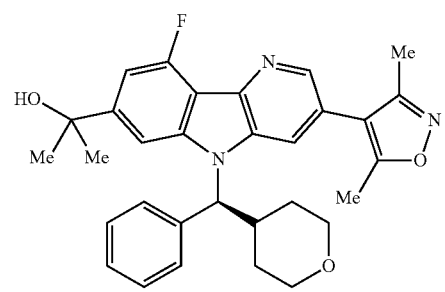 [SMILES: Cc1noc(C)c1-c1cnc2c3c(F)cc(C(C)(C)O)cc3n([C@H](c3ccccc3)C3CCOCC3)c2c1]

Step 1: Methyl 3-(3,5-dimethylisoxazol-4-yl)-9-fluoro-5H-pyrido[3,2-b]indole-7-carboxylate To a solution of (3,5-dimethylisoxazol-4-yl)boronic acid (0.166 g, 1.18 mmol) and methyl 3-bromo-9-fluoro-5H- pyrido[3,2-b]indole-7-carboxylate (0.190 g, 0.588 mmol) in DMF (3.92 mL) was added tripotassium phosphate (2M aqueous, 0.882 mL, 1.76 mmol). The solution was degassed with bubbling nitrogen, then PdCl$_2$(dppf)-DCM adduct (0.0480 g, 0.059 mmol) was added, and the reaction was heated to 90° C. After 2 h, the reaction was cooled and diluted with water. The reaction was extracted twice with EtOAc. The organic layers were washed with 10% LiCl solution, dried with sodium sulfate, and concentrated. The residue was purified via ISCO silica gel column chromatography (Hex/EtOAc; 0 to 100% gradient) to give methyl 3-(3,5-dimethylisoxazol-4-yl)-9-fluoro-5H-pyrido[3,2-b]indole-7-carboxylate (0.0440 g, 0.130 mmol, 22%); LCMS (M+H)=340.3; HPLC RT=0.79 min. Analytical HPLC Method 1.

Step 2: (S)-Methyl 3-(1,4-dimethyl-1H-1,2,3-triazol-5-yl)-9-fluoro-5-(phenyl(tetrahydro-2H-pyran-4-yl)methyl)-5H-pyrido[3,2-b]indole-7-carboxylate Following a procedure analogous to that for 2-[3-(dimethyl-1H-1,2,3-triazol-5-yl)-9-fluoro-5-[(S)-oxan-4-yl(phenyl)methyl]-5H-pyrido[3,2-b]indol-7-yl]propan-2-ol, (R)-phenyl(tetrahydro-2H-pyran-4-yl)methanol (0.0850 g, 0.442 mmol) and methyl 3-(1,4-dimethyl-1H-1,2,3-triazol-5-yl)-9-fluoro-5H-pyrido[3,2-b]indole-7-carboxylate (0.0600 g, 0.177 mmol) were converted to the title compound (3.70 mg, 6%). $^1$H NMR (400 MHz, CDCl$_3$) δ 9.28 (s, 1H), 8.62 (d, J=1.8 Hz, 1H), 8.06 (d, J=1.1 Hz, 1H), 7.74-7.64 (m, 2H), 3.99 (s, 3H), 2.49 (s, 3H), 2.34 (s, 3H); LCMS (M+H)=514.3; HPLC RT=0.86 min. Analytical HPLC Method 1.

Examples 371 & 372

[3-(Dimethyl-1H-1,2,3-triazol-5-yl)-5-[(S)-oxan-4-yl)phenyl)methyl]-5H-pyrido[3,2-b]indol-7-yl](imino)methyl-λ$^6$-sulfanone Diastereomer A, Example 371

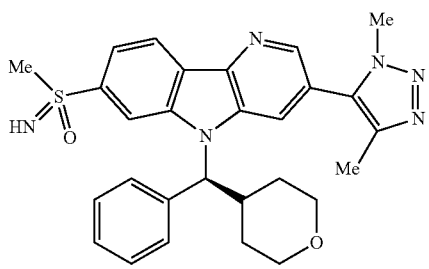

Diastereomer B, Example 372

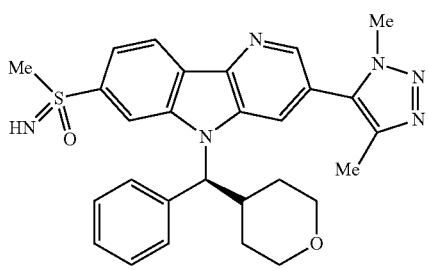

Step 1:
5-Bromo-2-(4-(methylthio)phenyl)-3-nitropyridine

To a solution of (4-(methylthio)phenyl)boronic acid (0.500 g, 2.98 mmol) and (4-(methylthio)phenyl)boronic acid (0.500 g, 2.98 mmol) in THF (9.92 ml) was added aq. tripotassium phosphate (2M, 2.98 ml, 5.95 mmol). The reaction was degassed with bubbling nitrogen, then PdCl$_2$(dppf)-DCM adduct (0.146 g, 0.179 mmol) was added, and the reaction was heated to 70° C. After ca. 1.5 h, the reaction was cooled, diluted with water, and extracted 3 times with EtOAc. The organic layer was concentrated. The residue was purified via ISCO silica gel column chromatography (40 g column; Hex/EtOAc; 0 to 50% gradient) to give 5-bromo-2-(4-(methylthio)phenyl)-3-nitropyridine (0.684 g, 71%). $^1$H NMR (400 MHz, CDCl$_3$) δ 8.89 (d, J=2.1 Hz, 1H), 8.92-8.86 (m, 1H), 8.26 (d, J=2.1 Hz, 1H), 7.51-7.45 (m, 2H), 7.36-7.29 (m, 2H), 2.53 (s, 3H).

Step 2:
3-Bromo-7-(methylthio)-5H-pyrido[3,2-b]indole

A suspension of 5-bromo-2-(4-(methylthio)phenyl)-3-nitropyridine (0.684 g, 2.10 mmol) and 1,2-bis(diphenylphosphino)ethane (1.05 g, 2.63 mmol) in o-dichlorobenzene (7.01 mL) was heated to 170° C. The suspended material was dissolved as the reaction was heated. After 1.5 h, the reaction was concentrated. The residue was purified via ISCO silica gel column chromatography (40 g column; Hex/EtOAc 0 to 100% gradient) to give 3-bromo-7-(methylthio)-5H-pyrido[3,2-b]indole (0.320 g, 1.09 mmol, 52%). $^1$H NMR (400 MHz, CDCl$_3$) δ 8.58 (d, J=2.0 Hz, 1H), 8.21 (d, J=8.3 Hz, 1H), 7.85 (d, J=2.0 Hz, 1H), 7.32 (s, 1H), 7.25 (d, J=1.6 Hz, 1H), 2.60 (s, 3H).

Step 3:
3-Bromo-7-(methylsulfinyl)-5H-pyrido[3,2-b]indole

To a solution of 3-bromo-7-(methylthio)-5H-pyrido[3,2-b]indole (0.220 g, 0.750 mmol) in THF (12.5 mL) and water (2.50 mL) was added NBS (0.160 g, 0.900 mmol). The reaction was stirred overnight, then concentrated. Water and sat. aq. NaHCO$_3$ solution were added, then the solid was filtered off and washed with water. Drying gave 3-bromo-7-(methylsulfinyl)-5H-pyrido[3,2-b]indole (0.183 g, 0.592 mmol, 79%). LCMS (M+H)=309.0; HPLC RT=0.87 min. Analytical HPLC Method 1.

Step 4: 3-Bromo-7-(methylsulfinyl)-5-((S)-phenyl(tetrahydro-2H-pyran-4-yl)methyl)-5H-pyrido[3,2-b]indole A suspension of (R)-phenyl(tetrahydro-2H-pyran-4-yl)methanol (0.280 g, 1.46 mmol), 3-bromo-7-(methylsulfinyl)-5H-pyrido[3,2-b]indole (0.180 g, 0.582 mmol), and triphenylphosphine (0.382 g, 1.46 mmol) in DCM (5.82 mL) was cooled in an ice bath. DIAD (0.283 mL, 1.46 mmol) was added; the suspended material dissolved. The reaction was stirred overnight, then concentrated. The residue was purified via ISCO silica gel column chromatography (40 g column; DCM/EtOAc 0 to 100% gradient, then DCM/MeOH 0 to 10% gradient) to give 3-bromo-7-(methylsulfinyl)-5-((S)-phenyl(tetrahydro-2H-pyran-4-yl)methyl)-5H-pyrido[3,2-b]indole (0.333 g, 0.689 mmol, 118%) as a mixture of 2 diastereomers at the sulfoxide position. LCMS (M+H)=483.2; HPLC RT=1.07 min. Analytical HPLC Method 1.

Step 5: 3-(1,4-Dimethyl-1H-1,2,3-triazol-5-yl)-7-(methylsulfinyl)-5-((S)-phenyl(tetrahydro-2H-pyran-4-yl)methyl)-5H-pyrido[3,2-b]indole A solution of 1,4-dimethyl-5-(tributylstannyl)-1H-1,2,3-triazole (0.319 g, 0.827 mmol), 3-bromo-7-(methylsulfinyl)-5-((S)-phenyl(tetrahydro-2H-pyran-4-yl)methyl)-5H-pyrido[3,2-b]indole (0.333 g, 0.689 mmol) (note: weight represents greater than 100% yield for previous reaction), triethylamine (0.192 mL, 1.38 mmol), and copper(I) iodide (0.0200 g, 0.103 mmol) in DMF (2.30 mL) was degassed with bubbling nitrogen. Tetrakis(triphenylphosphine)palladium(0) (0.0520 g, 0.0450 mmol) was added, and the reaction was heated to 90° C. After 2 h, the reaction was cooled and then diluted with water and EtOAc. The solid was filtered off, then ammonium hydroxide was added, and the aqueous layer was extracted twice with EtOAc. The combined organic layers were washed with brine, dried with sodium sulfate, and concentrated. The residue was purified via ISCO silica gel column chromatography (40 g column; DCM/MeOH; 0 to 10% gradient) to give 3-(1,4-dimethyl-1H-1,2,3-triazol-5-yl)-7-(methylsulfinyl)-5-((S)-phenyl(tetrahydro-2H-pyran-4-yl)methyl)-5H-pyrido[3,2-b]indole (0.111 g, 0.222 mmol, 32%) as a mixture of diastereomers at the sulfoxide position. LCMS (M+H)=500.4; HPLC RT=1.02 min. Analytical HPLC Method 1.

Step 6: [3-(Dimethyl-1H-1,2,3-triazol-5-yl)-5-[(S)-oxan-4-yl)phenyl)methyl]-5H-pyrido[3,2-b]indol-7-yl](imino)methyl-$\lambda^6$-sulfanone 3-(1,4-Dimethyl-1H-1,2,3-triazol-5-yl)-7-(methylsulfinyl)-5-((S)-phenyl(tetrahydro-2H-pyran-4-yl)methyl)-5H-pyrido[3,2-b]indole (0.111 g, 0.222 mmol), 4-nitrobenzenesulfonamide (0.0900 g, 0.444 mmol), iodobenzene diacetate (0.150 g, 0.467 mmol), and ferric acetylacetonate (0.0160 g, 0.0440 mmol) were dissolved in acetonitrile (2.222 mL). The reaction was stirred overnight, then additional 4-nitrobenzenesulfonamide (0.0900 g, 0.444 mmol), ferric acetylacetonate (0.0160 g, 0.0440 mmol), and iodobenzene diacetate (0.150 g, 0.467 mmol) were added. After an additional 5 h, the reaction was concentrated. The residue was purified via ISCO silica gel column chromatography (40 g column; DCM/MeOH; 0 to 100% gradient) to give the intermediate sulfoximine as a mixture of diastereomers. This intermediate was dissolved in acetonitrile (2.22 mL) and $Cs_2CO_3$ (0.289 g, 0.888 mmol) and thiophenol (0.0870 mL, 0.844 mmol) were added. After 6 h, additional $Cs_2CO_3$ (0.289 g, 0.888 mmol) and thiophenol (0.0870 mL, 0.844 mmol) were added. The reaction was stirred overnight, then diluted with acetonitrile and filtered. The filtrate was concentrated. The DCM-soluble portion of the residue was purified via ISCO silica gel column chromatography (24 g column; DCM/MeOH; 0 to 10% gradient) to give 3-(1,4-dimethyl-1H-1,2,3-triazol-5-yl)-7-(S-methylsulfonimidoyl)-5-((S)-phenyl(tetrahydro-2H-pyran-4-yl)methyl)-5H-pyrido[3,2-b]indole as a mixture of diastereomers, which were separated using chiral prep SFC (Column: Chiralpak IB 25×2 cm, 5 μm; Mobile Phase: 78/22 $CO_2$/MeOH; Flow: 50 mL/min). The faster eluting peak was assigned as Diastereomer A (13.0 mg, 11%); the slower eluting peak was assigned as Diastereomer B (11.6 mg, 10%). Diastereomer A: $^1$H NMR (400 MHz, $CD_3OD$) δ 8.64-8.59 (m, 2H), 8.57 (d, J=8.3 Hz, 1H), 8.42 (s, 1H), 7.99 (dd, J=8.3, 1.5 Hz, 1H), 7.65 (d, J=7.3 Hz, 2H), 7.40-7.34 (m, 2H), 7.31-7.25 (m, 1H), 5.88 (d, J=11.0 Hz, 1H), 4.04-3.96 (m, 4H), 3.81 (d, J=9.0 Hz, 1H), 3.61 (s, 1H), 3.45-3.39 (m, 2H), 3.29-3.27 (m, 3H), 2.33 (s, 3H), 1.98 (d, J=13.1 Hz, 1H), 1.73-1.59 (m, 1H), 1.52-1.38 (m, 1H), 1.06 (d, J=12.7 Hz, 1H); LCMS (M+H)=515.3; HPLC RT=0.67 min. Analytical HPLC Method 1. Diastereomer B: $^1$H NMR (400 MHz, $CD_3OD$) δ 8.63 (s, 1H), 8.60 (d, J=1.6 Hz, 1H), 8.57 (d, J=8.3 Hz, 1H), 8.41 (s, 1H), 7.99 (dd, J=8.3, 1.5 Hz, 1H), 7.64 (d, J=7.3 Hz, 2H), 7.41-7.34 (m, 2H), 7.30 (d, J=7.3 Hz, 1H), 5.88 (d, J=11.1 Hz, 1H), 4.04-3.96 (m, 4H), 3.82 (dd, J=11.5, 2.9 Hz, 1H), 3.61 (td, J=11.9, 2.1 Hz, 1H), 3.44-3.37 (m, 2H), 3.28 (s, 3H), 2.33 (s, 3H), 1.96 (d, J=13.1 Hz, 1H), 1.73-1.60 (m, 1H), 1.55-1.41 (m, 1H), 1.07 (d, J=13.3 Hz, 1H); LCMS (M+H)=515.3; HPLC RT=0.67 min. Analytical HPLC Method 1.

Examples 373 & 374

3-[3-(Dimethyl-1,2-oxazol-4-yl)-5-[(S)-oxan-4-yl(phenyl)methyl]-5H-pyrido[3,2-b]indol-7-yl]-3-hydroxypropanenitrile

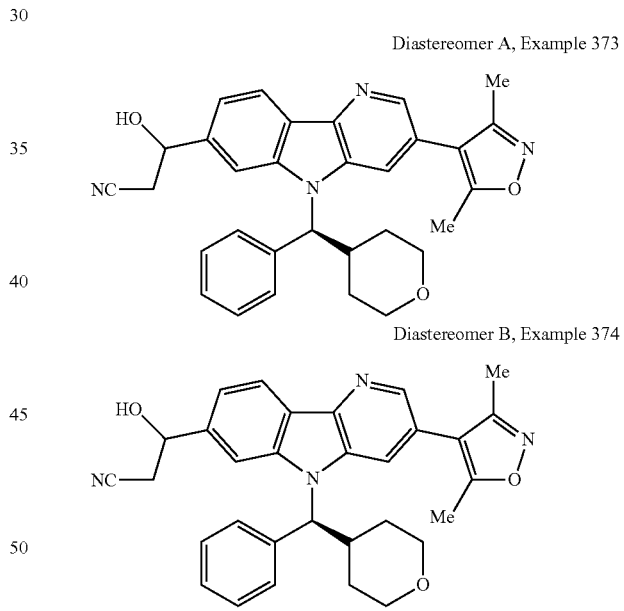

Diastereomer A, Example 373

Diastereomer B, Example 374

Step 1: (S)-3-(3-(3,5-Dimethylisoxazol-4-yl)-5-(phenyl(tetrahydro-2H-pyran-4-yl)methyl)-5H-pyrido[3,2-b]indol-7-yl)-3-oxopropanenitrile To a solution of acetonitrile (0.0160 mL, 0.303 mmol) in THF (0.5 mL) at −78° C. was added nBuLi (2.5 M in hexane, 0.121 mL, 0.303 mmol). After 1 h, a solution of (S)-methyl 3-(3,5-dimethylisoxazol-4-yl)-5-(phenyl(tetrahydro-2H-pyran-4-yl)methyl)-5H-pyrido[3,2-b]indole-7-carboxylate (0.0500 g, 0.101 mmol) in THF (0.5 mL) was added. After 2.75 h, the reaction was quenched with MeOH, then concentrated. The residue was purified via ISCO silica gel column chromatography (12 g column; DCM/EtOAc; 0 to 100% gradient) to give (S)-3-(3-(3,5-dimethylisoxazol-4-yl)-5-(phenyl(tetrahydro-2H-pyran-4-yl)methyl)-5H-pyrido[3,2-b]indol-7-yl)-3-oxopropanenitrile (0.0520 g, 0.103 mmol, 102%). ¹H NMR (400 MHz, CDCl₃) δ 8.55-8.47 (m, 2H), 8.41 (s, 1H), 7.83 (dd, J=8.3, 1.3 Hz, 1H), 7.66 (d, J=1.7 Hz, 1H), 7.46 (d, J=7.3 Hz, 2H), 7.40-7.29 (m, 3H), 5.59 (d, J=10.6 Hz, 1H), 4.24 (s, 2H), 4.06 (dd, J=11.7, 2.8 Hz, 1H), 3.85 (dd, J=11.7, 2.9 Hz, 1H), 3.55 (td, J=11.9, 1.9 Hz, 1H), 3.36 (td, J=11.9, 2.0 Hz, 1H), 3.14 (d, J=11.0 Hz, 1H), 2.42 (s, 3H), 2.26 (s, 3H), 2.01 (br. S., 1H), 1.71-1.56 (m, 1H), 1.44-1.32 (m, 1H), 1.14-1.03 (m, 1H); LCMS (M+H)=505.4; HPLC RT=0.91 min. Analytical HPLC Method 1.

Step 2: 3-[3-(Dimethyl-1,2-oxazol-4-yl)-5-[(S)-oxan-4-yl(phenyl)methyl]-5H-pyrido[3,2-b]indol-7-yl]-3-hydroxypropanenitrile To a solution of (S)-3-(3-(3,5-dimethylisoxazol-4-yl)-5-(phenyl(tetrahydro-2H-pyran-4-yl)methyl)-5H-pyrido[3,2-b]indol-7-yl)-3-oxopropanenitrile (0.0510 g, 0.101 mmol) in methanol (1.01 mL) and THF (1.01 mL) was added sodium borohydride (3.82 mg, 0.101 mmol). After 1 h, the reaction was quenched with a small amount of 1M aq. HCl and then concentrated. The material was dissolved in DCM and then washed with water. The DCM layer was dried with sodium sulfate and concentrated. The crude material was purified via preparative LC/MS with the following conditions: Column: Waters Xbridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 23-63% B over 25 min, then a 5-min hold at 100% B; Flow: 20 mL/min. Fractions containing the desired product were combined and dried via centrifugal evaporation. The diastereomers were separated using chiral prep SFC (Column: Chiracel OJ-H 25×3 cm, 5 μm; Mobile Phase: 75/25 CO₂/MeOH; Flow: 85 mL/min). The faster eluting peak was assigned as Diastereomer A (10.8 mg, 21%); the slower eluting peak was assigned as Diastereomer B (11.7 mg, 23%). Diastereomer A: ¹H NMR (500 MHz, DMSO-d₆) δ 8.39 (s, 1H), 8.19 (br d, J=8.1 Hz, 1H), 8.11 (br s, 1H), 7.64 (br d, J=7.4 Hz, 2H), 7.37 (br d, J=8.1 Hz, 1H), 7.32-7.26 (m, 2H), 7.24-7.16 (m, 1H), 6.30 (br d, J=4.0 Hz, 1H), 5.72 (br d, J=11.1 Hz, 1H), 5.15 (br d, J=4.7 Hz, 1H), 3.95-3.83 (m, 2H), 3.69 (br d, J=7.4 Hz, 1H), 3.53-3.43 (m, 1H), 3.36 (br d, J=11.4 Hz, 1H), 3.26 (br t, J=11.4 Hz, 1H), 2.99 (br d, J=7.4 Hz, 2H), 2.43 (s, 3H), 2.25 (br s, 3H), 1.68 (br d, J=10.8 Hz, 1H), 1.50 (br d, J=9.8 Hz, 1H), 1.29 (br d, J=7.7 Hz, 1H), 0.97 (br d, J=9.8 Hz, 1H); LCMS (M+H)=507.3; HPLC RT=1.66 min. Analytical HPLC Method 2. Diastereomer B: ¹H NMR (500 MHz, DMSO-d₆) δ 8.40 (s, 1H), 8.19 (d, J=8.1 Hz, 1H), 8.13 (br s, 1H), 7.65 (br d, J=7.4 Hz, 2H), 7.35 (br d, J=8.1 Hz, 1H), 7.31-7.26 (m, 2H), 7.25-7.18 (m, 1H), 6.26 (br d, J=4.0 Hz, 1H), 5.72 (br d, J=11.1 Hz, 1H), 5.17 (br d, J=5.0 Hz, 1H), 3.87 (br d, J=9.1 Hz, 1H), 3.68-3.59 (m, 2H), 3.51-3.33 (m, 2H), 3.27 (br t, J=11.8 Hz, 1H), 3.09-2.91 (m, 2H), 2.44 (s, 3H), 2.26 (br s, 3H), 1.68 (br d, J=12.1 Hz, 1H), 1.51 (br d, J=11.1 Hz, 1H), 1.28 (br d, J=8.8 Hz, 1H), 0.97 (br d, J=12.8 Hz, 1H); LCMS (M+H)=507.4; HPLC RT=1.66 min. Analytical HPLC Method 1.

Example 375

5-{8-Methanesulfonyl-5-[(S)-oxan-4-yl(phenyl)methyl]-5H-pyrido[3,2-b]indol-3-yl}-1,4-dimethyl-1H-1,2,3-triazole

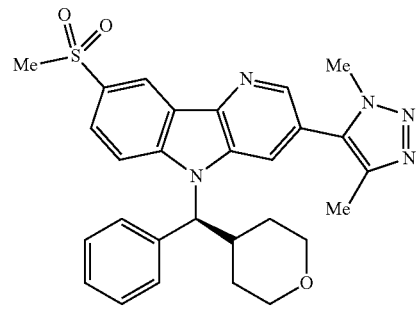 [SMILES: Cc1nnn(C)c1-c1cnc2c3cc(S(C)(=O)=O)ccc3n([C@H](c3ccccc3)C3CCOCC3)c2c1]

Step 1: 5-Bromo-2-(3-(methylsulfonyl)phenyl)-3-nitropyridine

Following a procedure analogous to that for methyl 4-(5-bromo-3-nitropyridin-2-yl)-3-fluorobenzoate, (3-(methylsulfonyl)phenyl)boronic acid (1.00 g, 5.00 mmol) and 2,5-dibromo-3-nitropyridine (1.41 g, 5.00 mmol) were converted to the title compound (0.740 g, 41%). LCMS (M+H)=357.1; HPLC RT=0.82 min. Analytical HPLC Method 1.

Step 2: 3-Bromo-6-(methylsulfonyl)-5H-pyrido[3,2-b]indole and 3-bromo-8-(methylsulfonyl)-5H-pyrido[3,2-b]indole Following a procedure analogous to that for methyl 3-bromo-9-fluoro-5H-pyrido[3,2-b]indole-7-carboxylate, 5-bromo-2-(3-(methylsulfonyl)phenyl)-3-nitropyridine (0.740 g, 2.07 mmol) was converted to 3-bromo-6-(methylsulfonyl)-5H-pyrido[3,2-b]indole (0.318 g, 47%) and 3-bromo-8-(methylsulfonyl)-5H-pyrido[3,2-b]indole (0.105 g, 16%). 3-Bromo-6-(methylsulfonyl)-5H-pyrido[3,2-b]indole; ¹H NMR (400 MHz, CDCl₃) δ 9.63 (br s, 1H), 8.70 (d, J=1.8 Hz, 1H), 8.62 (d, J=7.7 Hz, 1H), 8.03 (dd, J=0.7, 1.0 Hz, 1H), 8.01 (d, J=2.0 Hz, 1H), 7.51 (t, J=7.8 Hz, 1H), 3.21 (s, 3H). 3-Bromo-8-(methylsulfonyl)-5H-pyrido[3,2-b]indole; ¹H NMR (400 MHz, CDCl₃) δ 8.98 (s, 1H), 8.71 (d, J=2.0 Hz, 1H), 8.13 (dd, J=8.6, 1.9 Hz, 1H), 7.99 (d, J=2.0 Hz, 1H), 7.63 (d, J=8.6 Hz, 1H), 3.15 (s, 3H).

Step 3: 3-(1,4-Dimethyl-1H-1,2,3-triazol-5-yl)-8-(methylsulfonyl)-5H-pyrido[3,2-b]indole Following a procedure analogous to that for methyl 3-(1,4-dimethyl-1H-1,2,3-triazol-5-yl)-9-fluoro-5H-pyrido[3,2-b]indole-7-carboxylate, 3-bromo-8-(methylsulfonyl)-5H-pyrido[3,2-b]indole (110 mg, 0.338 mmol) was converted to the title compound (30.0 mg, 26%). LCMS (M+H)=342.1; HPLC RT=0.57 min. Analytical HPLC Method 1.

Step 4: 5-{8-Methanesulfonyl-5-[(S)-oxan-4-yl(phenyl)methyl]-5H-pyrido[3,2-b]indol-3-yl}-1,4-dimethyl-1H-1,2,3-triazole Following a procedure analogous to that for 3-bromo-7-(methylsulfinyl)-5-((S)-phenyl(tetrahydro-2H-pyran-4-yl)

methyl)-5H-pyrido[3,2-b]indole, 3-(1,4-dimethyl-1H-1,2,3-triazol-5-yl)-8-(methylsulfonyl)-5H-pyrido[3,2-b]indole (0.0300 g, 0.0880 mmol) was converted into the title compound (18.0 mg, 26%). ¹H NMR (400 MHz, CD₃OD) δ 8.98 (s, 1H), 8.61 (s, 1H), 8.40 (s, 1H), 8.32-8.25 (m, 1H), 8.20 (br d, J=9.0 Hz, 1H), 7.65 (br d, J=7.8 Hz, 2H), 7.39-7.33 (m, 2H), 7.30 (d, J=7.2 Hz, 1H), 5.88 (d, J=10.9 Hz, 1H), 4.00 (s, 4H), 3.80 (br s, 1H), 3.65-3.56 (m, 2H), 3.43-3.38 (m, 1H), 3.22 (s, 3H), 2.32 (s, 3H), 2.03-1.90 (m, 1H), 1.66 (s, 1H), 1.45 (s, 1H), 1.07 (br d, J=8.6 Hz, 1H);). LCMS (M+H)=516.4; HPLC RT=0.78 min. Analytical HPLC Method 1.

Example 376

5-{6-Methanesulfonyl-5-[(S)-oxan-4-yl(phenyl)methyl]-5H-pyrido[3,2-b]indol-3-yl}-1,4-dimethyl-1H-1,2,3-triazole

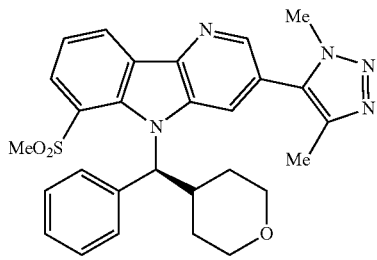 [SMILES: Cc1nnn(C)c1-c1cnc2c3cccc(S(C)(=O)=O)c3n([C@H](c3ccccc3)C3CCOCC3)c2c1]

Step 1: 3-(1,4-Dimethyl-1H-1,2,3-triazol-5-yl)-6-(methylsulfonyl)-5H-pyrido[3,2-b]indole A solution of 1,4-dimethyl-5-(tributylstannyl)-1H-1,2,3-triazole (0.449 g, 1.16 mmol), 3-bromo-6-(methylsulfonyl)-5H-pyrido[3,2-b]indole (0.315 g, 0.969 mmol), copper(I) iodide (0.221 g, 1.16 mmol) and triethylamine (0.162 mL, 1.16 mmol) in DMF (9.69 mL) was degassed with bubbling nitrogen. Tetrakis(triphenylphosphine)palladium(0) (0.112 g, 0.0970 mmol) was added and the reaction was heated to 100° C. After 7.5 h, 1,4-dimethyl-5-(tributylstannyl)-1H-1,2,3-triazole (0.449 g, 1.162 mmol), copper(I) iodide (0.221 g, 1.16 mmol), and tetrakis(triphenylphosphine)palladium (0) (0.112 g, 0.0970 mmol) were added, and the reaction was heated overnight. The reaction was cooled, then diluted with water and aq. ammonium hydroxide. The aqueous layer was extracted twice with EtOAc. The organic layers were washed twice with aq. 10% LiCl, dried with sodium sulfate, and concentrated. The residue was purified via ISCO silica gel column chromatography (40 g column; DCM/MeOH; 0 to 10% gradient) to give 3-(1,4-dimethyl-1H-1,2,3-triazol-5-yl)-6-(methylsulfonyl)-5H-pyrido[3,2-b]indole (0.0890 g, 0.261 mmol, 27%). LCMS (M+H)=342.2; HPLC RT=0.63 min. Analytical HPLC Method 1.

Step 2: 5-{6-Methanesulfonyl-5-[(S)-oxan-4-yl(phenyl)methyl]-5H-pyrido[3,2-b]indol-3-yl}-1,4-dimethyl-1H-1,2,3-triazole Following a procedure analogous to that for (S)-2-(3-(1,4-dimethyl-1H-1,2,3-triazol-5-yl)-9-fluoro-5-(phenyl(tetrahydro-2H-pyran-4-yl)methyl)-5H-pyrido[3,2-b]indol-7-yl)propan-2-ol, (R)-phenyl(tetrahydro-2H-pyran-4-yl)methanol (0.0510 g, 0.264 mmol) and 3-(1,4-dimethyl-1H-1,2,3-triazol-5-yl)-6-(methylsulfonyl)-5H-pyrido[3,2-b]indole (0.0450 g, 0.132 mmol) were converted to the title compound (15.0 mg, 22%). ¹H NMR (400 MHz, CD₃OD) δ 8.75 (dd, J=7.8, 1.2 Hz, 1H), 8.56 (d, J=1.7 Hz, 1H), 8.43 (dd, J=7.9, 1.2 Hz, 1H), 7.83 (d, J=1.7 Hz, 1H), 7.66-7.56 (m, 3H), 7.41-7.33 (m, 2H), 7.32-7.26 (m, 1H), 6.97 (d, J=10.0 Hz, 1H), 3.98 (br dd, J=11.3, 2.9 Hz, 1H), 3.77 (s, 3H), 3.73 (br dd, J=11.2, 3.6 Hz, 1H), 3.65-3.56 (m, 1H), 3.56 (s, 3H), 3.28-3.22 (m, 12H), 2.15 (s, 4H), 2.00-1.87 (m, 1H), 1.77 (qd, J=12.5, 4.5 Hz, 1H), 0.49 (br d, J=12.8 Hz, 1H); LCMS (M+H)=516.4; HPLC RT=0.82 min. Analytical HPLC Method 1.

Example 377

5-{6-Methanesulfonyl-5-[(1S)-4,4,4-trifluoro-1-phenylbutyl]-5H-pyrido[3,2-b]indol-3-yl}-1,4-dimethyl-1H-1,2,3-triazole

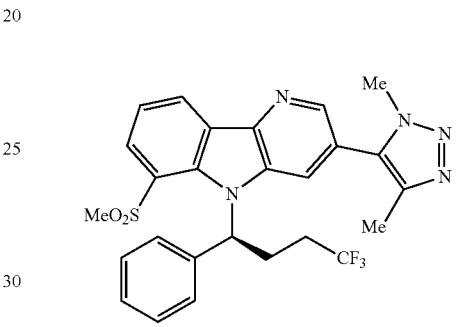

Following a procedure analogous to that for (S)-2-(3-(1,4-dimethyl-1H-1,2,3-triazol-5-yl)-9-fluoro-5-(phenyl(tetrahydro-2H-pyran-4-yl)methyl)-5H-pyrido[3,2-b]indol-7-yl)propan-2-ol, (R)-4,4,4-trifluoro-1-phenylbutan-1-ol (0.0540 g, 0.264 mmol) and 3-(1,4-dimethyl-1H-1,2,3-triazol-5-yl)-6-(methylsulfonyl)-5H-pyrido[3,2-b]indole (0.0450 g, 0.132 mmol) were converted to the title compound (10.5 mg, 15%). ¹H NMR (400 MHz, CD₃OD) δ 8.81 (dd, J=7.7, 1.1 Hz, 1H), 8.61 (d, J=1.8 Hz, 1H), 8.45 (dd, J=7.9, 1.1 Hz, 1H), 7.68-7.58 (m, 2H), 7.44-7.28 (m, 6H), 3.74 (s, 3H), 3.40 (s, 3H), 3.04 (s, 1H), 2.88-2.76 (m, 1H), 2.68-2.54 (m, 1H), 2.11 (s, 3H), 1.67-1.47 (m, 1H);). LCMS (M+H)=528.3; HPLC RT=0.92 min. Analytical HPLC Method 1.

Example 378

2-{3-[4-(²H₃)Methoxy-1-methyl-1H-1,2,3-triazol-5-yl]-5-[(S)-oxan-4-yl(phenyl)methyl]-5H-pyrido[3,2-b]indol-7-yl}propan-2-ol

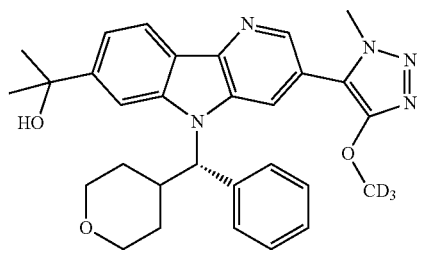 [SMILES: [2H]C([2H])([2H])Oc1nnn(C)c1-c1cnc2c3ccc(C(C)(C)O)cc3n([C@H](c3ccccc3)C3CCOCC3)c2c1]

Step 1: (Azidomethyl)trimethylsilane

A flask was charged with sodium azide (5.09 g, 78.0 mmol) and DMF (30 mL). To this was added (chloromethyl)trimethylsilane (8.00 g, 65.2 mmol). The flask was fitted with a balloon of nitrogen, placed in an 80° C. bath, and stirred at that temperature for 40 h. The reaction was allowed to cool to room temperature. The reaction flask was fitted with a jacketed vigreaux column and short path distillation head. The product was distilled under house vacuum to give a single fraction. Collection was discontinued when the head temperature began to rise and there was a visible change in the way the distillate interacted with the vigreaux column (went from being uniformly coated with distillate to a more irregular distribution on the glass of the vigreaux column). The distilled material weighed 7.60 g (85% pure by $^1$H NMR, 76%). The material was used without additional purification. $^1$H NMR (400 MHz, CDCl$_3$) δ 2.77 (s, 2H), 0.13 (s, 9H). $^{13}$C NMR (101 MHz, CDCl$_3$) δ 42.1, −2.6.

Step 2: 2-Chloro-1,1-bis($^2$H$_3$)methoxyethane

A flask was charged with 2-chloroacetaldehyde (50% in water, 20.0 g, 127 mmol) and D4-MeOH (10 mL). To this was added calcium chloride (16.5 g, 149 mmol), which gave a significant exotherm. When the exotherm ended, the reaction was placed in a 55° C. bath and held at that temperature overnight. In the morning, the reaction was poured into a separatory funnel and the layers separated. The lower, viscous aqueous layer was extracted with 15 mL of diethyl ether, which was added to the first organic layer. The organics were dried over MgSO$_4$, filtered, fitted with a jacketed vigereaux/shortpath distillation head, and warmed in a heating mantle. The fraction that distilled between 90° C. and 110° C. was retained to give 9.25 g (56%). $^1$H NMR (400 MHz, CDCl$_3$) δ 4.54 (t, J=5.4 Hz, 1H), 3.52 (d, J=5.3 Hz, 2H). $^{13}$C NMR (101 MHz, CDCl$_3$) δ 103.1, 53.1 (m), 43.0.

Step 3: ($^2$H$_3$)Methoxyethyne

To a solution of diethylamine (15.6 mL, 149 mmol) in THF (250 mL) at 0° C. was added nBuLi (2.5 M in hexanes, 59.7 mL, 149 mmol). After stirring for 10 min, the reaction was treated with 2-chloro-1,1-bis($^2$H$_3$)methoxyethane (5.67 mL, 49.8 mmol) over a few min. After stirring for 30 min at 0° C., the volatiles were removed via concentration under reduced pressure, venting the rotary evaporator to nitrogen. The resulting powder was pumped under high vacuum for 15 min before being immersed in a −78° C. bath. To this was added 125 mL of brine through an addition funnel as rapidly as possible, swirling the flask to aid in complete quenching of the reaction mixture. The flask was fitted with a 24/40→14/20 adapter and a jacketed vigereaux column/shortpath distillation apparatus. The receiving flask was immersed in a −78° C. bath. The boiling flask was heated with a heating mantle. A substantial fraction formed without any change in head temperature (Fraction 1). When the head temperature began to rise, the receiving flask was switched (Fraction 2). The temperature rose to 38° C. and stabilized at that temperature. Collection of Fraction 2 was discontinued when the head temperature began to fall. Both fractions were analyzed by HNMR. Fraction 1: 0.898 g, ca. 94% pure. $^1$H NMR (500 MHz, CDCl$_3$) δ 1.54 (s, 1H).

Step 4: 4-($^2$H$_3$)Methoxy-1-[(trimethylsilyl)methyl]-1H-1,2,3-triazole

To a solution of (azidomethyl)trimethylsilane (85.2% pure) (2.17 g, 14.3 mmol) and ($^2$H$_3$)methoxyethyne (0.898 g, ca. 94% pure, 14.3 mmol) in DCM (40.8 ml) at 0° C. was added a solution of copper (II) sulfate pentahydrate (0.467 g, 1.87 mmol) in water (30.7 mL). To this was slowly added sodium ascorbate (1.30 g, 6.54 mmol). Upon addition of the ascorbate, the reaction became very dark with precipitate, and stirring became difficult. The reaction was stirred at room temperature over the weekend. The resulting mixture was treated with Celite and filtered through a second pad of Celite, rinsing with additional DCM. The organics (the aqueous was removed in the Celite treatments) were dried over MgSO$_4$, filtered, and concentrated to give 0.750 g (28%) as a very dark oil. $^1$H NMR (500 MHz, CDCl$_3$) δ 6.88 (s, 1H), 3.83 (s, 2H), 0.16 (s, 9H). $^{13}$C NMR (126 MHz, CDCl$_3$) δ 161.3, 106.6, 56.65-55.97 (m, 1C), 43.07-42.42 (m, 1C), −2.16−−2.76 (m, 1C). LCMS (M+H)=189.1.

Step 5: Methyl 3-[4-($^2$H$_3$)methoxy-1-methyl-1H-1,2,3-triazol-5-yl]-5-[(S)-oxan-4-yl)phenyl)methyl]-5H-pyrido[3,2-b]indole-7-carboxylate A dry, N$_2$ (g) flushed, 1 dram vial was charged with tetramethylammonium acetate (22.2 mg, 0.167 mmol), bis(triphenylphosphine)palladium(II) dichloride (5.86 mg, 8.34 μmol), and (S)-methyl 3-bromo-5-(phenyl(tetrahydro-2H-pyran-4-yl)methyl)-5H-pyrido[3,2-b]indole-7-carboxylate (40.0 mg, 0.083 mmol, see Steps 1-2 of 2-[8-bromo-3-(4-bromo-1-methyl-1H-1,2,3-triazol-5-yl)-5-[(S)-oxan-4-yl(phenyl)methyl]-5H-pyrido[3,2-b]indol-7-yl]propan-2-ol and 2-[3-(4-bromo-1-methyl-1H-1,2,3-triazol-5-yl)-5-[(S)-oxan-4-yl(phenyl)methyl]-5H-pyrido[3,2-b]indol-7-yl]propan-2-ol). To this was added 4-($^2$H$_3$)methoxy-1-[(trimethylsilyl)methyl]-1H-1,2,3-triazole (31.4 mg, 0.167 mmol). The vial was again flushed with nitrogen. To this was added NMP (0.4 mL). The resulting mixture was stirred vigorously under a stream of nitrogen for 10 min. The vial was placed in a pre-heated oil bath at 95° C. and heated at that temperature overnight. The reaction was cooled to room temperature, diluted with EtOAc, washed with water (2×), then brine, dried over MgSO$_4$, filtered, and concentrated. The residue was purified by column chromatography (50% EtOAc/Hex 100% EtOAc) to give 32.0 mg (75%) as an off-white solid. $^1$H NMR (500 MHz, CDCl$_3$) δ 8.50 (s, 1H), 8.44 (s, 1H), 8.38 (d, J=8.4 Hz, 1H), 8.08 (d, J=8.4 Hz, 1H), 7.71 (s, 1H), 7.22 (t, J=7.3 Hz, 1H), 7.21 (d, J=7.5 Hz, 1H), 7.21 (d, J=7.5 Hz, 1H), 7.18 (dd, J=7.5, 7.3 Hz, 1H), 7.18 (dd, J=7.5, 7.3 Hz, 1H), 6.52 (d, J=5.8 Hz, 1H), 4.33 (s, 3H), 3.97 (s, 3H), 3.84 (ddd, J=11.6, 4.5, 3.5 Hz, 1H), 3.84 (ddd, J=11.6, 4.5, 3.5 Hz, 1H), 3.84 (ddd, J=11.8, 11.6, 4.5 Hz, 1H), 3.84 (ddd, J=11.8, 11.6, 4.5 Hz, 1H), 2.70 (tdt, J=7.5, 5.8, 3.4 Hz, 1H), 1.70 (dddd, J=4.5, 3.5, 3.4, −13.9 Hz, 1H), 1.67 (dddd, J=4.5, 3.5, 3.4, −13.9 Hz, 1H), 1.60 (dddd, J=11.8, 7.5, 4.5, −13.9 Hz, 1H), 1.57 (dddd, J=11.8, 7.5, 4.5, −13.9 Hz, 1H). LCMS (M+H)=515.5.

Step 6: 2-{3-[4-($^2$H$_3$)Methoxy-1-methyl-1H-1,2,3-triazol-5-yl]-5-[(S)-oxan-4-yl(phenyl)methyl]-5H-pyrido[3,2-b]indol-7-yl}propan-2-ol To a solution of methyl 3-[4-($^2$H$_3$)methoxy-1-methyl-1H-1,2,3-triazol-5-yl]-5-[(S)-oxan-4-yl(phenyl)methyl]-5H-pyrido[3,2-b]indole-7-carboxylate (32.0 mg, 0.0620 mmol) in THF (2 mL) at 0° C. was added methylmagnesiumbromide (3M in Et$_2$O, 0.311 mL, 0.933 mmol). The reaction was stirred for 30 min at that temperature. The reaction was quenched by addition of sat. aq. NH$_4$Cl. The reaction was diluted with ethyl acetate and poured into water. The layers were separated. The organics were concentrated and purified by silica gel column chromatography (100% EtOAc) to give mostly pure product. The solid was recrystallized from water/EtOH (2:1). The mother liquor was removed via pipette. The solid that came with it was collected in a syringe filter. The recrystallized solid was rinsed twice with additional cold water/EtOH (2:1). The rinses were again added to the syringe filter. The solid that remained in the filter was dissolved in EtOH and added back into the recrystallized solid. Concentration of the ethanol gave 27.0 mg (80%). $^1$H NMR (500 MHz, CDCl$_3$) δ 8.59 (d, J=1.9 Hz, 1H), 8.34 (d, J=8.2 Hz, 1H), 7.95 (s, 1H), 7.86 (d, J=1.9 Hz, 1H), 7.53-7.48 (m, 2H), 7.44 (dd, J=8.2, 1.4 Hz, 1H), 7.39-7.34 (m, 2H), 7.33-7.30 (m, 1H), 5.56 (d, J=10.7 Hz, 1H), 4.08 (dd, J=11.7, 2.6 Hz, 1H), 4.03 (s, 3H), 3.88 (dd, J=11.5, 2.8 Hz, 1H), 3.56 (td, J=11.9, 2.0 Hz, 1H), 3.37 (td, J=11.9, 2.0 Hz, 1H), 3.19-3.07 (m, 1H), 2.01 (d, J=13.6 Hz, 1H), 1.75 (s, 6H), 1.69-1.61 (m, 1H), 1.48-1.35 (m, 2H), 1.14 (d, J=13.2 Hz, 1H). LCMS (M+H)=515.6.

Example 379

2-[3-(4-Methoxy-1-Methyl-1H-1,2,3-triazol-5-yl)-5-[(S)-oxan-4-yl(phenyl)methyl]-5H-pyrido[3,2-b]indol-7-yl]propan-2-ol

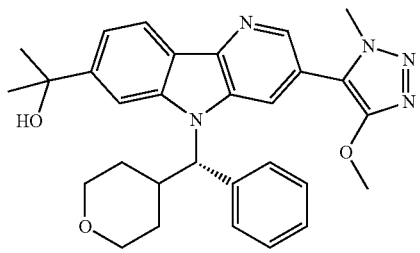 [SMILES: COc1nnn(C)c1-c1cnc2c3ccc(C(C)(C)O)cc3n([C@H](c3ccccc3)C3CCOCC3)c2c1]

Step 1: 4-Methoxy-1-((trimethylsilyl)methyl)-1H-1,2,3-triazole

The title compound was prepared following a procedure analogous to that described in the preparation of methyl 3-[4-($^2$H$_3$)methoxy-1-methyl-1H-1,2,3-triazol-5-yl]-5-[(S)-oxan-4-yl(phenyl)methyl]-5H-pyrido[3,2-b]indole-7-carboxylate, starting with commercially available 2-chloro-1,1-dimethoxyethane. $^1$H NMR (500 MHz, CDCl$_3$) δ 6.88 (s, 1H), 4.00 (s, 3H), 3.83 (s, 2H), 0.17 (s, 9H). $^{13}$C NMR (126 MHz, CDCl$_3$) δ 161.3, 106.6, 57.2, 42.8, −2.05-−2.90 (m, 1C). LCMS (M+H)=186.1.

Step 2: (S)-Methyl 3-(4-methoxy-1-methyl-1H-1,2,3-triazol-5-yl)-5-(phenyl(tetrahydro-2H-pyran-4-yl)methyl)-5H-pyrido[3,2-b]indole-7-carboxylate The title compound was prepared following a procedure analogous to that described in the preparation of methyl 3-[4-($^2$H$_3$)methoxy-1-methyl-1H-1,2,3-triazol-5-yl]-5-[(S)-oxan-4-yl(phenyl)methyl]-5H-pyrido[3,2-b]indole-7-carboxylate, starting with 4-methoxy-1-((trimethylsilyl)methyl)-1H-1,2,3-triazole. $^1$H NMR (500 MHz, CDCl$_3$) δ 8.66 (d, J=1.7 Hz, 1H), 8.48 (s, 1H), 8.44 (d, J=8.2 Hz, 1H), 8.07 (dd, J=8.2, 1.1 Hz, 1H), 7.94 (d, J=1.7 Hz, 1H), 7.51 (d, J=7.4 Hz, 2H), 7.40-7.35 (m, 2H), 7.34-7.29 (m, 1H), 5.59 (d, J=10.7 Hz, 1H), 4.16 (s, 3H), 4.11-4.06 (m, 1H), 4.05 (s, 3H), 4.04 (s, 3H), 3.87 (dd, J=11.8, 2.8 Hz, 1H), 3.56 (td, J=11.9, 2.0 Hz, 1H), 3.37 (td, J=11.9, 1.9 Hz, 1H), 3.21-3.10 (m, 1H), 2.01 (d, J=13.2 Hz, 1H), 1.70-1.58 (m, 1H), 1.49-1.37 (m, 1H), 1.10 (d, J=12.6 Hz, 1H). LCMS (M+H)=512.5.

Step 3: 2-[3-(4-Methoxy-1-methyl-1H-1,2,3-triazol-5-yl)-5-[(S)-oxan-4-yl(phenyl)methyl]-5H-pyrido[3,2-b]indol-7-yl]propan-2-ol To a solution of (S)-methyl 3-(4-methoxy-1-methyl-1H-1,2,3-triazol-5-yl)-5-(phenyl(tetrahydro-2H-pyran-4-yl)methyl)-5H-pyrido[3,2-b]indole-7-carboxylate (77.0 mg, 0.151 mmol) in THF (3 mL) at 0° C. was added methylmagnesium bromide (3M in Et$_2$O, 0.753 mL, 2.26 mmol). The reaction was stirred for 30 min at that temperature. The reaction was quenched by addition of sat. aq. NH$_4$Cl. The reaction was diluted with ethyl acetate and poured into water. The layers were separated. The organics were concentrated and purified by silica gel column chromatography (100% EtOAc) to give mostly pure product. The resulting residue was dissolved in EtOH (1.5 mL). To this was added water dropwise. With each drop, there was a flash of precipitate followed by dissolution. Upon addition of the final drop a large amount of solid precipitated. The resulting suspension was heated with a heat gun with vigorous stirring, but little went back into solution. The suspension was gently agitated on a shaker for 48 h. The resulting solid was collected by filtration in a Buchner funnel and rinsed with 2 mL of cold water/EtOH (2:1). The solid was air dried to give 50.0 mg (64%) as a fine white powder. $^1$H NMR (500 MHz, CDCl$_3$) δ 8.59 (d, J=1.7 Hz, 1H), 8.34 (d, J=8.2 Hz, 1H), 7.96 (s, 1H), 7.86 (d, J=1.7 Hz, 1H), 7.50 (d, J=7.3 Hz, 2H), 7.44 (dd, J=8.3, 1.3 Hz, 1H), 7.39-7.34 (m, 2H), 7.33-7.30 (m, 1H), 5.56 (d, J=10.7 Hz, 1H), 4.16 (s, 3H), 4.08 (dd, J=11.4, 2.4 Hz, 1H), 4.03 (s, 3H), 3.88 (dd, J=11.8, 2.7 Hz, 1H), 3.56 (td, J=11.9, 1.9 Hz, 1H), 3.37 (td, J=11.9, 2.0 Hz, 1H), 3.13 (q, J=11.2 Hz, 1H), 2.01 (d, J=12.5 Hz, 1H), 1.96 (s, 1H), 1.75 (s, 6H), 1.69-1.61 (m, 1H), 1.48-1.36 (m, 1H), 1.14 (d, J=13.2 Hz, 1H). LCMS (M+H)=512.6.

Example 380

2-{3-[4-($^2$H$_3$)Methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol

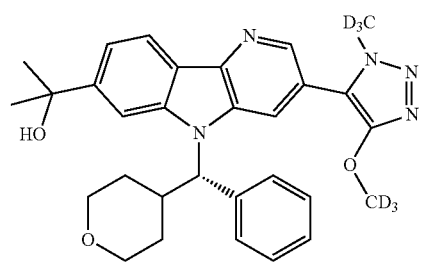 [SMILES: [2H]C([2H])([2H])Oc1nnn(C([2H])([2H])[2H])c1-c1cnc2c3ccc(C(C)(C)O)cc3n([C@H](c3ccccc3)C3CCOCC3)c2c1]

Step 1: 4-($^2$H$_3$)Methoxy-1-($^2$H$_3$)methyl-1H-1,2,3-triazole

To a solution of ($^2$H$_3$)methoxyethyne (ca. 11% in THF, 0.400 g, 0.745 mmol) and d3-iodomethane (0.0700 mL, 1.127 mmol) in THF (0.6 mL) at 0° C. was added a solution of sodium azide (0.0730 g, 1.12 mmol) in water (1 mL). The flask was sealed and stirred overnight at room temperature. The reaction was cooled to 0° C. and treated sequentially with copper(II) sulfate pentahydrate (0.0240 g, 0.0980 mmol) and sodium ascorbate (0.0740 g, 0.372 mmol). The mixture was stirred vigorously for 4 days. The resulting mixture was diluted with EtOAc, treated with Celite, filtered through a second pad of Celite, and concentrated. The crude product was purified by silica gel column chromatography (EtOAc/Hex) to give 0.0670 g (76%). $^1$H NMR (500 MHz, CDCl$_3$) δ 6.99 (s, 1H). LCMS (M+H)=120.1.

Step 2: Methyl 3-[4-($^2$H$_3$)methoxy-1-($^2$H$_3$)methyl-1H-1,2,3-triazol-5-yl]-5-[(S)-oxan-4-yl(phenyl) methyl]-5H-pyrido[3,2-b]indole-7-carboxylate A dry, N$_2$ (g) flushed, 1 dram vial was charged with tetramethylammonium acetate (16.7 mg, 0.125 mmol), bis (triphenylphosphine)palladium(II) dichloride (4.39 mg, 6.26 µmol), and (S)-methyl 3-bromo-5-(phenyl(tetrahydro-2H-pyran-4-yl)methyl)-5H-pyrido[3,2-b]indole-7-carboxylate (30.0 mg, 0.0630 mmol, see Steps 1-2 of 2-[8-bromo-3-(4-bromo-1-methyl-1H-1,2,3-triazol-5-yl)-5-[(S)-oxan-4-yl (phenyl)methyl]-5H-pyrido[3,2-b]indol-7-yl]propan-2-ol and 2-[3-(4-bromo-1-methyl-1H-1,2,3-triazol-5-yl)-5-[(S)-oxan-4-yl(phenyl)methyl]-5H-pyrido[3,2-b]indol-7-yl]propan-2-ol). To this was added 4-($^2$H$_3$)methoxy-1-($^2$H$_3$) methyl-1H-1,2,3-triazole (14.9 mg, 0.125 mmol). The vial was again flushed with nitrogen. To this was added NMP (0.5 mL). The resulting mixture was stirred vigorously under a stream of nitrogen for 10 min. The vial was placed in a pre-heated oil bath at 95° C. and heated at that temperature overnight. The reaction was cooled to room temperature, diluted with EtOAc, washed with water (2×), then brine, dried over MgSO$_4$, filtered, and concentrated. The residue was purified by column chromatography (50% EtOAc/Hex) to give 31.7 mg (98%) as clear oil. LCMS (M+H)=518.5. HPLC RT=1.58 min (Column: Phenomenex LUNA C18 2×30 mm; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Step 3: 2-{3-[4-($^2$H$_3$)Methoxy-1-($^2$H$_3$)methyl-1H-1, 2,3-triazol-5-yl]-5-[(5)-oxan-4-yl(phenyl)methyl]-5H-pyrido[3,2-b]indol-7-yl}propan-2-ol To a solution of methyl 3-[4-($^2$H$_3$)methoxy-1-($^2$H$_3$) methyl-1H-1,2,3-triazol-5-yl]-5-[(S)-oxan-4-yl(phenyl) methyl]-5H-pyrido[3,2-b]indole-7-carboxylate (31.7 mg, 0.0610 mmol) in THF (1 mL) at 0° C. was added methylmagnesium bromide (3M in Et$_2$O, 0.408 mL, 1.23 mmol). The reaction was stirred for 30 min at that temperature. The reaction was quenched by addition of sat. aq. NH$_4$Cl. The reaction was diluted with ethyl acetate and brine. The layers were separated. The organics were concentrated and purified by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min). The yield of the product was 16.2 mg (51%). $^1$H NMR (500 MHz, DMSO-d$_6$) δ 8.52 (s, 1H), 8.40 (br. s., 1H), 8.14 (d, J=8.4 Hz, 1H), 7.65 (d, J=7.7 Hz, 2H), 7.46 (d, J=8.1 Hz, 1H), 7.39-7.30 (m, 2H), 7.29-7.22 (m, 1H), 5.79 (d, J=11.4 Hz, 1H), 3.90 (d, J=8.4 Hz, 1H), 3.74 (d, J=11.4 Hz, 1H), 3.54-3.32 (m, 4H), 3.26 (t, J=11.6 Hz, 1H), 1.81-1.66 (m, 1H), 1.58 (s, 7H), 1.40-1.23 (m, 1H), 0.98 (d, J=13.6 Hz, 1H). LCMS (M+H)=518.5.

Example 381

2-{3-[4-Methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol

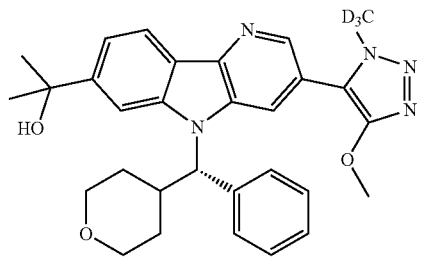 [SMILES: [2H]C([2H])([2H])n1nnc(OC)c1-c1cnc2c3ccc(C(C)(C)O)cc3n([C@H](c3ccccc3)C3CCOCC3)c2c1]

Step 1: 4-Methoxy-1-($^2$H$_3$)methyl-1H-1,2,3-triazole

The title compound was prepared according to the procedure of 2-{3-[4-($^2$H$_3$)methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol, starting with methoxyethyne (prepared by the procedure used to prepare ($^2$H$_3$)methoxyethyne, starting with commercially available 2-chloro-1,1-dimethoxyethane). $^1$H NMR (500 MHz, CDCl$_3$) δ 6.99 (s, 1H), 4.00 (s, 3H). $^{13}$C NMR (126 MHz, CDCl$_3$) δ 161.8, 106.7, 57.4 (CD$_3$ not observed). LCMS (M+H)=117.1.

Step 2: 2-{3-[4-Methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol The title compound was prepared according to the procedure of 2-{3-[4-($^2$H$_3$)methoxy-1-($^2$H$_3$)methyl-1H-1,2,3-triazol-5-yl]-5-[(S)-oxan-4-yl(phenyl)methyl]-5H-pyrido[3,2-b]indol-7-yl}propan-2-ol, starting with 4-methoxy-1-($^2$H$_3$)methyl-1H-1,2,3-triazole. $^1$H NMR (500 MHz, DMSO-d$_6$) δ 8.53 (s, 1H), 8.41 (br. s., 1H), 8.14 (d, J=8.1 Hz, 2H), 7.66 (d, J=7.3 Hz, 2H), 7.47 (d, J=8.4 Hz, 1H), 7.38-7.30 (m, 2H), 7.29-7.22 (m, 1H), 5.80 (d, J=11.0 Hz, 1H), 4.03 (s, 3H), 3.90 (d, J=8.8 Hz, 1H), 3.74 (d, J=9.2 Hz, 1H), 3.55-3.33 (m, 3H), 3.26 (t, J=11.9 Hz, 1H), 1.76-1.67 (m, 1H), 1.58 (s, 6H), 1.39-1.21 (m, 1H), 1.10-0.93 (m, 2H). LCMS (M+H)=515.6.

Example 382

2-[3-(4-Ethoxy-1-methyl-1H-1,2,3-triazol-5-yl)-5-[(S)-oxan-4-yl(phenyl)methyl]-5H-pyrido[3,2-b] indol-7-yl]propan-2-ol

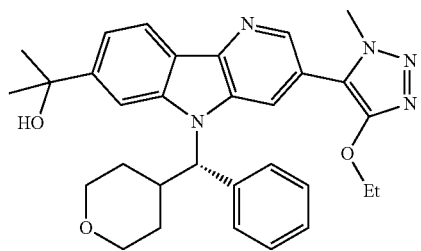

The title compound was prepared according to the procedure of 2-{3-[4-($^{2}H_{3}$)methoxy-1-methyl-1H-1,2,3-triazol-5-yl]-5-[(S)-oxan-4-yl(phenyl)methyl]-5H-pyrido[3,2-b]indol-7-yl}propan-2-ol, starting with commercially available ethoxyethyne. The title compound was purified by preparative HPLC with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. $^{1}$H NMR (500 MHz, DMSO-$d_{6}$) δ 8.55 (s, 1H), 8.42 (br. s., 1H), 8.14 (d, J=8.1 Hz, 2H), 7.67 (d, J=7.7 Hz, 2H), 7.47 (d, J=8.1 Hz, 1H), 7.38-7.30 (m, 2H), 7.29-7.21 (m, 1H), 5.82 (d, J=11.0 Hz, 1H), 4.40 (q, J=7.0 Hz, 2H), 4.07 (br. s., 3H), 3.96-3.86 (m, 1H), 3.74 (d, J=8.8 Hz, 1H), 3.56-3.33 (m, 2H), 3.27 (t, J=11.2 Hz, 1H), 3.18 (d, J=4.8 Hz, 1H), 1.73 (d, J=12.5 Hz, 1H), 1.59 (s, 7H), 1.36 (t, J=7.0 Hz, 3H), 1.34-1.25 (m, 1H), 1.00 (d, J=12.5 Hz, 1H). LCMS (M+H)=526.3.

Examples 383 & 384

2-[8-Bromo-3-(4-bromo-1-methyl-1H-1,2,3-triazol-5-yl)-5-[(S)-oxan-4-yl(phenyl)methyl]-5H-pyrido[3,2-b]indol-7-yl]propan-2-ol and 2-[3-(4-Bromo-1-methyl-1H-1,2,3-triazol-5-yl)-5-[(S)-oxan-4-yl(phenyl)methyl]-5H-pyrido[3,2-b]indol-7-yl]propan-2-ol

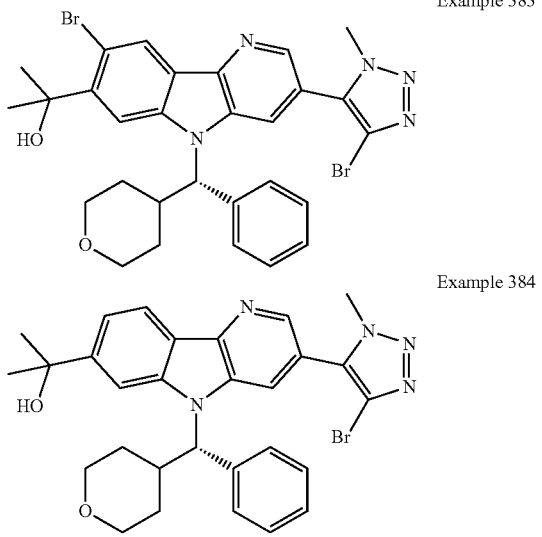

Example 383

Example 384

Step 1: (R)-Phenyl(tetrahydro-2H-pyran-4-yl)methyl methanesulfonate

To (R)-phenyl(tetrahydro-2H-pyran-4-yl)methanol (0.750 g, 3.90 mmol) in DCM (26.0 mL) was added triethylamine (0.952 mL, 6.83 mmol), it was cooled to 0° C., methanesulfonyl chloride (0.380 mL, 4.88 mmol) was then added dropwise, and it was stirred at 0° C. for 0.5 h, then room temperature for 0.5 h. The reaction was cooled to 0° C. and treated with 80 uL of MsCl. After 10 min, the ice bath was removed, and the reaction stirred at room temperature for 30 min. The reaction was diluted with ether, washed with water, then sat. aq. NaHCO$_{3}$, then brine, dried over MgSO$_{4}$, filtered, and concentrated to give a white solid. $^{1}$H NMR (400 MHz, CDCl$_{3}$) δ 7.50-7.34 (m, 5H), 5.22 (d, J=8.8 Hz, 1H), 4.07 (dd, J=11.7, 3.1 Hz, 1H), 3.93 (dd, J=11.7, 3.1 Hz, 1H), 3.40 (td, J=11.9, 2.3 Hz, 1H), 3.30 (td, J=11.8, 2.3 Hz, 1H), 2.63 (s, 3H), 2.20-2.07 (m, 1H), 2.06-1.97 (m, 1H), 1.58-1.50 (m, 1H), 1.39-1.28 (m, 1H), 1.19-1.10 (m, 1H).

Step 2: (S)-Methyl 3-bromo-5-(phenyl(tetrahydro-2H-pyran-4-yl)methyl)-5H-pyrido[3,2-b]indole-7-carboxylate A vial was charged with methyl 3-bromo-5H-pyrido[3,2-b]indole-7-carboxylate (600 mg, 1.97 mmol), (R)-phenyl(tetrahydro-2H-pyran-4-yl)methyl methanesulfonate (1060 mg, 3.93 mmol), cesium carbonate (1920 mg, 5.90 mmol), and DMF (5960 µL). The vial was sealed and heated at 30° C. overnight. The vial was warmed to 35° C. and held at that temperature 48 h. The vial was warmed to 45° C. and held at that temperature overnight. The reaction was cooled to room temperature and filtered to remove undissolved solids. The solids were rinsed with EtOAc. The organics were diluted with water/EtOAc, and the layers separated. The organics were washed with water, then brine, dried over MgSO$_{4}$, filtered, and concentrated. The resulting residue was suspended in 4 mL DCM. The resulting suspension was agitated occasionally over 5 min. The suspension was further diluted with 4 mL of 25% EtOAc/Hex. The resulting suspension was filtered through a plug of cotton and loaded on a silica gel column (150 mL SiO$_{2}$, 25% EtOAc/Hex), and eluted until the sample was adsorbed onto the column. The product was eluted using 25% EtOAc/Hex. Fractions were visualized 1st by UV (to show product and carboline) and then by PMA (to show benzyl alcohol (which shows blue upon charring)). Two sets of fractions were collected. The first fractions to come off were product, tainted by unreacted carboline. These fractions were collected together and concentrated. The resulting residue was dissolved in ether to give a fine white precipitate. The precipitate (unreacted carboline) was removed by filtration and discarded. Concentration of this mother liquor gave very pure product (502 mg, 53%). $^{1}$H NMR (400 MHz, CDCl$_{3}$) δ 8.61 (d, J=1.8 Hz, 1H), 8.42 (s, 1H), 8.38 (d, J=8.3 Hz, 1H), 8.05-7.98 (m, 2H), 7.49 (d, J=7.3 Hz, 2H), 7.41-7.34 (m, 2H), 7.31 (d, J=7.3 Hz, 1H), 5.46 (d, J=10.8 Hz, 1H), 4.07 (dd, J=11.4, 2.9 Hz, 1H), 4.03 (s, 3H), 3.86 (dd, J=11.8, 2.8 Hz, 1H), 3.57 (td, J=11.9, 1.6 Hz, 1H), 3.38 (td, J=11.9, 2.0 Hz, 1H), 3.22-3.06 (m, 1H), 1.99 (d, J=13.3 Hz, 1H), 1.68-1.51 (m, 1H), 1.47-1.31 (m, 1H), 1.04 (d, J=12.5 Hz, 1H). LCMS (M($^{81}$Br)+H)=481.2.

Step 3: (S)-Methyl 3-(1-methyl-1H-1,2,3-triazol-5-yl)-5-(phenyl(tetrahydro-2H-pyran-4-yl)methyl)-5H-pyrido[3,2-b]indole-7-carboxylate A dry, N$_{2}$ (g) flushed, 1 dram vial was charged with tetramethylammonium acetate (33.3 mg, 0.250 mmol), bis(triphenylphosphine)palladium dichloride (8.79 mg, 0.0130 mmol) and (S)-methyl 3-bromo-5-(phenyl(tetrahydro-2H-pyran-4-yl)methyl)-5H-pyrido[3,2-b]indole-7-carboxylate (60.0 mg, 0.125 mmol). To this was added 1-methyl-1H-1,2,3-triazole (20.8 mg, 0.250 mmol). The vial was again flushed with nitrogen. To this was added NMP (0.5 mL). The resulting mixture was stirred vigorously under a stream of nitrogen for 10 min. The vial was placed in a pre-heated oil bath at 95° C. and heated at that temperature overnight. The reaction was cooled to room temperature, diluted with EtOAc, washed with water (2×), then brine, dried over MgSO$_4$, filtered, and concentrated. The residue was purified by column chromatography (100% EtOAc→1% MeOH/EtOAc) to give 39.5 mg (66%) as an off-white solid. $^1$H NMR (500 MHz, CDCl$_3$) δ 8.61 (d, J=1.6 Hz, 1H), 8.50 (s, 1H), 8.47 (d, J=8.2 Hz, 1H), 8.10 (d, J=8.2 Hz, 1H), 7.82 (s, 1H), 7.75 (s, 1H), 7.53-7.45 (m, 2H), 7.42-7.35 (m, 2H), 7.35-7.30 (m, 1H), 5.63 (d, J=10.7 Hz, 1H), 4.11-4.03 (m, 4H), 3.98 (s, 3H), 3.86 (dd, J=11.7, 3.0 Hz, 1H), 3.57 (td, J=11.9, 1.7 Hz, 1H), 3.37 (td, J=11.9, 1.9 Hz, 1H), 3.22-3.09 (m, 1H), 2.11-2.01 (m, 1H), 1.72-1.59 (m, 1H), 1.50-1.38 (m, 1H), 1.07 (d, J=13.1 Hz, 1H). LCMS (M+H)=482.3.

Step 4: (S)-Methyl 3-(4-bromo-1-methyl-1H-1,2,3-triazol-5-yl)-5-(phenyl(tetrahydro-2H-pyran-4-yl)methyl)-5H-pyrido[3,2-b]indole-7-carboxylate and (S)-Methyl 8-bromo-3-(4-bromo-1-methyl-1H-1,2,3-triazol-5-yl)-5-(phenyl(tetrahydro-2H-pyran-4-yl)methyl)-5H-pyrido[3,2-b]indole-7-carboxylate To a solution of (S)-methyl 3-(1-methyl-1H-1,2,3-triazol-5-yl)-5-(phenyl(tetrahydro-2H-pyran-4-yl)methyl)-5H-pyrido[3,2-b]indole-7-carboxylate (39.5 mg, 0.0820 mmol) in DMF (0.5 mL) at room temperature was added NBS (16.1 mg, 0.0900 mmol). The reaction was placed in a preheated sand bath at 45° C. and held at that temperature for 2 h. The reaction was cooled to room temperature, diluted with DCM, and poured into water. The organics were washed with water (2×), then brine, dried over MgSO$_4$, filtered, and concentrated. Column chromatography (50%→100% EtOAc/Hex) gave two closely eluting spots which were collected together to give 21.0 mg (ca. 43%) as a mixture of the title compounds. LCMS (Column: Phenomenex Luna C18 2×50 mm; Mobile Phase A: 10:90 ACN:water with 0.1% TFA; Mobile Phase B: 90:10 ACN:water with 0.1% TFA; Temperature: 40° C.; Gradient: 0-100% B over 4 min; Flow: 0.8 mL/min) data: Mono-bromide:(M+H)=562.2. HPLC RT=3.14 min; Di-bromide: (M($^{79}$Br,$^{81}$Br)+H)=640.1. HPLC RT=3.37 min.

Step 5: 2-[8-Bromo-3-(4-bromo-1-methyl-1H-1,2,3-triazol-5-yl)-5-[(S)-oxan-4-yl(phenyl)methyl]-5H-pyrido[3,2-b]indol-7-yl]propan-2-ol and 2-[3-(4-Bromo-1-methyl-1H-1,2,3-triazol-5-yl)-5-[(S)-oxan-4-yl)phenyl)methyl]-5H-pyrido[3,2-b]indol-7-yl]propan-2-ol To a mixture of (S)-methyl 3-(4-bromo-1-methyl-1H-1,2,3-triazol-5-yl)-5-(phenyl(tetrahydro-2H-pyran-4-yl)methyl)-5H-pyrido[3,2-b]indole-7-carboxylate and (S)-methyl 8-bromo-3-(4-bromo-1-methyl-1H-1,2,3-triazol-5-yl)-5-(phenyl(tetrahydro-2H-pyran-4-yl)methyl)-5H-pyrido[3,2-b]indole-7-carboxylate (21.0 mg, 0.0350 mmol) in THF (350 μL) at 0° C. was added methylmagnesium bromide (3M in Et$_2$O, 117 μL, 0.350 mmol). The reaction was stirred for 30 min at that temperature. The reaction was quenched by addition of sat. aq. NH$_4$Cl. The reaction was diluted with ethyl acetate and poured into water. The layers were separated. The organics were washed with water, then brine, dried over MgSO$_4$, filtered, and concentrated. The resulting residue was purified by column chromatography (50%→100% EtOAc/Hexanes→1% MeOH/EtOAc) to give two fractions. The upper spot (Fraction1) was collected, concentrated, and re-purified by preparative HPLC (Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 min, then a 5-min hold at 100% B; Flow: 20 mL/min) to give Example 383 (6.30 mg, 28%). The lower spot (Fraction2) was collected to give Example 384 (9.40 mg, 43%). Example 383: $^1$H NMR (500 MHz, DMSO-d$_6$) δ 8.62 (s, 2H), 8.49 (br. s., 1H), 8.38 (s, 1H), 7.65 (d, J=7.7 Hz, 2H), 7.40-7.32 (m, 2H), 7.30-7.24 (m, 1H), 5.74 (d, J=11.0 Hz, 1H), 4.09 (s, 3H), 3.93-3.87 (m, 1H), 3.74 (d, J=8.8 Hz, 1H), 3.52-3.22 (m, 3H), 1.84-1.65 (m, 8H), 1.60-1.48 (m, 1H), 1.38-1.25 (m, 1H), 0.98 (d, J=12.1 Hz, 1H). LCMS (M($^{79}$Br,$^{81}$Br)+H)=640.1. Example 384: $^1$H NMR (500 MHz, CDCl$_3$) δ 8.53 (d, J=1.7 Hz, 1H), 8.38 (d, J=8.2 Hz, 1H), 8.01 (s, 1H), 7.83 (d, J=1.7 Hz, 1H), 7.50 (d, J=7.4 Hz, 2H), 7.47 (dd, J=8.3, 1.3 Hz, 1H), 7.38-7.33 (m, 2H), 7.30 (d, J=7.3 Hz, 1H), 5.59 (d, J=10.7 Hz, 1H), 4.07 (dd, J=12.1, 3.5 Hz, 1H), 4.02 (s, 3H), 3.87 (dd, J=11.8, 3.0 Hz, 1H), 3.56 (td, J=11.9, 1.9 Hz, 1H), 3.37 (td, J=11.9, 2.0 Hz, 1H), 3.22-3.09 (m, 1H), 2.03 (d, J=13.1 Hz, 1H), 1.76 (s, 6H), 1.69-1.57 (m, 2H), 1.48-1.37 (m, 1H), 1.12 (d, J=12.5 Hz, 1H). LCMS (M($^{81}$Br)+H)=562.2.

Example 385

2-[3-(4-Cyclopropyl-1-methyl-1H-1,2,3-triazol-5-yl)-5-[(S)-oxan-4-yl(phenyl)methyl]-5H-pyrido[3,2-b]indol-7-yl]propan-2-ol

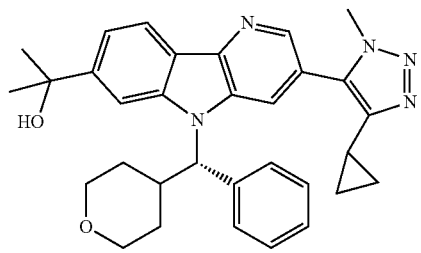 [SMILES: Cn1nnc(C2CC2)c1-c1cnc2c3ccc(C(C)(C)O)cc3n([C@H](c3ccccc3)C3CCOCC3)c2c1]

2-[3-(4-Bromo-1-methyl-1H-1,2,3-triazol-5-yl)-5-[(S)-oxan-4-yl(phenyl)methyl]-5H-pyrido[3,2-b]indol-7-yl]propan-2-ol (6.00 mg, 10.7 μmol), cyclopropylboronic acid (4.60 mg, 0.0540 mmol), bis(tricyclohexylphosphine)palladium dichloride (1.98 mg, 2.68 μmol), and potassium phosphate (11.4 mg, 0.0540 mmol) were placed in a vial, and the mixture was flushed with nitrogen. To this was added toluene (0.5 mL) and water (0.05 mL). The vial was flushed with nitrogen for 15 min with vigorous stirring. The vial was capped and placed in a preheated 110° C. bath. The reaction was held at 110° C. for 4 h, cooled to room temperature, and concentrated under a stream of nitrogen. The resulting residue was suspended in DCM/water and stirred vigorously. The mixture was diluted with EtOAc and the layers separated. The organics were dried over MgSO$_4$, filtered, and concentrated. The residue was purified by iterative preparative HPLC (1$^{st}$ HPLC: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. 2$^{nd}$ HPLC: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 min, then a 5-min hold at 100% B; Flow: 20 mL/min. 3$^{rd}$ HPLC: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 min, then a 5-min hold at 100% B; Flow: 20 mL/min) to give 3.8 mg (55%) as a TFA salt. $^1$H NMR (500 MHz, DMSO-d$_6$) δ 8.54 (s, 1H), 8.44 (br. s., 1H), 8.15 (d, J=8.4 Hz, 2H), 7.66 (d, J=7.3 Hz, 2H), 7.48 (d, J=8.1 Hz, 1H), 7.36-7.29 (m, 2H), 7.27-7.21 (m, 1H), 5.82 (d, J=11.4 Hz, 1H), 3.98 (s, 3H), 3.93-3.86 (m, 1H), 3.74 (d, J=11.0 Hz, 1H), 3.47 (t, J=12.1 Hz, 1H), 3.26 (t, J=11.7 Hz, 1H), 3.19-3.09 (m, 1H), 2.94 (br. s., 1H), 1.83 (br. s., 1H), 1.72 (d, J=12.1 Hz, 1H), 1.58 (s, 6H), 1.37-1.22 (m, 2H), 1.02 (d, J=12.5 Hz, 1H), 0.96-0.77 (m, 4H). LCMS (M+H)=522.3.

Examples 386 & 387

2-[8-Chloro-3-(4-chloro-1-methyl-1H-1,2,3-triazol-5-yl)-5-[(S)-oxan-4-yl(phenyl)methyl]-5H-pyrido[3,2-b]indol-7-yl]propan-2-ol, and 2-[3-(4-Chloro-1-methyl-1H-1,2,3-triazol-5-yl)-5-[(S)-oxan-4-yl(phenyl)methyl]-5H-pyrido[3,2-b]indol-7-yl]propan-2-ol

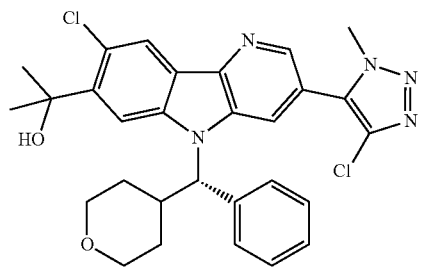

Example 386

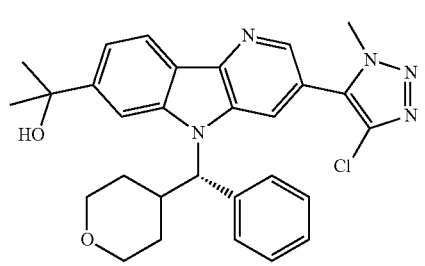

Example 387

The title compounds were prepared in an analogous manner to that used to prepare 2-[8-bromo-3-(4-bromo-1-methyl-1H-1,2,3-triazol-5-yl)-5-[(S)-oxan-4-yl(phenyl) methyl]-5H-pyrido[3,2-b]indol-7-yl]propan-2-ol and 2-[3-(4-bromo-1-methyl-1H-1,2,3-triazol-5-yl)-5-[(S)-oxan-4-yl (phenyl)methyl]-5H-pyrido[3,2-b]indol-7-yl]propan-2-ol, replacing N-bromosuccinimide with N-chlorosuccinimide. Isolation of the title compounds was accomplished by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-80% B over 40 min, then a 5-min hold at 100% B; Flow: 20 mL/min) to give Examples 386 & 387. Example 386: $^1$H NMR (500 MHz, DMSO-d$_6$) δ 8.62 (s, 2H), 8.48 (s, 1H), 8.18 (s, 1H), 7.65 (d, J=7.7 Hz, 2H), 7.39-7.31 (m, 2H), 7.30-7.23 (m, 1H), 5.74 (d, J=11.7 Hz, 1H), 4.09 (br. s., 3H), 3.94-3.87 (m, 1H), 3.74 (d, J=8.8 Hz, 1H), 3.51-3.32 (m, 2H), 3.27 (t, J=11.2 Hz, 1H), 1.73 (d, J=15.0 Hz, 7H), 1.59-1.49 (m, 1H), 1.32 (d, J=8.4 Hz, 1H), 0.97 (d, J=12.1 Hz, 1H). LCMS (M+H)=550.5. Example 387: $^1$H NMR (500 MHz, DMSO-d$_6$) δ 8.61-8.47 (m, 2H), 8.17 (d, J=8.1 Hz, 2H), 7.66 (d, J=7.3 Hz, 2H), 7.49 (d, J=8.1 Hz, 1H), 7.38-7.29 (m, 2H), 7.28-7.21 (m, 1H), 5.82 (d, J=11.4 Hz, 1H), 4.09 (s, 3H), 3.94-3.87 (m, 1H), 3.74 (d, J=9.2 Hz, 1H), 3.52-3.22 (m, 4H), 1.70 (d, J=13.2 Hz, 1H), 1.59 (s, 7H), 1.39-1.27 (m, 1H), 1.02 (d, J=11.7 Hz, 1H). LCMS (M+H)=516.4.

Example 388

2-[3-(4-Ethyl-1-methyl-1H-1,2,3-triazol-5-yl)-5-[(S)-oxan-4-yl(phenyl)methyl]-5H-pyrido[3,2-b]indol-7-yl]propan-2-ol

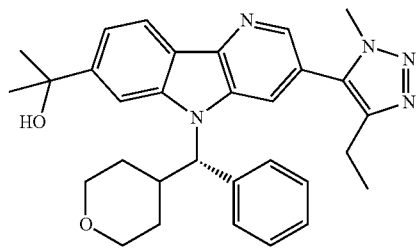 [SMILES: CCc1nnn(C)c1-c1cnc2c3ccc(C(C)(C)O)cc3n([C@H](c3ccccc3)C3CCOCC3)c2c1]

Step 1: 4-(((tert-Butyldimethylsilyl)oxy)methyl)-1-((trimethylsilyl)methyl)-1H-1,2,3-triazole To a solution of (azidomethyl)trimethylsilane (85% pure, 2.40 g, 15.7 mmol) and tert-butyldimethyl(prop-2-yn-1-yloxy)silane (2.95 g, 17.3 mmol) in t-butanol (40 mL) was added a solution of sodium ascorbate (3.12 g, 15.7 mmol) in water (20 mL). To this was slowly added a solution of copper (II) sulfate pentahydrate (0.785 g, 3.15 mmol) in water (20 mL). The resulting light yellow heterogeneous mixture was stirred vigorously overnight. The reaction was diluted with EtOAc/water which gave an emulsion that was partially separable. Multiple washings with aqueous ammonia (~10%) gave two easily separated layers. After concentration of the organics, the material was purified by column chromatography (12%→25% EtOAc/Hex) to give 4.36 g (92%) as a white solid. $^1$H NMR (400 MHz, CDCl$_3$) δ 7.35 (s, 1H), 4.85 (s, 2H), 3.91 (s, 2H), 0.92 (s, 9H), 0.15 (s, 9H), 0.10 (s, 6H). $^{13}$C NMR (101 MHz, CDCl$_3$) δ 148.5, 122.1, 58.1, 42.0, 25.9, 18.3, -2.5, -5.2. LCMS (M+H)=300.2.

Step 2: (S)-Methyl 3-(4-(((tert-butyldimethylsilyl) oxy)methyl)-1-((trimethylsilyl)methyl)-1H-1,2,3-triazol-5-yl)-5-(phenyl(tetrahydro-2H-pyran-4-yl) methyl)-5H-pyrido[3,2-b]indole-7-carboxylate To a solution of 4-(((tert-butyldimethylsilyl)oxy)methyl)-1-((trimethylsilyl)methyl)-1H-1,2,3-triazole (562 mg, 1.88 mmol) in THF (6.3 mL) at -78° C. was added n-BuLi (2.5M in pentane, 801 µL, 2.00 mmol). The resulting solution was stirred at -78° C. for 1 h. The resulting yellow solution was treated with zinc chloride (290 mg, 2.13 mmol). After stirring for 30 min, the ice bath was removed, and the reaction stirred 1 h longer to give a clear, colorless solution. The resulting solution was treated with (S)-methyl 3-bromo-5-(phenyl(tetrahydro-2H-pyran-4-yl)methyl)-5H-pyrido[3,2-b]indole-7-carboxylate (600 mg, 1.25 mmol), Pd$_2$dba$_3$ (22.9 mg, 0.0250 mmol), and Ru-Phos (46.7 mg, 0.100 mmol) as a mixture of solids in one portion under a constant stream of nitrogen. The resulting reddish-amber solution was sealed and immersed in a preheated oil bath at 70° C. The reaction was allowed to stir 20 h at that temperature. The reaction was diluted with DCM, poured into water, and the layers separated. The organics were washed with brine, dried over $MgSO_4$, filtered, and concentrated. Column chromatography (EtOAc/Hex) gave 650 mg (74%) as a foam solid. $^1H$ NMR (500 MHz, $CDCl_3$) δ 8.62 (d, J=1.7 Hz, 1H), 8.51 (s, 1H), 8.47 (d, J=8.2 Hz, 1H), 8.08 (dd, J=8.2, 1.3 Hz, 1H), 7.97 (br. s., 1H), 7.54 (d, J=7.3 Hz, 2H), 7.37-7.32 (m, 2H), 7.31-7.27 (m, 1H), 5.58 (d, J=10.9 Hz, 1H), 4.80 (s, 2H), 4.05 (s, 4H), 3.85 (dd, J=11.7, 2.8 Hz, 1H), 3.66-3.51 (m, 2H), 3.35 (td, J=11.9, 1.7 Hz, 1H), 3.18 (d, J=11.0 Hz, 1H), 1.99 (d, J=13.2 Hz, 1H), 1.67-1.55 (m, 1H), 1.48-1.37 (m, 1H), 1.12 (d, J=12.9 Hz, 1H), 0.82 (s, 10H), 0.09 (s, 3H), 0.07 (s, 3H), 0.02 (s, 9H). LCMS (M+H)=698.4.

Step 3: (S)-2-(3-(4-(((tert-Butyldimethylsilyl)oxy) methyl)-1-((trimethylsilyl)methyl)-1H-1,2,3-triazol-5-yl)-5-(phenyl(tetrahydro-2H-pyran-4-yl)methyl)-5H-pyrido[3,2-b]indol-7-yl)propan-2-ol To a solution of (S)-methyl 3-(4-(((tert-butyldimethylsilyl)oxy)methyl)-1-((trimethylsilyl)methyl)-1H-1,2,3-triazol-5-yl)-5-(phenyl(tetrahydro-2H-pyran-4-yl)methyl)-5H-pyrido[3,2-b]indole-7-carboxylate (650 mg, 0.931 mmol) in THF (4660 µL) at −20° C. was added methylmagnesium bromide (3M in $Et_2O$, 32483 µL, 7.45 mmol). The resulting solution was allowed to gradually warm to 0° C. and held at that temperature for 15 min. The reaction was quenched by the cautious addition of sat. aq. $NH_4Cl$. The reaction was diluted with ethyl acetate and poured into water. The layers were separated. The organics were washed with water, then brine, dried over $MgSO_4$, filtered, and concentrated to give 614 mg (94%). $^1H$ NMR (500 MHz, $CDCl_3$) δ 8.53 (d, J=1.6 Hz, 1H), 8.38 (d, J=8.2 Hz, 1H), 8.02 (s, 1H), 7.88 (br. s., 1H), 7.50 (d, J=7.3 Hz, 2H), 7.45 (dd, J=8.4, 1.3 Hz, 1H), 7.34-7.23 (m, 3H), 5.54 (d, J=10.9 Hz, 1H), 4.79 (s, 2H), 4.03 (dd, J=11.7, 2.7 Hz, 1H), 3.84 (dd, J=11.6, 2.6 Hz, 1H), 3.65-3.50 (m, 2H), 3.32 (td, J=11.9, 1.8 Hz, 1H), 3.19-3.09 (m, 1H), 1.96 (d, J=13.2 Hz, 1H), 1.75 (s, 6H), 1.61-1.51 (m, 1H), 1.44-1.35 (m, 1H), 1.13 (d, J=12.8 Hz, 1H), 0.86-0.79 (m, 11H), 0.07 (s, 3H), 0.05 (s, 3H), −0.01 (s, 9H). LCMS (M+H)=698.5.

Step 4: (S)-2-(3-(4-(Hydroxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol To a solution of (S)-2-(3-(4-(((tert-butyldimethylsilyl) oxy)methyl)-1-((trimethylsilyl)methyl)-1H-1,2,3-triazol-5-yl)-5-(phenyl(tetrahydro-2H-pyran-4-yl)methyl)-5H-pyrido [3,2-b]indol-7-yl)propan-2-ol (614 mg, 0.880 mmol) and water (0.0320 mL, 1.76 mmol) in THF (5.6 mL) at 0° C. was added tetrabutylammonium fluoride (1M in THF, 2.64 mL, 2.64 mmol). After 10 min at 0° C., the ice bath was removed and stirring continued for 1 h. The reaction was quenched by addition of sat. aq. $NH_4Cl$ and diluted with EtOAc. The mixture was poured into water, and the layers separated. The organics were washed with water, then brine, dried over $MgSO_4$, filtered, and concentrated. Column chromatography (2% MeOH/EtOAc 10% MeOH/EtOAc) gave 376 mg (84%) as a white solid. LCMS (M+H)=512.3. HPLC RT=1.98 min (Column: Phenomenex LUNA C18, 2×50 mm; Mobile Phase A: 10:90 ACN:water with 0.1% TFA; Mobile Phase B: 90:10 ACN:water with 0.1% TFA; Temperature: 40° C.; Gradient: 0-100% B over 4 min; Flow: 0.8 mL/min).

Step 5: (S)-(5-(7-(2-Hydroxypropan-2-yl)-5-(phenyl (tetrahydro-2H-pyran-4-yl)methyl)-5H-pyrido[3,2-b] indol-3-yl)-1-methyl-1H-1,2,3-triazol-4-yl)methyl methanesulfonate To a solution of (S)-2-(3-(4-(hydroxymethyl)-1-methyl-1H-1,2,3-triazol-5-yl)-5-(phenyl(tetrahydro-2H-pyran-4-yl) methyl)-5H-pyrido[3,2-b]indol-7-yl)propan-2-ol (125 mg, 0.244 mmol) and TEA (51.1 µL, 0.366 mmol) in DCM (1960 µL) at 0° C. was added methanesulfonyl chloride (20.9 µL, 0.269 mmol) dropwise. The reaction was held at 0° C. for 30 min. The reaction was diluted with EtOAc and quenched by addition of sat. aq. $NaHCO_3$. After stirring briefly at 0° C., the reaction was poured into a separatory funnel, and the layers separated. The organics were washed with water, then brine, dried over $MgSO_4$, filtered, and concentrated. The resulting residue was used without purification. LCMS (M+H)=590.1. HPLC RT=1.57 min (Column: Waters Aquity BEH C18, 2.1×50 mm; Mobile Phase A: water with 0.05% TFA; Mobile Phase B: ACN with 0.05% TFA; Temperature: 40° C.; Gradient: 2-50% B over 1.5 min; 0.5 min hold; Flow: 0.8 mL/min).

Step 6: 2-[3-(4-Ethyl-1-methyl-1H-1,2,3-triazol-5-yl)-5-[(S)-oxan-4-yl(phenyl)methyl]-5H-pyrido[3,2-b]indol-7-yl]propan-2-ol A flask was charged with copper(I) iodide (34.9 mg, 0.183 mmol) and flushed with nitrogen. To this was added THF (0.5 mL). The resulting suspension was vigorously stirred for 15 min, cooled to 0° C., and treated with methylmagnesium bromide (3M in $Et_2O$, 0.122 mL, 0.366 mmol). After stirring at 0° C. for 15 min, the heterogeneous mixture was treated with a solution of (S)-(5-(7-(2-hydroxypropan-2-yl)-5-(phenyl(tetrahydro-2H-pyran-4-yl(methyl)-5H-pyrido[3,2-b]indol-3-yl)-1-methyl-1H-1,2,3-triazol-4-yl)methyl methanesulfonate (18.0 mg, 0.0310 mmol) in THF (0.5 mL) dropwise. After stirring for 30 min, the reaction was quenched by addition of sat. aq. $NH_4Cl$ and diluted with EtOAc. The layers were separated. The organics were washed with 5% ammonia in water and concentrated. The resulting residue was purified by preparative HPLC (Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min) to give 5.50 mg (35%). $^1H$ NMR (500 MHz, DMSO-$d_6$) δ 8.52-8.32 (m, 2H), 8.16 (d, J=8.1 Hz, 2H), 7.67 (d, J=7.3 Hz, 2H), 7.48 (d, J=8.4 Hz, 1H), 7.37-7.29 (m, 2H), 7.28-7.20 (m, 1H), 5.82 (d, J=11.4 Hz, 1H), 3.99 (s, 3H), 3.94-3.85 (m, 1H), 3.75 (d, J=9.2 Hz, 1H), 3.56-3.34 (m, 2H), 3.27 (t, J=11.4 Hz, 1H), 2.77-2.53 (m, 3H), 1.71 (d, J=12.5 Hz, 1H), 1.64-1.51 (m, 7H), 1.40-1.27 (m, 1H), 1.17 (t, J=7.5 Hz, 3H), 1.03 (d, J=12.5 Hz, 1H). LCMS (M+H)=510.3.

Example 389

2-[3-(4-Amino-1-methyl-1H-1,2,3-triazol-5-yl)-5-[(S)-oxan-4-yl(phenyl)methyl]-5H-pyrido[3,2-b]indol-7-yl]propan-2-ol

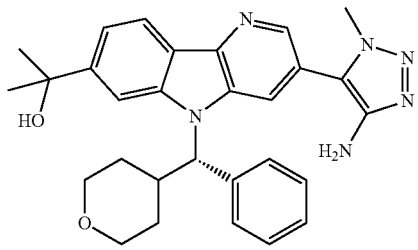 [SMILES: Cn1nnc(N)c1-c1cnc2c3ccc(C(C)(C)O)cc3n([C@H](c3ccccc3)C3CCOCC3)c2c1]

Step 1: (S)-5-(7-(2-Hydroxypropan-2-yl)-5-(phenyl(tetrahydro-2H-pyran-4-yl)methyl)-5H-pyrido[3,2-b]indol-3-yl)-1-methyl-1H-1,2,3-triazole-4-carbaldehyde To a solution of (S)-2-(3-(4-(hydroxymethyl)-1-methyl-1H-1,2,3-triazol-5-yl)-5-(phenyl(tetrahydro-2H-pyran-4-yl)methyl)-5H-pyrido[3,2-b]indol-7-yl)propan-2-ol (230 mg, 0.450 mmol) in DCM (2997 µL) at room temperature was added Dess-Martin Periodinane (229 mg, 0.539 mmol). After 1 h, the reaction was treated with a second portion of Dess-Martin Periodinane (115 mg). After 1 h, the reaction was quenched by addition of sodium thiosulfate (600 mg) in water (3 mL). After stirring at room temperature for 10 min, the mixture was diluted with EtOAc and sat. aq. NaHCO$_3$, and the layers separated. The organics were washed with sat. aq. NaHCO$_3$, then brine, dried over MgSO$_4$, filtered, and concentrated to give 220 mg (96%). $^1$H NMR (500 MHz, CDCl$_3$) δ 10.25 (s, 1H), 8.54 (d, J=1.7 Hz, 1H), 8.37 (d, J=8.2 Hz, 1H), 8.09 (d, J=1.7 Hz, 1H), 8.01 (s, 1H), 7.53 (d, J=7.3 Hz, 2H), 7.46 (dd, J=8.2, 1.3 Hz, 1H), 7.38-7.32 (m, 2H), 7.32-7.26 (m, 1H), 5.56 (d, J=10.9 Hz, 1H), 4.09-4.03 (m, 4H), 3.86 (dd, J=11.7, 2.8 Hz, 1H), 3.58 (td, J=11.9, 1.9 Hz, 1H), 3.47 (td, J=11.9, 1.9 Hz, 1H), 3.31-3.19 (m, 1H), 2.21 (s, 1H), 1.99 (d, J=13.2 Hz, 1H), 1.76 (d, J=1.3 Hz, 6H), 1.64-1.55 (m, 1H), 1.46-1.36 (m, 1H), 1.11 (d, J=12.5 Hz, 1H). LCMS (M+H)=510.5.

Step 2: (S)-5-(7-(2-Hydroxypropan-2-yl)-5-(phenyl(tetrahydro-2H-pyran-4-yl)methyl)-5H-pyrido[3,2-b]indol-3-yl)-1-methyl-1H-1,2,3-triazole-4-carboxylic acid A stock solution of oxidant was prepared by combining sodium chlorite (96.0 mg, 1.06 mmol), sodium dihydrogenphosphate monohydrate (73.1 mg, 0.530 mmol), and water (1.2 mL). Separately, (S)-5-(7-(2-hydroxypropan-2-yl)-5-(phenyl(tetrahydro-2H-pyran-4-yl)methyl)-5H-pyrido[3,2-b]indol-3-yl)-1-methyl-1H-1,2,3-triazole-4-carbaldehyde (135 mg, 0.265 mmol) was dissolved in t-BuOH (2 mL) and THF (1.3 mL), the reaction mixture cooled to 0° C., and treated with 2-methylbut-2-ene (0.312 mL, 2.65 mmol). To this was added 0.5 mL of the stock solution of oxidant. After stirring 10 min, the rest of the stock solution was added dropwise. After addition, the ice bath was removed, and the reaction stirred 2 h. The reaction was poured into water (3 mL) and diluted with EtOAc, which failed to solubilize the precipitate. The solid was collected in a Buchner funnel, rinsed with water, then EtOAc, and air dried to give 63.0 mg (45%). $^1$H NMR (500 MHz, DMSO-d$_6$) δ 8.74-8.48 (m, 2H), 8.20-8.05 (m, 2H), 7.67 (d, J=7.3 Hz, 2H), 7.48 (d, J=8.2 Hz, 1H), 7.33 (t, J=7.6 Hz, 2H), 7.27-7.21 (m, 1H), 5.77 (d, J=11.3 Hz, 1H), 3.99 (br. s., 3H), 3.90 (d, J=9.3 Hz, 1H), 3.74 (d, J=8.8 Hz, 1H), 3.54-3.22 (m, 5H), 1.72-1.49 (m, 8H), 1.38-1.26 (m, 1H), 1.04 (d, J=11.8 Hz, 1H). LCMS (M+H)=526.6.

Step 3: 2-[3-(4-Amino-1-methyl-1H-1,2,3-triazol-5-yl)-5-[(S)-oxan-4-yl(phenyl)methyl]-5H-pyrido[3,2-b]indol-7-yl]propan-2-ol and (S)-tert-butyl(5-(7-(2-hydroxypropan-2-yl)-5-(phenyl(tetrahydro-2H-pyran-4-yl)methyl)-5H-pyrido[3,2-b]indol-3-yl)-1-methyl-1H-1,2,3-triazol-4-yl)carbamate A vial was charged with (S)-5-(7-(2-hydroxypropan-2-yl)-5-(phenyl(tetrahydro-2H-pyran-4-yl)methyl)-5H-pyrido[3,2-b]indol-3-yl)-1-methyl-1H-1,2,3-triazole-4-carboxylic acid (63.0 mg, 0.120 mmol), t-BuOH (0.75 mL), TEA (0.0250 mL, 0.180 mmol), and diphenylphosphoryl azide (0.0310 mL, 0.144 mmol). The vial was sealed. The resulting white suspension was warmed to 85° C. and held at this temperature for 4 h. The reaction was treated with an additional portion of TEA (0.0250 mL, 0.180 mmol) and diphenylphosphoryl azide (0.0310 mL, 0.144 mmol). The reaction was sealed and heated at 85° C. for 8 h, cooled to room temperature, and concentrated under a stream of nitrogen. The residue was diluted with EtOAc and treated with sat. aq. NaHCO$_3$. The layers were separated. The organics were washed with water 3× and filtered through a Buchner funnel to remove undissolved solids, which were discarded. The eluent was concentrated and purified by column chromatography (100% EtOAc then 20% MeOH/EtOAc). The carbamate was first to elute, followed by the free amine. The free amine was repurified by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min) to give Example 389 (13.5 mg, 22%). Example 389. $^1$H NMR (500 MHz, DMSO-d$_6$) δ 8.52 (s, 1H), 8.35 (br. s., 1H), 8.16-8.03 (m, 2H), 7.67 (d, J=7.7 Hz, 2H), 7.45 (d, J=8.4 Hz, 1H), 7.37-7.29 (m, 2H), 7.28-7.22 (m, 1H), 5.79 (d, J=11.0 Hz, 1H), 4.90 (br. s., 2H), 3.99-3.86 (m, 4H), 3.74 (d, J=9.5 Hz, 1H), 3.49 (t, J=11.6 Hz, 1H), 3.42 (s, 4H), 3.27 (t, J=11.6 Hz, 1H), 1.72 (d, J=12.1 Hz, 1H), 1.57 (br. s., 7H), 1.32 (d, J=12.8 Hz, 1H), 1.00 (d, J=13.2 Hz, 1H). LCMS (M+H)=497.0. (S)-tert-butyl (5-(7-(2-hydroxypropan-2-yl)-5-(phenyl(tetrahydro-2H-pyran-4-yl)methyl)-5H-pyrido[3,2-b]indol-3-yl)-1-methyl-1H-1,2,3-triazol-4-yl)carbamate: $^1$H NMR (500 MHz, CDCl$_3$) δ 8.48 (d, J=1.7 Hz, 1H), 8.36 (d, J=8.2 Hz, 1H), 7.98 (s, 1H), 7.91 (br. s., 1H), 7.48 (d, J=7.4 Hz, 2H), 7.45 (dd, J=8.3, 1.3 Hz, 1H), 7.36-7.31 (m, 2H), 7.29-7.25 (m, 1H), 6.46 (s, 1H), 5.53 (d, J=10.7 Hz, 1H), 4.08-4.01 (m, 1H), 3.93-3.81 (m, 4H), 3.54 (td, J=11.9, 1.9 Hz, 1H), 3.38 (td, J=11.9, 1.9 Hz, 1H), 3.23-3.10 (m, 1H), 1.99-1.91 (m, 1H), 1.78-1.69 (m, 9H), 1.63-1.53 (m, 1H), 1.39 (d, J=4.1 Hz, 2H), 1.32 (br. s., 9H), 1.18-1.11 (m, 1H). LCMS (M+H)=597.7.

Example 390

2-{3-[1-Methyl-4-(methylamino)-1H-1,2,3-triazol-5-yl]-5-[(S)-oxan-4-yl(phenyl)methyl]-5H-pyrido[3,2-b]indol-7-yl}propan-2-ol

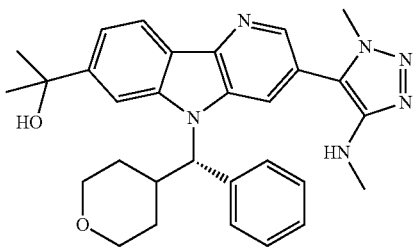 [SMILES: CNc1nnn(C)c1-c1cnc2c3ccc(C(C)(C)O)cc3n([C@H](c3ccccc3)C3CCOCC3)c2c1]

A vial was charged with (S)-tert-butyl (5-(7-(2-hydroxypropan-2-yl)-5-(phenyl(tetrahydro-2H-pyran-4-yl)methyl)-5H-pyrido[3,2-b]indol-3-yl)-1-methyl-1H-1,2,3-triazol-4-yl)carbamate (13.0 mg, 0.0220 mmol, see Step 3 of 2-[3-(4-amino-1-methyl-1H-1,2,3-triazol-5-yl)-5-[(S)-oxan-4-yl(phenyl)methyl]-5H-pyrido[3,2-b]indol-7-yl]propan-2-ol) and DMF (0.75 mL). The resulting solution was cooled to 0° C. and treated with sodium hydride (1.74 mg, 0.0440 mmol). The ice bath was removed and stirring continued 10 min. The reaction was re-cooled to 0° C. and treated with iodomethane (2.72 µL, 0.0440 mmol). The reaction was stirred at 0° C. for 15 min and quenched by addition of sat. aq. NH$_4$Cl. The reaction was diluted with EtOAc. The mixture was washed with water (2×), then brine, dried over MgSO$_4$, filtered, and concentrated. The crude Boc-protected product was dissolved in TFA/DCM (1:5 vol/vol). After 30 min, the reaction was concentrated and purified by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min) to give 11 mg (99%). $^1$H NMR (500 MHz, DMSO-d$_6$) δ 8.48 (s, 1H), 8.34 (br. s., 1H), 8.16-8.03 (m, 2H), 7.66 (d, J=7.7 Hz, 2H), 7.45 (d, J=8.1 Hz, 1H), 7.37-7.29 (m, 2H), 7.28-7.21 (m, 1H), 5.79 (d, J=11.0 Hz, 1H), 5.21 (d, J=5.1 Hz, 1H), 4.01-3.85 (m, 4H), 3.74 (d, J=8.4 Hz, 1H), 3.53-3.45 (m, 1H), 3.26 (t, J=11.6 Hz, 1H), 2.90 (s, 1H), 2.79 (d, J=5.1 Hz, 3H), 2.74 (s, 1H), 1.72 (d, J=13.2 Hz, 1H), 1.57 (s, 7H), 1.40-1.23 (m, 1H), 0.99 (d, J=12.5 Hz, 1H). LCMS (M+H)=511.1.

Example 391

5-{7-Methanesulfonyl-5-[(S)-oxan-4-yl(phenyl)methyl]-5H-pyrido[3,2-b]indol-3-yl}-4-methoxy-1-methyl-1H-1,2,3-triazole

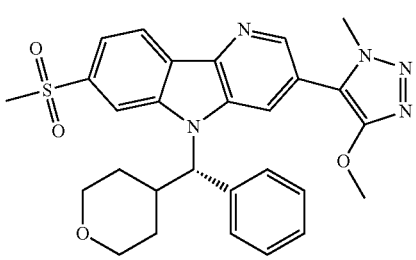 [SMILES: COc1nnn(C)c1-c1cnc2c3ccc(S(C)(=O)=O)cc3n([C@H](c3ccccc3)C3CCOCC3)c2c1]

Step 1: (S)-3-Bromo-7-(methylsulfonyl)-5-(phenyl(tetrahydro-2H-pyran-4-yl)methyl)-5H-pyrido[3,2-b]indole A vial was charged with 3-bromo-7-(methylsulfonyl)-5H-pyrido[3,2-b]indole (200 mg, 0.615 mmol) and cesium carbonate (601 mg, 1.85 mmol). To this was added a solution of (R)-phenyl(tetrahydro-2H-pyran-4-yl)methyl methanesulfonate (333 mg, 1.23 mmol) in DMF (3075 µL). The vial was flushed with nitrogen, sealed, and placed in a 50° C. bath. The reaction was stirred at this temperature for 4 days. The resulting mixture was diluted with EtOAc, filtered through a plug of cotton, and purified by silica gel column chromatography to give 215 mg (70%). $^1$H NMR (400 MHz, CDCl$_3$) δ 8.68 (d, J=2.0 Hz, 1H), 8.52 (d, J=8.3 Hz, 1H), 8.28 (s, 1H), 8.09 (d, J=1.7 Hz, 1H), 7.87 (dd, J=8.2, 1.3 Hz, 1H), 7.49 (d, J=7.3 Hz, 2H), 7.42-7.36 (m, 2H), 7.36-7.31 (m, 1H), 5.47 (d, J=11.0 Hz, 1H), 4.08 (dd, J=11.7, 2.9 Hz, 1H), 3.88 (dd, J=11.6, 3.1 Hz, 1H), 3.58 (td, J=12.0, 2.0 Hz, 1H), 3.40 (td, J=11.9, 2.0 Hz, 1H), 3.17-3.11 (m, 5H), 2.00 (d, J=13.0 Hz, 1H), 1.46-1.33 (m, 1H), 1.04 (d, J=12.5 Hz, 1H). LCMS (M ($^{81}$Br)+H)=501.3.

Step 2: 5-{7-Methanesulfonyl-5-[(S)-oxan-4-yl(phenyl)methyl]-5H-pyrido[3,2-b]indol-3-yl}-4-methoxy-1-methyl-1H-1,2,3-triazole A dry, N$_2$ (g) flushed, 1 dram vial was charged with tetramethyl ammonium acetate (18.7 mg, 0.140 mmol), bis(triphenylphosphine)palladium(II) dichloride (4.92 mg, 7.01 µmol), and (S)-3-bromo-7-(methylsulfonyl)-5-(phenyl(tetrahydro-2H-pyran-4-yl)methyl)-5H-pyrido[3,2-b]indole (35.0 mg, 0.0700 mmol). To this was added 4-methoxy-1-((trimethylsilyl)methyl)-1H-1,2,3-triazole (26.0 mg, 0.140 mmol). The vial was again flushed with nitrogen. To this was added NMP (0.4 mL). The resulting mixture was stirred vigorously under a stream of nitrogen for 10 min. The vial was placed in a pre-heated oil bath at 95° C. and heated at that temperature overnight. The reaction was cooled to room temperature, diluted with EtOAc, washed with water (2×), then brine, dried over MgSO$_4$, filtered, concentrated, and purified by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 min, then a 5-min hold at 100% B; Flow: 20 mL/min) to give 7.00 mg (18%). $^1$H NMR (500 MHz, DMSO-d$_6$) δ 8.75 (br. s., 1H), 8.68 (s, 1H), 8.53 (br. s., 1H), 8.48 (d, J=8.1 Hz, 1H), 7.86 (d, J=8.4 Hz, 1H), 7.68 (d, J=7.7 Hz, 2H), 7.40-7.32 (m, 2H), 7.31-7.24 (m, 1H), 6.01 (d, J=11.0 Hz, 1H), 4.08 (s, 3H), 4.04 (s, 3H), 3.91 (d, J=8.8 Hz, 1H), 3.72 (d, J=8.8 Hz, 1H), 3.26 (t, J=11.2 Hz, 1H), 2.51 (br. s., 4H), 1.79-1.57 (m, 2H), 1.42-1.18 (m, 2H), 0.92 (d, J=12.5 Hz, 1H). LCMS (M+H)=532.5.

Example 392

Propan-2-yl N-{3-[4-($^2$H$_3$)methoxy-1-methyl-1H-1,2,3-triazol-5-yl]-5-[(S)-oxan-4-yl(phenyl)methyl]-5H-pyrido[3,2-b]indol-7-yl}carbamate

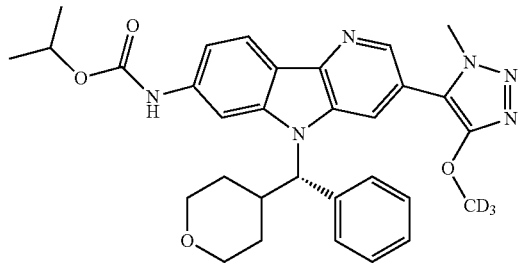 [SMILES: [2H]C([2H])([2H])Oc1nnn(C)c1-c1cnc2c3ccc(NC(=O)OC(C)C)cc3n([C@H](c3ccccc3)C3CCOCC3)c2c1]

Step 1: Phenyl(tetrahydro-2H-pyran-4-yl)methyl methanesulfonate

A solution of (R)-phenyl(tetrahydro-2H-pyran-4-yl)methanol (450 mg, 2.34 mmol) in DCM (15 mL) was treated with triethylamine (0.652 mL, 4.68 mmol). The resulting solution was cooled to 0° C. and treated with methanesulfonyl chloride (0.274 mL, 3.51 mmol) dropwise. It was stirred at 0° C. for 1 h then room temperature for 0.5 h. It was quenched with saturated aq. sodium bicarbonate and diluted with ether. The organic layer was washed with saturated aq. sodium bicarbonate, then brine, dried over magnesium sulfate, filtered, and concentrated to give 620 mg (quant. yield). $^1$H NMR (400 MHz, CDCl$_3$) δ 7.44-7.36 (m, 5H), 5.23 (d, J=8.78 Hz, 1H), 4.09-3.91 (m, 2H), 3.4-3.3 (m, 2H), 2.63 (s, 3H), 2.14-2.0 (m, 2H), 1.55 (m, 1H), 1.35-1.28 (m, 2H), 1.16-1.12 (m, 1H).

Step 2: (S)-Methyl 3-bromo-5-(phenyl(tetrahydro-2H-pyran-4-yl)methyl)-5H-pyrido[3,2-b]indole-7-carboxylate To a mixture of methyl 3-bromo-5H-pyrido[3,2-b]indole-7-carboxylate (1.20 g, 3.93 mmol) and cesium carbonate (2.56 g, 7.87 mmol) in DMF (6 mL) was added phenyl(tetrahydro-2H-pyran-4-yl)methyl methanesulfonate (1.17 g, 4.33 mmol) in DMF (6 mL). It was stirred at room temperature overnight. The reaction was warmed to 40° C. and held at that temperature 24 h. To this was added an additional portion of phenyl(tetrahydro-2H-pyran-4-yl)methyl methanesulfonate (1.06 g, 3.94 mmol) and cesium carbonate (1.28 g, 3.94 mmol). It was heated at 40° C. over the weekend. Solids were removed by filtration and discarded, and the filtrate concentrated. Biotage purification (30% EA/Hex) gave 300 mg product (16%). $^1$H NMR (400 MHz, CDCl$_3$) δ 8.6 (d, J=2.0 Hz, 1H), 8.43 (s, 1H), 8.39 (d, J=8.03 Hz, 1H), 8.05-8.01 (m, 2H), 7.50 (m, 2H), 7.39-7.35 (m, 2H), 7.32 (m, 1H), 5.489d, J–11.0 Hz, 1H), 4.07 (m, 1H), 4.03 (s, 3H), 3.86 (m, 1H), 3.57 (m, 1H), 3.4 (m, 1H), 3.14 (m, 1H), 2.99 (m, 1H), 1.6 (m, 1H), 1.4 (m, 1H), 1.06 (m, 1H); LCMS (M+H)=479.1/481.1

Step 3: Methyl 3-[4-($^2$H$_3$)methoxy-1-methyl-1H-1,2,3-triazole-5-yl]-5-[(S)-oxan-4-yl(phenyl)methyl-5H-pyrido[3,2-b]indole-7-carboxylate A dry, N$_2$ (g) flushed, 1 dram vial was charged with tetramethylammonium acetate (38.9 mg, 0.292 mmol), bis(triphenylphosphine)palladium(II) chloride (10.3 mg, 0.0150 mmol) and (S)-methyl 3-bromo-5-(phenyl(tetrahydro-2H-pyran-4-yl)methyl)-5H-pyrido[3,2-b]indole-7-carboxylate (70.0 mg, 0.146 mmol). To this was added 4-($^2$H$_3$)methoxy-1-[(trimethylsilyl)methyl]-1H-1,2,3-triazole (65.5 mg, 0.292 mmol). The vial was again flushed with nitrogen and NMP (1 mL) was then added. The resulting mixture was stirred vigorously under a stream of nitrogen for 10 min. The vial was placed in a pre-heated oil bath at 95° C. and heated at that temperature overnight. The reaction was cooled to room temperature, diluted with ethyl acetate, washed with water (2×), then brine, dried over magnesium sulfate, filtered, and concentrated. Biotage purification (70% EtOAc) gave 53.0 mg (71%) as yellow oil. LCMS (M+H)=515.5, LC RT=1.613 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 4: 3-[4-($^2$H$_3$)Methoxy-1-methyl-1H-1,2,3-triazole-5-yl]-5-[(S)-oxan-4-yl(phenyl)methyl-5H-pyrido[3,2-b]indole-7-carboxylic acid To a solution of methyl 3-[4-($^2$H$_3$)methoxy-1-methyl-1H-1,2,3-triazole-5-yl]-5-[(S)-oxan-4-yl(phenyl)methyl-5H-pyrido[3,2-b]indole-7-carboxylate (53.0 mg, 0.103 mmol) in THF (1 mL) was added potassium hydroxide (17.3 mg, 0.309 mmol). It was stirred at 50° C. overnight and concentrated. Water was added, and the resulting mixture extracted with EA (which were discarded). The aqueous layer was then acidified to pH 5. As the pH approached the acidic range, a white solid precipitated out. The mixture was extracted with ethyl acetate, dried over magnesium sulfate, filtered, and concentrated to give 42.0 mg (81%). $^1$H NMR (400 MHz, CDCl$_3$) δ 8.85 (s, 1H), 8.64 (s, 1H), 8.6 (d, J=8.0 Hz, 1H), 8.29 (d, J=8.3 Hz, 1H), 8.04 (d, J=1.5 Hz, 1H), 7.56 (m, 2H), 7.42-7.31 (m, 3H), 5.67 (d, J=10.8 Hz, 1H), 4.11 (s, 3H), 3.92 (m, 1H), 3.6 (m, 1H), 3.41 (m, 1H), 3.2 (m, 1H), 2.04 (m, 2H), 1.68 (m, 1H), 1.48 (m, 1H), 1.14 (m, 1H); LCMS (M+H)=501.4.

Step 5: 5-{7-Isocyanato-5-[(S)-oxan-4-yl(phenyl)methyl]-5H-pyrido[3,2-b]indol-3-yl}-4-($^2$H$_3$)methoxy-1-methyl-1H-1,2,3-triazole A vial was charged with 3-[4-($^2$H$_3$)methoxy-1-methyl-1H-1,2,3-triazole-5-yl]-5-[(S)-oxan-4-yl(phenyl)methyl-5H-pyrido[3,2-b]indole-7-carboxylic acid (42.0 mg, 0.0840 mmol), diphenylphosphoryl azide (0.0470 mL, 0.210 mmol), Et$_3$N (0.0290 mL, 0.210 mmol), and dioxane (1.7 mL). The mixture was heated at 60° C. for 2 h. The solution of isocyanate was used as is in the following reaction. LCMS (M+H)=498.25, LC RT=1.73 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 6: Propan-2-yl N-{3-[4-($^2$H$_3$)methoxy-1-methyl-1H-1,2,3-triazol-5-yl]-5-[(S)-oxan-4-yl(phenyl)methyl]-5H-pyrido[3,2-b]indol-7-yl}carbamate Isopropanol (210 μL, 2.73 mmol) was added to 5-{7-isocyanato-5-[(S)-oxan-4-yl(phenyl)methyl]-5H-pyrido[3,2-b]indol-3-yl}-4-($^2$H$_3$)methoxy-1-methyl-1H-1,2,3-triazole (41.8 mg, 0.0840 mmol). It was heated at 80° C. for 3 h. It was concentrated and purified by prep HPLC (Column: XBridge 19×200 mm, 5 μm; Mobile Phase A: 5:95 ACN:water with 10 mm ammonium acetate; Mobile Phase B: 95:5 ACN:water with 10 mm ammonium acetate; Gradient: 35-75% B over 20 min, 5-min hold; Flow Rate: 20 mL/min) to give 33.8 mg product (72%). $^1$H NMR (500 MHz, DMSO-d$_6$) δ 8.49 (s, 1H), 8.42 (bs, 1H), 8.25 (br. s., 1H), 8.10 (d, J=8.4 Hz, 1H), 7.63 (d, J=7.7 Hz, 2H), 7.40 (d, J=8.4 Hz, 1H), 7.35 (t, J=7.5 Hz, 2H), 7.29-7.23 (m, 1H), 5.6 (m, 1H), 5.06-4.91 (m, 1H), 4.08 (br. s., 3H), 3.91 (d, J=8.1 Hz, 1H), 3.75 (d, J=11.0 Hz, 1H), 3.34-3.23 (m, 2H), 1.69 (d, J=12.1 Hz, 1H), 1.50 (d, J=12.5 Hz, 1H), 1.32 (d, J=6.2 Hz, 8H), 1.05 (d, J=12.5 Hz, 1H); LCMS (M+H)=558.5, LC RT=1.49 min.

Example 393

2-{6-Chloro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol

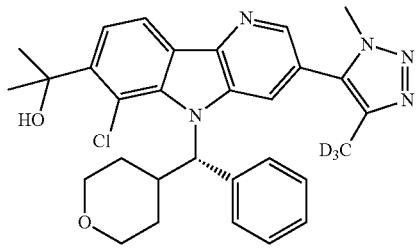 [SMILES: [2H]C([2H])([2H])c1nnn(C)c1-c1cnc2c3ccc(C(C)(C)O)c(Cl)c3n([C@H](c3ccccc3)C3CCOCC3)c2c1]

Step 1: Methyl 4-(5-bromo-3-nitropyridin-2-yl)-2-chlorobenzoate

A flask was charged with 2,5-dibromo-3-nitropyridine (6.55 g, 23.24 mmol) and (3-chloro-4-(methoxycarbonyl)phenyl)boronic acid (4.98 g, 23.24 mmol), flushed with nitrogen, and treated with tetrahydrofuran (65 mL), followed by 2M aqueous tripotassium phosphate (23.24 mL, 46.5 mmol). The resulting mixture was stirred while bubbling nitrogen through the mixture for 30 min. To this was added PdCl$_2$(dppf) (0.595 g, 0.813 mmol) and heated at 75° C. for 2 h. The reaction was cooled to room temperature and poured into a stirred mixture of water and ethyl acetate. The layers were separated, the organics washed with water (2×), then brine, dried over magnesium sulfate, filtered and concentrated. It was purified by silica gel column chromatography (100% DCM) to give 5.76 g product (67%) as white solid. $^1$H NMR (400 MHz, CDCl$_3$) δ 8.97 (m, 1H), 8.40 (m, 1H), 7.94 (m, 1H), 7.71 (m, 1H), 7.44 (m, 1H), 3.99 (s, 3H), LCMS (M+H)=373.2.

Step 2: Methyl 3-bromo-6-chloro-5H-pyrido[3,2-b]indole-7-carboxylate

A 250 mL flask, charged with methyl 4-(5-bromo-3-nitropyridin-2-yl)-2-chlorobenzoate (5.76 g, 15.5 mmol) and 1,2-bis(diphenylphosphino)ethane (6.79 g, 17.0 mmol) was flushed with nitrogen, treated with 1,2-dichlorobenzene (77 mL), and stirred under a stream of nitrogen for 15 min. The flask was sealed and immersed in an oil bath at 165° C. for 3 h. The reaction was allowed to cool to room temperature overnight. The resulting precipitate was collected by filtration, rinsed with a minimum of toluene, and discarded. The eluent was concentrated and purified by Biotage (5-50% EA/Hex) to give 398 mg product (8%). $^1$H NMR (400 MHz, DMSO-d$_6$) δ 12.23 (s, 1H), 8.67 (s, 1H), 8.25 (d, J=8.03 Hz, 1H), 8.17 (s, 1H), 7.76 (d, J=8.28 Hz, 1H), 3.94 (s, 3H); LCMS (M+H)=341.2.

Step 3: (S)-Methyl 3-bromo-6-chloro-5-(phenyl(tetrahydro-2H-pyran-4-yl)methyl)-5H-pyrido[3,2-b]indole-7-carboxylate A dry vial, charged with methyl 3-bromo-6-chloro-5H-pyrido[3,2-b]indole-7-carboxylate (160 mg, 0.471 mmol), triphenylphosphine (247 mg, 0.942 mmol), (R)-phenyl(tetrahydro-2H-pyran-4-yl)methanol (181 mg, 0.942 mmol), and THF (4712 μL), was cooled to 0° C. and treated with di-tert-butyl azodicarboxylate (217 mg, 0.942 mmol). The reaction was allowed to gradually warm to room temperature overnight. To this was added TFA (363 μL, 4.71 mmol), and the reaction mixture stirred for 10 min. Potassium phosphate (1.5 M) was added to the reaction mixture, followed by ethyl acetate. The layers were separated, and the organics concentrated. Biotage purification (25% EA/Hex) gave 246 mg product as off-white solid (57% purity by LCMS). LCMS (M+H)=515.3, LC RT=2.08 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 4: Methyl 6-chloro-3-[4-($^2$H$_3$)methyl-1-methyl-1H-1,2,3-triazol-5-yl]-5-[(S)-oxan-4-yl)phenyl)methyl]-5H-pyrido[3,2-b]indole-7-carboxylate (S)-Methyl 3-bromo-6-chloro-5-(phenyl(tetrahydro-2H-pyran-4-yl)methyl)-5H-pyrido[3,2-b]indole-7-carboxylate (30.0 mg, 0.0580 mmol), 4-($^2$H$_3$)methyl-1-methyl-5-(tributylstanny)-1H-1,2,3-triazole (34.1 mg, 0.0880 mmol), triethylamine (0.0160 mL, 0.117 mmol), and copper(I) iodide (1.11 mg, 5.84 μmol) in DMF (0.5 mL) was degassed with nitrogen. Tetrakis(triphenylphosphine)palladium(0) (3.37 mg, 2.92 μmol) was added (turning dark), and the reaction was heated at 90° C. for 3 h. LC/MS indicates product mass. It was diluted with ethyl acetate, washed with water (×3) and brine, dried over magnesium sulfate, filtered, and concentrated. Biotage purification (up to 100% EA/Hex) gave 11.0 mg product (35%) as clear oil. $^1$H NMR (400 MHz, CDCl$_3$) δ 8.5 (d, J=1.5 Hz, 1H), 8.41 (d, J=8.03 Hz, 1H), 7.71 (d, J=8.03 Hz, 1H), 7.57-7.52 (m, 3H), 7.41-7.38 (m, 2H), 7.33 (m, 1H), 4.08 (s, 3H), 3.86 (m, 1H), 3.77 (s, 3H), 3.57 (m, 1H), 3.31 (m, 1H), 3.02 (m, 1H), 2.17 (m, 1H), 1.75-1.6 (m, 2H), 1.35 (m, 1H), 0.72 (m, 1H); LCMS (M+H)=533.5.

Step 5: 2-{6-Chloro-3-[4-($^2$H$_3$)methyl-1-methyl-1H-1,2,3-triazol-5-yl]-5-[(5)-oxan-4-yl)phenyl)methyl]-5H-pyrido[3,2-b]indol-7-yl}propan-2-ol Following a procedure analogous to that described in 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol, methyl 6-chloro-3-[4-($^2$H$_3$)methyl-1-methyl-1H-1,2,3-triazol-5-yl]-5-[(5)-oxan-4-yl(phenyl)methyl]-5H-pyrido[3,2-b]indole-7-carboxylate (22.0 mg, 0.0410 mmol) was converted to 5.30 mg product (24%). $^1$H NMR (500 MHz, DMSO-d$_6$) δ 8.52 (s, 1H), 8.22 (d, J=8.4 Hz, 1H), 8.04 (s, 1H), 7.95 (d, J=8.1 Hz, 1H), 7.57 (d, J=7.7 Hz, 2H), 7.38-7.28 (m, 2H), 7.27-7.16 (m, 2H), 5.53 (s, 1H), 3.89 (d, J=9.2 Hz, 1H), 3.85 (s, 3H), 3.75 (d, J=9.9 Hz, 1H), 3.57-3.44 (m, 2H), 3.26 (t, J=11.6 Hz, 1H), 1.92 (d, J=12.5 Hz, 1H), 1.81 (d, J=11.7 Hz, 6H), 1.53-1.40 (m, 2H), 0.89 (d, J=12.1 Hz, 1H); LCMS (M+H)=533.5.

Examples 394 & 395

2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol Enantiomer A, Example 394

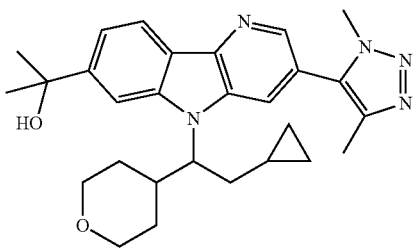

Enantiomer B, Example 395

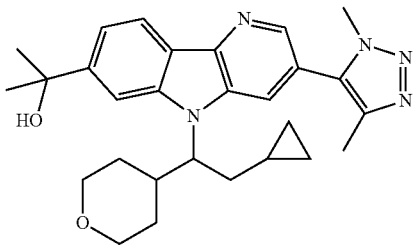

Step 1: Methyl 3-(1,4-dimethyl-1H-1,2,3-triazol-5-yl)-5H-pyrido[3,2-b]indole-7-carboxylate A mixture of methyl 3-bromo-5H-pyrido[3,2-b]indole-7-carboxylate (0.800 g, 2.62 mmol), 1,4-dimethyl-5-(tributylstannyl)-1H-1,2,3-triazole (1.11 g, 2.88 mmol), triethylamine (0.731 mL, 5.24 mmol), and DMF (7 mL) was purged under a stream of nitrogen. To this was added copper(I) iodide (0.0750 g, 0.393 mmol) and tetrakis(triphenylphosphine)palladium(0) (0.197 g, 0.170 mmol). The vial was sealed and heated at 85° C. for 1.5 h, then at 95° C. for 1 h. The resulting mixture was cooled to room temperature, purged again with nitrogen, treated with 1,4-dimethyl-5-(tributylstannyl)-1H-1,2,3-triazole (0.910 g, 2.36 mmol), copper(I)iodide (0.0750 g, 0.393 mmol), and tetrakis(triphenylphosphine)palladium(0) (0.197 g, 0.170 mmol). The vial was sealed and heated at 100° C. for 2 h. After cooling to room temperature, the reaction was diluted with water and extracted with ethyl acetate. The organics were washed with water, then aqueous NH$_4$OH, and then brine, dried over MgSO$_4$, filtered, and concentrated. The residue was suspended in a small amount of ethyl acetate. The resulting solid was triturated with little ethyl acetate and dried to give 325 mg product as pale yellow solid. The mother liquor was concentrated and purified by silica gel column chromatography (40 g SiO$_2$, 100% EA to 5-10% MeOH/CH$_2$Cl$_2$) to give another 175 mg product as pale yellow solid (0.500 g total, 59%). 1H NMR (400 MHz, DMSO-d6) δ 1.96 (s, 1H), 8.63 (d, J=2 Hz, 1H), 8.36 (d, J=8 Hz, 1H), 8.26 (s, 1H), 8.17 (d, J=1.76 Hz, 1H), 7.91 (dd, J1=1.25 Hz, J2=8 Hz, 1H), 4.03 (s, 3H), 3.94 (s, 3H), 2.31 (s, 3H); LCMS (M+H)=322.1.

Step 2: 2-Cyclopropyl-1-(tetrahydro-2H-pyran-4-yl)ethanol

A dry 50 mL flask was charged with magnesium (173 mg, 7.13 mmol) and a crystal of iodine. Under nitrogen, the solids were stirred vigorously while being warmed with the heat gun to aerosolize the iodine. Upon cooling to room temperature, it was treated with THF (4 mL). The mixture was warmed with a heat gun and treated with a solution of 4-bromotetrahydro-2H-pyran (0.530 mL, 4.76 mmol) in THF (4 mL) dropwise via a dry addition funnel. When addition was complete, the mixture was placed in a preheated oil bath, and the mixture held at reflux for 30 min. After cooling to room temperature, the solution was transferred to a stirred solution of 2-cyclopropylacetaldehyde (400 mg, 2.38 mmol) in THF (4 mL) at −78° C. After stirring for 5 min, the ice bath was removed, and the reaction allowed to warm to room temperature. The reaction was placed in a 0° C. bath and quenched by the cautious addition of sat. aq. NH$_4$Cl (~4 mL). The reaction was diluted with EtOAc and poured into brine (~10 mL). The layers were separated, and the aqueous was extracted with a second portion of EtOAc. The resulting organics were dried over magnesium sulfate, filtered, and concentrated to give product (410 mg, quant.) as near colorless oil, which was used without purification. $^1$H NMR (400 MHz, DMSO-d$_6$) δ 4.03-4.0 (m, 2H), 3.54-3.35 (m, 3H), 1.51-1.34 (m, 4H), 0.8 (m, 1H), 0.59-0.46 (m, 2H), 0.19-0.05 (m, 2H).

Step 3: Methyl 5-(2-cyclopropyl-1-(tetrahydro-2H-pyran-4-yl)ethyl)-3-(1,4-dimethyl-1H-1,2,3-triazol-5-yl)-5H-pyrido[3,2-b]indole-7-carboxylate A solution of triphenylphosphine (98.0 mg, 0.373 mmol) in THF (2 mL) was cooled to −20° C. and treated with DIAD (0.0730 mL, 0.373 mmol). After stirring at −20° C. for 30 min, methyl 3-(1,4-dimethyl-1H-1,2,3-triazol-5-yl)-5H-pyrido[3,2-b]indole-7-carboxylate (60.0 mg, 0.187 mmol) was added, and stirring continued at −20° C. for 30 min. To this was added a solution of 2-cyclopropyl-1-(tetrahydro-2H-pyran-4-yl)ethanol (63.6 mg, 0.373 mmol) in THF (1 mL) dropwise. The reaction was allowed to warm to room temperature overnight. It was concentrated and purified by silica gel column chromatography (0-1% MeOH/DCM) to give 89.0 mg product (79% purity) as sticky yellow oil. LCMS (M+H)=474.2, LC RT=1.40 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Step 4: 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol A solution of methyl 5-(2-cyclopropyl-1-(tetrahydro-2H-pyran-4-yl)ethyl)-3-(1,4-dimethyl-1H-1,2,3-triazol-5-yl)-5H-pyrido[3,2-b]indole-7-carboxylate (89.0 mg, 0.187 mmol) in THF (2 mL) was cooled to −78° C. under nitrogen. To this was added methylmagnesium bromide (3M in ether, 0.312 mL, 0.935 mmol) dropwise. After 10 min, the ice bath was removed and stirring continued for 1 h. The reaction was placed in a 0° C. bath and quenched by the cautious addition of sat. aq. ammonium chloride. The reaction was diluted with ethyl acetate and poured into brine. The layers were separated, and the aqueous was extracted with a second portion of ethyl acetate. The resulting organics were dried over magnesium sulfate, filtered, and concentrated. Prep HPLC (Column: XBridge 19×200 mm, 5 µm; Mobile Phase A: 5:95 ACN:water with 0.1% TFA; Mobile Phase B: 95:5 ACN:water with 0.1% TFA; Gradient: 10-60% B over 30 min, 5-min hold; Flow Rate: 20 mL/min) gave 17.5 mg (racemic, 20%), which was further purified by chiral prep SFC (Column: ChiralCel OD-H 30×250 mm, 5 μm; Mobile Phase: 85/15 CO$_2$/MeOH; Flow: 70 mL/min, Pressure: 150 bar, Temperature: 35° C., UV: 272 nm) to give: Enantiomer A (3.00 mg, 17%, SFC RT=14.6-16.75 min) $^1$H NMR (500 MHz, DMSO-d$_6$) δ 8.51 (d, J=14.67 Hz, 1H), 8.44-8.31 (m, 1H), 8.23-8.16 (m, 1H), 7.93-7.91 (d, J=13.57 Hz, 1H), 7.47-7.43 (m, 1H), 4.66 (br. s., 1H), 4.05 (d, J=7.3 Hz, 3H), 3.92 (d, J=11.4 Hz, 1H), 3.63 (m, 1H), 3.23-2.93 (m, 2H), 2.33 (d, J=4.4 Hz, 3H), 1.95-1.78 (m, 1H), 1.60 (br. s., 1H), 1.56 (s, 5H), 1.53 (br. s., 1H), 1.23-1.10 (m, 4H), 1.04 (br. s., 1H), 0.75 (d, J=13.6 Hz, 1H), 0.16--0.09 (m, 4H), −0.25 (d, J=14.7 Hz, 1H); LCMS (M+H)=474.2 and Enantiomer B (3.70 mg, 21%, SFC RT=18.75-21.75 min) 8.51 (d, J=14.67 Hz, 1H), 8.44-8.31 (m, 1H), 8.23-8.16 (m, 1H), 7.93-7.91 (d, J=13.57 Hz, 1H), 7.47-7.43 (m, 1H), 4.66 (br. s., 1H), 4.05 (d, J=7.3 Hz, 3H), 3.92 (d, J=11.4 Hz, 1H), 3.63 (m, 1H), 3.23-2.93 (m, 2H), 2.33 (d, J=4.4 Hz, 3H), 1.95-1.78 (m, 1H), 1.60 (br. s., 1H), 1.56 (s, 5H), 1.53 (br. s., 1H), 1.23-1.10 (m, 4H), 1.04 (br. s., 1H), 0.75 (d, J=13.6 Hz, 1H), 0.16--0.09 (m, 4H), −0.25 (d, J=14.7 Hz, 1H); LCMS (M+H)=474.2.

Examples 396 & 397

2-[3-(Dimethyl-1H-1,2,3-triazol-5-yl)-5-[(1S)-2-methoxy-1-(oxan-4-yl)ethyl]-5H-pyrido[3,2-b]indol-7-yl]propan-2-ol Enantiomer A, Example 396

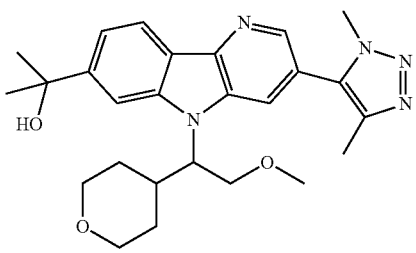

Enantiomer B, Example 397

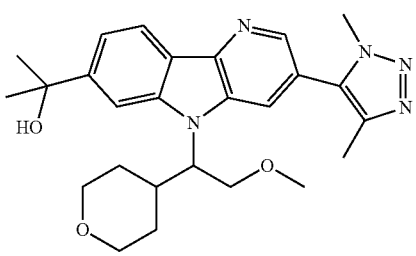

Step 1: N,2-Dimethoxy-N-methylacetamide

A solution of 2-methoxyacetic acid (1.70 mL, 22.2 mmol) in dichloromethane (10 mL) was treated with oxalyl chloride (2.14 mL, 24.4 mmol) at room temperature. To this was added 2 drops of DMF, and the reaction stirred overnight. This was added to a solution of N,O-dimethylhydroxylamine hydrochloride (3.25 g, 33.3 mmol) and TEA (6.19 mL, 44.4 mmol) in dichloromethane (10 mL) at 0° C. The ice bath was removed, and the resulting mixture stirred at room temperature overnight. The mixture was washed with water, then 1.5M potassium hydrogen phosphate, then 1N hydrochloric acid, then brine, and concentrated to give 535 mg (18%). $^1$H NMR (400 MHz, CDCl$_3$) δ 4.24 (s, 2H), 3.71 (s, 3H), 3.49 (s, 3H), 3.22 (s, 3H).

Step 2:
2-Methoxy-1-(tetrahydro-2H-pyran-4-yl)ethanone

A dry 50 mL flask under nitrogen was charged with magnesium (197 mg, 8.11 mmol) and a crystal of iodine. The solids were stirred vigorously while being warmed with the heat gun to aerosolize the iodine. Upon cooling to room temperature, it was treated with THF (4 mL). The mixture was warmed with a heat gun and treated with a solution of 4-bromotetrahydro-2H-pyran (0.678 mL, 6.08 mmol) in THF (4 mL) dropwise via a dry addition funnel. When addition was complete, the mixture was placed in a preheated oil bath, and the mixture held at reflux for 30 min. After cooling to room temperature, the solution was transferred to a stirred solution of N,2-dimethoxy-N-methylacetamide (270 mg, 2.03 mmol) in THF (12 mL) at −78° C. After stirring for 5 min, the ice bath was removed and the reaction allowed to warm to room temperature. The reaction was placed in a 0° C. bath, quenched by addition of sat. aq. ammonium chloride, concentrated, diluted with EtOAc, washed with water, then brine, dried over magnesium sulfate, filtered, and concentrated to give 260 mg (81%) as clear oil. Material was used without purification. $^1$H NMR (400 MHz, CDCl$_3$) δ 4.11 (s, 2H), 4.05-4.0 (m, 2H), 3.5-3.44 (m, 2H), 3.45 (s, 3H), 2.8 (m, 1H), 1.64 (m, 2H), 1.32 (m, 2H).

Step 3:
2-Methoxy-1-(tetrahydro-2H-pyran-4-yl)ethanol

A solution of 2-methoxy-1-(tetrahydro-2H-pyran-4-yl)ethanone (60.0 mg, 0.379 mmol) in methanol (1 mL) was treated with sodium borohydride (14.4 mg, 0.379 mmol) in portions (effervescence) at room temperature. After stirring for 2 h, it was concentrated, dissolved in EA, washed with sat. aq. ammonium chloride, then brine, dried over magnesium sulfate, filtered, and concentrated to give 60.0 mg (quant.). $^1$H NMR (400 MHz, CDCl$_3$) δ 4.07-3.96 (m, 2H), 3.59-3.47 (m, 1H), 3.46-3.31 (m, 4H), 1.87-1.77 (m, 1H), 1.74-1.58 (m, 4H), 1.53-1.40 (m, 2H), 1.32 (s, 1H).

Step 4: Methyl 3-(1,4-dimethyl-1H-1,2,3-triazol-5-yl)-5-(2-methoxy-1-(tetrahydro-2H-pyran-4-yl)ethyl)-5H-pyrido[3,2-b]indole-7-carboxylate A microwave vial was purged with nitrogen and charged with methyl 3-(1,4-dimethyl-1H-1,2,3-triazol-5-yl)-5H-pyrido[3,2-b]indole-7-carboxylate (60.0 mg, 0.187 mmol), 2-methoxy-1-(tetrahydro-2H-pyran-4-yl)ethanol (59.8 mg, 0.373 mmol), and degassed toluene (1.5 mL). The vial was flushed with nitrogen, charged with cyanomethylenetrimethylphosphorane (0.747 mL, 0.373 mmol, 0.5M in THF), sealed, and heated at 110° C. overnight. It was concentrated, diluted with ethyl acetate, washed with water, then brine, and concentrated to give 108 mg product (50% purity). $^1$H NMR (500 MHz, DMSO-d$_6$) δ 8.67 (br. s., 1H), 8.55-8.45 (m, 2H), 8.39 (br. s., 1H), 7.95 (d, J=13.2 Hz, 1H), 4.99 (br. s., 1H), 4.18 (br. s., 1H), 4.07 (s, 3H), 3.96 (s, 4H), 3.88 (br. s., 1H), 3.62 (d, J=9.5 Hz, 1H), 3.33 (br. s., 1H), 3.23-2.98 (m, 4H), 2.72-2.62 (m, 1H), 2.35 (s, 3H), 1.81 (br. s., 1H), 1.69 (br. s., 1H), 1.15 (br. s., 1H), 0.66 (br. s., 1H); LCMS (M+H)=464.2.

Step 5: 2-[3-(Dimethyl-1H-1,2,3-triazol-5-yl)-5-[(1S)-2-methoxy-1-(oxan-4-yl)ethyl]-5H-pyrido[3,2-b]indol-7-yl]propan-2-ol Following a procedure analogous to that described in 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol, methyl 3-(1,4-dimethyl-1H-1,2,3-triazol-5-yl)-5-(2-methoxy-1-(tetrahydro-2H-pyran-4-yl)ethyl)-5H-pyrido[3,2-b]indole-7-carboxylate (108 mg, 0.233 mmol) was converted to 40.2 mg product (racemic, 37%), which was further purified by chiral prep SFC (Column: ChiralPak AS-H 30×250 mm, 5 µm; Mobile Phase: 88/12 CO$_2$/MeOH; Flow Rate: 70 mL/min, Pressure: 150 bar, Temperature: 35° C., UV: 268 nm) to give: Enantiomer A (5.60 mg, 15%, SFC RT=8.75 min) $^1$H NMR (500 MHz, DMSO-d$_6$) δ 8.5 (br. s., 1H), 8.36-8.3 (m, 1H), 8.21-8.16 (m, 1H), 7.96 (s, 1H), 7.45 (d, J=8.4 Hz, 1H), 4.81 (br. s., 1H), 4.29-4.13 (m, 1H), 4.05 (s, 3H), 3.93-3.88 (m, 2H), 3.63 (d, J=9.2 Hz, 1H), 3.42-3.23 (m, 1H), 3.15 (s, 3H), 3.05 (m, 1H), 3.63 (m, 1H), 2.33 (s, 3H), 1.87 (m, 1H), 1.63 (d, J=12.1 Hz, 1H), 1.15 (dd, J=12.1, 4.0 Hz, 1H), 0.70 (br. s., 1H); LCMS (M+H)=464.2 and Enantiomer B (6.40 mg, 17%, SFC RT=10.52 min) $^1$H NMR (500 MHz, DMSO-d$_6$) δ 8.5 (br. s., 1H), 8.36-8.3 (m, 1H), 8.21-8.16 (m, 1H), 7.96 (s, 1H), 7.45 (d, J=8.4 Hz, 1H), 4.81 (br. s., 1H), 4.29-4.13 (m, 1H), 4.05 (s, 3H), 3.93-3.88 (m, 2H), 3.63 (d, J=9.2 Hz, 1H), 3.42-3.23 (m, 1H), 3.15 (s, 3H), 3.05 (m, 1H), 3.63 (m, 1H), 2.33 (s, 3H), 1.87 (m, 1H), 1.63 (d, J=12.1 Hz, 1H), 1.15 (dd, J=12.1, 4.0 Hz, 1H), 0.70 (br. s., 1H); LCMS (M+H)=464.2.

Examples 398 & 399

2-{5-[(S)-(4-Chlorophenyl)(oxan-4-yl)methyl]-3-(dimethyl-1H-1,2,3-triazol-5-yl)-5H-pyrido[3,2-b]indol-7-yl}propan-2-ol Enantiomer A, Example 398
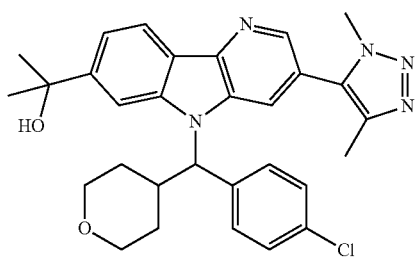

Enantiomer B, Example 399
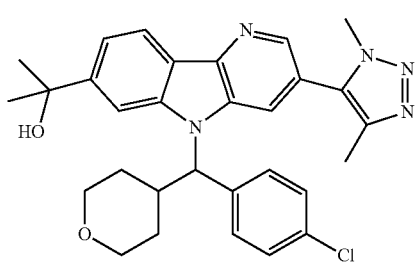

Step 1: (4-Chlorophenyl)(tetrahydro-2H-pyran-4-yl)methanol

Following a procedure analogous to that described in 2-cyclopropyl-1-(tetrahydro-2H-pyran-4-yl)ethanol, 4-chlorobenzaldehyde (200 mg, 1.42 mmol) was converted to 186 mg product (58%). $^1$H NMR (400 MHz, CDCl$_3$) δ 7.36-7.33 (m, 2H), 7.26 (m, 2H), 4.4 (m, 1H), 4.04 (m, 1H), 3.93 (m, 1H), 3.41-3.27 (m, 2H), 1.84-1.78 (m, 1H), 1.49-1.45 (m, 1H), 1.37-1.28 (m, 2H), 1.2-1.17 (m, 1H).

Step 2: Methyl 5-((4-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate Following a procedure analogous to that described in methyl 5-(2-cyclopropyl-1-(tetrahydro-2H-pyran-4-yl)ethyl)-3-(1,4-dimethyl-1H-1,2,3-triazol-5-yl)-5H-pyrido[3,2-b]indole-7-carboxylate, (4-chlorophenyl)(tetrahydro-2H-pyran-4-yl)methanol (141 mg, 0.622 mmol) was converted to 115 mg product (70%). LCMS (M+H)=530.2, LC RT=1.64 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 3: 2-{5-[(S)-(4-Chlorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described in 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol, methyl 5-((4-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate (115 mg, 0.217 mmol) was converted to racemic 2-{5-[(S)-(4-Chlorophenyl)(oxan-4-yl)methyl]-3-(dimethyl-1H-1,2,3-triazol-5-yl)-5H-pyrido[3,2-b]indol-7-yl}propan-2-ol, which was separated by chiral prep (Column: ChiralCel OD 21×250 mm, 10 µm; Mobile Phase: Solvent A 0.1% diethylamine/Heptane, Solvent B ethanol; Flow Rate: 15 mL/min; Isocratic: 20% B, 28 min; UV: 254 nm) to give: Enantiomer A (13.2 mg, 12%, SFC RT=12.4 min) $^1$H NMR (500 MHz, DMSO-d$_6$) δ 8.51 (s, 1H), 8.38 (m, 1H), 8.15 (d, J=8.1 Hz, 1H), 8.10 (m, 1H), 7.96 (s, 1H), 7.69 (d, J=8.4 Hz, 2H), 7.49 (d, J=8.1 Hz, 1H), 7.40 (d, J=8.4 Hz, 2H), 5.84 (d, J=11.4 Hz, 1H), 4.02 (br. s., 3H), 3.90 (d, J=7.7 Hz, 1H), 3.74 (d, J=8.8 Hz, 1H), 3.47 (t, J=11.4 Hz, 1H), 3.25 (t, J=11.2 Hz, 1H), 2.30 (s, 3H), 1.72-1.64 (m, 1H), 1.58 (br. s., 7H), 1.37-1.13 (m, 2H), 1.01 (d, J=12.1 Hz, 1H); LCMS (M+H)=530.3, LCMS (M+H)=530.3 and Enantiomer B (13.3 mg, 12%, SFC RT=22.5 min)$^1$H NMR (500 MHz, DMSO-d$_6$) δ 8.51 (s, 1H), 8.38 (m, 1H), 8.15 (d, J=8.1 Hz, 1H), 8.10 (m, 1H), 7.96 (s, 1H), 7.69 (d, J=8.4 Hz, 2H), 7.49 (d, J=8.1 Hz, 1H), 7.40 (d, J=8.4 Hz, 2H), 5.84 (d, J=11.4 Hz, 1H), 4.02 (br. s., 3H), 3.90 (d, J=7.7 Hz, 1H), 3.74 (d, J=8.8 Hz, 1H), 3.47 (t, J=11.4 Hz, 1H), 3.25 (t, J=11.2 Hz, 1H), 2.30 (s, 3H), 1.72-1.64 (m, 1H), 1.58 (br. s., 7H), 1.37-1.13 (m, 2H), 1.01 (d, J=12.1 Hz, 1H); LCMS (M+H)=530.3, LCMS (M+H)=530.3.

Examples 400 & 401

2-{5-[(S)-(3-Chlorophenyl)(oxan-4-yl)methyl]-3-(dimethyl-1H-1,2,3-triazol-5-yl)-5H-pyrido[3,2-b]indol-7-yl}propan-2-ol Enantiomer A, Example 400

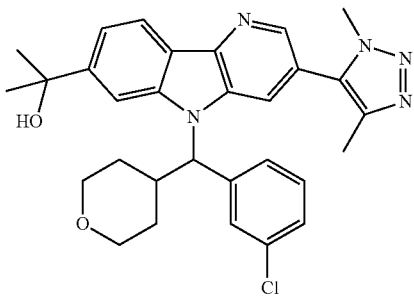

Enantiomer B, Example 401

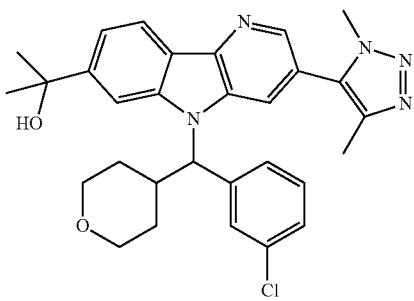

Step 1: (3-Chlorophenyl)(tetrahydro-2H-pyran-4-yl)methanol

Following a procedure analogous to that described in 2-cyclopropyl-1-(tetrahydro-2H-pyran-4-yl)ethanol, 3-chlorobenzaldehyde (200 mg, 0.162 mmol) was converted to 157 mg product (49%). $^1$H NMR (400 MHz, CDCl$_3$) δ 7.35-7.28 (m, 3H), 7.22-7.19 (m, 1H), 4.39 (d, J=7.28 Hz, 1H), 4.06-4.02 (m, 2H), 3.96-3.92 (m, 2H), 3.42-3.28 (m, 2H), 1.93-1.23 (m, 5H).

Step 2: Methyl 5-((3-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate Following a procedure analogous to that described in methyl 5-(2-cyclopropyl-1-(tetrahydro-2H-pyran-4-yl)ethyl)-3-(1,4-dimethyl-1H-1,2,3-triazol-5-yl)-5H-pyrido[3,2-b]indole-7-carboxylate, (3-chlorophenyl)(tetrahydro-2H-pyran-4-yl)methanol (141 mg, 0.622 mmol) was converted to 120 mg product (73%). LCMS (M+H)=530.3, LC RT=1.62 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 3: 2-{5-[(S)-(3-Chlorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described in 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol, methyl 5-((3-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate (120 mg, 0.226 mmol) was converted to racemic 2-{5-[(S)-(3-chlorophenyl)(oxan-4-yl)methyl]-3-(dimethyl-1H-1,2,3-triazol-5-yl)-5H-pyrido[3,2-b]indol-7-yl}propan-2-, which was separated by Chiral prep (Column: ChiralCel OD 21×250 mm, 10 μm; Mobile Phase: Solvent A 0.1% diethylamine/Heptane, Solvent B ethanol; Flow Rate: 15 mL/min; Isocratic: 15% B, 60 min; UV: 254 nm) to give: Enantiomer A (3.20 mg, 3%, SFC RT=18.1 min) $^1$H NMR (500 MHz, DMSO-d$_6$) δ 8.50-8.39 (m, 1H), 8.55-8.31 (m, 2H), 8.15 (d, J=8.1 Hz, 1H), 7.79 (s, 1H), 7.62 (d, J=7.3 Hz, 1H), 7.50 (d, J=8.1 Hz, 1H), 7.40-7.29 (m, 2H), 5.85 (d, J=11.4 Hz, 1H), 4.03 (br. s., 3H), 3.90 (d, J=7.7 Hz, 1H), 3.74 (d, J=11.0 Hz, 1H), 3.54-3.41 (m, 2H), 3.26 (t, J=11.4 Hz, 1H), 2.31 (s, 3H), 1.70-1.51 (m, 8H), 1.31 (d, J=9.2 Hz, 1H), 1.04 (d, J=12.5 Hz, 1H); LCMS (M+H)=530.3 and Enantiomer B (3.60 mg, 3%, SFC RT=32.3 min) $^1$H NMR (500 MHz, DMSO-d$_6$) δ 8.50-8.39 (m, 1H), 8.55-8.31 (m, 2H), 8.15 (d, J=8.1 Hz, 1H), 7.79 (s, 1H), 7.62 (d, J=7.3 Hz, 1H), 7.50 (d, J=8.1 Hz, 1H), 7.40-7.29 (m, 2H), 5.85 (d, J=11.4 Hz, 1H), 4.03 (br. s., 3H), 3.90 (d, J=7.7 Hz, 1H), 3.74 (d, J=11.0 Hz, 1H), 3.54-3.41 (m, 2H), 3.26 (t, J=11.4 Hz, 1H), 2.31 (s, 3H), 1.70-1.51 (m, 8H), 1.31 (d, J=9.2 Hz, 1H), 1.04 (d, J=12.5 Hz, 1H); LCMS (M+H)=530.3.

Examples 402 & 403

2-{5-[(S)-(2-Chlorophenyl)(oxan-4-yl)methyl]-3-(dimethyl-1H-1,2,3-triazol-5-yl)-5H-pyrido[3,2-b]indol-7-yl}propan-2-ol Enantiomer A, Example 402

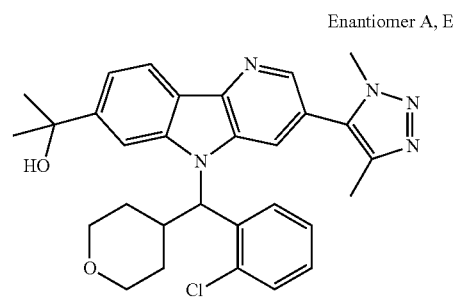

Enantiomer B, Example 403

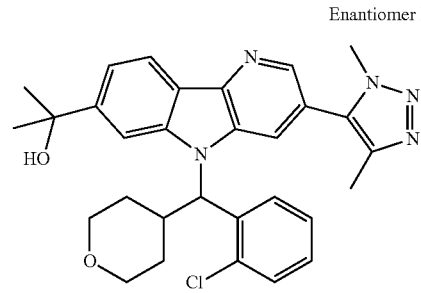

Step 1: (2-Chlorophenyl)(tetrahydro-2H-pyran-4-yl)methanol

Following a procedure analogous to that described in 2-cyclopropyl-1-(tetrahydro-2H-pyran-4-yl)ethanol, 2-chlorobenzaldehyde (200 mg, 0.162 mmol) was converted to 96.0 mg product (30%). $^1$H NMR (400 MHz, CDCl$_3$) δ 7.54-7.52 (m, 1H), 7.37-7.3 (m, 2H), 7.25-7.22 (m, 1H), 4.98 (m, 1H), 4.02 (m, 2H), 3.35 (m, 2H), 1.76 (m, 1H), 1.63 (m, 2H), 1.32 (m, 2H).

Step 2: Methyl 5-((2-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate Following a procedure analogous to that described in methyl 5-(2-cyclopropyl-1-(tetrahydro-2H-pyran-4-yl)ethyl)-3-(1,4-dimethyl-1H-1,2,3-triazol-5-yl)-5H-pyrido[3,2-b]indole-7-carboxylate, (2-chlorophenyl)(tetrahydro-2H-pyran-4-yl)methanol (85.0 mg, 0.373 mmol) was converted to 49.0 mg product (50%). LCMS (M+H)=530.2, LC RT=1.59 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Step 3: 2-{5-[(S)-(2-Chlorophenyl)(oxan-4-yl)methyl]-3-(dimethyl-1H-1,2,3-triazol-5-yl)-5H-pyrido[3,2-b]indol-7-yl}propan-2-ol Following a procedure analogous to that described in 2-{5-[(1R)-2-Cyclopropyl-1-(oxan-4-yl)ethyl]-3-(dimethyl-1H-1,2,3-triazol-5-yl)-5H-pyrido[3,2-b]indol-7-yl}propan-2-ol, methyl 5-((2-chlorophenyl)(tetrahydro-2H-pyran-4-yl)methyl)-3-(1,4-dimethyl-1H-1,2,3-triazol-5-yl)-5H-pyrido[3,2-b]indole-7-carboxylate (49.0 mg, 0.0920 mmol) was converted to racemic 2-{5-[(S)-(2-chlorophenyl)(oxan-4-yl)methyl]-3-(dimethyl-1H-1,2,3-triazol-5-yl)-5H-pyrido[3,2-b]indol-7-yl}propan-2-ol, which was separated by Chiral prep (Column: ChiralCel OD 21×250 mm, 10 μm; Mobile Phase: Solvent A 0.1% diethylamine/Heptane, Solvent B ethanol; Flow Rate: 15 mL/min; Isocratic: 30% B, 120 min; UV: 254 nm) to give; Enantiomer A (10.2 mg, 21%, SFC RT=7.38 min) $^1$H NMR (500 MHz, DMSO-d$_6$) δ 8.52 (s, 1H), 8.33 (d, J=7.7 Hz, 1H), 8.13 (d, J=8.1 Hz, 1H), 7.96 (s, 1H), 7.52 (t, J=7.5 Hz, 1H), 7.46 (d, J=8.4 Hz, 1H), 7.42 (s, 1H), 7.37 (d, J=7.3 Hz, 1H), 5.95 (d, J=11.7 Hz, 1H), 4.00 (br. s., 3H), 3.93-3.83 (m, 1H), 3.71 (d, J=10.6 Hz, 1H), 3.48 (t, J=11.7 Hz, 1H), 3.18 (t, J=11.6 Hz, 1H), 2.29 (m, 3H), 1.71 (br. s., 1H), 1.68-1.59 (m, 1H), 1.51 (br. s., 7H), 1.42 (d, J=12.5 Hz, 1H), 0.73 (br. s., 1H); LCMS (M+H)=530.3 and Enantiomer B (10.2 mg, 21%, SFC RT=14.17 min)$^1$H NMR (500 MHz, DMSO-d$_6$) δ 8.52 (s, 1H), 8.33 (d, J=7.7 Hz, 1H), 8.13 (d, J=8.1 Hz, 1H), 7.96 (s, 1H), 7.52 (t, J=7.5 Hz, 1H), 7.46 (d, J=8.4 Hz, 1H), 7.42 (s, 1H), 7.37 (d, J=7.3 Hz, 1H), 5.95 (d, J=11.7 Hz, 1H), 4.00 (br. s., 3H), 3.93-3.83 (m, 1H), 3.71 (d, J=10.6 Hz, 1H), 3.48 (t, J=11.7 Hz, 1H), 3.18 (t, J=11.6 Hz, 1H), 2.29 (m, 3H), 1.71 (br. s., 1H), 1.68-1.59 (m, 1H), 1.51 (br. s., 7H), 1.42 (d, J=12.5 Hz, 1H), 0.73 (br. s., 1H); LCMS (M+H)=530.3.

Example 405

[3-(Dimethyl-1H-1,2,3-triazol-5-yl)-5-[(S)-oxan-4-yl)phenyl)methyl]-5H-pyrido[3,2-b]indol-7-yl]methanol

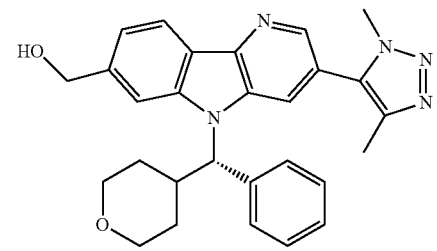 [SMILES: Cc1nnn(C)c1-c1cnc2c3ccc(CO)cc3n([C@H](c3ccccc3)C3CCOCC3)c2c1]

A solution of methyl 3-(dimethyl-1H-1,2,3-triazol-5-yl)-5-[(S)-oxan-4-yl(phenyl)methyl]-5H-pyrido[3,2-b]indole-7-carboxylate (188 mg, 0.379 mmol) in tetrahydrofuran (4.0 mL) was cooled in an ice water bath for 5 min, then lithium aluminum hydride 2.0 M in THF (0.379 mL, 0.759 mmol) was added dropwise over about 1 min. After 10 min the cooling bath was removed and stirring continued for 45 min. The mixture was cooled again in an ice water bath and quenched with 28 μL of water, 28 μL of 15% NaOH, and 84 μL of water. A small amount of sodium sulfate was added and the mixture stirred for 20 min, filtered, and rinsed with ethyl acetate. The eluent was concentrated. This material was purified on SiO$_2$ (4 g) equilibrated in 20% acetone/DCM, loaded in DCM, and eluted using 20% acetone/DCM (200 mL), 30% acetone/DCM (200 mL) 40% acetone/DCM (200 mL). The product containing fractions were concentrated to give the title compound (131 mg, 73%). A sample of the purest cut from these fractions (12.4 mg) was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. Fractions containing the desired product were combined and dried via centrifugal evaporation. $^1$H NMR (500 MHz, DMSO-d$_6$) δ 8.55-8.48 (m, 1H), 8.48-8.38 (m, 1H), 8.19 (d, J=8.1 Hz, 1H), 8.11-8.03 (m, 1H), 7.96 (s, 1H), 7.68 (d, J=7.3 Hz, 2H), 7.38-7.29 (m, 3H), 7.28-7.21 (m, 1H), 5.79 (d, J=11.4 Hz, 1H), 4.76 (s, 2H), 4.01 (br. s., 3H), 3.93-3.86 (m, 1H), 3.73 (d, J=11.4 Hz, 1H), 3.27 (t, J=11.4 Hz, 1H), 2.30 (s, 3H), 1.70 (d, J=12.8 Hz, 1H), 1.56 (br. s., 1H), 1.38-1.22 (m, 1H), 1.00 (d, J=13.9 Hz, 1H). LC/MS (468, [M+H]$^+$).

Example 406

{[3-(Dimethyl-1H-1,2,3-triazol-5-yl)-5-[(S)-oxan-4-yl(phenyl)methyl]-5H-pyrido[3,2-b]indol-7-yl]methyl}dimethylamine

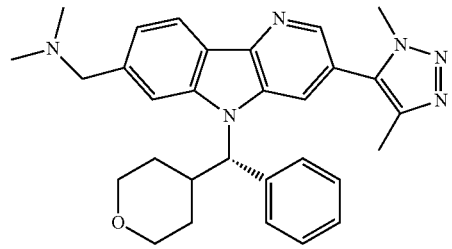 [SMILES: Cc1nnn(C)c1-c1cnc2c3ccc(CN(C)C)cc3n([C@H](c3ccccc3)C3CCOCC3)c2c1]

351

Step 1: 3-(Dimethyl-1H-1,2,3-triazol-5-yl)-5-[(S)-oxan-4-yl(phenyl)methyl]-5H-pyrido[3,2-b]indole-7-carbaldehyde To a solution of oxalyl chloride (0.0140 mL, 0.164 mmol) in 1.0 mL of DCM at −78° C. was added DMSO (0.0230 mL, 0.329 mmol). After 10 min, a solution of [3-(dimethyl-1H-1,2,3-triazol-5-yl)-5-[(S)-oxan-4-yl(phenyl)methyl]-5H-pyrido[3,2-b]indol-7-yl]methanol (64.0 mg, 0.137 mmol) in 0.5 mL of DCM was added dropwise (0.5 mL rinse). This mixture was stirred for about 10 min, then triethylamine (0.0570 mL, 0.411 mmol) was added, and the cooling bath was removed. After 2 h total reaction time, the ice bath was replaced, and the reaction quenched with water, allowed to warm to room temperature, and extracted into ethyl acetate. The combined organics were dried over $MgSO_4$, filtered, and concentrated. This material was purified on $SiO_2$ (4 g) loaded on dry column in DCM and eluted using 10-30% acetone/DCM to give the title compound (59.0 mg, 93%) as a yellow film. $^1$H NMR (400 MHz, $CDCl_3$) δ 10.25 (s, 1H), 8.60-8.56 (m, 1H), 8.54 (d, J=1.8 Hz, 1H), 8.31 (s, 1H), 7.92 (d, J=8.0 Hz, 1H), 7.69 (s, 1H), 7.51-7.44 (m, 2H), 7.41-7.29 (m, 3H), 5.64 (d, J=10.5 Hz, 1H), 4.07 (dd, J=11.4, 2.9 Hz, 1H), 3.90 (s, 3H), 3.88-3.83 (m, 1H), 3.56 (td, J=11.9, 1.9 Hz, 1H), 3.41-3.31 (m, 1H), 3.14 (d, J=11.0 Hz, 1H), 2.32-2.28 (m, 3H), 2.05 (d, J=13.3 Hz, 1H), 1.69-1.56 (m, 1H), 1.50-1.35 (m, 1H), 1.10 (d, J=13.3 Hz, 1H). LC/MS (466, [M+H]$^+$).

Step 2: {[3-(Dimethyl-1H-1,2,3-triazol-5-yl)-5-[(S)-oxan-4-yl(phenyl)methyl]-5H-pyrido[3,2-b]indol-7-yl]methyl}dimethylamine To a solution of 3-(dimethyl-1H-1,2,3-triazol-5-yl)-5-[(S)-oxan-4-yl(phenyl)methyl]-5H-pyrido[3,2-b]indole-7-carbaldehyde (24.9 mg, 0.0530 mmol) in DCM (1.0 mL) was added dimethylamine (2.0 M in methanol, 0.267 mL, 0.535 mmol). After 5 min, sodium triacetoxyborohydride (22.7 mg, 0.107 mmol) was added. The mixture was stirred at room temperature for 1 h. An additional 10 equivalents of dimethylamine was added followed by sodium triacetoxyborohydride (22.7 mg, 0.107 mmol). After 20 h, an additional 10 equivalents of dimethylamine was added followed by sodium triacetoxyborohydride (22.7 mg, 0.107 mmol), and the resulting mixture stirred 3 h longer. The mixture was concentrated and filtered through a 0.45 μm PVDF syringe filter using methanol. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. Fractions containing the desired product were combined and dried via centrifugal evaporation to give the title compound (5.10 mg, 19%). $^1$H NMR (500 MHz, DMSO-$d_6$) δ 8.52 (s, 1H), 8.45 (br. s., 1H), 8.18 (d, J=7.7 Hz, 1H), 8.04 (br. s., 1H), 7.67 (d, J=7.3 Hz, 2H), 7.38-7.21 (m, 4H), 5.81 (d, J=11.4 Hz, 1H), 4.01 (s, 3H), 3.92-3.87 (m, 1H), 3.73 (d, J=11.7 Hz, 1H), 3.70 (br. s., 2H), 3.48 (t, J=11.4 Hz, 1H), 3.37 (br. s., 1H), 3.26 (t, J=11.2 Hz, 1H), 2.30 (s, 3H), 2.25-2.18 (m, 6H), 1.69 (d, J=13.2 Hz, 1H), 1.62-1.51 (m, 1H), 1.37-1.26 (m, 1H), 1.03 (d, J=12.5 Hz, 1H). LC/MS (466, [M+H]$^+$).

352

Example 407

[3-(Dimethyl-1H-1,2,3-triazol-5-yl)-5-[(S)-oxan-4-yl(phenyl)methyl]-5H-pyrido[3,2-b]indol-7-yl]($^2$H$_2$)methanol

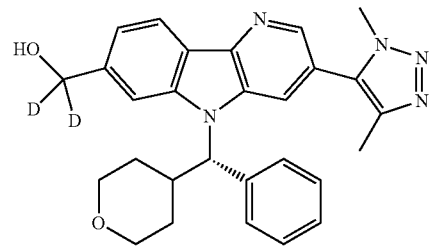 [SMILES: [2H]C([2H])(O)c1ccc2c3ncc(-c4c(C)nnn4C)cc3n([C@H](c3ccccc3)C3CCOCC3)c2c1]

A solution of methyl 3-(dimethyl-1H-1,2,3-triazol-5-yl)-5-[(S)-oxan-4-yl(phenyl)methyl]-5H-pyrido[3,2-b]indole-7-carboxylate (22.7 mg, 0.0460 mmol) in THF (4.0 mL) was cooled in an ice water bath for 5 min. To this was added lithium aluminum deuteride (2.10 mg, 0.0500 mmol) as a solid in one portion. After 1 h, the mixture was quenched with 2 drops of water, 2 drops of 15% NaOH solution, and 3 drops of water. Solid sodium sulfate was added, and this mixture was diluted with ethyl acetate and sonicated/filtered. The organics were further dried with a small amount of $MgSO_4$, filtered, and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. Fractions containing the desired product were combined and dried via centrifugal evaporation to give the title compound (8.50 mg, 39%). $^1$H NMR (500 MHz, DMSO-$d_6$) δ 8.52 (s, 1H), 8.44 (br. s., 1H), 8.19 (d, J=8.1 Hz, 1H), 8.08 (br. s., 1H), 7.68 (d, J=7.3 Hz, 2H), 7.39-7.29 (m, 3H), 7.29-7.23 (m, 1H), 5.80 (d, J=11.4 Hz, 1H), 4.01 (br. s., 3H), 3.94-3.87 (m, 1H), 3.73 (d, J=8.1 Hz, 1H), 3.53-3.43 (m, 2H), 3.42 (br. s., 1H), 3.27 (t, J=11.7 Hz, 1H), 2.30 (s, 3H), 1.70 (d, J=13.2 Hz, 1H), 1.61-1.48 (m, 1H), 1.31 (d, J=11.7 Hz, 1H), 1.01 (d, J=12.8 Hz, 1H). LC/MS (470, [M+H]$^+$).

Example 408

Dicyclopropyl[3-(dimethyl-1H-1,2,3-triazol-5-yl)-5-[(S)-oxan-4-yl)phenyl)methyl]-5H-pyrido[3,2-b]indol-7-yl]methanol

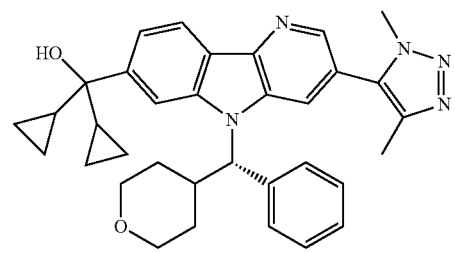 [SMILES: Cc1nnn(C)c1-c1cnc2c3ccc(C(O)(C4CC4)C4CC4)cc3n([C@H](c3ccccc3)C3CCOCC3)c2c1]

A solution of methyl 3-(dimethyl-1H-1,2,3-triazol-5-yl)-5-[(S)-oxan-4-yl(phenyl)methyl]-5H-pyrido[3,2-b]indole-7-carboxylate (25.5 mg, 0.0510 mmol) in THF (0.5 mL) was cooled in a dry ice-acetone bath. To this was added cyclopropylmagnesium bromide (1.0 M in 2-methyltetrahydrofuran, 0.515 mL, 0.515 mmol) over about 5 min. The mixture was stirred for 30 min then transferred to an ice water bath. After 2 h, the mixture was quenched with saturated aq. ammonium chloride solution, extracted into ethyl acetate, washed with brine, dried over MgSO$_4$, filtered, and concentrated to give 40 mg of a yellow film. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 min, then a 5-min hold at 100% B; Flow: 20 mL/min. Fractions containing the desired product were combined and dried via centrifugal evaporation to give the title compound (5.90 mg, 21%). $^1$H NMR (500 MHz, DMSO-d$_6$) δ 8.51 (s, 2H), 8.15 (d, J=8.1 Hz, 2H), 7.66 (d, J=7.7 Hz, 2H), 7.57 (d, J=8.1 Hz, 1H), 7.38-7.30 (m, 2H), 7.28-7.19 (m, 1H), 5.81 (d, J=11.0 Hz, 1H), 4.04 (s, 3H), 3.95-3.85 (m, 1H), 3.75 (d, J=9.5 Hz, 1H), 3.48 (t, J=11.2 Hz, 1H), 3.40 (br. s., 1H), 3.27 (t, J=11.2 Hz, 1H), 2.32 (s, 3H), 1.71 (d, J=12.5 Hz, 1H), 1.63-1.47 (m, 1H), 1.40-1.24 (m, 3H), 1.05 (d, J=13.9 Hz, 1H), 0.64 (br. s., 2H), 0.54-0.34 (m, 4H), 0.26 (dt, J=9.0, 4.3 Hz, 2H). LC/MS (548, [M+H]$^+$).

Example 409

2-[8-Chloro-3-(dimethyl-1H-1,2,3-triazol-5-yl)-5-[(S)-oxan-4-yl(phenyl)methyl]-5H-pyrido[3,2-b]indol-7-yl]propan-2-ol

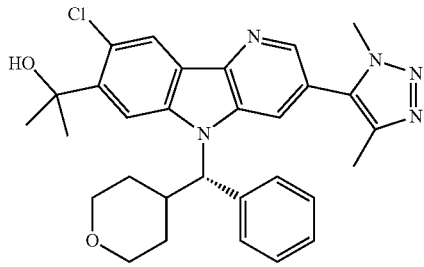 [SMILES: Cc1nnn(C)c1-c1cnc2c3cc(Cl)c(C(C)(C)O)cc3n([C@H](c3ccccc3)C3CCOCC3)c2c1]

Step 1: Methyl 8-chloro-3-(dimethyl-1H-1,2,3-triazol-5-yl)-5-[(S)-oxan-4-yl)phenyl)methyl]-5H-pyrido[3,2-b]indole-7-carboxylate A mixture of methyl 3-(dimethyl-1H-1,2,3-triazol-5-yl)-5-[(S)-oxan-4-yl(phenyl)methyl]-5H-pyrido[3,2-b]indole-7-carboxylate (26.0 mg, 0.0520 mmol) and NCS (7.36 mg, 0.0550 mmol) was dissolved in DMF (0.5 mL), and heated to 45° C. After 20 h at 45° C., the temperature was raised to 60° C. After 150 h, the mixture was cooled, diluted with DCM, washed with water, then brine, dried over MgSO$_4$, filtered, and concentrated to give 26.8 mg of a yellow film. This material was purified via preparative HPLC (XBridge C18 30×100 mm; A=95% water, 5% acetonitrile+10 mm ammonium acetate; B=95% acetonitrile, 5% water+10 mm ammonium acetate. Method was 30% B over 30 min at 30 mL/min, wavelength=254 nm) to give the title compound as a clear/white film (11.6 mg, 39%). $^1$H NMR (400 MHz, CDCl$_3$) δ 8.51 (d, J=1.8 Hz, 1H), 8.48 (s, 1H), 8.22 (s, 1H), 7.62 (s, 1H), 7.46-7.41 (m, 2H), 7.39-7.31 (m, 3H), 5.53 (d, J=10.5 Hz, 1H), 4.07 (s, 3H), 4.05 (s, 1H), 3.91-3.88 (m, 3H), 3.86 (br. s., 1H), 3.55 (td, J=11.9, 1.8 Hz, 1H), 3.36 (td, J=11.9, 2.0 Hz, 1H), 3.15-3.00 (m, J=11.0, 11.0, 11.0 Hz, 1H), 2.29 (s, 3H), 2.08-2.00 (m, 1H), 1.64 (s, 1H), 1.51-1.36 (m, J=13.1, 4.3 Hz, 1H), 1.07 (d, J=12.5 Hz, 1H). LC/MS (530, [M+H]$^+$).

Step 2: 2-[8-Chloro-3-(dimethyl-1H-1,2,3-triazol-5-yl)-5-[(S)-oxan-4-yl(phenyl)methyl]-5H-pyrido[3,2-b]indol-7-yl]propan-2-ol A solution of methyl 8-chloro-3-(dimethyl-1H-1,2,3-triazol-5-yl)-5-[(S)-oxan-4-yl(phenyl)methyl]-5H-pyrido[3,2-b]indole-7-carboxylate (8.50 mg, 0.0160 mmol) in THF (0.5 mL) was cooled in a dry ice/acetone bath and methylmagnesium bromide (1.0 M in THF, 0.160 mL, 0.160 mmol) was added slowly over about 5 min. After the addition was complete, the mixture was stirred at this temperature for 5 min, and then the cooling bath was removed. After 30 min, the mixture was re-cooled in a dry ice/acetone bath and quenched with a couple of drops of water, then allowed to come to room temperature and concentrated. The residue was partitioned between saturated aqueous ammonium chloride solution and dichloromethane. The aqueous portion was further extracted with 2 portions of dichloromethane. The combined organics were dried over MgSO$_4$, filtered, and concentrated to give 8.00 mg of a clear film. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 min, then a 5-min hold at 100% B; Flow: 20 mL/min. Fractions containing the desired product were combined and dried via centrifugal evaporation to give the title compound (4.00 mg, 47%). $^1$H NMR (500 MHz, DMSO-d$_6$) δ 8.56 (s, 1H), 8.46 (br. s., 2H), 8.16 (s, 1H), 7.66 (d, J=7.7 Hz, 2H), 7.40-7.31 (m, 2H), 7.30-7.24 (m, 1H), 5.74 (d, J=11.0 Hz, 1H), 4.01 (s, 3H), 3.93-3.86 (m, 1H), 3.74 (d, J=10.3 Hz, 1H), 3.46 (t, J=11.0 Hz, 1H), 3.36 (d, J=4.8 Hz, 1H), 3.31-3.22 (m, 1H), 2.30 (s, 3H), 1.73 (d, J=15.8 Hz, 7H), 1.60-1.47 (m, 1H), 1.31 (d, J=9.2 Hz, 1H), 0.97 (d, J=11.7 Hz, 1H). LC/MS (530, [M+H]$^+$).

Example 411

N-{2-[3-(Dimethyl-1H-1,2,3-triazol-5-yl)-5-[(S)-oxan-4-yl(phenyl)methyl]-5H-pyrido[3,2-b]indol-7-yl]propan-2-yl}methanesulfonamide

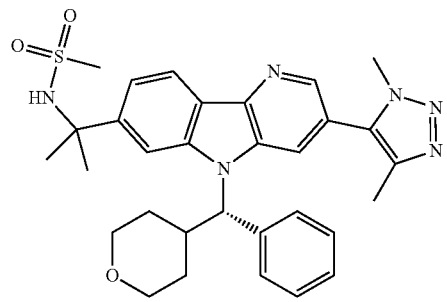 [SMILES: Cc1nnn(C)c1-c1cnc2c3ccc(C(C)(C)NS(C)(=O)=O)cc3n([C@H](c3ccccc3)C3CCOCC3)c2c1]

Step 1: 5-[7-(2-Azidopropan-2-yl)-5-[(S)-oxan-4-yl) phenyl)methyl]-5H-pyrido[3,2-b]indol-3-yl]-1,4-dimethyl-1H-1,2,3-triazole A solution of 2-[3-(dimethyl-1H-1,2,3-triazol-5-yl)-5-[(S)-oxan-4-yl(phenyl)methyl]-5H-pyrido[3,2-b]indol-7-yl]propan-2-ol (195 mg, 0.393 mmol) in DCM (5.0 mL) was cooled in an ice water bath and trimethylsilyl azide (0.131 mL, 0.984 mmol) was added. After 5 min, BF$_3$.OEt$_2$ (0.249 mL, 1.97 mmol) was added, and the mixture was stirred for 20 min before removing the cooling bath. After 18 h, the mixture was diluted with water and saturated aqueous bicarbonate, extracted into ethyl acetate, washed with brine, dried over MgSO$_4$, filtered, and concentrated to give the title compound (200 mg, 70%) as a yellow solid. This was consistent with desired product by 1HNMR but contained a significant impurity (72% purity). It was carried on without additional purification. $^1$H NMR (400 MHz, CDCl$_3$) δ 8.46 (d, J=1.8 Hz, 1H), 8.39 (d, J=8.3 Hz, 1H), 7.84 (d, J=1.0 Hz, 1H), 7.60 (s, 1H), 7.49-7.42 (m, 3H), 7.39-7.29 (m, 3H), 5.57 (d, J=10.0 Hz, 1H), 4.09-4.04 (m, 1H), 3.92-3.88 (m, 3H), 3.88-3.84 (m, 1H), 3.56 (td, J=12.0, 2.1 Hz, 1H), 3.36 (td, J=11.9, 1.9 Hz, 1H), 3.11 (dd, J=10.7, 3.6 Hz, 1H), 2.30 (s, 3H), 2.10-1.99 (m, 1H), 1.80 (s, 3H), 1.79 (s, 3H), 1.72-1.56 (m, 1H), 1.49-1.35 (m, 1H), 1.14 (d, J=13.1 Hz, 1H). LC/MS (521, [M+H]$^+$).

Step 2: 2-[3-(Dimethyl-1H-1,2,3-triazol-5-yl)-5-[(S)-oxan-4-yl)phenyl)methyl]-5H-pyrido[3,2-b]indol-7-yl]propan-2-amine A flask containing a solution of 5-[7-(2-azidopropan-2-yl)-5-[(S)-oxan-4-yl(phenyl)methyl]-5H-pyrido[3,2-b]indol-3-yl]-1,4-dimethyl-1H-1,2,3-triazole (200 mg, 0.384 mmol) in MeOH (5 mL) was vacuum purged with nitrogen. Pd/C (82.0 mg, 0.0770 mmol) was added and the flask was vacuum purged with H$_2$ (g) several times and eventually stirred at ambient temperature under a balloon of hydrogen. After 2 h, the mixture was vacuum purged several times with nitrogen, diluted with ethyl acetate, and filtered through Celite to give 146 mg of a white solid. This material was somewhat insoluble during the filtration. The crude material was purified (12 g SiO$_2$) eluting with 10% acetone/DCM (150 mL), 20% acetone/DCM (200 mL), 40% acetone/DCM (100 mL), 50% acetone/DCM (100 mL), 10% MeOH/DCM 100 mL. The desired product eluted in the MeOH/DCM fractions to give the title compound (56.0 mg, 30%) as a white solid. $^1$H NMR (400 MHz, CD$_3$OD) δ 8.49 (t, J=1.9 Hz, 1H), 8.40 (dd, J=8.3, 1.3 Hz, 1H), 8.30 (br. s., 1H), 8.13 (d, J=4.8 Hz, 1H), 7.66 (d, J=7.5 Hz, 2H), 7.55 (dd, J=8.5, 1.3 Hz, 1H), 7.42-7.34 (m, 2H), 7.32-7.25 (m, 1H), 5.86 (d, J=10.8 Hz, 1H), 4.04-3.96 (m, 4H), 3.82 (d, J=9.0 Hz, 1H), 3.62 (t, J=11.2 Hz, 1H), 3.49-3.37 (m, 1H), 2.34-2.26 (m, 3H), 2.00 (d, J=13.3 Hz, 1H), 1.82 (s, 6H), 1.72-1.60 (m, 1H), 1.46 (dd, J=12.4, 4.1 Hz, 1H), 1.07 (d, J=12.8 Hz, 1H), 0.93-0.80 (m, 1H). LC/MS (495, [M+H]$^+$).

Step 3: N-{2-[3-(Dimethyl-1H-1,2,3-triazol-5-yl)-5-[(S)-oxan-4-yl(phenyl)methyl]-5H-pyrido[3,2-b]indol-7-yl]propan-2-yl}methanesulfonamide To a suspension of 2-[3-(dimethyl-1H-1,2,3-triazol-5-yl)-5-[(S)-oxan-4-yl(phenyl)methyl]-5H-pyrido[3,2-b]indol-7-yl]propan-2-amine (17.5 mg, 0.0350 mmol) in DCM (1 mL) was added 2 drops of triethylamine (7.40 μL, 0.0530 mmol). The cloudy suspension became homogenous and was briefly cooled in an ice water bath and one drop of methanesulfonylchloride (3.03 μL, 0.0390 mmol) was added. The vial was removed from the bath. After 15 min, the mixture was diluted with DCM, washed with water and brine, dried over MgSO$_4$, filtered, and concentrated to give a clear film (20.4 mg). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 min, then a 5-min hold at 100% B; Flow: 20 mL/min. Fractions containing the desired product were combined and dried via centrifugal evaporation to give the title compound (9.70 mg, 48%). $^1$H NMR (500 MHz, DMSO-d$_6$) δ 8.53 (s, 1H), 8.19 (d, J=8.4 Hz, 2H), 7.72 (d, J=7.3 Hz, 3H), 7.50 (d, J=8.4 Hz, 1H), 7.41-7.28 (m, 2H), 7.27-7.22 (m, 1H), 5.82 (d, J=11.0 Hz, 1H), 4.03 (s, 3H), 3.95-3.88 (m, 1H), 3.73 (d, J=9.2 Hz, 1H), 3.53-3.42 (m, 2H), 3.35 (d, J=5.5 Hz, 1H), 3.29 (t, J=11.4 Hz, 1H), 2.45 (s, 3H), 2.32 (s, 3H), 1.79 (s, 3H), 1.76 (br. s., 3H), 1.71 (d, J=13.6 Hz, 1H), 1.60-1.47 (m, 1H), 1.31 (d, J=9.5 Hz, 1H), 1.01 (d, J=12.1 Hz, 1H). Two analytical LC/MS injections were used to determine the final purity; LC/MS (573, [M+H]$^+$).

Example 412

Methyl N-{2-[3-(dimethyl-1H-1,2,3-triazol-5-yl)-5-[(S)-oxan-4-yl(phenyl)methyl]-5H-pyrido[3,2-b]indol-7-yl]propan-2-yl}carbamate

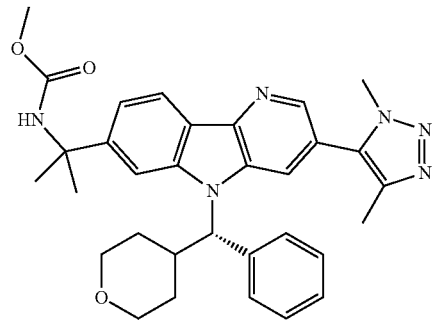 [SMILES: COC(=O)NC(C)(C)c1ccc2c3ncc(-c4c(C)nnn4C)cc3n([C@H](c3ccccc3)C3CCOCC3)c2c1]

To a suspension of 2-[3-(dimethyl-1H-1,2,3-triazol-5-yl)-5-[(S)-oxan-4-yl(phenyl)methyl]-5H-pyrido[3,2-b]indol-7-yl]propan-2-amine (23.0 mg, 0.0460 mmol) in THF (1 mL) and DCM (1 mL) was added Hünig's base (0.0160 mL, 0.0930 mmol). The mixture was briefly cooled in an ice water bath and methyl chloroformate (4.31 μl, 0.0560 mmol) was added. After 3 h, an additional drop of chloroformate was added. After 30 min, the mixture was concentrated, taken up in methanol, and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 min, then a 5-min hold at 100% B; Flow: 20 mL/min. Fractions containing the desired product were combined and dried via centrifugal evaporation to give the title compound (21.5 mg, 83%). $^1$H NMR (500 MHz, DMSO-d$_6$) δ 8.51 (s, 1H), 8.47 (br. s., 1H), 8.14 (d, J=8.4 Hz, 1H), 8.00 (br. s., 1H), 7.75 (br. s., 1H), 7.66 (d, J=7.7 Hz, 2H), 7.33 (t, J=8.1 Hz, 3H), 7.28-7.23 (m, 1H), 5.79 (d, J=11.4 Hz, 1H), 4.03 (s, 3H), 3.95-3.86 (m, 2H), 3.75 (d, J=9.2 Hz, 1H), 3.57-3.41 (m, 2H), 3.36 (d, J=4.4 Hz, 1H), 3.27 (t, J=11.2 Hz, 1H), 2.31 (s, 3H), 1.68 (d, J=4.8 Hz, 7H), 1.54 (d, J=16.1 Hz, 1H), 1.30 (d, J=8.4 Hz, 1H), 1.03 (d, J=12.8 Hz, 1H). LC/MS (553, [M+H]$^+$).

Example 413

5-[7-(3-Fluoroazetidine-1-carbonyl)-5-[(S)-oxan-4-yl(phenyl)methyl]-5H-pyrido[3,2-b]indol-3-yl]-1,4-dimethyl-1H-1,2,3-triazole

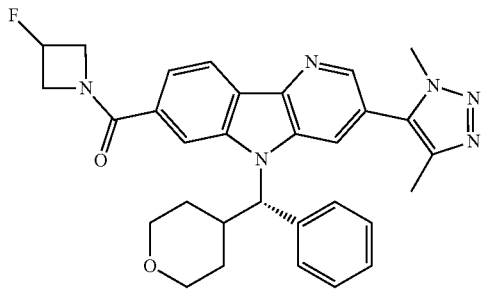 [SMILES: Cc1nnn(C)c1-c1cnc2c3ccc(C(=O)N4CC(F)C4)cc3n([C@H](c3ccccc3)C3CCOCC3)c2c1]

Step 1: 3-(Dimethyl-1H-1,2,3-triazol-5-yl)-5-[(S)-oxan-4-yl)phenyl)methyl]-5H-pyrido[3,2-b]indole-7-carboxylic acid A 20 mL pressure vial was charged with methyl 3-(dimethyl-1H-1,2,3-triazol-5-yl)-5-[(S)-oxan-4-yl(phenyl)methyl]-5H-pyrido[3,2-b]indole-7-carboxylate (200 mg, 0.404 mmol), THF (3363 µL), and water (673 µL). The resulting solution was treated with potassium hydroxide (67.9 mg, 1.21 mmol), and the vial sealed. After 3 h, the reaction mixture was heated to 50° C. and stirred at that temperature overnight. After 19 h, the organics were removed under a stream of nitrogen, and the aqueous was transferred to a separatory funnel. The basic solution was extracted with ethyl acetate (2×), which was discarded. The aqueous was acidified to a pH of ~4 using 1 mL of 1N aq. HCl. This mixture was then adjusted to pH~5 using a 2M solution of aqueous tripotassium phosphate. The resulting mixture was extracted with ethyl acetate (3×). The combined organics were dried over magnesium sulfate and concentrated under reduced pressure to give the title compound (192 mg, 99%) as a white solid. $^1$H NMR (400 MHz, CDCl$_3$) δ 8.59 (s, 1H), 8.55 (d, J=1.5 Hz, 1H), 8.52 (d, J=8.3 Hz, 1H), 8.17 (dd, J=8.3, 1.0 Hz, 1H), 7.66 (d, J=1.5 Hz, 1H), 7.48 (d, J=7.3 Hz, 2H), 7.41-7.29 (m, 4H), 5.66 (d, J=10.5 Hz, 1H), 4.13-4.05 (m, 1H), 3.92-3.86 (m, 4H), 3.63-3.53 (m, 1H), 3.38 (td, J=12.0, 1.5 Hz, 1H), 3.14 (d, J=11.0 Hz, 1H), 2.32 (s, 3H), 2.10-2.02 (m, 1H), 1.74-1.61 (m, 1H), 1.55-1.43 (m, 1H), 1.11 (d, J=14.3 Hz, 1H). LC/MS (481, [M+H]$^+$).

Step 2: 5-[7-(3-Fluoroazetidine-1-carbonyl)-5-[(S)-oxan-4-yl)phenyl)methyl]-5H-pyrido[3,2-b]indol-3-yl]-1,4-dimethyl-1H-1,2,3-triazole A mixture of 3-(dimethyl-1H-1,2,3-triazol-5-yl)-5-[(S)-oxan-4-yl)phenyl)methyl]-5H-pyrido[3,2-b]indole-7-carboxylic acid (10.8 mg, 0.0220 mmol), 3-fluoroazetidine hydrochloride (5.00 mg, 0.0450 mmol), Hünig's base (7.83 µL, 0.0450 mmol), and HATU (12.8 mg, 0.0340 mmol) in DMF (0.5 mL) was stirred at room temperature. After 1.5 h, the mixture was filtered through a 0.45 µm PVDF syringe filter and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min. Fractions containing the desired product were combined and dried via centrifugal evaporation to give the title compound (7.10 mg, 56%). $^1$H NMR (500 MHz, DMSO-d$_6$) δ 8.60 (s, 1H), 8.49 (br. s., 1H), 8.31 (d, J=8.1 Hz, 1H), 7.68 (d, J=7.7 Hz, 2H), 7.59 (d, J=8.1 Hz, 1H), 7.40-7.29 (m, 2H), 7.29-7.22 (m, 1H), 5.96 (d, J=11.0 Hz, 1H), 5.56 (br. s., 1H), 5.45 (br. s., 1H), 4.52 (br. s., 3H), 4.17 (br. s., 1H), 4.01 (br. s., 3H), 3.94-3.88 (m, 1H), 3.72 (d, J=9.5 Hz, 1H), 3.56-3.34 (m, 3H), 3.31-3.19 (m, 1H), 2.30 (br. s., 3H), 1.79-1.68 (m, 1H), 1.61 (d, J=11.0 Hz, 1H), 1.31 (br. s., 1H), 0.95 (br. s., 1H). LC/MS (539, [M+H]$^+$).

Example 414

5-[7-(3,3-Difluoroazetidine-1-carbonyl)-5-[(S)-oxan-4-yl)phenyl)methyl]-5H-pyrido[3,2-b]indol-3-yl]-1,4-dimethyl-1H-1,2,3-triazole

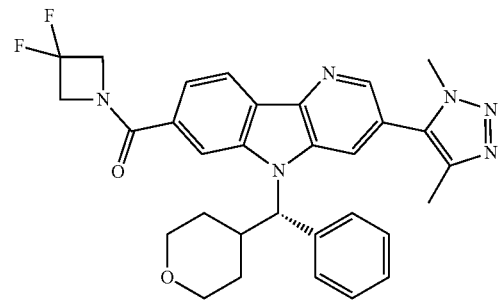 [SMILES: Cc1nnn(C)c1-c1cnc2c3ccc(C(=O)N4CC(F)(F)C4)cc3n([C@H](c3ccccc3)C3CCOCC3)c2c1]

A mixture of 3-(dimethyl-1H-1,2,3-triazol-5-yl)-5-[(S)-oxan-4-yl(phenyl)methyl]-5H-pyrido[3,2-b]indole-7-carboxylic acid (10.0 mg, 0.0210 mmol), 3,3-difluoroazetidine hydrochloride (5.38 mg, 0.0420 mmol), Hünig's base (7.25 µL, 0.0420 mmol), and HATU (11.8 mg, 0.0310 mmol) in DMF was stirred at room temperature for 1.5 h. The mixture was filtered through a 0.45 µm PVDF syringe filter and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 min, then a 5-min hold at 100% B; Flow: 20 mL/min. Fractions containing the desired product were combined and dried via centrifugal evaporation to give the title compound (6.40 mg, 53%). $^1$H NMR (500 MHz, DMSO-d$_6$) δ 8.61 (s, 1H), 8.48 (br. s., 1H), 8.33 (d, J=8.1 Hz, 1H), 7.69 (d, J=7.7 Hz, 2H), 7.64 (d, J=8.1 Hz, 1H), 7.39-7.30 (m, 2H), 7.30-7.18 (m, 1H), 5.97 (d, J=11.4 Hz, 1H), 4.90 (br. s., 1H), 4.58 (br. s., 1H), 4.01 (br. s., 1H), 3.90 (d, J=6.6 Hz, 1H), 3.73 (d, J=8.8 Hz, 1H), 3.49 (t, J=11.4 Hz, 1H), 3.40-3.32 (m, 4H), 3.25 (t, J=11.7 Hz, 1H), 2.30 (br. s., 3H), 1.73 (d, J=13.2 Hz, 1H), 1.62 (d, J=10.3 Hz, 1H), 1.33 (d, J=10.3 Hz, 1H), 0.95 (d, J=12.1 Hz, 1H). LC/MS (557, [M+H]$^+$).

Examples 415 & 416

1-Cyclopropyl-1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol

Example 417

5-{7-Methanesulfonyl-5-[(S)-oxan-4-yl(phenyl)methyl]-5H-pyrido[3,2-b]indol-3-yl}-1,4-dimethyl-1H-pyrazole

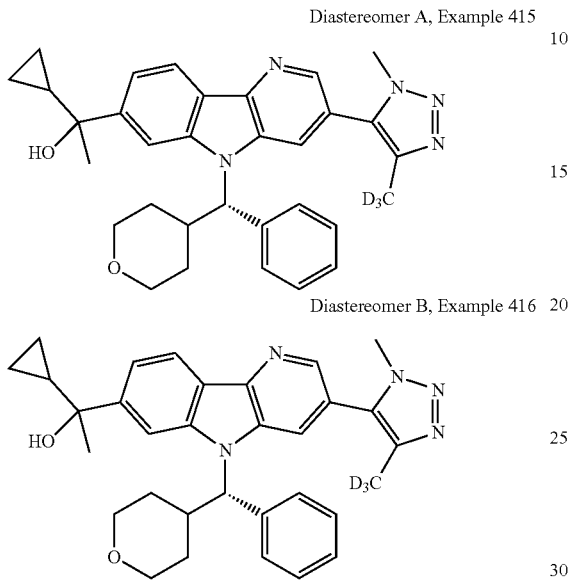

Diastereomer A, Example 415

Diastereomer B, Example 416

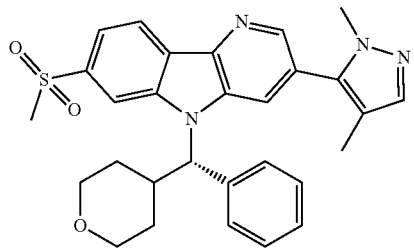 [SMILES: Cc1cnn(C)c1-c1cnc2c3ccc(S(C)(=O)=O)cc3n([C@H](c3ccccc3)C3CCOCC3)c2c1]

1-Cyclopropyl-1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol was prepared as a mixture of diastereomers according to the procedures described for 1-cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol. Separation of the diastereomer mixture generated in the last step was performed using chiral preparative SFC to give Diastereomer A and Diastereomer B: Chiralpak OJ-H preparative column, 30×250 mm, 5 µm; Mobile Phase: 10% MeOH in CO$_2$, 150 bar; Temp: 35° C.; Flow rate: 70.0 mL/min. for 47 min. UV monitored at 270 nm. Injection: 0.75 mL of ~6 mg/mL solution in MeOH (~19 mg purified by stacked injection). Diastereomer A: $^1$H NMR (500 MHz, DMSO-d$_6$) δ 8.49 (s, 1H), 8.43 (br. s., 1H), 8.15 (d, J=8.4 Hz, 1H), 8.11 (br. s., 1H), 7.66 (d, J=7.7 Hz, 2H), 7.50 (d, J=8.1 Hz, 1H), 7.33 (t, J=7.3 Hz, 2H), 7.28-7.18 (m, 1H), 5.80 (d, J=11.0 Hz, 1H), 4.01 (s, 3H), 3.89 (d, J=8.8 Hz, 1H), 3.74 (d, J=10.3 Hz, 1H), 3.49 (s, 1H), 3.41 (br. s., 1H), 3.26 (t, J=11.6 Hz, 1H), 1.75-1.66 (m, 1H), 1.57 (br. s., 3H), 1.51 (br. s., 1H), 1.29 (br. s., 2H), 1.02 (d, J=12.8 Hz, 1H), 0.52 (br. s., 1H), 0.41 (d, J=6.2 Hz, 2H), 0.26 (d, J=7.3 Hz, 1H). SFC retention time: 33 min. Diastereomer B: $^1$H NMR (500 MHz, DMSO-d$_6$) δ 8.49 (s, 1H), 8.44 (br. s., 1H), 8.15 (d, J=8.1 Hz, 1H), 8.11 (br. s., 1H), 7.65 (d, J=7.7 Hz, 2H), 7.49 (d, J=8.1 Hz, 1H), 7.32 (t, J=7.3 Hz, 2H), 7.27-7.21 (m, 1H), 5.80 (d, J=11.4 Hz, 1H), 4.01 (br. s., 3H), 3.89 (br. s., 1H), 3.74 (d, J=10.3 Hz, 1H), 3.50 (d, J=3.3 Hz, 1H), 3.39 (br. s., 1H), 3.26 (t, J=11.7 Hz, 1H), 1.71 (d, J=13.2 Hz, 1H), 1.56 (br. s., 3H), 1.54-1.50 (m, 1H), 1.31 (d, J=8.8 Hz, 2H), 1.03 (d, J=13.2 Hz, 1H), 0.51 (br. s., 1H), 0.41 (d, J=7.2 Hz, 2H), 0.25 (br. s., 1H). SFC retention time: 39 min.

Step 1: 5-Bromo-2-(4-(methylsulfonyl)phenyl)-3-nitropyridine

Into a mixture of PdCl$_2$(dppf)-CH$_2$Cl$_2$ adduct (0.732 g, 1.00 mmol), potassium phosphate (21.2 g, 100 mmol), (4-(methylsulfonyl)phenyl)boronic acid (10.0 g, 50.0 mmol), and 2,5-dibromo-3-nitropyridine (14.1 g, 50.0 mmol) in THF (100 mL) was bubbled N$_2$ (g) for 10 min. The pressure bottle was sealed and heated at 80° C. in an oil bath for 3 h. The mixture was cooled and poured into water and EtOAc, then filtered through a layer of Celite. The organic layer was washed with water and brine, then dried over sodium sulfate to afford a solid, which was washed with Et$_2$O thoroughly to afford 7.40 g. $^1$H NMR (400 MHz, CDCl$_3$) δ 8.99 (d, J=2.3 Hz, 1H), 8.43 (d, J=2.0 Hz, 1H), 8.10-8.02 (m, 2H), 7.78-7.72 (m, 2H), 3.13 (s, 3H). LC/MS Method 1; RT=1.8 min., M+H=356.

Step 2: 3-Bromo-7-(methylsulfonyl)-5H-pyrido[3,2-b]indole

A 100 mL round bottomed flask was charged with 5-bromo-2-(4-(methylsulfonyl)phenyl)-3-nitropyridine (2.00 g, 5.60 mmol), triphenylphosphine (3.67 g, 14.0 mmol), and 1,2-dichlorobenzene (50 mL). The flask was placed in an oil bath, the flask was capped with a condenser and heated to 170° C. for 1.5 h. The volatiles were removed under high vacuum at 70° C., then under a stream of nitrogen for 36 h to afford a black oil. The residue was dissolved in methylene chloride and purified on a 220 g ISCO column, eluting with 100% methylene chloride to 40% EtOAc/methylene chloride over 1800 mL, then 40% EtOAc/methylene chloride to 80% EtOAc/methylene chloride over 1800 mL. Fractions that contained the desired product were concentrated to afford 920 mg of a light-tan solid. $^1$H NMR (400 MHz, DMSO-d$_6$) δ 12.07 (s, 1H), 8.66 (d, J=2.0 Hz, 1H), 8.44 (d, J=8.3 Hz, 1H), 8.37 (d, J=2.0 Hz, 1H), 8.30-8.12 (m, 1H), 7.82 (dd, J=8.2, 1.6 Hz, 1H), 3.31 (s, 3H). LC/MS Method 2; RT=0.92 min. M+H=325.

Step 3: (S)-3-Bromo-7-(methylsulfonyl)-5-(phenyl(tetrahydro-2H-pyran-4-yl)methyl)-5H-pyrido[3,2-b]indole 3-Bromo-7-(methylsulfonyl)-5H-pyrido[3,2-b]indole (0.920 g, 2.83 mmol), (R)-phenyl(tetrahydro-2H-pyran-4-yl)methanol (0.816 g, 4.24 mmol), and triphenylphosphine (1.11 g, 4.24 mmol) were dissolved in 100 mL of THF and cooled to 0° C. To this was added DIAD (0.825 ml, 4.24 mmol) dropwise via an 18 gauge needle. After 15 min, the ice bath was removed, and the reaction stirred for 1 h longer. The volatiles were removed under reduced pressure, and the crude material was dissolved in methylene chloride and purified on an 80 g ISCO column, eluting with 0% EtOAc/methylene chloride to 40% EtOAc/methylene chloride over 800 mL. Fractions containing the product were concentrated to afford 1.52 g as a light-brown solid. LC/MS Method 2 showed a major peak with masses consistent with the title compound in 32% purity; RT=1.17 min. M+H=499.

Step 4: 5-{7-Methanesulfonyl-5-[(S)-oxan-4-yl(phenyl)methyl]-5H-pyrido[3,2-b]indol-3-yl}-1,4-dimethyl-1H-pyrazole (S)-3-Bromo-7-(methylsulfonyl)-5-(phenyl(tetrahydro-2H-pyran-4-yl)methyl)-5H-pyrido[3,2-b]indole (80.0 mg, 0.0800 mmol) and 1,4-dimethyl-5-(4,4,5,5-tetramethyl-1,3,2-dioxaborolan-2-yl)-1H-pyrazole (35.6 mg, 0.160 mmol) were dissolved in 2 mL of DMSO. To this was added sodium carbonate (25.5 mg, 0.240 mmol) and 0.1 mL of water. Argon was bubbled through this mixture for 5 min before adding PdCl$_2$(dppf)-CH$_2$Cl$_2$ adduct (6.54 mg, 8.01 μmol), and then bubbled in argon while sonicating for 30 seconds. The vial was capped and heated in the microwave at 150° C. for 15 min. The crude material was purified via preparative LC/MS (Preparative HPLC Method 1): Fractions containing the desired product were combined and dried via centrifugal evaporation. The yield of the product was 14.1 mg (33%), and its estimated purity by LCMS analysis was 98%. Two analytical LC/MS injections were used to determine the final purity. Injection 1 conditions LC/MS Method 3; HPLC RT=1.67 min. Injection 2 conditions: LC/MS Method 4; HPLC RT=2.51 min. $^1$H NMR (500 MHz, DMSO-d$_6$) δ 8.74 (br. s., 1H), 8.60 (s, 1H), 8.48 (d, J=8.4 Hz, 2H), 7.96 (s, 1H), 7.87 (d, J=8.4 Hz, 1H), 7.69 (d, J=7.7 Hz, 3H), 7.46 (s, 1H), 7.38-7.30 (m, 3H), 7.30-7.21 (m, 1H), 6.03 (d, J=11.0 Hz, 1H), 3.95-3.86 (m, 2H), 3.73 (d, J=8.4 Hz, 1H), 3.57-3.43 (m, 2H), 3.37 (br. s., 1H), 3.27 (t, J=12.1 Hz, 1H), 2.90 (s, 3H), 2.74 (s, 3H), 2.03 (s, 3H), 1.81-1.69 (m, 1H), 1.68-1.54 (m, 1H), 1.45-1.28 (m, 1H).

Example 418

5-{7-Methanesulfonyl-5-[(S)-oxan-4-yl(phenyl)methyl]-5H-pyrido[3,2-b]indol-3-yl}-1-methyl-1H-pyrazole

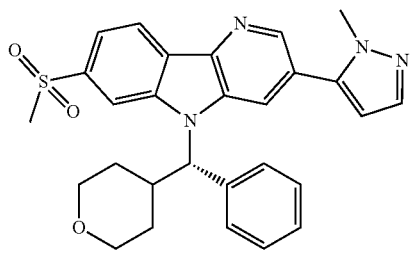 [SMILES: Cn1nccc1-c1cnc2c3ccc(S(C)(=O)=O)cc3n([C@H](c3ccccc3)C3CCOCC3)c2c1]

(S)-3-Bromo-7-(methylsulfonyl)-5-(phenyl(tetrahydro-2H-pyran-4-yl)methyl)-5H-pyrido[3,2-b]indole (40.0 mg, 0.0400 mmol) and 1-methyl-5-(4,4,5,5-tetramethyl-1,3,2-dioxaborolan-2-yl)-1H-pyrazole (16.7 mg, 0.0800 mmol) were dissolved in 2 mL of DMSO. To this was added sodium carbonate (12.7 mg, 0.120 mmol) and 0.1 mL of water. Argon was bubbled through the reaction mixture for 5 min while sonicating. To this was added PdCl$_2$(dppf)-CH$_2$Cl$_2$ adduct (3.27 mg, 4.00 μmol) and bubbled in argon while sonicating for 30 seconds. The vial was and heated in the microwave at 150° C. for 15 min. Reaction was filtered and purified via preparative LC/MS (Preparative HPLC Method 2). Fractions containing the desired product were combined and dried via centrifugal evaporation. The yield of the product was 3.10 mg (16%), and its estimated purity by LCMS analysis was 100%. Two analytical LC/MS injections were used to determine the final purity. Injection 1 conditions: LC/MS Method 3; HPLC RT=1.54 min. Injection 2 conditions: LC/MS Method 4; HPLC RT=2.48 min. $^1$H NMR (500 MHz, DMSO-d$_6$) δ 8.69 (s, 1H), 8.55 (br. s., 1H), 8.47 (d, J=8.1 Hz, 1H), 7.86 (d, J=8.1 Hz, 1H), 7.70 (d, J=7.7 Hz, 2H), 7.60 (s, 1H), 7.40-7.32 (m, 2H), 7.28 (d, J=7.7 Hz, 1H), 6.64 (s, 1H), 6.03 (d, J=11.0 Hz, 1H), 3.91 (br. s., 3H), 3.72 (d, J=10.3 Hz, 1H), 3.56-3.45 (m, 2H), 3.35 (d, J=5.5 Hz, 3H), 3.26 (t, J=11.4 Hz, 1H), 1.80-1.69 (m, 1H), 1.63 (d, J=9.5 Hz, 1H), 1.37 (d, J=12.5 Hz, 1H).

Example 419

1-[3-(Dimethyl-1H-1,2,3-triazol-5-yl)-5-[(S)-oxan-4-yl)phenyl)methyl]-5H-pyrido[3,2-b]indol-7-yl]cyclopropan-1-ol

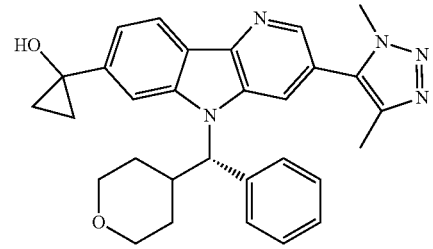 [SMILES: Cc1nnn(C)c1-c1cnc2c3ccc(C4(O)CC4)cc3n([C@H](c3ccccc3)C3CCOCC3)c2c1]

Step 1: Methyl 4-(5-bromo-3-nitropyridin-2-yl)benzoate

A 24/40-500 ml, round bottom flask was charged with 2,5-dibromo-3-nitropyridine (8.07 g, 28.6 mmol), 4-methoxycarbonylphenylboronic acid (4.97 g, 27.6 mmol), THF (143 mL), 1,1'-bis(diphenylphosphino)ferrocenedichloropalladium(II) (1.05 g, 1.43 mmol) and potassium phosphate tribasic (2M, 11.6 mL, 23.1 mmol). The flask was sealed with a rubber septum, and the reaction mixture was degassed using ultra pure argon and sonicated for 5 min. The flask was transferred to an oil bath preheated to 65° C. and held there for 4 h. The mixture was quenched with water, diluted with ethyl acetate, and filtered through a pad of Celite. The contents of the flask were transferred into a reparatory funnel and the layers were separated. The organic was washed with water (2×) and brine (2×). The combined aqueous was back extracted with ethyl acetate, and the aqueous discarded. The combined organics were dried with magnesium sulfate, concentrated under reduced pressure, and purified by silica gel column chromatography (80 g ISCO RediSep Rf, loaded in/with: DCM and dried, initial waste: 0 mL, fraction size: 9 mL 13×100 mm, and eluted with dichloromethane in hexanes 0% [200 mL], 0-20% [300 mL], 20% [1000 mL], 20-50% [500 mL], 50% [300 mL]) to give 1.39 g (59%). ¹H NMR (400 MHz, CDCl₃) δ 8.95 (d, J=2.0 Hz, 1H), 8.36 (d, J=2.0 Hz, 1H), 8.18-8.11 (m, 2H), 7.66-7.58 (m, 2H), 3.96 (s, 3H). Mass found 337 [M+H]⁺.

Step 2: Methyl 3-bromo-5H-pyrido[3,2-b]indole-7-carboxylate

A 14/20-100 mL round bottom flask was charged with methyl 4-(5-bromo-3-nitropyridin-2-yl)benzoate (6.68 g, 19.81 mmol) and 1,2-bis(diphenylphosphino)ethane (9.87 g, 24.8 mmol). The mixture was suspended in 1,2-dichlorobenzene (20 mL) and the flask was sealed and vented with a balloon full of nitrogen. The flask was placed into an oil bath preheated to 160° C. and held there for 1 h. Upon cooling, the solution was diluted with ether, causing a brown precipitate to form which was removed by filtration and discarded. The supernatant was concentrated under reduced pressure and purified by silica gel column chromatography (80 g ISCO RediSep Rf, loaded in/with: DCM and dried, initial waste: 0 mL, fraction size: 9 mL 13×100 mm, and eluted with dichloromethane in hexanes 0% [200 mL], 0-100% [300 mL], 100% [1500 mL]) to give 2.80 g (46%) as a beige solid. ¹H NMR (400 MHz, CDCl₃) δ 8.95 (d, J=2.0 Hz, 1H), 8.36 (d, J=2.0 Hz, 1H), 8.18-8.11 (m, 2H), 7.66-7.58 (m, 2H), 3.96 (s, 3H). Mass found 305 [M+H]⁺.

Step 3: Methyl 3-(1,4-dimethyl-1H-1,2,3-triazol-5-yl)-5H-pyrido[3,2-b]indole-7-carboxylate A 40 mL pressure vial was charged with 1,4-dimethyl-5-(tributylstannyl)-1H-1,2,3-triazole (3.90 g, 10.1 mmol) and diluted with DMF (23 mL). To that solution was added methyl 3-bromo-5H-pyrido[3,2-b]indole-7-carboxylate (2.80 g, 9.18 mmol), copper(I) iodide (0.262 g, 1.38 mmol), triethylamine (2.56 mL, 18.4 mmol) and Pd(Ph₃P)₄ (0.636 g, 0.551 mmol). The vial was sealed, and the reaction mixture was degassed using ultra pure argon and sonication for 3 min. After which, the vial was placed into a reaction block preheated to 100° C. After 30 min, the mixture was diluted with ethyl acetate and water, and the contents of the vial were filtered through a pad of Celite. The mixture was concentrated under reduced pressure and purified by silica gel column chromatography (40 g ISCO RediSep Rf, loaded in/with: DCM and dried, initial waste: 0 mL, fraction size: 9 mL 13×100 mm, and eluted with acetone in DCM 0% [100 mL], 0-30% [150 mL], 30% [300 mL], 30-60% [500 mL], 60% [200 mL]) to give 1.75 g (59%) as a light-tan solid. ¹H NMR (400 MHz, DMSO-d₆) δ 11.94 (s, 1H), 8.61 (d, J=2.0 Hz, 1H), 8.35 (dd, J=8.3, 0.5 Hz, 1H), 8.25 (dd, J=1.4, 0.6 Hz, 1H), 8.16 (d, J=1.8 Hz, 1H), 7.90 (dd, J=8.2, 1.4 Hz, 1H), 4.02 (s, 3H), 3.93 (s, 3H), 2.30 (s, 3H). Mass found 321 [M+H]⁺.

Step 4: (S)-Methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate A 24/40-50 mL round bottom flask was charged with methyl 3-(1,4-dimethyl-1H-1,2,3-triazol-5-yl)-5H-pyrido[3,2-b]indole-7-carboxylate (250 mg, 0.778 mmol), (R)-phenyl(tetrahydro-2H-pyran-4-yl)methanol (299 mg, 1.56 mmol), and triphenylphosphine (408 mg, 1.56 mmol). The mixture was suspended in THF (7780 µL) and cooled to 0° C. Di-tert-butyl azodicarboxylate (358 mg, 1.56 mmol) was added in 1 portion. After 30 min at 0° C., the reaction was warmed to room temperature and the reaction slowly turned to a deep red. After 30 min at room temperature, the reaction mixture was quenched with TFA (300 µL, 3.89 mmol) and stirred for 30 min. The mixture was concentrated under reduced pressure, diluted with ethyl acetate, and neutralized using a 1.5M potassium phosphate. The contents of the flask were transferred into a separatory funnel, and the layers were separated. The organic was washed with brine, dried over magnesium sulfate, concentrated under reduced pressure, and purified by silica gel column chromatography (24 g ISCO RediSep Rf, loaded in/with: DCM and dried, fraction size: 21 mL 16×150 mm, and eluted with acetone in dichloromethane 0% [50 mL], 0-20% [200 mL], 20% [150 mL], 20-30% [150 mL], 30% [350 mL]). Collected fractions to give 338 mg (88%). ¹H NMR (400 MHz, CDCl₃) δ 8.51 (d, J=1.8 Hz, 1H), 8.47 (d, J=8.3 Hz, 1H), 8.10 (dd, J=8.3, 1.3 Hz, 1H), 7.63 (d, J=1.8 Hz, 1H), 7.46 (d, J=7.3 Hz, 2H), 7.40-7.29 (m, 3H), 5.63 (d, J=10.5 Hz, 1H), 4.11-4.01 (m, 4H), 3.92-3.82 (m, 4H), 3.61-3.51 (m, 1H), 3.41-3.31 (m, 1H), 3.12 (q, J=11.3 Hz, 1H), 2.30 (s, 3H), 2.05 (d, J=13.3 Hz, 1H), 1.71-1.52 (m, 2H), 1.51-1.37 (m, 1H), 1.09 (d, J=12.3 Hz, 1H). Mass found 495 [M+H]⁺.

Step 5: (S)-Methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate A 14/20-15 mL round bottom flask was charged with titanium(IV) isopropoxide (29.6 µL, 0.101 mmol) and diluted with THF (1000 µL). To that solution was added (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate (100 mg, 0.202 mmol). Ethyl magnesium bromide (1.0M in THF, 1210 µL, 1.210 mmol) was then added at room temperature. After 20 min, the reaction mixture was quenched with methanol and concentrated under reduced pressure. The crude material was purified via preparative LC/MS with the following conditions: Column: XBridge C18, 19×200 mm, 5-µm particles; Mobile Phase A: 5:95 Acetonitrile: water with 10-mM ammonium acetate; Mobile Phase B: 95:5 Acetonitrile: water with 10-mM ammonium acetate; Gradient: 25-65% B over 15 min, then a 5-min hold at 100% B; Flow: 20 mL/min. The fractions were collected to give 8.3 mg (8.17%). ¹H NMR (500 MHz, DMSO-d₆) δ 8.49 (s, 1H), 8.39 (br. s., 1H), 8.12 (d, J=8.4 Hz, 1H), 7.95 (br. s., 1H), 7.65 (d, J=7.3 Hz, 2H), 7.36-7.29 (m, 2H), 7.27-7.21 (m, 1H), 7.15 (d, J=7.0 Hz, 1H), 6.17 (s, 1H), 5.80 (d, J=11.4 Hz, 1H), 4.05-3.94 (m, 3H), 3.89 (d, J=10.6 Hz, 1H), 3.73 (d, J=8.8 Hz, 1H), 3.47 (t, J=11.2 Hz, 1H), 3.42-3.31 (m, 1H), 3.26 (t, J=11.0 Hz, 1H), 2.34-2.23 (m, 3H), 1.71 (d, J=13.2 Hz, 1H), 1.61-1.50 (m, 1H), 1.38-1.08 (m, 5H), 0.99 (d, J=12.5 Hz, 1H). Mass found 494 [M+H].

Example 420

1,4-Dimethyl-5-{5-[(S)-oxan-4-yl)phenyl)methyl]-7-(prop-1-en-2-yl)-5H-pyrido[3,2-b]indol-3-yl}-1H-1,2,3-triazole

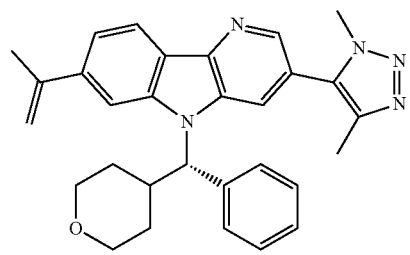 [SMILES: C=C(C)c1ccc2c3ncc(-c4c(C)nnn4C)cc3n([C@H](c3ccccc3)C3CCOCC3)c2c1]

Step 1: 5-Bromo-2-(4-chlorophenyl)-3-nitropyridine

A 24/40-3 neck 500 mL round bottom flask was charged with 2,5-dibromo-3-nitropyridine (12.1 g, 42.9 mmol) and (4-chlorophenyl)boronic acid (7.48 g, 47.8 mmol). The mixture was suspended with THF (150 mL) and potassium phosphate tribasic, (2M, 42.9 mL, 86.0 mmol). PdCl$_2$(dppf) (0.314 g, 0.429 mmol) was added, and the flask was sealed and degassed using sonication and ultra pure argon for 5 min. The mixture was heated to 65° C. After 2 h, the contents of the flask was transferred into a 1 L-round bottom flask and concentrated under reduced pressure. The resulting black slurry was diluted with ethyl acetate and water and filtered through a pad of Celite. The contents of the flask were transferred to a separatory funnel, and the organic was washed with brine (3×). The organics were dried with magnesium sulfate, concentrated under reduced pressure, and purified by silica gel column chromatography (120 g ISCO RediSep Rf, loaded in/with: DCM and dried, fraction size: 18 mL 16×150 mm, and eluted with dichloromethane in hexanes 0% [300 mL], 0-20% [450 mL], 20% [1503 mL], 20-50% [756 mL], 50% [450 mL]). The fractions were collected to 10.8 g (80%). 1H NMR consistent with desired. $^1$H NMR (400 MHz, CDCl$_3$) δ 8.92 (d, J=2.0 Hz, 1H), 8.31 (d, J=2.0 Hz, 1H), 7.53-7.43 (m, 4H). Mass found 314 [M+H]$^+$.

Step 2: 3-Bromo-7-chloro-5H-pyrido[3,2-b]indole

A 24/40-250 mL round bottom flask was charged with 5-bromo-2-(4-chlorophenyl)-3-nitropyridine (8.83 g, 28.2 mmol) and 1,2-bis(diphenylphosphino)ethane (22.4 g, 36.6 mmol). The mixture was suspended in 1,2-dichlorobenzene (60 mL). The flask was sealed and vented into a nitrogen-filled balloon. The reaction vessel was placed into an oil bath preheated to 160° C. After 2 h, the mixture was concentrated under reduced pressure to give a black slurry. The slurry was suspended in DCM, which gave a grey precipitate that was collected by filtration to give 1.5 g of product. The supernatant was loaded onto a column and purified by silica gel column chromatography (80 g ISCO RediSep Rf, loaded in/with: DCM and dried, initial waste: 0 mL, fraction size: 9 mL 13×100 mm, and eluted with dichloromethane in hexanes 0% [200 mL], 0-100% [300 mL], 100% [1500 mL]). The fractions were collected and combined with the product previously collected to give 3.17 g (40%). $^1$H NMR (400 MHz, DMSO-d$_6$) δ 11.75 (br. s., 1H), 8.56 (d, J=2.0 Hz, 1H), 8.22 (d, J=2.0 Hz, 1H), 8.19 (d, J=8.0 Hz, 1H), 7.69 (d, J=1.5 Hz, 1H), 7.32 (dd, J=8.3, 1.8 Hz, 1H). Mass found 280 [M+H]$^+$.

Step 3: 7-Chloro-3-(1,4-dimethyl-1H-1,2,3-triazol-5-yl)-5H-pyrido[3,2-b]indole A 40 mL-pressure vial was charged with 1,4-dimethyl-5-(tributylstannyl)-1H-1,2,3-triazole (5.10 g, 13.2 mmol) and diluted with DMF (16.5 mL). To that solution was added 3-bromo-7-chloro-5H-pyrido[3,2-b]indole (1.86 g, 6.61 mmol), copper(I) iodide (0.189 g, 0.991 mmol), triethylamine (1.01 mL, 7.27 mmol), and Pd(Ph$_3$P)$_4$ (0.229 g, 0.198 mmol), respectively. The vial was sealed and degassed using sonication and ultra pure argon for 2 min. The vial was placed into a reaction block preheated to 100° C. After 45 min, the mixture was diluted with ethyl acetate and water and filtered through a pad of Celite. The contents of the flask were transferred to a separatory funnel and further diluted with ethyl acetate and brine. The layers were separated, and the organic was washed with water (2×) and brine (2×). The combined aqueous was extracted with ethyl acetate (2×), and the aqueous discarded. The combined organics were washed with brine (2×), dried with magnesium sulfate, and concentrated under reduced pressure. The residue was suspended in DCM to give a yellow solid, which was collected by filtration to give 520 mg of desired product. The supernatant was purified by silica gel column chromatography (40 g ISCO RediSep Rf, loaded in/with: DCM and dried, initial waste: 38 mL, fraction size: 9 mL 13×100 mm, and eluted with acetone in dichloromethane 0% [151 mL], 0-100% [501 mL], 100% [250 mL]). The fractions were collected and combined with the product previously collected to give 1.56 (79%). $^1$H NMR (400 MHz, CDCl$_3$) δ 8.68 (br. s., 1H), 8.53 (d, J=1.8 Hz, 1H), 8.32 (d, J=8.5 Hz, 1H), 7.70 (d, J=2.0 Hz, 1H), 7.56 (d, J=1.3 Hz, 1H), 7.37 (dd, J=8.5, 1.8 Hz, 1H), 4.04 (s, 3H), 2.39 (s, 3H). Mass found 298 [M+H]$^+$.

Step 4: (S)-7-Chloro-3-(1,4-dimethyl-1H-1,2,3-triazol-5-yl)-5-(phenyl(tetrahydro-2H-pyran-4-yl)methyl)-5H-pyrido[3,2-b]indole A 24/40-100 mL round bottom flask was charged with 7-chloro-3-(1,4-dimethyl-1H-1,2,3-triazol-5-yl)-5H-pyrido[3,2-b]indole (250 mg, 0.840 mmol), triphenylphosphine (440 mg, 1.68 mmol), and (R)-phenyl(tetrahydro-2H-pyran-4-yl)methanol (242 mg, 1.26 mmol). The mixture was dissolved in THF (8397 µL) and cooled to 0° C. Di-tert-butyl azodicarboxylate (387 mg, 1.68 mmol) was added in one portion. After 15 min, the ice bath was removed. After 1 h, the mixture was concentrated under reduced pressure and purified by silica gel column chromatography (24 g ISCO RediSep Rf, loaded in/with: DCM and dried, initial waste: 0 mL, fraction size: 9 mL 13×100 mm, and eluted with acetone in dichloromethane 0% [75 mL], 15% [102 mL], 20% [150 mL], 20-60% [402 mL]). The fractions were collected to give 286 mg (72%). $^1$H NMR (400 MHz, CDCl$_3$) δ 8.46 (d, J=1.8 Hz, 1H), 8.32 (d, J=8.3 Hz, 1H), 7.71 (d, J=1.5 Hz, 1H), 7.58 (d, J=1.5 Hz, 1H), 7.46-7.41 (m, 2H), 7.40-7.30 (m, 4H), 5.45 (d, J=10.5 Hz, 1H), 4.06 (dd, J=11.7, 2.9 Hz, 1H), 3.92-3.84 (m, 4H), 3.55 (td, J=11.8, 2.0 Hz, 1H), 3.36 (td, J=11.9, 2.0 Hz, 1H), 3.14-3.00 (m, 1H), 2.29 (s, 3H), 2.03 (d, J=14.1 Hz, 1H), 1.67-1.53 (m, 1H), 1.50-1.34 (m, 1H), 1.10 (d, J=13.3 Hz, 1H). Mass found 472 [M+H]$^+$.

Step 5: 1,4-Dimethyl-5-{5-[(S)-oxan-4-yl(phenyl)methyl]-7-(prop-1-en-2-yl)-5H-pyrido[3,2-b]indol-3-yl}-1H-1,2,3-triazole A 2-5 mL microwave vial was charged with dioxane (10.1 mL) and tricyclohexylphosphine (20 wt % in toluene, 0.784 mL, 0.503 mmol). To that mixture was added (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (475 mg, 1.01 mmol), cesium carbonate (656 mg, 2.01 mmol), Pd$_2$(dba)$_3$ (230 mg, 0.252 mmol), and isopropenylboronic acid pinacol ester (338 mg, 2.01 mmol). The vial was sealed, and the reaction mixture was degassed using sonication and ultra pure argon for 2 min. The vial was placed into an oil bath preheated to 130° C. After 4 h, the mixture was cooled to room temperature and filtered through a pad of Celite, concentrated under reduced pressure, and purified by silica gel column chromatography (40 g ISCO RediSep Rf, loaded in/with: DCM and dried, initial waste: 0 mL, fraction size: 9 mL 13×100 mm, and eluted with acetone in dichloromethane 0% [105 mL], 15% [201 mL], 20% [201 mL], 30% [201 mL], 30-100% [402 mL]). The fractions were collected to give 390 mg (81%). $^1$H NMR (400 MHz, CDCl$_3$) δ 8.45 (d, J=1.8 Hz, 1H), 8.35 (d, J=8.3 Hz, 1H), 7.74 (s, 1H), 7.56 (td, J=4.1, 1.3 Hz, 2H), 7.48-7.42 (m, 2H), 7.40-7.29 (m, 3H), 5.57 (s, 1H), 5.28 (t, J=1.4 Hz, 1H), 4.07 (d, J=12.0 Hz, 1H), 3.92-3.83 (m, 5H), 3.61-3.51 (m, 1H), 3.41-3.29 (m, 1H), 3.10 (q, J=11.1 Hz, 1H), 2.36-2.26 (m, 5H), 2.10-1.99 (m, 1H), 1.71-1.53 (m, 2H), 1.50-1.38 (m, 1H), 1.13 (d, J=13.3 Hz, 1H). Mass found 477 [M+H]$^+$.

Example 421

1-[3-(Dimethyl-1H-1,2,3-triazol-5-yl)-5-[(S)-oxan-4-yl)phenyl)methyl]-5H-pyrido[3,2-b]indol-7-yl]ethan-1-one

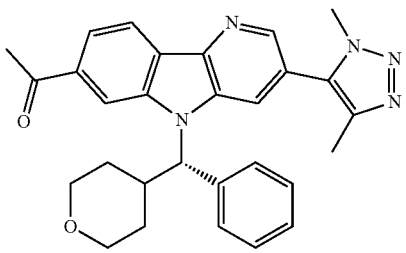 [SMILES: CC(=O)c1ccc2c3ncc(-c4c(C)nnn4C)cc3n([C@H](c3ccccc3)C3CCOCC3)c2c1]

A 40 mL pressure vial was charged with (S)-3-(1,4-dimethyl-1H-1,2,3-triazol-5-yl)-5-(phenyl(tetrahydro-2H-pyran-4-yl)methyl)-7-(prop-1-en-2-yl)-5H-pyrido[3,2-b]indole (200 mg, 0.419 mmol) and dissolved in 1,4-dioxane (4188 µL). To that stirring solution was added water (4188 µL) followed by sodium periodate (269 mg, 1.26 mmol) and osmium tetroxide 2.5% Wt in t-butanol (500 µL, 0.0400 mmol). The reaction mixture was stirred overnight. After 18.5 h, the contents of the vial were transferred into a reparatory funnel, and the mixture was diluted with DCM and water. The layers were separated, the aqueous was extracted with DCM (2×), and the aqueous discarded. The combined organics were dried with magnesium sulfate, concentrated under reduced pressure, and purified by silica gel column chromatography (24 g ISCO RediSep Rf, loaded in/with: DCM and dried, initial waste: 12 mL, fraction size: 9 mL 13×100 mm, and eluted with acetone in dichloromethane 0% [75 mL], 0-100% [300 mL], 100% [150 mL]). The fractions were collected fractions to give 112 mg (56%). $^1$H NMR (500 MHz, DMSO-d$_6$) δ 8.71 (br. s., 1H), 8.62 (s, 1H), 8.53 (br. s., 1H), 8.34 (d, J=8.4 Hz, 1H), 7.91 (d, J=8.1 Hz, 1H), 7.70 (d, J=7.7 Hz, 2H), 7.37-7.30 (m, 2H), 7.28-7.21 (m, 1H), 6.02 (d, J=11.4 Hz, 1H), 4.01 (s, 3H), 3.94-3.85 (m, 1H), 3.72 (d, J=8.4 Hz, 1H), 3.47 (q, J=11.1 Hz, 2H), 3.25 (t, J=11.4 Hz, 1H), 2.78 (s, 3H), 2.30 (s, 3H), 1.76-1.70 (m, 1H), 1.69-1.55 (m, 1H), 1.43-1.29 (m, 1H), 0.96 (d, J=12.8 Hz, 1H). Mass found 480 [M+H]$^+$.

Examples 422 & 423

1-Cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol Enantiomer A, Example 422

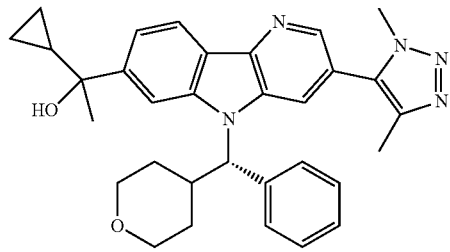

Enantiomer B, Example 423

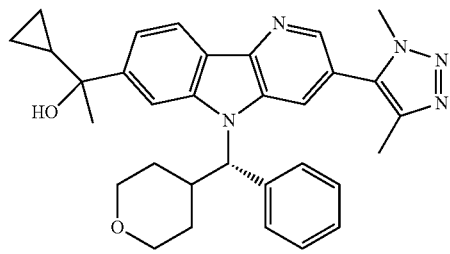

Step 1: 1-Cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol A flame dried 2.0-5.0 microwave vial was charged with 1-[3-(dimethyl-1H-1,2,3-triazol-5-yl)-5-[(S)-oxan-4-yl(phenyl)methyl]-5H-pyrido[3,2-b]indol-7-yl]ethan-1-one (75.0 mg, 0.156 mmol) and sealed. The vial was evacuated and purged with nitrogen. THF (1 mL) was added and the mixture was cooled to −78° C. Cyclopropylmagnesium bromide 1.0M in 1-methyltetrahydrofuran (0.938 mL, 0.938 mmol) was added drop wise turning the solution from a yellow to brown color. After 15 min, the vial was removed from the ice bath and allowed to warm to room temperature. After 2.5 h, the reaction was quenched with a saturated solution of aq. ammonium chloride and diluted with ethyl acetate. The contents of the flask were transferred to a reparatory funnel, and the layers were separated. The organic was washed with brine, dried with magnesium sulfate, concentrated under reduced pressure, and purified using silica gel flash chromatography (4 g ISCO RediSep Rf, loaded in/with: DCM and dried, initial waste: 0 mL, fraction size: 9 mL 13×100 mm, and eluted with acetone in dichloromethane 0% [51 mL], 0-60% [501 mL], 60% [99 mL]). The fractions were collected to give the desired product as a diastereomeric mixture. The mixture was separated by Chiral SFC: Chiral OJ-H prep column, 30×250 mm, 5 mm, Mobile phase: 10% MeOH in CO$_2$, 150 bar, Temp: 35° C., Flow rate: 70 mL/min for 46 min. UV monitored at 270 nm. Injection: 0.75 mL of ~5 mg/mL in MeOH (20 mg purified by stacked injection) to give Enantiomer A (9.10 mg, 17%) and Enantiomer B (10.5 mg, 19%). Enantiomer A: $^1$H NMR (400 MHz, METHANOL-d) δ 8.44 (d, J=1.5 Hz, 1H), 8.32-8.21 (m, 2H), 8.12 (s, 1H), 7.62 (d, J=7.3 Hz, 2H), 7.53 (dd, J=8.4, 1.1 Hz, 1H), 7.38-7.30 (m, 2H), 7.30-7.22 (m, 1H), 5.76 (d, J=11.0 Hz, 1H), 4.00 (s, 4H), 3.87-3.78 (m, 1H), 3.65-3.55 (m, 1H), 3.45-3.34 (m, 2H), 2.32 (s, 3H), 1.96 (d, J=12.8 Hz, 1H), 1.71-1.55 (m, 4H), 1.49-1.20 (m, 2H), 1.12 (d, J=13.3 Hz, 1H), 0.89 (d, J=7.3 Hz, 1H), 0.53 (t, J=6.8 Hz, 2H), 0.50-0.38 (m, 2H). SFC retention time 33.12 min. Mass found 521 [M+H]+. Enantiomer B: $^1$H NMR (400 MHz, CD$_3$OD) δ 8.44 (d, J=1.8 Hz, 1H), 8.31-8.25 (m, 2H), 8.13 (s, 1H), 7.63 (d, J=7.3 Hz, 2H), 7.56 (dd, J=8.3, 1.3 Hz, 1H), 7.38-7.31 (m, 2H), 7.29-7.23 (m, 1H), 5.76 (d, J=11.0 Hz, 1H), 4.03-3.94 (m, 4H), 3.82 (dd, J=11.4, 2.9 Hz, 1H), 3.59 (td, J=11.9, 1.9 Hz, 1H), 3.45-3.34 (m, 2H), 2.32 (s, 3H), 1.95 (d, J=12.8 Hz, 1H), 1.71-1.54 (m, 4H), 1.50-1.33 (m, 2H), 1.12 (d, J=12.8 Hz, 1H), 0.96-0.82 (m, 1H), 0.61-0.51 (m, 2H), 0.50-0.38 (m, 2H). SFC retention time 40.02 min. Mass found 521 [M+H]+.

Example 424

2-[3-(Dimethyl-1H-1,2,3-triazol-5-yl)-5-[(S)-oxan-4-yl(phenyl)methyl]-5H-pyrido[3,2-b]indol-7-yl]propane-1,2-diol

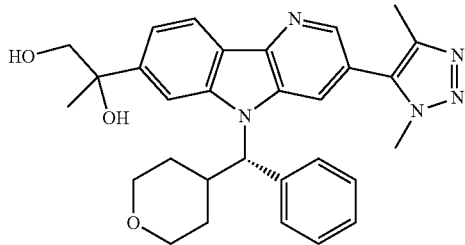 [SMILES: Cc1nnn(C)c1-c1cnc2c3ccc(C(C)(O)CO)cc3n([C@H](c3ccccc3)C3CCOCC3)c2c1]

A 20 mL scintillation vial was charged with 1,4-dimethyl-5-{5-[(S)-oxan-4-yl(phenyl)methyl]-7-(prop-1-en-2-yl)-5H-pyrido[3,2-b]indol-3-yl}-1H-1,2,3-triazole (100 mg, 0.209 mmol), which was subsequently suspended in n-PrOH (2094 μL). To that suspension was added NMO 50% in H$_2$O (66.3 μL, 0.314 mmol) followed by osmium tetroxide 4% in H$_2$O (133 μL, 0.0210 mmol). After ~5 min, the reaction mixture became homogenous. After 2.5 h, the volatiles were evaporated using a stream of nitrogen, and the resulting yellow oil was diluted with ethyl acetate and water and transferred to a reparatory funnel where the layers were separated. The organic was washed with water and brine. The combined aqueous was extracted with ethyl acetate (2×) and the aqueous discarded. The combined organics were dried with magnesium sulfate, concentrated under reduced pressure, and purified by silica gel column chromatography (4 g ISCO RediSep Rf, loaded in/with: DCM and dried, initial waste: 0 mL, fraction size: 6 mL 13×100 mm, and eluted with acetone in dichloromethane 0% [30 mL], 0-100% [201 mL], 100% [100 mL]). Collected fractions to give 67.0 mg (63%). $^1$H NMR (400 MHz, CDCl$_3$) δ 8.45 (d, J=1.8 Hz, 1H), 8.39 (d, J=8.0 Hz, 1H), 8.01 (s, 1H), 7.58 (d, J=1.8 Hz, 1H), 7.45 (d, J=7.8 Hz, 2H), 7.40-7.29 (m, 4H), 5.60 (d, J=10.3 Hz, 1H), 4.07 (d, J=8.8 Hz, 1H), 4.01-3.93 (m, 1H), 3.91-3.78 (m, 5H), 3.56 (t, J=11.9 Hz, 1H), 3.35 (t, J=11.8 Hz, 1H), 3.10 (d, J=11.0 Hz, 1H), 2.30 (s, 3H), 2.04 (d, J=11.5 Hz, 1H), 1.85-1.77 (m, 1H), 1.70 (s, 3H), 1.64 (dd, J=13.4, 4.4 Hz, 1H), 1.49-1.36 (m, 1H), 1.12 (d, J=12.8 Hz, 1H). Mass found 512 [M+H].

Example 427

1-[3-(Dimethyl-1H-1,2,3-triazol-5-yl)-5-[(S)-oxan-4-yl(phenyl)methyl]-5H-pyrido[3,2-b]indole-8-carbonyl]-3-methylazetidin-3-ol

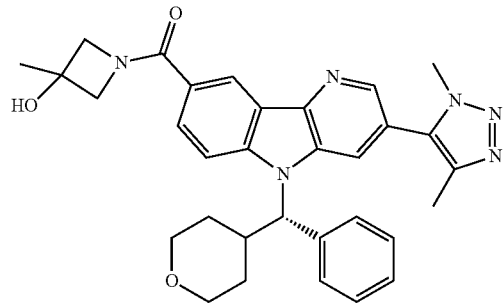 [SMILES: Cc1nnn(C)c1-c1cnc2c3cc(C(=O)N4CC(C)(O)C4)ccc3n([C@H](c3ccccc3)C3CCOCC3)c2c1]

Step 1: 2-Chloro-5-(1,4-dimethyl-1H-1,2,3-triazol-5-yl)pyridin-3-amine

A 24/40-250 ml, round bottom flask was charged with 1,4-dimethyl-5-(tributylstannyl)-1H-1,2,3-triazole (5.00 g, 13.0 mmol) and diluted with DMF (43.2 mL). To that solution was added 5-bromo-2-chloropyridin-3-amine (5.37 g, 25.9 mmol), copper (I) iodide (0.370 g, 1.94 mmol), triethylamine (3.61 mL, 25.9 mmol), and finally Pd(Ph$_3$P)$_4$ (1.12 g, 0.971 mmol). The flask was sealed and degassed using ultra pure argon and sonication for 5 min. The flask was placed into an oil bath preheated to 100° C. After 15 h, the reaction mixture was cooled and filtered through a pad of Celite. The black liquid was concentrated under reduced pressure. The resulting black slurry was diluted with DCM and brine and transferred into a separatory funnel. A thick emulsion made it impossible to separate the layers. The mixture was re-filtered through Celite. The layers were separated and the organic was washed with brine (2×), dried with magnesium sulfate, concentrated under reduced pressure, and purified by silica gel column chromatography (80 g ISCO RediSep Rf, loaded in/with: DCM and dried, initial waste: 102 mL, fraction size: 21 mL 16×150 mm, and eluted with acetone in dichloromethane 0% [201 mL], 0-20% [501 mL], 20-50% [1002 mL]). The fractions were collected to 898 mg (31%). $^1$H NMR (400 MHz, CDCl$_3$) δ 7.76 (d, J=2.0 Hz, 1H), 6.96 (d, J=2.0 Hz, 1H), 4.32 (br. s., 2H), 3.97 (s, 3H), 2.33 (s, 3H). Mass found 223 [M+H]+.

Step 2: Methyl 4-((2-chloro-5-(1,4-dimethyl-1H-1,2,3-triazol-5-yl)pyridin-3-yl)amino)benzoate A 24/40-100 ml, round bottom flask was charged with 2-chloro-5-(1,4-dimethyl-1H-1,2,3-triazol-5-yl)pyridin-3-amine (300 mg, 1.34 mmol), 4-methoxycarbonylphenylboronic acid (966 mg, 5.37 mmol), and copper(II) Acetate (609 mg, 3.35 mmol). 6 g of 4 Å molecular sieve powder was added, and the vial was sealed and evacuated and flushed with argon, twice. To that mixture was added CHCl$_3$ (13.4 mL) followed by pyridine (432 μL, 5.37 mmol). The sealed flask was degassed using oxygen and sonication for 4 min, and the reaction stirred under an atmosphere of oxygen. After 17 h, the reaction mixture was quenched with ammonium hydroxide (1000 μL, 25.1 mmol) and diluted with chloroform. Celite and sand was added to aid in filtration.

The mixture was filtered, concentrated under reduced pressure, and purified by silica gel column chromatography (12 g ISCO RediSep Rf, loaded in/with: DCM and dried, initial waste: 0 mL, fraction size: 9 mL 13×100 mm, and eluted with acetone in dichloromethane 0% [51 mL], 5% [51 mL], 10% [150 mL], 15% [150 mL], 15-30% [252 mL]). Collected fractions to give 160 mg (33.3%). $^1$H NMR (400 MHz, CDCl$_3$) δ 8.10-8.03 (m, 2H), 7.93 (d, J=2.0 Hz, 1H), 7.56 (d, J=2.0 Hz, 1H), 7.23-7.18 (m, 2H), 6.48 (s, 1H), 3.99 (s, 3H), 3.92 (s, 3H), 2.38-2.31 (m, 3H). Mass found 357 [M+H]$^+$.

Step 3: Methyl 3-(1,4-dimethyl-1H-1,2,3-triazol-5-yl)-5H-pyrido[3,2-b]indole-8-carboxylate A 2.0-5.0 mL microwave vial was charged with methyl 4-((2-chloro-5-(1,4-dimethyl-1H-1,2,3-triazol-5-yl)pyridin-3-yl)amino)benzoate (276 mg, 0.771 mmol) and dissolved in DMA (5 mL). To that solution was added sodium acetate trihydrate (0.181 mL, 1.93 mmol) and bis(triphenylphosphine)palladium(II) dichloride (54.1 mg, 0.0770 mmol). The vial was sealed and degassed using ultra pure argon and sonication for 2 min. The reaction mixture was placed into a reaction block preheated to 110° C. After 30 min, the reaction was cooled, and the contents of the microwave vial were transferred to a 100 mL round bottom flask, and the DMA was concentrated under reduced pressure to give a brown oil. The contents of the flask were transferred into a separatory funnel and diluted with ethyl acetate and a saturated aq. solution of ammonium chloride. The combined organics were washed with brine (2×), dried with magnesium sulfate, concentrated under reduced pressure, and purified by silica gel column chromatography (12 g ISCO RediSep Rf, loaded in/with: DCM and dried, initial waste: 0 mL, fraction size: 9 mL 13×100 mm, and eluted with acetone in dichloromethane 0% [51 mL], 5% [51 mL], 10% [150 mL], 15% [150 mL], 15-30% [252 mL], 30-60% [500 mL]). The fractions were collected to give 165 mg (67%). $^1$H NMR (400 MHz, CDCl$_3$) δ 9.20-9.15 (m, 1H), 8.58 (d, J=2.0 Hz, 2H), 8.32 (dd, J=8.7, 1.6 Hz, 1H), 7.73 (d, J=2.0 Hz, 1H), 7.63-7.53 (m, 1H), 4.04 (s, 3H), 4.00 (s, 3H), 2.40 (s, 3H). Mass found 306 [M+H]$^+$.

Step 4: (R)-Phenyl(tetrahydro-2H-pyran-4-yl)methyl methanesulfonate

A 24/40-100 mL round bottom flask was charged with (R)-phenyl(tetrahydro-2H-pyran-4-yl)methanol (1.07 g, 5.57 mmol) and dissolved in DCM (27.8 mL). To that solution was added triethylamine (2.33 mL, 16.7 mmol), and the mixture was cooled with an ice bath to 0° C. Mesyl chloride (0.651 mL, 8.35 mmol) was added drop wise. The ice bath was allowed to expire, and after 2 h the mixture was quenched with a saturated solution of sodium bicarbonate, vigorously stirred, and transferred into a separatory funnel where the layers were separated. The organic was washed with a saturated aq. solution of sodium bicarbonate, brine, and dried with magnesium sulfate. The mixture was concentrated under reduced pressure several times using diethyl ether to afford 1.51 g (100%). $^1$H NMR (400 MHz, CDCl$_3$) δ 7.46-7.38 (m, 3H), 7.38-7.34 (m, 2H), 5.21 (d, J=9.0 Hz, 1H), 4.05 (dd, J=11.7, 3.1 Hz, 1H), 3.91 (ddd, J=11.5, 4.4, 1.1 Hz, 1H), 3.38 (td, J=11.9, 2.3 Hz, 1H), 3.29 (td, J=11.8, 2.3 Hz, 1H), 2.61 (s, 3H), 2.18-2.05 (m, 1H), 2.05-1.96 (m, 1H), 1.60-1.48 (m, 1H), 1.39-1.26 (m, 1H), 1.17-1.10 (m, 1H).

Step 5: (S)-Methyl 3-(1,4-dimethyl-1H-1,2,3-triazol-5-yl)-5-(phenyl(tetrahydro-2H-pyran-4-yl)methyl)-5H-pyrido[3,2-b]indole-8-carboxylate A 2-dram pressure vial was charged with methyl 3-(1,4-dimethyl-1H-1,2,3-triazol-5-yl)-5H-pyrido[3,2-b]indole-8-carboxylate (165 mg, 0.513 mmol) and dissolved in DMF (5135 µL). To that solution was added cesium carbonate (1000 mg, 3.08 mmol) followed by (R)-phenyl(tetrahydro-2H-pyran-4-yl)methyl methanesulfonate (833 mg, 3.08 mmol). The vial was sealed and placed into an oil bath preheated to 40° C. After 65 h, the reaction mixture was quenched with water, and the contents of the vial were transferred to a separatory funnel where it was diluted with ethyl acetate and a brine solution. The layers were separated, and the organic was washed with brine (2×). The combined aqueous was extracted with ethyl acetate (2×), and the aqueous discarded. The combined organics were washed with water, dried with magnesium sulfate, concentrated under reduced pressure, and purified by silica gel column chromatography (12 g ISCO RediSep Rf, loaded in/with: DCM and dried, initial waste: 0 mL, fraction size: 9 mL 13×100 mm, and eluted with acetone in dichloromethane 0% [51 mL], 20% [150 mL], 25% [252 mL], 25-100% [150 mL]). The fractions were collected to give 147 mg (58%). $^1$H NMR (400 MHz, CDCl$_3$) δ 9.16 (d, J=1.3 Hz, 1H), 8.52 (d, J=1.8 Hz, 1H), 8.36 (dd, J=8.8, 1.8 Hz, 1H), 7.76 (d, J=8.8 Hz, 1H), 7.62 (d, J=1.8 Hz, 1H), 7.45 (d, J=7.0 Hz, 2H), 7.40-7.29 (m, 3H), 5.56 (d, J=10.8 Hz, 1H), 4.09-4.03 (m, 1H), 4.00 (s, 3H), 3.93-3.84 (m, 4H), 3.60-3.51 (m, 1H), 3.40-3.31 (m, 1H), 3.10 (d, J=11.0 Hz, 1H), 2.30 (s, 3H), 2.09-1.99 (m, 1H), 1.68-1.58 (m, 1H), 1.44-1.35 (m, 1H), 1.10 (d, J=12.8 Hz, 1H). Mass found 496 [M+H]$^+$.

Step 6: (S)-3-(1,4-Dimethyl-1H-1,2,3-triazol-5-yl)-5-(phenyl(tetrahydro-2H-pyran-4-yl)methyl)-5H-pyrido[3,2-b]indole-8-carboxylic acid A 24/40-50 mL round bottom flask was charged with (S)-methyl 3-(1,4-dimethyl-1 H-1,2,3-triazol-5-yl)-5-(phenyl(tetrahydro-2H-pyran-4-yl)methyl)-5H-pyrido[3,2-b]indole-8-carboxylate (148 mg, 0.299 mmol) and dissolved in THF (2489 µL) and diluted with water (498 µL). To that mixture was added potassium hydroxide (50.3 mg, 0.896 mmol). The vial was sealed with a rubber septum and placed into an oil bath preheated to 50° C. After 17.5 h, the reaction mixture was concentrated under reduced pressure. The mixture was dissolved in 2 mL of water and acidified to a pH of ~5 using 5N aq. HCl. As the pH approached the acidic range, a white solid precipitated out. The mixture was transferred into a reparatory funnel and extracted with ethyl acetate (×4), dried with magnesium sulfate, and concentrated under reduced pressure to give 128 mg (89%). $^1$H NMR (400 MHz, CDCl$_3$) δ 9.56 (d, J=1.5 Hz, 1H), 8.59 (d, J=1.8 Hz, 1H), 8.43 (dd, J=8.8, 1.8 Hz, 1H), 7.81 (d, J=8.8 Hz, 1H), 7.67 (d, J=1.8 Hz, 1H), 7.46 (d, J=7.3 Hz, 2H), 7.41-7.30 (m, 3H), 5.59 (d, J=11.0 Hz, 1H), 4.10-4.04 (m, 1H), 3.94-3.84 (m, 4H), 3.61-3.52 (m, 1H), 3.41-3.32 (m, 1H), 3.12 (d, J=11.3 Hz, 1H), 2.32 (s, 3H), 2.06 (s, 1H), 1.70-1.56 (m, 2H), 1.46-1.40 (m, 1H), 1.12 (d, J=13.3 Hz, 1H). Mass found 482 [M+H]$^+$.

Step 7: 1-[3-(Dimethyl-1H-1,2,3-triazol-5-yl)-5-[(S)-oxan-4-yl(phenyl)methyl]-5H-pyrido[3,2-b]indole-8-carbonyl]-3-methylazetidin-3-ol A 1-dram vial was charged with (S)-3-(1,4-dimethyl-1H-1,2,3-triazol-5-yl)-5-(phenyl(tetrahydro-2H-pyran-4-yl)methyl)-5H-pyrido[3,2-b]indole-8-carboxylic acid (20.0 mg, 0.0420 mmol) and dissolved in DMF (500 µL). To that solution was added 3-methylazetidin-3-ol hydrochloride (10.3 mg, 0.0830 mmol), Hünig's base (14.5 µL, 0.0830 mmol), and HATU (23.7 mg, 0.0620 mmol). After 1 h, the mixture was diluted with 800 µL of methanol and purified by preparative HPLC: Column: Waters XBridge C18 100×30 mm 5 u, Solvents: A: 95% MeCN 5% Water B: 95% Water 5% MeCN Buffer: 10 mm Ammonium Acetate), flow Rate: 30 mL/min, 1 injection. The fractions were collected to give 9.70 mg (42%). $^1$H NMR (400 MHz, CDCl$_3$) δ 8.64 (d, J=1.5 Hz, 1H), 8.49 (d, J=1.5 Hz, 1H), 8.11 (dd, J=8.7, 1.6 Hz, 1H), 7.79 (d, J=8.8 Hz, 1H), 7.63 (d, J=1.8 Hz, 1H), 7.44 (d, J=7.0 Hz, 2H), 7.39-7.30 (m, 3H), 5.54 (d, J=10.5 Hz, 1H), 4.54-4.17 (m, 4H), 4.09-4.02 (m, 1H), 3.92-3.83 (m, 4H), 3.59-3.49 (m, 1H), 3.40-3.31 (m, 1H), 3.17-3.03 (m, 1H), 2.40 (s, 1H), 2.30 (s, 3H), 2.02 (d, J=13.6 Hz, 1H), 1.59 (s, 4H), 1.47-1.34 (m, 1H), 1.12 (d, J=12.0 Hz, 1H). Mass found 550 [M+H]$^+$.

Example 428

5-[8-(3,3-Difluoroazetidine-1-carbonyl)-5-[(S)-oxan-4-yl)phenyl)methyl]-5H-pyrido[3,2-b]indol-3-yl]-1,4-dimethyl-1H-1,2,3-triazole

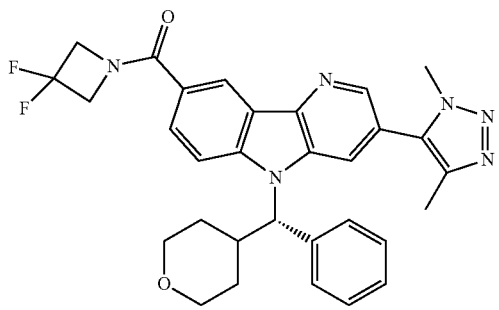 [SMILES: Cc1nnn(C)c1-c1cnc2c3cc(C(=O)N4CC(F)(F)C4)ccc3n([C@H](c3ccccc3)C3CCOCC3)c2c1]

5-[8-(3,3-Difluoroazetidine-1-carbonyl)-5-[(S)-oxan-4-yl(phenyl)methyl]-5H-pyrido[3,2-b]indol-3-yl]-1,4-dimethyl-1H-1,2,3-triazole (14.6 mg, 63%) was prepared from 3,3-difluoroazetidine hydrochloride following the procedures analogous to those described in the synthesis of 1-[3-(dimethyl-1H-1,2,3-triazol-5-yl)-5-[(S)-oxan-4-yl(phenyl)methyl]-5H-pyrido[3,2-b]indole-8-carbonyl]-3-methylazetidin-3-ol. $^1$H NMR (500 MHz, DMSO-d$_6$) δ 8.62 (s, 1H), 8.56 (s, 1H), 8.25 (br. s., 1H), 8.00-7.92 (m, 1H), 7.69 (d, J=7.3 Hz, 2H), 7.38-7.30 (m, 2H), 7.29-7.22 (m, 1H), 5.89 (d, J=11.4 Hz, 1H), 4.02 (br. s., 3H), 3.93-3.85 (m, 1H), 3.73 (d, J=8.4 Hz, 1H), 3.51-3.44 (m, 1H), 3.43-3.35 (m, 6H), 3.27 (t, J=11.6 Hz, 1H), 2.31 (s, 3H), 1.70 (d, J=12.8 Hz, 1H), 1.61-1.49 (m, 1H), 1.37-1.25 (m, 1H), 0.99 (d, J=11.4 Hz, 1H). Mass found 556 [M+H]$^+$.

Example 429

1-[3-(Dimethyl-1H-1,2,3-triazol-5-yl)-5-[(S)-oxan-4-yl)phenyl)methyl]-5H-pyrido[3,2-b]indole-8-cabonyl]azetidine-3-ol

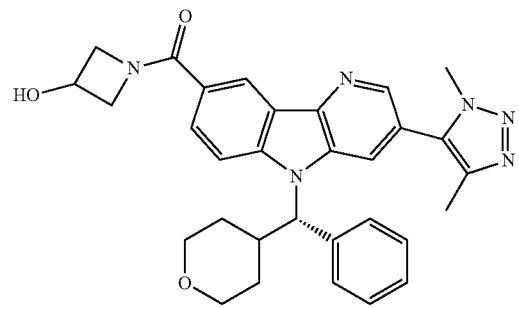 [SMILES: Cc1nnn(C)c1-c1cnc2c3cc(C(=O)N4CC(O)C4)ccc3n([C@H](c3ccccc3)C3CCOCC3)c2c1]

The title compound was prepared from 3-hydroxyazetidine hydrochloride following the procedures analogous to those described in the synthesis of 1-[3-(dimethyl-1 H-1,2,3-triazol-5-yl)-5-[(S)-oxan-4-yl(phenyl)methyl]-5H-pyrido[3,2-b]indole-8-carbonyl]-3-methylazetidin-3-ol to give 20.7 mg (63%). $^1$H NMR (500 MHz, DMSO-d6) δ 8.61 (s, 1H), 8.48 (s, 1H), 8.22 (br. s., 1H), 7.91 (d, J=6.6 Hz, 1H), 7.69 (d, J=7.3 Hz, 2H), 7.37-7.30 (m, 2H), 7.29-7.23 (m, 1H), 5.87 (d, J=11.4 Hz, 1H), 4.68-4.47 (m, 2H), 4.32 (br. s., 1H), 4.15 (br. s., 1H), 4.02 (br. s., 3H), 3.93-3.82 (m, 3H), 3.73 (d, J=9.2 Hz, 1H), 3.51-3.43 (m, 1H), 3.43-3.36 (m, 2H), 3.27 (t, J=11.6 Hz, 1H), 2.31 (s, 3H), 1.69 (d, J=11.7 Hz, 1H), 1.60-1.49 (m, 1H), 1.31 (d, J=9.2 Hz, 1H), 1.00 (d, J=12.5 Hz, 1H). Mass found 536 [M+H]$^+$.

Example 430

5-[8-(3-Fluoroazetidine-1-carbonyl)-5-[(S)-oxan-4-yl(phenyl)methyl]-5H-pyrido[3,2-b]indol-3-yl]-1,4-dimethyl-1H-1,2,3-triazole

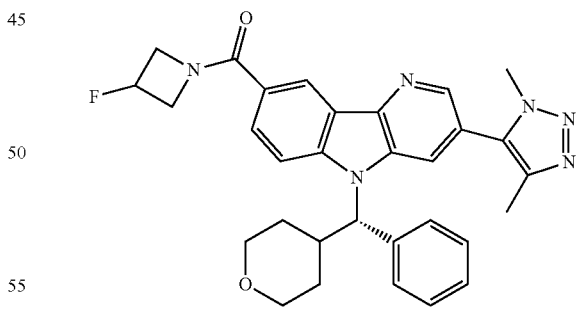

The title compound was prepared from 3-fluoroazetidine following procedures analogous to those described in the synthesis of 1-[3-(dimethyl-1H-1,2,3-triazol-5-yl)-5-[(S)-oxan-4-yl(phenyl)methyl]-5H-pyrido[3,2-b]indole-8-carbonyl]-3-methylazetidin-3-ol to give 17.2 mg (77%). $^1$H NMR (500 MHz, DMSO-d$_6$) δ 8.62 (s, 1H), 8.51 (s, 1H), 8.55 (br. s., 1H), 8.24 (br. s., 1H), 7.93 (d, J=8.8 Hz, 1H), 7.70 (d, J=7.7 Hz, 2H), 7.38-7.30 (m, 2H), 7.29-7.22 (m, 1H), 5.89 (d, J=11.0 Hz, 1H), 5.58-5.38 (m, 1H), 4.85-4.34 (m, 3H), 4.17 (br. s., 1H), 4.03 (s, 3H), 3.94-3.86 (m, 1H), 3.74 (d, J=8.1 Hz, 1H), 3.53-3.40 (m, 2H), 3.37-3.23 (m, 1H), 2.31 (s, 3H), 1.70 (d, J=12.5 Hz, 1H), 1.56 (d, J=10.3 Hz, 1H), 1.38-1.20 (d, J=12.5 Hz, 1H). Mass found 538 [M+H]+.

Examples 431 & 432

(1S)-1-Cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol and (1R)-1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol Diastereomer A, Example 431

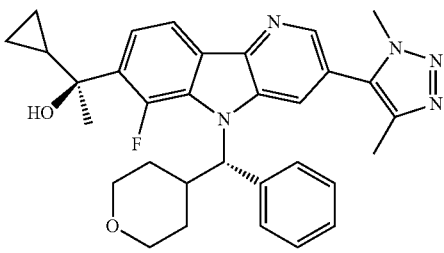

Diastereomer B, Example 432

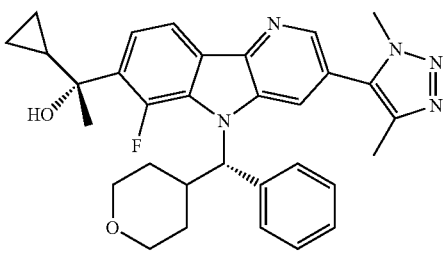

Step 1: 5-Bromo-2-(4-chloro-3-fluorophenyl)-3-nitropyridine

A 24/40-3 neck 500 mL round bottom flask was charged with 2,5-dibromo-3-nitropyridine (12.1 g, 42.9 mmol) and 4-chloro-3-fluorophenylboronic acid (7.48 g, 42.9 mmol). The mixture was diluted with THF (150 mL) and aq. potassium phosphate tribasic, 2.0M (42.9 mL, 86 mmol). PdCl$_2$(dppf) (0.314 g, 0.429 mmol) was added, and the flask was sealed and degassed using sonication and ultra pure argon for 5 min. The mixture was heated to 65° C. After 2 h, the mixture was concentrated under reduced pressure, diluted with ethyl acetate and water, and filtered through Celite. The contents of the vial were transferred into a separatory funnel, and the organic was washed with brine (3×), dried with magnesium sulfate, concentrated under reduced pressure, and purified by silica gel column chromatography (120 g ISCO RediSep Rf, loaded in/with: DCM and dried, fraction size: 18 mL 16×150 mm, and eluted with dichloromethane in hexanes 0% [300 mL], 0-20% [450 mL], 20% [1503 mL], 20-50% [756 mL], 50% [450 mL]). Only fractions containing pure mono-couple product were collected and set aside. The remaining impure fractions were collected, concentrated under reduced pressure, and re-purified by flash chromatography: (80 g ISCO RediSep Rf, loaded in/with: DCM and dried, initial waste: collected by threshold, fraction size: 18 mL 16×150 mm, and eluted with dichloromethane in hexanes 0% [200 mL], 0-20% [300 mL], 20% [1000 mL], 20-50% [500 mL], 50% [275 mL]). The fractions were combined to give 10.77 g (67%). $^1$H NMR (400 MHz, CDCl$_3$) δ 8.93 (d, J=2.0 Hz, 1H), 8.34 (d, J=2.0 Hz, 1H), 7.50 (dd, J=8.2, 7.4 Hz, 1H), 7.41 (dd, J=9.4, 2.1 Hz, 1H), 7.26-7.22 (m, 1H). Mass found 331 [M+H]+.

Step 2: 3-Bromo-7-chloro-6-fluoro-5H-pyrido[3,2-b]indole & 3-bromo-7-chloro-8-fluoro-5H-pyrido[3,2-b]indole A 350 mL-wide neck pressure flask was charged with 5-bromo-2-(4-chloro-3-fluorophenyl)-3-nitropyridine (10.7 g, 32.5 mmol) and 1,2-bis(diphenylphosphino)ethane (19.4 g, 48.7 mmol). The mixture was suspended in 1,2-dichlorobenzene (65 mL). The flask was sealed and placed into an oil bath preheated to 160° C. After 30 min, the mixture was concentrated under reduced pressure. The resulting solids were diluted with DCM to give a tan solid, which was collected by filtration to give 3.2 g of the regioisomer mixture. The supernatant was concentrated under reduced pressure and purified by flash chromatography: (80 g ISCO RediSep Rf, loaded in/with: DCM and dried, fraction size: 18 mL 16×150 mm, and eluted with dichloromethane in hexanes 0% [200 mL], 0-100% [500 mL], 100% [1500 mL]). The fractions were collected and combined with the product previously collected. NMR showed a 1.5:1 ratio of 8F:6F. The mixture was separated by chiral SFC: Chiralpak IB prep column, 30×250 mm, 5 μm. Mobile phase: 10% MeOH in CO$_2$, 150 bar. Temp: 35° C. Flow rate: 70 mL/min. for 10 min. UV monitored at 316 nm. Injection: 1.25 mL of ~20 mg/mL in 1:1:1 DMSO:MeOH:CHCl$_3$ (4.9 g purified by stacked injection). Regioisomer 1: 3-bromo-7-chloro-6-fluoro-5H-pyrido[3,2-b]indole (1.69 g, 5.64 mmol, 17%) was isolated as a white solid. $^1$H NMR (400 MHz, CDCl$_3$) δ 8.65 (d, J=1.8 Hz, 1H), 8.30 (br. s., 1H), 8.02 (d, J=8.5 Hz, 1H), 7.96 (d, J=2.0 Hz, 1H), 7.33 (dd, J=8.5, 6.3 Hz, 1H). SFC retention time: 15.4 min. Mass found 300 [M+H]+. Regioisomer 2: 3-bromo-7-chloro-8-fluoro-5H-pyrido[3,2-b]indole (2.51 g, 8.38 mmol, 25.8%) was isolated as a white solid. $^1$H NMR (400 MHz, CDCl$_3$) δ 8.62 (d, J=1.8 Hz, 1H), 8.06 (d, J=8.5 Hz, 2H), 7.91 (d, J=1.8 Hz, 1H), 7.53 (d, J=5.8 Hz, 1H). SFC retention time: 19.67 min. Mass found 300 [M+H]+.

Step 3: (S)-3-Bromo-7-chloro-6-fluoro-5-(phenyl(tetrahydro-2H-pyran-4-yl)methyl)-5H-pyrido[3,2-b]indole A 24/40-250 mL round bottom flask was charged with triphenylphosphine (2.63 g, 10.0 mmol) and THF (30 mL) and placed into an ice bath. A solution of di-tert-butyl azodicarboxylate (2.31 g, 10.0 mmol) dissolved in THF (5 mL) was added drop wise, and the mixture was stirred. After 30 min, (R)-phenyl(tetrahydro-2H-pyran-4-yl)methanol (1.93 g, 10.0 mmol) was added in one portion, and the mixture was let stir for 30 min. 3-Bromo-7-chloro-6-fluoro-5H-pyrido[3,2-b]indole (1.50 g, 5.01 mmol) was added in small portions over the course of 20 min at 0° C. After 15 min, the ice bath was removed. After 1 h, TFA (3.86 mL, 50.1 mmol) was added, and the mixture was let stir for 30 min and concentrated under reduced pressure. The mixture was diluted with ethyl acetate, and the contents of the flask were transferred into a separatory funnel where the organic was neutralized with a 1.5M aq. potassium phosphate solution. The layers were separated, and the organics washed with brine (2×), dried over magnesium sulfate, concentrated under reduced pressure, and purified by silica gel column chromatography (80 g ISCO RediSep Rf, loaded in/with: DCM and dried, initial waste: 0 mL, fraction size: 21 mL 16×150 mm, and eluted with dichloromethane in hexanes 0% [150 mL], 0-100% [500 mL], 100% [1000 mL], 2% ethyl acetate in DCM [500 mL]). The fractions were collected to give 1.97 g (83%). $^1$H NMR (400 MHz, CDCl$_3$) δ 8.56 (s, 1H), 8.03 (d, J=7.8 Hz, 1H), 7.94 (br. s., 1H), 7.55-7.43 (m, 2H), 7.41-7.28 (m, 4H), 5.92 (br. s., 1H), 4.10-3.99 (m, 1H), 3.95-3.83 (m, 1H), 3.56 (td, J=11.9, 2.1 Hz, 1H), 3.46-3.34 (m, 1H), 3.06 (br. s., 1H), 1.98 (d, J=14.1 Hz, 1H), 1.64-1.37 (m, 2H), 1.01 (d, J=13.6 Hz, 1H). Mass found 473 [M+H]$^+$.

Step 4: (S)-7-Chloro-3-(1,4-dimethyl-1H-1,2,3-triazol-5-yl)-6-fluoro-5-(phenyl(tetrahydro-2H-pyran-4-yl)methyl)-5H-pyrido[3,2-b]indole A 2.0-5.0 mL microwave vial was charged with 1,4-dimethyl-5-(tributylstannyl)-1H-1,2,3-triazole (164 mg, 0.423 mmol) and DMF (3251 μL). To this was added (S)-3-bromo-7-chloro-6-fluoro-5-(phenyl(tetrahydro-2H-pyran-4-yl)methyl)-5H-pyrido[3,2-b]indole (154 mg, 0.325 mmol), triethylamine (49.8 μL, 0.358 mmol), and copper(I) iodide (9.29 mg, 0.0490 mmol). Pd(Ph$_3$P)$_4$ (28.2 mg, 0.0240 mmol) was added last, and the vial was sealed and degassed using ultra pure argon and sonication for 1 min. The vial was placed into a reaction block preheated to 100° C. After 20 min, the reaction was diluted with water and ethyl acetate and filtered through a pad of Celite to remove the black emulsion. The filtered solution was transferred into a separatory funnel, and the layers were separated. The organics were washed with water (2×) and brine. The combined aqueous was extracted with ethyl acetate, and the aqueous discarded. The combined organics were washed with brine, dried with magnesium sulfate, concentrated under reduced pressure, and purified by silica gel column chromatography (40 g ISCO RediSep Rf, loaded in/with: DCM and dried, initial waste: 0 mL, fraction size: 18 mL 16×150 mm, and eluted with acetone in dichloromethane 0% [102 mL], 0-20% [150 mL], 20% [300 mL], 20-60% [507 mL], 60% [200 mL]). The fractions were collected to give 1.10 g (89%). $^1$H NMR (400 MHz, CDCl$_3$) δ 8.47 (d, J=1.8 Hz, 1H), 8.12 (dd, J=8.3, 0.5 Hz, 1H), 8.03 (s, 1H), 7.49 (d, J=7.3 Hz, 2H), 7.44-7.30 (m, 4H), 6.06 (br. s., 1H), 4.10-4.01 (m, 1H), 3.93-3.86 (m, 1H), 3.83 (s, 3H), 3.55 (td, J=11.9, 2.0 Hz, 1H), 3.40-3.29 (m, 1H), 3.03 (d, J=11.0 Hz, 1H), 2.05 (d, J=13.6 Hz, 1H), 1.70-1.46 (m, 5H), 1.01 (d, J=13.1 Hz, 1H). Mass found 493 [M+H]$^+$.

Step 5: (5)-1-(3-(1,4-Dimethyl-1H-1,2,3-triazol-5-yl)-6-fluoro-5-(phenyl(tetrahydro-2H-pyran-4-yl)methyl)-5H-pyrido[3,2-b]indol-7-yl)ethanone A 10-20 mL microwave vial was charged with tributyl(1-ethoxyvinyl)tin (1.84 mL, 5.79 mmol) and dissolved in dioxane (19.3 mL). To this was added (S)-7-chloro-3-(1,4-dimethyl-1H-1,2,3-triazol-5-yl)-6-fluoro-5-(phenyl(tetrahydro-2H-pyran-4-yl)methyl)-5H-pyrido[3,2-b]indole (1.89 g, 3.86 mmol), cesium carbonate (2.51 g, 7.71 mmol), Pd2(dba)3 (0.265 g, 0.289 mmol), and tricyclohexylphosphine (20 wt % in toluene, 0.901 mL, 0.579 mmol). The vial was sealed and degassed using ultra pure argon and sonication for 1 min. The vial was placed into an oil bath preheated to 130° C. After 15 h, the mixture was cooled to room temperature and HCl (3.0N, 12.9 mL, 38.6 mmol) was added. After 30 min, the mixture was filtered through a pad of Celite, quenched with a 1.5M solution of aq. potassium phosphate and diluted with ethyl acetate. The contents of the flask were transferred into a separatory funnel where the layers were separated. The organics were washed with a saturated solution of sodium bicarbonate, then water and then brine. The combined organics were dried with magnesium sulfate, concentrated under reduced pressure, and purified by silica gel column chromatography (24 g ISCO RediSep Rf, loaded in/with: DCM and dried, initial waste: 0 mL, fraction size: 9 mL 13×100 mm, and eluted with acetone in dichloromethane 0% [75 mL], 5% [51 mL], 10% [150 mL],10-35% [300 mL], 40% [300 mL]. The fractions were collected to give 1.34 g (70%). $^1$H NMR (400 MHz, CDCl$_3$) δ 8.51 (d, J=1.8 Hz, 1H), 8.22 (d, J=8.3 Hz, 1H), 7.84 (dd, J=8.3, 5.8 Hz, 1H), 7.60 (br. s., 1H), 7.50 (d, J=7.5 Hz, 2H), 7.43-7.36 (m, 2H), 7.34 (d, J=7.0 Hz, 1H), 6.24-6.10 (m, 1H), 4.07 (dd, J=11.9, 2.9 Hz, 1H), 3.90 (dd, J=11.8, 2.5 Hz, 1H), 3.83 (s, 3H), 3.57 (td, J=11.9, 1.9 Hz, 1H), 3.36 (td, J=11.8, 1.5 Hz, 1H), 3.13-2.99 (m, 1H), 2.85 (d, J=5.3 Hz, 3H), 2.26 (s, 3H), 2.10 (d, J=15.6 Hz, 1H), 1.59 (s, 2H), 1.00 (d, J=9.5 Hz, 1H). Mass found 526 [M+H]$^+$.

Step 6: (1S)-1-Cyclopropyl-1-[3-(dimethyl-1H-1,2,3-triazol-5-yl)-6-fluoro-5-[(S)-oxan-4-yl)phenyl)methyl]-5H-pyrido[3,2-b]indol-7-yl]ethan-1-ol and (1R)-1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol A 10-20 mL microwave vial was charged with (S)-1-(3-(1,4-dimethyl-1H-1,2,3-triazol-5-yl)-6-fluoro-5-(phenyl(tetrahydro-2H-pyran-4-yl)methyl)-5H-pyrido[3,2-b]indol-7-yl)ethanone (221 mg, 0.444 mmol) and sealed. The vial was evacuated and purged with nitrogen. THF (2961 μL) was added and the mixture cooled to −78° C. Cyclopropylmagnesium bromide (1.0M in 1-methyltetrahydrofuran, 2670 μL, 2.66 mmol) was added drop wise. After 15 min, the vial was removed from the ice bath and allowed to warm to room temperature. After 2.5 h, the reaction was quenched with a saturated solution of ammonium chloride and diluted with ethyl acetate. The contents of the flask were transferred to a separatory funnel, and the layers were separated. The organics were washed with brine, dried with magnesium sulfate, concentrated under reduced pressure, and purified by silica gel column chromatography (12 g ISCO RediSep Rf, loaded in/with: DCM and dried, initial waste: 0 mL, fraction size: 9 mL 13×100 mm, and eluted with acetone in dichloromethane 0% [75 mL], 0-10% [201 mL], 15% [201 mL], 15-60% [300 mL], 60% [150 mL]). The fractions containing both diastereomers were collected to give 189 mg. The diastereomers were further purified by preparative HPLC: Column: Waters XBridge C18 100×30 mm 5 u, Solvents: A: 95:5 water/Acetonitrile; B: 95:5 Acetonitrile/water; Buffer: 10 mm ammonium acetate, % B gradient (time): 33% (40 min), Flow Rate: 30 mL/min, UV monitored: 254 nm. The diastereomers were separated using Chiral SFC to give Diastereomers A and B: Chiralcel OJ-H prep column, 30×250 mm, 5 μm; Mobile phase: 10% MeOH in CO$_2$, 150 bar; Temp: 35° C. Flow rate: 70 mL/min. for 35 min. UV monitored at 220 nm. Injection: 0.25 mL of ~50 mg/mL in MeOH. Diastereomer A: $^1$H NMR (400 MHz, CDCl$_3$) δ 8.42 (s, 1H), 8.13 (d, J=8.3 Hz, 1H), 7.66 (dd, J=7.9, 6.7 Hz, 1H), 7.58-7.45 (m, 3H), 7.41-7.28 (m, 3H), 6.16 (br. s., 1H), 4.05 (d, J=9.3 Hz, 1H), 3.87 (d, J=9.3 Hz, 1H), 3.80 (s, 3H), 3.56 (t, J=11.2 Hz, 1H), 3.40-3.29 (m, 1H), 3.05 (d, J=8.8 Hz, 1H), 2.37 (d, J=18.1 Hz, 1H), 2.24 (s, 3H), 2.07 (d, J=13.3 Hz, 1H), 1.80 (s, 3H), 1.71-1.46 (m, 3H), 1.01 (d, J=11.8 Hz, 1H), 0.70-0.57 (m, 2H), 0.53 (dd, J=8.2, 5.6 Hz, 2H). SFC retention time: 25 min. HPLC retention time: 25 min. Mass found 539 [M+H]$^+$. Diastereomer B: $^1$H NMR (400 MHz, CDCl$_3$) δ 8.43 (d, J=1.5 Hz, 1H), 8.14 (d, J=8.3 Hz, 1H), 7.67 (dd, J=8.2, 6.7 Hz, 1H), 7.56-7.45 (m, 3H), 7.40-7.33 (m, 2H), 7.33-7.28 (m, 1H), 6.17 (br. s., 1H), 4.05 (dd, J=11.5, 2.5 Hz, 1H), 3.89 (dd, J=11.7, 2.4 Hz, 1H), 3.80 (s, 3H), 3.56 (td, J=11.8, 1.8 Hz, 1H), 3.40-3.30 (m, 1H), 3.04 (d, J=7.8 Hz, 1H), 2.27-2.14 (m, 4H), 2.08 (d, J=13.6 Hz, 1H), 1.81 (s, 3H), 1.70-1.45 (m, 3H), 1.03 (d, J=13.1 Hz, 1H), 0.70-0.58 (m, 2H), 0.57-0.45 (m, 2H). SFC retention time 30 min. HPLC retention time: 28 min. Mass found 539 [M+H]$^+$.

Alternate synthesis of 3-bromo-7-chloro-6-fluoro-5H-pyrido[3,2-b]indole

Step 1:
5-Bromo-N-(3-chloro-2-fluorophenyl)pyridin-3-amine

A 20 mL microwave vial was charged with 3-chloro-2-fluoroaniline (473 μL, 4.22 mmol) and diluted with 1,4-dioxane (16.9 mL). To that solution was added 3,5-dibromopyridine (1000 mg, 4.22 mmol), sodium tert-butoxide (568 mg, 5.91 mmol), xantphos (48.9 mg, 0.0840 mmol), and tris(dibenzylideneacetone)dipalladium(0) (38.7 mg, 0.0420 mmol). The vial was sealed and degassed using ultra pure argon and sonication for 1 min. The vial was placed into a reaction block preheated to 80° C. After 1 h, the contents of the vial were transferred to a flask, and the volatiles were concentrated under reduced pressure. The resulting brown solids were dissolved with ethyl acetate and water. The contents of the flask were transferred into a separatory funnel where the layers were separated. The organic was washed with water and brine, dried over magnesium sulfate, and purified by silica gel flash chromatography. Upon dissolving the sample with DCM, a white solid persisted, which was collected by filtration and washed with hexanes to give 541 mg of desired product. The supernatant was concentrated under reduced pressure and purified by silica gel column chromatography (24 g ISCO RediSep Rf, loaded in/with: DCM and dried, initial waste: 0 mL, fraction size: 9 mL 13×100 mm, and eluted with ethyl acetate in dichloromethane 0% [75 mL], 0-5% [201 mL], 5% [300 mL]). The fractions were collected and combined with the previously collected solids to give 921 mg (72%). $^1$H NMR (400 MHz, CDCl$_3$) δ 8.35 (d, J=2.5 Hz, 1H), 8.31 (d, J=1.8 Hz, 1H), 7.58 (t, J=2.1 Hz, 1H), 7.22-7.14 (m, 1H), 7.08-7.01 (m, 2H), 5.86 (br. s., 1H). Mass found 302 [M+H]$^+$.

Step 2:
3-Bromo-7-chloro-6-fluoro-5H-pyrido[3,2-b]indole

A 10-20 mL microwave vial was charged with 5-bromo-N-(3-chloro-2-fluorophenyl)pyridin-3-amine (541 mg, 1.79 mmol) and dissolved in TFA (8971 μL). To that solution was added palladium (II) acetate (604 mg, 2.69 mmol). The vial was sealed and placed into an oil bath preheated to 85° C. After 30 min, an additional 200 mg (0.50 equiv.) of palladium acetate was added, and the reaction stirred 1 h longer. After 1 h, the contents of the microwave vial were transferred into a round bottom flask, and the TFA was concentrated under reduced pressure to give a brown solid. The solids were dissolved with ethyl acetate and 35 mL of aqueous ammonia (27-35%) was added and stirred for 15 min. The contents of the flask were transferred into a separatory funnel, and the layers were separated. The organic was washed with brine (3×) and set aside. The combined aqueous was extracted with ethyl acetate (2×), and the aqueous discarded. The combined organics were dried over magnesium sulfate, concentrated under reduced pressure, and purified by silica gel column chromatography (40 g ISCO RediSep Rf, loaded in/with: DCM and dried, initial waste: 0 mL, fraction size: 21 mL 16×150 mm, and eluted with ethyl acetate in dichloromethane 0% [150 mL], 0-5% [150 mL], 5% [400 mL]). The fractions containing product were collected, and the volatiles were removed under reduced pressure to give the title compound (194 mg, 36%). $^1$H NMR (400 MHz, CDCl$_3$) δ 8.65 (d, J=1.8 Hz, 1H), 8.30 (br. s., 1H), 8.02 (d, J=8.5 Hz, 1H), 7.96 (d, J=2.0 Hz, 1H), 7.33 (dd, J=8.5, 6.3 Hz, 1H). Mass found 299 [M+H]$^+$.

Example 433 & Example 434

(1S)-1-cyclopropyl-1-{6-fluoro-3-[4-($^2$H$_3$)methyl-1-methyl-1H-1,2,3-triazol-5-yl]-5-[(S)-oxan-4-yl)phenyl)methyl]-5H-pyrido[3,2-b]indol-7-yl}ethan-1-ol
and (1R)-1-cyclopropyl-1-{6-fluoro-3-[4-($^2$H$_3$) methyl-1-methyl-1H-1,2,3-triazol-5-yl]-5-[(S)-oxan-4-yl(phenyl)methyl]-5H-pyrido[3,2-b]indol-7-yl}ethan-1-ol

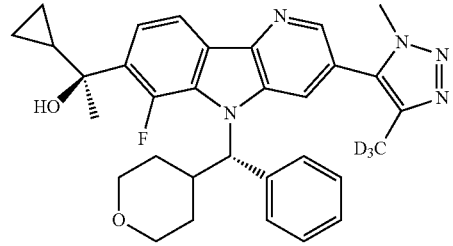

Diastereomer A, Example 433

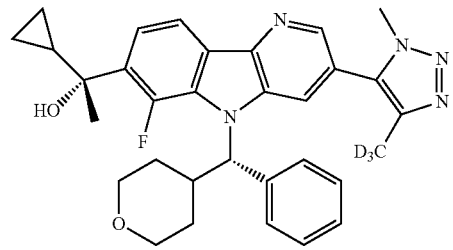

Diastereomer B, Example 434

Diastereomeric mixture 1-cyclopropyl-1-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol was prepared according to the procedures described for Examples 431 and 432 substituting 1,4-dimethyl-5-(tributylstannyl)-1H-1,2,3-triazole with 4-($^2$H$_3$)methyl-1-methyl-5-(tributylstannyl)-1H-1,2,3-triazole in Step 4. Separation of the diastereomeric mixture generated in the last step was performed using chiral prep SFC to give Diastereomer A and B: ChiralCel OJ-H prep column, 30×250 mm, 5 μm; Mobile phase: 10% MeOH in CO$_2$, 150 bar; Temp: 35° C. Flow rate: 70 mL/min. for 35 min. UV monitored at 220 nm. Injection: 0.25 mL of ~50 mg/mL in MeOH (34 8 mg purified by stacked injection). Diastereomer A: $^1$H NMR (400 MHz, CDCl$_3$) δ 8.44 (d, J=1.8 Hz, 1H), 8.14 (d, J=8.3 Hz, 1H), 7.65 (dd, J=8.3, 6.5 Hz, 1H), 7.54-7.46 (m, 3H), 7.40-7.34 (m, 2H), 7.31 (t, J=7.5 Hz, 1H), 6.16 (br. s., 1H), 4.06 (d, J=9.0 Hz, 1H), 3.90 (d, J=12.0 Hz, 1H), 3.81 (s, 3H), 3.57

(t, J=10.9 Hz, 1H), 3.41-3.31 (m, 1H), 3.04 (br. s., 1H), 1.80 (s, 3H), 1.27 (s, 5H), 1.02 (d, J=13.8 Hz, 1H), 0.69-0.58 (m, 2H), 0.57-0.48 (m, 2H). SFC retention time: 25 min. Mass found 543 [M+H]⁺. Diastereomer B: ¹H NMR (500 MHz, DMSO-d₆) δ 8.54 (br. s., 1H), 8.01 (d, J=8.4 Hz, 1H), 7.78-7.06 (m, 7H), 6.00 (br. s., 1H), 4.20-3.82 (m, 4H), 3.77 (d, J=10.3 Hz, 1H), 3.49 (t, J=11.4 Hz, 1H), 3.43-3.35 (m, 1H), 3.29 (t, J=11.6 Hz, 1H), 1.88-1.46 (m, 6H), 1.35 (d, J=9.9 Hz, 2H), 1.12 (d, J=12.5 Hz, 1H), 0.65-0.18 (m, 4H). SFC retention time 30 min. Mass found 543 [M+H]⁺.

Examples 435 & 436

1-Cyclopropyl-1-[3-(dimethyl-1H-1,2,3-triazol-5-yl)-6-fluoro-5-[(S)-(2-fluorophenyl)(oxan-4-yl)methyl]-5H-pyrido[3,2-b]indol-7-yl]ethan-1-ol

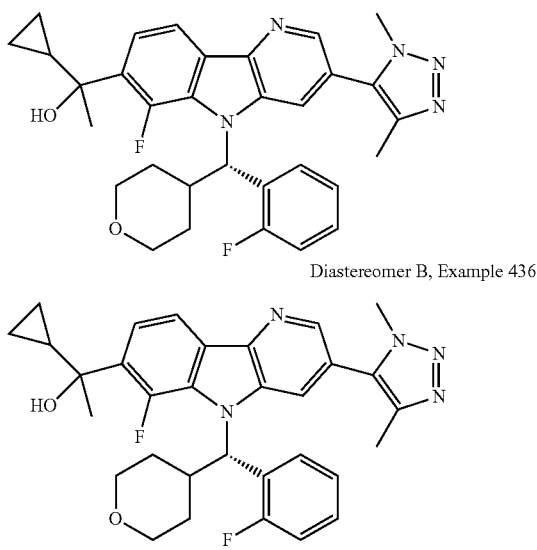

Diastereomer A, Example 435

Diastereomer B, Example 436

Diastereomeric mixture 1-cyclopropyl-1-[3-(dimethyl-1H-1,2,3-triazol-5-yl)-6-fluoro-5-[(S)-(2-fluorophenyl)(oxan-4-yl)methyl]-5H-pyrido[3,2-b]indol-7-yl]ethan-1-ol was prepared according to the procedures described for Example 431 and 432 substituting (R)-phenyl(tetrahydro-2H-pyran-4-yl)methanol for (R)-(2-fluorophenyl)(tetrahydro-2H-pyran-4-yl)methanol in Step 3. The diastereomers generated in the last step were separated by preparative HPLC: Column: Waters XBridge C18 100×30 mm 5 u, Solvents: A:95:5 water/Acetonitrile; B:95:5 Acetonitrile/water; Buffer:10 mm ammonium acetate, % B gradient (time): 32% (50 min), Flow Rate: 30 mL/min; 5 injections. Diastereomer A: ¹H NMR (400 MHz, CDCl₃) δ 8.45 (s, 1H), 8.12 (d, J=8.3 Hz, 1H), 7.77-7.60 (m, 3H), 7.37-7.29 (m, 1H), 7.26-7.19 (m, 1H), 7.06-6.97 (m, 1H), 6.37 (br. s., 1H), 4.10-4.02 (m, 1H), 3.96-3.81 (m, 4H), 3.59-3.50 (m, 1H), 3.43-3.29 (m, 2H), 3.17-2.99 (m, 1H), 2.43-2.34 (m, 1H), 2.29 (br. s., 3H), 1.97 (d, J=15.3 Hz, 1H), 1.80 (s, 3H), 1.59 (s, 1H), 0.97-0.81 (m, 2H), 0.70-0.56 (m, 2H), 0.50 (d, J=6.5 Hz, 2H). Mass found 557 [M+H]⁺. HPLC retention time: 39 min. Diastereomer B: ¹H NMR (400 MHz, CDCl₃) δ 8.12 (d, J=8.3 Hz, 1H), 7.77-7.60 (m, 3H), 7.36-7.29 (m, 1H), 7.26-7.20 (m, 1H), 7.06-6.98 (m, 1H), 6.38 (br. s., 1H), 4.10-4.02 (m, 1H), 3.96-3.81 (m, 4H), 3.60-3.50 (m, 1H), 3.42-3.29 (m, 2H), 3.20-2.97 (m, 1H), 2.29 (br. s., 3H), 2.08-2.02 (m, 1H), 1.97 (d, J=13.6 Hz, 1H), 1.80 (s, 3H), 1.59 (br. s., 2H), 1.10 (br. s., 1H), 0.95-0.80 (m, 1H), 0.60 (t, J=7.3 Hz, 2H), 0.53 (d, J=6.5 Hz, 2H). Mass found 557 [M+H]⁺. HPLC retention time: 44 min.

Example 437 & Example 438

1-Cyclopropyl-1-{6-fluoro-5-[(S)-(2-fluorophenyl)(oxan-4-yl)methyl]-3-[4-(²H₃)methyl-1-methyl-1H-1,2,3-triazol-5-yl]-5H-pyrido[3,2-b]indol-7-yl}ethan-1-ol

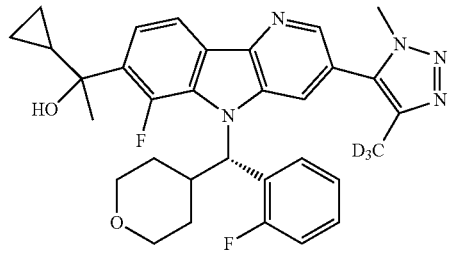

Diastereomer A, Example 437

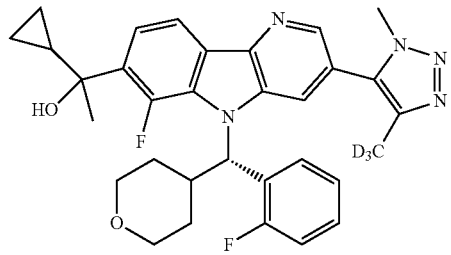

Diastereomer B, Example 438

Diastereomeric mixture 1-cyclopropyl-1-{6-fluoro-5-[(S)-(2-fluorophenyl)(oxan-4-yl)methyl]-3-[4-(²H₃)methyl-1-methyl-1H-1,2,3-triazol-5-yl]-5H-pyrido[3,2-b]indol-7-yl}ethan-1-ol was prepared according to the procedures described for Example 431 and 432 substituting (R)-phenyl(tetrahydro-2H-pyran-4-yl)methanol for (R)-(2-fluorophenyl)(tetrahydro-2H-pyran-4-yl)methanol in Step 3 and 1,4-dimethyl-5-(tributylstannyl)-1H-1,2,3-triazole with 4-(²H₃)methyl-1-methyl-5-(tributylstannyl)-1H-1,2,3-triazole in Step 4. The diastereomers generated in the last step were separated by preparative HPLC: Column: Waters XBridge C18 100×30 mm 5 u, Solvents: A:95:5 water/Acetonitrile; B:95:5 Acetonitrile/water; Buffer:10 mm ammonium acetate, % B gradient (time): 32% (50 min), Flow Rate: 30 mL/min; 5 injections. Diastereomer A: ¹H NMR (500 MHz, DMSO-d₆) δ 8.52 (br. s., 1H), 8.30-8.06 (m, 2H), 8.03-7.91 (m, 2H), 7.59 (br. s., 1H), 7.32 (d, J=8.1 Hz, 2H), 7.10 (br. s., 1H), 6.30 (br. s., 1H), 4.10 (br. s., 1H), 3.89 (br. s., 4H), 3.78 (d, J=9.9 Hz, 1H), 3.49 (t, J=11.6 Hz, 1H), 3.43-3.34 (m, 1H), 3.27 (t, J=11.6 Hz, 1H), 3.17 (br. s., 3H), 1.81 (d, J=12.5 Hz, 1H), 1.73 (br. s., 3H), 1.54 (br. s., 1H), 1.39 (br. s., 2H), 1.06 (br. s., 1H). HPLC retention time: 33 min. Diastereomer B: ¹H NMR (500 MHz, DMSO-d₆) δ 8.52 (br. s., 1H), 8.30-8.08 (m, 2H), 8.03-7.92 (m, 2H), 7.61 (br. s., 1H), 7.33 (dd, J=15.0, 7.0 Hz, 2H), 7.09 (br. s., 1H), 6.30 (br. s., 1H), 4.07 (br. s., 1H), 3.96-3.83 (m, 4H), 3.78 (d, J=9.9 Hz, 1H), 3.54-3.41 (m, 2H), 3.26 (t, J=11.7 Hz, 1H), 3.17 (br. s., 3H), 1.82 (d, J=12.8 Hz, 1H), 1.72 (br. s., 3H), 1.57-1.29 (m, 3H), 1.04 (d, J=11.0 Hz, 1H). HPLC retention time: 36 min. Mass found 557 [M+H]⁺.

Examples 439 & 440

1-Cyclopropyl-1-[6-fluoro-3-(4-methoxy-1-methyl-1H-1,2,3-triazol-5-yl)-5-[(S)-oxan-4-yl)phenyl)methyl]-5H-pyrido[3,2-b]indol-7-yl]ethan-1-ol

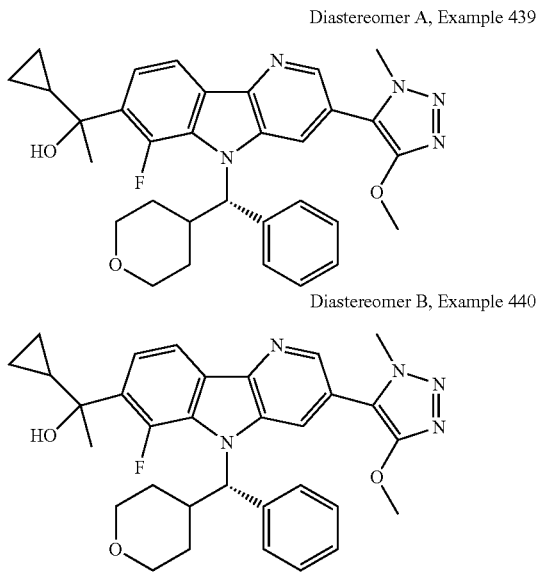

Diastereomer A, Example 439

Diastereomer B, Example 440

Step 1: (S)-7-Chloro-6-fluoro-3-(4-methoxy-1-methyl-1H-1,2,3-triazol-5-yl)-5-(phenyl(tetrahydro-2H-pyran-4-yl)methyl)-5H-pyrido[3,2-b]indole A 2.0-5.0 mL microwave vial was charged with 4-methoxy-1-((trimethylsilyl)methyl)-1H-1,2,3-triazole (156 mg, 0.844 mmol) and diluted with NMP (2111 μL). (S)-3-bromo-7-chloro-6-fluoro-5-(phenyl(tetrahydro-2H-pyran-4-yl)methyl)-5H-pyrido[3,2-b]indole (200 mg, 0.422 mmol) was added followed by bis(triphenylphosphine)palladium(II) dichloride (29.6 mg, 0.042 mmol) and tetramethylammonium acetate (112 mg, 0.844 mmol). The vial was sealed and degassed using ultra pure argon and sonication for 1 min. The vial was placed into a reaction block preheated to 95° C. After 2 h, the reaction was diluted with ethyl acetate and a saturated solution of sodium bicarbonate. The contents of the vial were transferred into a separatory funnel where the layers were separated. The organics were washed with water (2×) and brine, dried with magnesium sulfate, concentrated under reduced pressure, and purified by silica gel column chromatography (24 g ISCO RediSep Rf, loaded in/with: DCM and dried, initial waste: 0 mL, fraction size: 18 mL 16×150 mm, and eluted with acetone in dichloromethane 0% [75 mL], 0-20% [150 mL], 20% [300 mL], 20-60% [300 mL], 60% [200 mL]). Collected fractions to give 218 mg (100%) as a yellow, amorphous solid. ¹H NMR (400 MHz, CDCl₃) δ 8.61 (d, J=1.8 Hz, 1H), 8.08 (d, J=8.3 Hz, 1H), 7.87 (br. s., 1H), 7.73-7.63 (m, 1H), 7.59-7.44 (m, 2H), 7.42-7.29 (m, 3H), 6.01 (br. s., 1H), 4.15 (s, 3H), 4.06 (dd, J=11.8, 2.8 Hz, 1H), 3.97 (s, 3H), 3.89 (dd, J=12.0, 2.5 Hz, 1H), 3.54 (td, J=11.9, 1.9 Hz, 1H), 3.44-3.31 (m, 1H), 3.14-2.99 (m, 1H), 2.09-1.95 (m, 1H), 1.67-1.42 (m, 2H), 1.02 (d, J=12.0 Hz, 1H). Mass found 505 [M+H]⁺.

Step 2: (S)-1-(6-Fluoro-3-(4-methoxy-1-methyl-1H-1,2,3-triazol-5-yl)-5-(phenyl(tetrahydro-2H-pyran-4-yl)methyl)-5H-pyrido[3,2-b]indol-7-yl)ethanone Following a procedure analogous to the one described in the synthesis of 1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol, (S)-7-chloro-6-fluoro-3-(4-methoxy-1-methyl-1H-1,2,3-triazol-5-yl)-5-(phenyl(tetrahydro-2H-pyran-4-yl)methyl)-5H-pyrido[3,2-b]indole (218 mg, 0.431 mmol) was converted to (S)-1-(6-fluoro-3-(4-methoxy-1-methyl-1H-1,2,3-triazol-5-yl)-5-(phenyl(tetrahydro-2H-pyran-4-yl)methyl)-5H-pyrido[3,2-b]indol-7-yl)ethanone (152 mg, 0.296 mmol, 69%). ¹H NMR (400 MHz, CDCl₃) δ 8.65 (d, J=1.8 Hz, 1H), 8.18 (d, J=8.0 Hz, 1H), 7.90 (br. s., 1H), 7.72-7.64 (m, 1H), 7.59-7.51 (m, 2H), 7.42-7.29 (m, 3H), 6.13 (br. s., 1H), 4.14 (s, 3H), 4.07 (dd, J=11.9, 2.4 Hz, 1H), 3.97 (s, 3H), 3.89 (dd, J=11.7, 2.6 Hz, 1H), 3.55 (td, J=11.8, 1.8 Hz, 1H), 3.43-3.31 (m, 1H), 3.08 (d, J=7.8 Hz, 1H), 2.83 (d, J=5.0 Hz, 3H), 2.04 (d, J=13.1 Hz, 1H), 1.69-1.45 (m, 2H), 1.00 (d, J=12.5 Hz, 1H). Mass found 513 [M+H]⁺.

Step 3: 1-Cyclopropyl-1-[6-fluoro-3-(4-methoxy-1-methyl-1H-1,2,3-triazol-5-yl)-5-[(S)-oxan-4-yl)phenyl)methyl]-5H-pyrido[3,2-b]indol-7-yl]ethan-1-ol Following a procedure analogous to the one described in the synthesis of 1-cyclopropyl-1-[3-(dimethyl-1H-1,2,3-triazol-5-yl)-6-fluoro-5-[(S)-oxan-4-yl(phenyl)methyl]-5H-pyrido[3,2-b]indol-7-yl]ethan-1-ol, 1-cyclopropyl-1-[6-fluoro-3-(4-methoxy-1-methyl-1H-1,2,3-triazol-5-yl)-5-[(S)-oxan-4-yl(phenyl)methyl]-5H-pyrido[3,2-b]indol-7-yl]ethan-1-ol (75 mg, 0.146 mmol) was converted to 1-cyclopropyl-1-(6-fluoro-3-(4-methoxy-1-methyl-1H-1,2,3-triazol-5-yl)-5-((S)-phenyl(tetrahydro-2H-pyran-4-yl)methyl)-5H-pyrido[3,2-b]indol-7-yl)ethanol. The diastereomers were separated by preparative HPLC: 58 mg dissolved in 3 mL of methanol (19 mg/mL), Column: Waters XBridge C18 100×30 mm 5 u, Solvents: A:95:5 water/acetonitrile; B:95:5 acetonitrile/water; Buffer:10 mm ammonium acetate, % B gradient (time): 35% (40 min), Flow Rate: 30 mL/min. Diastereomer A: ¹H NMR (400 MHz, CDCl₃) δ 8.58 (d, J=1.5 Hz, 1H), 8.11 (d, J=8.3 Hz, 1H), 7.80 (s, 1H), 7.63 (dd, J=8.3, 6.5 Hz, 1H), 7.53 (d, J=7.5 Hz, 2H), 7.41-7.29 (m, 3H), 6.12 (br. s., 1H), 4.14 (s, 3H), 4.06 (dd, J=11.5, 2.3 Hz, 1H), 3.94 (s, 3H), 3.88 (dd, J=11.7, 2.4 Hz, 1H), 3.56 (td, J=11.8, 1.8 Hz, 1H), 3.41-3.29 (m, 1H), 3.06 (d, J=8.0 Hz, 1H), 2.11-1.98 (m, 2H), 1.79 (s, 3H), 1.71-1.42 (m, 2H), 1.03 (d, J=11.8 Hz, 1H), 0.92-0.78 (m, 1H), 0.69-0.58 (m, 2H), 0.57-0.45 (m, 2H). HPLC retention time: 33 min. Mass found 555 [M+H]⁺. Diastereomer B: ¹H NMR (400 MHz, CDCl₃) δ 8.58 (d, J=1.8 Hz, 1H), 8.11 (d, J=8.3 Hz, 1H), 7.81 (s, 1H), 7.62 (dd, J=8.3, 6.5 Hz, 1H), 7.53 (d, J=7.5 Hz, 2H), 7.41-7.28 (m, 3H), 6.11 (br. s., 1H), 4.14 (s, 3H), 4.06 (dd, J=11.8, 2.5 Hz, 1H), 3.95 (s, 3H), 3.88 (dd, J=11.8, 2.5 Hz, 1H), 3.55 (td, J=11.9, 1.9 Hz, 1H), 3.41-3.28 (m, 1H), 3.06 (d, J=7.8 Hz, 1H), 2.14-1.97 (m, 2H), 1.79 (s, 3H), 1.70-1.43 (m, 2H), 1.03 (d, J=12.8 Hz, 1H), 0.93-0.79 (m, 1H), 0.69-0.57 (m, 2H), 0.56-0.47 (m, 2H). HPLC retention time: 37 min. Mass found [M+H]⁺.

Example 441 & Example 442

2-[3-(Dimethyl-1H-1,2,3-triazol-5-yl)-6-fluoro-5-[(S)-oxan-4-yl(phenyl)methyl]-5H-pyrido[3,2-b]indol-7-yl]-1,1,1-trifluoropropan-2-ol

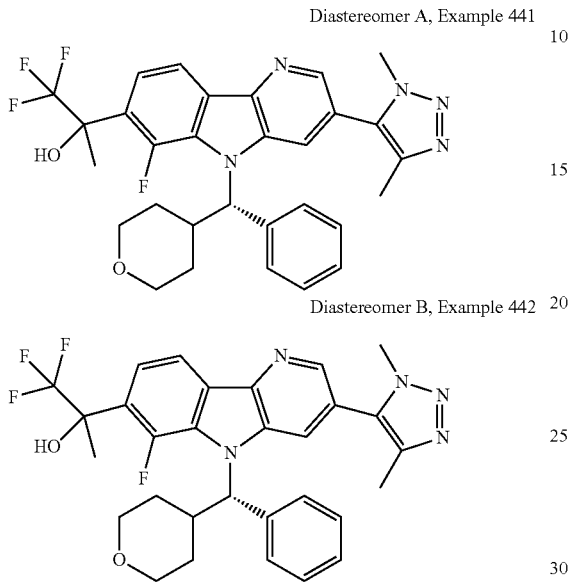

Diastereomer A, Example 441

Diastereomer B, Example 442

(S)-1-(3-(1,4-Dimethyl-1H-1,2,3-triazol-5-yl)-6-fluoro-5-(phenyl(tetrahydro-2H-pyran-4-yl)methyl)-5H-pyrido[3,2-b]indol-7-yl)ethanone (100 mg, 0.201 mmol) was dissolved in THF (4020 µL). To that solution was added (trifluoromethyl)trimethylsilane (297 µL, 2.01 mmol), and the mixture was cooled to 0° C. TBAF (1.0 M in THF, 52.5 mg, 0.201 mmol) was added drop wise. After 2.5 h, 2 mL of 3N aq. HCl was added. The mixture was diluted with ethyl acetate and quenched with a 1.5 M aq. potassium phosphate solution. The contents of the flask were transferred into a reparatory funnel where the layers were separated. The organic was washed with water (2×) and brine (2×), dried with magnesium sulfate, concentrated under reduced pressure, and purified by silica gel column chromatography (12 g ISCO RediSep Rf, loaded in/with: DCM and dried, initial waste: 0 mL, fraction size: 9 mL 13×100 mm, and eluted with acetone in dichloromethane 0% [75 mL], 0-10% [201 mL], 15% [201 mL], 15-60% [300 mL], 60% [150 mL]). The diastereomers were separated by preparative HPLC: The crude mixture was dissolved in 2.5 mL of methanol. Column: Waters XBridge C18 100×30 mm 5 u, Solvents: A:95:5 water/Acetonitrile; B:95:5 Acetonitrile/water; Buffer:10 mm ammonium acetate, % B gradient (time): 38% (22 min), Flow Rate: 30 mL/min, ~16 mg/mL per injection. Diastereomer A (17.5 mg, 0.0300 mmol, 15%): $^1$H NMR (400 MHz, CDCl$_3$) δ 8.47 (d, J=1.8 Hz, 1H), 8.22 (d, J=8.3 Hz, 1H), 7.65 (dd, J=8.3, 6.8 Hz, 1H), 7.56 (s, 1H), 7.48 (d, J=7.5 Hz, 2H), 7.41-7.29 (m, 3H), 6.14 (br. s., 1H), 4.06 (dd, J=11.7, 2.6 Hz, 1H), 3.89 (dd, J=11.8, 2.8 Hz, 1H), 3.82 (s, 3H), 3.56 (td, J=11.9, 1.8 Hz, 1H), 3.47 (d, J=6.3 Hz, 1H), 3.34 (td, J=11.9, 1.9 Hz, 1H), 3.10-2.96 (m, 1H), 2.25 (s, 3H), 2.13-2.02 (m, 4H), 1.70-1.44 (m, 2H), 1.01 (d, J=12.5 Hz, 1H). HPLC retention time: 16 min. Mass found 567 [M+H]$^+$. Diastereomer B (19.5 mg, 0.0340 mmol, 17%). $^1$H NMR (400 MHz, CDCl$_3$) δ 8.47 (d, J=1.8 Hz, 1H), 8.22 (d, J=8.3 Hz, 1H), 7.68 (dd, J=8.3, 6.8 Hz, 1H), 7.56 (s, 1H), 7.48 (d, J=7.3 Hz, 2H), 7.41-7.28 (m, 3H), 6.14 (br. s., 1H), 4.06 (dd, J=11.8, 2.5 Hz, 1H), 3.89 (dd, J=11.5, 2.5 Hz, 1H), 3.81 (s, 3H), 3.56 (td, J=11.9, 1.9 Hz, 1H), 3.48 (d, J=5.8 Hz, 1H), 3.35 (td, J=11.8, 1.8 Hz, 1H), 3.11-2.97 (m, 1H), 2.25 (s, 3H), 2.14-2.02 (m, 4H), 1.71-1.42 (m, 2H), 1.00 (d, J=13.1 Hz, 1H). HPLC retention time: 19 min. Mass found 567 [M+H]$^+$.

Examples 443 & 444

1-Cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol

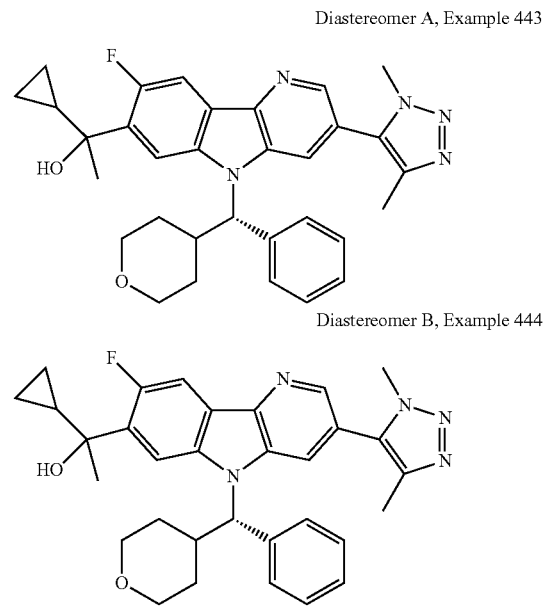

Diastereomer A, Example 443

Diastereomer B, Example 444

Step 1: (S)-1-(3-(1,4-Dimethyl-1H-1,2,3-triazol-5-yl)-8-fluoro-5-(phenyl(tetrahydro-2H-pyran-4-yl)methyl)-5H-pyrido[3,2-b]indol-7-yl)ethanone 1-Cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol was prepared according to the procedures described in the synthesis of Example 431 and 432 by using 3-bromo-7-chloro-8-fluoro-5H-pyrido[3,2-b]indole instead of 3-bromo-7-chloro-6-fluoro-5H-pyrido[3,2-b]indole. The regioisomers were separated at Step 5 by chiral chromatography: Column: Chiralpak OD 21×250 mm 10µ, Solvents: A: 0.1% diethylamine/heptane; B: Ethanol, % B gradient (time): 15% isocratic (50 min), Flow Rate: 15 mL/min; ~20 mg per injection. Peak 1 was isolated as (S)-1-(3-(1,4-dimethyl-1H-1,2,3-triazol-5-yl)-8-fluoro-5-(phenyl(tetrahydro-2H-pyran-4-yl)methyl)-5H-pyrido[3,2-b]indol-7-yl)ethanone. $^1$H NMR (400 MHz, CDCl$_3$) δ 8.50 (d, J=1.8 Hz, 1H), 8.30 (d, J=5.3 Hz, 1H), 8.13 (d, J=10.5 Hz, 1H), 7.64 (d, J=1.8 Hz, 1H), 7.46-7.40 (m, 2H), 7.39-7.29 (m, 3H), 5.56 (d, J=10.5 Hz, 1H), 4.09-4.02 (m, 1H), 3.90 (s, 3H), 3.89-3.82 (m, 1H), 3.59-3.49 (m, 1H), 3.41-3.29 (m, 1H), 3.09 (d, J=11.3 Hz, 1H), 2.82 (d, J=5.8 Hz, 3H), 2.31 (s, 3H), 2.00 (d, J=13.6 Hz, 1H), 1.41 (qd, J=12.4, 4.6 Hz, 2H), 1.09 (d, J=12.8 Hz, 1H). Mass found 497 [M+H]+.

Step 2: 1-Cyclopropyl-1-[3-(dimethyl-1H-1,2,3-triazol-5-yl)-8-fluoro-5-[(S)-oxan-4-yl)phenyl)methyl]-5H-pyrido[3,2-b]indol-7-yl]ethan-1-ol 1-Cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol was prepared according to the procedures described in the synthesis of 1-cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol. The diastereomers generated in the last step were separated by Chiral SFC: Chiralpak OJ-H prep column, 30×250 mm, 5 μm. Mobile phase: 20% MeOH in CO$_2$, 130 bar. Temp: 35° C. Flow rate: 70 mL/min. for 12 min. UV monitored at 270 nm. Injection: 0.4 mL of ~10 mg/mL in MeOH (41 mg purified by stacked injection). Diastereomer A: $^1$H NMR (400 MHz, CDCl$_3$) δ 8.44 (d, J=1.8 Hz, 1H), 8.06-7.97 (m, 2H), 7.57 (d, J=1.8 Hz, 1H), 7.43 (d, J=7.0 Hz, 2H), 7.38-7.28 (m, 3H), 5.54 (d, J=10.5 Hz, 1H), 4.06 (dd, J=11.8, 2.8 Hz, 1H), 3.93-3.83 (m, 4H), 3.62-3.48 (m, 1H), 3.36 (td, J=11.9, 2.1 Hz, 1H), 3.16-2.99 (m, 1H), 2.30 (s, 3H), 2.02 (d, J=13.6 Hz, 1H), 1.94 (d, J=2.3 Hz, 1H), 1.76 (d, J=1.3 Hz, 3H), 1.69-1.51 (m, 1H), 1.47-1.35 (m, 1H), 1.14 (d, J=12.0 Hz, 1H), 0.93-0.80 (m, 1H), 0.67-0.54 (m, 2H), 0.50-0.42 (m, 2H). SFC retention time: 7.35 min. Mass found 539 [M+H]+. Diastereomer B: $^1$H NMR (400 MHz, CDCl$_3$) δ 8.43 (d, J=1.8 Hz, 1H), 8.07-7.98 (m, 2H), 7.57 (d, J=1.8 Hz, 1H), 7.46-7.40 (m, 2H), 7.38-7.29 (m, 3H), 5.54 (d, J=10.3 Hz, 1H), 4.05 (dd, J=11.7, 2.9 Hz, 1H), 3.92-3.84 (m, 4H), 3.59-3.50 (m, 1H), 3.35 (td, J=11.9, 2.1 Hz, 1H), 3.08 (q, J=10.9 Hz, 1H), 2.30 (s, 3H), 2.04-1.94 (m, 2H), 1.76 (d, J=1.0 Hz, 3H), 1.68-1.52 (m, 1H), 1.48-1.35 (m, 1H), 1.11 (d, J=13.1 Hz, 1H), 0.93-0.81 (m, 1H), 0.69-0.57 (m, 2H), 0.51-0.40 (m, 2H). SFC retention time: 9.31 min. Mass found 539 [M+H]+.

Examples 445 & 446

1-Cyclopropyl-1-{8-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol Diastereomer A, Example 445

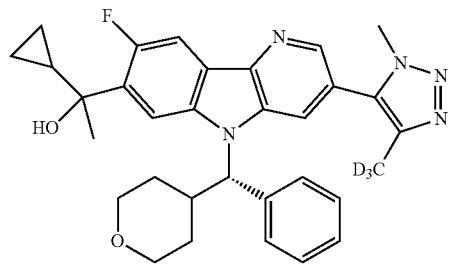

Diastereomer B, Example 446

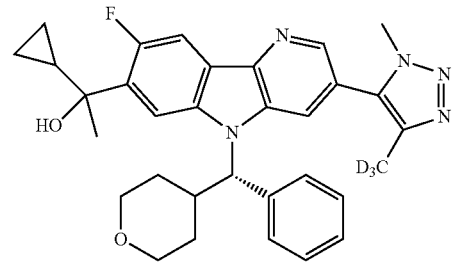

1-Cyclopropyl-1-{8-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}ethan-1-ol was prepared according to the procedures described for 1-cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol. In step 3, 1,4-dimethyl-5-(tributylstannyl)-1H-1,2,3-triazole was replaced with 4-($^2$H$_3$)methyl-1-methyl-5-(tributylstannyl)-1H-1,2,3-triazole. The diastereomers generated in the last step were separated by Chiral SFC: Chiralcel OJ-H prep column, 30×250 mm, 5 μm. Mobile phase: 20% MeOH in CO$_2$, 130 bar. Temp: 35° C. Flow rate: 70 mL/min. for 12 min. UV monitored at 270 nm. Injection: 0.4 mL of ~10 mg/mL in MeOH (41 mg purified by stacked injection). Diastereomer A: $^1$H NMR (400 MHz, CDCl$_3$) δ 8.43 (d, J=1.8 Hz, 1H), 8.05-7.98 (m, 2H), 7.58 (d, J=1.8 Hz, 1H), 7.43 (d, J=7.3 Hz, 2H), 7.38-7.29 (m, 3H), 5.55 (d, J=10.5 Hz, 1H), 4.06 (dd, J=11.8, 3.0 Hz, 1H), 3.93-3.84 (m, 4H), 3.55 (td, J=11.9, 1.8 Hz, 1H), 3.36 (td, J=11.9, 1.9 Hz, 1H), 3.08 (q, J=11.0 Hz, 1H), 2.06-1.94 (m, 2H), 1.76 (d, J=1.3 Hz, 3H), 1.68-1.50 (m, 1H), 1.48-1.36 (m, 1H), 1.13 (d, J=13.1 Hz, 1H), 0.93-0.80 (m, 1H), 0.68-0.55 (m, 2H), 0.51-0.40 (m, 2H). SFC retention time: 7.05. Mass found 542 [M+H]+. Diastereomer B: $^1$H NMR (400 MHz, CDCl$_3$) δ 8.43 (d, J=1.8 Hz, 1H), 8.06-7.99 (m, 2H), 7.57 (d, J=1.8 Hz, 1H), 7.46-7.41 (m, 2H), 7.38-7.29 (m, 3H), 5.55 (d, J=10.5 Hz, 1H), 4.05 (dd, J=11.8, 2.8 Hz, 1H), 3.93-3.84 (m, 4H), 3.54 (td, J=11.9, 1.9 Hz, 1H), 3.35 (td, J=11.9, 1.8 Hz, 1H), 3.15-3.01 (m, 1H), 2.06-1.96 (m, 2H), 1.76 (d, J=1.0 Hz, 3H), 1.69-1.54 (m, 1H), 1.48-1.35 (m, 1H), 1.10 (d, J=12.3 Hz, 1H), 0.89 (t, J=6.8 Hz, 1H), 0.69-0.57 (m, 2H), 0.51-0.41 (m, 2H). SFC retention Time: 8.91 min. Mass found 542 [M+H]+.

Examples 447 & 448

1-Cyclopropyl-1-[3-(dimethyl-1H-1,2,3-triazol-5-yl)-8-fluoro-5-[(S)-(2-fluorophenyl)(oxan-4-yl)methyl]-5H-pyrido[3,2-b]indol-7-yl]ethan-1-ol Diastereomer A, Example 447

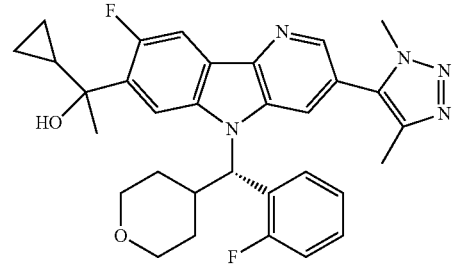

-continued

Diastereomer B, Example 448

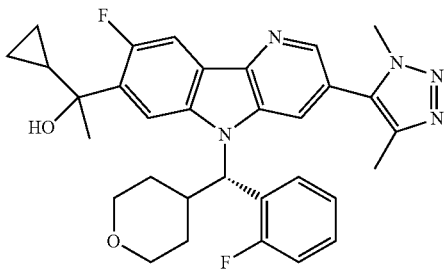

1-Cyclopropyl-1-[3-(dimethyl-1H-1,2,3-triazol-5-yl)-8-fluoro-5-[(S)-(2-fluorophenyl)(oxan-4-yl)methyl]-5H-pyrido[3,2-b]indol-7-yl]ethan-1-ol was prepared according to the procedures described for 1-cyclopropyl-1-[3-(dimethyl-1H-1,2,3-triazol-5-yl)-8-fluoro-5-[(S)-oxan-4-yl(phenyl)methyl]-5H-pyrido[3,2-b]indol-7-yl]ethan-1-ol. (R)-phenyl(tetrahydro-2H-pyran-4-yl)methanol was replaced for (R)-(2-fluorophenyl)(tetrahydro-2H-pyran-4-yl)methanol. The diastereomers generated in the last step were separated by Chiralcel OJ-H prep column, 30×250 mm, 5 μm, Mobile phase: 20% MeOH in CO$_2$, 130 bar. Temp: 35° C. Flow rate: 70 mL/min. for 10 min. UV monitored at 270 nm. Injection: 0.3 mL of ~6 mg/mL in 1:1 MeOH:CHCl$_3$ (35 mg purified by stacked injection). Diastereomer A: $^1$H NMR (400 MHz, CDCl$_3$) δ 8.47 (d, J=1.8 Hz, 1H), 8.05 (d, J=6.0 Hz, 1H), 8.00 (d, J=11.3 Hz, 1H), 7.82 (s, 1H), 7.75 (t, J=6.9 Hz, 1H), 7.35-7.29 (m, 1H), 7.25-7.20 (m, 1H), 7.08-7.01 (m, 1H), 5.72 (d, J=11.3 Hz, 1H), 4.05 (dd, J=12.0, 3.0 Hz, 1H), 4.01 (s, 3H), 3.88 (dd, J=11.9, 2.9 Hz, 1H), 3.57-3.47 (m, 1H), 3.38-3.30 (m, 1H), 3.21-3.09 (m, 1H), 2.38 (s, 3H), 1.97 (d, J=3.0 Hz, 1H), 1.88 (d, J=12.5 Hz, 1H), 1.76 (d, J=1.3 Hz, 3H), 1.64-1.49 (m, 1H), 1.46-1.32 (m, 1H), 1.13 (d, J=13.8 Hz, 1H), 0.88 (d, J=11.3 Hz, 1H), 0.67-0.54 (m, 2H), 0.49-0.37 (m, 2H). SFC retention Time: 6.43 min. Mass found 557 [M+H]$^+$. Diastereomer B: $^1$H NMR (400 MHz, CDCl$_3$) δ 8.46 (d, J=1.5 Hz, 1H), 8.06 (d, J=6.0 Hz, 1H), 8.00 (d, J=11.5 Hz, 1H), 7.81 (s, 1H), 7.74 (t, J=6.8 Hz, 1H), 7.36-7.29 (m, 1H), 7.25-7.20 (m, 1H), 7.09-7.02 (m, 1H), 5.72 (d, J=11.5 Hz, 1H), 4.05 (dd, J=11.8, 2.8 Hz, 1H), 4.00 (s, 3H), 3.88 (dd, J=11.7, 2.6 Hz, 1H), 3.52 (td, J=11.9, 2.0 Hz, 1H), 3.33 (td, J=11.9, 2.0 Hz, 1H), 3.21-3.07 (m, 1H), 2.37 (s, 3H), 1.98 (d, J=2.3 Hz, 1H), 1.87 (d, J=13.6 Hz, 1H), 1.76 (d, J=1.3 Hz, 3H), 1.66-1.50 (m, 1H), 1.46-1.32 (m, 1H), 1.09 (d, J=12.8 Hz, 1H), 0.95-0.78 (m, 1H), 0.69-0.55 (m, 2H), 0.52-0.39 (m, 2H). SFC retention Time: 7.59 min. Mass found 557 [M+H]$^+$.

Examples 449 & 450

1-Cyclopropyl-1-[3-(dimethyl-1H-1,2,3-triazol-5-yl)-6,8-difluoro-5-[(S)-oxan-4-yl(phenyl)methyl]-5H-pyrido[3,2-b]indol-7-yl]ethan-1-ol Diastereomer A, Example 449

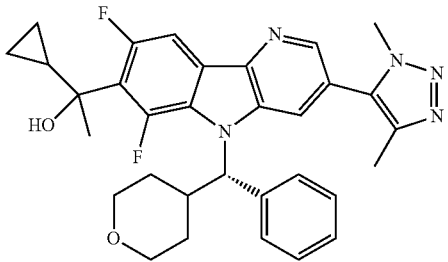

-continued

Diastereomer B, Example 450

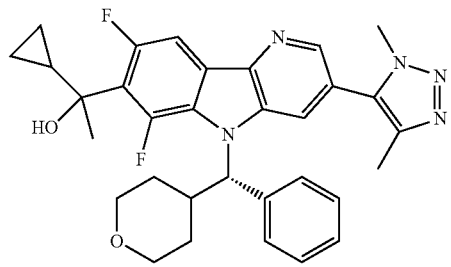

Step 1: 2-(4-Chloro-3,5-difluorophenyl)-4,4,5,5-tetramethyl-1,3,2-dioxaborolane

A dry 24/40-250 mL round bottom flask was charged with 5-bromo-2-chloro-1,3-difluorobenzene (5.00 g, 22.0 mmol) and diluted with DMSO (44.0 mL). Bis(pinacol)diborane (6.42 g, 25.3 mmol) was added followed by potassium acetate (4.32 g, 44.0 mmol), and [1,1'-bis(diphenylphosphino)ferrocene] dichloropalladium(II) (0.161 g, 0.220 mmol). The flask was sealed and degassed using ultra pure argon and sonication for 5 min. The reaction mixture was placed into an oil bath preheated to 80° C. and vented into a balloon partially filled with nitrogen. After 10 h, the mixture was diluted with ethyl acetate and water and transferred to a separatory funnel where the organic was washed with several volumes of water. The combined organics were dried with magnesium sulfate, concentrated under reduced pressure, and purified by flash chromatography: (40 g ISCO RediSep Rf, loaded in/with: DCM and dried, initial waste: 0 mL, fraction size: 9 mL 13×100 mm, and eluted with ethyl acetate in hexanes 0% [201 mL], 0-5% [150 mL], 5-10% [252 mL]). Collected fractions to give 3.53 g (59%). $^1$H NMR (400 MHz, CDCl$_3$) δ 7.40-7.35 (m, 2H), 1.35 (s, 12H).

Step 2: 5-Bromo-2-(4-chloro-3,5-difluorophenyl)-3-nitropyridine

A 24/40-100 mL round bottom flask was charged with 2,5-dibromo-3-nitropyridine (2.00 g, 7.09 mmol) and 2-(4-chloro-3,5-difluorophenyl)-4,4,5,5-tetramethyl-1,3,2-dioxaborolane (1.95 g, 7.09 mmol). The mixture was diluted with THF (30 mL), and PdCl$_2$(dppf) (0.0520 g, 0.0710 mmol) was added followed by aq. potassium phosphate tribasic, (2.0 M, 7.09 mL, 14.2 mmol). The vial was sealed and degassed using ultra pure argon and sonication for 2 min. The vial was placed in an oil bath preheated to 65° C. After 35 min, the reaction mixture was concentrated under reduced pressure, diluted with ethyl acetate and a brine solution, and filtered through a pad of Celite. The contents of the flask were transferred into a separatory funnel, and the organic was washed with brine (3×) and then back extracted with ethyl acetate. The combined organics were dried with magnesium sulfate, concentrated under reduced pressure, and purified by silica gel column chromatography (40 g ISCO RediSep Rf, loaded in/with: DCM and dried, initial waste: 0 mL, fraction size: 9 mL 13×100 mm, and eluted with dichloromethane in hexanes 0% [102 mL], 0-20% [150 mL], 20% [501 mL], 20-50% [252 mL], 50% [150 mL]). The fractions were collected to give 1.59 g (64%). $^1$H NMR (400 MHz, CDCl$_3$) δ 8.94 (d, J=2.0 Hz, 1H), 8.37 (d, J=2.3 Hz, 1H), 7.23-7.16 (m, 2H). Mass found 350 [M+H]$^+$.

Step 3: 3-Bromo-7-chloro-6,8-difluoro-5H-pyrido[3,2-b]indole

A 40 mL pressure vial was charged with 5-bromo-2-(4-chloro-3,5-difluorophenyl)-3-nitropyridine (1.59 g, 4.55 mmol) and 1,2-bis(diphenylphosphino)ethane (2.72 g, 6.82 mmol). The mixture was suspended in 1,2-dichlorobenzene (15 mL), and the vial was sealed and placed into a reaction block preheated to 160° C. After 15 min, the contents of the vial were transferred into a 250 mL round bottom flask and concentrated under reduced pressure. The brown oil was purified by silica gel column chromatography (24 g ISCO RediSep Rf, loaded in/with: DCM and dried, initial waste: 0 mL, fraction size: 9 mL 13×100 mm, and eluted with ethyl acetate in dichloromethane 0% [1500 mL]). The fractions were collected to give 722 mg (50%). $^1$H NMR (400 MHz, CD$_3$OD) δ 8.57 (s, 1H), 8.16 (s, 1H), 7.94 (d, J=8.5 Hz, 1H). Mass found 317 [M+H]$^+$.

Step 4: (S)-3-Bromo-7-chloro-6,8-difluoro-5-(phenyl(tetrahydro-2H-pyran-4-yl)methyl)-5H-pyrido[3,2-b]indole A 24/40-100 mL round bottom flask was charged with 3-bromo-7-chloro-6,8-difluoro-5H-pyrido[3,2-b]indole (349 mg, 1.10 mmol), triphenylphosphine (432 mg, 1.65 mmol), and (R)-phenyl(tetrahydro-2H-pyran-4-yl)methanol (317 mg, 1.65 mmol). The mixture was dissolved in THF (22 mL) and cooled to 0° C. DIAD (342 µL, 1.65 mmol) was then added drop wise. The ice bath was allowed to expire. After 5 h, the mixture was concentrated under reduced pressure and purified by silica gel column chromatography (24 g ISCO RediSep Rf, loaded in/with: DCM and dried, initial waste: 0 mL, fraction size: 9 mL 13×100 mm, and eluted with dichloromethane in hexanes 0% [75 mL], 0-100% [150 mL], 100% [1002 mL]). The fractions were collected to give 445 mg (82%). $^1$H NMR (400 MHz, CDCl$_3$) δ 8.56 (s, 1H), 7.95 (br. s., 1H), 7.90 (dd, J=0.7, 1.6 Hz, 1H), 7.47 (d, J=7.0 Hz, 2H), 7.42-7.29 (m, 3H), 5.82 (br. s., 1H), 4.05 (dd, J=11.7, 2.6 Hz, 1H), 3.89 (dd, J=11.9, 2.4 Hz, 1H), 3.56 (td, J=11.9, 2.0 Hz, 1H), 3.44-3.35 (m, 1H), 3.02 (br. s., 1H), 1.97 (d, J=11.0 Hz, 1H), 1.59-1.51 (m, 1H), 1.45 (d, J=7.0 Hz, 1H), 1.02 (d, J=12.5 Hz, 1H). Mass found 491 [M+H]$^+$.

Step 5: (S)-7-Chloro-3-(1,4-dimethyl-1H-1,2,3-triazol-5-yl)-6,8-difluoro-5-(phenyl(tetrahydro-2H-pyran-4-yl)methyl)-5H-pyrido[3,2-b]indole A 2-5 mL microwave vial was charged with (S)-3-bromo-7-chloro-6,8-difluoro-5-(phenyl(tetrahydro-2H-pyran-4-yl)methyl)-5H-pyrido[3,2-b]indole (150 mg, 0.305 mmol) and dissolved in DMF (3050 µL). To that solution was added copper(I) iodide (11.6 mg, 0.0610 mmol), triethylamine (85.0 µL, 0.610 mmol) and 1,4-dimethyl-5-(tributylstannyl)-1H-1,2,3-triazole (141 mg, 0.366 mmol). Pd(Ph$_3$P)$_4$ (35.2 mg, 0.0310 mmol) was added last, and the vial was sealed and degassed using ultra pure argon and sonication for 2 min. The vial was placed into a reaction block preheated to 100° C. After 30 min, the reaction was diluted with water and ethyl acetate and filtered through a pad of Celite to remove the black emulsion. The filtered solution was transferred into a reparatory funnel and the layers were separated. The organics were washed with water (2×) and brine. The combined aqueous was extracted with ethyl acetate, and the aqueous discarded. The combined organics were washed with brine, dried with magnesium sulfate, concentrated under reduced pressure, and purified by silica gel column chromatography (40 g ISCO RediSep Rf, loaded in/with: DCM and dried, initial waste: 0 mL, fraction size: 9 mL 13×100 mm, and eluted with acetone in dichloromethane 0% [99 mL], 0-10% [201 mL], 10% [201 mL], 15% [150 mL], 20% [150 mL], 30% [150 mL]). The fractions were collected to give 159 mg (103%). $^1$H NMR (400 MHz, CDCl$_3$) δ 8.47 (d, J=1.8 Hz, 1H), 7.99 (dd, J=0.7, 1.6 Hz, 1H), 7.58 (br. s., 1H), 7.51-7.29 (m, 5H), 6.00 (br. s., 1H), 4.09-4.01 (m, 1H), 3.90 (dd, J=11.7, 2.9 Hz, 1H), 3.84 (s, 3H), 3.55 (td, J=11.9, 2.0 Hz, 1H), 3.41-3.30 (m, 1H), 3.02 (d, J=8.0 Hz, 1H), 2.27 (s, 3H), 2.08-2.00 (m, 1H), 1.67-1.44 (m, 2H), 1.01 (d, J=12.5 Hz, 1H). Mass found 508 [M+H]$^+$.

Step 6: (S)-3-(1,4-Dimethyl-1H-1,2,3-triazol-5-yl)-6,8-difluoro-5-(phenyl(tetrahydro-2H-pyran-4-yl)methyl)-7-(prop-1-en-2-yl)-5H-pyrido[3,2-b]indole (S)-3-(1,4-Dimethyl-1H-1,2,3-triazol-5-yl)-6,8-difluoro-5-(phenyl(tetrahydro-2H-pyran-4-yl)methyl)-7-(prop-1-en-2-yl)-5H-pyrido[3,2-b]indole was synthesized using a procedure analogous to the one described in the synthesis of 1-[3-(Dimethyl-1H-1,2,3-triazol-5-yl)-5-[(S)-oxan-4-yl(phenyl)methyl]-5H-pyrido[3,2-b]indol-7-yl]ethan-1-one. $^1$H NMR (400 MHz, CDCl$_3$) δ 8.43 (d, J=1.8 Hz, 1H), 7.88 (dd, J=8.3, 0.8 Hz, 1H), 7.56 (s, 1H), 7.49 (d, J=7.3 Hz, 2H), 7.41-7.28 (m, 3H), 6.05 (br. s., 1H), 5.61-5.57 (m, 1H), 5.27 (s, 1H), 4.08-4.01 (m, 1H), 3.89 (dd, J=11.7, 2.6 Hz, 1H), 3.85-3.78 (m, 3H), 3.54 (td, J=11.9, 1.9 Hz, 1H), 3.40-3.30 (m, 1H), 3.12-2.95 (m, 1H), 2.25 (s, 6H), 2.04 (d, J=13.6 Hz, 1H), 1.66-1.44 (m, 2H), 1.00 (d, J=12.5 Hz, 1H). Mass found 513 [M+H]$^+$.

Step 7: (5)-1-(3-(1,4-Dimethyl-1H-1,2,3-triazol-5-yl)-6,8-difluoro-5-(phenyl(tetrahydro-2H-pyran-4-yl)methyl)-5H-pyrido[3,2-b]indol-7-yl)ethanone (S)-1-(3-(1,4-Dimethyl-1H-1,2,3-triazol-5-yl)-6,8-difluoro-5-(phenyl(tetrahydro-2H-pyran-4-yl)methyl)-5H-pyrido[3,2-b]indol-7-yl)ethanone was synthesized using a procedure analogous to the one described in 1-cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol. $^1$H NMR (400 MHz, CDCl$_3$) δ 8.49 (d, J=1.8 Hz, 1H), 7.95 (d, J=8.0 Hz, 1H), 7.59 (br. s., 1H), 7.50-7.43 (m, 2H), 7.42-7.29 (m, 3H), 6.04 (br. s., 1H), 4.11-4.01 (m, 1H), 3.90 (d, J=8.8 Hz, 1H), 3.84 (s, 3H), 3.60-3.48 (m, 1H), 3.35 (t, J=11.0 Hz, 1H), 2.99 (br. s., 1H), 2.78 (s, 3H), 2.27 (s, 3H), 2.09-2.01 (m, 1H), 1.65-1.45 (m, 2H), 1.05-0.94 (m, 1H). Mass found 515 [M+H]$^+$.

Step 8: 1-Cyclopropyl-1-[3-(dimethyl-1H-1,2,3-triazol-5-yl)-6,8-difluoro-5-[(S)-oxan-4-yl)phenyl)methyl]-5H-pyrido[3,2-b]indol-7-yl]ethan-1-ol 1-Cyclopropyl-1-[3-(dimethyl-1H-1,2,3-triazol-5-yl)-6,8-difluoro-5-[(S)-oxan-4-yl(phenyl)methyl]-5H-pyrido[3,2- b]indol-7-yl]ethan-1-ol was synthesized using a procedure analogous to the one described in 1-cyclopropyl-1-[3-(dimethyl-1H-1,2,3-triazol-5-yl)-5-[(S)-oxan-4-yl(phenyl)methyl]-5H-pyrido[3,2-b]indol-7-yl]ethan-1-ol. The diastereomers were separated by chiral SFC: Column: ChiralCel OJ-H, 30×250 mm, 5 μm Mobile Phase: 10% MeOH/90% CO$_2$ Pressure: 120 bar, Temperature: 35° C. Flow Rate: 70 mL/min UV: 270 nm Injection: 0.75 mL (~6 mg/mL in MeOH:CHCl$_3$). Diastereomer A: $^1$H NMR (400 MHz, CDCl$_3$) δ 8.45 (s, 1H), 7.96 (d, J=12.0 Hz, 1H), 7.58 (br. s., 1H), 7.52-7.29 (m, 5H), 6.09 (br. s., 1H), 4.06 (d, J=8.0 Hz, 1H), 3.91 (d, J=9.0 Hz, 1H), 3.82 (br. s., 3H), 3.56 (t, J=10.8 Hz, 1H), 3.42-3.30 (m, 1H), 3.01 (br. s., 1H), 2.25 (br. s., 3H), 2.08 (d, J=13.3 Hz, 1H), 1.89 (br. s., 3H), 1.69-1.45 (m, 4H), 1.03-0.94 (m, 1H), 0.93-0.79 (m, 2H), 0.67-0.49 (m, 2H). SFC retention time: 30.6 min. Mass found 557 [M+H]$^+$. Diastereomer B: $^1$H NMR (400 MHz, CDCl$_3$) δ 8.44 (d, J=1.5 Hz, 1H), 7.88 (dd, J=11.8, 1.0 Hz, 1H), 7.53 (s, 1H), 7.49-7.43 (m, 2H), 7.41-7.29 (m, 3H), 6.08 (br. s., 1H), 4.06 (dd, J=11.5, 2.5 Hz, 1H), 3.90 (dd, J=11.7, 2.4 Hz, 1H), 3.81 (s, 3H), 3.56 (td, J=11.9, 1.9 Hz, 1H), 3.35 (t, J=11.0 Hz, 1H), 3.09 (dd, J=10.0, 4.0 Hz, 1H), 3.05-2.94 (m, 1H), 2.25 (s, 3H), 2.06 (d, J=13.6 Hz, 1H), 1.90 (br. s., 3H), 1.69-1.46 (m, 2H), 1.39-1.18 (m, 1H), 1.00 (d, J=13.6 Hz, 1H), 0.94-0.79 (m, 2H), 0.69-0.47 (m, 2H). SFC retention time: 37.1 min. Mass found 557 [M+H]$^+$.

Example 451

2-[3-(Dimethyl-1H-1,2,3-triazol-5-yl)-6,8-difluoro-5-[(S)-oxan-4-yl(phenyl)methyl]-5H-pyrido[3,2-b]indol-7-yl]propan-2-ol

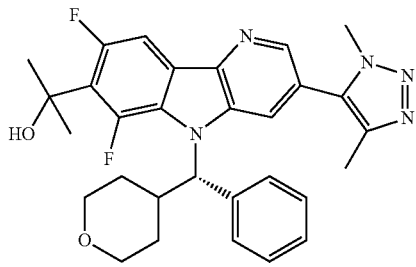 [SMILES: Cc1nnn(C)c1-c1cnc2c3cc(F)c(C(C)(C)O)c(F)c3n([C@H](c3ccccc3)C3CCOCC3)c2c1]

2-[3-(Dimethyl-1H-1,2,3-triazol-5-yl)-6,8-difluoro-5-[(S)-oxan-4-yl(phenyl)methyl]-5H-pyrido[3,2-b]indol-7-yl]propan-2-ol was prepared according to the procedures described for the synthesis of 1-cyclopropyl-1-[3-(dimethyl-1H-1,2,3-triazol-5-yl)-6,8-difluoro-5-[(S)-oxan-4-yl(phenyl)methyl]-5H-pyrido[3,2-b]indol-7-yl]ethan-1-ol by substituting cyclopropylmagnesium bromide 1.0 M in 2-methyltetrahydrofuran for methyllithium 1.6 M in diethyl ether in Step 8. The compound was purified by preparative HPLC: Column: Waters XBridge C18 100×30 mm 5 u, Solvents: water/Acetonitrile/10 mm ammonium acetate, % B gradient (time): 40% (12 min), Flow Rate: 30 mL/min, 6.8 mg per injection. $^1$H NMR (400 MHz, CDCl$_3$) δ 8.44 (d, J=1.8 Hz, 1H), 7.89 (dd, J=11.8, 1.0 Hz, 1H), 7.53 (s, 1H), 7.47-7.43 (m, 2H), 7.41-7.29 (m, 3H), 6.09 (br. s., 1H), 4.06 (dd, J=11.7, 2.6 Hz, 1H), 3.90 (dd, J=11.7, 2.9 Hz, 1H), 3.81 (s, 3H), 3.55 (td, J=11.9, 2.0 Hz, 1H), 3.40-3.29 (m, 1H), 3.21 (d, J=6.5 Hz, 1H), 3.07-2.94 (m, 1H), 2.25 (s, 3H), 2.10-2.02 (m, 1H), 1.92 (s, 6H), 1.68-1.43 (m, 2H), 0.96 (d, J=12.0 Hz, 1H). HPLC retention time: 7 min. Mass found 531 [M+H]$^+$.

Example 452

2-{6,8-Difluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol

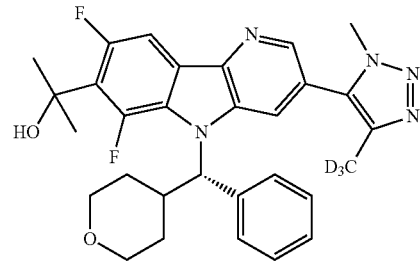 [SMILES: [2H]C([2H])([2H])c1nnn(C)c1-c1cnc2c3cc(F)c(C(C)(C)O)c(F)c3n([C@H](c3ccccc3)C3CCOCC3)c2c1]

2-{6,8-Difluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol was prepared according to the procedures described for 1-cyclopropyl-1-[3-(dimethyl-1H-1,2,3-triazol-5-yl)-6,8-difluoro-5-[(S)-oxan-4-yl(phenyl)methyl]-5H-pyrido[3,2-b]indol-7-yl]ethan-1-ol by substituting 1,4-dimethyl-5-(tributylstannyl)-1H-1,2,3-triazole with 4-($^2$H$_3$)methyl-1-methyl-5-(tributylstannyl)-1H-1,2,3-triazole in Step 5. Also substituting cyclopropylmagnesium bromide 1.0 M in 2-methyltetrahydrofuran for methyllithium 1.6 M in diethyl ether in Step 8 of the same example. The compound was purified by preparative HPLC: Column: Waters XBridge C18 100×30 mm 5 u, Solvents: water/Acetonitrile/ammonium acetate, % B gradient (time): 37% (25 min), Flow Rate: 30 mL/min, 2×250 μL injections (10.8 mg per injection) $^1$H NMR (400 MHz, CDCl$_3$) δ 8.44 (d, J=1.8 Hz, 1H), 7.89 (dd, J=11.8, 1.0 Hz, 1H), 7.53 (s, 1H), 7.46 (d, J=7.5 Hz, 2H), 7.41-7.29 (m, 3H), 6.08 (br. s., 1H), 4.06 (dd, J=11.7, 2.6 Hz, 1H), 3.90 (dd, J=11.7, 2.6 Hz, 1H), 3.81 (s, 3H), 3.55 (td, J=11.9, 1.9 Hz, 1H), 3.34 (td, J=11.9, 1.6 Hz, 1H), 3.21 (d, J=6.3 Hz, 1H), 3.01 (d, J=7.8 Hz, 1H), 2.11-2.02 (m, 1H), 1.92 (br. s., 6H), 1.69-1.45 (m, 2H), 0.96 (d, J=13.3 Hz, 1H). HPLC retention time: 9 min. Mass found 534 [M+H]$^+$.

Example 453

5-{7-Methanesulfonyl-5-[(S)-oxan-4-yl(phenyl)methyl]-5H-pyrido[3,2-b]indol-3-yl}-1-methyl-1H-1,2,3-triazole

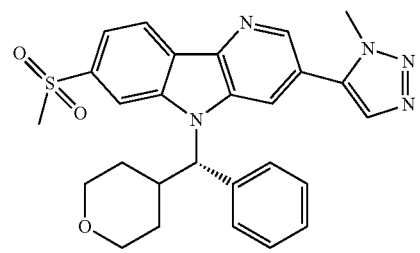 [SMILES: Cn1nncc1-c1cnc2c3ccc(S(C)(=O)=O)cc3n([C@H](c3ccccc3)C3CCOCC3)c2c1]

Step 1: 5-Bromo-2-(4-(methylsulfonyl)phenyl)-3-nitropyridine

In a pressure bottle, a mixture PdCl$_2$(dppf)-CH$_2$Cl$_2$ adduct (0.732 g, 1.00 mmol), potassium phosphate (21.2 g, 100 mmol), (4-(methylsulfonyl)phenyl)boronic acid (10.0 g, 50.0 mmol), and 2,5-dibromo-3-nitropyridine (14.1 g, 50.0 mmol) in THF (100 mL) was bubbled with nitrogen for 10 min. The bottle was sealed and heated at 80° C. for 3 h. After cooling, the mixture was diluted with EtOAc and filtered through a layer of SiO$_2$. The organic layer was washed with water and brine, dried over sodium sulfate, and concentrated. The resulting solid was washed with ether to afford 7.40 g (41%) of a solid. $^1$H NMR (400 MHz, CDCl$_3$) δ 8.99 (d, J=2.0 Hz, 1H), 8.43 (d, J=2.0 Hz, 1H), 8.07 (d,d J=1.6, 8 Hz, 2H), 7.63 (d,d J=1.6, 8 Hz, 2H), 3.14 (s, 3H).

Step 2: 3-Bromo-7-(methylsulfonyl)-5H-pyrido[3,2-b]indole

A 100 mL round bottomed flask was charged with 5-bromo-2-(4-(methylsulfonyl)phenyl)-3-nitropyridine (2.00 g, 5.60 mmol), triphenylphosphine (3.67 g, 14.0 mmol) and 1,2-dichlorobenzene (50 mL). The flask was placed in an oil bath, fitted with a condenser, and heated to 170° C. for 1.5 h. The volatiles were removed on a rotovap under high vacuum at 70° C., then under a stream of nitrogen for 36 h to afford a black oil. The residue was taken up in methylene chloride and purified on a 220 g ISCO column, eluting with 100% methylene chloride to 40% EtOAc/methylene chloride over 1800 mL, then 40% EtOAc/methylene chloride to 80% EtOAc/methylene chloride over 1800 mL. Fractions containing the title compound were concentrated to afford 920 mg of a light tan solid, which was contaminated with triphenylphosphine oxide. LC/MS using LC/MS Method 2 indicated the title compound with HPLC RT=0.93 min and triphenylphosphine oxide with HPLC RT=1.01 min.

Step 3: (S)-3-Bromo-7-(methylsulfonyl)-5-(phenyl(tetrahydro-2H-pyran-4-yl)methyl)-5H-pyrido[3,2-b]indole 3-Bromo-7-(methylsulfonyl)-5H-pyrido[3,2-b]indole (0.92 g, 2.83 mmol), (R)-phenyl(tetrahydro-2H-pyran-4-yl)methanol (0.816 g, 4.24 mmol) and triphenylphosphine (1.11 g, 4.24 mmol) were dissolved in 100 mL of THF and cooled to 0° C. To this was added DIAD (0.825 mL, 4.24 mmol) dropwise via an 18 gauge needle. After 15 min, the ice bath was removed, and the reaction stirred for 1 h. Volatiles were removed on a rotovap. The residue was dissolved in methylene chloride and purified on an 80 g ISCO column, eluting with 0% EtOAc/methylene chloride to 40% EtOAc/methylene chloride over 800 mL. Fractions containing the title compound were concentrated to afford 1.52 g of a white solid. LC/MS using LC/MS Method 2 indicated impure product with HPLC RT=1.18 min.

Step 4: (S)-(7-(Methylsulfonyl)-5-(phenyl(tetrahydro-2H-pyran-4-yl)methyl)-5H-pyrido[3,2-b]indol-3-yl)boronic acid A mixture of (S)-3-bromo-7-(methylsulfonyl)-5-(phenyl (tetrahydro-2H-pyran-4-yl)methyl)-5H-pyrido[3,2-b]indole (0.700 g, 1.40 mmol), 4,4,4',4',5,5,5',5'-octamethyl-2,2'-bi (1,3,2-dioxaborolane) (0.427 g, 1.68 mmol), PdCl$_2$(dppf)-CH$_2$Cl$_2$ adduct (0.0570 g, 0.0700 mmol), and potassium acetate (0.275 g, 2.80 mmol) was dissolved in 10 mL of dioxane. Argon was bubbled through the mixture for 5 min while sonicating. The vial was capped and heated at 90° C. overnight. Volatiles were removed, and the residue dissolved in EtOAc. The organics were washed with water and brine, dried over MgSO$_4$, and concentrated to afford 0.980 g of a brown oil. The oil was dissolved in 11 mL of DMSO and purified by HPLC in 1.5 mL aliquots. Column: Luna 10 u C18; 30×100 mm. Method: 10% B to 100% B over 17 min. A=90% water/10% methanol/0.1% TFA. B=10% water/90% methanol/0.1% TFA. Fractions that eluted from 11-12 min were collected and concentrated to afford 210 mg of a yellow oil. $^1$H NMR (400 MHz, CD$_3$OD) δ 8.71 (br. s., 1H), 8.60-8.40 (m, 3H), 7.85 (dd, J=8.3, 1.5 Hz, 1H), 7.70-7.58 (m, 2H), 7.42-7.30 (m, 2H), 7.30-7.16 (m, 1H), 5.87-5.78 (m, 1H), 4.02 (d, J=15.1 Hz, 1H), 3.81 (d, J=11.0 Hz, 1H), 3.64 (t, J=11.5 Hz, 1H), 3.52-3.37 (m, 2H), 3.25-3.20 (m, 3H), 1.77-1.58 (m, 1H), 1.04 (d, J=12.0 Hz, 1H). LC/MS Method 2; HPLC RT=0.83 min.

Step 5: 5-{7-Methanesulfonyl-5-[(S)-oxan-4-yl(phenyl)methyl]-5H-pyrido[3,2-b]indol-3-yl}-1-methyl-1H-1,2,3-triazole (S)-(7-(Methylsulfonyl)-5-(phenyl(tetrahydro-2H-pyran-4-yl)methyl)-5H-pyrido[3,2-b]indol-3-yl)boronic acid (30 mg, 0.065 mmol) and 5-bromo-1-methyl-1H-1,2,3-triazole (10.5 mg, 0.0650 mmol) were dissolved in 1.5 mL of dioxane and 0.5 mL of water. To this was added potassium carbonate (26.8 mg, 0.194 mmol) and PdCl$_2$(dppf)-CH$_2$Cl$_2$ adduct (3.69 mg, 4.52 µmol) and bubbled in argon while sonicating for 5 min. The vial was capped and heated at 100° C. for 1 h. The volatiles were removed. The residue was dissolved in 1.5 mL of DMSO, filtered and purified on preparative HPLC using Preparative HPLC Method 1, but with a gradient of 20% B-80% B over 20 min. Fractions containing the desired product were combined and dried via centrifugal evaporation. The yield of the product was 6.30 mg (18%), and its estimated purity by LCMS analysis was 94%. Two analytical LC/MS injections were used to determine the final purity. Injection 1: LC/MS Method 3; HPLC RT=1.39 min. Injection 2: LC/MS Method 4; HPLC RT=2.20 min. $^1$H NMR (400 MHz, DMSO-d$_6$) δ 8.79-8.68 (m, J=1.5 Hz, 2H), 8.64 (br. s., 1H), 8.48 (d, J=8.3 Hz, 1H), 8.11 (s, 1H), 7.86 (dd, J=8.2, 1.4 Hz, 1H), 7.69 (d, J=7.3 Hz, 2H), 7.41-7.31 (m, 2H), 7.31-7.23 (m, 1H), 6.01 (d, J=11.3 Hz, 1H), 4.12 (s, 3H), 3.94-3.91 (m, 1H), 3.71 (d, J=8.5 Hz, 1H), 3.56-3.42 (m, 2H), 3.38 (s, 3H), 2.32 (t, J=1.8 Hz, 1H), 1.74 (d, J=12.5 Hz, 1H), 1.68-1.56 (m, 1H), 1.36 (d, J=8.3 Hz, 1H), 0.91 (d, J=13.8 Hz, 1H).

Example 454

5-{7-Methanesulfonyl-5-[(S)-oxan-4-yl(phenyl)methyl]-5H-pyrido[3,2-b]indol-3-yl}-1,4-dimethyl-1H-imidazole

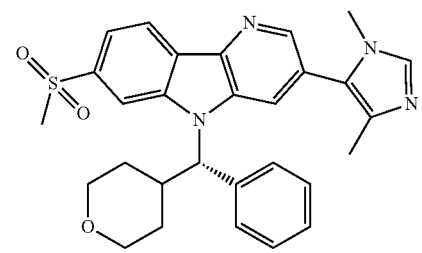 [SMILES: Cc1ncn(C)c1-c1cnc2c3ccc(S(C)(=O)=O)cc3n([C@H](c3ccccc3)C3CCOCC3)c2c1]

(S)-(7-(Methylsulfonyl)-5-(phenyl(tetrahydro-2H-pyran-4-yl)methyl)-5H-pyrido[3,2-b]indol-3-yl)boronic acid (30.0 mg, 0.0650 mmol) and 5-bromo-1,4-dimethyl-1H-imidazole (11.3 mg, 0.0650 mmol) were dissolved in 1.5 mL of dioxane and 0.5 mL of water. To this was added potassium carbonate (26.8 mg, 0.194 mmol) and $PdCl_2(dppf)\text{-}CH_2Cl_2$ adduct (3.69 mg, 4.52 μmol), and the reaction mixture was degassed by bubbling in argon while sonicating for 5 min. The vial was capped and heated at 100° C. for 1 h. The crude material was purified via preparative LC/MS (Preparative HPLC Method 1) with the following modifications: Gradient 30-70% B over 20 min. Fractions containing the desired product were combined and dried via centrifugal evaporation. The yield of the product was 5.80 mg, and its estimated purity by LCMS analysis was 91%. Two analytical LC/MS injections were used to determine the final purity. Injection 1: LC/MS Method 3, HPLC RT=1.32 min. Injection 2: LC/MS Method 4, HPLC RT=2.32 min. $^1$H NMR (500 MHz, DMSO-$d_6$) δ 8.58 (s, 1H), 8.45 (d, J=8.1 Hz, 1H), 7.85 (d, J=8.4 Hz, 1H), 7.74 (s, 1H), 7.68 (d, J=7.7 Hz, 2H), 7.34 (t, J=7.5 Hz, 2H), 7.30-7.23 (m, 1H), 6.01 (d, J=11.0 Hz, 1H), 3.91-3.84 (m, 1H), 3.73 (d, J=8.1 Hz, 1H), 3.54-3.45 (m, 1H), 3.26 (t, J=11.7 Hz, 1H), 2.17 (s, 3H), 1.91 (s, 6H), 1.73 (br. s., 1H), 1.63 (d, J=8.8 Hz, 1H), 1.46-1.28 (m, 1H), 0.94 (d, J=11.7 Hz, 1H).

Example 455

4-{7-Methanesulfonyl-5-[(S)-oxan-4-yl(phenyl)methyl]-5H-pyrido[3,2-b]indol-3-yl}-3-methyl-1H-pyrazole

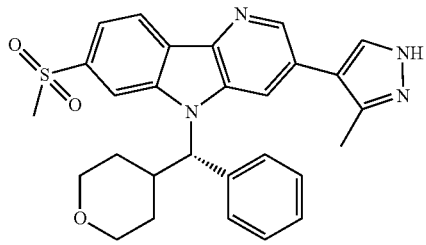 [SMILES: Cc1n[nH]cc1-c1cnc2c3ccc(S(C)(=O)=O)cc3n([C@H](c3ccccc3)C3CCOCC3)c2c1]

(S)-(7-(Methylsulfonyl)-5-(phenyl(tetrahydro-2H-pyran-4-yl)methyl)-5H-pyrido[3,2-b]indol-3-yl)boronic acid (20.0 mg, 0.0430 mmol) and 4-bromo-3-methyl-1H-pyrazole (13.9 mg, 0.0860 mmol) were dissolved in 1.5 mL of dioxane and 0.2 mL of water. To this was added potassium carbonate (17.9 mg, 0.129 mmol) and $PdCl_2(dppf)\text{-}CH_2Cl_2$ adduct (2.46 mg, 3.02 μmol), and argon was bubbled in while sonicating for 5 min. The vial was capped, heated at 100° C. for 50 min, and filtered. The crude material was purified via preparative LC/MS (Preparative HPLC Method 1) with the following modifications: Gradient 10-50% B over 40 min. Fractions containing the desired product were combined and dried via centrifugal evaporation. The yield of the product was 1.20 mg, and its estimated purity by LCMS analysis was 96%. Two analytical LC/MS injections were used to determine the final purity Injection 1: LC/MS Method 3, HPLC RT=1.83 min. Injection 2: LC/MS Method 4, HPLC RT=2.37 min. $^1$H NMR (500 MHz, DMSO-$d_6$) δ 8.69 (s, 2H), 8.42 (d, J=8.4 Hz, 1H), 8.27 (br. s., 1H), 8.01 (s, 1H), 7.82 (d, J=8.4 Hz, 1H), 7.67 (d, J=7.7 Hz, 2H), 7.36 (t, J=7.5 Hz, 2H), 7.27 (t, J=7.3 Hz, 1H), 5.99 (d, J=11.0 Hz, 1H), 3.90 (s, 2H), 3.72 (d, J=9.9 Hz, 2H), 3.60 (br. s., 2H), 3.52 (t, J=11.2 Hz, 3H), 3.27 (t, J=11.6 Hz, 1H), 2.43 (s, 3H), 1.85-1.73 (m, 1H), 1.72-1.58 (m, 1H), 1.46-1.27 (m, 1H), 0.89 (d, J=12.1 Hz, 1H).

Examples 456-459

The compounds in Table 15 were prepared from commercially available or previously described starting materials according to analogous procedures described for 2-{5-[(5-methyl-1,2-oxazol-3-yl)(oxan-4-yl)methyl]-3-[4-($^2$H$_3$)methyl-1-methyl-1H-1,2,3-triazol-5-yl]-5H-pyrido[3,2-b]indol-7-yl}propan-2-ol or 2-{6-fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}propan-2-ol. All compounds are homochiral:

TABLE 15

| Example | Structure | HPLC RT (min) | HPLC Method | MS (M + H) |
|---|---|---|---|---|
| 456 Enantiomer A | 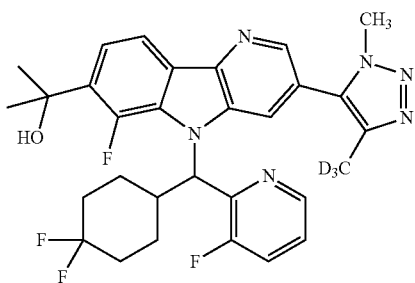 [SMILES: [2H]C([2H])([2H])c1nnn(C)c1-c1cnc2c3ccc(C(C)(C)O)c(F)c3n(C(c3ncccc3F)C3CCC(F)(F)CC3)c2c1] | 9.07 | A | 570.3 |

TABLE 15-continued

| Example | Structure | HPLC RT (min) | HPLC Method | MS (M + H) |
|---|---|---|---|---|
| 457 Enantiomer B | 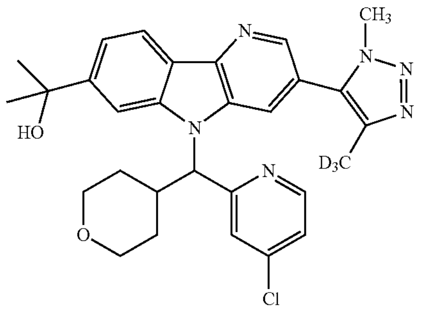 [SMILES: [2H]C([2H])([2H])c1nnn(C)c1-c1cnc2c3ccc(C(C)(C)O)cc3n(C(c3cc(Cl)ccn3)C3CCOCC3)c2c1] | 55.05 | B | 534.6 |
| 458 Enantiomer B | 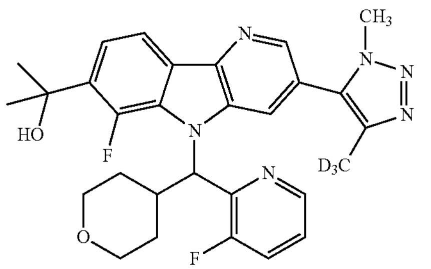 [SMILES: [2H]C([2H])([2H])c1nnn(C)c1-c1cnc2c3ccc(C(C)(C)O)c(F)c3n(C(c3ncccc3F)C3CCOCC3)c2c1] | 6.73 | C | 536.3 |
| 459 Enantiomer A | 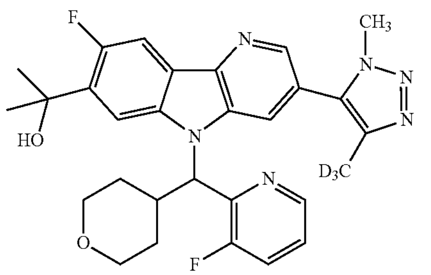 [SMILES: [2H]C([2H])([2H])c1nnn(C)c1-c1cnc2c3cc(F)c(C(C)(C)O)cc3n(C(c3ncccc3F)C3CCOCC3)c2c1] | 10.06 | D | 536.2 |

HPLC Conditions for Table 15: Method A: Column: Chiralcel OJ-H preparative column, 30×250 mm, 5 µm; Mobile Phase: 10% methanol in CO₂, 150 Bar; Flow: 70 mL/min. Method B: Column: Chiralpak OJ 21×250 mm 10 µm; Mobile Phase: 12:88 ethanol:heptane with 0.1% diethylamine; Flow: 15 mL/min. Method C: Column: Chiralcel OJ-H preparative column, 30×250 mm, 5 µm; Mobile Phase: 15% methanol in CO₂, 150 Bar; Flow: 70 mL/min. Method D: Column: Chiralpak OD 21×250 mm 10 µm; Mobile Phase: 25:75 ethanol:heptane with 0.1% diethylamine; Flow: 15 mL/min.

Example 460

3-(Dimethyl-1H-1,2,3-triazol-5-yl)-6-fluoro-5-[(S)-oxan-4-yl(phenyl)methyl]-5H-pyrido[3,2-b]indole-7-carboxamide

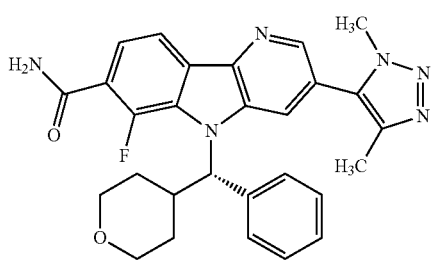 [SMILES: Cc1nnn(C)c1-c1cnc2c3ccc(C(N)=O)c(F)c3n([C@H](c3ccccc3)C3CCOCC3)c2c1]

Step 1: (S)-3-(1,4-Dimethyl-1H-1,2,3-triazol-5-yl)-6-fluoro-5-(phenyl(tetrahydro-2H-pyran-4-yl) methyl)-5H-pyrido[3,2-b]indole-7-carboxylic acid To a solution of (S)-methyl 3-(1,4-dimethyl-1H-1,2,3-triazol-5-yl)-6-fluoro-5-(phenyl(tetrahydro-2H-pyran-4-yl) methyl)-5H-pyrido[3,2-b]indole-7-carboxylate (see Step 2 of Example 70) (330 mg, 0.643 mmol) in THF (7 mL) was added a solution of potassium hydroxide (124 mg, 1.928 mmol) in water (1.4 mL). The reaction was stirred at 50° C. overnight. The reaction was concentrated to remove the THF. The reaction was diluted with water and extracted with EtOAc (which was discarded). The aqueous was acidified to pH 5 which gave a precipitate. The mixture was extracted with ethyl acetate, washed with brine, dried over magnesium sulfate, and concentrated to give 274 mg (85%) which was used without purification. LCMS (M+H)=500.4.

Step 2: 3-(Dimethyl-1H-1,2,3-triazol-5-yl)-6-fluoro-5-[(S)-oxan-4-yl(phenyl)methyl]-5H-pyrido[3,2-b] indole-7-carboxamide To a solution of (S)-3-(1,4-dimethyl-1H-1,2,3-triazol-5-yl)-6-fluoro-5-(phenyl(tetrahydro-2H-pyran-4-yl)methyl)-5H-pyrido[3,2-b]indole-7-carboxylic acid (10.0 mg, 0.020 mmol) in CH₂Cl₂ (0.5 mL) was added CDI (2.82 mg, 0.020 mmol). After stirring for 1 h at room temperature, saturated ammonium hydroxide (0.03 mL) was added and stirring continued overnight. The reaction was concentrated and purified by Prep HPLC (Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min) to give 8.3 mg (83%). LCMS: RT=1.58 min; MS (ES): m/z=499.1 [M+H]+ (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.0 mL/min; Detection: UV at 220 nm); HPLC RT=1.37 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min; Detection: UV at 220 nm)

Example 461

2-[3-(Dimethyl-1H-1,2,3-triazol-5-yl)-6-fluoro-5-[(S)-oxan-4-yl(phenyl)methyl]-5H-pyrido[3,2-b]indol-7-yl]propan-2-amine

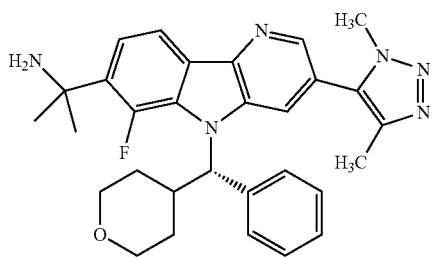 [SMILES: Cc1nnn(C)c1-c1cnc2c3ccc(C(C)(C)N)c(F)c3n([C@H](c3ccccc3)C3CCOCC3)c2c1]

Step 1: (S)-7-(2-Azidopropan-2-yl)-3-(1,4-dimethyl-1H-1,2,3-triazol-5-yl)-6-fluoro-5-(phenyl(tetrahydro-2H-pyran-4-yl)methyl)-5H-pyrido[3,2-b]indole A solution of 2-[3-(dimethyl-1H-1,2,3-triazol-5-yl)-6-fluoro-5-[oxan-4-yl(phenyl)methyl]-5H-pyrido[3,2-b]indol-7-yl]propan-2-ol-Enantiomer A (Example 70) (250 mg, 0.487 mmol) in DCM (6 mL) was cooled to 0° C. and treated with trimethylsilylazide (0.162 mL, 1.217 mmol). After 5 min, BF$_3$.OEt$_2$ (0.308 mL, 2.434 mmol) was added and the mixture stirred for 20 min. The ice bath was removed and the reaction stirred overnight. The mixture was diluted with water and saturated aqueous bicarbonate, and extracted with ethyl acetate. The organics were washed with brine, dried over MgSO$_4$, filtered, and concentrated to give 236 mg (90%) which was used without purification. LCMS (M+H)=539.4.

Step 2: 2-[3-(Dimethyl-1H-1,2,3-triazol-5-yl)-6-fluoro-5-[(S)-oxan-4-yl(phenyl)methyl]-5H-pyrido[3,2-b]indol-7-yl]propan-2-amine To a solution of (S)-7-(2-azidopropan-2-yl)-3-(1,4-dimethyl-1H-1,2,3-triazol-5-yl)-6-fluoro-5-(phenyl(tetrahydro-2H-pyran-4-yl)methyl)-5H-pyrido[3,2-b]indole (235 mg, 0.436 mmol) in THF (7 mL) was added trimethylphosphine (1M in THF, 0.873 mL, 0.873 mmol) and the resulting solution stirred overnight. The solution was treated with water (0.1 mL) and the reaction stirred overnight. The reaction was concentrated, diluted with EtOAc, and poured into water. The organics were washed with water (3×), then brine, dried over MgSO$_4$, filtered, and concentrated to give 200 mg crude product. A small portion of the reaction mixture was purified by Prep HPLC (Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-90% B over 40 min, then a 5-min hold at 100% B; Flow: 20 mL/min) to give 10.9 mg (5%). $^1$H NMR (500 MHz, DMSO-d$_6$) δ 8.53 (br. s., 1H), 8.20 (br. s., 1H), 8.01 (d, J=8.1 Hz, 1H), 7.72-7.50 (m, 3H), 7.40-7.20 (m, 3H), 5.99 (br. s., 1H), 3.99-3.83 (m, 4H), 3.76 (d, J=8.8 Hz, 1H), 3.50-3.46 (m, 1H), 3.28 (t, J=11.9 Hz, 1H), 2.23 (br. s., 3H), 1.89 (s, 6H), 1.80 (d, J=12.1 Hz, 1H), 1.64 (br. s., 3H), 1.35 (d, J=8.4 Hz, 2H), 1.07 (d, J=12.5 Hz, 1H). LCMS (M+H)=513.0.

Example 462

N-{2-[3-(Dimethyl-1H-1,2,3-triazol-5-yl)-6-fluoro-5-[(S)-oxan-4-yl)phenyl)methyl]-5H-pyrido[3,2-b]indol-7-yl]propan-2-yl}acetamide

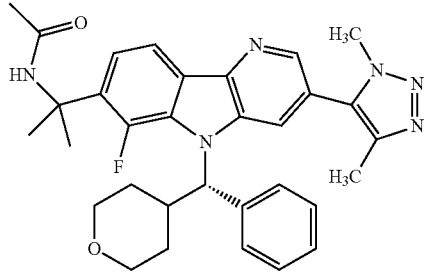 [SMILES: CC(=O)NC(C)(C)c1ccc2c3ncc(-c4c(C)nnn4C)cc3n([C@H](c3ccccc3)C3CCOCC3)c2c1F]

To a solution of 2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-amine (20 mg, 0.039 mmol) in DCM (1 mL) was added acetyl chloride (0.039 mL, 0.039 mmol) and triethylamine (5.44 μl, 0.039 mmol). After stirring for 1 h at room temperature, the reaction was concentrated and purified by Prep HPLC (Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-90% B over 35 min, then a 5-min hold at 100% B; Flow: 20 mL/min) to give 8.6 mg (39%). $^1$H NMR (500 MHz, DMSO-d$_6$) δ 8.53 (br. s., 1H), 8.39 (br. s., 1H), 8.20 (br. s., 1H), 7.96 (d, J=8.1 Hz, 1H), 7.61 (br. s., 2H), 7.38-7.22 (m, 4H), 5.96 (br. s., 1H), 4.02-3.82 (m, 4H), 3.77 (d, J=11.0 Hz, 1H), 3.48 (d, J=10.6 Hz, 1H), 3.28 (t, J=11.2 Hz, 1H), 2.23 (br. s., 3H), 1.90 (d, J=12.8 Hz, 4H), 1.77 (br. s., 7H), 1.32 (br. s., 2H), 1.10 (d, J=12.8 Hz, 1H). LCMS (M+H)=555.5.

Example 463

N-{2-[3-(Dimethyl-1H-1,2,3-triazol-5-yl)-6-fluoro-5-[(S)-oxan-4-yl(phenyl)methyl]-5H-pyrido[3,2-b]indol-7-yl]propan-2-yl}methanesulfonamide

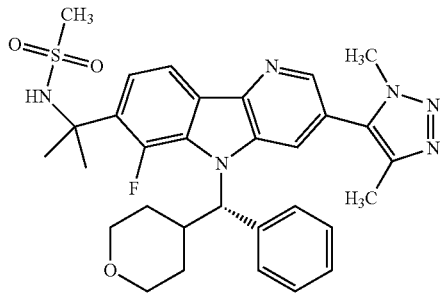 [SMILES: Cc1nnn(C)c1-c1cnc2c3ccc(C(C)(C)NS(C)(=O)=O)c(F)c3n([C@H](c3ccccc3)C3CCOCC3)c2c1]

To a solution of 2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-amine (30.0 mg, 0.059 mmol) in DCM (1 mL) was added methanesulfonyl chloride (4.54 µl, 0.059 mmol) and triethylamine (0.016 mL, 0.117 mmol). After stirring for 30 min, the reaction was diluted with DCM, filtered to remove solids (which were discarded), and concentrated. The residue was purified by Prep HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-90% B over 35 min, then a 5-min hold at 100% B; Flow: 20 mL/min) to give 10.2 mg (28%). $^1$H NMR (500 MHz, DMSO-$d_6$) δ 8.54 (br. s., 1H), 8.23 (br. s., 1H), 8.03 (d, J=8.1 Hz, 1H), 7.79 (br. s., 1H), 7.69-7.54 (m, 2H), 7.46 (br. s., 1H), 7.39-7.22 (m, 3H), 5.98 (br. s., 1H), 3.99-3.84 (m, 4H), 3.75 (d, J=12.1 Hz, 1H), 3.55-3.44 (m, 4H), 3.28 (t, J=11.2 Hz, 1H), 2.22 (br. s., 3H), 1.86 (br. s., 8H), 1.35 (br. s., 2H), 1.09 (br. s., 1H). LCMS (M+H)=591.4.

Example 464

Methyl N-{2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-yl}carbamate

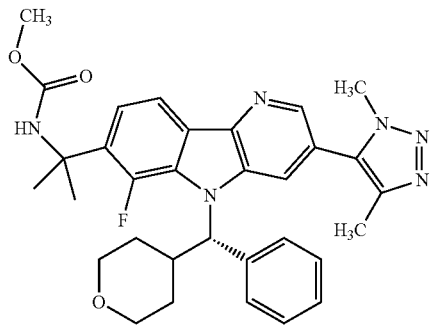 [SMILES: COC(=O)NC(C)(C)c1ccc2c3ncc(-c4c(C)nnn4C)cc3n([C@H](c3ccccc3)C3CCOCC3)c2c1F]

To a solution of 2-[3-(dimethyl-1H-1,2,3-triazol-5-yl)-6-fluoro-5-[(S)-oxan-4-yl(phenyl)methyl]-5H-pyrido[3,2-b]indol-7-yl]propan-2-amine (30.0 mg, 0.059 mmol) in DCM (1 mL) was added methyl chloroformate (4.52 µl, 0.059 mmol) and potassium carbonate (8.09 mg, 0.059 mmol). The reaction was stirred overnight at room temperature. The reaction was diluted with DCM, filtered to remove solids (which were discarded) and concentrated. The resulting residue was purified by Prep HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-90% B over 20 min, then a 5-min hold at 100% B; Flow: 20 mL/min) to give 10.1 mg (30%). $^1$H NMR (500 MHz, DMSO-$d_6$) δ 8.54 (br. s., 1H), 8.22 (br. s., 1H), 7.98 (d, J=8.1 Hz, 1H), 7.85 (br. s., 1H), 7.62 (br. s., 2H), 7.39-7.21 (m, 4H), 5.97 (br. s., 1H), 4.00-3.83 (m, 4H), 3.77 (d, J=8.8 Hz, 1H), 3.49-3.39 (m, 4H), 3.29 (t, J=11.2 Hz, 1H), 2.24 (br. s., 3H), 1.77 (br. s., 8H), 1.32 (br. s., 2H), 1.10 (d, J=11.0 Hz, 1H). LCMS (M+H)=571.5.

Evaluation of Biological Activity

Exemplary compounds were tested for inhibition of BRD2, BRD3, BRD4 and BRDT activity. Experimental procedures and results are provided below.

Cloning, Expression, and Purification of Human Bromodomains for Thermal Shift Assays (TSA)

Recombinant DNA clones encoding bromodomains of human proteins were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) (SEQ ID NO: 1) were immediately followed by bromodomain proteins with the amino acid residue sequences (followed by accessions referenced from and numbered according to the Uniprot Knowledgebase; Uniprot Consortium; www.uniprot.org) as follows:

CECR2(420-543), Q9BXF3-1; FALZ(2917-3037), Q12830-1; GCN5(731-837), Q92830-1; PCAF(715-831), Q92831-1; BRD2(24-472), P25440-1; BRD3(1-434), Q15059-1; BRD4 (44-168), BRD4(333-460), BRD4(44-460), O60885-1; BRDT(1-383), Q58F21-1; BAZ1B(1340-1457), Q9UIG0-1; CREBBP(1081-1197), Q92793-1; EP300(1040-1161), Q09472-1; WDR9(1310-1430), Q9NSI6-1; ATAD2(981-1108), Q6PL18-1; BRD1(556-688), O95696-1; BRD7(129-236), Q9NPI1-1; BRD9(134-239), Q9H8M2-1; BRPF1 (626-740), P55201-2; ATAD2B(952-1086), Q9ULI0-1; BAZ2B(2054-2168), Q9UIF8-1; SP140L(400-580), Q9H930-4; 5P140(687-862), Q13342-1; TIF1(896-1014), O15164-1; TRIM28(619-805), Q13263-1; BRWD3(1295-1443), Q6R145-1; TAF1(1377-1503), TAF1(1501-1635), P21675-1; TAF1L(1402-1522), TAF1L(1523-1654), Q8IZX4-1; ASH1L(2433-2564), Q9NR48-1; PB1(43-156), PB1(178-291), PB1(388-494), PB1(645-766), PB1(773-917), Q86U86-1; SMARCA2(1367-1511), P51531-1; SMARCA2-2(1367-1493), P51531-2.

The recombinant vectors were transformed into *E. coli* BL21(DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 hours. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD2, BRD3, BRD4 and BRDT were optimized for E. coli expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by E. coli biotin ligase (BirA). The non-native amino acids (MGSSHHHHHHSSGETVRFQGLN-DIFEAQKIEWHEDTGHM) (SEQ ID NO: 2) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), O60885-1.

Each of the recombinant vectors were co-transformed into E. coli BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 µg/ml kanamycin, 35 µg/ml chloramphenicol, and 100 µM biotin. At a cell density corresponding to an OD600 nm=0.6, the cultures were induced with 0.5 mM IPTG and incubated in the shaker for an additional 20 hours at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 hours at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responsed test compound are incubated together to reach thermodynamic equilibrium. In the absence of a test compound, the bromodomain and small molecule are bound, resulting in a high fluorescent signal. In the presence of a sufficient concentration of inhibitor, this intercation is disrupted resulting in a lost of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responsed test compound or dmso vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, ($\lambda$ex=340 nm, acceptor $\lambda$Em=520 nm, and donor $\lambda$Em=615 nm, LANCE D400 mirror). Time resolved fluorescence intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the IC50, and 'd' is the maximum. Histone peptide: Purchased from GenScript H4K5K8K12K16 Biotin-AHA-SGRGK (Ac)GGK(Ac)GLGK(Ac)GGAK(Ac)RHRKV (SEQ ID NO: 3)

The fluorescently labeled small molecule used was a BRD4 inhibitor known in the art 1. F. Degorce, A. Card, S. Soh, E. Trinquet, G. P. Knapik and B. Xie, HTRF: A technology tailored for drug discovery—a review of theoretical aspects and recent applications. Current Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with dmso but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6(2001) 429-440.
2. M. D. Cummings, M. A. Farnum, M. I. Nelen, Universal screening methods and application of Thermo-Fluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37 C for 4 hrs, cells were fixed in 4% Formaldehyde at room temperature for 30 min and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% $CO_2$ before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 μl/well into T0 plates followed by incubation at 37° C. in 5% $CO_2$ for three hours. Absorbance at 490 nm was measured on an Envision reader (Perkin Elmer, Boston, Mass.). On the same day, the remaining cell plates (T72 plates) were treated with compounds at 37° C. in 5% $CO_2$. After 72 hours, 4 ul MTS reagents were then added onto those cell plates. The plates were further incubated at 37° C. in 5% $CO_2$ for three hours and the absorbance values at A490 were measured on an Envision reader.

Human Tumor Xenograft Models in Mice

All rodents were obtained from Jackson Laboratory. (Bar Harbor, Me.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in NSG (NOD scid IL2 receptor gamma chain knockout) mice (Jackson Lab). Tumors were propagated as subcutaneous transplants using tumor fragments obtained from donor mice.

Preclinical Chemotherapy Trials

The required numbers of animals needed to detect a meaningful response were pooled at the start of the experiment and each was given bilateral subcutaneous implants of two tumor fragments (~20 mg) with a 13-gauge trocar. Tumors were allowed to grow to the pre-determined size window (tumors outside the range were excluded) and animals were evenly distributed to various treatment and control groups. There were typically 6-8 mice per treatment and control groups, consisting of 10-12 tumors. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width$^2$)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e. TGI≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

For administration of BET inhibitors to rodents, compounds were dissolved in 90% PEG300/10% TPGS/10% Ethanol. BET inhibitors were typically administered orally on a schedule of QDx7 or QDx10 (5 day-on-2 day-off), although other schedules had also been evaluated and shown to be efficacious Results:

The following Table shows the results of certain compounds of the invention against the H187 Human Small Cell Carcinoma and the JJN3R multiple myeloma cell line.

|     | Cell Line | Dose (mg/kg) | Treatment Schedule | % TGI | LCK |
| --- | --- | --- | --- | --- | --- |
| 1   | H187  | 15 | 2QDx7 | 104.0 | 1.2 |
| 1   | H187  | 5  | 2QDx7 | 88.0  | 1.0 |
| 54  | H187  | 10 | QDx7  | 102.0 | 0.9 |
| 54  | H187  | 5  | QDx7  | 100.0 | 0.7 |
| 70  | H187  | 10 | QDx7  | 96.0  | 1.6 |
| 70  | H187  | 3  | QDx7  | 90.0  | 1.0 |
| 70  | H187  | 1  | QDx7  | 82.0  | 0.7 |
| 203 | JJN3R | 4  | QDx7  | 105   | >1.4 |
| 203 | JJN3R | 1  | QDx7  | 93    | 0.7 |
| 263 | JJN3R | 4  | QDx7  | 52    | 0.3 |
| 263 | JJN3R | 1  | QDx7  | 6     | 0.2 |
| 267 | JJN3R | 4  | QDx7  | 67    | 0.6 |
| 267 | JJN3R | 1  | QDx7  | 10    | 0   |
| 276 | JJN3R | 4  | QDx7  | 95    | 1   |
| 276 | JJN3R | 1  | QDx7  | 56    | 0.3 |
| 278 | JJN3R | 4  | QDx7  | 110   | >1.4 |
| 278 | JJN3R | 1  | QDx7  | 103   | 1   |
| 279 | JJN3R | 4  | QDx7  | 110   | >1.4 |
| 279 | JJN3R | 1  | QDx7  | 88    | 0.6 |
| 432 | JJN3R | 4  | QDx7  | 102   | 1.4 |
| 432 | JJN3R | 1  | QDx7  | 51    | 0.4 |
| 433 | JJN3R | 1  | QDx7  | 54    | 0.5 |
| 434 | JJN3R | 1  | QDx7  | 82    | 0.5 |
| 436 | JJN3R | 4  | QDx7  | 116   | 0.9 |
| 436 | JJN3R | 1  | QDx7  | 71    | 0.6 |

The activity data shown below is based on the use of one of the FRET assays described. Compounds with an $IC_{50}$ less than 1500 nM are shown with (+), compounds with an $IC_{50}$ less than 25 nM are shown with (++) and those with an $IC_{50}$ less than 5 nM are shown with (+++).

| Example # | FRET BRD4 $IC_{50}$ (nM) |
| --- | --- |
| Example 1 | +++ |
| Example 2 | +++ |
| Example 3 | +++ |
| Example 4 | ++ |
| Example 5 | +++ |
| Example 6 | ++ |
| Example 7 | ++ |
| Example 8 | +++ |
| Example 9 | +++ |
| Example 10 | ++ |
| Example 11 | ++ |
| Example 12 | ++ |
| Example 13 | +++ |
| Example 14 | ++ |
| Example 15 | +++ |
| Example 16 | ++ |
| Example 17 | ++ |
| Example 18 | + |
| Example 19 | +++ |
| Example 20 | ++ |
| Example 21 | +++ |
| Example 22 | +++ |
| Example 23 | +++ |
| Example 24 | + |
| Example 25 | +++ |
| Example 26 | ++ |
| Example 27 | +++ |
| Example 28 | +++ |
| Example 29 | +++ |
| Example 30 | +++ |
| Example 31 | +++ |
| Example 32 | +++ |
| Example 33 | +++ |
| Example 34 | +++ |
| Example 35 | ++ |
| Example 36 | ++ |
| Example 37 | +++ |
| Example 38 | ++ |
| Example 39 | + |
| Example 40 | ++ |
| Example 41 | + |
| Example 42 | ++ |
| Example 43 | + |
| Example 44 | +++ |
| Example 45 | +++ |
| Example 46 | + |
| Example 47 | ++ |
| Example 48 | ++ |
| Example 49 | +++ |
| Example 50 | + |
| Example 51 | + |
| Example 52 | ++ |
| Example 53 | + |
| Example 54 | +++ |
| Example 55 | +++ |
| Example 56 | +++ |
| Example 57 | +++ |
| Example 58 | +++ |
| Example 59 | +++ |
| Example 60 | +++ |
| Example 61 | +++ |
| Example 62 | ++ |
| Example 63 | ++ |
| Example 64 | +++ |
| Example 65 | +++ |
| Example 66 | +++ |
| Example 67 | ++ |
| Example 69 | +++ |
| Example 70 | +++ |
| Example 71 | +++ |
| Example 72 | ++ |
| Example 73 | +++ |
| Example 74 | ++ |
| Example 75 | +++ |
| Example 76 | +++ |
| Example 77 | +++ |
| Example 78 | +++ |
| Example 79 | ++ |
| Example 80 | ++ |
| Example 81 | +++ |
| Example 82 | ++ |

-continued

| Example # | FRET BRD4 IC$_{50}$ (nM) |
|---|---|
| Example 83 | ++ |
| Example 84 | + |
| Example 85 | + |
| Example 86 | +++ |
| Example 87 | + |
| Example 88 | +++ |
| Example 89 | ++ |
| Example 90 | +++ |
| Example 91 | ++ |
| Example 92 | +++ |
| Example 93 | +++ |
| Example 94 | +++ |
| Example 95 | +++ |
| Example 96 | ++ |
| Example 97 | +++ |
| Example 98 | +++ |
| Example 99 | +++ |
| Example 100 | +++ |
| Example 101 | ++ |
| Example 102 | +++ |
| Example 103 | +++ |
| Example 104 | +++ |
| Example 105 | +++ |
| Example 106 | +++ |
| Example 107 | +++ |
| Example 108 | +++ |
| Example 109 | +++ |
| Example 110 | +++ |
| Example 111 | +++ |
| Example 112 | +++ |
| Example 113 | + |
| Example 114 | +++ |
| Example 115 | +++ |
| Example 116 | ++ |
| Example 117 | +++ |
| Example 118 | +++ |
| Example 119 | +++ |
| Example 120 | +++ |
| Example 121 | ++ |
| Example 122 | +++ |
| Example 123 | +++ |
| Example 124 | +++ |
| Example 125 | +++ |
| Example 126 | ++ |
| Example 127 | +++ |
| Example 128 | ++ |
| Example 129 | + |
| Example 130 | +++ |
| Example 131 | +++ |
| Example 132 | +++ |
| Example 133 | +++ |
| Example 134 | +++ |
| Example 135 | +++ |
| Example 136 | +++ |
| Example 137 | +++ |
| Example 138 | +++ |
| Example 139 | +++ |
| Example 140 | +++ |
| Example 141 | ++ |
| Example 142 | +++ |
| Example 143 | +++ |
| Example 144 | +++ |
| Example 145 | +++ |
| Example 146 | +++ |
| Example 147 | +++ |
| Example 148 | ++ |
| Example 149 | +++ |
| Example 150 | +++ |
| Example 151 | +++ |
| Example 152 | +++ |
| Example 153 | +++ |
| Example 154 | ++ |
| Example 155 | ++ |
| Example 156 | +++ |
| Example 157 | +++ |

-continued

| Example # | FRET BRD4 IC$_{50}$ (nM) |
|---|---|
| Example 158 | +++ |
| Example 159 | +++ |
| Example 160 | +++ |
| Example 161 | +++ |
| Example 162 | +++ |
| Example 163 | +++ |
| Example 164 | +++ |
| Example 165 | +++ |
| Example 166 | +++ |
| Example 167 | +++ |
| Example 168 | +++ |
| Example 169 | +++ |
| Example 170 | + |
| Example 171 | +++ |
| Example 172 | +++ |
| Example 173 | +++ |
| Example 174 | +++ |
| Example 175 | +++ |
| Example 176 | +++ |
| Example 177 | +++ |
| Example 178 | +++ |
| Example 179 | +++ |
| Example 180 | +++ |
| Example 181 | +++ |
| Example 182 | +++ |
| Example 183 | +++ |
| Example 184 | +++ |
| Example 185 | +++ |
| Example 186 | +++ |
| Example 187 | +++ |
| Example 188 | +++ |
| Example 189 | +++ |
| Example 190 | +++ |
| Example 191 | +++ |
| Example 192 | +++ |
| Example 193 | +++ |
| Example 194 | +++ |
| Example 195 | +++ |
| Example 196 | ++ |
| Example 197 | +++ |
| Example 198 | +++ |
| Example 199 | +++ |
| Example 200 | +++ |
| Example 201 | +++ |
| Example 202 | +++ |
| Example 203 | +++ |
| Example 204 | +++ |
| Example 205 | +++ |
| Example 206 | +++ |
| Example 207 | +++ |
| Example 208 | +++ |
| Example 209 | +++ |
| Example 210 | +++ |
| Example 211 | +++ |
| Example 212 | +++ |
| Example 213 | +++ |
| Example 214 | +++ |
| Example 216 | +++ |
| Example 217 | +++ |
| Example 218 | +++ |
| Example 219 | +++ |
| Example 221 | +++ |
| Example 222 | +++ |
| Example 223 | ++ |
| Example 225 | ++ |
| Example 226 | +++ |
| Example 227 | +++ |
| Example 228 | +++ |
| Example 229 | +++ |
| Example 230 | +++ |
| Example 231 | +++ |
| Example 233 | +++ |
| Example 235 | +++ |
| Example 236 | + |
| Example 239 | +++ |

| Example # | FRET BRD4 IC$_{50}$ (nM) |
|---|---|
| Example 240 | +++ |
| Example 243 | +++ |
| Example 244 | +++ |
| Example 245 | +++ |
| Example 246 | + |
| Example 247 | +++ |
| Example 248 | + |
| Example 249 | +++ |
| Example 250 | ++ |
| Example 251 | +++ |
| Example 252 | +++ |
| Example 253 | +++ |
| Example 254 | +++ |
| Example 255 | +++ |
| Example 256 | +++ |
| Example 257 | +++ |
| Example 258 | +++ |
| Example 259 | +++ |
| Example 260 | +++ |
| Example 261 | +++ |
| Example 262 | +++ |
| Example 263 | +++ |
| Example 264 | +++ |
| Example 265 | +++ |
| Example 266 | +++ |
| Example 267 | +++ |
| Example 268 | +++ |
| Example 269 | +++ |
| Example 270 | +++ |
| Example 271 | +++ |
| Example 272 | +++ |
| Example 273 | +++ |
| Example 274 | +++ |
| Example 275 | +++ |
| Example 276 | +++ |
| Example 277 | +++ |
| Example 278 | +++ |
| Example 279 | +++ |
| Example 280 | +++ |
| Example 281 | +++ |
| Example 282 | +++ |
| Example 283 | +++ |
| Example 284 | +++ |
| Example 285 | +++ |
| Example 286 | +++ |
| Example 287 | ++ |
| Example 288 | +++ |
| Example 289 | +++ |
| Example 290 | +++ |
| Example 291 | +++ |
| Example 292 | +++ |
| Example 293 | +++ |
| Example 294 | +++ |
| Example 295 | +++ |
| Example 296 | +++ |
| Example 297 | +++ |
| Example 298 | ++ |
| Example 299 | +++ |
| Example 300 | ++ |
| Example 301 | +++ |
| Example 302 | +++ |
| Example 303 | +++ |
| Example 304 | +++ |
| Example 305 | +++ |
| Example 306 | +++ |
| Example 307 | ++ |
| Example 308 | +++ |
| Example 309 | ++ |
| Example 310 | +++ |
| Example 311 | +++ |
| Example 312 | +++ |
| Example 313 | +++ |
| Example 314 | +++ |
| Example 315 | +++ |
| Example 316 | +++ |
| Example 317 | +++ |
| Example 318 | +++ |
| Example 319 | +++ |
| Example 320 | +++ |
| Example 321 | +++ |
| Example 322 | +++ |
| Example 323 | ++ |
| Example 324 | ++ |
| Example 325 | +++ |
| Example 326 | ++ |
| Example 327 | +++ |
| Example 328 | ++ |
| Example 329 | ++ |
| Example 330 | ++ |
| Example 331 | +++ |
| Example 332 | +++ |
| Example 333 | +++ |
| Example 334 | +++ |
| Example 335 | +++ |
| Example 336 | +++ |
| Example 337 | +++ |
| Example 338 | +++ |
| Example 339 | +++ |
| Example 340 | +++ |
| Example 341 | +++ |
| Example 342 | ++ |
| Example 343 | +++ |
| Example 344 | +++ |
| Example 345 | +++ |
| Example 346 | +++ |
| Example 347 | +++ |
| Example 348 | +++ |
| Example 351 | +++ |
| Example 352 | ++ |
| Example 353 | +++ |
| Example 354 | +++ |
| Example 355 | +++ |
| Example 356 | +++ |
| Example 357 | +++ |
| Example 364 | +++ |
| Example 365 | +++ |
| Example 366 | +++ |
| Example 367 | +++ |
| Example 369 | +++ |
| Example 370 | +++ |
| Example 371 | +++ |
| Example 372 | +++ |
| Example 373 | +++ |
| Example 374 | +++ |
| Example 375 | +++ |
| Example 376 | +++ |
| Example 377 | +++ |
| Example 378 | +++ |
| Example 379 | +++ |
| Example 380 | +++ |
| Example 381 | +++ |
| Example 382 | +++ |
| Example 383 | +++ |
| Example 384 | +++ |
| Example 385 | +++ |
| Example 386 | +++ |
| Example 387 | +++ |
| Example 388 | +++ |
| Example 389 | +++ |
| Example 390 | +++ |
| Example 391 | +++ |
| Example 392 | +++ |
| Example 393 | +++ |
| Example 394 | +++ |
| Example 395 | +++ |
| Example 396 | +++ |
| Example 397 | ++ |
| Example 398 | +++ |
| Example 399 | +++ |
| Example 400 | +++ |

| Example # | FRET BRD4 IC$_{50}$ (nM) |
|---|---|
| Example 401 | +++ |
| Example 402 | +++ |
| Example 403 | +++ |
| Example 405 | +++ |
| Example 406 | +++ |
| Example 407 | +++ |
| Example 408 | +++ |
| Example 409 | +++ |
| Example 411 | +++ |
| Example 412 | +++ |
| Example 413 | +++ |
| Example 414 | +++ |
| Example 415 | +++ |
| Example 416 | +++ |
| Example 417 | +++ |
| Example 418 | ++ |
| Example 419 | +++ |
| Example 420 | +++ |
| Example 421 | +++ |
| Example 422 | +++ |
| Example 423 | +++ |
| Example 424 | +++ |
| Example 427 | +++ |
| Example 428 | +++ |
| Example 429 | +++ |
| Example 430 | +++ |
| Example 431 | +++ |
| Example 432 | +++ |
| Example 433 | +++ |
| Example 434 | +++ |
| Example 435 | +++ |
| Example 436 | +++ |
| Example 437 | +++ |
| Example 438 | +++ |
| Example 439 | +++ |
| Example 440 | +++ |
| Example 441 | +++ |
| Example 442 | +++ |
| Example 443 | +++ |
| Example 444 | +++ |
| Example 445 | +++ |
| Example 446 | +++ |
| Example 447 | +++ |
| Example 448 | +++ |
| Example 449 | +++ |
| Example 450 | +++ |
| Example 451 | +++ |
| Example 452 | +++ |
| Example 453 | +++ |
| Example 454 | ++ |
| Example 455 | ++ |
| Example 456 | +++ |
| Example 457 | +++ |
| Example 458 | +++ |
| Example 459 | +++ |
| Example 460 | +++ |
| Example 461 | +++ |
| Example 462 | +++ |
| Example 463 | +++ |
| Example 464 | +++ |

What is claimed is:

1. A compound of the formula

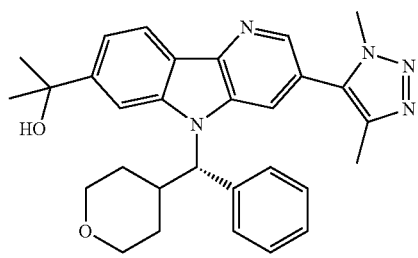 [SMILES: Cc1nnn(C)c1-c1cnc2c3ccc(C(C)(C)O)cc3n([C@H](c3ccccc3)C3CCOCC3)c2c1]

or a pharmaceutically acceptable salt, tautomer or stereoisomer thereof.

2. A pharmaceutical composition which comprises a compound according to claim 1 or a pharmaceutically acceptable salt thereof and one or more pharmaceutically acceptable carriers, diluents or excipients.

3. A method of treating cancer comprising administering a therapeutically effective amount of a compound according to claim 1 or a pharmaceutically acceptable salt thereof wherein the cancer is small cell lung cancer, non-small cell lung cancer, colorectal cancer, multiple myeloma or AML.

* * * * *

UNITED STATES PATENT AND TRADEMARK OFFICE
CERTIFICATE OF CORRECTION

| | | |
|---|---|---|
| PATENT NO. | : 9,458,156 B2 | Page 1 of 1 |
| APPLICATION NO. | : 14/580355 | |
| DATED | : October 4, 2016 | |
| INVENTOR(S) | : Norris et al. | |

It is certified that error appears in the above-identified patent and that said Letters Patent is hereby corrected as shown below:

On the Title Page

Column 1, please insert:
-- (60) Provisional Application Ser. No. 61/920,500 filed on 12/24/2013 --

Signed and Sealed this
Twenty-ninth Day of May, 2018

Andrei Iancu
*Director of the United States Patent and Trademark Office*